(12) United States Patent
Kempsell et al.

(10) Patent No.: US 11,674,188 B2
(45) Date of Patent: Jun. 13, 2023

(54) BIOMARKERS AND COMBINATIONS THEREOF FOR DIAGNOSING TUBERCULOSIS

(71) Applicant: The Secretary of State for Health, London (GB)

(72) Inventors: Karen Kempsell, Salisbury (GB); Nigel Silman, Salisbury (GB); Sally Sharpe, Salisbury (GB); Ann Williams, Salisbury (GB); Richard Vipond, Salisbury (GB); Sajid Javed, Macclesfield (GB)

(73) Assignee: The Secretary of State for Health, London (GB)

( * ) Notice: Subject to any disclaimer, the term of this patent is extended or adjusted under 35 U.S.C. 154(b) by 140 days.

(21) Appl. No.: 15/309,348

(22) PCT Filed: May 7, 2015

(86) PCT No.: PCT/GB2015/051349
§ 371 (c)(1),
(2) Date: Nov. 7, 2016

(87) PCT Pub. No.: WO2015/170108
PCT Pub. Date: Nov. 12, 2015

(65) Prior Publication Data
US 2017/0073737 A1     Mar. 16, 2017

(30) Foreign Application Priority Data
May 7, 2014   (GB) ..................... 1408100

(51) Int. Cl.
*C12Q 1/689*   (2018.01)
*C12Q 1/6883*  (2018.01)

(52) U.S. Cl.
CPC .......... *C12Q 1/689* (2013.01); *C12Q 1/6883* (2013.01); *C12Q 2600/158* (2013.01)

(58) Field of Classification Search
CPC .............................. A61K 39/00; A61K 39/04
USPC .................... 424/184.1, 185.1, 234.1, 248.1; 536/23.1, 23.7, 24.3, 24.32
See application file for complete search history.

(56) References Cited

U.S. PATENT DOCUMENTS

| | | | | |
|---|---|---|---|---|
| 7,598,080 B2 * | 10/2009 | Deirmengian | ....... | C12Q 1/6809 435/325 |
| 7,666,596 B2 * | 2/2010 | Halloran | ............ | C12Q 1/6881 435/6.16 |
| 10,519,216 B2 * | 12/2019 | Sonntag | ............... | C12N 5/0636 |
| 2006/0134663 A1 * | 6/2006 | Harkin | ................ | C12Q 1/6837 435/6.11 |
| 2009/0142301 A1 * | 6/2009 | Bevec | .................... | A61K 31/57 424/85.5 |
| 2011/0196614 A1 * | 8/2011 | Banchereau | ....... | G01N 33/5695 702/19 |
| 2012/0142544 A1 * | 6/2012 | Hare | .................... | C12Q 1/6883 506/7 |
| 2013/0316933 A1 * | 11/2013 | Osta Pinzolas | ...... | C12Q 1/6883 506/9 |
| 2018/0028608 A1 * | 2/2018 | Yu | ........................ | C12Q 1/6883 |
| 2019/0209576 A1 * | 7/2019 | Beeharry | ................ | A61P 35/04 |

FOREIGN PATENT DOCUMENTS

| | | |
|---|---|---|
| WO | 2009/158521 A2 | 12/2009 |
| WO | 2013/177502 A1 | 11/2013 |
| WO | 2013/190321 A1 | 12/2013 |
| WO | 2014/019977 A1 | 2/2014 |
| WO | 2014/067943 A1 | 5/2014 |
| WO | 2014/093872 A1 | 6/2014 |
| WO | 2015/170108 A1 | 11/2015 |

OTHER PUBLICATIONS

Berry, M.P.R., et al., "An Interferon-Inducible Neutrophil-Driven Blood Transcriptional Signature in Human Tuberculosis," Nature Letters 466(7309):973-977, Aug. 2010.
Fu, T., and J. Xie, "Progress on the Biomarkers for Tuberculosis Diagnosis," Critical Reviews™ in Eukaryotic Gene Expression 21(4):379-391, 2011.
Great Britain Search Report Under Section 17(5), dated Jan. 13, 2015, issued in corresponding Application No. GB1408100.4, filed May 7, 2014, 3 pages.
International Preliminary Report on Patentability dated Jul. 11, 2016, issued in corresponding International Application No. PCT/GB2015/051349, filed May 7, 2015, 23 pages.
International Search Report and Written Opinion dated Aug. 20, 2015, issued in corresponding International Application No. PCT/GB2015/051349, filed May 7, 2015, 27 pages.
Lesho, E., et al., "Transcriptional Responses of Host Peripheral Blood Cells to Tuberculosis Infection," Tuberculosis 91(5):390-399, Sep. 2011.
Operon Biotechnologies GmbH, "Operon Microarray Slides—OpArrays™," Jan. 9, 2006, <http://178.250.165.133/ex/downloads/flyer/EU_OpArray_Flyer.pdf> [retrieved Mar. 24, 2016], 1 page.
Second Written Opinion dated Apr. 12, 2016, issued in corresponding International Application No. PCT/GB2015/051349, filed May 7, 2015, 9 pages.
Stanton, L.-A., et al., "Immunophenotyping of Macrophages in Human Pulmonary Tuberculosis and Sarcoidosis," International Journal of Experimental Pathology 84(6):289-304, Dec. 2003.
Stern, J.N.H., et al., "Molecular Signatures Distinguishing Active From Latent Tuberculosis in Peripheral Blood Mononuclear Cells, After In Vitro Antigenic Stimulation With Purified Protein Derivative of Tuberculin (PPD) or Candida: A Preliminary Report," Immunologic Research 45(1):1-12, Oct. 2009.

(Continued)

*Primary Examiner* — Mary Maille Lyons
(74) *Attorney, Agent, or Firm* — Christensen O'Connor Johnson Kindness PLLC

(57) ABSTRACT

This invention relates to the detection and diagnosis of tuberculosis. More specifically, the invention relates to new biomarkers and combinations thereof that enable the accurate detection and diagnosis of tuberculosis.

14 Claims, 12 Drawing Sheets

Specification includes a Sequence Listing.

(56) References Cited

OTHER PUBLICATIONS

Office Action dated Mar. 27, 2018, issued in EP Application No. 15722572.3, filed Nov. 23, 2016, 3 pages.
Mukundan, H., et al., "Rapid Detection of *Mycobacterium tuberculosis* Biomarkers Using a Waveguide-Based Biosensor," Tuberculosis 92(5):407-416, Sep. 2012.
"DNA Arrays : Order Minimum : 500 Arrays : Contact MI for Pricing," © Microarrays Inc 2020, Huntsville, Ala., [retrieved Oct. 22, 2020] <http://www.microarrays.com/dna-arrays.php>, 1 page.
"Human MI ReadyArray Genelist," © Microarrays Inc 2020, Huntsville, Ala., [retrieved Oct. 22, 2020] <http://www.microarrays.com/docs/HS1100_Human_MI_ReadyArray_genelist.xls>.
Examination Report dated May 6, 2020, issued in IN Application No. 201617037590, filed Mar. 11, 2016, 8 pages.
Extended European Search Report dated Jul. 30, 2020, issued in EP Application No. 20170712.2, filed May 7, 2015, 12 pages.
Examination Report dated Aug. 3, 2020, issued in AU Application No. 2015257483, filed May 7, 2015, 5 pages.
"Anti-GBP1 Antibody [EPR8285] ab131255," abcam Product Datasheet, © 1998-2021 Abcam plc, Boston, MA, <https://www.abcam.com/gbp1-antibody-epr8285-ab131255.html> [retrieved May 24, 2021], 6 pages.
"Anti-SNX10 Antibody Produced in Mouse," Sigma-Aldrich Product Datasheet, © 2021 Merck KGaA, Darmstadt, Germany <https://www.sigmaaldrich.com/catalog/product/sigma/sab1407388?lang=en®ion-AU> [retrieved May 24, 2021], 5 pages.
Examination Report No. 2 dated May 24, 2021, issued in Australian Application No. 2015257483, filed May 7, 2015, 4 pages.

* cited by examiner

SEQUENCE LISTING

<160> NUMBER OF SEQ ID NOS: 171

<210> SEQ ID NO 1
<211> LENGTH: 70
<212> TYPE: DNA
<213> ORGANISM: Artificial Sequence
<220> FEATURE:
<223> OTHER INFORMATION: probe

<400> SEQUENCE: 1
caggcccaat gtgcctcatt gagaacacta atgggcgact gatggcgaat ccagaagctc    60
tgaagatcct                                                           70

<210> SEQ ID NO 2
<211> LENGTH: 70
<212> TYPE: DNA
<213> ORGANISM: Artificial Sequence
<220> FEATURE:
<223> OTHER INFORMATION: probe

<400> SEQUENCE: 2
gaacagcacc aagtggaacg tgtgaaagct gagtctgcac aggcttcagc aaaaatgttg    60
cagcaaatgc                                                           70

<210> SEQ ID NO 3
<211> LENGTH: 71
<212> TYPE: DNA
<213> ORGANISM: Artificial Sequence
<220> FEATURE:
<223> OTHER INFORMATION: probe

<400> SEQUENCE: 3
cttcttccca gactttgtgt tgacactgag agatttctag cattacagaa agcgcttttg    60
gacaaaactg t                                                         71

<210> SEQ ID NO 4
<211> LENGTH: 70
<212> TYPE: DNA
<213> ORGANISM: Artificial Sequence

```
<220> FEATURE:
<223> OTHER INFORMATION: probe

<400> SEQUENCE: 4
aggagatgct gttcttggcg ttgctgctcc tgccagttgt ggtcgccttc gccagagctg     60
aagctgaaga                                                           70

<210> SEQ ID NO 5
<211> LENGTH: 70
<212> TYPE: DNA
<213> ORGANISM: Artificial Sequence
<220> FEATURE:
<223> OTHER INFORMATION: probe

<400> SEQUENCE: 5
agctactagc tgcctaagtg tgcactttca atctaactgt gaaagaatct tctgatgttt     60
gtattatcct                                                           70

<210> SEQ ID NO 6
<211> LENGTH: 70
<212> TYPE: DNA
<213> ORGANISM: Artificial Sequence
<220> FEATURE:
<223> OTHER INFORMATION: probe

<400> SEQUENCE: 6
ttccagtggg agttcttggg tttcattgcc gggaaagatg aggaaagaga tccttgaggc     60
tcgcaccttg                                                           70

<210> SEQ ID NO 7
<211> LENGTH: 70
<212> TYPE: DNA
<213> ORGANISM: Artificial Sequence
<220> FEATURE:
<223> OTHER INFORMATION: probe

<400> SEQUENCE: 7
gttcctgtat gggctcgacg tctctggaaa acttctgcag gtcgccaaag gtctccacaa     60
gttgcagcca                                                           70

<210> SEQ ID NO 8
<211> LENGTH: 70
<212> TYPE: DNA
<213> ORGANISM: Artificial Sequence
<220> FEATURE:
<223> OTHER INFORMATION: probe

<400> SEQUENCE: 8
gatgtcgact cctttgcttc ggactctaca caagattatt taacaggaca ctaagatggg     60
gaaacgtcct                                                           70

<210> SEQ ID NO 9
<211> LENGTH: 70
<212> TYPE: DNA
<213> ORGANISM: Artificial Sequence
<220> FEATURE:
<223> OTHER INFORMATION: probe

<400> SEQUENCE: 9
ggttgataag gattttattc ctggactcat gtacatccga gacaatgaag ccacctcaga     60
ggagtttgaa                                                           70
```

```
<210> SEQ ID NO 10
<211> LENGTH: 70
<212> TYPE: DNA
<213> ORGANISM: Artificial Sequence
<220> FEATURE:
<223> OTHER INFORMATION: probe

<400> SEQUENCE: 10
gcctttggtc aaatattctt ctgattactt ccaagccccc tctgactaca gatactaccc     60
ctaccagtcc                                                           70

<210> SEQ ID NO 11
<211> LENGTH: 70
<212> TYPE: DNA
<213> ORGANISM: Artificial Sequence
<220> FEATURE:
<223> OTHER INFORMATION: probe

<400> SEQUENCE: 11
caccattgcc tacgaaaaca aagccctgat gctctgcgaa gggctcttcg tggcagacgt     60
caccgatttc                                                           70

<210> SEQ ID NO 12
<211> LENGTH: 70
<212> TYPE: DNA
<213> ORGANISM: Artificial Sequence
<220> FEATURE:
<223> OTHER INFORMATION: probe

<400> SEQUENCE: 12
tgggaaaata gccacctcct tgttaacagc tttgcagaca cacccgtcg ttttatgccc      60 ctgagcgatg                                                           70

<210> SEQ ID NO 13
<211> LENGTH: 70
<212> TYPE: DNA
<213> ORGANISM: Artificial Sequence
<220> FEATURE:
<223> OTHER INFORMATION: probe

<400> SEQUENCE: 13
tagttctggg gtgatccacg tcatgctgaa tggttcagag ccaacaggag cctatcccat     60
caaaggtttt                                                           70

<210> SEQ ID NO 14
<211> LENGTH: 69
<212> TYPE: DNA
<213> ORGANISM: Artificial Sequence
<220> FEATURE:
<223> OTHER INFORMATION: probe

<400> SEQUENCE: 14
agttcatgcc atccaggcat ttaagagcga tcctcatccc ttcagcaata tgtatttgag     60
ttcacacta                                                            69

<210> SEQ ID NO 15
<211> LENGTH: 70
<212> TYPE: DNA
<213> ORGANISM: Artificial Sequence
<220> FEATURE:
<223> OTHER INFORMATION: probe

<400> SEQUENCE: 15
```

```
gataactagg ataacttgtt gctttgttac ccagcctaat tgaagagtgg cagaggctac    60
tacaaaaagc                                                          70

<210> SEQ ID NO 16
<211> LENGTH: 69
<212> TYPE: DNA
<213> ORGANISM: Artificial Sequence
<220> FEATURE:
<223> OTHER INFORMATION: probe

<400> SEQUENCE: 16
cctggtattc ttttataagt aaagtttacc caggcatgga ccagcttcag ccagggacaa    60
aatcccctc                                                           69

<210> SEQ ID NO 17
<211> LENGTH: 70
<212> TYPE: DNA
<213> ORGANISM: Artificial Sequence
<220> FEATURE:
<223> OTHER INFORMATION: probe

<400> SEQUENCE: 17
tggtgcttct gaataaatct tgccaagata gacaaacaat gatgaaactc agatggagct    60
tcctactcac                                                          70

<210> SEQ ID NO 18
<211> LENGTH: 70
<212> TYPE: DNA
<213> ORGANISM: Artificial Sequence
<220> FEATURE:
<223> OTHER INFORMATION: probe

<400> SEQUENCE: 18
cacccagtaa tgtggaccaa gttagcacac caccggctgc gaaaaagtca cgaatctgac    60
tttgtccttc                                                          70

<210> SEQ ID NO 19
<211> LENGTH: 70
<212> TYPE: DNA
<213> ORGANISM: Artificial Sequence
<220> FEATURE:
<223> OTHER INFORMATION: probe

<400> SEQUENCE: 19
gagtcattgc cacaaagtca agtgaacagt caagatctgt aaatattgct tcaaaacttt    60
ctctccaaga                                                          70

<210> SEQ ID NO 20
<211> LENGTH: 70
<212> TYPE: DNA
<213> ORGANISM: Artificial Sequence
<220> FEATURE:
<223> OTHER INFORMATION: probe

<400> SEQUENCE: 20
aaaagtaacc atcactggtt gcacttatga tttcatgtgc ggggatcatc tgccgtgcct    60
ggatcctgaa                                                          70

<210> SEQ ID NO 21
<211> LENGTH: 70
<212> TYPE: DNA
```

```
<213> ORGANISM: Artificial Sequence
<220> FEATURE:
<223> OTHER INFORMATION: probe

<400> SEQUENCE: 21
tcttctatga acactgctca gacctgctag acatgccata ggagtggcgt gcacatctct      60
ctctcttcca                                                              70

<210> SEQ ID NO 22
<211> LENGTH: 70
<212> TYPE: DNA
<213> ORGANISM: Artificial Sequence
<220> FEATURE:
<223> OTHER INFORMATION: probe

<400> SEQUENCE: 22
tccaccgccc tcatgccgc cctttggagg aaagtgaaag tgaaaggagg aagaggaggc       60
ttcatggctg                                                              70

<210> SEQ ID NO 23
<211> LENGTH: 70
<212> TYPE: DNA
<213> ORGANISM: Artificial Sequence
<220> FEATURE:
<223> OTHER INFORMATION: probe

<400> SEQUENCE: 23
acctgcaagg attcaaagaa gaaagcagag tgagggcact cactgccatc ctgtggaagc      60
caccatcatc                                                              70

<210> SEQ ID NO 24
<211> LENGTH: 70
<212> TYPE: DNA
<213> ORGANISM: Artificial Sequence
<220> FEATURE:
<223> OTHER INFORMATION: probe

<400> SEQUENCE: 24
acagcaggca tcgcaacttt ctgcatgttg atgcccgaag aaaatttcac tgccgaccat      60
ccattccttt                                                              70

<210> SEQ ID NO 25
<211> LENGTH: 70
<212> TYPE: DNA
<213> ORGANISM: Artificial Sequence
<220> FEATURE:
<223> OTHER INFORMATION: probe

<400> SEQUENCE: 25
acatccgatg cgtagattct tgaccatgta gtaatctata aaattgctat atcctcctga      60
tagccatggg                                                              70

<210> SEQ ID NO 26
<211> LENGTH: 70
<212> TYPE: DNA
<213> ORGANISM: Artificial Sequence
<220> FEATURE:
<223> OTHER INFORMATION: probe

<400> SEQUENCE: 26
tgccggtgtg gaccatcgag tcatcttggg caatgaactg ccaaaattct atgatgagtg      60
aaccttcccc                                                              70
```

<210> SEQ ID NO 27
<211> LENGTH: 70
<212> TYPE: DNA
<213> ORGANISM: Artificial Sequence
<220> FEATURE:
<223> OTHER INFORMATION: probe

<400> SEQUENCE: 27
aataaactct ctagggccaa aacctggtat ggtcattggg aaatgagtgc tcagggagat    60
ggagcttagg                                                          70

<210> SEQ ID NO 28
<211> LENGTH: 69
<212> TYPE: DNA
<213> ORGANISM: Artificial Sequence
<220> FEATURE:
<223> OTHER INFORMATION: probe

<400> SEQUENCE: 28
agatggtaaa tactgactta cgaaagttga attgggtgag gcgggcaaat cacctgaggt    60
cagcagttt                                                           69

<210> SEQ ID NO 29
<211> LENGTH: 70
<212> TYPE: DNA
<213> ORGANISM: Artificial Sequence
<220> FEATURE:
<223> OTHER INFORMATION: probe

<400> SEQUENCE: 29
cgtatcgtat ttagaagatt ctgccttccc tagtagtagg gactgacaga atacacttaa    60
cacaaacctc                                                          70

<210> SEQ ID NO 30
<211> LENGTH: 70
<212> TYPE: DNA
<213> ORGANISM: Artificial Sequence
<220> FEATURE:
<223> OTHER INFORMATION: probe

<400> SEQUENCE: 30
ctcaagctcc tggagacaac cacgtggtgc ctgtactgcg ctaactcctg attaatacaa    60
tggaagtttc                                                          70

<210> SEQ ID NO 31
<211> LENGTH: 70
<212> TYPE: DNA
<213> ORGANISM: Artificial Sequence
<220> FEATURE:
<223> OTHER INFORMATION: probe

<400> SEQUENCE: 31
ctggctgagg tggaggtgaa gaagttcaag cagatgacag aggccatagg ccccagcacc    60
atcagggacc                                                          70

<210> SEQ ID NO 32
<211> LENGTH: 70
<212> TYPE: DNA
<213> ORGANISM: Artificial Sequence
<220> FEATURE:
<223> OTHER INFORMATION: probe

```
<400> SEQUENCE: 32
tgtggcaaag gctggacttg cctctcggtg gacaaacttg gggacagtca atgcagctgc      60
accagctcag                                                            70

<210> SEQ ID NO 33
<211> LENGTH: 70
<212> TYPE: DNA
<213> ORGANISM: Artificial Sequence
<220> FEATURE:
<223> OTHER INFORMATION: probe

<400> SEQUENCE: 33
atgaatgata acagcacaaa gtcactgatg gtggatgagc ggcagctggc ccgagatgtt      60
ctggacaacc                                                            70

<210> SEQ ID NO 34
<211> LENGTH: 70
<212> TYPE: DNA
<213> ORGANISM: Artificial Sequence
<220> FEATURE:
<223> OTHER INFORMATION: probe

<400> SEQUENCE: 34
aaatggttgg gcagaacagc aaggggttca tatggctata ttaaaacaac tgctgtagag      60
attgactatg                                                            70

<210> SEQ ID NO 35
<211> LENGTH: 70
<212> TYPE: DNA
<213> ORGANISM: Artificial Sequence
<220> FEATURE:
<223> OTHER INFORMATION: probe

<400> SEQUENCE: 35
atggctgcat ctatgacaat gactagcact caactttggt cattctgctg tgttcattag      60
gtgccaatgt                                                            70

<210> SEQ ID NO 36
<211> LENGTH: 70
<212> TYPE: DNA
<213> ORGANISM: Artificial Sequence
<220> FEATURE:
<223> OTHER INFORMATION: probe

<400> SEQUENCE: 36
cgtatgtacc cagaaccctc aagacagtca gtgggaccgc aaagacctgg gcctctgctt      60
tgataactgc                                                            70

<210> SEQ ID NO 37
<211> LENGTH: 70
<212> TYPE: DNA
<213> ORGANISM: Artificial Sequence
<220> FEATURE:
<223> OTHER INFORMATION: probe

<400> SEQUENCE: 37
ccaagaaggc ctgcgcattc aaaactggct ttcagcaaaa gttaggaagc aactacgact      60
aaagccattt                                                            70

<210> SEQ ID NO 38
<211> LENGTH: 70
```

```
<212> TYPE: DNA
<213> ORGANISM: Artificial Sequence
<220> FEATURE:
<223> OTHER INFORMATION: probe

<400> SEQUENCE: 38
atattctgat cccgaatcaa ttatagggg ctatgcagaa ttcctgtacc aaattggctt    60
gttggatgag                                                          70

<210> SEQ ID NO 39
<211> LENGTH: 70
<212> TYPE: DNA
<213> ORGANISM: Artificial Sequence
<220> FEATURE:
<223> OTHER INFORMATION: probe

<400> SEQUENCE: 39
tgtcacaagt aacatgacct tgcgtgacag agacttcccc tggaccacaa cgctctccat    60
gctttacatt                                                          70

<210> SEQ ID NO 40
<211> LENGTH: 70
<212> TYPE: DNA
<213> ORGANISM: Artificial Sequence
<220> FEATURE:
<223> OTHER INFORMATION: probe

<400> SEQUENCE: 40
tatatactaa taaaacatga actgcccact cttcatgcct gccaaacttg gggcaattga    60
tgctaaatgg                                                          70

<210> SEQ ID NO 41
<211> LENGTH: 70
<212> TYPE: DNA
<213> ORGANISM: Artificial Sequence
<220> FEATURE:
<223> OTHER INFORMATION: probe

<400> SEQUENCE: 41
ttgtatatcc cctaccagta ccgggatctg cacacatctt tttgcagtta cctcttcata    60
gccatgaacc                                                          70

<210> SEQ ID NO 42
<211> LENGTH: 70
<212> TYPE: DNA
<213> ORGANISM: Artificial Sequence
<220> FEATURE:
<223> OTHER INFORMATION: probe

<400> SEQUENCE: 42
gttgatgcca gacatcacca ggttgtagaa gttgacaggc agtgccatgg gggcaacagc    60
caaaataggg                                                          70

<210> SEQ ID NO 43
<211> LENGTH: 70
<212> TYPE: DNA
<213> ORGANISM: Artificial Sequence
<220> FEATURE:
<223> OTHER INFORMATION: probe

<400> SEQUENCE: 43
caatgccata atccacctct tctgcttcag ttgaggtgac acgtctcagc cttagccctg    60
```

```
tgccccctga                                                             70

<210> SEQ ID NO 44
<211> LENGTH: 70
<212> TYPE: DNA
<213> ORGANISM: Artificial Sequence
<220> FEATURE:
<223> OTHER INFORMATION: probe

<400> SEQUENCE: 44
gcattcaaac gtacaattgt atctgtggga agagaataga ctctattttc tctgattcgg      60
tgtgcgccaa                                                             70

<210> SEQ ID NO 45
<211> LENGTH: 70
<212> TYPE: DNA
<213> ORGANISM: Artificial Sequence
<220> FEATURE:
<223> OTHER INFORMATION: probe

<400> SEQUENCE: 45
actctgtttc tcaatgttgg acctaagata ttgaagacag gctggagccc agagccttca      60
ttcaatctca                                                             70

<210> SEQ ID NO 46
<211> LENGTH: 70
<212> TYPE: DNA
<213> ORGANISM: Artificial Sequence
<220> FEATURE:
<223> OTHER INFORMATION: probe

<400> SEQUENCE: 46
tgcttcaata aagtaacagg ctattgcagg aagaaatgca aggtaggaga aagatatgaa      60
ataggatgtc                                                             70

<210> SEQ ID NO 47
<211> LENGTH: 70
<212> TYPE: DNA
<213> ORGANISM: Artificial Sequence
<220> FEATURE:
<223> OTHER INFORMATION: probe

<400> SEQUENCE: 47
tgtgtcattt aagaagccac atcaacattc tggtgagaag ctgagtgtgc tgcaggatta      60
catcatctta                                                             70

<210> SEQ ID NO 48
<211> LENGTH: 70
<212> TYPE: DNA
<213> ORGANISM: Artificial Sequence
<220> FEATURE:
<223> OTHER INFORMATION: probe

<400> SEQUENCE: 48
attttaattg aactaacaat cctagtttga tactcccagt cttgtcattg ccagctgtgt      60
tggtagtgct                                                             70

<210> SEQ ID NO 49
<211> LENGTH: 70
<212> TYPE: DNA
<213> ORGANISM: Artificial Sequence
<220> FEATURE:
<223> OTHER INFORMATION: probe
```

```
<400> SEQUENCE: 49
aaagaactga gagtgattga gagtggacca cactgcgcca acacagaaat tattgtaaag    60
ctttctgatg                                                          70

<210> SEQ ID NO 50
<211> LENGTH: 70
<212> TYPE: DNA
<213> ORGANISM: Artificial Sequence
<220> FEATURE:
<223> OTHER INFORMATION: probe

<400> SEQUENCE: 50
agctggtacc actcaggaga agtttattct tccagatgac cagcagtaga caaatggata    60
ctgagcagag                                                          70

<210> SEQ ID NO 51
<211> LENGTH: 70
<212> TYPE: DNA
<213> ORGANISM: Artificial Sequence
<220> FEATURE:
<223> OTHER INFORMATION: probe

<400> SEQUENCE: 51
tctccagagg aaggtggaag aaaccatggg caggagtagg aattgagtga taaacaattg    60
ggctaatgaa                                                          70

<210> SEQ ID NO 52
<211> LENGTH: 70
<212> TYPE: DNA
<213> ORGANISM: Artificial Sequence
<220> FEATURE:
<223> OTHER INFORMATION: probe

<400> SEQUENCE: 52
atcccagggc tggctctgca ctaagagaaa attgcactaa atgaatctcg ttcccaaaga    60
actacccct                                                           70

<210> SEQ ID NO 53
<211> LENGTH: 70
<212> TYPE: DNA
<213> ORGANISM: Artificial Sequence
<220> FEATURE:
<223> OTHER INFORMATION: probe

<400> SEQUENCE: 53
agccctcaac aggcccaggg agggaagtgt gagcgccttg gtatgactta aaattggaaa    60
tgtcatctaa                                                          70

<210> SEQ ID NO 54
<211> LENGTH: 70
<212> TYPE: DNA
<213> ORGANISM: Artificial Sequence
<220> FEATURE:
<223> OTHER INFORMATION: probe

<400> SEQUENCE: 54
taccacctcg aactttgaca gcgacaagaa gtggggcttc tgcccggacc aaggatacag    60
tttgttcctc                                                          70

<210> SEQ ID NO 55
```

<211> LENGTH: 70
<212> TYPE: DNA
<213> ORGANISM: Artificial Sequence
<220> FEATURE:
<223> OTHER INFORMATION: probe

<400> SEQUENCE: 55
ttctactggc gcgtgagttc ccggagtgag ttgaaccagg tggaccaagt gggctacgtg  60
acctatgaca  70

<210> SEQ ID NO 56
<211> LENGTH: 70
<212> TYPE: DNA
<213> ORGANISM: Artificial Sequence
<220> FEATURE:
<223> OTHER INFORMATION: probe

<400> SEQUENCE: 56
tgcatggtcg gtggaaaaca gcagcacgga ttcttgggtc cttctttcta agggtataaa  60
ggaggataat  70

<210> SEQ ID NO 57
<211> LENGTH: 70
<212> TYPE: DNA
<213> ORGANISM: Artificial Sequence
<220> FEATURE:
<223> OTHER INFORMATION: probe

<400> SEQUENCE: 57
ggaggtattc acactcaggg tcatgcactt gcacaatgtt gagaatgagt accactctca  60
ccattggtat  70

<210> SEQ ID NO 58
<211> LENGTH: 70
<212> TYPE: DNA
<213> ORGANISM: Artificial Sequence
<220> FEATURE:
<223> OTHER INFORMATION: probe

<400> SEQUENCE: 58
tgtcccgctg aacattatca gaaaagctgg tgaaaccccg aagatcaaca cgcttcaaac  60
tcagcccctt  70

<210> SEQ ID NO 59
<211> LENGTH: 70
<212> TYPE: DNA
<213> ORGANISM: Artificial Sequence
<220> FEATURE:
<223> OTHER INFORMATION: probe

<400> SEQUENCE: 59
tagcaagata ttatcggcac agtggtttct tagaggtaaa tagcgcctca cgtgtgttag  60
atgctgaatc  70

<210> SEQ ID NO 60
<211> LENGTH: 70
<212> TYPE: DNA
<213> ORGANISM: Artificial Sequence
<220> FEATURE:
<223> OTHER INFORMATION: probe

<400> SEQUENCE: 60
agaccaccac caccaattcc aagagagagg agaagctttt caatgtgacc agcacactga  60

```
gaatcaacac                                                            70

<210> SEQ ID NO 61
<211> LENGTH: 70
<212> TYPE: DNA
<213> ORGANISM: Artificial Sequence
<220> FEATURE:
<223> OTHER INFORMATION: probe

<400> SEQUENCE: 61
taacccatta atactctggt tgacctaatc ttattctcag acctcaagtg tctgtgcagt    60
atctgttcca                                                            70

<210> SEQ ID NO 62
<211> LENGTH: 70
<212> TYPE: DNA
<213> ORGANISM: Artificial Sequence
<220> FEATURE:
<223> OTHER INFORMATION: probe

<400> SEQUENCE: 62
atcccacttt tgccagacgc tcattcagca tctgacctct accttcataa gatctgttat    60
ttttataaga                                                            70

<210> SEQ ID NO 63
<211> LENGTH: 70
<212> TYPE: DNA
<213> ORGANISM: Artificial Sequence
<220> FEATURE:
<223> OTHER INFORMATION: probe

<400> SEQUENCE: 63
tgctgaaggt ggtcctggag gattacctgc ggctcaaaaa gctctttgca cagcggatgg    60
tgcaaaaagc                                                            70

<210> SEQ ID NO 64
<211> LENGTH: 70
<212> TYPE: DNA
<213> ORGANISM: Artificial Sequence
<220> FEATURE:
<223> OTHER INFORMATION: probe

<400> SEQUENCE: 64
gggactgaat cctctgaatg catactccga tctcgctgag ttcctggaga cggaatgtta    60
tcagacacca                                                            70

<210> SEQ ID NO 65
<211> LENGTH: 70
<212> TYPE: DNA
<213> ORGANISM: Artificial Sequence
<220> FEATURE:
<223> OTHER INFORMATION: probe

<400> SEQUENCE: 65
gagacagagg aggaaaacag agcatcagaa gcctgcagtg gtggttgtga cgggtaggac    60
gataggaaga                                                            70

<210> SEQ ID NO 66
<211> LENGTH: 70
<212> TYPE: DNA
<213> ORGANISM: Artificial Sequence
<220> FEATURE:
```

<223> OTHER INFORMATION: probe

<400> SEQUENCE: 66
aggcctatgc ctccaccgcc aagtgcctga acatctgggc cctgattctg ggcatcctca    60
tgaccattct                                                            70

<210> SEQ ID NO 67
<211> LENGTH: 70
<212> TYPE: DNA
<213> ORGANISM: Artificial Sequence
<220> FEATURE:
<223> OTHER INFORMATION: probe

<400> SEQUENCE: 67
tgatcttcca ggcctatgga tagatcagga ggcatcactg aggccaggag ctctgcccat    60
gacctgtatc                                                            70

<210> SEQ ID NO 68
<211> LENGTH: 70
<212> TYPE: DNA
<213> ORGANISM: Artificial Sequence
<220> FEATURE:
<223> OTHER INFORMATION: probe

<400> SEQUENCE: 68
gaccagcaac aaaattctta tgcagctaca agcagacatt ctgtatatac cagtagtgaa    60
gccctcaatg                                                            70

<210> SEQ ID NO 69
<211> LENGTH: 70
<212> TYPE: DNA
<213> ORGANISM: Artificial Sequence
<220> FEATURE:
<223> OTHER INFORMATION: probe

<400> SEQUENCE: 69
aactcatgga ttcccaagat gtgagctttt tacataatga aagaacccag caattctgtc    60
tcttaatgca                                                            70

<210> SEQ ID NO 70
<211> LENGTH: 70
<212> TYPE: DNA
<213> ORGANISM: Artificial Sequence
<220> FEATURE:
<223> OTHER INFORMATION: probe

<400> SEQUENCE: 70
ttgattgttg gcccctgcct tgcccagatg tggagtgtga attcagcatt ctcccagaga    60
atgagtgctg                                                            70

<210> SEQ ID NO 71
<211> LENGTH: 70
<212> TYPE: DNA
<213> ORGANISM: Artificial Sequence
<220> FEATURE:
<223> OTHER INFORMATION: probe

<400> SEQUENCE: 71
taccgtgaca tcctgaaccc tggatagaaa gcctgagccc attggatctg tgaaagcctc    60
tagcttcact                                                            70

```
<210> SEQ ID NO 72
<211> LENGTH: 70
<212> TYPE: DNA
<213> ORGANISM: Artificial Sequence
<220> FEATURE:
<223> OTHER INFORMATION: probe

<400> SEQUENCE: 72
cagcctttct gtcatcatct ccacagccca cccatcccct gagcacacta accacctcat     60
gcaggcccca                                                            70

<210> SEQ ID NO 73
<211> LENGTH: 70
<212> TYPE: DNA
<213> ORGANISM: Artificial Sequence
<220> FEATURE:
<223> OTHER INFORMATION: probe

<400> SEQUENCE: 73
ttggtggcct agctatggct tgccatgact ccttcctcaa ggctgtccct tcccagaagc     60
ggacctgagg                                                            70

<210> SEQ ID NO 74
<211> LENGTH: 70
<212> TYPE: DNA
<213> ORGANISM: Artificial Sequence
<220> FEATURE:
<223> OTHER INFORMATION: probe

<400> SEQUENCE: 74
ataacagcaa gagggaacct ggcaaggaag ctattcctat aatccaggaa agagatgagg     60
aaggcttgga                                                            70

<210> SEQ ID NO 75
<211> LENGTH: 70
<212> TYPE: DNA
<213> ORGANISM: Artificial Sequence
<220> FEATURE:
<223> OTHER INFORMATION: probe

<400> SEQUENCE: 75
actggaaatc ctctgtgaaa atgagtgtac agagacagac atcgagaaag acaaatctaa     60
attcctggag                                                            70

<210> SEQ ID NO 76
<211> LENGTH: 70
<212> TYPE: DNA
<213> ORGANISM: Artificial Sequence
<220> FEATURE:
<223> OTHER INFORMATION: probe

<400> SEQUENCE: 76
cctgacatca ttcgcaatta caaagtcatg gctgctgaga atattcctga gaatcccctg     60
aagtatctgt                                                            70

<210> SEQ ID NO 77
<211> LENGTH: 70
<212> TYPE: DNA
<213> ORGANISM: Artificial Sequence
<220> FEATURE:
<223> OTHER INFORMATION: probe

<400> SEQUENCE: 77
```

```
gatacaccca aagtatcagg acgagaatga gggtcctttg ggaaaggaga agttaagcaa    60
catctagcaa                                                          70

<210> SEQ ID NO 78
<211> LENGTH: 70
<212> TYPE: DNA
<213> ORGANISM: Artificial Sequence
<220> FEATURE:
<223> OTHER INFORMATION: probe

<400> SEQUENCE: 78
gactgtgacc tccctctgca tctacttgga tctgccctgg tatctcagga tggtgtgcca    60
gtggacccag                                                          70

<210> SEQ ID NO 79
<211> LENGTH: 70
<212> TYPE: DNA
<213> ORGANISM: Artificial Sequence
<220> FEATURE:
<223> OTHER INFORMATION: probe

<400> SEQUENCE: 79
attcccaaca agtaccacaa gctgaaggct ctcatgacgc agcggactta tttgcagtgg    60
cccaaggaga                                                          70

<210> SEQ ID NO 80
<211> LENGTH: 70
<212> TYPE: DNA
<213> ORGANISM: Artificial Sequence
<220> FEATURE:
<223> OTHER INFORMATION: probe

<400> SEQUENCE: 80
ccaaggagtc ctggcctccg cagatgcttc attttgaccc ttggctgcag tggaagtcag    60
cacagagcag                                                          70

<210> SEQ ID NO 81
<211> LENGTH: 70
<212> TYPE: DNA
<213> ORGANISM: Artificial Sequence
<220> FEATURE:
<223> OTHER INFORMATION: probe

<400> SEQUENCE: 81
cctggcctct gtaagcctgt gtatgttatc aatactgttt cttcctgtga gttccattat    60
ttctatctct                                                          70

<210> SEQ ID NO 82
<211> LENGTH: 70
<212> TYPE: DNA
<213> ORGANISM: Artificial Sequence
<220> FEATURE:
<223> OTHER INFORMATION: probe

<400> SEQUENCE: 82
ggaagagcag tgcaaacggc gcaccatcct gacagccata cactgcttcc cttatgtgaa    60
gaagcgcatc                                                          70

<210> SEQ ID NO 83
<211> LENGTH: 70
<212> TYPE: DNA
<213> ORGANISM: Artificial Sequence
```

```
<220> FEATURE:
<223> OTHER INFORMATION: probe

<400> SEQUENCE: 83
acatcttcaa cgccatcagt gggactccaa caagcacaat ggttcacggg atgaccagct     60
cgtcttcggt                                                            70

<210> SEQ ID NO 84
<211> LENGTH: 70
<212> TYPE: DNA
<213> ORGANISM: Artificial Sequence
<220> FEATURE:
<223> OTHER INFORMATION: probe

<400> SEQUENCE: 84
ttctgcaaaa cgtctccagt gaggatgcag gcacctatta ctgtgtaaag tttcagagga     60
aacccaacag                                                            70

<210> SEQ ID NO 85
<211> LENGTH: 70
<212> TYPE: DNA
<213> ORGANISM: Artificial Sequence
<220> FEATURE:
<223> OTHER INFORMATION: probe

<400> SEQUENCE: 85
tattagaatg caggttcagc aactataaca aagctcttaa ataacagtgg cttaaaccag     60
tggaaatcaa                                                            70

<210> SEQ ID NO 86
<211> LENGTH: 70
<212> TYPE: DNA
<213> ORGANISM: Artificial Sequence
<220> FEATURE:
<223> OTHER INFORMATION: probe

<400> SEQUENCE: 86
agacttttgg tctgtgggcc atttaacctg gatgccacca ttttatgggg ataatgatgc     60
ttaccatggt                                                            70

<210> SEQ ID NO 87
<211> LENGTH: 70
<212> TYPE: DNA
<213> ORGANISM: Artificial Sequence
<220> FEATURE:
<223> OTHER INFORMATION: probe

<400> SEQUENCE: 87
tcaagttcac catggccgta atccttctaa gggaaacact aaagttgttg tagtctccac     60
ttcagtcaga                                                            70

<210> SEQ ID NO 88
<211> LENGTH: 70
<212> TYPE: DNA
<213> ORGANISM: Artificial Sequence
<220> FEATURE:
<223> OTHER INFORMATION: probe

<400> SEQUENCE: 88
catcatgaac tcgtttgtaa acgacgtgtt tgagcagctg gcgtgtgagg ctgcccggct     60
ggcccagtac                                                            70
```

<210> SEQ ID NO 89
<211> LENGTH: 70
<212> TYPE: DNA
<213> ORGANISM: Artificial Sequence
<220> FEATURE:
<223> OTHER INFORMATION: probe

<400> SEQUENCE: 89
cagccatgac ttcagactca ttcagcaggt tgcacaggaa atttgggtct gtgagaagca    60
gacaatcacc                                                           70

<210> SEQ ID NO 90
<211> LENGTH: 70
<212> TYPE: DNA
<213> ORGANISM: Artificial Sequence
<220> FEATURE:
<223> OTHER INFORMATION: probe

<400> SEQUENCE: 90
tactgccttc ataagatcaa gtcaccactg ttacacagct gacatatagt gtattacctt    60
tgcagctagt                                                           70

<210> SEQ ID NO 91
<211> LENGTH: 70
<212> TYPE: DNA
<213> ORGANISM: Artificial Sequence
<220> FEATURE:
<223> OTHER INFORMATION: probe

<400> SEQUENCE: 91
ggaggaaatg tgatctggct gtgtttgtct tctgtacaaa gcctgaagtg cttatggttt    60
tttggctaac                                                           70

<210> SEQ ID NO 92
<211> LENGTH: 70
<212> TYPE: DNA
<213> ORGANISM: Artificial Sequence
<220> FEATURE:
<223> OTHER INFORMATION: probe

<400> SEQUENCE: 92
ggtggttctg tcagatgaaa gcaaagcgag gctggatccc agcatccttc ctcgagcccc    60
tggacagtcc                                                           70

<210> SEQ ID NO 93
<211> LENGTH: 70
<212> TYPE: DNA
<213> ORGANISM: Artificial Sequence
<220> FEATURE:
<223> OTHER INFORMATION: probe

<400> SEQUENCE: 93
gacgtcacag gctactttcc gtccatgtac ctgcaaaagt cggggcaaga cgtgtcccag    60
gcccaacgcc                                                           70

<210> SEQ ID NO 94
<211> LENGTH: 70
<212> TYPE: DNA
<213> ORGANISM: Artificial Sequence
<220> FEATURE:
<223> OTHER INFORMATION: probe

<400> SEQUENCE: 94

```
actgattccg accagggcac ccccttcaga gctagggacg aacagcagta tgctcccacc    60
tcagggcctt                                                           70
```

<210> SEQ ID NO 95
<211> LENGTH: 70
<212> TYPE: DNA
<213> ORGANISM: Artificial Sequence
<220> FEATURE:
<223> OTHER INFORMATION: probe

<400> SEQUENCE: 95

```
aggcttctag aagcatctgg gccagggctc atggctggat aatttcccta ggcttaacaa    60
cccaagcaag                                                           70
```

<210> SEQ ID NO 96
<211> LENGTH: 70
<212> TYPE: DNA
<213> ORGANISM: Artificial Sequence
<220> FEATURE:
<223> OTHER INFORMATION: probe

<400> SEQUENCE: 96

```
tgacattctc tcatgggaca atgttggggt ttttcagact gacaggactg caagagggag    60
aaaggaattt                                                           70
```

<210> SEQ ID NO 97
<211> LENGTH: 70
<212> TYPE: DNA
<213> ORGANISM: Artificial Sequence
<220> FEATURE:
<223> OTHER INFORMATION: probe

<400> SEQUENCE: 97

```
tcacaatatt ctctctcaga aatcaatggc atttgaacca ccaaaaagaa ataaagggct    60
gagtgcggtg                                                           70
```

<210> SEQ ID NO 98
<211> LENGTH: 70
<212> TYPE: DNA
<213> ORGANISM: Artificial Sequence
<220> FEATURE:
<223> OTHER INFORMATION: probe

<400> SEQUENCE: 98

```
cattttctat cccctcaggg actgaacaaa tggaaataac tcccaggcag tatcaggtgg    60
tcactacaga                                                           70
```

<210> SEQ ID NO 99
<211> LENGTH: 70
<212> TYPE: DNA
<213> ORGANISM: Artificial Sequence
<220> FEATURE:
<223> OTHER INFORMATION: probe

<400> SEQUENCE: 99

```
ctgggctttc cctaatgtgg ttgggagtta tgccctagac taactgtatt gtcctagtca    60
cagctccttg                                                           70
```

<210> SEQ ID NO 100
<211> LENGTH: 70
<212> TYPE: DNA

<213> ORGANISM: Artificial Sequence
<220> FEATURE:
<223> OTHER INFORMATION: probe

<400> SEQUENCE: 100
cgctagaaac cagtgtggat ttgattacaa ctggggactt catgtccagg ttctgttcca    60
acctttgtct                                                           70

<210> SEQ ID NO 101
<211> LENGTH: 70
<212> TYPE: DNA
<213> ORGANISM: Artificial Sequence
<220> FEATURE:
<223> OTHER INFORMATION: probe

<400> SEQUENCE: 101
tctctgtggc agcggcagct atttacatgg cctcacaggc atcagctgaa aagaggaccc    60
aaaaagaaat                                                           70

<210> SEQ ID NO 102
<211> LENGTH: 70
<212> TYPE: DNA
<213> ORGANISM: Artificial Sequence
<220> FEATURE:
<223> OTHER INFORMATION: probe

<400> SEQUENCE: 102
agctactctc aggctgcgtg cagcgacagt gcccagggct ctgatgtgtc tctcacagct    60
tgaaaagcct                                                           70

<210> SEQ ID NO 103
<211> LENGTH: 70
<212> TYPE: DNA
<213> ORGANISM: Artificial Sequence
<220> FEATURE:
<223> OTHER INFORMATION: probe

<400> SEQUENCE: 103
gcataatgtg aggaggtgga gagacagccc acccttgtgt ccactgtgac ccctgttccc    60
atgctgacct                                                           70

<210> SEQ ID NO 104
<211> LENGTH: 70
<212> TYPE: DNA
<213> ORGANISM: Artificial Sequence
<220> FEATURE:
<223> OTHER INFORMATION: probe

<400> SEQUENCE: 104
atcacccagc gcttctatga ggcagaggaa tatgcagagg agttcaggac ctacctggag    60
ggcgagtgcc                                                           70

<210> SEQ ID NO 105
<211> LENGTH: 70
<212> TYPE: DNA
<213> ORGANISM: Artificial Sequence
<220> FEATURE:
<223> OTHER INFORMATION: probe

<400> SEQUENCE: 105
gagatcacgc tgacctggca gcgggatggg gaggaacaga cccaggacac agagcttgtg    60
gagaccaggc                                                           70

<210> SEQ ID NO 106
<211> LENGTH: 70
<212> TYPE: DNA
<213> ORGANISM: Artificial Sequence
<220> FEATURE:
<223> OTHER INFORMATION: probe

<400> SEQUENCE: 106
tcactgggtc accagagttt gagagagtat ttcgggcaca acaaaactgt gtggagtttt    60
atcctatatt                                                          70

<210> SEQ ID NO 107
<211> LENGTH: 70
<212> TYPE: DNA
<213> ORGANISM: Artificial Sequence
<220> FEATURE:
<223> OTHER INFORMATION: probe

<400> SEQUENCE: 107
acggatcacc ggtttccgac tgagtctggg gattttggcc ttgttgaccc tcctaggtgc    60
cctgggaatt                                                          70

<210> SEQ ID NO 108
<211> LENGTH: 70
<212> TYPE: DNA
<213> ORGANISM: Artificial Sequence
<220> FEATURE:
<223> OTHER INFORMATION: probe

<400> SEQUENCE: 108
cacaaacgga cgtctataat gacagtacta acttggcatg ccgcaatgga catctccagt    60
cagaaagtgg                                                          70

<210> SEQ ID NO 109
<211> LENGTH: 70
<212> TYPE: DNA
<213> ORGANISM: Artificial Sequence
<220> FEATURE:
<223> OTHER INFORMATION: probe

<400> SEQUENCE: 109
ttaggaatgt ggacagcaac cttgctaacc ttataatgaa tgaaattgtg gacaatggaa    60
cagctgttaa                                                          70

<210> SEQ ID NO 110
<211> LENGTH: 70
<212> TYPE: DNA
<213> ORGANISM: Artificial Sequence
<220> FEATURE:
<223> OTHER INFORMATION: probe

<400> SEQUENCE: 110
gttttgtaga gtgaagccat gggaagccat gtgtaacaga gcttagacat ccaaaactaa    60
tcaatgctga                                                          70

<210> SEQ ID NO 111
<211> LENGTH: 70
<212> TYPE: DNA
<213> ORGANISM: Artificial Sequence
<220> FEATURE:
<223> OTHER INFORMATION: probe

<400> SEQUENCE: 111

```
ggtgctgact gctgttctta gccatcacaa aacgctaaat ttgtgtaatt ggagcttcct    60
gctgttatct                                                          70
```

<210> SEQ ID NO 112
<211> LENGTH: 1234
<212> TYPE: DNA
<213> ORGANISM: Homo sapiens

<400> SEQUENCE: 112

```
aaaatattag tccaaggatc cagtgagaga cacagaagtg ctagaagcca ctcctcatga    60
actaaggaga aaagaacag acaagggaac accccagaca tggtatcaga gatccacatg   120
acaggcccaa tgtgcctcat tgagaacact aatgggcgac tgatggcgaa tccagaagct   180
ctgaagatcc tttctgccat tacgcagcct gtggtggtgg tggcgactgt gggccgctag   240
cgcacaggaa atcctacct gattaacaag ctggctcaga agaaaaaggg cttctctctg   300
ggctccacag tgcagtctca cactaaagga atctggatgt ggtgtatgcc ccatcccaag   360
aagccaggcc acatcctagt tctgctggac accgagggtc tgggagatgt agagaagggt   420
gacaaccaga atgactcctg gatcttcgcc ctggccgtcc tcctgaacag cacttccatg   480
tacaatagca taggaaccat taaccagcag gccatggacc aactgcagta tcctttgtga   540
cccagaacag caccaagtgg aacgtgtgaa agctgagtct gcacaggctt cagcaaaaat   600
gttgcagcaa atgcaaagaa agaatgagca gatgatggaa cagaaggaga ggagttatca   660
ggaacacttg aaacaactga ctgagaagat ggagagcgac agggtccagt tgctggaaga   720
gcaagagagg accctcgctc ttaaacttca ggtgtctaat tgcatcacct tgaggtttct   780
gttttttctgt tttctctcca ttctccccga tcacaggctt actgtggcag agagaacatg   840
aagcccaggg gaagaaccct gcttgcttac ttgtactttt caattcctgt ctgtccagcc   900
tgaactggct actgccaagt ctggtcacta aactgcaaat attgcagttg tgtcacattc   960
agtgctttat ctatatatcc ttcatttcaa ggcaggtatt atctgctagc catcattaaa  1020
gtatctgtat ctcttgctta ataccatgtg aagcaagaac tatattctta ttacttagga  1080
gaagaaacaa agtttccaaa aataataaat aaatagagtc acacagctag taaatgtatc  1140
aaagctgtct tcatcactta gtggaatcca caatgattat ttttttctgt gacacctagt  1200
atgaaattaa acttaagaaa acctttgtga gcag                             1234
```

<210> SEQ ID NO 113
<211> LENGTH: 17257
<212> TYPE: DNA
<213> ORGANISM: Homo sapiens

<400> SEQUENCE: 113

```
aaaatattag tccaaggatc cagtgagaga cacagaagtg ctagaagcca ctcctcatga    60
actaaggaga aaagaacag gtaagaactt ttactacttc tcattaagca gctttctctt   120
tagctccaaa ggatctcagc tcagggatat ggaacccata aggttgtggc agggatggga   180
aggaatttat aaaggtcagt tcattttctt aaacatcgtc agaaccaaat taggctgcag   240
atgagcctga agtgggacgc aggtcagatg aaatcctggt gttatcaggg acagcatggc   300
cttaagtgac actacagtgt ttgtgttgaa ttaggcacca gtagacaggg gctaaactga   360
gagtttgaaa tgcactagga tagtcttttct ctttgttgtc attctctgtg ttgactggag   420
acatgattac atttccatta tcagtgatgg agcttgctga atcctgctcc tatgcagcta   480
```

```
agaaatggaa agagctacaa atgggttctt ttcataagga aagaacagca aatgagaagc    540
agagtaatca gcccactgac atggttaaag acaaagaaaa aactgaaact cagcctgaaa    600
gatgaagatt catgaaaaca gtatactttt tattacactt gtgaacttcg tttcagaatg    660
gattactttc tttagaaata gtccagactc actaatttcc tagtgcccac tgatccctgt    720
cccttagaag tgaaattcaa ccccactgct tcactaaagt gcttccaatt ttgtcttctt    780
ttagtagaga ctggggccta aagtgtttcc tctttaattc tcctgtaatg catctctaga    840
gaaaatatct ttgcttattt taacctctct atgcaatcag actactttaa tcctgccttc    900
tggaaagtcc tcgcctgaat tccttgtcaa gacactagcc tcattcatca ccttctggtc    960
tgatagctct ttctcgctct ctctctctct ctctctctct ctctctctca               1020
cacacacaca cacacacaca caaacacaca cacaccttcc cagccccttc tcctcctcct   1080
ctccactcct actattcctc ctctatttct cttctcccta ccctaccaaa tggaaaacag   1140
aacaaaacag aaatcctaaa gctgtatcgc tggaaatata tttcatttga caacttcct    1200 aggtagctct ctttatctgc ctcttgatct tttaatcctt atttcattat ctggggaaa    1260 cattcagcat ttgcaatttt gcattcatac cctcactgag ttagaggcta ccttattgtg   1320
actctaacgc agcttaagtt tcagggccct tctcttggac atgacccttc agagtccttg   1380
gaaggttcct cagccatgtg tttcacatgt ttgtatagtt ttctaaaatt tgcaaaagta   1440
tgttacgttg tttccacttc cagaatggca ccgtgaaaag ctttattgat cctcattgcg   1500
gtgaaataag cataaccact tgaagatgga ggaaggaaca catttaaaaa tctttggaaa   1560
ttgttctaag ggtaaacatc aaactatgaa tactgattca ctgtattatt cactgtaaga   1620
attaataagt aaatcaatat tgaattcctt atacacagcc aggatgcaaa ataaatcctc   1680
taaatcctgt tctatcttcc attaattgac tagtgaaaat atttaaaaag aatccaaaaa   1740
gaaagttttc cactataaat taaatgaaat atttgagttg tgagcatagt tgagtgttga   1800
tgaggcagga aattaaagaa aaatacaatt aaaaataaaa agaaataagt tttcctgtat   1860
taggctgact tgtcccagag gcagcaacag gcacagacca gacccaggaa aagtcttgat   1920
aatactatct aaggtgctct ggagactctc ccagcactcc ctcaacatag gaagaagaaa   1980
aataaatttt cctttgtttt atggaaaagt ttgtagattc ctgttctctg taactagtga   2040
cttcaagtat tctgttttat ctaagaagta gagtgaaggt catgagaagc ctgaataggc   2100
ctgaactaca gctgcctggg caccatagtg aaggttataa tataaaccag tgcaaggctc   2160
tttagagcaa aacgtagata acagacatct gggttgcttg gcaatggtca tgtgtaatcc   2220
tgagtttgtc ctgcctctat atccctgctt tcatgccact gtaagcttgc ttcaagctag   2280
cccacctgct tttgtgaagt gtgtataaaa gtcaagtgct gtctttgcat gtgagtgtgc   2340
tggggcctga gtgtactcaa taaaaattct cctgttttaa cccgaggtct ctctctcgtc   2400
ctcctggatc ccacaacatt gataagtcac tgtcatgcta acattttttg taatgagcta   2460
ctttgacaat acttccataa ttttctcaaa tgatacagat tttgcctcat ctctctcgct   2520
gtcacacaca aaacttttgg ccataatggg gaatcttatg attctcccct ataattgcaa   2580
aacactagaa actctcattt atttcacctc ttctcttgca gacaagggaa cacccccagac  2640 atggtatcag agatccacat gacaggccca atgtgcctca ttgagaacac taatgggcga   2700
ctgatggcga atccagaagc tctgaagatc ctttctgcca ttacgcagcc tgtggtggtg   2760
gtggcgactg tgggccgcta gcgcacagga aaatcctacc tgattaacaa gctggctcag   2820
```

```
aagaaaaagg gtgagtggca tgagcaaagc tctgccaagt cccttctgtc catctacaca    2880
gtcagcctcc atcatgagga tgtgaagaga gaaagagatg aggatgaata tggaaagcta    2940
actttccatt cacagtcggg ctccttatct tcacgctgct ctaagggata attttaaatt    3000
cattaattat tcccatgata cattagtttc cctttcaaaa gcacaaactg tgcctttcct    3060
aaaaggagta agactgtaat aaaaataatt aatgtacata ataataacta taataaacta    3120
caatttttat gccataacag cgagtttaca gtgatcttta aggttgaaaa aatgtttgtc    3180
tgtattggat attcttttt attgttgtaa aaaaataaca taaaatttaa cctcgtaacc    3240
atttttaagt gtacagctct gtggcattaa ttaaattcac attgttatac agctgtcacc    3300
tccatccata tccagaaatc tttcatcttg cctaacagaa actctgtact aactaaacaa    3360
aagctccaca taaacccatt gcctgccatc attctacatt ctatctctat gaattttact    3420
actacagaaa cctcatataa gtggaattat tcaatatttg tccttttatg actggcttat    3480
ttcaattcat atgtcttcaa ggttcatcag tgtgttagca tgtgtcaaaa ctcttccttt    3540
ttaaggctta gtaattgtac atgtatacta atttgtttat ctcttcatct gtcaatggac    3600
aattggattg cttccacctt ttgtctatta taaataatgc taataggaac atgggtgtct    3660
gaatatctgt tcaagtccct gctttcactt cttttgggaa tatacccaga agggtaattg    3720
ctggctcatg cagtcattcc atgttaactt tttttttttt taagaaatca ctatactatt    3780
ttccacagtg actgtactgt tttacattcc caacagaaat gcacagggc tctaatttct     3840
ctacctcctc accaacattt tttattttca gtgttttttt tgatagtggc catatgaatg    3900
gatgttaagt agtatctcac tatggttttg attttcattt tcctaatgac tggtgatact    3960
gggcatcttt tcatgtgctt attggccacc tgtatatctt ctttgggaaa atgtctattc    4020
aagtcctttc ttcattatt tttttttttt aaattcagaa aaatttctt ccacttgaaa      4080
atgttaaaac tcttcattaa acaactatta gatcaagtag aaaatacaaa tcaaaatagg    4140
tgaacatata aacatcaaaa tagtgatata tatatcagaa tctatggaat ataatgaaaa    4200
taattatcaa aaacaatttg tagtctttaa atcatatatc aatagaatta taaattaaaa    4260
tacataaatc taatgtgaaa cacagaaagc tagaaaaaag atcaagaaaa taagcaaaa     4320
ggaaacataa cagacataaa gagataagag cagaacttca gttagttctg attgtaagct    4380
atgttataaa ttaatcaaca tgctagttct ttgaatagaa cataaacaaa atatgcaaac    4440
caacatccaa cctaatcaag aaaaacaggg agaaaacaaa gttacacaga ataatacacg    4500
aaacaagagg aaatcatact aaaactaagg acatttttaa acttttgagt taaatcattt    4560
tacacagctc taagcaggta gatataaaag cctacataaa atgggtaatc ccatagggaa    4620
attattaaca gtgataccaa tggagacaga aagtttaaga aaatgagaaa gttattaaat    4680
tactactccc acccaaaagt acaagacaca gatgacttta taatggaatt ttatgaattt    4740
ttcaaatatt agataatacc aatgctacat agactgttct taaaaagaga ttgccaagct    4800
atggccagtg ggacaaatat ggcctgccgg ttattatttt attttatttt attttatttt    4860
ttaaatcaat gtatatttta ttttatttta ttatttattt atttatttat tttattata     4920
ctttaagttt tagggtacat gtgcacattg tgcaggttag ttacatatgt atacatgtgc    4980
catgctgctg cgctgcaccc actaacttgt catctagcat taggtatatc ccccaatgct    5040
atccctcccc cctcccccca ccccacaaca gtccccagag tgtgatattc cccttcctgt    5100
gtccatgtga tctcattgtt caattcccac ctatgagtga gaatatgcgg tgtttggttt    5160
tttgttcttg tgatagttta ctgagaatga tgatttccaa tttcatccat gtccctacaa    5220
```

```
aggacatgaa ctcatcattt tttatggctg catagtattc catggtgtat atgtgccaca   5280
ttttcttaat ccagtctatc attgttggac atttgggttg gttccaagtc tttgctattg   5340
tgaataatgc cacaataaac atacgtgtgc atgtgtcttt atagcagcat gatttatagt   5400
cctttggata tatacccagt agtgggatgg ctgggtcaaa tggtatttct agttctagat   5460
tcctgaggaa tcgccacact gacttccgca atggttgaac tagtttacag tcccaccaac   5520
agtgtaaaag tgttcctatt tctccacatc ctctccagca cctgttgttt cctgactttt   5580
taatgatcgc cattctaact ggtgtgagat gatatctcat tgtggttttg atttgcattt   5640
ctctgatggc cagtgatgat gagcattttt tcaagtgttt tttggctgca taaaggtctt   5700
cttttgagaa gtgtctgttc atgtcctttg cccactttt gatggggttg tttgtttttt   5760
tcttgtaaat ttgttggagt tcattgtaga ttctggatat tagccctttt tcagatgaat   5820
aggttgcaaa aatttctcc cattttatag gttgcctgtt cactctgatg gtagtttctt   5880
ttgctgtgca gaagctcttc agttcaatta gatcccattt gtcaattttg gcttttgttg   5940
ccattgcttt tggtgtttta gacatgaaat ccttgcccat gcctatgtcc tgaatggtaa   6000
tgcctagatt ttcttctagg gttttttatgg ttttaggtct aacttttaag tctttaatcc   6060
accttgaatt aattttgta taaggtgtaa ggaagggatc cagtttcagc tatctacata   6120
tggctagcca gttttcccag caccatttat taaatagga atcctctccc cattgcttgt   6180
ttttctcagg tttgtcaaag atcagatagt tgtagatatg cggcgttatt tctgagggct   6240
ctgttctgtt ccattgatct atatctctgt tttggtacca gtaccatgct gttttggtta   6300
ctgtagcctt gtagtatagt ttgaagttag gtagtgtgat gcctccagct ttgttctttt   6360
ggcttaggat tgacttggtg atgtgggctc ttttttggtt ccatatgaac tttaaagtag   6420 tttttttccaa ttctgtgaag aaagtcattg gtagcttgat ggggatggca ttgaatctgt   6480
aaattacctt gggcagtacg gccattttca cgatattgag tcttcctact catgagcatg   6540
gaatgttctt ccatttgttt gtatcctctt ttatttcctt gagcagtggt ttgtagttct   6600
ccttgaagag gtccttcaca tcccttgtaa gttgtattcc taggtatttt attctctttg   6660
aagcaattgt gaatgggagt tcactcatga tttggctctc tgtttgtctg ttgttggtgt   6720
acaagaatgc ttgtgatttt ggtacattga ttttgtatcc tgagactttg ctaaagttgc   6780
ttatcagctt aaggagattt tgggctgaga cgatgggggtt ttctagatat acaatcatgt   6840
cgtctgcaaa cagggacaat ttgacttcct cttttcctaa ttgaataccc tttatttcct   6900
tctcctgcct aattgccctg ccagaacctt ccaacactat gttgaatagg agtggtgaga   6960
gagggcatcc ctgtcttgtg ccagttttca aagggaatgc ttccagtttt tgcccattca   7020
gtatgatatt ggctgtgggt ttgtcataga tagctcttat tattttgaaa tatgtcccat   7080 caataccctaa tttattgaga gtttttagca tgaagggttg ttgaattttg tcaaaggctt   7140
tttctgcatc tattgagata atcatgtggt ttttgtcttt ggctctgttt atatgctgga   7200
ttacatttat tgatttgcat atattgaacc agccttgcat cccagggatg aagcccactt   7260
gatcatggtg gataagcttt tgatgtgct gctggattcg gtttgccagt attttattga   7320 ggattttgc atcaatgttc atcaaggata ttggtctaaa attctctttt ttggttgtgt   7380
ctctgcccgg ctttggtatc agaatgatgc tggcctcata aaatgagtta gggaggattc   7440 cctcttttc tattgattgg aatagtttca gaaggaatgg taccatttcc tccttgtacc   7500
tctggtagaa ttcggctgtg aatccatctg gtcctggact ctttttggtt ggtaagctat   7560
```

```
tgattattgc cacaatttca gagcctgtta ttggtctatt cagagattca acttcttcct   7620
ggtttagtct tgggagagtg tatgtgtcca ggaatttatc catttcttct agatgttcta   7680
gtttatttgc atagaggtgt tgtagtata ctctgatggt agtttgtatt tctgtgggat    7740
cgctggtgat atcccctta tcatttttta ttgcgtctat ttgattcttc tctcttttt    7800
tctttattag tcttgctagc ggtctatcaa ttttgttgat cctttcaaaa aaccagctcc   7860
tggattcatt gatttttga agggttttt gtgtctctat ttccttcagt tctgctctga    7920
ttttagttat ttcttgcctt ctgctagctt tgaatgtgt ttgctcttgc ttttctagtt   7980
cttttaattg tgatgttagg gtgtcaattt tggatctttc ctgcttttct tgtgggcatt   8040
tagtgctata aatttccctt tacacactgc tttgaatgcg tcccagagat tctggtatgt   8100
tgtgtcgttg ttctcgttgg tttcaaagaa catctttatt tctgccttca tttcattatg   8160
tacccagtag tcattcaggt gcaggttgtt cagtttccat gtagttgagc cgttttgagt   8220
gagattctta atcctgagtc ctagtttgat tgcactgtgg tctgagaaat agtttgttat   8280
aatctctgtt cttttacatt tgctgaggag agctttactt ccaagtatgt ggtcaatttt   8340
ggataggtg tggtgtggtg ctgaaaaata tgtatattct gttgatttgg ggtggagagt   8400
tctgtagatg tctattaggt ctgcttggtg cagagctgag ttcaattcct gggtatcctt   8460
gttgactttc tgtctcgttg atctgtctaa tgttgacagt ggggtgttaa agtctcccat   8520
tattaatgtg tgggagtcta agtctctttg taggtcactc aggacttgct ttatgaatct   8580
gggtgctcct gtattgggtg catatatatt taggatagtt agctcttctt gttgaattga   8640
tcccttacc attatgtaat ggccttcttt gtctcttttg atcttttttg ttttgacatc    8700
tgttttatca gagactagga ttgcaacccc tgcctttttt tgttttccat ttgcttggta   8760
gatcttcctc catccttta ttttgagcct atgtgtgtct ctgcacgtga gatgggtttc    8820
ctgggtacag cacactgatg ggtcttgact cttatccaa tttgccagtc tgtgtctttt    8880
aattggagca tttagtccat ttacatttaa agttaatatt gttatgtgtg aatttgatcc   8940
tgttgttatg atgttagctg gttattttgc tcattagttg atgcaatttc ttcctagact   9000
tgatgatcat gcaaaatttt ggcatgattt tgcagcggct ggtaccggtt gttcctttcc   9060
atgtttagcg tttccttcag gagctctttt agggcaggcc tggtggtgac aaaaatctct   9120
cagcatttga ttgtctgtaa agtattttat ttctccttca cttatgaagc ttagtttggc   9180
tggatatgaa attctgggtt gaaaattctt ttctttaaga atgttgaata ttggccccca   9240
ctctcttctg gcttgtaggg tttctgccga gagatctgct gttagtctga tgggcttccc   9300
tttgtgggta acccgacctt tctctctggc tgcccttaac attttttcct tcatttcaac   9360
tttggtgaat ctgacaatta tgtgtcttgg agttgctctt cttgaggagt atctttgtgg   9420
cgttctctgt atttcctgaa tctgaacgtt ggcctgcctt gctagattgg ggaagttctc   9480
ctggataata tcctgcagag tgttttccaa cttggttcca ttctccccat cactttcagg   9540
tacaccaatc agacgtagat ttggtctttt cacatagtcc catatttctt ggaggctttg   9600
ctcatttctt tttattcttt tgtctctaaa cttcccttct cacttcattt cattcatttc   9660
atcttccatt gctgataccc tttcttccag ttgatcgcat cggctcctca ggcttctgca   9720
ttcttcacgt agttctcgag ccttggcttt cagctccatc agctccttta agcacttctc   9780
tgtattggtt attctagtta tacattcttc taaatttttt ttcaaagttt tcaacttctt   9840
tgcctttggt ttgaatgtcc tcctgtagtt cagtgtaatt tgatagtctg aagccttctt   9900
ctctcagctc gtcaaagtca ttctccatcc agctttgttc cgttgctggt gaggaactgc   9960
```

```
gttcctttgg aggaggagag gcgctctgct ttttagagtt tccagttttt ctgttctgtt    10020
ttttccccat ctttgtggtt ttatctactt ttggtctttg atgatggtga tgtacggatg    10080 ggttttggt gtggatgtcc tttctgtttg ttagtcttcc ttctaacaga caggaccctc     10140
agctgcaggt ctgttggaat accctgccgt gtgaggtgtc agtgtgcccc tgctgggggg    10200
tgcctcccag ttaggctgct cgggggtcag gggtcaggga accacttgag gaggcagtct    10260
gcccgttctc agatctccag ctgcgtgctg ggagaaccac tgctctcttc aaagctgtca    10320
gacagggaca tttaagtctg cagaggttgc tgctgtcttt ttgtttgtct gtgccctgcc    10380
cccagaggtg gagcctacag aggcaggcag gcctccttga gctgtggtgg gctccaccca    10440
gttcgagctt cctggctgct ttgtttacct aagcaagcct gggcaatggt gggcgcccct    10500
cccccagcct cgctgccgcc ttgcagtttg atctcagact gctgtgctag caatcagcga    10560
gactccgtgg gcgtaggacc ctccgagcca ggtgcgggat ataatctcgt ggtgcaccgt    10620 tttttaagc ccgtcggaaa agcgcagtat tcgggtggga gtgacccgat tttccaggtg     10680
cgtccgtcac tcctttcttt gactgggaaa gggaactccc tgaccccttg cacttcccaa    10740
gtgaggcaat gcctcgccct gcttcggctc gcgcacggtg cgcgcaccca ctgacctgtg    10800
cccactgtct ggcactccct agtgagatga acccgttacc tcagatggaa atgcagaaat    10860
cacccgtctt ctgcgtcgct caggctggga gctgtagacc ccagctgttc ctattcggcc    10920
atcttggctc ctcctccttt attcatttat taatctggtt gtttatctgt gttgctttgt    10980 aaatttttt tatattttct agatataaat cccttatcat atacatgttt aacaaatatt     11040
ttcttacatt ctgtgtgttg cttttttta actctgttga tagtgtctgt taatacacaa     11100
aagttttaaa tgttgatgaa gtcaactaat ctatttttc ttttattgtc tatacttttg     11160
gtttcttatt aaaaaaaatc attgccaaat ccaatattat ataacttttta cccttgtttt    11220 cttctacaaa ttttatagtt ttaactctaa tgtttggttc tttgatccat tttgagttca    11280
tatttgtaag ttataaggta agagcccaac tttttttaag gagatatctc atttcctcaa    11340
catcatttgt taaagagact cttctttctt aattaaatga tcttgacacc catcctggaa    11400
atcactgacc atatatgtca gagtatattc atgggctgtc ttttctattc cattggttta    11460
tatgtcagtc tttataccag taccacacat ggttttgtaa taagtttcag aactcagaaa    11520
ctgtaagact ccaactttgc tcttcctctc ttccttttta agattatttt cataattagg    11580
ggatctctgg aaatttcata tgaaagttat ggtagatttt tctatttata caaagtaatt    11640
ggaatgttag tagaattacc tcaaacctgt acatcacttt gggtagtagt gacatcttaa    11700
gaatattaag tcttccaatt cataaacgca ggatgttttt ctaatgattt atgtcatcta    11760
caatttcttt aaagggtgtt tgaagttttc actcgacaac tcttgcgcct gcttggttaa    11820
gcttattcct aagtgattta ttcttttgat gctgttaaat gggattgttt tcaaaatttc    11880
cttttctttt tgtttaggaa ggaaattaga attcctgttc taattctatt tttatacact    11940
agcaactgat ttctccatat tggctttgca tcctgcaact ttgatgaatt cttttaatag    12000
ttctaatagt ttttttgtgga atatttaatg ttttccacaa attagatact accgtcggca    12060
gacagagata attttacttt ttcattacca attaggatgc ctcctttatg cttttcttgt    12120
ctaattactc tggataggac ttgcagtgtt ctgtggaatg caattggcaa aagtaggcat    12180 cctttttcttg ttcctgatgt tataggaaaa gctatgacac ttcatcatta aatgtgaagt    12240
gagctgtggg ttttttaatat atggccttta ttatgttgag gtattgtctt tctatttcta    12300
```

```
ctttgttgat tattttatc gtgaaagcct cctgaattt tccatgcatt ggatattcaa    12360
atttcctatt tctttgattg taagtaagta aggtgaatac tgattgttgt ttcagttctc    12420
tctcttaacc ttaaaatacg ctacctttc cttcagttgc tagaactgcc tgttactaaa    12480
tccccatctc tggtctcctc tctcccttgc aggcttctct ctgggctcca cagtgcagtc    12540
tcacactaaa ggaatctgga tgtggtgtat gccccatccc aagaagccag gccacatcct    12600
agttctgctg gacaccgagg gtctgggaga tgtagagaag gtgagactca aggatccaat    12660
tgtggagtga gccctcttc tctgaatatt ttatgcactg tttaattgtt tattaaccat    12720
taactacagg ctgtaatatg tgtgggttaa cacagatgca taagggagc acaaataatc    12780 ccagtgtcat gagtcttatc ctgcacagaa ctttagttaa gaattgggt gctaaagccc    12840 cgtgactttg tatttaaatt taaattctgt cactaattca gtagcctgag aaaattgacc    12900
tattttagcc tcagcattct aagctttaaa atgtatggaa aagacctatg ttggccacat    12960
agtataattt tgaatattta ataagaaaat acgtgtcagg tgtatattaa ttattcgata    13020
aaacagcaac taatagtacc aatcttatat gtgaattctg ttattgaaaa agaagagaa    13080 aattttaaat ttacattgta ctcaggcctt aaaatgccca ccaaccttga attttaattt    13140
tacaattatc tgttgatgat cattagaaga cctagtaagg atcattgtaa cccaaaacat    13200
tcatcgaaaa actacccaaa agccacatcc tactgagaat actttttgta tttggcttct    13260
ttgataggtc attagtgcta aagaacaaac aaacaaaaaa ccaaaaaccc tctaacatat    13320
gaacatagtt ttactactct tactctggaa agtgctgtga ctacgaaacg tgctcctgac    13380
tccagtgtgt cttgacttcc agggtgacaa ccagaatgac tcctggatct tcgccctggc    13440
cgtcctcctg aacagcactt ccatgtacaa tagcatagga accattaacc agcaggccat    13500
ggaccaactg cagtatcctt tgtgacccag aacagcacca aggtcagagg gcacctgtgt    13560
tcataaacca gctgcctgac tgtgaatcct gatgaatcaa gctcaaaagg agaaaacata    13620
aaatacataa agtacagagg agtgatccca tatatccact ttagacttga cacttaggtt    13680
aagaacaaag gaaaatggaa ggtttgggaa tgtgttgaac taatatggga tgaggtccat    13740 gttcatttg tcacatttct ttagttagct actcagctat gtgacagagc tgacacatcg    13800
agtccaacca aaatcttcac ctgatgagaa tgagaatgag gattcagctg actttgagag    13860
cttcttccca gactttgtgt tgacactgag agatttctag cattacagaa agcgcttttg    13920
gacaaaactg tgataaaata aactaaatgg aggactttt tttattggaa tagtttcatt    13980
tgtttcatac atattgatca aatgcttact atgaatagac tgaagataca gatataaatg    14040
aaatagatat ggttcctgtc ctaatgttgc ttggggttaa aatggatgca aacattcaat    14100
taacacaggt ctatgtaatc tagtacaaga actctcaaat gttggtatgc atacgtatct    14160
tctgaggatc ttaccaaaga caaaagtcta attcaataga tcttggacag ggtctaagag    14220
tctgtatttc tgaaaaaaaa aaaaaaaaaa aaaaaaaaaa agaattacag gaatagaga    14280 ctttctttac tacaagaaac attagcattt gttctccata ggcaggtcta gagagcctgg    14340
tgctgaccta tgtcaatgcc atcagcagtg gggatctacc ctgcatggag aacgcagtcc    14400
tggccttggc ccagatagag aactcagccg cagtgcaaaa ggctattgcc cactatgaaa    14460
agcagatggg ccagaaggtg cagctgccca cagaaaccct ccaggagctg ctggacctgc    14520
acagggacag tgagagcaag gccactgaag ttttcatcag gagttccttc aaagatgtgg    14580
accatctatt tcaaaggag ttagcggtaa ttttgtctc aaatttatat ggtttagggt    14640
catggaagac aaagtactac aaagaaagaa aacgagtatt attttgatag aagtaattct    14700
```

```
tcctagcttt cataatggtg acaacaacag atttgtaatc acatcaatca agaggaccaa    14760
ctgtattatt acagactcaa agttttaaaa cattttttcc tgaataattt tccctttacc    14820
taaatgcata caactgataa ccagagcttc taataaaatt acctgcccac tcttctcaga    14880
ctgatttgat attctagcca aacacaaaga aaactttcat cctgcttatc ttgagcatgc    14940
ttctgttcag ccacatttat tccatatgaa atcattagtc caatatgcaa aaccagagtt    15000
ttcctctaac ggttgacata aagctatcaa tctcggtcct gaacctcacc tccaaaaaga    15060
aagcgacttc agtagaaagt ggggtcagaa ggaagagtgt ggtcctggtg aggagtctgt    15120
caatttctcc agcatcattg acttttattt tcagaagtca ttcccgaaat tctgaggtca    15180
agctaacatc ctttccctgt tactcttttt acttcctatt tttacattaa aggcccagct    15240
agacaaaaag cgggatgact tttgtaaaca gaatcaggaa gcatcatcag atcgttgctc    15300
agctttactt caggtcattt tcagtcctct agaagaagaa gtgaaggcgg aatttattc     15360 gaaaccaggg ggctatcgtc tctttattca gaagttacaa gacctggaga aaaagtacta    15420
tgaggaaccg aggaagggga tacaggtaac caaaattcat ctgtcgatta tggaaacctg    15480
ctgacctgcc tcctacaaac accaaggtga ccaagcttca ctgcacacag atgtgctttt    15540
ttgtttgcat aacattcatg ctttcattca ataacatatg caaagaggct gttattccag    15600
atatgcccta ggtgctcatc aaggagagtg caattaacta ctgagttaca aattcaacta    15660
gcagatgaag caccaagttg tcattatcat cattacagct gggcttttcc tgttgcaaga    15720
gacaggaacc taatgatggc tgcttaaaca aaaatagtaa ttcattgatt taggctgcaa    15780
actggcttta caggacaggt gggtctaagg tttcaagtaa catcatgaac tgtctctctg    15840
tccagtgttc ccccatcccc acagttttct ccctcccacc ctccctctat ctgagtcact    15900
ctgatatttg ctttctcaat gatggcttca ttccccagca ggctcagccc atatgggacc    15960
acagcattaa cagttccaaa cttagagccc ttaatctaaa caggacagag actctccttt    16020
tcccagtatc tatattagcc tactaaaaat gactgctaag taggatgctc tgatcagctt    16080
gccaggagca tgtgcctctc gctctgacag ggaatttcac caccaaggac aacagggcaa    16140
aggaaagaat tcccagagga aaggatggca ggaagacaaa caggaacacc tgcttacagc    16200
cgtctcctac ttctcacttt gtgttctctg ggtcctaagg ctgaagagat tctgcagaca    16260
tacttgaaat ccaaggagtc tatgactgat gcaattctcc agacagacca gactctcaca    16320
gaaaaagaaa aggagattga aggtgaggag tgagttaaga gattagatgg cctcaaaagc    16380
tccaaaaatt gaaataactt gactggataa acatgggacc cttttaactag agcaagatcc    16440 acaaaggtgt gtcttacttg ccgaggtcat ctctgagtag ggcatatgca gtcagcaaca    16500
acgacaggta agtgtataag gaacaatgag gcaacaagat aaccccacac aaattttcct    16560
tctttctttt cctccacagt ggaacgtgtg aaagctgagt ctgcacaggc ttcagcaaaa    16620
atgttgcagc aaaatgcaaag aaagaatgag cagatgatgg aacagaagga gaggagttat    16680
caggaacact tgaaacaact gactgagaag atggagagcg acagggtcca gttgctggaa    16740
gagcaagaga ggaccctcgc tcttaaactt caggtgtcta attgcatcac cttgaggttt    16800
ctgttttcct gttttctctc cattctcccc gatcacaggc ttactgtggc agagagaaca    16860
tgaagcccag gggaagaacc ctgcttgctt acttgtactt tcaattcct gtctgtccag     16920 cctgaactgg ctactgccaa gtctggtcac taaactgcaa atattgcagt tgtgtcacat    16980
tcagtgcttt atctatatat ccttcatttc aaggcaggta ttatctgcta gccatcatta    17040
```

```
aagtatctgt atctcttgct taataccatg tgaagcaaga actatattct tattacttag    17100
gagaagaaac aaagtttcca aaaataataa ataaatagag tcacacagct agtaaatgta    17160
tcaaagctgt cttcatcact tagtggaatc cacaatgatt attttttct gtgacaccta     17220 gtatgaaatt aaacttaaga aaacctttgt gagcaga                             17257
```

<210> SEQ ID NO 114
<211> LENGTH: 2277
<212> TYPE: DNA
<213> ORGANISM: Homo sapiens

<400> SEQUENCE: 114

```
aatcgaaagt agactctttt ctgaagcatt tcctgggatc agcctgacca cgctccatac      60
tgggagaggc ttctgggtca aaggaccagt ctgcagaggg atcctgtggc tggaagcgag     120
gaggctccac acggccgttg cagctaccgc agccaggatc tgggcatcca ggcacggcca    180
tgacccctcc gaggctcttc tgggtgtggc tgctggttgc aggaacccaa ggcgtgaacg    240
atggtgacat gcggctggcc gatggggcg ccaccaacca gggccgcgtg agatcttct     300 acagaggcca gtggggcact gtgtgtgaca acctgtggga cctgactgat gccagcgtcg    360
tctgccgggc cctgggcttc gagaacgcca cccaggctct gggcagagct gccttcgggc    420
aaggatcagg ccccatcatg ctggatgagt ccagtgcac gggaaccgag gcctcactgg     480
ccgactgcaa gtccctgggc tggctgaaga caactgcag gcacgagaga gacgctggtg    540
tggtctgcac caatgaaacc aggagcaccc acccctggaa cctctccagg gagctctcgg    600
aggcccttgg ccagatcttt gacagccagc ggggctgcga cctgtccatc agcgtgaatg    660
tgcagggcga ggacgccctg ggcttctgtg ccacacggt catcctgact gccaacctgg    720
aggcccaggc cctgtggaag gagccgggca gcaatgtcac catgagtgtg atgctgagt     780 gtgtgcccat ggtcagggac cttctcaggt acttctactc ccgaaggatt gacatcaccc    840
tgtcgtcagt caagtgcttc cacaagctgg cctctgccta tggggccagg cagctgcagg    900
gctactgcgc aagcctcttt gccatcctcc tccccaggga cccctcgttc agatgccccc   960
tggacctgta tgcctatgca gtggccacag gggacgccct gctggagaag ctctgcctac    1020
agttcctggc ctggaacttc gaggccttga cgcaggccga ggcctggccc agtgtcccca    1080
cagacctgct ccaactgctg ctgcccagga gcgacctggc ggtgcccagc gagctggccc    1140
tactgaaggc cgtggacacc tggagctggg gggagcgtgc ctcccatgag gaggtggagg    1200
gcttggtgga aagatccgc ttccccatga tgctccctga ggagctcttt gagctgcagt     1260
tcaacctgtc cctgtactgg agccacgagg ccctgttcca aagaagact ctgcaggccc     1320 tggaattcca cactgtgccc ttccagttgc tggcccggta caaaggcctg aacctcaccg    1380
aggataccta caagcccgg atttacacct cgcccacctg gagtgccttt gtgacagaca    1440
gttcctggag tgcacggaag tcacaactgg tctatcagtc cagacggggg cctttggtca    1500
aatattcttc tgattacttc caagcccct ctgactacag atactacccc taccagtcct      1560
tccagactcc acaacacccc agcttcctct tccaggacaa gagggtgtcc tggtccctgg    1620
tctacctccc caccatccag agctgctgga actacggctt ctcctgctcc tcggacgagc    1680
tccctgtcct gggcctcacc aagtctggcg gctcagatcg caccattgcc tacgaaaaca    1740
aagccctgat gctctgcgaa gggtcttcg tggcagacgt caccgatttc gagggctgga    1800
aggctgcgat tccagtgcc ctggacacca acagctcgaa gagcacctcc tccttccct     1860 gcccggcagg gcacttcaac ggcttccgca cggtcatccg ccccttctac ctgaccaact    1920
```

| | | | |
|---|---|---|---|
| cctcaggtgt | ggactagacg gcgtggccca agggtggtga gaaccggaga | accccaggac | 1980 |
| gccctcactg | caggctcccc tcctcggctt ccttcctctc tgcaatgacc | ttcaacaacc | 2040 |
| ggccaccaga | tgtcgcccta ctcacctgag cgctcagctt caagaaatta | ctggaaggct | 2100 |
| tccactaggg | tccaccagga gttctcccac cacctcacca gtttccaggt | ggtaagcacc | 2160 |
| aggacgccct | cgaggttgct ctgggatccc cccacagccc ctggtcagtc | tgcccttgtc | 2220 |
| actggtctga | ggtcattaaa attacattga ggttcctaca aaaaaaaaaa | aaaaaaa | 2277 |

<210> SEQ ID NO 115
<211> LENGTH: 1497
<212> TYPE: DNA
<213> ORGANISM: Homo sapiens

<400> SEQUENCE: 115

| | | | |
|---|---|---|---|
| aaagtgctgg | gattacaggc atgagccgcc gcgccccgcc ccacgctcag | tcttgaaatt | 60 |
| gtctggaacg | ggaaacggca acagcgagat atccgagcg agagtcccgc | cctgcatcag | 120 |
| tttgcggaac | cgccttggta aaggagaga aggggagtgg aggaagcacg | ggactggagg | 180 |
| gaccaaagtt | ccccgatggc ggcccagggg tgcgcggcat cgcggctgct | ccagctgctg | 240 |
| ctgcagcttc | tgcttctact gttgctgctg gcggcgggcg gggcgcgcgc | gcggtggcgc | 300 |
| ggggagggca | ccagcgcaca cttgcgggac atcttcctgg gccgctgcgc | cgagtaccgc | 360 |
| gcactgctga | gtcccgagca gcggaacaag aactgcacag ccatctggga | agcctttaaa | 420 |
| gtggcgctgg | acaaggatcc ctgctccgtg ctgccctcag actatgacct | ttttattaac | 480 |
| ttgtccaggc | actctattcc cagagataag tccctgttct gggaaaatag | ccacctcctt | 540 |
| gttaacagct | ttgcagacaa cacccgtcgt tttatgcccc tgagcgatgt | tctgtatggc | 600 |
| agggttgcag | atttcttgag ctggtgtcga cagaaaaatg actctggact | cgattaccaa | 660 |
| tcctgcccta | catcgaagat ctgtgaaaat aatcctgtgg attccttttg | gaaagggca | 720 |
| tccatccagt | attccaagga tagttctggg gtgatccacg tcatgctgaa | tggttcagag | 780 |
| ccaacaggag | cctatcccat caaaggtttt tttgcagatt atgaaattcc | aaacctccag | 840 |
| aaggaaaaaa | ttacacgaat cgagatctgg gttatgcatg aaattggggg | acccaatgtg | 900 |
| gaatcctgcg | gggaaggcag catgaaagtc ctgaaaaga ggctgaagga | catgggttc | 960 |
| cagtacagct | gtattaatga ttaccgacca gtgaagctct acagtgcgt | ggaccacagc | 1020 |
| acccatcctg | actgtgcctt aaagtcggca gcagccgcta ctcaaagaaa | agccccaagt | 1080 |
| ctttatacag | aacaaaggc gggtcttatc attccctct ttctggtgct | ggcttccagg | 1140 |
| actcaactgt | aactggaaac tgtgttgctc taaccctcct ccagccctgc | agcctcccct | 1200 |
| tgcagtcatc | attcgtgttc tgtgtatacc aaatgattct gttatctaaa | gaagcttttt | 1260 |
| gctgggaaaa | cgatgtcctg aaaatggtat ttcaatgagg catatgttca | ggatttcaga | 1320 |
| aacaagaagt | tagttctatt tagcaggtta aaaaatgctg cattagaatt | aaagcaagtt | 1380 |
| attttcttat | ttgtataatg acacaaagca ttgggagtca gactgcttgt | atattatcaa | 1440 |
| acattttaag | agaattctaa taaagctgta ttttacatca aaaaaaaaaa | aaaaaaa | 1497 |

<210> SEQ ID NO 116
<211> LENGTH: 2638
<212> TYPE: DNA
<213> ORGANISM: Homo sapiens

<400> SEQUENCE: 116

-continued

```
gctgagcgcg ggcgcggggc cgctacgtgc gcggggagcg cggggagcgc ggggagcgcg      60
gggctgcgct cgtgtgcgct cctgggcgct cgccgccgcc gctgccgccg cgcgcctttg     120
agtcagcaaa ctccgcggcc cgcaagcccg gctcggcccg gccctgctct gttctgcccg     180
gaggagccgc ccgtaagtga caagagaccc gctgagggg cctccctgc accgcccaga      240
ttgatcgtgt cctgtgctga agatgtttcc ggaacaacag aaagaggaat tgtaagtgt      300
ctgggttcga gatcctagga ttcagaagga ggacttctgg cattcttaca ttgactatga     360
gatatgtatt catactaata gcatgtgttt tacaatgaaa acatcctgtg tacgaagaag     420
atatagagaa ttcgtgtggc tgaggcagag actccaaagt aatgcgttgc tggtacaact     480
gccagaactt ccatctaaaa acctgttttt caacatgaac aatcgccagc acgtggatca     540
gcgtcgccag ggtctggaag atttcctcag aaaagtccta cagaatgcac ttttgctttc     600
agatagcagc cttcacctct tcttacagag ccatctgaat tcagaagaca ttgaggcgtg     660
tgtttctggg cagactaagt actctgtgga agaagcaatt cacaagtttg ccttaatgaa     720
tagacgtttc cctgaagaag atgaagaagg aaaaaaagaa aatgatatag attatgattc     780
agaaagttca tcctctgggc ttggacacag tagtgatgac agcagttcac atggatgtaa     840
agtaaataca gctccgcagg aatcctgaaa ataattcta atgttactat cttaggaata     900
gcaaattatg tccagtcata gagaagaaag cttcataata atacattctt acctaaagct     960
cactgtcatg atgttaggta tttaaattct taaagatgtt gggttgttta ttagtggtat    1020
ttttatgttg tcttatttta ggtaagcttc tgtgtaaagc taaaaatcct gtgaatacaa    1080
tactatcctt tacaggcaga cattattggt aaacaagatc ttgccctcca atgaaatgac    1140
ttacatgttt taaaaaaccg agttggtttt attgaattta aaagatagg taactaagta     1200
gcatttaaaa tcaagataga gcattccttc ttgtatcagt ggggcagtgt taccataaac    1260
acggtgtata tgttgttaaa ccctatgaag agtaacagtg tagaccagac tgcctctctc    1320
agatatgtgc ctgatatttt gtggatacct ccctgcact ggcaaaacac tatgcttttg     1380
ggtgttagac tgaaatattt taagagtatt taacctttcc agtattctgt ttcacgctta    1440
gatgaaatg tatcttatga atagagacat attaaaataa tgtttacatc ttagaaaaaa     1500
catagatagt gctagtaata ttacttataa ctgtaatata tagattcaga aatacatttt    1560
cattatccaa aatcagcttc aacaaatggt ttctggagac aaataatttg ttttcattat    1620
cattgtataa tcaggttaat gatttatttt ttgactaaat gtgcaatttc ttatcactag    1680
ataactttca gtatcagtgg tggttactta ttacttaaat cagaggaagg attttataaa    1740
gattaataaa tttaatttta ccaataaata ttcccataat ttagaaaagg atgtcgactt    1800
gctaatttca gaataatta ttcatttta aaaagcccct tttaaagcat ctacttgaag      1860
attggtataa ttttcataaa atgtcttttt ttttagtgtc ccaaagatat cttagataaa    1920
ctattttgaa gttcagattt cagatgaggc aacattttct tgagataatt acccaagttt    1980
catccatgtt gaatggtaca aaatatttct gtgaaactaa caggaagata ttttcagata    2040
actaggataa cttgttgctt tgttacccag cctaattgaa gagtggcaga ggctactaca    2100
aaaagcaacc ttttcatttt cactaagagt ttaaagcta ttgtattatt aaaaagtctt     2160
tacaatgctt gtttcaaaga accaacagaa aaaaagcta agaaaactga aactaacat      2220
taaaaaaatt aaatttagaa taagaatgat ttctttaatt tgtccttttt ttctttggtc    2280
taaaacatta ttaaattttt gtaaatattt tgatttaatg tgtcttagat cctcattatt    2340
ttaatacagg aaaagaaaag atttagtaat ttcttaccat gctaatatgt aaagttcatg    2400
```

```
ccatccaggc atttaagagc gatcctcatc ccttcagcaa tatgtatttg agttcacact    2460
atttctgttt tacagcagtt ttgaaaaaca catactatgc caccaattgt catattattt    2520
ttagatgatg taacatagcc atcaaaatta atattatgta atgcctaata cttagtatgt    2580
aaatgtcacg agatcatttt tacattaaac gtgaaaaaaa atcaaaaaaa aaaaaaaa     2638

<210> SEQ ID NO 117
<211> LENGTH: 5441
<212> TYPE: DNA
<213> ORGANISM: Homo sapiens

<400> SEQUENCE: 117
aattcctact tcctgaaact gaagccgttt atgagaaaca gtgtgtttca gagaggctgt      60
accagaatta actctgctca gagttagatt tgctggtctt aaagtacttt tcctctttaa     120
gataaaagaa gttcttctaa atcaggaatg gattgaaatc taatgaaccg aaactttggg     180
tacttcggcc ttcaaggggc tcctttattg agaatcaatg tcttctccta ggtaattgat     240
caccctagac ccagggacac ccaattcatc gtaatcatca tgaataatca aaaagtggta     300
gctgtgctac tgcaagagtg caagcaagtg ctggatcagc tcttgttgga agcgccagat     360
gtgtcggaag aggacaagag cgaggaccag cgctgcagag ctttactccc cagcgagtta     420
aggaccctga tccaggaggc aaaggaaatg aagtggccct tcgtgcctga aaagtggcag     480
tacaaacaag ccgtgggccc agaggacaaa acaaacctga aggatgtgat tggcgccggg     540
ttgcagcagt tactgcgtcc ctgagggcc tccatcctcg ctcgggactg tgcggctgcg     600
gcggctattg tgttcttggt ggaccggttc ctgtatgggc tcgacgtctc tggaaaactt     660
ctgcaggtcg ccaaaggtct ccacaagttg cagccagcca cgccaattgc cccgcaggtg     720
gttattcgcc aagcccgaat ctccgtgaac tcaggaaaac ttttaaaagc agagtatatt     780
ctgagcagtc taataagcaa caatggagca acgggtacct ggctgtacag aaatgaaagt     840
gacaaggtcc tggtgcagtc ggtctgtata cagatcagag ggcagattct gcaaaagctg     900
gggatgtggt acgaagcagc agagttaata tgggcctcca ttgtaggata tttggcactt     960
cctcagccgg ataaaaaggg cctctccacg tcgctaggta tactggcaga catctttgtt    1020
tccatgagca agaacgatta tgaaaagttt aaaaacaatc cacaaattaa tttgagcctg    1080
ctgaaggagt ttgaccacca tttgctgtcc gctgcagaag cctgcaagct ggcagctgcc    1140
ttcagtgcct atacgccgct cttcgtgctc acagctgtga atatccgtgg cacgtgttta    1200
ttgtcctaca gtagttcaaa tgactgtcct ccagaattga aaaacttaca tctgtgtgaa    1260
gccaaagagg cctttgagat tggcctcctc accaagagag atgatgagcc tgttactgga    1320
aaacaggagc ttcacagctt tgtcaaagct gctttcggtc tcaccacagt gcacagaagg    1380
ctccatgggg agacagggac ggtccatgca gcaagtcagc tctgtaagga agcaatgggg    1440
aagctgtaca atttcagcac ttcctccaga agtcaggaca gagaagctct gtctcaagaa    1500
gttatgtctg tgattgccca ggtgaaggaa catttacaag ttcaaagctt ctcaaatgta    1560
gatgacagat cttatgttcc cgagagtttc gagtgcaggt tggataaact tatcttgcat    1620
gggcaagggg atttccaaaa aatccttgac acctattcac agcaccatac ttcggtgtgt    1680
gaagtatttg aaagtgattg tggaaacaac aaaaatgaac agaaagatgc aaaaacagga    1740
gtctgcatca ctgctctaaa aacagaaata aaaaacatag atactgtgag tactactcaa    1800
gaaaagccac attgtcaaag agacacagga atatcttcct ccctaatggg taagaatgtt    1860
```

-continued

```
cagagggaac tcagaagggg aggaaggaga aactggaccc attctgatgc atttcgagtc    1920
tccttggatc aagatgtgga gactgagact gagccatcgg actacagcaa tggtgaggga    1980
gctgttttca acaagtctct gagtggcagc cagacttcca gtgcttggag caacttatca    2040
gggtttagtt cctctgcaag ctgggaggaa gtgaattatc acgttgacga caggtcagcc    2100
agaaaagagc ctggcaaaga acatctggtg gacactcagt gttccactgc cttgtctgag    2160
gagctagaga tgacaggga aggcagagct atgcattcat tgcattcaca gcttcatgat    2220
ctctctcttc aggaacccaa caatgacaat ttggagcctt ctcaaaatca gccacagcaa    2280
cagatgccct tgacacccett ctcgcctcat aatacccag gcatttcett ggccctggt      2340 gcagggcttc tagaaggagc tccagaaggt atccaggaag tcagaaatat gggacccaga    2400
aatacttctg ctcactccag accctcatat cgttctgctt cttggtcttc tgattctggt    2460
aggcccaaga atatgggcac acatccttca gtccaaaaag aagaagcctt tgaaataatt    2520
gttgagtttc cagaaaccaa ctgcgatgtc aaagacaggc aggggaaaga gcagggagaa    2580
gaaattagtg aaagaggcgc aggccctaca tttaaagcta gtccctcctg ggttgaccca    2640
gaaggagaaa cagcagaaag cactgaagat gcacccttag actttcacag ggtcctgcac    2700
aattctctgg gaaacatttc catgctgcca tgtagtcctt cacccctaa ttggcctgtt     2760 caaaatcctg actccagaaa aagtggtggc ccagtcgcag agcagggcat cgaccctgat    2820
gcctccacag tggatgagga ggggcaactg ctcgacagca tggatgttcc ctgcacaaat    2880
gggcacggct ctcatagact gtgcattctg agacagccgc ctggtcagag ggcggagacc    2940
cccaattcct ctgtaagcgg taacatcctc ttccctgtcc tcagcgagga ctgcactacc    3000
acagaggaag gaaatcagcc tggaaacatg ctaaactgca gccagaactc cagctcatcc    3060
tcagtgtggt ggctgaaatc acctgcattt tccagtggtt cttctgaggg ggacagccct    3120
tggtcctatc tgaattccag tgggagttct tgggtttcat tgccgggaaa gatgaggaaa    3180
gagatccttg aggctcgcac cttgcaacct gatgactttg aaaagctgtt ggcaggagtg    3240
aggcatgatt ggctgttttca gagactagag aatacggggg ttttttaagcc cagtcaactc    3300 caccgagcac atagtgctct tttgttaaaa tattcaaaaa aatctgaact gtggacggcc    3360
caggaaacta ttgtctattt gggggactac ttgactgtga agaaaaaagg cagacaaaga    3420
aatgcttttt gggttcatca tcttcatcaa gaagaaattc tggggaggta tgttgggaaa    3480
gactataagg agcagaaggg gctctggcac cacttcactg atgtggagcg acagatgacc    3540
gcacagcact atgtgacaga atttaacaag agactctatg aacaaaacat tcccacccag    3600
atattctaca tcccatccac aatactactg attttagagg acaagacaat aaagggatgt    3660
atcagtgtgg agccttacat actggggagaa tttgtaaaat tgtcaaataa cacgaaagtg    3720
gtgaaaacag aatacaaagc cacagaatat ggcttggcct atggccatttt tcttatgag    3780 ttttctaatc atagagatgt tgtggtcgat ttacaaggtt gggtaaccgg taatggaaaa    3840
ggactcatct acctcacaga tccccagatt cactccgttg atcagaaagt tttcactacc    3900
aattttggaa agagaggaat ttttttactttc tttaataacc agcatgtgga atgtaatgaa    3960
atctgccatc gtctttcttt gactagacct tcaatggaga aaccatgcac atagaatacg    4020
gcacagtctg gtcctttggg gcttgggcag ggccgtgaca caggttctgg ccaatgatttt   4080 gcaagaggaa ttgatcagta tcactttaag tcctgcattt aattggcagc acaagatcct    4140
gcagagcctc tttccctctg ccacagttat caagaatggg tcaggagacc gctgcttctg    4200
ggcataagtc ctgcaaggaa agcaacatgg aaaacagccc caactcaccc atgagggatg    4260
```

```
aaaagcactc ttgagaaagg catgtgttgt ttaagccatt gagattttag agcttttgt      4320 cactatctgt caagactgat actactgggg cttttcctat tgatttggga gttcttaca      4380 tattaaaaaa atgtgagcct ttgtgatacg aattcaattt gttttcctgt cttttgacat     4440
ttgactttgc ataaaagttt atctgtgcat aattttatat gtagttgaat tcatcaatct     4500
tttattttgt atggcttttt ggttatgtat aatacttaga tcctccttat actctgagtt     4560
tctttctttt taattctcct gtatttcctt ctagtataat taaatctgta aaagtaaga     4620 tggaagagtg gtacagtttt ctttatccag tctgtccttg atgggcattt aggtagactg     4680
gataaagaaa atgtggtaca tatacaccat ggaacactat gtgtattaat ccactctcac     4740
actgctatga agagatacct gagactgggt aatttagaaa gaaagaggt ttaattaact      4800 cacagttcca catggctggg gagacctcag gaaacttaca atcatggcag aaggcacctc     4860
ttcataaggt agcaggagag agaatgagtg ccagcagggg aaatgccaga tgcttataaa     4920
gccatcagat cttgtgagaa ttcattcact ctcacgagaa cagcatggga aaaactgcct     4980
caattacctc ctaccaggtc cttcccatga cacatgggaa ttatgggact acaattcgag     5040
atgagatttg ggtggggaca caaagccaaa ccatatcaca atgtaaccat aaaaaagaat     5100
gagatcatgt cctttgcagg gacatggata gagctggagg ccattatttt tagcaaacta     5160
atgcaagaac agaaaactaa ataccacttg ttctcactta taggtgagag ctaagtgatg     5220
agagtaggtg gacacataga gggaacaaca cacaccaggg cttatcagag ggtggacagt     5280
gggaggaggg agaggatcag gaaaaataac taatgggtac taggctgaat acctgggtga     5340
tgaagtaatt cgcacaacaa acccccatga cacaaacctg cacatgtacc cctgaactta     5400
aaataaaagt aaaaaaaaaa aaaaaaaaaa aaaaaaaaaa a                         5441
```

<210> SEQ ID NO 118
<211> LENGTH: 2048
<212> TYPE: DNA
<213> ORGANISM: Homo sapiens

<400> SEQUENCE: 118

```
ggcggggcct gggcgcgccg agctccggct gggtccctgc aggtcttggg gcccgggact       60
cttcctggag acaccgccat ggccgggcta tcccgcgggt ccgcgcgcgc actgctcgcc      120
gccctgctgg cgtcgacgct gttggcgctg ctcgtgtcgc ccgcgcgggg tcgcggcggc      180
cgggaccacg gggactggga cgaggcctcc cggctgccgc cgctaccacc ccgcgaggac      240
gcggcgcgcg tggcccgctt cgtgacgcac gtctccgact ggggcgctct ggccaccatc     300
tccacgctgg aggcggtgcg cggccggccc ttcgccgacg tcctctcgct cagcgacggg     360 cccccggggcg cgggcagcgg cgtgcccctat ttctacctga gcccgctgca gctctccgtg     420
agcaacctgc aggagaatcc atatgctaca ctgaccatga ctttggcaca gaccaacttc     480
tgcaagaaac atgatttga tccacaaagt cccctttgtg ttcacataat gctgtcagga     540
actgtgacca aggtgaatga aacagaaatg gatattgcaa agcattcgtt attcattcga     600 cacccctgaga tgaaacctg gccttccagc cataattggt tctttgctaa gttgaatata     660
accaatatct gggtcctgga ctactttggt ggaccaaaaa tcgtgacacc agaagaatat     720
tataatgtca cagttcagtg aagcagactg tggtgaattt agcaacactt atgaagtttc     780
ttaaagtggc tcatacacac ttaaaaggct taatgtttct ctggaaagcg tcccagaata     840
ttagccagtt ttctgtcaca tgctggtttg tttgcttgct tgtttacttg cttgtttacc     900
```

```
aatagagttg acctgttatt ggatttcctg gaagatgtgg tagctacttt tttcctattt      960
tgaagccatt ttcgtagaga aatatccttc actataatca aataagtttt gtcccatcaa     1020
ttccaaagat gtttccagtg gtgctcttga agaggaatga gtaccagttt taaattgccc     1080
attggcattt gaaggtagtt gagtatgtgt tctttattcc tagaagccac tgtgcttggt     1140
agagtgcatc actcaccaca gctgcctcct gagctgcctg agcctggtgc aaaaggattg     1200
gcccccatta tggtgcttct gaataaatct tgccaagata gacaaacaat gatgaaactc     1260
agatggagct tcctactcac gttgatttat gtctcacaat cctgggtatt gttaattcaa     1320
catagggtga aactatttct gataaagaac ttttgaaaaa cttttttatac tctaaagtga     1380
tactcagaac aaaagaaagt cataaaactc ctgaatttaa tttccccacc taagtcgaaa     1440
cagtattatc aaaacacatg tgcacacaga ttattttttg gctccaaaac tggattgcaa     1500
agaaagagg agaagaatat tttgtgtgtt cctggtattc ttttataagt aaagtttacc      1560
caggcatgga ccagcttcag ccagggacaa aatcccctcc caaaccactc tccacagctt     1620
tttaaaaata cttctactct taacaattac ctaaggcttc tcaactgcc ccaaatctct      1680
taatagcttc tagtgctgct acaatctaag tcaggtcacc agagggaaga gaacatggca     1740
ttaaaagaat cacatcttca gaagagaaga cactaatatt attacccata tacatgattt     1800
cagaagatga cataagattc ctcttaaaga ggaaatgtca ggaatcaagc cactgaatcc     1860
ttaaagagaa aagttgaata tgagtcattg tgtctgaaaa ctgcaaagtg aacttaactg     1920
agatccagca aacaggttct gtttaagaaa aataatttat actaaattta gtaaaatgga     1980
cttcttattc aaagcatcaa taattaaaag aattattttta atgaaaaaaa aaaaaaaaa     2040
aaaaaaaa                                                             2048

<210> SEQ ID NO 119
<211> LENGTH: 6031
<212> TYPE: DNA
<213> ORGANISM: Homo sapiens

<400> SEQUENCE: 119
cttttcccat cgtgtagtca agagtctgtg ccagacttga aggctttact ttgttagcca       60
tgtgtttatg aaccccagc gctttcccta gatcttttgg ctgataatct caaacatgga      120
ggatgcttct gaatcttcac gagggggttgc tccattaatt aataatgtag ttctcccagg     180
ctctccgctg tctcttcctg tatcagtgac aggctgtaaa agtcatcgag tagccaataa     240
aaaggtagaa gcgaggagtg aaaagctcct cccaacagct cttcctcctt cagagccgaa     300
agtagatcag aaacttccca ggagctccga gaggcgggga agtggcggtg ggacgcaatt     360
ccccgcgcgg agtcgggcag tggcagcggg agaagcggca gccaggggcg cggcggggcc     420
ggagagaggc ggtcccctgg gaggacgggg tctcccctcg ttgcctttgt agtggagaag     480
gtggacaagt ggcagtcggc gtgatcgcag ggaagcgggg ccggcgcggg cggccgaggg     540
tccaggcgag cccgcgggcg gacgggagat gccgctgcta caccgaaagc cgtttgtgag     600
acagaagccg cccgcggacc tgcggcccga cgaggaagtt ttctactgta aagtcaccaa     660
cgagatcttc cgccactacg atgactttt tgaacgaacc attctgtgca acagccttgt     720
gtggagttgt gctgtgacgg gtagacctgg actgacgtat caggaagcac ttgagtcaga     780
aaaaaaagca agacagaatc ttcagagttt tccagaacca ctaattattc cagttttata     840
cttgaccagc cttaccccatc gttcgcgctt acatgaaatt tgtgatgata tctttgcata     900
tgtcaaggat cgatattttg tcgaagaaac tgtggaagtc attaggaaca atggtgcaag     960
```

```
gttgcagtgt aggattttgg aagtcctccc tccatcacat caaaatggtt ttgctaatgg   1020
acatgttaac agtgtggatg gagaaactat tatcatcagt gatagtgatg attcagaaac   1080
acaaagctgt tcttttcaaa atgggaagaa aaagatgca attgatccct tactattcaa    1140
gtataaagtg caacccacta aaaagaatt acatgagtct gctattgtta aagcaacaca    1200
aatcagccgg agaaaacacc tattttctcg tgataaacta agcttttttc tgaagcaaca   1260
ctgtgaacca caagatggag tcattaaaat aaaggcatca tctctttcaa cgtataaaat   1320
agcagaacaa gattttctt atttcttccc tgatgatcca cccacattta tcttcagtcc    1380
tgctaacaga cgaagaggga gacctcccaa acgaatacat attagtcaag aggacaatgt   1440
tgctaataaa cagactcttg caagttatag gagcaaagct actaagaaa gagataaact    1500 tttgaaacaa gaagaaatga agtcactggc ttttgaaaag gctaaattaa aaagagaaaa   1560
agcagatgcc ctagaagcga agaaaaaga aaagaagat aaagagaaaa agagggaaga    1620
attgaaaaaa attgttgaag aagagagact aagaaaaaa gaagaaaaag agaggcttaa    1680
agtagaaaga gaaaaggaaa gagagaagtt acgtgaagaa aagcgaaagt atgtggaata   1740
cttaaaacag tggagtaaac ctagagaaga tatggaatgt gatgacctta aggaacttcc   1800
agaaccaaca ccagtgaaaa ctagactacc tcctgaaatc tttggtgatg ctctgatggt   1860
tttggagttc cttaatgcat ttgggggaact ttttgatctt caagatgagt ttcctgatgg   1920
agtaacccta gaagtattag aggaagctct tgtaggaaat gacagtgaag gcccactgtg   1980
tgaattgctt ttttttcttcc tgactgcaat cttccaggca atagctgaag aagaaggaga   2040
agtagccaaa gagcaactaa ctgatgctga caccaaagat ttaacagagg ctttggatga   2100
agatgcagac cccacaaaat ctgcactgtc tgcagttgca tctttggcag ctgcatggcc   2160
acagttacac cagggctgca gtttgaaaag tttggatctt gatagctgca ctcttttcaga   2220 aatcctcaga ctgcacatct tagcttcagg tgctgatgta acatcagcaa atgcaaagta   2280
tagatatcaa aaacgaggag gatttgatgc tacagatgat gcttgtatgg agcttcgttt   2340
gagcaatccc agtctagtga agaaaactgtc aagcacctca gtgtatgatt tgacaccagg   2400
agaaaaaatg aagatactcc atgctctctg tggaaagcta ctgaccctag tttcaactag   2460 ggatttatt gaagattatg ttgatatatt acgacaggca aagcaggagt tccgggaatt    2520
aaaagcagaa caacatcgaa agagaggga agaagcagct gccagaattc gtaaaaggaa   2580
ggaagaaaaa cttaaggagc aagaacaaaa aatgaaagag aaacaagaaa aactgaaaga   2640
agatgagcaa agaaattcaa cggcagatat atctattggg gaggaagaaa gggaagattt   2700
tgatactagc attgagagca agacacaga gcaaaaggaa ttagatcaag atatggtcac    2760
tgaagatgaa gatgacccag gatcacataa agaggcaga aggggaaaa gaggacaaaa    2820 tggatttaaa gaatttacaa ggcaagaaca gatcaactgt gtaacaagag agcctcttac   2880
tgctgatgag gaagaagcat taaaacagga acaccaacga aaagagaaag agctcttaga   2940
aaaaatccaa agtgccatag cctgtaccaa tatctttccc ttgggtcgcg accgcatgta   3000
tagacgatac tggattttcc cttctattcc tggactcttt attgaagagg attattctgg   3060
tcttactgaa gacatgctgt tgcctagacc ttcatcattt cagaataatg tacagtctca   3120
agatcctcag gtatccacta aaactggaga gcctttgatg tctgaatcta cctccaacat   3180
tgaccaaggt ccacgtgacc attctgtgca gctgccaaaa ccagtgcata agccaaatcg   3240
gtggtgcttt tacagttctt gtgaacagct agaccagctt attgaagctc ttaattctag   3300
```

-continued

```
aggacataga gaaagtgcct taaaagaaac tttgttacaa gagaaaagca gaatatgtgc    3360
acagctagcc cgttttctg aagagaaatt tcattttca gacaaacctc agcctgatag      3420
caaaccaaca tatagtcggg gaagatcttc caatgcatat gatccatctc agatgtgtgc   3480
agaaaagcaa cttgaactaa ggctgagaga ttttctttta gatattgaag atagaatcta   3540
ccaaggaaca ttaggagcca tcaaggttac agatcgacat atctggagat cagcattaga   3600
aagtggacgg tatgagctgt taagtgagga aaacaaggaa aatgggataa ttaaaactgt   3660
gaatgaagac gtagaagaga tggaaattga tgaacaaaca aaggtcatag taaaagacag   3720
acttttgggg ataaaaacag aaactccaag tactgtatca acaaatgcaa gtacaccaca   3780
atcagtgagc agtgtggttc attatctggc aatggcactc tttcaaatag agcagggcat   3840
tgagcggcgt tttctgaaag ctccacttga tgccagtgac agtgggcgtt cttataaaac   3900
agttctggac cgttggagag agtctctcct ttcttctgct agtctatccc aagtttttct   3960
tcacctatcc accttggatc gtagcgtgat atggtctaaa tctatactga atgcgcgttg   4020
caagatatgt cgaaagaaag gcgatgctga aaacatggtt ctttgtgatg ctgtgatag    4080 gggtcatcat acctactgtg ttcgaccaaa gctcaagact gtgcctgaag agactggtt    4140 ttgtccagaa tgtcgaccaa agcaacgttc tagaagactc tcctctagac agagaccatc   4200
cttggaaagt gatgaagatg tggaagacag tatgggaggt gaggatgatg aagttgatgg   4260
cgatgaagaa gaaggtcaaa gtgaggagga agagtatgag gtagaacaag atgaagatga   4320
ctctcaagaa gaggaagaag tcagcctacc caaacgagga agaccacaag ttagattgcc   4380
agttaaaaca gagggaaac ttagctcttc tttctcaagt cgtggccaac aacaagaacc    4440
tggaagatac ccttcaagga gtcagcagag cacacccaaa acaactgttt cttctaaaac   4500
tggtagaagc ctaagaaaga taaactctgc tcctcctaca gaaacaaaat ctttaagaat   4560
tgccagtcgt tctactcgcc acagtcatgg cccactgcaa gcagatgtat tgtggaatt    4620 gcttagtcct cgtagaaaac gcagaggcag gaaaagtgct aataatacac cagaaaatag   4680
tcccaacttc cctaacttca gagtcattgc cacaaagtca agtgaacagt caagatctgt   4740
aaatattgct tcaaaacttt ctctccaaga gagtgaatcc aaaagaagat gcagaaaaag   4800
acaatctcca gagccatcgc ctgtgacact gggtcgaagg agttctggcc gacagggagg   4860
agttcatgaa ttgtctgctt ttgaacaact tgttgtagaa ttggtacgac atgatgacag   4920
ctggcctttt ttgaaacttg tttctaaaat ccaggtccca gactactatg acatcatcaa   4980
aaagcccatt gccttaaata taattcgtga aaaagtgaat aagtgtgaat ataaattagc   5040
atctgagttt attgatgaca ttgagttaat gttttcgaac tgctttgaat caaccctcg    5100 taacacaagt gaagcaaaag ctggaactag gcttcaagca tttttcata ttcaggctca    5160 aaagcttgga ctccacgtca cacccagtaa tgtggaccaa gttagcacac caccggctgc   5220
gaaaaagtca cgaatctgac tttgtccttc taaaggatat attttgaagaa aaacaaattg   5280 ttcatgaaaa tggaacatta aatcatgctg tataaagcaa taacaattga ttgaccacat   5340
gaaagtgtgg cctgcactat attctcaatt ttaatattaa gcactcagga gaatgtagga   5400
aagatatcct ttgctacagt tttgttcagt atctaataag tttgatagat gtattggata   5460
cagtactggt ttacagaggt ttttgtacat ttttgagatc attcatgtgt ccagagatct   5520
tggaaaatat ttttcaccc acgatttatt ttgttattga tgattttttt ttaaagtggt    5580
ggtattaagg gagagttatc tacatggatg agtcttccgc tatagcacag tttagaaaag   5640
gtgtttatgt cttaattaat tgtttgagta cattctttca acactacaca tgaatgaatc   5700
```

```
caatcttata accttgaagt gctgtaccag tgctggctgc aggtattaag tccaagttta    5760
ttaactagat atttatttag tattgagagt aatttgtgaa tttgttttgt atttataaaa    5820
tttatacctg aaaaatgttc cttaatgttt taaacctttt actgtgtttt tattcctcta    5880
acttccttaa tgatcaatca aaaaagtaa caccctccct ttttcctgac agttctttca     5940
gctttacaga actgtattat aagtttctat gtataacttt ttaactgtac aaataaaata    6000 acatttttc aaataaaaaa aaaaaaaaaa a                                    6031
```

<210> SEQ ID NO 120
<211> LENGTH: 4095
<212> TYPE: DNA
<213> ORGANISM: Homo sapiens

<400> SEQUENCE: 120

```
agacagccag ttcctctccc gccgcgccgg gccgcgctgc cgctcgctcc ccggccgtgg      60
cgcctccggg ccagacgcgc tgcagcctcc agcccgcggc aagcggggcg gccgcgccac    120
ccccggcccc gcgccagcag cccctcgccg cgcgtccagc gttcccggcc agcagcctcc    180
ccatacgcag gtcctgctgg gccgccccgt cgcgcccccc actctgaact caagtcaccg    240
tggagctccg ccgccccgaa actttcaccg cgagcgggaa atatgggatg tataaaatca    300
aaagggaaag acagcttgag tgacgatgga gtagatttga agactcaacc agttccagaa    360
tctcagcttt tacctggaca gaggtttcaa actaaagatc cagaggaaca aggagacatt    420
gtggtagcct tgtaccccta tgatggcatc cacccggacg acttgtcttt caagaaagga    480
gagaagatga aagtcctgga ggagcatgga gaatggtgga agcaaagtc ccttttaaca     540 aaaaaagaag gcttcatccc cagcaactat gtggccaaac tcaacacctt agaaacagaa    600
gagtggtttt tcaaggatat aaccaggaag gacgcagaaa ggcagctttt ggcaccagga    660
aatagcgctg gagcttttcct tattagaaa agtgaaacat taaaaggaag cttctctctg    720
tctgtcagag actttgaccc tgtgcatggt gatgttatta gcactacaa aattagaagt     780 ctggataatg ggggctatta catctctcca cgaatcactt ttccctgtat cagcgacatg    840
attaaacatt accaaaagca ggcagatggc ttgtgcagaa gattggagaa ggcttgtatt    900
agtcccaagc cacagaagcc atgggataaa gatgcctggg agatccccg ggagtccatc     960 aagttggtga aaaggcttgg cgctgggcag tttgggaag tctggatggg ttactataac    1020
aacagtacca aggtggctgt gaaaacctg aagccaggaa ctatgtctgt gcaagccttc    1080
ctggaagaag ccaacctcat gaagaccctg cagcatgaca agctcgtgag gctctacgct    1140
gtggtcacca gggaggagcc catttacatc atcaccgagt acatggccaa gggcagtttg    1200
ctggatttcc tgaagagcga tgaaggtggc aaagtgctgc ttccaaagct cattgacttt    1260
tctgctcaga ttgcagaggg aatggcatac atcgagcgga gaactacat tcaccgggac    1320 ctgcgagcag ctaatgttct ggtctccgag tcactcatgt gcaaaattgc agattttggc    1380
cttgctagag taattgaaga taatgagtac acagcaaggg aaggtgctaa gttccctatt    1440
aagtggacgg ctccagaagc aatcaacttt ggatgtttca ctattaagtc tgatgtgtgg    1500
tcctttggaa tcctcctata cgaaattgtc acctatggga aaattcccta cccagggaga    1560
actaatgccg acgtgatgac cgccctgtcc cagggctaca ggatgccccg tgtggagaac    1620
tgcccagatg agctctatga cattatgaaa atgtgctgga agaaaagc agaagagaga    1680 ccaacgtttg actacttaca gagcgtcctg gatgatttct acacagccac ggaagggcaa    1740
```

```
taccagcagc agccttagag cacagggaga cccgtccatt tggcaggggt ggctgcctca    1800
tttagagagg aaaagtaacc atcactggtt gcacttatga tttcatgtgc ggggatcatc    1860
tgccgtgcct ggatcctgaa atagaggcta aattactcag gaagaacacc ctctaaatgg    1920
gaaagtattc tgtactctta gatggattct ccactcagtt gcaacttgga cttgtcctca    1980
gcagctggta atcttgctct gcttgacaac atctgagtgc agccgtttga aagaaaaca     2040 tctattctct ccaaaaatgc acccaactag ctctatgttt acaaatggac ataggactca    2100
aagtttcaga gaccattgca atgaatcccc aataattgca gaactaaact catttataaa    2160
gctaaaataa ccggatatat acatagcatg acatttcttt gtgctttggc ttacttgttt    2220
aaaaaaaaaa aaaactaat ccaacctgtt agattttgca ggtgaagtca gcagcttaaa     2280
aatgtctttc ccagatttca atgattttt tccccctacc tcccaaaatc tgagactgtt     2340
aaaacatttt tcttctatga acactgctca gacctgctag acatgccata ggagtggcgt    2400
gcacatctct ctctcttcca gcaggaggag cccgtgagca cgcacagctg ccctgtctgc    2460
tcacccgaag gcaccgggct cacctggacc tcccaggaaa gggagaagag cctcagaaac    2520
tgctctgtgt ttagaaggaa tattttaag agtccagctt tttcatttcc acaatttcct     2580
atatccagat ttgttttgac aatgtagttt ggaagaacta agattctaat ctctgaagaa    2640
ccttataggg ccttctaaaa cataagagtt tcctttgttg cttcaaatat ttgaacatta    2700
tgttaaagat caagtattaa ttttagttgt actctagaaa gctaaagtgc cacattcggg    2760 gctatttta tgattcagca atcttttcta aattgtgtag catgtgtatg agactattta     2820
tacccaagga tatgaaggaa cataagtgac tacaaggctc taataagcca cggtggcagg    2880
aggttcaagc ggttctgttc actaaatttt tctcctgtaa gctttgaatg gaaacttctg    2940
tatcacatga tgtgtttcac ttatgctgtt gtgtatatac ctaatatttc tatttttgat    3000 tttatttaa tacacctcgt ccaataacat ctcaagcttt ttatttgcat ttacattttc     3060
agctgtggtc agtgtaaaaa ttggtcatca gctgggggcg gggtggttag aagtgattca    3120
acagagctac atgctttaaa cttgcccaag ttctacctcc ttcctttgaa catttcagat    3180
tggagaacca aggagttgat tgcctgaaca cctgaacatc cgtttatggg ggccagatag    3240
aatttgtttt caaataggct taacaggcat cattaaaatt tcattctgtg tgttttgttt    3300
aggcttgagg tgcttagaag atgggataaa atattctact ttttttctaaa ttttaacttt   3360 gtttcctatg tgattttttt aaatgtcctt tctaaaatat tctaaaatta ttgattcaca    3420
agtgccatgt tcagaactat agaatattac tgttacataa tgtctgcaca gctggtccct    3480
tgattcagtg gtaaggtttt tgtgtacacc cccctgcttg catttatttt cagaaccaca    3540
agtattaccc aatatgttac atggagagga actataaaga atccctaagg caaaagaag     3600 tctctagaaa atgactagag gttttttttt tagcataaca aatttattta agaaaatta    3660 ttaaatttat cttcgccttg ttttgcttct cccagttcct cctcttcttg ccattttcca    3720
cttgtctttc cctcccaatc aagcctgtga tccttacctc catgtgggcc cttcaccagc    3780
ttgggcctca tctctggtgt ccagcatgtg tggaagtcac acgttccctt gatgaacagc    3840
acacacagtc tccttactta gctataggtt tccagcctcc ctgtgacaga caggcataat    3900
gaggggctga ataggtgttt gtagcatttt cgggtatcca gtggtgtgca aaatggctca    3960
tgtcatcaca cctcaggtta ttgtagagaa ctggaaagac agaatccata ctccctaccg    4020
ccaagattct gacttagctg ttgtgcagcg ggagatgtat gtcagtctat tttaaaagct    4080
tctccagtca gctag                                                     4095
```

<210> SEQ ID NO 121
<211> LENGTH: 3779
<212> TYPE: DNA
<213> ORGANISM: Homo sapiens

<400> SEQUENCE: 121

| | | | | | |
|---|---|---|---|---|---:|
| ggggacgcgg | cacagatagg | gggaagccgg | agtaatggtt | ttcgggcaag | tggatgttgg | 60 |
| agagcacaca | caggagttgg | ggggcggggg | agggcctggg | gttggggagg | gctcgaactc | 120 |
| ggggctgctg | ggtagtccag | gagggcgcgg | taaggctggg | gtgtcctggt | gagaactgga | 180 |
| gaggatctac | ccgggtccct | gcctggccag | tggggaaaca | ccggtccccc | aggcaccttc | 240 |
| acctaaccag | agcggggatt | tccaccgccc | ctcatgccgc | cctttggagg | aaagtgaaag | 300 |
| tgaaaggagg | aagaggaggc | ttcatggctg | aggaggtcgc | agcgccatga | agtccctgtc | 360 |
| tctgctcctc | gctgtggctt | tgggcctggc | gaccgccgtc | tcagcaggac | ccgcggtgat | 420 |
| cgagtgttgg | ttcgtggagg | atgcgagcgg | aaagggcctg | ccaagagac | ccggtgcact | 480 |
| gctgttgcgc | cagggaccgg | gggaaccgcc | gccccggccg | gacctcgacc | ctgagctcta | 540 |
| tctcagtgta | cacgaccccg | cgggcgccct | ccaggctgcc | ttcaggcggt | atccccgggg | 600 |
| cgcccccgca | ccacactgcg | agatgagccg | cttcgtgcct | ctccccgcct | ctgcgaaatg | 660 |
| ggccagcggc | ctgaccccg | cgcagaactg | cccgcgggcc | ctggatgggg | cttggctgat | 720 |
| ggtcagcata | tccagcccag | tcctcagcct | ctccagcctc | ttgcgaccac | agccagagcc | 780 |
| tcagcaggag | cctgttctca | tcaccatggc | aacagtggta | ctgactgtcc | tcacccacac | 840 |
| ccctgcccct | cgagtgagac | tgggacaaga | tgctctgctg | gacttgagct | tgcctacat | 900 |
| gcccccacc | tccgaggccg | cctcatctct | ggctccgggt | ccccctcct | ttgggctaga | 960 |
| gtggcgacgc | cagcacctgg | gtaagggaca | tctgctcctg | gctgcaactc | ctgggctgaa | 1020 |
| tgccagatg | ccagcagccc | aagaaggggc | cgtggcattt | gctgcttggg | atgatgatga | 1080 |
| gccatggggc | ccatggaccg | gaaatgggac | cttctggctg | cctacagttc | aaccctttca | 1140 |
| ggagggcacc | tatctggcca | ccatacacct | gccatacctg | caaggacagg | tcaccctgga | 1200 |
| gcttgctgtg | tacaaacccc | ccaaagtgtc | cctgatgcca | gcaaccttg | cacgggccgc | 1260 |
| cccaggggag | gcacccccgg | aattgctctg | ccttgtgtcc | cacttctacc | cttctggggg | 1320 |
| cctggaggtg | gagtgggaac | tccggggtgg | cccaggggc | cgctctcaga | aggccgaggg | 1380 |
| gcagaggtgg | ctctcggccc | tgcgccacca | ttccgatggc | tctgtcagcc | tctctgggca | 1440 |
| cttgcagccg | cccccagtca | ccactgagca | gcatggggca | cgctatgcct | gtcgaattca | 1500 |
| ccatcccagc | ctgcctgcct | cggggcgcag | cgctgaggtc | accctggagg | tagcaggtct | 1560 |
| ttcagggccc | tcccttgagg | acagcgtagg | ccttttcctg | tctgcctttc | ttctgcttgg | 1620 |
| gctcttcaag | gcactgggct | gggctgctgt | ctacctgtcc | acctgcaagg | attcaaagaa | 1680 |
| gaaagcagag | tgagggcact | cactgccatc | ctgtggaagc | caccatcatc | tctgccccaa | 1740 |
| gcttctgtag | tagctcccta | aaataatacc | ctatcatctg | ctcctaatcc | ctccaatctc | 1800 |
| tctccactga | gtggctggaa | tgctttttt | ttttctttc | acttatataa | gggataattt | 1860 |
| ttcttttttt | tttttttttg | agacggagtc | tcactcttcc | gcccaggctg | cagtgcagtg | 1920 |
| gcatgatctt | ggcttactgc | aacctccgcc | tcctgggttc | aagcaattct | gtggcttcag | 1980 |
| cctccggagt | agctgggatt | acaggcacat | gccaccacac | ccagtgaatt | tttgtatttt | 2040 |
| tagtagagac | ggggtttcac | catgttggcc | aggctggtct | tgaattcctg | acctcaggtg | 2100 |

| | |
|---|---|
| atctgcccac ctcagcctcc caaagtgctg ggattacagg cgtgagccac cacaccaggc | 2160 |
| ccgagaaatg ctttttttaaa aaacacacat cttatggcat tcaccttctt ggagctctag | 2220 |
| gacagtggtt ctcaaaattt ttttctctca ggacctctta aaaatcatca aggacccaa | 2280 |
| aaagcttttg ggtatgtggg ttatagctat caatatttat ggtactagaa cttaaaagtg | 2340 |
| agaaaaattt aaaacacgag aatacatagg cacacattct attcatcgtg ggaaccatgg | 2400 |
| tgtcaataca tatcatgtag cttctgaaaa actccactgt acacttatag aatgaagaag | 2460 |
| gcaaaaaact ttttttttt tttttttgag acggagtctc gctctgtcgc ccaggctgga | 2520 |
| gtgcagtggc gcgatctcgg ctcactgcaa gctccgcctc tcgggttcac gccattctcc | 2580 |
| tgcctcagcc tcccaagtag ctcggactac aggcgtcctc caccatgcct ggctaatatt | 2640 |
| ttgtattttt tagtagagac ggggtttcac cgtgttagcc aggatggtct cgatctccta | 2700 |
| acctggtgat ccgcccgcct cggcctccca agtattggg attacccgcg tgagccaccg | 2760 |
| cgcccggctg caaataatct ttctttttt ctgagacaga gtctcgctct gttgcccagg | 2820 |
| ctggagtgca gtggcacgat ctcggctcac ggcacgctcc gcctcccggg ttcacgccat | 2880 |
| tctcctgcct cagcttcccg agtagctggg actacagggg cccgccacca cgcccggcta | 2940 |
| acttttgtg ttttagtag agacggggtt tcaccgtgtt agccaggatg gtctcgatct | 3000 |
| cctgaccttg tgatctgccc gcctcggcct cccaaagtgc tgggattaca ggcgtgagcc | 3060 |
| accgcgcccg gcgcgaaac acgatattgt actaacatct taattttgtt ataaaatctc | 3120 |
| acaaaccccc tgacatagtc tcagagatct gtagggccga ggttacattt ggagaacccg | 3180 |
| tactctaggg ccaaatccat tcttcttgcc ctggctcact tgtcccccc accgcccgc | 3240 |
| gctggagcca ctgcctagtt cttcagccct agatggtgct cgccagacct cctctcaatg | 3300 |
| ctcatcacac acagggctat tccttcctc caatgaacca aacgcctccc gcccacctcc | 3360 |
| aggtcccagt cctctgttcc ctttgcctgg tccacccttg ccctccctgg gtcgcagacg | 3420 |
| aggtcggcct cgtcattccc cgcagaccgc gcgcgtccc tcttgtgcgg ttcaccacag | 3480 |
| ttgtatttaa gtgatcgtgt gagtcgtcgt taaatgcctg tctccccgcg gatcatgggc | 3540 |
| tcctcgagga cagggactgg cctgtctgtc cactgctgta accccgcgcc ggcataggga | 3600 |
| cctaaggccc actggagggc gctcatcaag tagctgctgg atgttgacga aggaagcggc | 3660 |
| ggcgcagctc agggatctcc gagtcaggac ggtcggccag acccacgggg taacgggtct | 3720 |
| aatcgtgtag gaataaagct gtattccagt gcttccaaaa aaaaaaaaa aaaaaaaaa | 3779 |

<210> SEQ ID NO 122
<211> LENGTH: 2678
<212> TYPE: DNA
<213> ORGANISM: Homo sapiens

<400> SEQUENCE: 122

| | |
|---|---|
| agaaagaagc cgcgcccctg aggagggcgc tgcccggaag ccacgctcac ttctgcttgc | 60 |
| acttaggcga cctcgggagc tcggactcct acgcagtcac cgggaagggc cgccgccccg | 120 |
| cccgcggctg ctggcccggg tgacgcttcc gcctgctata agagcagcgg ccctcggtgc | 180 |
| ctccttcctg acctcgcacc cagctcggag cccgagcgt gcctcggcgg cctgtcggtt | 240 |
| ttcaccatgg agcagctgag ctcagcaaac accgcttcg ccttggacct gttcctggcg | 300 |
| ttgagtgaga caatccggc tggaaacatc ttcatctctc ccttcagcat ttcatctgct | 360 |
| atggccatgt ttttctgggg gaccagaggt aacacggcag cacagctgtc caagactttc | 420 |
| catttcaaca cggttgaaga ggttcattca agattccaga gtctgaatgc tgatatcaac | 480 |

```
aaacgtggag cgtcttatat tctgaaactt gctaatagat tatatggaga gaaaacttac    540
aatttccttc ctgagttctt ggtttcgact cagaaaacat atggtgctga cctggccagt    600
gtggattttc agcatgcctc tgaagatgca aggaagacca taaaccagtg ggtcaaagga    660
cagacagaag gaaaaattcc ggaactgttg gcttcgggca tggttgataa catgaccaaa    720
cttgtgctag taaatgccat ctatttcaag ggaaactgga aggataaatt catgaaagaa    780
gccacgacga atgcaccatt cagattgaat aagaaagaca gaaaaactgt gaaaatgatg    840
tatcagaaga aaaaatttgc atatggctac atcgaggacc ttaagtgccg tgtgctggaa    900
ctgccttacc aaggcgagga gctcagcatg gtcatcctgc tgccggatga cattgaggac    960
gagtccacgg gcctgaagaa gattgaggaa cagttgactt tggaaaagtt gcatgagtgg   1020
actaaacctg agaatctcga tttcattgaa gttaatgtca gcttgcccag gttcaaactg   1080
gaagagagtt acactctcaa ctccgacctc gcccgcctag tgtgcagga tctctttaac    1140 agtagcaagg ctgatctgtc tggcatgtca ggagccagag atattttat atcaaaaatt    1200 gtccacaagt catttgtgga agtgaatgaa gagggaacag aggcggcagc tgccacagca   1260
ggcatcgcaa ctttctgcat gttgatgccc gaagaaaatt tcactgccga ccatccattc   1320 cttttctttta ttcggcataa ttcctcaggt agcatcctat tcttggggag attttcttcc   1380
ccttagaaga aagagactgt agcaatacaa aaatcaagct tagtgcttta ttacctgagt   1440
ttttaataga gccaatatgt cttatatctt taccaataaa accactgttc agaaacaagt   1500
ctttcatttt ctttgtaagt ttggctctgt tggctgttta cacccatgaa ttttggcatg   1560
ggtatctatt tttctttttt acattgaaaa aaatccagtg gttgcttttg aatgcatcaa   1620
gtaaagaaga agaaaagaat acatccgatg cgtagattct tgaccatgta gtaatctata   1680
aaattgctat atcctcctga tagccatggg aaaacatgat aagatggtca tttatttgc    1740 agttagaatt ttggaagcca caaaatagac agacaccctg actgttgaag ggaggtttaa   1800
aaacagatat tcaattgaaa tgtaagagag cacccccaatt gagagcccag gttacgaaga   1860
caagcttgcc tcgcctgact tttctgtccc ttgttctgca ggattagtat tctgttacag   1920
acctctagtt tttagactct tcaattaaag ggccaatggt tataacctgc attccctttt   1980
ttgttcttct ttatgtataa tatatagttc atgtggcgct gcatgaaatc aagaagtggg   2040
tgtcttagga taaaagatac caagagtcta caaaaataac catgtagtaa gataaactgc   2100
tgaacaaagg ttttactgtt agccaccttc tcatgtgttt tcttttctct ttttcttttt   2160
ctttctttct ttctttttttt ttttttgag acagagtctt gctctgttac ccaggctgga   2220
gtgcagtggc acgatctcag ctcaccgcaa cctctgcctc ctgggttcaa gtgattctct   2280
tgcttcagcc tcctgagtag ctgggattat aggcatgcac cactaggcct ggctaatttt   2340
tgtattttta gtagagatgg ggttttttcca tgttggccag gctggtcccg aactcctgac   2400
ctcaggtgat ccgcgcacct cagcctccca aagtgctggg attacaggca tgagctacca   2460
tgcctggcct tctcatgtgt tttctgatta aggctcttga cttccaaggc tgtgtgggga   2520
gatggggtgg gggctcttgg actgatataa aactttgtca aatgtagttc tttgaatgga   2580
gcttgaaacg ccgcatattc ttgctcccac aaggatagtg ggcatcatga attaataaaa   2640
cgtcctagga ttctgcaagc taaaaaaaaa aaaaaaaa                           2678

<210> SEQ ID NO 123
<211> LENGTH: 1048
<212> TYPE: DNA
```

<213> ORGANISM: Homo sapiens

<400> SEQUENCE: 123

| | | | | | |
|---|---|---|---|---|---|
| gcgcgttgtg | cgctgtccca | ggttggaaac | cagtgcccca | ggcggcgagg | agagcggtgc | 60 |
| cttgcaggga | tgctgcgggc | gggagcacca | accggggact | taccccgggc | gggagaagtc | 120 |
| cacaccggga | ccaccatcat | ggcagtggag | tttgacgggg | gcgttgtgat | gggttctgat | 180 |
| tcccgagtgt | ctgcaggcga | ggcggtggtg | aaccgagtgt | ttgacaagct | gtccccgctg | 240 |
| cacgagcgca | tctactgtgc | actctctggt | tcagctgctg | atgcccaagc | cgtggccgac | 300 |
| atggccgcct | accagctgga | gctccatggg | atagaactgg | aggaacctcc | acttgttttg | 360 |
| gctgctgcaa | atgtggtgag | aaatatcagc | tataaatatc | gagaggactt | gtctgcacat | 420 |
| ctcatggtag | ctggctggga | ccaacgtgaa | ggaggtcagg | tatatggaac | cctgggagga | 480 |
| atgctgactc | gacagccttt | tgccattggt | ggctccggca | gcacctttat | ctatggttat | 540 |
| gtggatgcag | catataagcc | aggcatgtct | cccgaggagt | gcaggcgctt | caccacagac | 600 |
| gctattgctc | tggccatgag | ccgggatggc | tcaagcgggg | gtgtcatcta | cctggtcact | 660 |
| attacagctg | ccggtgtgga | ccatcgagtc | atcttgggca | tgaactgcc | aaaattctat | 720 |
| gatgagtgaa | ccttccccag | acttctcttt | cttattttgt | aataaactct | ctagggccaa | 780 |
| aacctggtat | ggtcattggg | aaatgagtgc | tcagggagat | ggagcttagg | ggaggtgggt | 840 |
| gcttccctcc | tagatgtcag | catacactct | ttcttctttt | gtcccaggtc | taaaacatct | 900 |
| ttcctagaga | aaacaaaagg | gactaaacta | gaaatataaa | gagccctata | catgacaggt | 960 |
| gatcacgtac | tgaatgattt | tgaagtagta | caaacaataa | aaattctcat | tccgcatcat | 1020 |
| catgcggtcc | atgatgatga | ggccgcaa | | | | 1048 |

<210> SEQ ID NO 124
<211> LENGTH: 2849
<212> TYPE: DNA
<213> ORGANISM: Homo sapiens

<400> SEQUENCE: 124

| | | | | | |
|---|---|---|---|---|---|
| agatatctcc | ggcgccgccc | gccattttga | ctccagtgtc | tcgtttgcag | tcggcgcttt | 60 |
| aggggaactg | tcttcctccg | caggcgcgag | gctgggtaca | gggtctattg | tctgtggttg | 120 |
| actccgtact | ttggtctgag | gccttcggga | gctttcccga | ggcagttagc | agaagccgca | 180 |
| gcggccgccc | ccgcccgtct | cctctgtccc | tgggcccggg | agggaccaac | ttggcgtcac | 240 |
| gcccctcagc | ggtcgccact | ctcttctctg | ttgtttgggtc | cgcatcgtat | tcccggaatc | 300 |
| agacggtgcc | ccatagatgg | ccagctttcc | cccgagggtc | aacgagaaag | agatcgtgag | 360 |
| attacgtact | ataggtgaac | ttttagctcc | tgcagctcct | tttgacaaga | aatgtggtcg | 420 |
| tgaaaattgg | actgttgctt | tgctccaga | tggttcatac | tttgcttggt | cacaaggaca | 480 |
| tcgcacagta | aagcttgttc | cgtggtccca | gtgccttcag | aactttctct | tgcatggcac | 540 |
| caagaatgtt | accaattcaa | gcagtttaag | attgccaaga | caaatagtg | atggtggtca | 600 |
| gaaaaataag | cctcgtgaac | atattataga | ctgtggagat | atagtctgga | gtcttgcttt | 660 |
| tgggtcatca | gttccagaaa | aacagagtcg | ctgtgtaaat | atagaatggc | atcgcttcag | 720 |
| atttggacaa | gatcagctac | ttcttgctac | agggttgaac | aatgggcgta | tcaaaatatg | 780 |
| ggatgtatat | acaggaaaac | tcctccttaa | cttggtagat | catactgaag | tggtcagaga | 840 |
| tttaactttt | gctccagatg | gaagcttgat | cctggtgtca | gcttcaagag | acaaaactct | 900 |
| cagagtatgg | gacctgaaag | atgatggaaa | catgatgaaa | gtattgaggg | ggcatcagaa | 960 |

```
ttgggtgtac agctgtgcat tctctcctga ctcttctatg ctgtgttcag tcggagccag    1020
taaagcagtt ttcctttgga atatggataa atacaccatg atacggaaac tagaaggaca    1080
tcaccatgat gtggtagctt gtgactttc tcctgatgga gcattactgg ctactgcatc    1140
ttatgatact cgagtatata tctgggatcc acataatgga gacattctga tggaatttgg    1200
gcacctgttt cccccaccta ctccaatatt tgctggagga gcaaatgacc ggtgggtacg    1260
atctgtatct tttagccatg atggactgca tgttgcaagc cttgctgatg ataaaatggt    1320
gaggttctgg agaattgatg aggattatcc agtgcaagtt gcacctttga caatggtct    1380 ttgctgtgcc ttctctactg atggcagtgt tttagctgct gggacacatg acggaagtgt    1440 gtattttgg gccactccac ggcaggtccc tagcctgcaa catttatgtc gcatgtcaat    1500
ccgaagagtg atgcccaccc aagaagttca ggagctgccg attccttcca gcttttgga    1560 gtttctctcg tatcgtattt agaagattct gccttcccta gtagtaggga ctgacagaat    1620
acacttaaca caaacctcaa gcttactga cttcaattat ctgttttaa agacgtagaa    1680 gatttattta atttgatatg ttcttgtact gcattttgat cagttgagct tttaaaatat    1740
tatttataga caatagaagt atttctgaac atatcaaata taattttttt taaagatcta    1800
actgtgaaaa catacatacc tgtacatatt tagatataag ctgctatatg ttgaatggac    1860
ccttttgctt ttctgatttt tagttctgac atgtatatat tgcttcagta gagccacaat    1920
atgtatcttt gctgtaaagt gcaaggaaat tttaaattct gggacactga gttagatggt    1980
aaatactgac ttacgaaagt tgaattgggt gaggcgggca aatcacctga ggtcagcagt    2040
ttgagactag cctggcaaac atgatgaaac cctgtctcta ctaaaaatac aaaaaaaaaa    2100
aaaattagcc aggcgtggtg gtgcacacct gtagtcctag ctacttggga ggctgaggca    2160
ggagaattgc ttgaacccag gaggtggagg ttgcagtaag ccaagatcac accactgcac    2220
tccaacctgg acaacagagc gagactccat ctcaaaaaaa aaaaaaatt gtgttgcctc    2280 atacgaaatg tatttggttt tgttggagag tgtcagactg atctggaagt gaaacacagt    2340
ttatgtacag ggaaaaggat tttattatcc ttaggaatgt catccaagac gtagagcttg    2400
aatgtgacgt tatttaaaaa caacaacaaa gaaggcagag ccaggatata actagaaaaa    2460
ggatgtcttt ttttttttt ttactccccc tctaaacact gctgctgcct taattttaga    2520
aagcagctta ctagtttacc cttgtggtat aaagtattat aaattgttgt gaatttgaag    2580
aatccgtcta ctgtattatt gctaaatatt tgtttatac taagggacaa ttatttttaag    2640 accatggatt taaaaaaaaa aaaaaaaact ctgtttctgc aggggatgat attggtgagt    2700
tgccaaagaa gcaatacagc atatctgctt ttgccttctg ttgtttatct tacctgcaga    2760
tattaagaat gtatgcatta tgtaaaatgc tcaattatat attttgttg agttttttaa    2820 ttaaagactt gttaaaaaaa aaaaaaaa                                       2849

<210> SEQ ID NO 125
<211> LENGTH: 2902
<212> TYPE: DNA
<213> ORGANISM: Homo sapiens

<400> SEQUENCE: 125
aactcccaag ccccaccct gggcttggcc tgccttgccc tgccgggaag tgatccccaa       60
ggcagggtga gagttcccca tctgaggcgt ttgttgcagc tacctgcact tctagattca     120
tcttcttgtg agccctgggc ttaggagtca ccatggcaac tgaagagttc atcatccgca     180
```

```
tcccccccata ccactatatc catgtgctgg accagaacag caacgtgtcc cgtgtggagg    240
tcgggccaaa gacctacatc cggcaggaca atgagagggt actgtttgcc cccatgcgca    300
tggtgaccgt ccccccacgt cactactgca cagtggccaa ccctgtgtct cgggatgccc    360
agggcttggt gctgtttgat gtcacagggc aagttcggct tcgccacgct gacctcgaga    420
tccggctggc ccaggacccc ttccccctgt acccagggga ggtgctggaa aaggacatca    480
caccccctgca ggtggttctg cccaacactg ccctccatct aaaggcgctg cttgattttg    540
aggataaaga tggagacaag gtggtggcag agatgagtg gcttttcgag ggacctggca    600
cgtacatccc ccggaaggaa gtggaggtcg tggagatcat tcaggccacc atcatcaggc    660
agaaccaggc tctgcggctc agggcccgca aggagtgctg ggaccgggac ggcaaggaga    720
gggtgacagg ggaagaatgg ctggtcacca cagtaggggc gtacctccca gcggtgtttg    780
aggaggttct ggatttggtg gacgccgtca tccttacgga aaagacagcc ctgcacctcc    840
gggctcggcg gaacttccgg gacttcaggg gagtgtcccg ccgcactggg gaggagtggc    900
tggtaacagt gcaggacaca gaggcccacg tgccagatgt ccacgaggag gtgctggggg    960
ttgtgcccat caccaccctg gccccccaca actactgcgt gattctcgac cctgtcggac   1020
cggatggcaa gaatcagctg gggcagaagc gcgtggtcaa gggagagaag tcttttttcc   1080
tccagccagg agagcagctg gaacaaggca tccaggatgt gtatgtgctg tcggagcagc   1140
aggggctgct gctgagggcc ctgcagcccc tggaggaggg ggaggatgag gagaaggtct   1200
cacaccaggc tggggaccac tggctcatcc gcggacccct ggagtatgtg ccatctgcca   1260
aagtggaggt ggtggaggag cgccaggcca tccctctaga cgagaacgag gcatctatg    1320
tgcaggatgt caagaccgga aaggtgcgcg ctgtgattgg aagcacctac atgctgaccc   1380
aggacgaagt cctgtgggag aaagagctgc ctcccgggt ggaggagctg ctgaacaagg   1440
ggcaggaccc tctggcagac aggggtgaga aggacacagc taagagcctc cagcccttgg   1500
cgccccggaa caagacccgt gtggtcagct accgcgtgcc ccacaacgct gcggtgcagg   1560
tgtacgacta ccgagagaag cgagcccgcg tggtcttcgg gcctgagctg gtgtcgctgg   1620
gtcctgagga gcagttcaca gtgttgtccc tctcagctgg gcggcccaag cgtccccatg   1680
cccgccgtgc gctctgcctg ctgctggggc ctgacttctt cacagacgtc atcaccatcg   1740
aaacggcgga tcatgccagg ctgcaactgc agctggccta caactggcac tttgaggtga   1800
atgaccggaa ggaccccaca gagacggcca agctcttttc agtgccagac tttgtaggtg   1860
atgcctgcaa agccatcgca tcccgggtgc gggggccgt ggcctctgtc actttcgatg   1920
acttccataa gaactcagcc cgcatcattc gcactgctgt ctttggcttt gagacctcgg   1980
aagcgaaggg ccccgatggc atggccctgc ccaggccccg ggaccaggct gtcttccccc   2040
aaaacgggct ggtggtcagc agtgtggacg tgcagtcagt ggagcctgtg gatcagagga   2100
cccgggacgc cctgcaacgc agcgtccagc tggccatcga gatcaccacc aactcccagg   2160
aagcggcggc caagcatgag gctcagagac tggagcagga agcccgcggc cggcttgagc   2220
ggcagaagat cctggaccag tcagaagccg agaaagctcg caaggaactt ttggagctgg   2280
aggctctgag catggccgtg gagagcaccg gggactgccaa ggcggaggcc gagtcccgtg   2340
cggaggcagc ccggattgag ggagaagggt ccgtgctgca ggccaagcta aaagcacagg   2400
ccttggccat tgaaacggag gctgagctcc agagggtcca gaaggtccga gagctggaac   2460
tggtctatgc ccgggcccag ctggagctgg aggtgagcaa ggctcagcag ctggctgagg   2520
tggaggtgaa gaagttcaag cagatgacag aggccatagg ccccagcacc atcagggacc   2580
```

```
ttgctgtggc tgggcctgag atgcaggtaa aactgctcca gtccctgggc ctgaaatcaa    2640
ccctcatcac cgatggctcc actcccatca acctcttcaa cacagccttt gggctgctgg    2700
ggatggggcc cgagggtcag cccctgggca aagggtggc cagtgggccc agccctgggg     2760 agggatatc cccccagtct gctcaggccc ctcaagctcc tggagacaac cacgtggtgc     2820
ctgtactgcg ctaactcctg attaatacaa tggaagtttc tgggcattta caatttcaac    2880
acttaaaaaa aaaaaaaaaa aa                                              2902

<210> SEQ ID NO 126
<211> LENGTH: 2659
<212> TYPE: DNA
<213> ORGANISM: Homo sapiens

<400> SEQUENCE: 126
tctcagtctt tggtggaacc atcactaggc cccaatccct tagtccctct tgcgtcgagg      60
ctgcaaaatg gttccattcg ccaggagacg ctcctgagag aagggcgcgc gcggcacagg     120
ggccttcctt gcacctcgga gcaaagcagc tcggatagcg ccacacgtct gcgcgctgcg    180
tgggaagggc agggctgaca gcacttcctc cccggggcag cgacctggag cccgggtgcg    240
gcagtctgca ccgcgcgtcg ctttcccggc cggagtctcg ccgccttccc gcgccccgca    300
gcgccccgca gagcagtcga gatgggtgag tcaagtgaag acatagacca aatgttcagc    360
actttgctgg agagatgga tcttctgact cagagtttag gagttgacac tctccctcct    420
cctgacccta atccacccag agctgaattt aactacagtg tggggtttaa agatttaaat    480
gagtccttaa atgcactgga agaccaagat ttagatgctc tcatggcaga tctggtagca    540
gacataagtg aggctgagca gaggacaatc caggcacaga aagagtcctt gcagaatcaa    600
catcattcag catctctaca agcatcaatt ttcagtggtg cagcctctct tggttatgga    660
acaaatgttg ctgccactgg tatcagccaa tatgaggatg acttaccacc tccaccagcc    720
gatcctgtgt tagaccttcc actgccacca ccacctcctg aacctctctc tcaggaagag    780
gaagaagccc aagccaaggc tgataaaatt aagctggcgc tggaaaaact gaaggaggcc    840
aaggttaaga agctcgtcgt caaggtgcac atgaatgata cagcacaaa gtcactgatg     900 gtggatgagc ggcagctggc ccgagatgtt ctggacaacc ttttcgagaa aactcattgt    960
gactgcaatg tagactggtg tctttatgaa atctacccgg aactacaaat tgagaggttt    1020
tttgaagacc atgaaaatgt tgttgaagtc ttatcagact ggacaagaga cacagaaaat    1080
aaaatactat ttttggagaa agaggagaaa tatgctgtat ttaaaaaccc ccagaatttc    1140
tacttggata acagaggaaa aaagaaagc aaggaaacta atgagaaaat gaatgctaag    1200
aacaaggaat ccttacttga ggaaagtttc tgtggaacat ctatcattgt accagaactg    1260
gaaggagctc tttatttgaa agaagatgga agaaatcct ggaaaaggcg ctatttctt     1320 ttacgggctt ctggaattta ttatgtaccc aaaggaaaga ctaagacatc tcgagatctg    1380
gcgtgtttta tacagtttga aaatgtcaac atttactatg ggactcagca taaaatgaaa    1440
tataaagcgc ccactgacta ttgctttgtt ttaaagcacc cccaaattca gaaggagtcc    1500
cagtatatca agtatctctg ctgtgatgac acaagaaccc ttaaccagtg ggtcatggga    1560
atacggatag ccaagtatgg gaagactctc tatgataact accagcgggc tgtggcaaag    1620
gctggacttg cctctcggtg gacaaacttg ggacagtca atgcagctgc accagctcag    1680
ccatctacag gacctaaaac aggcaccacc cagcccaatg acagattcc ccaggctaca    1740
```

```
cattctgtca gtgctgttct ccaagaggcc cagagacatg ctgaaacatc gaaggataag    1800
aagccagccc tcgggaacca ccacgacccg gcagtgcccc gggccccgca cgcccccaag    1860
tccagcctgc ccccgccccc tccggtgcgg aggtcctccg acaccagcgg cagtcccgcc    1920
acgcccctca aggccaaggg cacaggcggc gggggcttgc ccgccccacc cgacgacttc    1980
ctgccgccgc cgccaccgcc gccgcccctc gatgaccctg agctcccgcc gccgccccg     2040
gacttcatgg agccgccccc agacttcgtg ccccgccccc cgccgtcgta cgcagggatc    2100
gcgggctcag agctgccccc gccgccgccg ccgccgcccg cgcccgcgcc cgcccccgtc    2160
cccgactccg ccaggccgcc cccgcgcgtg gccaagaggc ctcctgtgcc ccccaagagg    2220
caagagaacc cagggcaccc cggcggagca ggaggcgggg agcaagattt catgtcagac    2280
ctcatgaaag ctttgcaaaa gaagagaggc aacgtgtcct agggacgggc atgatgagtg    2340
ttccagaggg agaagcatcg ctgaccccga gcgcaggttt tgctagcaga ttgccctgac    2400
atcttgttca tttcagataa aatgtgatgg gaaacttctc actgatgtgc tcaagtacag    2460
gcataaccat taacccagta gagttcagaa tatctgccca aatgtacata tcgttcccat    2520
gtattttaac ctaaatggaa tgtatcttcc cttccaagct gcctaaagcg ctgttttagg    2580
ttcatttatt ttattatgtt cagaagcatc aaataaaagt taaacgtttt tccggaaaaa    2640
aaaaaaaaaa aaaaaaaaa                                                 2659

<210> SEQ ID NO 127
<211> LENGTH: 4811
<212> TYPE: DNA
<213> ORGANISM: Homo sapiens

<400> SEQUENCE: 127
gcatagctaa cttgcacatt cactatccaa gctgcaccat cttcggggtc attgtgtgcc      60
aggcatatca actcttttca ataaaaatgg atggaaaggc agatgtaaag tccctcatgg     120
cgaaatataa cacgggggc aacccgacag aggatgtctc agtcaatagc cgacccttca      180
gagtcacagg gccaaactca tcttcaggaa tacaagcaag aaagaactta ttcaacaacc     240
aaggaaatgc cagccctcct gcaggaccca gcaatgtacc taagtttggg tccccaaagc     300
cacctgtggc agtcaaacct tcttctgagg aaaagcctga caaggaaccc aagcccccgt     360
ttctaaagcc cactggagca ggccaaagat tcggaacacc agccagcttg accaccagag     420
accccgaggc gaaagtggga tttctgaaac ctgtaggccc caagcccatc aacttgccca     480
aagaagattc caaacctaca tttccctggc ctcctggaaa caagccatct cttcacagtg     540
taaaccaaga ccatgactta aagccactag gcccgaaatc tgggcctact cctccaacct     600
cagaaaatga acagaagcaa gcgtttccca aattgactgg ggttaaaggg aaatttatgt     660
cagcatcaca agatcttgaa cccaagcccc tcttccccaa acccgccttt ggccagaagc     720
cgccctaag taccgagaac tcccatgaag acgaaagccc catgaagaat gtgtcttcat     780
caaaagggtc cccagctccc ctgggagtca ggtccaaaag cggccctta aaaccagcaa      840
gggaagactc agaaaataaa gaccatgcag gggagatttc aagtttgccc tttcctggag     900
tggttttgaa acctgctgcg agcaggggag gcccaggtct ctccaaaaat ggtgaagaaa     960
aaaaggaaga taggaagata gatgctgcta agaacaccct tccagagcaaa ataaatcagg    1020
agagttggc ctcagggact cctcctgcca ggttccctaa ggcccttct aagctgacag       1080
tgggggggc atgggccaa agtcaggaaa aggaaaggg agacaagaat tcagccaccc        1140
cgaaacagaa gccattgcct cccttgttta ccttgggtcc acctccacca aaacccaaca    1200
```

-continued

```
gaccaccaaa tgttgacctg acgaaattcc acaaaacctc ttctggaaac agtactagca    1260
aaggccagac gtcttactca acaacttccc tgccaccacc tccaccatcc catccggcca    1320
gccaaccacc attgccagca tctcacccat cacaaccacc agtcccaagc ctacctccca    1380
gaaacattaa acctccgttt gacctaaaaa gccctgtcaa tgaagacaat caagatggtg    1440
tcacgcactc tgatggtgct ggaaatctag atgaggaaca agacagtgaa ggagaaacat    1500
atgaagacat agaagcatcc aaagaaagag agaagaaaag ggaaaggaa gaaaagaaga    1560 ggttagagct ggagaaaaag gaacagaaag agaaagaaaa gaaagaacaa gaaataaaga    1620
agaaatttaa actaacaggc cctattcaag tcatccatct tgcaaaagct tgttgtgatg    1680
tcaaaggagg aaagaatgaa ctgagcttca agcaaggaga gcaaattgaa atcatccgca    1740
tcacagacaa cccagaagga aaatggttgg gcagaacagc aagggttca tatggctata    1800 ttaaaacaac tgctgtagag attgactatg attctttgaa actgaaaaaa gactctcttg    1860
gtgccccttc aagacctatt gaagatgacc aagaagtata tgatgatgtt gcagagcagg    1920
atgatattag cagccacagt cagagtggaa gtggagggat attccctcca ccaccagatg    1980
atgacattta tgatgggatt gaagaggaag atgctgatga tggctccaca ctacaggttc    2040
aagagaagag taatacgtgg tcctgggga ttttgaagat gttaaaggga aagatgaca    2100 gaaagaaaag tatacgagag aaacctaaag tctctgactc agacaataat gaaggttcat    2160
ctttccctgc tcctcctaaa caattggaca tgggagatga agtttacgat gatgtggata    2220
cctctgattt ccctgtttca tcagcagaga tgagtcaagg aactaatgtt ggaaaagcta    2280
agacagaaga aaaggacctt aagaagctaa aaaagcagga aaagaagaa aaagacttca    2340 ggaaaaaatt taaatatgat ggtgaaatta gagtcctata ttcaactaaa gttacaactt    2400
ccataacttc taaaaagtgg ggaaccagag atctacaggt aaaacctggt gaatctctag    2460
aagttataca aaccacagat gacacaaaag ttctctgcag aaatgaagaa gggaaatatg    2520
gttatgtcct tcggagttac ctagcggaca atgatggaga gatctatgat gatattgctg    2580
atggctgcat ctatgacaat gactagcact caactttggt cattctgctg tgttcattag    2640
gtgccaatgt gaagtctgga ttttaattgg catgttattg ggtatcaaga aaattaatgc    2700
acaaaaccac ttattatcat ttgttatgaa atcccaatta tctttacaaa gtgtttaaag    2760
tttgaacata gaaaataatc tctctgctta attgttaact cagaagacta cattagtgag    2820
atgtaagaat tattaaatat tccatttccg ctttggctac aattatgaag aagttgaagg    2880
tacttctttt agaccaccag taaataatcc tccttcaaaa aataaaaata aagaaaaag    2940 gaaaatcatt caggaagaaa tgacctgtct aaaaaaacct aaggaagaat aataatataa    3000
gaaaggaaat ttaaaaacat tccacaagaa gaaaaattat tgtttatact tctacttatg    3060
gttatatctt atattctcta ttcaagtgac ctgtctttta aaaaggcagt gctgtcttac    3120
ctcttgctag tgggtaaat gttttcaaaa attatagcag tagtagaagt tttgtataaa    3180
atttgtcctt atttgttaat tgtatataaa tgttaattat ttgatacgaa tgttatgcat    3240
ttagtatgca cattgaagtc taaactgtag aagagtctaa aacaagttct cttttttgcag    3300 attcacatac taatggttta attctgtgct ctgtttaaag tactattata actagagtag    3360
atctgaatga ggataaccct aaaatcatga ggaatggaag aatggacctt gaaactacct    3420
aggcttttat gcatggcacc tctttataat gaagacactt tttaaagttt ttgttttgt    3480 ttcaattacc gctagatttt tttttctctt tttttaaaat ccatttact ggaaagttgg    3540
```

| | |
|---|---|
| ccagcagagg gagtagaaat tattaaaatt ctagtgtttg gattgggccc ttctctaaca | 3600 |
| gtacatactc attcccaaag caatccaaaa acaaaatgtg aaccatttgg gtttcaaatg | 3660 |
| ttaagaacac taaatagcat gatttaaaaa atgaaaaatg ctaacaccca agaaaagaag | 3720 |
| atattaagtg cttttttaaca actcctagag tacaaaatga gtacatcata atgctggctc | 3780 |
| ttctactaat gaaccatcga gtgatattga ataaattatt tatcttctca gtttccttat | 3840 |
| ctgtaaatta caatattaga ctaagtaagt ttttccaact cttcactacc aattaccta | 3900 |
| ggcttttata atgctccgcc tacttcagtc ccatgtttca gaagcttttg tctatttttt | 3960 |
| aaactcattg attaaataat gattaatgca ttctccacat tttaatattg caaaggccca | 4020 |
| ttggagtttc tgaagtggct ccacagaatt gaaataattt caaataactg taaaggaact | 4080 |
| gaaaatcttc acagagatga agtggggttt ccattaggtg ctttgaaatt tgataacaaa | 4140 |
| tcatcaactt ccactggtca atatatagat tttgggtgtc tgaggcccca agattagatg | 4200 |
| ccactaatct ccaaagattc cctccaatta tgaaatattt taatgtctac ttttagagag | 4260 |
| cactagccag tatatgacca tgtgattaat ttcttttcac actagataaa attacctggt | 4320 |
| tcaaaagtgg tttttgttta ttaaatttgg taataaatat atataataca cagacaggat | 4380 |
| agttttatg ctgaagtttt tggccagctt tagtttgagg actccttgat aagcttgcta | 4440 |
| aactttcaga gtgccctgag acacttccag ccatccctcc tcctgccttc attggggcag | 4500 |
| acttgcattg cagtctgaca gtaatttttt ttctgattga gaattatgta aattcagtac | 4560 |
| aatgtcagtt tttaaaagtc aaagttagat caagagaata tttcagagtt ttggtttaca | 4620 |
| catcaagaaa cagacacaca tacctaggaa agatttacac aatagataat catcttaatg | 4680 |
| tgaaagatat ttgaagtatt aattttaata tattaaatat gatttctgtt atagtcttct | 4740 |
| gtatggaatt ttgtcactta agatgagctg caaataaata ataccttcaa tggataaaaa | 4800 |
| aaaaaaaaaa a | 4811 |

<210> SEQ ID NO 128
<211> LENGTH: 1802
<212> TYPE: DNA
<213> ORGANISM: Homo sapiens

<400> SEQUENCE: 128

| | |
|---|---|
| agcctggggt tcccctttcgg gtcgcagact cttgtgtgcc cgccagtagt gcttggtttc | 60 |
| caacagctgc tgctggctct tcctcttgcg gccttttcct gaaacggatt cttctttcgg | 120 |
| ggaacagaaa gcgccagcca tgcagccttg gcacggaaag gccatgcaga gagcttccga | 180 |
| ggccggagcc actgccccca aggcttccgc acggaatgcc aggggcgccc cgatggatcc | 240 |
| caccgagtct ccggctgccc ccgaggccgc cctgcctaag gcgggaaagt tcggccccgc | 300 |
| caggaagtcg ggatcccggc agaaaaagag cgccccggac acccaggaga ggccgcccgt | 360 |
| ccgcgcaact ggggcccgcg ccaaaaaggc ccctcagcgc gcccaggaca cgcagccgtc | 420 |
| tgacgccacc agcgcccctg gggcagaggg gctggagcct cctgcggctc gggagccggc | 480 |
| tctttccagg gctggttctt gccgccagag gggcgcgcgc tgctccacga agccaagacc | 540 |
| tccgcccggg ccctgggacg tgcccagccc cggcctgccg gtctcggccc ccattctcgt | 600 |
| acggagggat gcggcgcctg gggcctcgaa gctccgggcg gttttggaga agttgaagct | 660 |
| cagccgcgat gatatctcca cggcggcggg gatggtgaaa ggggttgtgg accacctgct | 720 |
| gctcagactg aagtgcgact ccgcgttcag aggcgtcggg ctgctgaaca ccggagcta | 780 |
| ctatgagcac gtgaagattt ctgcacctaa tgaatttgat gtcatgttta aactggaagt | 840 |

```
cccccagaatt caactagaag aatattccaa cactcgtgca tattactttg tgaaatttaa    900
aagaaatccg aaagaaaatc ctctgagtca gttttagaa ggtgaaatat tatcagcttc    960
taagatgctg tcaaagttta ggaaaatcat taaggaagaa attaacgaca ttaaagatac   1020
agatgtcatc atgaagagga aaagaggagg gagccctgct gtaacacttc ttattagtga   1080
aaaaatatct gtggatataa ccctggcttt ggaatcaaaa agtagctggc ctgctagcac   1140
ccaagaaggc ctgcgcattc aaaactggct ttcagcaaaa gttaggaagc aactacgact   1200
aaagccattt taccttgtac ccaagcatgc aaaggaagga aatggtttcc aagaagaaac   1260
atggcggcta tccttctctc acatcgaaaa ggaaattttg aacaatcatg aaaatctaa   1320
aacgtgctgt gaaaacaaag aagagaaatg ttgcaggaaa gattgtttaa aactaatgaa   1380
ataccttta gaacagctga agaaaggtt taaagacaaa aaacatctgg ataaaattctc   1440
ttcttatcat gtgaaaactg ccttctttca cgtatgtacc cagaaccctc aagacagtca   1500
gtgggaccgc aaagacctgg gcctctgctt tgataactgc gtgacatact ttcttcagtg   1560
cctcaggaca gaaaaacttg agaattattt tattcctgaa ttcaatctat tctctagcaa   1620
cttaattgac aaaagaagta aggaatttct gacaaagcaa attgaatatg aaagaaacaa   1680
tgagtttcca gttttgatg aattttgaga ttgtattttt agaaagatct aagaactaga   1740
gtcaccctaa atcctggaga atacaagaaa aatttgaaaa ggggccagac gctgtggctc   1800
ac                                                                  1802

<210> SEQ ID NO 129
<211> LENGTH: 1778
<212> TYPE: DNA
<213> ORGANISM: Homo sapiens

<400> SEQUENCE: 129
gtgactgggt ggggctgcct cacttctgcc tgatttggga agcgctgcaa ggacaaccgg     60
ctggggtcct tgcgcgccgc ggctcaggga ggagcaccga ctgcgccgcg taagtgccgc    120
ctgccctgcg tgggtcgtgc cagctcagcg ggacaggtcc tcgcctcggt ccctcggact    180
tagggagcgc ggggcagacc ctgagagatg gttggtgcca tgtggaaggt gattgtttcg    240
ctggtcctgt tgatgcctgg cccctgtgat gggctgtttc gctccctata cagaagtgtt    300
tccatgccac ctaagggaga ctcaggacag ccattatttc tcaccccta cattgaagct    360
gggaagatcc aaaaggaag agaattgagt ttggtcggcc ctttcccagg actgaacatg    420
aagagttatg ccggcttcct caccgtgaat aagacttaca cagcaacct cttcttctgg    480
ttcttcccag ctcagataca gccagaagat gccccagtag ttctctggct acagggtggg    540
ccgggaggtt catccatgtt tggactcttt gtggaacatg ggccttatgt tgtcacaagt    600
aacatgacct tgcgtgacag agacttcccc tggaccacaa cgctctccat gctttacatt    660
gacaatccag tgggcacagg cttcagtttt actgatgata cccacggata tgcagtcaat    720
gaggacgatg tagcacggga tttatacagt gcactaattc agttttccca gatatttcct    780
gaatataaaa ataatgactt ttatgtcact ggggagtctt atgcagggaa atatgtgcca    840
gccattgcac acctcatcca ttccctcaac cctgtgagag aggtgaagat caacctgaac    900
ggaattgcta ttggagatgg atattctgat cccgaatcaa ttataggggg ctatgcagaa    960
ttcctgtacc aaattggctt gttggatgag aagcaaaaaa agtacttcca gaagcagtgc   1020
catgaatgca tagaacacat caggaagcag aactggtttg aggcctttga atactggat   1080
```

| | |
|---|---|
| aaactactag atggcgactt aacaagtgat ccttcttact tccagaatgt tacaggatgt | 1140 |
| agtaattact ataactttt gcggtgcacg gaacctgagg atcagcttta ctatgtgaaa | 1200 |
| tttttgtcac tcccagaggt gagacaagcc atccacgtgg ggaatcagac tttaatgat | 1260 |
| ggaactatag ttgaaaagta cttgcgagaa gatacagtac agtcagttaa gccatggtta | 1320 |
| actgaaatca tgaataatta taaggttctg atctacaatg gccaactgga catcatcgtg | 1380 |
| gcagctgccc tgacagagcg ctccttgatg ggcatggact ggaaaggatc ccaggaatac | 1440 |
| aagaaggcag aaaaaaagt ttggaagatc tttaaatctg acagtgaagt ggctggttaa | 1500 |
| tccggcaagc gggtgacttc catcaggtaa ttattcgagg tggaggacat attttaccct | 1560 |
| atgaccagcc tctgagagct tttgacatga ttaatcgatt catttatgga aaaggatggg | 1620 |
| atccttatgt tggataaact accttcccaa aagagaacat cagaggtttt cattgctgaa | 1680 |
| aagaaaatcg taaaaacaga aaatgtcata ggaataaaaa aattatcttt tcatatctgc | 1740 |
| aagatttttt tcatcaataa aaattatcct tgaaacaa | 1778 |

<210> SEQ ID NO 130
<211> LENGTH: 3074
<212> TYPE: DNA
<213> ORGANISM: Homo sapiens

<400> SEQUENCE: 130

| | |
|---|---|
| acattaaccc ctgactcaca gctggaccgc cccggcccgc agcgccacgt cccgggtggg | 60 |
| gcctgccacg gcaaagcagc agtccggcct cgagcggccc ctcggggggcg gcggggtggg | 120 |
| cgccaacagc agtcaggcct gacaagcggc gacctccaag ggtgaggcct ctgcgggccc | 180 |
| ccgactcacg cgcgtccggg ctctgcaagc gcggtgggga gcaggctgct gtggtcgcgg | 240 |
| ggactgggtt gcggcgcgcc gcgtacggga cggccccaaa ctctcgacgc ccggggcaag | 300 |
| acgcccaccc cctgggcgct ctcgctgggc cagaaaggaa gacagaaaag ccgcgggctg | 360 |
| actgtggtgg cgctcgcctg cagattgaaa agaaatgctg agaaatacat aaagtttcc | 420 |
| tcttctgcct tggatattta atgggtat cgggaagtct aaaataaatt cctgccctct | 480 |
| ttctctctct tggggtaaaa ggcacagtgt ggatacaagt ccaggatatc atgagtcaga | 540 |
| ttccaagaag tctgaagatc tatccttgtg taatgttgct gagcacagca atacaacaga | 600 |
| ggggccaaca ggaaagcagg agggagctca gagcgtggaa gagatgtttg aagaagaagc | 660 |
| tgaagaagag gtgttcctca aatttgtgat attgcatgca aagatgaca cagatgaagc | 720 |
| cctcagagtc cagaatctgc tacaagatga ctttggtatc aaacccggaa taatctttgc | 780 |
| tgagatgcca tgtggcagac agcatttaca gaatttagat gatgctgtaa atgggtctgc | 840 |
| atggacaatc ttattactga ctgaaaaactt tttaagagat acttggtgta atttccagtt | 900 |
| ctatacgtcc ctaatgaact ccgttaacag gcagcataaa tacaactctg ttatacccat | 960 |
| gcggcccctg aacaatcccc ttccccgaga aaggactccc tttgccctcc aaaccatcaa | 1020 |
| tgccttagag gaagaaagtc gtggatttcc tacacaagta gaaagaattt ttcaggagtc | 1080 |
| tgtgtataag acacaacaaa ctatatggaa agagacaaga aatatggtac aaagacaatt | 1140 |
| tattgcctga tgaaacat ataacatgtg gctggctctt gttttgtaaa ccaaatgatt | 1200 |
| aatcttcact tgagaaagca gtttctagga aatgtttaaa taaagagag tcttcacctt | 1260 |
| aaagaaacct atggagcaca agaaagataa atttctgcag gacagcctat aaaattgtgg | 1320 |
| tacttttga tgtttcagta aacttgacat tgtcagagtt tcaaggactt ttctttcaca | 1380 |
| atttcctag ttcatggata tgaaaaagga attctcaatc catattcctt gtattgaacc | 1440 |

```
ttgaacaaaa acttgtatga cagacatttt taaaaatgtg acaacacttt tattctctga    1500
attttgatct caaaggacac agaaaaaaaa tggccccagg agatctgatc acacttcctc    1560
ctgaggcacc tctcatggat gttgcaataa gcattcgggt actatcaccc agaaatatga    1620
attgccagaa tagaacattt agcatgttaa gcgttgatgc atataaaatc agaaatagat    1680
gtgagaatgg tggaactttt taaaagaacc cagtcaaatg tattttctgc tgaaatctgc    1740
atatttggag gcatttccca ccaccgattc acagcccatt tgatagtgtg gtagttaggg    1800
acttcgtgga gtggtgttca gacgtcccct ggggcttaaa tctcttcata ttagtcatca    1860
tttgtaacta tggctttatt tgcagagctt ctaaaaggcg tataactgtg tgagtggcca    1920
gatattcact ttttaaatca aaacctctc ttatggaagc tttaaaagtt ccgtcacac     1980 acaattctct tctcaggaag tatttctcat ttaggtcttc aaagtagcct gactgtgtgc    2040
atgtgtgtgt gtgataggtt atttataaag actttggata gaaggagatg tatttttatta   2100 cctcctattc tagagcccca tgctcctaac aagccagaga ggccccaaac aggattgttt    2160 cttttcctcca cagcccttct gcccatctga gattgaggga gcatcgtcca cttgagatca   2220
gggatggggt ggagaatggg tcatgtcatg taatgagaaa agccctcttc gggatcatga    2280
gacttggttc tagtccaatt tctgccactg aggatgaatg taactgtggg caaactattt    2340
accctccttt atctgtgaaa tgaaagggtt gaattgatgg atctctaaag gcttttgtcc    2400
tctatgagga tgtgaaaaac tagggaccac aaaagggaac aagcaaaaaa gtttggattc    2460
gataaagtga tatgtaatag ttgcagaagg ctttatatat gcttataatg aaaagatatt    2520
ttttgtatat tgacagcata atttatttt aatgctgtca ttacacttaa agtcacagga     2580
aaaaaatata catgcttact caggctttct taaaaataaa tttttataga gatccttgag    2640
taaagacatt ttgcttaatt tctttttct tattccccac ttgtatatcc cctaccagta     2700
ccgggatctg cacacatctt tttgcagtta cctcttcata gccatgaacc aaaacgttct    2760
atgaggagca tgcaagtaag tcaagcctcc tattctgtta gtacttatta gaggaggaga    2820
tggttttcat tgcatagtga cattttctta gccttaacgt tctgatagta gcttactact    2880
cacttctctt tttcagtttt cataataagt attcattttt ttgccataat gcttcctgta    2940
aagccaattt tatatactaa taaaacatga actgcccact cttcatgcct gccaaacttg    3000
gggcaattga tgctaaatgg tatttttaaa ataaatgttt ttattcttta ctcttgaaaa    3060
aaaaaaaaaa aaaa                                                     3074
```

<210> SEQ ID NO 131
<211> LENGTH: 523
<212> TYPE: DNA
<213> ORGANISM: Homo sapiens

<400> SEQUENCE: 131

```
ctcctggttc aaaagcagct aaaccaaaag aagcctccag acagccctga gatcacctaa     60
aaagctgcta ccaagacagc cacgaagatc ctaccaaaat gaagcgcttc ctcttcctcc    120
tactcaccat cagcctcctg gttatggtac agatacaaac tggactctca ggacaaaacg    180
acaccagcca aaccagcagc ccctcagcat ccagcaacat aagcggaggc attttccttt    240
tcttcgtggc caatgccata atccacctct tctgcttcag ttgaggtgac acgtctcagc    300
cttagccctg tgcccctga aacagctgcc accatcactc gcaagagaat ccctccatc     360 tttgggaggg gttgatgcca gacatcacca ggttgtagaa gttgacaggc agtgccatgg    420
```
gggcaacagc caaaataggg gggtaatgat gtaggggcca agcagtgccc agctggggt      480 caataaagtt acccttgtac ttgcaaaaaa aaaaaaaaa aaa                        523

<210> SEQ ID NO 132
<211> LENGTH: 15340
<212> TYPE: DNA
<213> ORGANISM: Homo sapiens

<400> SEQUENCE: 132
gcgccggctg agccagcggc tcttgggagg ctgcgtccgc gcgccggcga ggcgaggcgg      60
ccgggccctg cgcgtcaggc ctgagacctg ggaggaagct ggagaaaaga tgccctctga     120
atctttctgt ttggctgccc aggctcgcct cgactccaaa tggttgaaaa cagatataca     180
gcttgcattc acaagagatg ggctctgtgg tctgtggaat gaaatggtta agatggagg      240 aattgtatac actggaacag aatcaaccca gaacggagag ctccctccta gaaaagatga     300
tagtgtcgaa ccaagtggaa caaagaaaga agatctgaat gacaaagaga aaaaagatga     360
agaagaaact cctgcaccta tatagggc caagtcaatt ctggacagct gggtatgggg      420
caagcaacca gatgtgaatg aactgaagga gtgtctttct gtgctggtta agagcagca      480 ggccctggcc gtccagtcag ccaccaccac cctctcagcc ctgcgactca agcagaggct     540
ggtgatcttg gagcgctatt tcattgcctt gaatagaacc gttttcagg agaatgtcaa      600 agttaagtgg aaaagcagcg gtatttctct gcctcctgtg gacaaaaaaa gttcccggcc     660
tgcgggcaaa ggtgtggagg ggctcgccag agtgggatcc cgagcggcgc tgtcttttgc     720 cttttgcctttc ctgcgcaggg cctggcgatc aggcgaggat gcggacctct gcagtgagct     780
gttgcaggag tcctggacg ccctgcgagc acttcccgag gcctcgctct ttgacgagag     840
caccgtgtcc tctgtgtggc tggaggtggt ggagagagcg accaggttcc tcaggtccgt     900
cgtgacgggg gatgttcacg gaacgccagc caccaaaggg ccaggaagca tcccccctgca    960 ggaccagcac ttggccctgg ccatcctgct ggagctggct gtgcagagag gcacgctgag   1020
ccaaatgttg tctgccatcc tgttgttgct tcagctgtgg acagcgggg cacaggagac   1080 tgacaatgag cgttccgccc agggcaccag cgccccactt ttgcccttgc tgcaaaggtt   1140
ccagagcatc atttgcagga aggatgcacc ccactccgag ggcgacatgc accttttgtc   1200
tggccctctg agcccaatg agagtttcct gaggtacctc acccttccac aagcaacga   1260 gcttgccatt gatctgcgac aaacggcggt tgttgtcatg gcccatttag accgtctggc   1320
tacgccctgt atgcctccgc tgtgtagctc tccgacatct cataagggat cattgcaaga   1380
ggtcataggt tgggggttaa taggatggaa atactatgcc aatgtgattg gtccaatcca   1440
gtgcgaaggc ctggccaacc tgggagtcac acagattgcc tgtgcagaga gcgtttcct   1500 gattctgtca cgcaatggcc gcgtgtacac acaggcctat aatagtgaca cgctggcccc   1560
acagctggtc caaggccttg cctccagaaa cattgtaaaa attgctgccc attctgatgg   1620
tcaccactac ctagccttgg ctgctactgg agaggtgtac tcctgggct gtggggacgg   1680 cggacggctg ggccatgggg acactgtgcc tttggaggag cctaaggtga tctccgcctt   1740
ctctggaaag caggccggga agcacgtggt gcacatcgct tgcgggagca cttacagtgc   1800
ggccatcact gccgagggg agctgtacac ctggggccgc gggaactacg gccggctggg   1860
ccatggctcc agtgaggacg aggccattcc gatgctggta gccgggctta aaggactgaa   1920
ggtcatcgat gtgcgtgtg ggagtgggga tgctcaaacc ctggctgtca ctgagaacgg   1980
gcaagtgtgg tcttggggag atggtgacta tgggaaattg gcagaggtg gtagtgatgg   2040

```
ctgcaaaacc ccaaagctga ttgaaaagct tcaagacttg gatgtggtca aagtccgctg    2100
tggaagtcag ttttccattg ctttgacgaa agatggccaa gtttattcat ggggaaaagg    2160
tgacaaccag agacttggac atggaacaga ggaacatgtt cgttatccaa aactcttaga    2220
aggcttgcaa gggaagaagg tgattgatgt ggctgcaggc tccacccact gcctggctct    2280
gactgaggac agcgaggtcc acagctgggg gagcaacgac cagtgccagc actttgacac    2340
cttgcgcgtg accaagccag aacctgcagc attgccagga ctggacacca aacacatagt    2400
gggaattgcc tgtgggcctg cccagagctt tgcttggtca tcatgttctg agtggtccat    2460
tggcctccgt gtccctttg tggtggacat ctgctcaatg acttttgagc agctggatct    2520
cctgcttcgg caggtgagtg aggggatgga tggttccgcg gactggcccc cgccccagga    2580
gaaagagtgt gtgccgtgg caacgctgaa tcttctacga cttcagttgc atgctgccat    2640
tagtcaccag gttgacccgg aattccttgg tttaggtctg ggcagcatcc tcctgaacag    2700
cctgaagcag acggtggtga ccctggccag cagtgcgggc gtgctgagca ccgtgcagtc    2760
ggccgcccag gccgtgctgc agagtggctg gtccgtgctg ctgcccaccg cggaggagcg    2820
ggcccgggca ctctctgctc tcctgccctg cgcagtttca ggcaatgaag tgaacataag    2880
tccaggtcgt cgattcatga ttgatcttct ggtgggcagc ttgatggctg atggagggtt    2940
ggagtcagcc ttacacgcag ccattactgc agagatccag gatattgaag ccaaaaaaga    3000
agcacagaag gaaaaagaaa ttgatgaaca ggaagcgaat gcctcaacat tcatagaag     3060 caggactcca ctggataaag accttattaa tacggggatc tgtgagtctt ctggcaaaca    3120
gtgtttgcct ctggttcagc tcatacaaca gcttcttaga aacattgctt ctcagactgt    3180
agccagattg aaagatgttg cccgtcggat ttcatcatgt ctggactttg agcaacacag    3240
tcgtgaaaga tctgcttcat ggatttgtt actgcgtttt caacgtttgc ttattagtaa     3300
actttatcca ggagaaagta ttggtcagac ctcagatatt tctagtccag agctaatggg    3360
tgttggttcc ttgctgaaga gtacacagc cctcctgtgc acgcacattg gagatatact     3420
gcctgtggcc gccagcattg cttctaccag ctggcggcac ttcgcggagg tggcttacat    3480
tgtggaaggg gactttactg tgttctcct tccagaacta gtagtttcta tagtgcttct     3540
gctcagtaaa aatgctggtc tcatgcaaga ggctggagct gtacctctgc tgggtggcct    3600 gttgaacat ctggatcggt tcaaccatct ggcaccagga aaggaacggg atgatcatga     3660
agagttagcc tggcctggca taatggagtc attttttaca ggtcagaact gtagaaataa    3720
tgaggaagtg acacttatac gcaaagctga tttggagaac cataataaag atggaggctt    3780
ctggactgtg attgacggga aggtgtatga tataaaggac ttccagacac agtcgttaac    3840
aggaaatagt attcttgctc agtttgcagg ggaagaccca gtggtagctt tggaagctgc    3900
tttgcagttt gaagacaccc gggaatccat gcacgcgttt tgtgttggcc agtatttgga    3960
gcctgaccaa gaaatcgtca ccataccaga tctggggagt ctctcttcac ctctgataga    4020
cacagagagg aatctgggcc tgcttctcgg attacacgct tcgtatttgg caatgagcac    4080
accgctgtct cctgtcgaga ttgaatgtgc caaatggctt cagtcatcca tcttctctgg    4140
aggcctgcag accagccaga tccactacag ctacaacgag gagaaagacg aggaccactg    4200
cagctcccca gggggcacac ctgccagcaa atctcgactc tgctcccaca gacgggccct    4260
gggggaccat tccaggcat ttctgcaagc cattgcagac aacaacattc aggatcacaa     4320
cgtgaaggac ttttgtgtc aaatagaaag gtactgtagg cagtgccatt tgaccacacc     4380
```

```
gatcatgttt ccccccgagc atcccgtgga agaggtcggt cgcttgttgt tatgttgcct    4440
cttaaaacat gaagatttag gtcatgtggc attatcttta gttcatgcag gtgcacttgg    4500
tattgagcaa gtaaagcaca gaacgttgcc taagtcagtg gtggatgttt gtagagttgt    4560
ctaccaagca aaatgttcgc tcattaagac tcatcaagaa cagggccgtt cttacaagga    4620
ggtctgcgct cctgtcatcg aacgtttgag attcctcttt aatgaattga gacctgctgt    4680
ttgtaatgac ctctctataa tgtctaagtt taaattgtta agttctttgc cccgttggag    4740
gaggatagct caaaagataa ttcgagaacg aaggaaaaag agagttccta agaagccaga    4800
atctacggat gatgaagaaa aaattggaaa cgaagagagt gatttagaag aagcttgcat    4860
tttgcctcat agtccaataa atgtggacaa gagacccatt gcaattaaat cacccaagga    4920
caaatggcag ccgctgttga gtactgttac aggtgttcac aaatacaagt ggttgaagca    4980
gaatgtgcag ggtctttatc cgcagtctcc actcctcagt acaattgctg aatttgccct    5040
taaagaagag ccagtggatg tggaaaaaat gagaaagtgc ctactaaaac agttggagag    5100
agcagaggtt cgcctggaag ggatagatac aattttaaaa ctggcgagca agaatttctt    5160
acttccatct gtgcagtatg cgatgttttg tggatggcaa agacttattc ctgagggaat    5220
cgatataggg gaacctctta ctgattgttt aaaggatgtt gatttgatcc cgccttttaa    5280
tcggatgctg ctggaagtca cctttggcaa gctgtacgct tgggctgtac agaacattcg    5340
aaatgttttg atggatgcca gtgccaaatt taaagagctt ggtatccagc cggttcccct    5400
gcaaaccatc accaatgaga acccgtcagg accgagcctg ggaccatcc cgcaagcccg    5460
cttcctcctg gtgatgctca gcatgctcac cctgcagcac ggcgcaaaca acctcgacct    5520
tctgctcaat tccggcatgc tggccctcac gcagacggca ctgcgcctga ttggccccag    5580
ttgtgacaac gttgaggaag atatgaatgc ttctgctcaa ggtgcttctg ccacagtttt    5640
ggaagaaaca aggaaggaaa cggctcctgt gcagctccct gtttcaggac cagaactggc    5700
tgccatgatg aagattggaa caagggtcat gagaggtgtg gactggaaat ggggcgatca    5760
ggatgggcct cctccaggcc taggccgcgt gattggtgag ctgggagagg acggatggat    5820
aagagtccag tgggacacag gcagcaccaa ctcctacagg atggggaaag aaggaaaata    5880
cgacctcaag ctggcagagc tgccggctgc tgcacagccc tcagcagagg attcggacac    5940
agaggatgac tctgaagccg aacaaactga aaggaacatt cacccactg caatgatgtt    6000
taccagcact attaacttac tgcagactct ttgtctgtct gctggagttc atgctgagat    6060
catgcagagc gaagccacca agactttatg cggactgctg cgaatgttag tggaaagcgg    6120
aacgacggac aagacatctt ctccaaacag gctggtgtac agggagcaac accggagctg    6180
gtgcacgctg gggtttgtgc ggagcatcgc tctcacgccg caggtatgcg cgcccctcag    6240
ctcccccgcag tggatcacgc tgctcatgaa ggtcgtggaa gggcacgcac ccttcactgc    6300
cacctcgctg cagaggcaga tcttagctgt gcatttgttg caagcagtcc ttccatcatg    6360
ggacaagacc gaaagggcga gggacatgaa atgcctcgtg gagaagctgt ttgacttctt    6420
gggaagcttg ctcactacct gctcctctga cgtgccatta ctcagagagt ccacgctgag    6480
gcggcgcagg gtgcgcccgc aggcctcgct gactgccacc cacagcagca cactggcgga    6540
ggaggtggtg gcactgctgc gcacgctgca ctccctgact cagtggaatg ggctcatcaa    6600
caagtacatc aactcccagc tccgctccat caccccacagc tttgtgggaa ggccttccga    6660
aggggcccag ttagaggact acttccccga ctccgagaac cctgaagtgg ggggcctcat    6720
ggcagtcctg gctgtgattg gaggcatcga tggtcgcctg cgcctgggcg gtcaagttat    6780
```

```
gcacgatgag tttggagaag gcactgtgac tcgcatcacc ccaaagggca aaatcaccgt   6840
gcagttctct gacatgcgga cgtgtcgcgt ttgcccattg aatcagctga aaccactccc   6900
tgccgtggcc tttaatgtga acaacctgcc cttcacagag cccatgctgt ctgtctgggc   6960
tcagttggtg aacctcgctg gaagcaagtt agaaaagcac aaaataaaga aatcgactaa   7020
acaggccttt gcaggacaag tggacctgga cctgctgcgg tgccagcagt tgaagctata   7080
catcctgaaa gcaggtcggg cgctgctctc ccaccaggat aaactgcggc agatcctgtc   7140
tcagccagct gttcaggaga ctggaactgt tcacacagat gatggagcag tggtatcacc   7200
tgaccttggg gacatgtctc ctgaagggcc gcagcccccc atgatcctct tgcagcagct   7260
gctggcctcg ccacccagc cgtctcctgt gaaggccata tttgataaac aggaacttga   7320
ggctgctgca ctgccgtttt gccagtgctt ggctgtggag tccactcacc cttcgagccc   7380
aggatttgaa gactgcagct ccagtgaggc caccacgcct gtcgccgtgc agcacatccg   7440
ccctgccaga gtgaagaggc gcaagcagtc gcccgttccc gctctgccga tcgtggtgca   7500
gctcatggag atgggatttt ccagaaggaa catcgagttt gccctgaagt ctctcactgg   7560
tgcttccggg aatgcatcca gcttgcctgg tgtggaagcc ttggtcgggt ggctgctgga   7620
ccactccgac atacaggtca cggagctctc agatgcagac acggtgtccg acgagtattc   7680
tgacgaggag gtggtggagg acgtggatga tgccgcctac tccatgtcta ctggtgctgt   7740
tgtgacggag agccagacgt acaaaaaacg agctgatttc ttgagtaatg atgattatgc   7800
tgtatatgtg agagagaata ttcaggtggg aatgatggtt agatgctgcc gagcgtatga   7860
agaagtgtgc gaaggtgatg ttggcaaagt catcaagctg gacagagatg gattgcatga   7920
tctcaatgtg cagtgtgact ggcagcagaa agggggcacc tactgggtta ggtacattca   7980
tgtggaactt ataggctatc ctccaccaag ttcttcttct cacatcaaga ttggtgataa   8040
agtgcgggtc aaagcctctg tcaccacacc aaaatacaaa tggggatctg tgactcatca   8100
gagtgtgggg gttgtgaaag ctttcagtgc caatggaaaa gatatcattg tcgactttcc   8160
ccagcagtct cactgggactg ggttgctatc agaaatggag ttggtaccca gtattcatcc   8220
tggggttacg tgtgatggat gtcagatgtt tcctatcaat ggatccagat tcaaatgcag   8280
aaactgtgat gactttgatt tttgtgaaac gtgtttcaag accaaaaaac acaataccag   8340
gcatacattt ggcagaataa atgaaccagg tcagtctgcg gtattttgtg gccgttctgg   8400
aaaacagctg aagcgttgcc acagcagcca gccaggcatg ctgctggaca gctggtcccg   8460
catggtgaag agcctgaatg tgtcgtcctc cgtgaaccag gcatcccgtc tcattgacgg   8520
cagcgagccc tgctggcagt catcggggtc gcaaggaaag cactggattc gtttggagat   8580
ttccccagat gttcttgttc atagattaaa aatgatcgta gatcctgctg acagtagcta   8640
catgccgtcc ctggttgtag tgtcaggtgg aaattccctg aataacctta ttgaactaaa   8700
gacaatcaat attaacccctt ctgacaccac agtgcccctt ctgaatgact gcacagagta   8760
tcacaggtat attgaaattg ctataaagca gtgcaggagc tcaggaatcg attgtaaaat   8820
ccatggtctc atcctgctgg gacggatccg tgcagaagag gaagatttgg ctgcagttcc   8880
tttcttagct tcgataatg aagaggagga ggatgagaaa ggcaacagcg gaagcctcat   8940
tagaaagaag gctgctgggc tggaatcagc agctacgata agaaccaagg tgtttgtgtg   9000
gggcctgaat gacaaggacc agctgggcgg gctgaaaggc tccaagataa aggttccttc   9060
gttctctgag acactgtcag ctttgaatgt ggtacaggtg gctggtggat ctaaaagttt   9120
```

```
gtttgcagtg actgtggaag ggaaggtgta tgcctgtgga gaagccacga atggccggct    9180
ggggctgggc atttccagcg ggacggtgcc catcccacgg cagatcacag ctctcagcag    9240
ctacgtggtc aagaaggtgg ctgttcactc aggtggccgg cacgcgacgg ctttaactgt    9300
cgatggaaaa gtgttttcgt ggggcgaagg tgacgatgga aaacttggac acttcagcag    9360
aatgaactgt gacaaaccaa ggctgatcga ggccctgaaa accaagcgta tccgggatat    9420
cgcctgtggg agctcgcaca gcgcagccct cacatccagc ggagaactgt acacctgggg    9480
cctcggcgag tacggccggc tgggacatgg ggataatacg acacagctaa agcccaaaat    9540
ggtgaaagtc cttctcggtc acagagtaat ccaggttgca tgtgggagta gagacgcgca    9600
gaccctggct ctgaccgatg aaggtttggt attttcctgg ggtgatggtg actttggaaa    9660
actgggccgg ggcggaagtg aaggctgtaa cattccccag aacattgaga gactaaatgg    9720 acaggggtg tgccagattg agtgtggagc tcagttctcc ctggcgctca ccaagtctgg    9780
agtggtgtgg acatgggaa aggggattta cttcagattg gccacggct ctgacgtgca    9840 cgtgcggaaa ccacaggtgg tggaagggct gagagggaag aagatcgtgc atgtggctgt    9900
cggggccctg cactgcctgg cggtcacgga ctcggggcag gtgtatgctt ggggtgacaa    9960
cgaccacggc cagcagggca atggcacgac cacggttaac aggaagccca cactcgtgca   10020
aggcttagaa ggccagaaga tcacacgcgt ggcttgtggg tcgtcccaca gtgtggcgtg   10080
gacaactgtg gatgtggcca cgccctctgt ccacgagccc gtcctcttcc agactgcaag   10140
agacccttta ggtgcttcct atttaggcgt gccttcagat gctgattctt ctgctgccag   10200
taataaaata agtggtgcaa gtaattctaa gccaaatcgc ccttctcttg ccaagattct   10260
cttgtcattg gatggaaatc tggccaaaca gcaggcctta tcacatattc ttacagcatt   10320
gcaaatcatg tatgccagag atgctgttgt cggggccctg atgccggccg ccatgatcgc   10380
cccggtggag tgcccctcgt tctcctcggc ggccccttcc gacgcatctg cgatggctag   10440
tcccatgaat ggagaagaat gcatgctggc tgttgatatc gaagacagac tgagtccaaa   10500
tccatggcaa gaaaagagag agattgtttc ctctgaggac gcagtgaccc cctctgcagt   10560
gactccgtcg gcccccctcag cctccgctcg gccttttatc ccagtgacgg atgacctggg   10620
agccgcaagc atcattgcag aaaccatgac caaaaccaaa gaggatgttg aaagccaaaa   10680
taaagcagca ggtccggagc tcaggcctt ggatgagttc accagtctgc tgattgcgga   10740
tgacactcgt gtggtggtag acctgctcaa gctgtcagtg tgcagccggg ccggggacag   10800
gggcagggat gtgctctccg cggtgctttc cggcatgggg accgcctacc acaggtggc   10860 agatatgctg ttggagctct gtgtcaccga gttggaggat gtggccacag actcgcagag   10920
cggccgcctc tcttctcagc ctgtggtggt ggagagtagc cacccttaca ccgacgacac   10980
ctccaccagt ggcacagtga agataccagg tgcagaagga ctcagggtag aatttgaccg   11040
gcagtgctcc acagagaggc gccacgaccc tctcacagtc atggacggcg tcaacaggat   11100
cgtctccgtg cggtcaggcc gagagtggtc cgactggtcc agcgagctgc gcatcccagg   11160
ggatgagtta aagtggaagt tcatcagcga tgggtctgtg aatggctggg gctggcgctt   11220
caccgtctat cccatcatgc cagctgctgg ccctaaagaa ctcctctctg accgctgcgt   11280
cctctcctgt ccatccatgg acttggtgac gtgtctgtta gacttccgac tcaaccttgc   11340
ctctaacaga agcatcgtcc ctcgccttgc ggcctcgctg cagcttgtg cacagctgag   11400 tgccctagct gccagtcaca gaatgtgggc ccttcagaga ctgaggaagc tgcttacaac   11460
tgaatttggg cagtcaatta acataaatag gctgcttgga gaaaatgatg gggaaacaag   11520
```

```
agctttgagt tttacaggta gtgctcttgc tgctttggtg aaaggtcttc cagaagcttt    11580
gcaaaggcag tttgaatatg aagatcctat tgtgaggggt ggcaaacagc tgctccacag    11640
cccattcttt aaggtactgg tagctcttgc ttgtgacctg agctggaca ctctgccttg     11700 ctgtgccgag acgcacaagt gggcctggtt ccggaggtac tgcatggcct cccgtgttgc    11760
tgtggcccct gacaaaagaa caccgttgcc ccgtctgttt cttgatgagg tggctaagaa    11820
aattcgtgaa ttaatggcag acagcgaaaa catggatgtt ctgcatgaga gccatgacat    11880 tttaaaaga gagcaagacg aacaacttgt gcagtggatg aacaggcgac cagatgactg     11940
gactctctct gctggtggca gtggaacaat ttatggatgg ggacataatc acaggggcca    12000 gctcggggc attgaaggcg caaaagtcaa agttcccact ccctgtgaag cccttgcaac     12060
tctcagaccc gtgcagttaa tcggagggga acagaccctc tttgctgtga cggctgatgg    12120
gaagctgtat gccactgggt atggtgcagg tggcagacta ggcattggag gacagagtc     12180 ggtgtccacc ccaacattgc ttgaatccat tcagcatgtg tttattaaga agtagctgt     12240 gaactctgga ggaaagcact gccttgccct gtcttcagaa ggagaagttt actcttgggg    12300
tgaggcagaa gatgggaagt tggggcatgg caacagaagt ccgtgtgacc gccctcgtgt    12360
catcgagtct ctgagaggaa ttgaagtggt cgatgttgct gctggcggag cccacagcgc    12420
ctgtgtcaca gcagccgggg acctctacac atggggcaaa ggccgctacg gccggctggg    12480
gcacagcgac agtgaggacc agctgaagcc gaagctggtg gaggcgctgc agggccaccg    12540
tgtggttgac atcgcctgtg gcagtggaga tgcccagacc ctctgcctca cagatgacga    12600
cactgtctgg tcctggggg acggggacta cggcaagctc ggccggggag gcagcgatgg    12660
ctgtaaagtg cctatgaaga ttgattctct tactggtctt ggagtagtta aagtggaatg    12720
cggatcccag ttttctgttg cccttaccaa atctggagct gtttatacct ggggcaaagg    12780
cgattatcac aggttgggcc atggatcaga tgaccatgtt cgaaggcctc ggcaggtcca    12840
agggttgcag gggaagaaag tcatcgccat cgccactggc tccctgcact gtgtgtgctg    12900
cacagaggat ggtgaggttt atacatgggg cgacaatgat gagggacaac tgggagacgg    12960
aaccaccaat gccatccaga ggcctcggtt ggtagctgcc cttcagggta agaaggtcaa    13020
ccgtgtggcc tgtggctcag cacatacccct cgcctggtcg accagcaagc ccgccagtgc    13080
tggcaaactc cctgcacagg tccccatgga gtacaatcac ctgcaggaga tccccatcat    13140
tgcgctgagg aaccgtctgc tgctgctgca ccacctctcc gagctcttct gcccctgcat    13200
ccccatgttc gacctggaag gctcgctcga cgaaactgga ctcgggcctt ctgttgggtt    13260
cgacactctc cgaggaattc tgatatccca gggaaggag gcggctttcc ggaaagtagt     13320
acaagcaact atggtacgcg atcgtcagca tggccccgtc gtggagctga accgcatcca    13380
ggtcaaacga tcaaggagca aaggcgggct ggccggcccc gacggcacca agtctgtctt    13440
tgggcagatg tgtgctaaga tgagctcgtt tggtcccgac agcctcctcc ttcctcaccg    13500
tgtctggaaa gtcaagtttg tgggtgaatc tgtgatgac tgtgggggcg gctacagcga    13560
gtccatagct gagatctgtg aggagctgca gaacggactc acgcccctgc tgatcgtgac    13620
acccaacggg agggatgagt ctggggccaa ccgagactgc tacctgctca gcccggccgc    13680
cagagcaccc gtgcacagca gcatgttccg cttcctgggt gtgttgctgg gcattgccat    13740
ccgaaccggg agtcccctga gcctcaacct tgccgagcct gtctgaagc agctggctgg     13800 gatgagcctc accatcgcgg acctcagtga ggttgataag gatttattc ctggactcat     13860
```

```
gtacatccga gacaatgaag ccacctcaga ggagtttgaa gccatgagcc tgcccttcac    13920
agtgccaagt gccagtggcc aggacattca gttgagctcc aagcacacac acatcacect    13980 ggacaaccgc gcggagtacg tgcggctggc gataaactat agactccatg aatttgatga    14040
gcaggtggct gctgttcggg aaggaatggc ccgcgttgtg cctgttcccc tcctctctct    14100
gttcaccggc tacgaactgg agacgatggt gtgtggcagc cctgacatcc cgctgcacct    14160
tctcaagtcg gtggccacct ataaaggcat cgagccttcc gcatcgctga tccagtggtt    14220
ctgggaggtg atggagtcct tctccaacac agagcgctct cttttccttc gcttcgtctg    14280
gggccggacg aggctgccca ggaccatcgc cgacttccgg ggccgagact tcgtcatcca    14340
ggtgttggat aaatacaacc ctccagacca cttcctccct gagtcctaca cctgtttctt    14400
cttgctgaag ctgcccaggt attcctgcaa gcaggtgctg gaggagaagc tcaagtacgc    14460
catccacttc tgcaagtcca tagacacaga tgactacgct cgcatcgcac ttacaggaga    14520
gccagccgcc gacgacagca gcgacgattc agataacgag gatgtcgact cctttgcttc    14580
ggactctaca caagattatt taacaggaca ctaagatggg gaaacgtcct cgtgagatga    14640
gagcctgagc caggcagcag agcgctcgct gctgtgtaga ctgtaggctg cctggtgtgt    14700
ctgatgagaa gcgtccgtcc tcgagccagg cgggaggagg gagtggagag actgactggc    14760
cgtgatggga atgacagtga aaggtccgc ctgtgcgcgt ggaacactgt ggacgctcga    14820
cttccaaggg tcttctcacc cgtaatgctg cattacatgt aggactgtgt ttactaaagt    14880
gtgtaaatgt ttatataaat accaaattgc agcatcccca aaatgaataa agccttttta    14940
cttgtgggtg caatcgattt tttttctttc tcctttcttt caagtgtcgt gagtcgtctt    15000
gattgtatat tggaaataac tgtgtaacaa atcgtattat aaatatttca attaatttta    15060
ctctgaattt gtttattaaa agacttttga acatgaaatg attagtatta cttgaatgca    15120
tccagaggat atttaaacca aaatgaaaaa ccagaaggcc atttggtgtc cccctcca    15180 ggtgtcccct tgtagcatat gcattatgtc atctgaattg aggcctttct gtgaacagca    15240
tcataacttc tatcatggaa agtgtactat atataatgtt tgtgtcatgt atatgcctaa    15300 atttttaatta tctataaata aaacatctga cataaaagtg                          15340
```

```
<210> SEQ ID NO 133
<211> LENGTH: 2208
<212> TYPE: DNA
<213> ORGANISM: Homo sapiens

<400> SEQUENCE: 133
ttcagccctc aaatattgat tttgaacatt attttgcaaa gagtactaag tggttggtta       60
gttgagatag aggaatatgc agcttttgac tatctttcct ttcccgtcag taccagcttt      120
catgatacaa tttcctctta tcactttggt caagaggtgg ggcagaaaat tttgagttac      180
agtatcattc gaagagaatt tatttctgcc tttcatgtta tagcccctaa gggatccagg      240
acccgaaagg ccagcttctc cctcattttg aaatcagttt tctccacctg caccactgca      300
tagcacagat acagaaacca tcctatttca ggatttgaat gcaaaactta ccttcttact      360
ctaaagatga atgatcaggg agagatttat tcaaccctga dattttgca gtctccttca      420 gagtcacaga atagattaag gcctgatgat actcaaaggc ctgggaaaac tgatgacaaa      480
gaattttcag tgccctggca cctcattgca gtgactcttg ggatcctctg tttacttctt      540
ctgatgatag tcacagtgtt ggtgacaaat atctttcagt gtattcaaga aaaacatcaa      600
cggcaggaaa ttctaagaaa ctgtagtgaa aagtacatca tgcaaaatga caactactta      660
```

```
aaagagcaga ttttgacaaa taagacttta aaatttgacg ttctcaaaaa tagcttttcag      720 cagaaaaagg aactggattc acgccttata caaaagaaca gatgtcatag agaaaatgag      780
atcgttttta aagttttgca aaatacaggc aaattctctg aagaccacgg gtcctgttgt      840
ggagtaaact gttattattt taccatgcag aagaaagact ggaagggatg taaacagact      900
tgtcaacatt gtagatcatc ccttttgaag atagatgaca agatgaact cgtatttac        960 attcactttt attctcttgg actctgtttc tcaatgttgg acctaagata ttgaagacag     1020
gctggagccc agagccttca ttcaatctca gatttatgaa ataattact ggattggatt      1080 atcatatgat gaaagggaaa gtaagtggaa atggattgat aatggcacat ctcctggaat     1140
taattctaca ataatgcgtt tttcttctgg gagaggagaa tgtgcatttt tgacctcaac     1200
aagaatggca actattgatt gcattcaaac gtacaattgt atctgtggga agagaataga     1260 ctctatttc tctgattcgg tgtgcgccaa aagaaaagg tgaaaatgga atgttttctt      1320
tttttgtttc ccataataat ttctgattat aaatcattgc ttttaactgt gggacttagt     1380
taattcttca aagataaag atgaacagga agaaaaagaa aattattttg gactatgact      1440
ttaaagatca gatgccatct ttcttcctgg agaagaggag attttctctt ttgagagtgg     1500
ttgttccttc ctttaatgtc cctgaggaat tattcattct ttctaattct cagaactacc     1560
tatacaacca gttagagaac tctgatatta tatcctgggt cttttttctt atcaatagga     1620
taaatcattc cagcatcttc tggttttgaa agcagttgtg aactagaatg tagttatttt     1680
tttcttccca tctagaagtt acctcatctt taaaacatt tgttttgcta caaaatataa      1740
cttcaaactt actgaaagtt gcaagcatag tacaaggaac ttctatataa cctttactca     1800
tacttactag ttgtttatat tttgctctgc tttatatttc tctctttcta tcttccactt     1860 aataataat tgaggacttc atgtcccttt gtctaaatat tttccaagat caagggcttt      1920
gttttatata atcacagtgc aattatcaaa ctcaggaaat ttagcattag tacagtacta     1980
tgatctaatc tgtaatccat gttcaaattt tgtcaattgt cccaataatg ccatttatgt     2040
gtatttctta aaaatccatg ttcaggataa ttcaatgcat ttgattgtaa tgtctcttta     2100
gtcttcttta atctgaaaca gttctttagg cttttttcttg accttgacat tttaaaaatt    2160
aactttattg agttatactt ttcatgcaat aaaatgcact cactttaa                  2208

<210> SEQ ID NO 134
<211> LENGTH: 741
<212> TYPE: DNA
<213> ORGANISM: Homo sapiens

<400> SEQUENCE: 134
actgcctgca gaaccccagc ccgactttcc ctgcgcactg ggatcctgct ggaacctcag       60
ctgcaacatg agctccgcag ccaggtcccg cctcacccgc gccacccgcc aggagatgct      120
gttcttggcg ttgctgctcc tgccagttgt ggtcgccttc gccagagctg aagctgaaga      180
agatggggac ctgcagtgcc tgtgtgtgaa gaccaccctcc caggtccgtc ccaggcacat      240
caccagcctg gaggtgatca aggccggacc ccactgcccc actgcccaac tcatagccac      300
gctgaagaat gggaggaaaa tttgcttgga tctgcaagcc ctgctgtaca agaaaatcat      360
taaggaacat ttggagagtt agctactagc tgcctaagtg tgcactttca atctaactgt      420
gaaagaatct tctgatgttt gtattatcct tcttatatta tattaacaaa ataaatcaag      480
ttgtggtata gtcaatctat ttcttaataa tactgcaaaa ataatgctga cacatcacaa      540
```

```
tttcatattt taaaatttcc agaattttaa gcaaaaagca ttatgaagga aggcttggtt      600
taataaagac tgattttgtt cagtgttata tgttagctga tacatatttg ttcatttatg      660
tgattgcagt actttatagc tacatattta ccttgaatgt tacaattagc ttgccaataa      720
atattagtag ctcttaagca t                                                741

<210> SEQ ID NO 135
<211> LENGTH: 282
<212> TYPE: DNA
<213> ORGANISM: Homo sapiens

<400> SEQUENCE: 135
atgaagctgt ttctggttct cattattctg ctgtttgagg tactcacaga cggggcaaga       60
ctcaaaaaat gcttcaataa agtaacaggc tattgcagga agaaatgcaa ggtaggagaa      120
agatatgaaa taggatgtct aagtgggaaa ttatgttgtg ctaatgatga agaagagaaa      180
aaacatgtgt catttaagaa gccacatcaa cattctggtg agaagctgag tgtgctgcag      240
gattacatca tcttacccac catcaccatt ttcacagtct aa                         282

<210> SEQ ID NO 136
<211> LENGTH: 1718
<212> TYPE: DNA
<213> ORGANISM: Homo sapiens

<400> SEQUENCE: 136
gagggtgcat aagttctcta gtagggtgat gatataaaaa gccaccggag cactccataa       60
ggcacaaact ttcagagaca gcagcagcaca caagcttcta ggacaagagc caggaagaaa      120
ccaccggaag gaaccatctc actgtgtgta acatgactt ccaagctggc cgtggctctc       180
ttggcagcct cctgatttc tgcagctctg tgtgaaggtg cagttttgcc aaggagtgct      240
aaagaactta gatgtcagtg cataaagaca tactccaaac ctttccaccc caaatttatc      300
aaagaactga gagtgattga gagtggacca cactgcgcca acacagaaat tattgtaaag      360
ctttctgatg gaagagagct ctgtctggac cccaaggaaa actgggtgca gagggttgtg      420
gagaagtttt tgaagagggc tgagaattca taaaaaaatt cattctctgt ggtatccaag      480
aatcagtgaa gatgccagtg aaacttcaag caaatctact tcaacacttc atgtattgtg      540
tgggtctgtt gtagggttgc cagatgcaat acaagattcc tggttaaatt tgaatttcag      600
taaacaatga atagtttttc attgtaccat gaaatatcca gaacatactt atatgtaaag      660
tattatttat ttgaatctac aaaaaacaac aaataatttt taaatataag gattttccta      720
gatattgcac gggagaatat acaaatagca aaattgaggc caagggccaa gagaatatcc      780
gaactttaat ttcaggaatt gaatgggttt gctagaatgt gatatttgaa gcatcacata      840
aaaatgatgg gacaataaat tttgccataa agtcaaattt agctggaaat cctggatttt      900
tttctgttaa atctggcaac cctagtctgc tagccaggat ccacaagtcc ttgttccact      960
gtgccttggt ttctccttta tttctaagtg gaaaaagtat tagccaccat cttacctcac     1020
agtgatgttg tgaggacatg tggaagcact ttaagttttt tcatcataac ataaattatt     1080
ttcaagtgta acttattaac ctatttatta tttatgtatt tatttaagca tcaaatattt     1140
gtgcaagaat ttggaaaaat agaagatgaa tcattgattg aatagttata aagatgttat     1200
agtaaattta ttttatttta gatattaaat gatgttttat tagataaatt tcaatcaggg     1260 ttttagatt aaacaaacaa acaattgggt acccagttaa attttcattt cagataaaca     1320
acaaataatt ttttagtata agtacattat tgtttatctg aaattttaat tgaactaaca     1380
```

| | | | | |
|---|---|---|---|---|
| atcctagttt | gatactccca | gtcttgtcat | tgccagctgt | gttggtagtg ctgtgttgaa | 1440 |
| ttacggaata | atgagttaga | actattaaaa | cagccaaaac | tccacagtca atattagtaa | 1500 |
| tttcttgctg | gttgaaactt | gtttattatg | tacaaataga | ttcttataat attatttaaa | 1560 |
| tgactgcatt | tttaaataca | aggctttata | tttttaactt | taagatgttt ttatgtgctc | 1620 |
| tccaaatttt | ttttactgtt | tctgattgta | tggaaatata | aaagtaaata tgaaacattt | 1680 |
| aaatatataat | ttgttgtcaa | agtaaaaaaa | aaaaaaaa | | 1718 |

<210> SEQ ID NO 137
<211> LENGTH: 1485
<212> TYPE: DNA
<213> ORGANISM: Homo sapiens

<400> SEQUENCE: 137

| | | | | |
|---|---|---|---|---|
| tcagccaatt | agagctccag | ttgtcactcc | tacccacact | gggcctgggg gtgaagggaa | 60 |
| gtgtttatta | ggggtacatg | tgaagccgtc | cagaagtgtc | agagtctttg tagctttgaa | 120 |
| agtcacctag | gttatttggg | catgctctcc | tgagtcctct | gctagttaag ctctctgaaa | 180 |
| agaaggtggc | agacccggtt | tgctgatcgc | cccaggggatc | aggaggctga tcccaaagtt | 240 |
| gtcagatgga | gagtaaatac | aaggagatac | tcttgctaac | aggcctggat aacatcactg | 300 |
| atgaggaact | ggataggttt | aagttctttc | tttcagacga | gtttaatatt gccacaggca | 360 |
| aactacatac | tgcaaacaga | atacaagtag | ctaccttgat | gattcaaaat gctggggcgg | 420 |
| tgtctgcagt | gatgaagacc | attcgtattt | ttcagaagtt | gaattatatg cttttggcaa | 480 |
| aacgtcttca | ggaggagaag | gagaaagttg | ataagcaata | caaatcggta acaaaaccaa | 540 |
| agccactaag | tcaagctgaa | atgagtcctg | ctgcatctgc | agccatcaga atgatgtcg | 600 |
| caaagcaacg | tgctgcacca | aaagtctctc | ctcatgttaa | gcctgaacag aaacagatgg | 660 |
| tggcccagca | ggaatctatc | agagaagggt | ttcagaagcg | ctgtttgcca gttatggtac | 720 |
| tgaaagcaaa | gaagcccttc | acgtttgaga | cccaagaagg | caagcaggag atgtttcatg | 780 |
| ctacagtggc | tacagaaaag | gaattcttct | ttgtaaaagt | ttttaataca ctgctgaaag | 840 |
| ataaattcat | tccaaagaga | ataattataa | tagcaagata | ttatcggcac agtggtttct | 900 |
| tagaggtaaa | tagcgcctca | cgtgtgttag | atgctgaatc | tgaccaaaag gttaatgtcc | 960 |
| cgctgaacat | tatcagaaaa | gctggtgaaa | ccccgaagat | caacacgctt caaactcagc | 1020 |
| cccttggaac | aattgtgaat | ggtttgtttg | tagtccagaa | ggtaacagaa aagaagaaaa | 1080 |
| acatattatt | tgacctaagt | gacaacactg | ggaaaatgga | agtactgggg gttagaaacg | 1140 |
| aggacacaat | gaaatgtaag | gaaggagata | aggttcgact | tacattcttc acactgtcaa | 1200 |
| aaaatggaga | aaaactacag | ctgacatctg | gagttcatag | caccataaag gttattaagg | 1260 |
| ccaaaaaaaa | aacatagaga | agtaaaaagg | accaattcaa | gccaactggt ctaagcagca | 1320 |
| tttaattgaa | gaatatgtga | tacagcctct | tcaatcagat | tgtaagttac ctgaaagctg | 1380 |
| cagttcacag | gctcctctct | ccaccaaatt | aggatagaat | aattgctgga taaacaaatt | 1440 |
| cagaatatca | acagatgatc | acaataaaca | tctgtttctc | attcc | 1485 |

<210> SEQ ID NO 138
<211> LENGTH: 3691
<212> TYPE: DNA
<213> ORGANISM: Homo sapiens

<400> SEQUENCE: 138

-continued

```
ggcgcaacgc tgagcagctg cgcgtcccg cgcggcccca gttctgcgca gcttcccgag      60
gctccgcacc agccgcgctt ctgtccgcct gcagggcatt ccagaaagat gaggatattt    120 gctgtctttta tattcatgac ctactggcat tgctgaacg catttactgt cacggttccc    180
aaggacctat atgtggtaga gtatggtagc aatatgacaa ttgaatgcaa attcccagta    240
gaaaaacaat tagacctggc tgcactaatt gtctattggg aaatggagga taagaacatt    300
attcaatttg tgcatggaga ggaagacctg aaggttcagc atagtagcta cagacagagg    360
gcccggctgt tgaaggacca gctctcccctg ggaaatgctg cacttcagat cacagatgtg    420
aaattgcagg atgcaggggt gtaccgctgc atgatcagct atggtggtgc cgactacaag    480
cgaattactg tgaaagtcaa tgccccatac aacaaaatca ccaaagaat tttggttgtg    540 gatccagtca cctctgaaca tgaactgaca tgtcaggctg agggctaccc caaggccgaa    600
gtcatctgga caagcagtga ccatcaagtc ctgagtggta agaccaccac caccaattcc    660
aagagagagg agaagcttt caatgtgacc agcacactga gaatcaacac aacaactaat    720
gagattttct actgcacttt taggagatta gatcctgagg aaaaccatac agctgaattg    780
gtcatcccag aactacctct ggcacatcct ccaaatgaaa ggactcactt ggtaattctg    840
ggagccatct tattatgcct tggtgtagca ctgacattca tcttccgttt aagaaaaggg    900
agaatgatgg atgtgaaaaa atgtggcatc caagatacaa actcaaagaa gcaaagtgat    960
acacatttgg aggagacgta atccagcatt ggaacttctg atcttcaagc agggattctc   1020
aacctgtggt ttaggggttc atcgggctg agcgtgacaa gaggaaggaa tgggcccgtg   1080
ggatgcaggc aatgtgggac ttaaaaggcc caagcactga aatgaacc tggcgaaagc   1140 agaggaggag aatgaagaaa gatggagtca acagggagc ctggagggag accttgatac   1200
tttcaaatgc ctgagggct catcgacgcc tgtgacaggg agaaaggata cttctgaaca   1260
aggagcctcc aagcaaatca tccattgctc atcctaggaa gacgggttga gaatccctaa   1320
tttgagggtc agttcctgca gaagtgccct ttgcctccac tcaatgcctc aatttgtttt   1380
ctgcatgact gagagtctca gtgttggaac gggacagtat ttatgtatga gttttcctta   1440
tttattttga gtctgtgagg tcttcttgtc atgtgagtgt ggttgtgaat gatttctttt   1500
gaagatatat tgtagtagat gttacaattt tgtcgccaaa ctaaacttgc tgcttaatga   1560
tttgctcaca tctagtaaaa catggagtat ttgtaaggtg cttggtctcc tctataacta   1620
caagtataca ttggaagcat aaagatcaaa ccgttggttg cataggatgt cacctttatt   1680
taacccatta atactctggt tgacctaatc ttattctcag acctcaagtg tctgtgcagt   1740
atctgttcca tttaaatatc agctttacaa ttatgtggta gcctacacac ataatctcat   1800
ttcatcgctg taaccaccct gttgtgataa ccactattat tttacccatc gtacagctga   1860
ggaagcaaac agattaagta acttgcccaa accagtaaat agcagacctc agactgccac   1920
ccactgtcct tttataatac aatttacagc tatatttac tttaagcaat tcttttattc   1980
aaaaaccatt tattaagtgc ccttgcaata tcaatcgctg tgccaggcat tgaatctaca   2040
gatgtgagca agacaaagta cctgtcctca aggagctcat agtataatga ggagattaac   2100
aagaaaatgt attattacaa tttagtccag tgtcatagca taaggatgat gcgagggaa   2160 aacccgagca gtgttgccaa gaggaggaaa taggccaatg tggtctggga cggttggata   2220
tacttaaaca tcttaataat cagagtaatt ttcatttaca aagagaggtc ggtacttaaa   2280
ataaccctga aaaataacac tggaattcct tttctagcat tatatttatt cctgatttgc   2340
ctttgccata taatctaatg cttgtttata tagtgtctgg tattgtttaa cagttctgtc   2400
```

```
ttttctattt aaatgccact aaattttaaa ttcataccttt tccatgattc aaaattcaaa    2460
agatcccatg ggagatggtt ggaaaatctc cacttcatcc tccaagccat tcaagtttcc    2520
tttccagaag caactgctac tgcctttcat tcatatgttc ttctaaagat agtctacatt    2580
tggaaatgta tgttaaaagc acgtattttt aaaattttttt tcctaaatag taacacattg    2640
tatgtctgct gtgtactttg ctattttat ttattttagt gtttcttata tagcagatgg    2700
aatgaatttg aagttcccag ggctgaggat ccatgccttc tttgtttcta agttatcttt    2760
cccatagctt ttcattatct ttcatatgat ccagtatatg ttaaatatgt cctacatata    2820
catttagaca accaccattt gttaagtatt tgctctagga cagagtttgg atttgtttat    2880
gtttgctcaa aaggagaccc atgggctctc caggtgcac tgagtcaatc tagtcctaaa     2940
aagcaatctt attattaact ctgtatgaca gaatcatgtc tggaacttttt gttttctgct   3000 ttctgtcaag tataaacttc actttgatgc tgtacttgca aaatcacatt ttctttctgg    3060
aaattccggc agtgtacctt gactgctagc taccctgtgc cagaaaagcc tcattcgttg    3120
tgcttgaacc cttgaatgcc accagctgtc atcactacac agccctccta agaggcttcc    3180
tggaggtttc gagattcaga tgccctggga gatcccagag tttcctttcc ctcttggcca    3240
tattctggtg tcaatgacaa ggagtacctt ggctttgcca catgtcaagg ctgaagaaac    3300
agtgtctcca acagagctcc ttgtgttatc tgtttgtaca tgtgcatttg tacagtaatt    3360
ggtgtgacag tgttctttgt gtgaattaca ggcaagaatt gtggctgagc aaggcacata    3420
gtctactcag tctattccta agtcctaact cctccttgtg gtgttggatt tgtaaggcac    3480 tttatcccttt ttgtctcatg tttcatcgta aatggcatag gcagagatga tacctaattc   3540
tgcatttgat tgtcactttt tgtacctgca ttaattttaat aaaatattct tatttatttt   3600
gttacttggt acaccagcat gtccattttc ttgtttattt tgtgtttaat aaaatgttca    3660
gtttaacatc ccagtggaga aagttaaaaa a                                    3691
```

<210> SEQ ID NO 139  
<211> LENGTH: 4481  
<212> TYPE: DNA  
<213> ORGANISM: Homo sapiens

<400> SEQUENCE: 139

```
ttcctgtcta cgtttcattt cctgggggct tgccaagtga taaacagacc caggcgtgtg      60
tggtagagtt cgggtttttt agcacgaagt gggtggctgg agtttgcttg aaaacatcaa     120
ttgactttgt gatcattaca gaaatgctgg tgtaaggtgt tcagaagaca atggagaaaa     180
aatggaaata ctgtgctgtc tattacatca tccagataca ttttgtcaag ggagtttggg     240
aaaaaacagt caacacagaa gaaaatgttt atgctcacact tggctctgat gtcaacctga     300
cctgccaaac acagacagta ggcttcttcg tgcagatgca atggtccaag gtcaccaata     360
agatagacct gattgctgtc tatcatcccc aatacggctt ctactgtgcc tatgggagac     420
cctgtgagtc acttgtgact ttcacagaaa ctcctgagaa tgggtcaaaa tggactctgc     480
acttaaggaa tatgtcttgt tcagtcagtg gaaggtacga gtgtatgctt gttctgtatc     540
cagagggcat tcagactaaa atctacaacc ttctcattca gacacacgtt acagcagatg     600
aatggaacag caaccatacg atagaaatag agataaatca gactctggaa ataccatgct     660
ttcaaaatag ctcctcaaaa atttcatctg agttcaccta tgcatggtcg gtggaaaaca    720
gcagcacgga ttcttgggtc cttctttcta agggtataaa ggaggataat ggaactcagg    780
```

```
aaacacttat ctcccaaaat cacctcatca gcaattccac attacttaaa gatagagtca   840
agcttggtac agactacaga ctccacctct ctccagtcca aatcttcgat gatgggcgga   900
agttctcttg ccacattaga gtcggtccta acaaaatctt gaggagctcc accacagtca   960 aggttttgc taaaccagaa atccctgtga ttgtggaaaa taactccacg gatgtcttgg   1020
tagagagaag atttacctgc ttactaaaga atgtatttcc caaagcaaat atcacatggt   1080
ttatagatgg aagttttctt catgatgaaa aagaaggaat atatattact aatgaagaga   1140
gaaaaggcaa agatggattt ttggaactga agtctgtttt aacaagggta catagtaata   1200
aaccagccca atcagacaac ttgaccattt ggtgtatggc tctgtctcca gtcccaggaa   1260
ataaagtgtg gaacatctca tcagaaaaga tcactttct cttaggttct gaaatttcct   1320
caacagaccc tccactgagt gttacagaat ctacccttga cacccaacct tctccagcca   1380
gcagtgtatc tcctgcaaga tatccagcta catcttcagt gacccttgta gatgtgagtg   1440
ccttgaggcc aaacaccact cctcaaccca gcaattccag tatgactacc cgaggcttca   1500
actatccctg gacctccagt gggacagata ccaaaaaatc agtttcacgg ataccatagtg  1560 aaacatacag ttcatccccg tcaggtgcag gctcaacact tcatgacaat gtctttacca   1620
gcacagccag agcattttca gaagtcccca caactgccaa tggatctacg aaaactaatc   1680
acgtccatat cactggtatt gtggtcaata agcccaaaga tggaatgtcc tggccagtga   1740
ttgtagcagc tttactcttt tgctgcatga tattgtttgg tcttggagtg agaaaatggt   1800
gtcagtacca aaaagaaata atggaaagac ctccacccttt caagccacca ccacctccca   1860
tcaagtacac ttgcattcaa gagcccaacg aaagtgatct gccttatcat gagatggaga   1920
ccctctagtc tcgtgagact ttgccccatg gcagaactct gctggaatcc tattgagaag   1980
gtagacattg tgctttatta atatagtcgc tcttcagcca tgcctttgct gcagctgaaa   2040
tggaagtcag aagtgagtga cctgttttcc cagcaactca ccctcttcca tctccaaacg   2100
cctgaagctt aaccaagagt gagaggatat gtcatgttca cactcaatgc aattcgtagt   2160
ggttttcttg cttatgtaag aagtacatat tagtctgcca tctttaaaaa aaaatacagt   2220
atttcatttt aaattctctg atggagggac aacaatggtt tcaactgtat gcccatgcct   2280
gatcctctta tttgaacatc tatcaacatt gtaaactctt tgccaaaatc ctggggcttt   2340
gctgcattcc ctaagataat tacaggaaaa agaaaatgta aaagtgctaa caaggctgcc   2400
aagtaatgga gaagtatggt tagtcttcat attgaaattc tgttgcttat tttcatggaa   2460
ggaaacagaa tactttgcac aggaaccaca ttttcaatcc tccttcactg tcttcctacc   2520
atgttcagcc cagactcctg ccacatggac caggatgaag agggatcaaa gagataatta   2580
gccaaaaacc cagtagccta gaagatacaa aactccactg gcctctaaaa ttatattagc   2640
caagagtggt ttcatttgag tgccttcgtg tgtatgtcca tcaaactgga accaaactgt   2700
tttgtaagta aacaggcagc ctaagcccaa ccctactttc taattccagt tattctcttt   2760
ttcatctggg gatttacctg ttcatttaat ctgcctgttt tgatctgttt tgaaaaagat   2820
aaagagcctc aaatcagacc agcactgatt aattaaccct gctcctacca atctttttta   2880
aagcagttga agcagaatgt ataggtgtca gagaagaaac ctagtcagcc agacgtgctc   2940
tgtattcagc aatagtttgt gaatgaataa attactaatc ctccttgtcg cttgaaacct   3000
tcccacactc cctgctccag gagggaaaaa cagatgttgt tgacagatag agtgataggc   3060
aaattctgtg tggactttag tcccaaaagg aaacttagt tcacttgcag tatgcttatc   3120
cttgactgca catgagaatg ccttgtgcag agttatttgg agattatgtc ttttcttaa   3180
```

```
acaccatggc tgtcacactt cagttcaatt aaatcagaat gtctgaggag tgagacacag    3240
gcatcaacac tctcaaatga ttcacatgtt cagccaaagt tgagaaccat cgagcctgtg    3300
gaagttcttt ctcatggctc agaatcttag gtaggtgctt aactcttgtg gtggccagcc    3360
tccaagatga gccccagtgt tcttgcctcc tactattcac atctttatgt ggtcccctcc    3420
aatgctgaat acagatgatt tgtgtaacct gaggccagga ttaaggggag gcaatcaatg    3480
cacctaggga aaaaatttaa ggaggtattc acactcaggg tcatgcactt gcacaatgtt    3540
gagaatgagt accactctca ccattggtat agccaaaaaa gcttggaagt gaccaaggct    3600
aggtcacaaa atacactgtg gcttcttctt tgatctctct ttgaccatac tgacactggg    3660
aaaagcccat tcccatgcca tgaagacacc aaggcagccc tattgagaaa tctacctgtc    3720
gtggccgggc gcagtggctc acgcctgtaa tcccagcact tgggaggcc gaggtgggtg    3780 gatcacgagg tcaggagatc gagaccatcc tggctaacac agtgaaaccc cgtctctact    3840
aaaaatacaa aaaattagcc gggtgtggtg tcgggcacct gtagtcccag ctactcagga    3900
ggctgaggca ggagaagggt gggaacccgg gaggcagagc ttgcagtgag ccgagattgt    3960
gccactgcac actccaatct gggtgaaaga ccgagactcc gcctcaaaaa aaaaaaaaa    4020 agaaagaaag aaagaaagaa agaaatctac ctgtcaagga actaaggtat tttgctaaca    4080
agcaccaact tgccagccat gtaagggagc catcttggaa gcagatcctc cagcctccag    4140
tcaagtcttc agataattgc aacttcagtt gatcttttga ccaagacctc aagagagcca    4200
gaactaccca gctaagcctt ttactaaatt tctgaacttc taacactatt agataataag    4260
tgcttattgt ttaacaccat taattttgag tataatttgt tacatagcga cagataacta    4320
tacagctcaa caactagaaa aataaactgt ttacctgcct taattattta tctttagttc    4380
cttattagtt ctcaagaaac aaatgctagc ttcatatgta tggctgttgc tttgcttcat    4440
gtgtatggct atttgtattt aacaagactt aatcatcagt a                       4481

<210> SEQ ID NO 140
<211> LENGTH: 11134
<212> TYPE: DNA
<213> ORGANISM: Homo sapiens

<400> SEQUENCE: 140
gcggcggcgg cggctcggga gagagggacg cgggctgcag gcgcgatgct tggctagagg      60
acgcgtccga cggcggccgg acgctgaggt ggtcggggct agtcagcccg gcctgggcat     120
ggagcgcggg gtggcagagc ctctggacgt ttggggcgcg cccagtccga gcccccggcg     180
cgcctgaagt tgcgagcggc gagcggcgag cggcgagcgg cccgcggaga cccaggagct     240
gccggcacgc cgcggatgag ccttcgcgcc ggcgggaaga cgcggcggtg gccagggcca     300
gagcaggcgg cccgcggggg ccgatccggc ggagagcaga gcccgaggcg aggcgaggcg     360
cggcgccgct gcacacacgc acacggagcc atggggcgcc atgttgccac cagctgccac     420
gtggcctggc ttttggtgct gatctctgga tgctggggcc aggtgaaccg gctgcccttc     480
ttcaccaacc acttctttga tacatacctg ctgatcagcg aggacacgcc tgtgggttct     540
tctgtgaccc agttgctggc ccaagacatg gacaatgacc cctggtgtt tggcgtgtct     600 ggggaggagg cctctcgctt ctttgcagtg gagcctgaca ctggcgtggt gtggctccgg     660
cagccactgg acagagagac caagtcagag ttcaccgtgg agttctctgt cagcgaccac    720
cagggggtga tcacacggaa ggtgaacatc caggttgggg atgtgaatga caacgcgccc    780
```

```
acatttcaca atcagccnta cagcgtccgc atccctgaga atacaccagt ggggacgccc    840
atcttcatcg tgaatgccac agaccccgac ttgggggcag gggcagcgt cctctactcc     900
ttccagcccc cctcccaatt cttcgccatt gacagcgccc gcggtatcgt cacagtgatc    960
cgggagctgg actacgagac cacacaggcc taccagctca cggtcaacgc cacagatcaa   1020
gacaagacca ggcctctgtc caccctggcc aacttggcca tcatcatcac agatgtccag   1080
gacatggacc ccatcttcat caacctgcct tacagcacca acatctacga gcattctcct   1140
ccgggcacga cggtgcgcat catcaccgcc atagaccagg ataaaggacg tccccggggc   1200
attggctaca ccatcgtttc agggaatacc aacagcatct ttgccctgga ctacatcagc   1260
ggagtgctga ccttgaatgg cctgctggac cgggagaacc ccctgtacag ccatggcttc   1320
atcctgactg tgaagggcac ggagctgaac gatgaccgca ccccatctga cgctacagtc   1380
accacgacct tcaatatcct ggttattgac atcaatgaca atgccccgga gttcaacagc   1440
tccgagtaca cgctggccat cactgagctg gcacaggtcg gctttgccct tccactcttc   1500
atccaggtgg tggacaagga tgagaatttg ggcctgaaca gcatgtttga ggtgtacttg   1560
gtggggaaca actcccacca cttcatcatc tccccgacct ccgtccaggg gaaggcggac   1620
attcgtattc gggtggccat cccactggac tacgagaccg tggaccgcta cgactttgat   1680
ctctttgcca atgagagtgt gcctgaccat gtgggctatg ccaaggtgaa gatcactctc   1740
atcaatgaaa atgacaaccg gcccatcttc agccagccac tgtacaacat cagcctgtac   1800
gagaacgtca ccgtggggac ctctgtgctg acagtcctgg caactgacaa tgatgcaggc   1860
acctttgggg aagtcagcta cttcttcagt gatgaccctg acaggttctc gctggacaag   1920
gacacgggac tcatcatgct gattgccagg ctggactatg agctcatcca gcgcttcacc   1980
ctgacgatca ttgcccggga cggggcggc gaggagacca caggccgggt caggatcaat   2040
gtgttggatg tcaacgacaa cgtgcccacc ttccagaagg atgcctacgt gggtgctctg   2100
cgggagaacg agccttctgt cacacagctg gtgcggctcc gggcaacaga tgaagactcc   2160
cctcccaaca accagatcac ctacagcatt gtcagtgcat ctgccttgg cagctacttc   2220
gacatcagcc tgtacgaggg ctatggagtg atcagcgtca gtcgccccct ggattatgaa   2280
cagatatcca atgggctgat ttatctgacg gtcatggcca tggatgctgg caaccccccct   2340
ctcaacagca ccgtccctgt caccatcgag gtgtttgatg agaatgacaa ccctcccacc   2400
ttcagcaagc ccgcctactt cgtctccgtg gtggagaaca tcatggcagg agccacggtg   2460
ctgttcctga atgccacaga cctggaccgc tcccggagt acggccagga gtccatcatc   2520
tactccttgg aaggctccac ccagtttcgg atcaatgccc gctcagggga aatcaccacc   2580
acgtctctgc ttgaccgaga gaccaagtct gaatacatcc tcatcgttcg cgcagtggac   2640
gggggtgtgg ccacaaccca gaaaactggc atcgccaccg taaacatcac cctcctggac   2700
atcaatgaca ccacccccac gtggaaggac gcaccctact acatcaacct ggtggagatg   2760
accctccag actctgatgt gaccacggtg gtggctgttg acccagacct ggggagaat    2820
ggcaccctgg tgtacagcat ccagccaccc aacaagttct acagcctcaa cagcaccacg   2880
ggcaagatcc gcaccaccca cgccatgctg accgggaga accccgaccc catgaggcc    2940
gagctgatgc gcaaaatcgt cgtctctgtt actgactgtg gcaggccccc tctgaaagcc   3000
accagcagtg ccacagtgtt tgtgaacctc ttggatctca atgacaatga ccccaccttt   3060
cagaacctgc ctttttgtggc cgaggtgctt gaaggcatcc cggcggggt ctccatctac   3120
caagtggtgg ccatcgacct cgatgagggc ctgaacggcc tggtgtccta ccgcatgccg   3180
```

```
gtgggcatgc cccgcatgga cttcctcatc aacagcagca gcggcgtggt ggtcaccacc    3240
accgagctgg accgcgagcg catcgcggag taccagctgc gggtggtggc cagtgatgca    3300
ggcacgccca ccaagagctc caccagcacg ctcaccatcc atgtgctgga tgtgaacgac    3360
gagacgccca ccttcttccc ggccgtgtac aatgtgtctg tgtccgagga cgtgccacgc    3420
gagttccggg tggtctggct gaactgcacg gacaacgacg tgggcctcaa tgcagagctc    3480
agctacttca tcacaggtgg caacgtggat gggaagttca gcgtgggtta ccgcgatgcc    3540
gttgtgagaa ccgtggtggg cctggaccgg agaccacag ccgcctacat gctcatcctg     3600
gaggccatcg acaacggccc tgtagggaag cgacacacgg gcacagccac cgtgttcgtc    3660
actgtcctgg atgtgaatga caaccggccc atctttctgc agagcagcta tgaggccagc    3720
gtccctgagg acatccctga aggccacagc atcttgcagc tgaaagccac ggacgcagat    3780
gagggcgagt ttgggcgtgt gtggtaccgc atcctccatg gtaaccatgg caacaacttc    3840
cggatccatg tcagcaatgg gctcctgatg cgagggcccc ggcccctgga ccgggagcgg    3900
aactcatccc acgtgctgat agtggaggcc tacaaccacg acctgggccc catgcggagc    3960
tccgtcaggg tgattgtgta cgtggaggac atcaacgatg aggcccccgt gttcacacag    4020
cagcagtaca gccgtctggg gcttcgagag accgcaggca ttggaacgtc agtcatcgtg    4080
gtccaagcca cagaccgaga ctctggggat ggtggcctgg tgaactaccg catcctgtcg    4140
ggcgcagagg ggaagtttga gattgacgag agcacagggc ttatcatcac cgtgaattac    4200
ctggactacg agaccaagac cagctacatg atgaatgtgt cggccactga ccaggccccg    4260
cccttcaacc agggcttctg cagcgtctac atcactctgc tcaacgagct ggacgaggcc    4320
gtgcagttct ccaatgcctc atacgaggct gccatcctgg agaatctggc actgggtact    4380
gagattgtgc gggtccaggc ctactccatc gacaacctca accaaatcac gtaccgcttc    4440
aacgcctaca ccagcaccca ggccaaagcc tcttcaagaa tagacgccat cacgggtgtg    4500
atcacagtcc agggcctggt ggaccgtgag aagggcgact tctataccttt gacagtggtg   4560 gcagatgacg gcggccccaa ggtggactcc accgtgaagg tctacatcac tgtgctggac    4620
gagaatgaca acagccccg gtttgacttc acctccgact cggcggtcag cataccccgag   4680 gactgccctg tgggccagcg agtggctact gtcaaggcct gggaccctga tgctggcagc    4740
aatgggcagg tggtcttctc cctggcctct ggcaacatcg cgggggcctt tgagatcgtc    4800
accaccaatg actccattgg cgaagtgttt gtggccaggc ccctggacag agaagagctg    4860
gatcactaca tcctccaggt tgtggcttct gaccgaggca cccctccacg gaagaaggac    4920
cacatcctgc aggtgaccat cctggacatc aatgacaacc ctccagtcat cgagagcccc    4980
tttggataca atgtcagtgt gaatgagaac gtgggtggag gtactgctgt ggtccaggtg    5040
agagccactg accgtgacat cgggatcaac agtgttctgt cctactacat caccgagggc    5100
aacaaggaca tggccttccg catgaccgc atcagcggtg agatcgccac acggcctgcc    5160
ccgcctgacc gcgagcgcca gagcttctac cacctggtgg ccactgtgga ggacgagggc    5220
accccaaccc tgtcggccac cacgcacgtg tacgtgacca ttgtggatga aatgataac    5280 gcgcccatgt tccagcagcc ccactatgag gtgctgctgg atgagggccc agacacgctc    5340
aacaccagcc tcatcaccat ccaggcactg gacctggatg agggtcccaa cggcacagtc    5400
acctatgcca tcgtcgcagg caacatcgtc aacaccttcc gcatcgacag acacatgggt    5460
gtcatcactg ctgccaaaga gctggactac gagatcagcc acggccgcta cacctgatc    5520
```

```
gtcactgcca cagaccagtg ccccatctta tcccaccgcc tcacctctac caccacggtg    5580
cttgtgaatg tgaatgacat caacgacaat gtgcctacct tcccccggga ctatgaggga    5640
ccatttgaag tcactgaggg ccagccgggg cccagagtgt ggaccttcct ggcccatgac    5700
cgagactcag gacccaacgg gcaggtggag tacagcatca tggatggaga ccctctgggg    5760
gagtttgtga tctctcctgt ggaggggtg ctaagggtcc ggaaggacgt ggagctggac    5820
cgggagacca tcgccttcta caacctgacc atctgtgccc gtgaccgggg gatgccccca    5880
ctcagctcca caatgctggt ggggatccgg gtgctggaca tcaacgacaa cgaccctgtg    5940
ctgctgaacc tgcccatgaa catcaccatc agcgagaaca gccctgtctc cagctttgtc    6000
gcccatgtcc tggccagtga cgctgacagt ggctgcaatg cacgcctcac cttcaacatc    6060
actgcgggca accgcgagcg ggccttcttc atcaatgcca cgacagggat cgtcactgtg    6120
aaccggcccc tggaccgcga gcggatccca gagtacaagc tgaccatttc tgtgaaggac    6180
aacccggaga atccacgcat agccaggagg gattatgact tgcttctgat cttcctttct    6240
gatgagaatg acaaccaccc cctcttcact aaaagcacct accaggcaga ggtgatggaa    6300
aactctcccg ctggcacccc tctcacggtg ctcaatgggc ccatcctggc cctggatgca    6360
gaccaagaca tctacgccgt ggtgacctac cagctgctgg gtgcccagag tggcctctct    6420
gacatcaaca gcagcaccgg tgtggtgacc gtgaggtcag gtgtcatcat tgaccgggag    6480
gcattctcgc cacccatcct ggagctgctg ctgctggctg aggacatcgg gctgctcaac    6540
agcacggccc acctgctcat caccatcctg gatgacaatg acaaccggcc cacctttagc    6600
cctgccaccc tcactgtcca tctgctagag aactgcccgc ctggattctc agtccttcaa    6660
gtcacagcca cagatgagga cagtggcctc aatggggagc tggtctaccg aatagaagct    6720 gggggctcagg accgcttcct cattcatctg gtcaccgggg tcatccgtgt tggtaatgcc    6780
accatcgaca gagaggagca ggagtcctac aggctaacgg tggtggccac cgaccggggc    6840
accgttcctc tctcgggcac agccattgtc accattctga tcgatgacat caatgactcc    6900
cgccccgagt tcctcaaccc catccagaca gtgagcgtgc tggagtcggc tgagccaggc    6960
actgtcattg ccaatatcac ggccattgac cacgacctca acccaaagct agagtaccac    7020
attgtcggca ttgtggccaa ggacgacact gatcgcctgg tgcccaacca ggaggacgcc    7080
tttgctgtga atatcaacac aggatctgta atggtgaagt cccccatgaa tcggagctg    7140 gttgccacct atgaggtcac tctctcagtg attgacaatg ccagcgacct accagagcgc    7200
tctgtcagtg tgccaaatgc caagctgact gtcaacgtcc tggacgtcaa tgacaatacg    7260
ccccagttca agccctttgg gatcacctac tacatggagc ggatcctgga gggggccacc    7320
cctgggacca cactcattgc tgtggcagcc gtggaccctg acaagggcct taatgggctg    7380
gtcacctaca ccctgctgga cctggtgccc cagggtatg tccagctgga ggactcctcg    7440
gcagggaagg tcattgccaa ccggacagtg actacgagg aggtgcactg gctcaactttt    7500 accgtgaggg cctcagacaa cgggtccccg ccccgggcag ctgagatccc tgtctacctg    7560
gaaatcgtgg acatcaatga caacaacccc atctttgacc agccctccta ccaggaggct    7620
gtctttgagg atgtgcctgt gggcacaatc atcctgacag tcactgccac tgatgctgac    7680
tcaggcaact ttgcactcat tgagtacagc cttggagatg agagagcaa gtttgccatc    7740 aaccccacca cgggtgacat ctatgtgctg tcttctctgg accgggagaa gaaggaccac    7800
tatatcctga ctgccttggc caaagacaac cctggggat tagccagcaa ccgtcgcgaa    7860
aattcagtgc aggtggtgat ccaagtgctg gatgtcaatg actgccggcc acagttctcc    7920
```

```
aagccccagt tcagcacaag cgtgtatgag aatgagccgg cgggcacctc ggtcatcacc   7980
atgatggcca ctgaccagga tgaaggtccc aatggagagt tgacctactc acttgagggc   8040
cctggcgtgg aggccttcca tgtggacatg gactcgggct tggtgaccac acagcggcca   8100
ctgcagtcct acgagaagtt cagtctgacc gtggtggcca cagatggtgg agagcccca    8160
ctctggggca ccaccatgct cctggtggag gtcatcgacg tcaatgacaa ccgccctgtc   8220
tttgtgcgcc cacccaacgg caccatcctc cacatcagag aggagatccc gctgcgctcc   8280
aacgtgtacg aggtctacgc cacggacaag gatgagggcc tcaacggggc ggtgcgctac   8340
agcttcctga agactgcggg caaccgggac tgggagttct tcatcatcga cccaatcagc   8400
ggcctcatcc agactgctca gcgcctggac cgcgagtcgc aggcggtgta cagcctcatc   8460
ttggtggcca gcgacctggg ccagccagtg ccatacgaga ctatgcagcc gctgcaggtg   8520
gccctggagg acatcgatga caacgaaccc ttttcgtga ggcctccaaa aggcagcccc    8580
cagtaccagc tgctgacagt gcctgagcac tcaccacgcg gcaccctcgt gggcaacgtg   8640
acaggcgcag tggatgcaga tgagggcccc aacgcgatcg tgtactactt catcgcagcc   8700
ggcaacgaag agaagaactt ccatctgcag cccgatgggt gtctgctggt gctgcgggac   8760
ctggaccggg agcgagaagc catcttctcc ttcatcgtca aggcctccag caatcgcagc   8820
tggacacctc cccgtggacc ctccccaacc ctcgacctgg ttgctgacct cacactgcag   8880
gaggtgcgcg ttgtgctaga ggacatcaac gaccagccac cacgcttcac caaggctgag   8940
tacactgcag gggtggccac cgacgccaag gtgggctcag agttgatcca ggtgctggcc   9000
ctggatgcag acattggcaa caacagcctt gtcttctaca gcattctggc catccactac   9060
ttccgggccc ttgccaacga ctctgaagat gtgggccagg tcttcaccat ggggagcatg   9120
gacggcattc tgcgcacctt cgacctcttc atggcctaca gccccggcta cttcgtggtg   9180
gacattgtgg cccgagacct ggcaggccac aacgacacgg ccatcatcgg catctacatc   9240
ctgagggacg accagcgcgt caagatcgtc attaacgaga tccccgaccg tgtgcgcggc   9300
ttcgaggagg agttcatcca cctgctctcc aacatcactg ggccattgt caatactgac    9360
aatgtgcagt ccatgtggga caagaagggc cgggtgaact tgcgcagac agaactgctt    9420
atccacgtgg tgaaccgcga taccaaccgc atcctggacg tggaccgggt gatccagatg   9480
atcgatgaga acaaggagca gctacggaat cttttccgga actacaacgt cctggacgtg   9540
cagcctgcca tctctgtccg gctgccggat gacatgtctg ccctgcagat ggcgatcatc   9600
gtcctggcta tcctcctgtt cctggccgcc atgctctttg tcctcatgaa ctggtactac   9660
aggactgtac acaagaggaa gctcaaggcc attgtggctg gctcagctgg gaatcgtggc   9720
ttcatcgaca tcatggacat gcctaacacc aacaagtact ccttttgatgg agccaaccct   9780
gtgtggctgg atcccttctg tcggaacctg agctggccg cccaggcgga gcatgaggat     9840
gacctaccgg agaacctgag tgagatcgcc gacctgtgga acagcccac gcgcacccat     9900
ggaacttttg ggcgtgagcc agcagctgtc aagcctgatg atgaccgata cctgcgggct   9960
gccatccagg agtatgacaa cattgccaag ctgggccaga tcattcgtga ggggccaatc  10020
aagggctcgc tgctgaaggt ggtcctggag gattacctgc ggctcaaaaa gctctttgca  10080
cagcggatgg tgcaaaaagc ctcctcctgc cactcctcca tctctgagct gatacagact  10140
gagctggacg aggagccagg agaccacagc ccagggcagg gtagcctgcg cttccgccac  10200
aagccaccag tggagctcaa ggggcccgat gggatccatg tggtgcacgg cagcacgggc  10260
```

| | |
|---|---|
| acgctgctgg ccaccgacct caacagcctg cccgaggaag accagaaggg cctgggccgc | 10320 |
| tcgctggaga cgctgaccgc tgccgaggcc actgccttcg agcgcaacgc ccgcacagaa | 10380 |
| tccgccaaat ccacacccct gcacaaactt cgcgacgtga tcatggagac ccccctggag | 10440 |
| atcacagagc tgtgactaga cagggaagcc ttgtgggtgt gagcagcacc catccaccgt | 10500 |
| cccctcccag ggagcaaggg cagggacagg gccggtcggg ggggacccct caaggccagg | 10560 |
| ccttggggac aaccttggct tggccctggc agcccgcatc agctgctcag atcccacttt | 10620 |
| tgccagacgc tcattcagca tctgacctct accttcataa gatctgttat ttttataaga | 10680 |
| aaaccaaaca aaaatgttaa gcatctaagg acaaggtaag gagggtcact ggggcccaag | 10740 |
| agtctgggga ccagcttggc tcaggctgag ctgaaagagg ccaaacaggc cctcctccct | 10800 |
| cccagctcca ccccgcaagc accatcccct ccggctaagc aggcgcaagg gaggcccagc | 10860 |
| gcggacatcc cctgctggcc ggacacccga ctccagtcca agtctcgcta catttccgcc | 10920 |
| acatccctct ctgctggacg tccaggtgga ggtggcatcc ccacgtggac aagaaagtca | 10980 |
| atgtcaatga acaagcattc tctccatttc actggcttcc caaatgtgtg cccagcttat | 11040 |
| aaacagaagt gactgatgtt ccctccggtt ttgaatgtgg agtgtttgtg tgtgttcctt | 11100 |
| ttttaaatta agttattccc tcaaaaaaaa aaaa | 11134 |

<210> SEQ ID NO 141
<211> LENGTH: 3567
<212> TYPE: DNA
<213> ORGANISM: Homo sapiens

<400> SEQUENCE: 141

| | |
|---|---|
| agagctcgcc actccttagt cgaggcaaga cgtgcgcccg agcccgccg aaccgaggcc | 60 |
| acccggagcc gtgcccagtc cacgccggcc gtgcccggcg gccttaagaa cccggcaacc | 120 |
| tctgccttct tccctcttcc actcggagtc gcgctccgcg cgccctcact gcagcccctg | 180 |
| cgtcgccggg accctcgcgc gcgaccgccg aatcgctcct gcagcagagc caacatgccc | 240 |
| atcactcgga tgcgcatgag accctggcta gagatgcaga ttaattccaa ccaaatcccg | 300 |
| gggctcatct ggattaataa agaggagatg atcttccaga tcccatggaa gcatgctgcc | 360 |
| aagcatggct gggacatcaa caaggatgcc tgtttgttcc ggagctgggc cattcacaca | 420 |
| ggccgataca aagcagggga aaaggagcca gatcccaaga cgtggaaggc caactttcgc | 480 |
| tgtgccatga actccctgcc agatatcgag gaggtgaaag accagagcag gaacaagggc | 540 |
| agctcagctg tgcgagtgta ccggatgctt ccacctctca ccaagaacca gagaaaagaa | 600 |
| agaaagtcga agtccagccg agatgctaag agcaaggcca agaggaagtc atgtgggggat | 660 |
| tccagccctg ataccttctc tgatggactc agcagctcca ctctgcctga tgaccacagc | 720 |
| agctacacag ttccaggcta catgcaggac ttggaggtgg agcaggccct gactccagca | 780 |
| ctgtcgccat gtgctgtcag cagcactctc cccgactggc acatcccagt ggaagttgtg | 840 |
| ccggacagca ccagtgatct gtacaacttc caggtgtcac ccatgccctc cacctctgaa | 900 |
| gctacaacag atgaggatga ggaagggaaa ttacctgagg acatcatgaa gctcttggag | 960 |
| cagtcggagt ggcagccaac aaacgtggat gggaagggt acctactcaa tgaacctgga | 1020 |
| gtccagccca cctctgtcta tggagacttt agctgtaagg aggagccaga aattgacagc | 1080 |
| ccaggggggg atattgggct gagtctacag cgtgtcttca cagatctgaa gaacatggat | 1140 |
| gccacctggc tggacagcct gctgacccca gtccggttgc cctccatcca ggccattccc | 1200 |
| tgtgcaccgt agcagggccc ctgggcccct cttattcctc taggcaagca ggacctggca | 1260 |

```
tcatggtgga tatggtgcag agaagctgga cttctgtggg cccctcaaca gccaagtgtg    1320 acccactgc caagtgggga tggggcctcc ctccttgggt cattgacctc tcagggcctg    1380
gcaggccagt gtctgggttt ttcttgtggt gtaaagctgg ccctgcctcc tgggaagatg    1440
aggttctgag accagtgtat caggtcaggg acttggacag gagtcagtgt ctggcttttt    1500
cctctgagcc cagctgcctg gagagggtct cgctgtcact ggctggctcc taggggaaca    1560
gaccagtgac cccagaaaag cataacacca atcccaggc tggctctgca ctaagagaaa    1620
attgcactaa atgaatctcg ttcccaaaga actacccct tttcagctga gccctgggga    1680
ctgttccaaa gccagtgaaa tgtgaaggaa agtggggtcc ttcggggcga tgctccctca    1740
gcctcagagg agctctaccc tgctccctgc tttggctgag gggcttggga aaaaaacttg    1800
gcactttttc gtgtggatct tgccacattt ctgatcagag gtgtacacta acatttcccc    1860
cgagctcttg gcctttgcat ttatttatac agtgccttgc tcggcgccca ccaccccctc    1920
aagccccagc agccctcaac aggcccaggg agggaagtgt gagcgccttg gtatgactta    1980
aaattggaaa tgtcatctaa ccattaagtc atgtgtgaac ataaggac gtgtgtaaat    2040 atgtacattt gtctttttat aaaaagtaaa ttgtttataa ggggtgtggc cttttttagag    2100 agaaatttaa cttgtagatg attttacttt ttatggaaac actgatggac ttattattgg    2160
catcccgcct gaacttgact ttggggtgaa caggacatg catctattat aaaatccttt    2220
cggccaggcg cggtggctca cctgtaat cccagcactt tgggaggccg agatgggtgg    2280
atcacctgag gtcaggagtt cgagaccagc ctggtgaaac tccatttcta ctaaaaatgc    2340
aaaaattagc tgggcgtggt tgcgggtgct tgtaatccca gctactcagg aggctgaggc    2400
aagagaatcg cttgaacctg ggaggtggag gttgcagtga gccgagaaca tgccattgca    2460
ctccagcccg ggcaccaaaa aaaaaaaaa aaaaaaaac ctttcatttg gccgggcatg    2520
gtggcttatg cctgtaatcc tggcactttg ggaggccaag gtgggcagat cacctgaggt    2580
caggagtttg agaccagcct ggccaacatg gtgaaacctc atctctacta aaaatacaaa    2640
aattaggccg ggcacggtgg ctcacgcctg taatcccagc actttgggag gcagaggcgg    2700
gcggatcacg aggtcaggag atcaagacca tcctggctaa cacggtgaaa ccccgtctct    2760
actaaaaata taaaaaatta gccgggccta gtggcgggtg cctgtagtcc cagctactcg    2820
ggaggctgag gcaggagaat ggcatgaacc ccggaggcag agcttgcagt gagccgagat    2880
tgcaccactg cactcagcc tgggcgacag agcgagactc cgtctcaaaa aaaaaaaaa    2940 aaattagccg ggcctggtgg cgggcgcctg taatcccagc tactgtggag gctgaagcac    3000
aagaatcact tgaacccggg agatggaggt tgcagtgagc tgagactgtg ccactgcact    3060
ccagcctggg tgacaagagt gagactttgt ctcaaaaaaa aaaaaatcct tttgtttatg    3120
ttcacataga caatggcaga aggaggggac attcctgtca taggaacatg cttatataaa    3180
catagtcacc tgtccttgac tatcaccagg gctgtcagtt gattctgggc tcctggggcc    3240
caaggagtgt taagttttga ggcatgtgcc ataggtgatg tgtcctgcta acacacagat    3300
gctgctccaa aaagtcagtt gatatgacac agtcacagac agaacagtca gcagcccaag    3360
aaaggtcctc acgctgctg tgctgggtag cacttgccat ccagtttcta gagtgatgaa    3420
atgctctgtc tgtaccgttc aatacagtag gcactggcac tagccacatg tgccagctaa    3480
gcacttgaaa tgtggccagt gcaataagga attgaacttt taattgcatt taataaactg    3540
tatgtaaata gtcaaaaaaa aaaaaaa                                      3567
```

<210> SEQ ID NO 142
<211> LENGTH: 3050
<212> TYPE: DNA
<213> ORGANISM: Homo sapiens

<400> SEQUENCE: 142

| | | | | | |
|---|---|---|---|---|---|
| ggagtcagtg | atttgaacga | agtactttca | gtttcatatt | actctaaatc | cattacaaat | 60 |
| ctgcttagct | tctaaatatt | tcatcaatga | ggaaatccca | gccctacaac | ttcggaacag | 120 |
| tgaaatatta | gtccagggat | ccagtgagag | acacagaagt | gctagaagcc | agtgctcgtg | 180 |
| aactaaggag | aaaaagaaca | gacaagggaa | cagcctggac | atggcatcag | agatccacat | 240 |
| gacaggccca | atgtgcctca | ttgagaacac | taatgggcga | ctgatggcga | atccagaagc | 300 |
| tctgaagatc | ctttctgcca | ttacacagcc | tatggtggtg | gtggcaattg | tgggcctcta | 360 |
| ccgcacaggc | aaatcctacc | tgatgaacaa | gctggctgga | agaaaaagg | gcttctctct | 420 |
| gggctccacg | gtgcagtctc | acactaaagg | aatctggatg | tggtgtgtgc | cccaccccaa | 480 |
| gaagccaggc | cacatcctag | ttctgctgga | caccgagggt | ctgggagatg | tagagaaggg | 540 |
| tgacaaccag | aatgactcct | ggatcttcgc | cctggccgtc | ctcctgagca | gcaccttcgt | 600 |
| gtacaatagc | ataggaacca | tcaaccagca | ggctatggac | caactgtact | atgtgacaga | 660 |
| gctgacacat | agaatccgat | caaaatcctc | acctgatgag | aatgagaatg | aggttgagga | 720 |
| ttcagctgac | tttgtgagct | tcttcccaga | cttttgtgtgg | acactgagag | atttctccct | 780 |
| ggacttggaa | gcagatggac | aaccctcac | accagatgag | tacctgacat | actccctgaa | 840 |
| gctgaagaaa | ggtaccagtc | aaaaagatga | aactttaaac | ctgcccagac | tctgtatccg | 900 |
| gaaattcttc | ccaaagaaaa | atgctttgt | ctttgatcgg | cccgttcacc | gcaggaagct | 960 |
| tgcccagctc | gagaaactac | aagatgaaga | gctggacccc | gaatttgtgc | aacaagtagc | 1020 |
| agacttctgt | tcctacatct | ttagtaattc | caaaactaaa | actctttcag | gaggcatcca | 1080 |
| ggtcaacggg | cctcgtctag | agagcctggt | gctgacctac | gtcaatgcca | tcagcagtgg | 1140 |
| ggatctgccg | tgcatggaga | acgcagtcct | ggccttggcc | cagatagaga | actcagctgc | 1200 |
| agtgcaaaag | gctattgccc | actatgaaca | gcagatgggc | cagaaggtgc | agctgcccac | 1260 |
| agaaaccctc | caggagctgc | tggacctgca | cagggacagt | gagagagagg | ccattgaagt | 1320 |
| cttcatcagg | agttccttca | aagatgtgga | ccatctatt | caaaggagt | tagcggccca | 1380 |
| gctagaaaaa | aagcgggatg | acttttgtaa | acagaatcag | gaagcatcat | cagatcgttg | 1440 |
| ctcagcttta | cttcaggtca | ttttcagtcc | tctagaagaa | gaagtgaagg | cgggaattta | 1500 |
| ttcgaaacca | gggggctatc | gtctctttgt | tcagaagcta | caagacctga | gaaaaagta | 1560 |
| ctatgaggaa | ccgaggaagg | ggatacaggc | tgaagagatt | ctgcagacat | acttgaaatc | 1620 |
| caaggagtct | atgactgatg | caattctcca | gacagaccag | actctcacag | aaaaagaaaa | 1680 |
| ggagattgaa | gtgaacgtg | tgaaagctga | gtctgcacag | gcttcagcaa | aaatgttgca | 1740 |
| ggaaatgcaa | agaaagaatg | agcagatgat | ggaacagaag | gagaggagtt | atcaggaaca | 1800 |
| cttgaaacaa | ctgactgaga | agatggagaa | cgacagggtc | cagttgctga | agagcaaga | 1860 |
| gaggaccctc | gctcttaaac | ttcaggaaca | ggagcaacta | ctaaagagg | gatttcaaaa | 1920 |
| agaaagcaga | ataatgaaaa | atgagataca | ggatctccag | acgaaaatga | gacgacgaaa | 1980 |
| ggcatgtacc | ataagctaaa | gaccagagcc | ttcctgtcac | ccctaaccaa | ggcataattg | 2040 |
| aaacaatttt | gaatttgga | acaagcgtca | ctacatttga | taataattag | atcttgcatc | 2100 |
| ataacaccaa | aagtttataa | aggcatgtgg | tacaatgatc | aaaatcatgt | ttttcttaa | 2160 |

```
aaaaaaaaaa agactgtaaa ttgtgcaaca aagatgcatt tacctctgta tcaactcagg    2220
aaatctcata agctggtacc actcaggaga agtttattct tccagatgac cagcagtaga    2280
caaatggata ctgagcagag tcttaggtaa aagtcttggg aaatatttgg gcattggtct    2340
ggccaagtct acaatgtccc aatatcaagg acaaccaccc tagcttctta gtgaagacaa    2400
tgtacagtta tccgttagat caagactaca cggtctatga gcaataatgt gatttctgga    2460
cattgcccat gtataatcct cactgatgat ttcaagctaa agcaaccac cttatacaga     2520 gatctagaat ctctttatgt tctccagagg aaggtggaag aaaccatggg caggagtagg    2580
aattgagtga taaacaattg ggctaatgaa gaaaacttct cttattgttc agttcatcca    2640
gattataact tcaatgggac actttagacc attagacaat tgacactgga ttaaacaaat    2700
tcacataatg ccaaatacac aatgtattta tagcaacgta taatttgcaa agatggactt    2760
taaaagatgc tgtgtaacta aactgaaata attcaattac ttattattta gaatgttaaa    2820
gcttatgata gtcttttcta actcttaaca ctcatacttg aaaactttct gagtttcccc    2880
agaagagaat atgggatttt ttttgacatt tttgactcat ttaataatgc tcttgtgttt    2940
acctagtata tgtagacttt gtcttatgtg tgaaaagtcc taggaaagtg gttgatgttt    3000
cttatagcaa ttaaaaatta tttttgaact gaaaatacaa tgtatttcac                3050

<210> SEQ ID NO 143
<211> LENGTH: 2552
<212> TYPE: DNA
<213> ORGANISM: Homo sapiens

<400> SEQUENCE: 143
attttcctcc tcccaacgat tttaaattag tttcactttc cagtttcctc ttccttcccc      60
taaaagcaat tactcaaaaa cggagaaaac atcagctgat gcgtgcccta ctctcccacc    120
cctttatata gttccttcag tatttacttg aggcagacag gaagacttct gaagaacaaa    180
tcagcctggt caccagcttt tcggaacagc agagacacag agggcagtca tgagtgaggt    240
caccaagaat tccctggaga aaatccttcc acagctgaaa tgccatttca cctggaactt    300
attcaaggaa gacagtgtct caagggatct agaagataga gtgtgtaacc agattgaatt    360
tttaaacact gagttcaaag ctacaatgta caacttgttg gcctacataa aacacctaga    420
tggtaacaac gaggcagccc tggaatgctt acggcaagct gaagagttaa tccagcaaga    480
acatgctgac caagcagaaa tcagaagtct agtcacttgg ggaaactacg cctgggtcta    540
ctatcacttg ggcagactct cagatgctca gatttatgta gataaggtga acaaacctg     600 caagaaattt tcaaatccat acagtattga gtattctgaa cttgactgtg aggaagggtg    660
gacacaactg aagtgtggaa gaaatgaaag ggcgaaggtg tgttttgaga aggctctgga    720
agaaaagccc aacaacccag aattctcctc tggactggca attgcgatgt accatctgga    780
taatcaccca gagaaacagt tctctactga tgttttgaag caggccattg agctgagtcc    840
tgataaccaa tacgtcaagg ttctcttggg cctgaaactg cagaagatga ataagaagc     900 tgaaggagag cagtttgttg aagaagcctt ggaaaagtct ccttgccaaa cagatgtcct    960
ccgcagtgca gccaaatttt acagaagaaa aggtgaccta gacaaagcta ttgaactgtt   1020
tcaacgggtg ttggaatcca caccaaacaa tggctacctc tatcaccaga ttgggtgctg   1080
ctacaaggca aaagtaagac aaatgcagaa tacaggagaa tctgaagcta gtggaaataa   1140
agagatgatt gaagcactaa agcaatatgc tatggactat tcgaataaag ctcttgagaa   1200
```

```
gggactgaat cctctgaatg catactccga tctcgctgag ttcctggaga cggaatgtta      1260
tcagacacca ttcaataagg aagtccctga tgctgaaaag caacaatccc atcagcgcta      1320
ctgcaacctt cagaaatata tgggaagtc tgaagacact gctgtgcaac atggtttaga       1380
gggtttgtcc ataagcaaaa aatcaactga caaggaagag atcaaagacc aaccacagaa      1440
tgtatctgaa aatctgcttc cacaaaatgc accaaattat tggtatcttc aaggattaat      1500
tcataagcag aatggagatc tgctgcaagc agccaaatgt tatgagaagg aactgggccg      1560
cctgctaagg gatgccccttt caggcatagg cagtattttc ctgtcagcat ctgagcttga     1620
ggatggtagt gaggaaatgg gccagggcgc agtcagctcc agtcccagag agctcctctc      1680
taactcagag caactgaact gagacagagg aggaaaacag agcatcagaa gcctgcagtg      1740
gtggttgtga cgggtaggac gataggaaga caggggggccc caacctggga ttgctgagca     1800
gggaagcttt gcatgttgct ctaaggtaca ttttttaaaga gttgtttttt ggccgggcgc     1860
agtggctcat gcctgtaatc ccagcacttt ggaggccga ggtgggcgga tcacgaggtc       1920
tggagtttga gaccatcctg gctaacacag tgaaatcccg tctctactaa aaatacaaaa      1980
aattagccag gcgtggtggc tggcacctgt agtcccagct acttgggagg ctgaggcagg      2040
agaatggcgt gaacctggaa ggaagaggtt gcagtgagcc aagattgcgc ccctgcactc      2100
cagcctgggc aacagagcaa gactccatct caaaaaaaaa aaaaaaaaa aaaaagagtt       2160 gttttctcat gttcattata gttcattaca gttacatagt ccgaaggtct tacaactaat      2220
cactggtagc aataaatgct tcaggcccac atgatgctga ttagttctca gttttcattc     2280
agttcacaat ataaccacca ttcctgccct ccctgccaag ggtcataaat ggtgactgcc      2340
taacaacaaa atttgcagtc tcatctcatt ttcatccaga cttctggaac tcaaagatta      2400
acttttgact aaccctggaa tatctcttat ctcacttata gcttcaggca tgtatttata     2460
tgtattcttg atagcaatac cataatcaat gtgtattcct gatagtaatg ctacaataaa      2520
tccaaacatt tcaactctgt taaaaaaaaa aa                                    2552

<210> SEQ ID NO 144
<211> LENGTH: 678
<212> TYPE: DNA
<213> ORGANISM: Homo sapiens

<400> SEQUENCE: 144
aggaaaagga aactgttgag aaaccgaaac tactggggaa agggagggct cactgagaac       60
catcccagta acccgaccgc cgctggtctt cgctggacac catgaatcac actgtccaaa      120
ccttcttctc tcctgtcaac agtggccagc cccccaacta tgagatgctc aaggaggagc      180
acgaggtggc tgtgctgggg cgcccccaca ccctgctcc cccgacgtcc accgtgatcc       240
acatccgcag cgagacctcc gtgcccgacc atgtcgtctg gtccctgttc aacaccctct      300
tcatgaaccc ctgctgcctg gcttcatag cattcgccta ctccgtgaag tctagggaca      360
ggaagatggt tggcgacgtg accggggccc aggcctatgc ctccaccgcc aagtgcctga      420
acatctgggc cctgattctg ggcatcctca tgaccattct gctcatcgtc atcccagtgc      480
tgatcttcca ggcctatgga tagatcagga ggcatcactg aggccaggag ctctgcccat      540
gacctgtatc ccacgtactc caacttccat tcctcgccct gccccggag ccgagtcctg       600 tatcagccct ttatcctcac acgctttttct acaatggcat tcaataaagt gcacgtgttt    660
ctggtgctaa aaaaaaaa                                                    678
```

```
<210> SEQ ID NO 145
<211> LENGTH: 4503
<212> TYPE: DNA
<213> ORGANISM: Homo sapiens

<400> SEQUENCE: 145
gggccggagg ggcggggtga gaaggctgcg cgcgggtaaa ggggccgcct cgagcgcggt      60
ccgagcgttc agcggacgcg cgcggcctcg atctctggac tcgtcacctg cccctccccc     120
tcccgccgcc gtcacccagg aaaccggccg caatcgccgg ccgacctgaa gctggtttca     180
tggcagcctc aaagaaggca gttttgggggc cattggtggg ggcggtggac cagggcacca    240
gttcgacgcg cttttttggtt ttcaattcaa aaacagctga actacttagt catcatcaag    300
tagaaataaa acaagagttc ccaagagaag gatgggtgga acaggaccct aaggaaattc     360
tacattctgt ctatgagtgt atagagaaaa catgtgagaa acttggacag ctcaatattg     420
atatttccaa cataaaagct attggtgtca gcaaccagag ggaaaccact gtagtctggg     480
acaagataac tggagagcct ctctacaatg ctgtggtgtg gcttgatcta agaacccagt     540
ctaccgttga gagtcttagt aaaagaattc caggaaataa taactttgtc aagtccaaga     600
caggccttcc acttagcact tacttcagtg cagtgaaact tcgttggctc cttgacaatg     660
tgagaaaagt tcaaaaggcc gttgaagaaa aacgagctct ttttgggact attgattcat     720
ggcttatttg gagtttgaca ggaggagtca atggaggtgt ccactgtaca gatgtaacaa     780
atgcaagtag gactatgctt tcaacattc attctttgga atgggataaa caactctgcg     840 aatttttttgg aattccaatg gaaattcttc caaatgtccg gagttcttct gagatctatg     900
gcctaatgaa aatctctcat agcgtgaaag ctggggcctt ggaaggtgtg ccaatatctg     960
ggtgtttagg ggaccagtct gctgcattgg tgggacaaat gtgcttccag attggacaag    1020
ccaaaaatac gtatggaaca ggatgttttct tactatgtaa tacaggccat aagtgtgtat    1080
tttctgatca tggccttctc accacagtgg cttacaaact tggcagagac aaaccagtat    1140
attatgcttt ggaaggttct gtagctatag ctggtgctgt tattcgctgg ctaagagaca    1200
atcttggaat tataaagacc tcagaagaaa ttgaaaaact tgctaaagaa gtaggtactt    1260
cttatggctg ctacttcgtc ccagcatttt cggggttata tgcaccttat tgggagccca    1320
gcgcaagagg gataatctgt ggactcactc agttcaccaa taaatgccat attgcttttg    1380
ctgcattaga agctgtttgt ttccaaactc gagagatttt ggatgccatg aatcgagact    1440
gtggaattcc actcagtcat ttgcaggtag atggaggaat gaccagcaac aaaaattctta    1500 tgcagctaca agcagacatt ctgtatatac agtagtgaa gccctcaatg cccgaaacca     1560
ctgcactggg tgcggctatg gcggcagggg ctgcagaagg agtcggcgta tggagtctcg    1620
aacccgagga tttgtctgcc gtcacgatgg agccgtttga acctcagatt aatgcggagg    1680
aaagtgaaat tcgttattct acatggaaga agctgtgat gaagtcaatg ggttgggtta     1740
caactcaatc tccagaaagt ggtattccat aaaacctacc aactcatgga ttcccaagat    1800
gtgagctttt tacataatga aagaacccag caattctgtc tcttaatgca atgacactat    1860
tcatagactt tgattttatt tataagccac ttgctgcatg accctccaag tagacctgtg    1920
gcttaaaata aagaaaatgc agcaaaaaga atgctataga aatatttggt ggttttttttt     1980 ttttttaaac atccacagtt aaggttgggc cagctacctt tgggggctgac ccccctccatt  2040 gccataacat cctgctccat tccctctaag atgtaggaag aattcggatc cttaccattg    2100
gaatcttcca tcgaacatac tcaaacactt ttggaccagg atttgagtct ctgcatgaca    2160
```

```
tatacttgat taaaaggtta ttactaacct gttaaaaatc agcagctctt tgcttttaac    2220 agacaccta aaagtcttct tttctacata gttgaagaca gcaacatctt cactgaatgt     2280
ttgaatagaa acctctacta aattattaaa atagacattt agtgttctca cagcttggat    2340 attttctga aaagttattt gccaaaactg aaatccttca gatgttttcc atggtcccac     2400
taattataat gacttctgt ctggatctta taggaaaaga tactttcttt tttcttccat     2460 ctttccttt tatattttt actttgtatg tataacatac atgcctatat attttataca     2520
ctgagggtag cccatttata aattaagagc acattatatt cagaaggttc taacagggct    2580
ggtcttaagt gaaccactgt gtatataaat atgttggaaa acagctgtat acattttgg     2640 gcaacggtta tgcataatat ttaccaggag aattttttc ttaacaagcc aacatttaaa     2700
atttatgttt tatgtcaata aaagaaaata tactttattg tgacttcaac tatatttctt    2760
atcccttaca tttttatta attgtcttag cttaaaaaaa gaagaaactg tggaatacta     2820
cagtaaatat tgttttcaaa cacaagcaat aattcaaata gttatttttc ttttgaatta    2880
attttagaca tattttggat cctattgagg ggataagagg atgtcaaaaa agttaaatac    2940
ctaagtagaa aaaatatag aaataaagcc aagaatctct ttcagttcaa atgttatcaa     3000
ttgttaataa gaaattgcta tctgggatga cagaattacc tctgcttagt atctcattat    3060
aactgaaaga aggtttatca ttacaaatac cttccaatga aaccaagaat ttctcaaaat    3120
atttaatgtc acatattata agaagttacc taatcctgct tcttaacatc aatttttaaa    3180
aatatcttaa aattactttg ttttgtagta aacagtgaag aaaagattgc ctcctaatta    3240
tttttttcaa tgagtgctga atgggaaaac atttatatct tactataaaa ggttctgttt    3300
tgtttggaat caatggtagc tttattgact gttctgattg tgctgtttct aatttattga    3360
atctgctagg ttttattgat gcagccacca cttaagtgac ataaatatta tagaaaggta    3420
ctgtgaaatg atcactttgt ggcagggta cttttaaaca taaatgtttc tacaaaagta    3480
ggttgagttc attgtaaata attgtgaaag ccactgttca aataatttta agattacatt    3540 aattttcta taaattggaa gattataaa tgtttgaaat tgtacacatt gatatttaat     3600
gacaaattta cttaaaataa attgacccct tgttcttact tgcatttctc atttacagac    3660
tagaacttag ttgaaagtta aattaagaaa gatgtttcag aggccgggca cggtggctga    3720
cgcctgtaat cccagcactt tgggaggccg aggtgggcag atcacctgag gtcaggagtt    3780
cgggactagc ctaaccgaca tggagaaacc ctatctctac taaaaaaaaa aaaagatgtt    3840
tcaggacatg tgaaacttgg ctgttagcgc ttgatagggc acactctgaa gagttaacca    3900
acagccaaag aagtaatttc tgtaatgatg aacactttaa tcattctatt agaagaaact    3960
acactgtccc atctcagcat ttgcaaaaaa taatgttggt aaggtcagca gccattatca    4020
acagggcctt gcatggctaa ctttgaccac catttttctc tcaacctgat aggcaacacc    4080
tcaatccttt gttctccaac taatcagtaa aataagtaat gcatctctgc ttctgtaatg    4140
atatcttaga attttagta tgtttctttt gaagtgccca aagcccaatt ctttgggata    4200
tcttttgggt atctggtatc atgtgggagt gaagaaagaa agttttgga gaaaccaaca     4260 aatgaaagct gtgatagcac agaagctaat ggcattgaca gtggagtagg tagtatttaa    4320
tctgtagtgt ttacaacata gtagatagaa gtacaaaaat ttttttaact ataactcttt    4380
aatagcttgt tttatctagt aatatttaaa taatgaagtt ccttgatcc tttgcttttg     4440 caacctaaca actttaataa taagttcaca caataaacaa attagtagaa aaaaaaaaa     4500 aaa                                                                  4503
```

<210> SEQ ID NO 146
<211> LENGTH: 3385
<212> TYPE: DNA
<213> ORGANISM: Homo sapiens

<400> SEQUENCE: 146

| | | | | | |
|---|---|---|---|---|---|
| ctctacctac | tttgcccagc | tccacctcgg | cagtgcagcg | tgttttggtg | gccttcctcc | 60 |
| gcacgccctg | gaggggagt | gccctgcacc | ccggggctgc | tccggagccc | agtgcacgag | 120 |
| tgcacatggg | cttccctcct | ttgcttaaag | ggcaggcgag | cgctactcgc | tccagccttg | 180 |
| cctcctgcag | ctgggtggtc | ttttttctct | cctgtctttc | aagacacgcg | cccgaaatcg | 240 |
| agggagggag | acgatggact | gagctgatcc | gcaccatgga | gtctcgggtc | ttactgagaa | 300 |
| cattctgttt | gatcttcggt | ctcggagcag | tttgggggct | tggtgtggac | ccttccctac | 360 |
| agattgacgt | cttaacagag | ttagaacttg | gggagtccac | gaccggagtg | cgtcaggtcc | 420 |
| cggggctgca | taatgggacg | aaagcctttc | tctttcaaga | tactcccaga | agcataaaag | 480 |
| catccactgc | tacagctgaa | cagttttttc | agaagctgag | aaataaacat | gaatttacta | 540 |
| ttttggtgac | cctaaaacag | acccacttaa | attcaggagt | tattctctca | attcaccact | 600 |
| tggatcacag | gtacctggaa | ctggaaagta | gtggccatcg | gaatgaagtc | agactgcatt | 660 |
| accgctcagg | cagtcaccgc | cctcacacag | aagtgtttcc | ttacattttg | gctgatgaca | 720 |
| agtggcacaa | gctctcctta | gccatcagtg | cttcccattt | gattttacac | attgactgca | 780 |
| ataaaattta | tgaaagggta | gtagaaaagc | cctccacaga | cttgcctcta | ggcacaacat | 840 |
| tttggctagg | acagagaaat | aatgcgcatg | gatattttaa | gggtataatg | caagatgtcc | 900 |
| aattacttgt | catgccccag | ggatttattg | ctcagtgccc | agatcttaat | cgcacctgtc | 960 |
| caacttgcaa | tgacttccat | ggacttgtgc | agaaaatcat | ggagctacag | gatatttag | 1020 |
| ccaaaacatc | agccaagctg | tctcgagctg | aacagcgaat | gaatagattg | gatcagtgct | 1080 |
| attgtgaaag | gacttgcacc | atgaagggaa | ccacctaccg | agaatttgag | tcctggatag | 1140 |
| acggctgtaa | gaactgcaca | tgcctgaatg | gaaccatcca | gtgtgaaact | ctaatctgcc | 1200 |
| caaatcctga | ctgcccactt | aagtcggctc | ttgcgtatgt | ggatggcaaa | tgctgtaagg | 1260 |
| aatgcaaatc | gatatgccaa | tttcaaggac | gaacctactt | tgaaggagaa | agaaatacag | 1320 |
| tctattcctc | ttctggagta | tgtgttctct | atgagtgcaa | ggaccagacc | atgaaacttg | 1380 |
| ttgagagttc | aggctgtcca | gctttggatt | gtccagagtc | tcatcagata | accttgtctc | 1440 |
| acagctgttg | caaagtttgt | aaaggttatg | acttttgttc | tgaaaggcat | aactgcatgg | 1500 |
| agaattccat | ctgcagaaat | ctgaatgaca | gggctgtttg | tagctgtcga | gatggtttta | 1560 |
| gggctcttcg | agaggataat | gcctactgtg | aagacatcga | tgagtgtgct | gaagggcgcc | 1620 |
| attactgtcg | tgaaaataca | atgtgtgtca | acacccgggg | ttcttttatg | tgcatctgca | 1680 |
| aaactggata | catcagaatt | gatgattatt | catgtacaga | acatgatgag | tgtatcacaa | 1740 |
| atcagcacaa | ctgtgatgaa | aatgctttat | gcttcaacac | tgttggagga | cacaactgtg | 1800 |
| tttgcaagcc | gggctataca | gggaatggaa | cgacatgcaa | agcattttgc | aaagatggct | 1860 |
| gtaggaatgg | aggagcctgt | attgccgcta | atgtgtgtgc | ctgcccacaa | ggcttcactg | 1920 |
| gacccagctg | tgaaacggac | attgatgaat | gctctgatgg | ttttgttcaa | tgtgacagtc | 1980 |
| gtgctaattg | cattaacctg | cctggatggt | accactgtga | gtgcagagat | ggctaccatg | 2040 |
| acaatgggat | gttttcacca | agtggagaat | cgtgtgaaga | tattgatgag | tgtgggaccg | 2100 |

```
ggaggcacag ctgtgccaat gataccattt gcttcaattt ggatggcgga tatgattgtc    2160
gatgtcctca tggaaagaat tgcacagggg actgcatcca tgatggaaaa gttaagcaca    2220
atggtcagat ttgggtgttg gaaaatgaca ggtgctctgt gtgctcatgt cagaatggat    2280
tcgttatgtg tcgacggatg gtctgtgact gtgagaatcc cacagttgat ctttttttgct    2340 gccctgaatg tgacccaagg cttagtagtc agtgcctcca tcaaaatggg gaaactttgt    2400
ataacagtgg tgcacctgg gtccagaatt gtcaacagtg ccgctgcttg caaggggaag    2460
ttgattgttg gcccctgcct tgcccagatg tggagtgtga attcagcatt ctcccagaga    2520
atgagtgctg cccgcgctgt gtcacagacc cttgccaggc tgacaccatc cgcaatgaca    2580
tcaccaagac ttgcctggac gaaatgaatg tggttcgctt caccgggtcc tcttggatca    2640
aacatggcac tgagtgtact ctctgccagt gcaagaatgg ccacatctgt tgctcagtgg    2700
atccacagtg ccttcaggaa ctgtgaagtt aactgtctca tgggagattt ctgttaaaag    2760
aatgttcttt cattaaaaga ccaaaaagaa gttaaaactt aaattgggtg atttgtgggc    2820
agctaaatgc agctttgtta atagctgagt gaactttcaa ttatgaaatt tgtggagctt    2880
gacaaaatca caaaggaaa attactgggg caaaattaga cctcaagtct gcctctactg    2940
tgtctcacat caccatgtag aagaatgggc gtacagtata taccgtgaca tcctgaaccc    3000
tggatagaaa gcctgagccc attggatctg tgaaagcctc tagcttcact ggtgcagaaa    3060
attttcctct agatcagaat cttcaagaat cagttaggtt cctcactgca agaaataaaa    3120
tgtcaggcag tgaatgaatt atattttcag aagtaaagca agaagctat aacatgttat    3180 gtacagtaca ctctgaaaag aaatctgaaa caagttattg taatgataaa aataatgcac    3240
aggcatggtt acttaatatt ttctaacagg aaaagtcatc cctatttcct tgttttactg    3300
cacttaatat tatttggttg aatttgttca gtataagctc gttcttgtgc aaaattaaat    3360
aaatatttct cttaccttat aacac                                          3385
```

<210> SEQ ID NO 147
<211> LENGTH: 595
<212> TYPE: DNA
<213> ORGANISM: Homo sapiens

<400> SEQUENCE: 147

```
gggcaaggct gggccgggaa gggcgtgggt tgaggagagg ctccagaccc gcacgccgcg     60
cgcacagagc tctcagcgcc gctcccagcc acagcctccc gcgcctcgct cagctccaac    120
atggcaaaaa tctccagccc tacagagact gagcggtgca tcgagtccct gattgctgtc    180
ttccagaagt atgctggaaa ggatggttat aactacactc tctccaagac agagttccta    240
agcttcatga atacagaact agctgccttc acaaagaacc agaaggaccc tggtgtcctt    300
gaccgcatga tgaagaaact ggacaccaac agtgatggtc agctagattt ctcagaattt    360
cttaatctga ttggtggcct agctatggct tgccatgact ccttcctcaa ggctgtccct    420
tcccagaagc ggacctgagg accccttggc cctggccttc aaacccaccc ctttccttc    480 cagccttttct gtcatcatct ccacagccca cccatcccct gagcacacta accacctcat    540
gcaggcccca cctgccaata gtaataaagc aatgtcactt ttttaaaaca tgaaa        595
```

<210> SEQ ID NO 148
<211> LENGTH: 7133
<212> TYPE: DNA
<213> ORGANISM: Homo sapiens

<400> SEQUENCE: 148

-continued

```
aaagtcagag tactgggaga acagaagact tcacaattta atgcctcagt ttttaaaaaa        60
ggatccttac acttcatgtc tcctagccat cagaagagga atgagacagc aaaagttcaa       120
atggcctgtt tcaagtttct gatataaaac gatgacattt tcaggaaaat cctgcatttc       180
cagagagaga ctggctggtt aaatttctga agaggacac cagctaaaag aaggtattgc        240
atctcacccg agcagactgt gtctgtggaa agtgtaagcc ccttgccaga gagcagctt        300
cccagcaaag gcagagggtg aaaacagcaa aggtcttaag acactgggga cctagagtca       360
aaagggacct cctccaggga aaacgctgtg tgagaaatgg cctcattcgg tgactgtgag       420
tgacacagca gaaagttggg tcattccggc tgcttttttg agaagtccct gaagagatca       480
ataacagcaa gagggaacct ggcaaggaag ctattcctat aatccaggaa agagatgagg       540
aaggcttgga ccaggtggta gtggtgtcag gtagtcaaat gctgggtata ttttgaagat       600
acacccata ggatttgctc cacattgaat gtggaatgct ggaagagaga taaagtgtac        660
ctgtcacata cttttttgagt tttatttatt ttcttagaag taagtacaca aagagatgct      720
acctaggaga agggtattct tttcactatt cttttcaaatt ttctgtatgt tcgaacattt     780
tcatagtaga aagttggggg gaaaatctgt ttcataaaca tttcctcagc agcagtccag       840
tctattgcat tttaattggt tgtgatatca ttgttttatg caatacgttc tcaacaagta      900
tatcctccgg caaactgaac aaggaccaag tctgttctgc ctacagctct gcttcctcat      960
agctgctttc cagaacgtga ctcttgcaaa ttatcaagaa aggggaacta atctaaggga     1020
tccagatcaa acagcctcat gaagacttat tttatgtttc taatataaag atagaagttt      1080
tcagaaaagc cctgctacac agaggatcag agcaggggtg ggcctgctgg gctgcagctg      1140
ggattctgag catcctttcc cggaggcacg gaaagtgagt gagtgagccc agtgaggaag     1200
aagttgaagc tttgatatga gtaaacaagt atctctacct gaaatgatta aagactggac      1260
caaagagcat gtgaaaaaat gggtaaatga agaccttaag attaatgagc aatacgggca    1320
aattctgctc agtgaagaag taacaggatt agtcctgcag gaattaactg agaaggacct    1380
tgtagaaatg gggctaccat ggggtccagc acttttgata aaacgttcat acaacaaatt     1440
gaatagtaag tcccctgaaa gtgacaatca tgatccggga caattagata attcaaaacc    1500
gtccaaaaca gaacaccaga aaaatccaaa acacaccaaa aaggaagaag aaaattcaat    1560
gtcatctaat attgattatg atcccagaga gatcagagat atcaaacaag aagaatcaat   1620
tcttatgaaa gaaatgtgt tagatgaagt agcaaatgct aaacacaaga aaaagggtaa     1680
gctaaaacct gaacaattga cttgtatgcc atatcctttt gatcagttcc atgacagcca     1740
tcgctacata gaacattata ctctacaacc tgaaacagga gcactcaatc tcattgatcc      1800
aatacatgag ttcaaagctc tcacaaacac agaaacagcc acggaagtgg acattaagat    1860
gaaattcagc aatgaagtct tccgatttgc atcagcttgt atgaattcac gcaccaatgg    1920
caccatccat tttggagtca aggacaaacc ccatggagaa attgttggtg tgaaaatcac    1980
cagtaaggct gccttcattg accacttcaa tgtaatgatc aaaaagtatt ttgaagaaag   2040
tgagatcaat gaagccaaga agtgtattcg ggagccaagg tttgtggaag tccttctgca    2100
gaacaataca ccatctgaca gatttgtcat tgaagttgat actattccaa acactctctat   2160
atgtaatgat aagtatttct acattcagat gcaaatttgt aaagataaaa tatggaaaca    2220
aaaccaaaat ctttcactgt ttgtaagaga aggggctagc tctagggata tcctggccaa    2280
ttccaagcaa cgggatgtag atttcaaggc atttttacaa aatttaaagt cactggtagc   2340
```

```
atctagaaaa gaggctgaag aagagtatgg aatgaaggca atgaagaagg agagtgaagg    2400
actaaagctg gttaaacttc tcataggaaa ccgagactca ctggataatt catactatga    2460
ctggtacatt cttgtaacaa ataaatgcca tccaaaccaa ataaagcact tagattttt     2520 aaaagaaatt aaatggtttg ctgtgttgga gtttgatcct gaatctatga tcaatggagt    2580
ggtcaaagct tacaaagaaa gtcgggtggc aaaccttcac tttccaaatc aatatgaaga    2640
caagacaact aacatgtggg agaagatttc tactcttaat cttaccaac agcccagctg     2700 gattttctgc aacggcagat cagacctgaa aagcgagaca tataaacctc tagaaccaca    2760
tttatggcag agagaaagag cttcagaagt caggaaacta attttatttc tcacagatga    2820
aaatataatg acaagaggaa aattttggt agtgtttcta ttactctctt cagtggaaag     2880
cccaggagat ccactcattg aaactttctg ggctttctat caagctctca aaggaatgga    2940
aaatatgttg tgtatctctg taaactcaca tatttatcaa cgatggaaag atctactaca    3000
aacaagaatg aagatggaag atgaactaac aaaccacagt atttccactt taatatagaa    3060
actggtaaac agcactatcc ttaaactaaa atcggtgact cggtcatcaa gaaggttttt    3120
gcccgcccgt ggatcttctt cagttatcct agagaaaaag aaagaggatg tcttgactgc    3180
actgaaaatc ctctgtgaaa atgagtgtac agagacagac atcgagaaag acaaatctaa    3240
attcctggag tttaagaaat caaaagaaga acactttat cgaggtggca agtatcctg      3300 gtggaacttc tattttctt ctgaaaacta ttcttcagat tttgttaaaa gggacagtta     3360
tgaaaagctt aaagatttaa tacactgctg ggcagagtct cctaaaccaa tatttgcaaa    3420
aatcatcaat cttatcatc atccaggctg tggaggtacc acactggcta tgcatgttct     3480
ctgggactta aagaaaaact tcagatgtgc tgtgttaaaa acaagacaa ctgattttgc     3540 agaaattgca gagcaagtga tcaatctggt cacctatagg gcaaagagcc atcaggatta    3600
cattcctgtg cttctccttg tggatgattt tgaagaacaa gaaaatgtct actttctaca    3660
aaatgccatc cattccgttt tagcagaaaa ggatttgcga tatgaaaaaa cattggtaat    3720
tatcttaaac tgcatgagat cccggaatcc agatgaaagt gcaaaattgg cagacagtat    3780
tgcactaaat taccaacttt cttccaagga acaaagagct tttggtgcca aactgaagga    3840
aattgaaaag cagcacaaga actgtgaaaa cttttattcc ttcatgatca tgaaaagcaa    3900
ttttgatgaa acatatatag aaaatgtagt caggaatatc ctaaaaggac aggatgttga    3960
cagcaaggaa gcacaactca tttccttcct ggctttactc agctcttatg ttactgactc    4020
tacaatttca gtttcacagt gtgaaatatt tttgggaatc atatacacta gtacaccctg    4080
ggaacctgaa agcttagaag acaagatggg aacttattct acacttctaa taaaaacaga    4140
agttgcagaa tatgggagat acacaggtgt gcgtatcatt caccctctga ttgccctgta    4200
ctgtctaaaa gaactggaaa gaagctatca cttggataaa tgtcaaattg cattgaatat    4260
attagaagag aatttattct atgattctgg aataggaaga acaaatttc aacatgatgt     4320 tcaaactctt ctgcttacaa gacagcgcaa ggtgtatgga gatgaaacag acactctgtt    4380
ttccccatta atggaagctt tacagaataa agacattgaa aaggtcttga gtgcaggaag    4440
tagacgattc ccacaaaatg cattcatttg tcaagcctta gcaagacatt tctacattaa    4500
agagaaggac tttaacacag ctctggactg ggcacgtcag gccaaaatga agcacctaa     4560 aaattcctat atttcagata cactaggtca agtctacaaa agtgaaatca atggtggtt     4620 ggatgggaac aaaaactgta ggagcattac tgttaatgac ctaacacatc tcctagaagc    4680
tgcggaaaaa gcctcaagag cttttcaaga atcccaaagg caaactgata gtaaaaacta    4740
```

```
tgaaaccgag aactggtcac cacagaagtc ccagagacga tatgacatgt ataacacagc    4800
ttgtttcttg ggtgaaatag aagttggtct ttacactatc cagattcttc agctcactcc    4860 cttttttccac aaagaaaatg aattatccaa aaaacatatg gtgcaatttt tatcaggaaa   4920
gtggaccatt cctcctgatc ccagaaatga atgttatttg gctcttagca agttcacatc    4980
ccacctaaaa aatttacaat cagatctgaa aaggtgcttt gactttttta ttgattatat    5040
ggttcttctg aaaatgaggt atcccaaaa agaaattgca gaaatcatgt taagcaagaa     5100
agtcagtcgt tgtttcagga aatacacaga acttttctgt catttggatc catgtctatt    5160
acaaagtaaa gagagtcaat tactccagga ggagaattgc aggaaaaagc tagaagctct    5220
gagagcagat aggtttgctg gactcttgga atatcttaat ccaaactaca aagatgctac    5280
caccatggaa agtatagtga atgaatatgc cttcctactg cagcaaaact caaaaaagcc    5340
catgacaaat gagaaacaaa attccatttt ggccaacatt attctgagtt gtctaaagcc    5400
caactccaag ttaattcaac cacttaccac gctaaaaaaa caactccgag aggtcttgca    5460
atttgtagga ctaagtcatc aatatccagg tccttatttc ttggcctgcc tcctgttctg    5520
gccagaaaat caagagctag atcaagattc caaactaata gaaaagtatg tttcatcctt    5580
aaatagatcc ttcaggggac agtacaagcg catgtgcagg tccaagcagg caagcacact    5640
tttctatctg ggcaaaagga agggtctaaa cagtattgtt cacaaggcca aaatagagca    5700
gtactttgat aaagcacaaa atacaaattc cctctggcac agtggggatg tgtggaaaaa    5760
aaatgaagtc aaagacctcc tgcgtcgtct aactggtcag gctgaaggca agctaatctc    5820
tgtagaatat ggaacagagg aaaaaataaa aataccagta atatctgttt attcaggtcc    5880
actcagaagt ggtaggaaca tagaaagagt gtctttctac ctaggatttt ccattgaagg    5940
ccctctggca tatgatatag aagtaattta agacaataca tcacctgtag ttcaaatacg    6000
tttatttata tctttatgat tttattctct ctctctattc tcatggcact ttcataacat    6060
tatggctaac ctctaattac agattttgct tttgcctccc tgaatgaatt acaagccttt    6120
ttaagatatg aaatatgcct acccgcagag cttggcacaa agtggagtca atctttttaat   6180 gttttaaata tgcattttca gactcaaata attaagaagt tcattgata tccactggtc     6240 acatcataac tgtctatagg gcaataaaat ctgtgttaaa ctcaattgct tttataagtt    6300
ttctaaatta tttcttcact gtgacagcaa agatttaaat aagatgaatg taaaagagaa    6360
agcttattgg actcaaaccc acagatccac accagagttc tatttacctc atcttggtat    6420
caataaaaac ttatgtggaa ggtaaatata ttgttcccca tccaccacat aacactctcc    6480
ccaacacaca cacacacaca cacacacaca cacacacaca cacacactcc ttgtacccct    6540
tgcccttctc ccagctcatt gctccaggag agagaagagt tcaaaaaata aagtaatcat    6600
aaacttgaac tctctccatt ctcttgttcc catttacagg tgaatctctt cctttaagcc    6660
atttttgtct cctgtgaata cagccttatc tccacctgtt tcttagatcc catctcccct    6720
ggcttatttt ttccattcat taccctcttt gttcccttta cttctcaacc tgtgctatat    6780
acatgctgtt ctctctgttg agattgcctt atttccatct aacattctct ctcctgctat    6840
tctgatttgt cattcacaac tgatttcaag agtcaccttc accaggaagt cttccttgac    6900
caccatcatt cctgcctgat tagagggctt cctcatggta atatgtgttc tcaagttttc    6960
agtgtcaagg aatgccatcc cagaagctca ttctcagatg cacaacagcc agaacagtct    7020
caagcagcat tctagagctt ggaatttaag aactacgcat tgcctataaa gtgaaacata    7080
```

```
ggctaatata gattaaattg aatattgaat aaaaaatata tttatttatc cac         7133

<210> SEQ ID NO 149
<211> LENGTH: 4326
<212> TYPE: DNA
<213> ORGANISM: Homo sapiens

<400> SEQUENCE: 149
gctgagcgcg gagccgcccg gtgattggtg ggggcggaag ggggccgggc gccagcgctg   60
ccttttctcc tgccgggtag tttcgctttc ctgcgcagag tctgcggagg ggctcggctg  120
caccgggggg atcgcgcctg gcagacccca gaccgagcag aggcgaccca gcgcgctcgg  180
gagaggctgc accgccgcgc ccccgcctag cccttccgga tcctgcgcgc agaaaagttt  240
catttgctgt atgccatcct cgagagctgt ctaggttaac gttcgcactc tgtgtatata  300
acctcgacag tcttggcacc taacgtgctg tgcgtagctg ctcctttggt tgaatcccca  360
ggcccttgtt ggggcacaag gtggcaggat gtctcagtgg tacgaacttc agcagcttga  420
ctcaaaattc ctggagcagg ttcaccagct ttatgatgac agttttccca tggaaatcag  480
acagtacctg gcacagtggt tagaaaagca agactgggag cacgctgcca atgatgtttc  540
atttgccacc atccgttttc atgacctcct gtcacagctg gatgatcaat atagtcgctt  600
ttctttggag aataacttct tgctacagca taacataagg aaaagcaagc gtaatcttca  660
ggataatttt caggaagacc caatccagat gtctatgatc atttacagct gtctgaagga  720
agaaaggaaa attctggaaa acgcccagag atttaatcag gctcagtcgg ggaatattca  780
gagcacagtg atgttagaca aacagaaaga gcttgacagt aaagtcagaa atgtgaagga  840
caaggttatg tgtatagagc atgaaatcaa gagcctggaa gatttacaag atgaatatga  900
cttcaaatgc aaaaccttgc agaacagaga cacgagacc aatggtgtgg caaagagtga  960
tcagaaacaa gaacagctgt tactcaagaa gatgtatttta atgcttgaca ataagagaaa  1020
ggaagtagtt cacaaaataa tagagttgct gaatgtcact gaacttaccc agaatgccct  1080
gattaatgat gaactagtgg agtggaagcg gagacagcag agcgcctgta ttgggggggcc  1140 gcccaatgct tgcttggatc agctgcagaa ctggttcact atagttgcgg agagtctgca  1200
gcaagttcgg cagcagctta aaagttggag ggaattggaa cagaaatacc ctacgaaca  1260 tgaccctatc acaaaaaaca aacaagtgtt atgggaccgc accttcagtc ttttccagca  1320
gctcattcag agctcgtttg tggtggaaag acagccctgc atgccaacgc accctcagag  1380
gccgctggtc ttgaagacag gggtccagtt cactgtgaag ttgagactgt tggtgaaatt  1440
gcaagagctg aattataatt tgaaagtcaa agtcttattt gataaagatg tgaatgagag  1500
aaatacagta aaaggattta ggaagttcaa cattttgggc acgcacacaa agtgatgaa  1560 catggaggag tccaccaatg gcagtctggc ggctgaattt cggcacctgc aattgaaaga  1620
acagaaaaat gctggcacca gaacgaatga gggtcctctc atcgttactg aagagcttca  1680
ctcccttagt tttgaaaccc aattgtgcca gcctggtttg gtaattgacc tcgagacgac  1740
ctctctgccc gttgtggtga tctccaacgt cagccagctc ccgagcggtt gggcctccat  1800
cctttggtac aacatgctgg tggcggaacc caggaatctg tccttcttcc tgactccacc  1860
atgtgcacga tgggctcagc tttcagaagt gctgagttgg cagttttctt ctgtcaccaa  1920
aagaggtctc aatgtggacc agctgaacat gttgggagag aagcttcttg gtcctaacgc  1980
cagccccgat ggtctcattc cgtggacgag gttttgtaag gaaaatataa atgataaaaa  2040
tttccccttc tggctttgga ttgaaagcat cctagaactc attaaaaaac acctgctccc  2100
```

```
tctctggaat gatgggtgca tcatgggctt catcagcaag gagcgagagc gtgccctgtt    2160
gaaggaccag cagccgggga ccttcctgct gcggttcagt gagagctccc gggaaggggc    2220
catcacattc acatgggtgg agcggtccca gaacggaggc gaacctgact tccatgcggt    2280
tgaaccctac acgaagaaag aactttctgc tgttactttc cctgacatca ttcgcaatta    2340
caaagtcatg gctgctgaga atattcctga gaatccctg aagtatctgt atccaaatat    2400
tgacaaagac catgcctttg gaaagtatta ctccaggcca aaggaagcac cagagccaat    2460
ggaacttgat ggccctaaag gaactggata tatcaagact gagttgattt ctgtgtctga    2520
agttcaccct tctagacttc agaccacaga caacctgctc cccatgtctc ctgaggagtt    2580
tgacgaggtg tctcggatag tgggctctgt agaattcgac agtatgatga acacagtata    2640
gagcatgaat ttttttcatc ttctctggcg acagttttcc ttctcatctg tgattccctc    2700
ctgctactct gttccttcac atcctgtgtt tctagggaaa tgaaagaaag gccagcaaat    2760
tcgctgcaac ctgttgatag caagtgaatt tttctctaac tcagaaacat cagttactct    2820
gaagggcatc atgcatctta ctgaaggtaa aattgaaagg cattctctga agagtgggtt    2880
tcacaagtga aaacatcca gatacaccca agtatcagg acgagaatga gggtcctttg    2940
ggaaaggaga agttaagcaa catctagcaa atgttatgca taaagtcagt gcccaactgt    3000
tataggttgt tggataaatc agtggttatt tagggaactg cttgacgtag gaacggtaaa    3060
tttctgtggg agaattctta catgtttct ttgctttaag tgtaactggc agttttccat    3120
tggtttacct gtgaaatagt tcaaagccaa gtttatatac aattatatca gtcctctttc    3180
aaaggtagcc atcatggatc tggtaggggg aaaatgtgta ttttattaca tctttcacat    3240
tggctattta aagacaaaga caaattctgt tccttgagaa gagaatatta gctttactgt    3300
ttgttatggc ttaatgacac tagctaatat caatagaagg atgtacattt ccaaattcac    3360
aagttgtgtt tgatatccaa agctgaatac attctgcttt catcttggtc acatacaatt    3420 attttttacag ttctcccaag ggagttaggc tattcacaac cactcattca aaagttgaaa    3480
ttaaccatag atgtagataa actcagaaat ttaattcatg tttcttaaat gggctacttt    3540 gtccttttttg ttattagggt ggtatttagt ctattagcca caaaattggg aaaggagtag    3600
aaaaagcagt aactgacaac ttgaataata caccagagat aatatgagaa tcagatcatt    3660
tcaaaactca tttcctatgt aactgcattg agaactgcat atgtttcgct gatatatgtg    3720
tttttcacat ttgcgaatgg ttccattctc tctcctgtac ttttttccaga cacttttttg    3780 agtggatgat gtttcgtgaa gtatactgta ttttaccctt tttccttcct tatcactgac    3840
acaaaaagta gattaagaga tgggtttgac aaggttcttc cctttacat actgctgtct    3900 atgtggctgt atcttgtttt tccactactg ctaccacaac tatattatca tgcaaatgct    3960
gtattcttct ttggtggaga taaagatttc ttgagttttg ttttaaaatt aaagctaaag    4020
tatctgtatt gcattaaata taatatgcac acagtgcttt ccgtggcact gcatacaatc    4080
tgaggcctcc tctctcagtt tttatataga tggcgagaac ctaagtttca gttgatttta    4140
caattgaaat gactaaaaaa caagaagac aacattaaaa caatattgtt tctaattgct    4200
gaggtttagc tgtcagttct ttttgccctt tgggaattcg gcatggtttc attttactgc    4260
actagccaag agactttact tttaagaagt attaaaattc taaaattcaa aaaaaaaaaa    4320
aaaaaa                                                               4326
```

<210> SEQ ID NO 150

<211> LENGTH: 5891
<212> TYPE: DNA
<213> ORGANISM: Homo sapiens

<400> SEQUENCE: 150

```
aattgtattt ccgttcattt acaagttatt ttctcttctt ctgaaaaaga gatcttgaat      60
ttggactcat atcaagatgc tctgaagaag aacaacccct taggatagcc actgcaacat     120
catgaccaaa gacaagaac ctattgttaa aagcttccat tttgtttgcc ttatgatcat      180
aatagttgga accagaatcc agttctccga cggaaatgaa tttgcagtag acaagtcaaa     240
aagaggtctt attcatgttc caaaagacct accgctgaaa accaaagtct tagatatgtc     300
tcagaactac atcgctgagc ttcaggtctc tgacatgagc tttctatcag agttgacagt     360
tttgagactt tcccataaca gaatccagct acttgattta agtgttttca gttcaacca     420
ggatttagaa tatttggatt tatctcataa tcagttgcaa aagatatcct gccatcctat     480
tgtgagtttc aggcatttag atctctcatt caatgatttc aaggccctgc ccatctgtaa     540
ggaatttggc aacttatcac aactgaattt cttgggattg agtgctatga agctgcaaaa     600
attagatttg ctgccaattg ctcacttgca tctaagttat atccttctgg atttaagaaa     660
ttattatata aagaaaatg agacagaaag tctacaaatt ctgaatgcaa aaacccttca     720
ccttgttttt cacccaacta gtttattcgc tatccaagtg aacatatcag ttaatacttt     780
agggtgctta caactgacta atattaaatt gaatgatgac aactgtcaag ttttcattaa     840
attttatca gaactcacca gaggttcaac cttactgaat tttaccctca accacataga     900
aacgacttgg aaatgcctgg tcagagtctt tcaattctt tggcccaaac ctgtggaata     960
tctcaatatt tacaatttaa caataattga agcattcgt gaagaagatt ttacttattc    1020
taaaacgaca ttgaaagcat tgacaataga acatatcacg aaccaagttt ttctgttttc    1080
acagacagct ttgtacaccg tgttttctga gatgaacatt atgatgttaa ccatttcaga    1140
tacaccttt atacacatgc tgtgtcctca tgcaccaagc acattcaagt ttttgaactt    1200
tacccagaac gttttcacag atagtatttt tgaaaaatgt tccacgttag ttaaattgga    1260
gacacttatc ttacaaaaga atggattaaa agacctttc aaagtaggtc tcatgacgaa    1320
ggatatgcct tctttggaaa tactggatgt tagctggaat tctttggaat ctggtagaca    1380
taaagaaaac tgcacttggg ttgagagtat agtggtgtta aatttgtctt caaatatgct    1440
tactgactct gttttcagat gtttacctcc caggatcaag gtacttgatc ttcacagcaa    1500
taaaataaag agcgttccta aacaagtcgt aaaactggaa gctttgcaag aactcaatgt    1560
tgctttcaat tctttaactg accttcctgg atgtggcagc tttagcagcc tttctgtatt    1620
gatcattgat cacaattcag tttcccaccc atcggctgat ttcttccaga gctgccagaa    1680
gatgaggtca ataaaagcag gggacaatcc attccaatgt acctgtgagc taagagaatt    1740
tgtcaaaaat atagaccaag tatcaagtga agtgttagag ggctggcctg attcttataa    1800
gtgtgactac ccagaaagtt atagaggaag cccactaaag gactttcaca tgtctgaatt    1860
atcctgcaac ataactctgc tgatcgtcac catcggtgcc accatgctgg tgttggctgt    1920
gactgtgacc tccctctgca tctacttgga tctgccctgg tatctcagga tggtgtgcca    1980
gtggaccag actcggcgca gggccaggaa catacccta gaagaactcc aaagaaacct    2040
ccagttcat gcttttattt catatagtga acatgattct gcctgggtga aagtgaatt    2100
ggtaccttac ctagaaaaag aagatataca gatttgtctt catgagagaa ctttgtccc    2160
tggcaagagc attgtggaaa atatcatcaa ctgcattgag aagagttaca gtccatctt    2220
```

```
tgttttgtct cccaactttg tccagagtga gtggtgccat tacgaactct attttgccca    2280
tcacaatctc tttcatgaag gatctaataa cttaatcctc atcttactgg aacccattcc    2340
acagaacagc attcccaaca agtaccacaa gctgaaggct ctcatgacgc agcggactta    2400
tttgcagtgg cccaaggaga aaagcaaacg tgggctcttt tgggctaaca ttagagccgc    2460
ttttaatatg aaattaacac tagtcactga aaacaatgat gtgaaatctt aaaaaaattt    2520
aggaaattca acttaagaaa ccattattta cttggatgat ggtgaatagt acagtcgtaa    2580
gtaactgtct ggaggtgcct ccattatcct catgccttca ggaaagactt aacaaaaaca    2640
atgtttcatc tggggaactg agctaggcgg tgaggttagc ctgccagtta gagacagccc    2700
agtctcttct ggtttaatca ttatgtttca aattgaaaca gtctcttttg agtaaatgct    2760 cagttttttca gctcctctcc actctgcttt cccaaatgga ttctgttgtg agcaagagtt    2820
tatatggctt catggcagca agggaacagt caacttcagc atcatatgca ccagtcctcg    2880
gagtgccctg tgaatcatat tggtctttgg gtcagtgtca tcattctctt caagtctggg    2940
gcttggggaa aaaattagat cagctacggc atataaaaaa gtcttttgtt tcacatatgt    3000
gtaatagctt atttaatttt ttatcctgct acacaaatat gtaattaacc aatgaggact    3060
catgacttga tagtgtatgt atgtaaaggg atatatggac ttaatcataa gctgttgagg    3120
tgaaagacgt ggatccacct gctttccaag aaaactcggc caaatttatt tgcagctgga    3180
tattgaatgg gacttttctg gttgtcttag aattctggct aaaggctcaa agctgacgaa    3240
agacagtaac tgcaccaaca tgatactaga cacagccagt ctggacttat caaaagagca    3300
gaaagagacc aatgactccc agtccgtatt atccatctct agaagactag agtcaaaagc    3360
gtgattaaag agtcattaag cggaggttct aggccatagg gagattgctt tgaatttctt    3420
gcagacaagt gtgagggact cagcatggta gaaggtagcc tggcatccca ctccaagact    3480
gaaagcttgc agagtaacag gagcacacag gttcagtgca gcagatgtgg tgtggcttga    3540
gaattcttgg aagagcttga tgagtgtttg ctggagtccg agggtgggca ctgggaacac    3600
agagactggt aaatagtgtt tggcaaatac aagtgcttga tgaatatttg ttgaatgaat    3660
agatgagttc ttccccccctg gggaattcag gaggtgaaag gttggcttga gcacccaaaa    3720
tggcaggatg agagaagaga agcactgata gcaacctgcc ctcccattat tgacatggta    3780
aaaggatgtg aatttcttca catggctttg actatgaagt agtagctggg cttgcattgt    3840
catgacggga tatcagccaa cagggtagcc tgttgtgcaa agaaactata gcagtaagag    3900
gacacggggt taggcagaag aggggtttgg ggtggaggtt gctgcaagag gtcagccaga    3960
taatgtggcc ctgcatcatg gaactgtgca atgtggggta cactcaaggc cctccaataa    4020
ctcacagatg tgcccctatga aaaagccagc atttggactc tgccatagca gctggcagga    4080
tcatgctggc ctgtctgcct tattcaatag ttaactacag gaagatctgc tcctctttgt    4140 gtaatacccct cttcccttgc aatggcatag ggacatctag aatatagaga agacagagac    4200
aatggaggaa gagtaaagaa actgactata tgccttcgtc atttcactgc aaggaaggcc    4260
aagcagattt ttgaatgagg tgtgagattg ctgttaaatt ggactggcct ggacatttta    4320
atcccttaaa tagaggtgca atgactaaag tgagatttgt cactaaaatt tatggtatct    4380
gcccaagatt caggagtgat gatgggagga gatccaacag aactttgttg taaggcaatg    4440
gttagagaaa aatgaagccc tcgctttctg gacttagttc attcaataaa ccagtttcgg    4500
ccaggcacgt tggctcacat ctataatccc agtactgtgg gaggctgagg caggtggatc    4560
```

| | |
|---|---|
| acttgaggtc aggagttcga gaccagcctg gccaacatgg tgaaaccctg tctgtactaa | 4620 |
| aaatacaaaa attagccggg tgtggtggtg tgcacctgta gtcccagcta ctcgggaggc | 4680 |
| tgaggcagga aaatcacttg aacctgggag acagaggctg tagtgagctg agacagcgct | 4740 |
| actgtactcc ccgctgggca acagagtgag actccatctc aaaaaagtta aagaaaaaa | 4800 |
| aatctggttt cataatagct gtaacgaaat aagccttaat gatattttat tagcatcatc | 4860 |
| ttctgtctgc attagccctt ccttgctctt caggagaaca catttgtttt cctccctag | 4920 |
| gctctatccc aaacggcaca ttcttccaca acccctgttg aacagatttt ttaaactgtt | 4980 |
| gcctaatcta aaaacaataa aaacaacaaa caaccacagt aacaacaacg acaaaaaaaa | 5040 |
| ctgccacaga ttctaaataa tcagatcttt ttaaatggta tcaatgtttc ccacaaaata | 5100 |
| ttgttgacat tgaaaatata gaattttagc attaattttg ttaaacctac atccctcgg | 5160 |
| cagaggggcc tccctgcatc ccagtggaaa gtaggttcct cacagtcctc tccgtcacat | 5220 |
| tcttcccatt tcttttcttc acagaacaca tcactgtcta aaattatctt gtttgcttag | 5280 |
| ttgcttactc atcttcttct tctctcctct gaagtctaag ctccaggaaa aagggagact | 5340 |
| tctccacctg ttccctgcct ctccccagtg ccgaggggac actgtgcacc ccattgtaga | 5400 |
| tgcgcagtaa aaactcgtgg gatgagcaaa tgactctgaa acggtcccat gcgggaaatg | 5460 |
| tccatgaagt cctggatttt atctaaaaag cccaggcagg ggggggcggg ggcggcgggg | 5520 |
| ctacagttcc acgctgagct gcctcctggc cgctcgtccc cgccgcagtg cctgggcggc | 5580 |
| ccgggcgccc gaccttggcc gtggacacct tcgcggtggg tgctgctcct ccccatctgc | 5640 |
| cactggaaga tgctggggcg acccggctcc aggtttagca ggacactgag aaaagggaat | 5700 |
| ggctgccttt cggaggctgg gtgagccctt ctctgtgcct cacctgcccg ccccacagcg | 5760 |
| gccctgcacc tcgtcccacg gggcccattg ccccggtagg atgcgcgctt ttgttttgag | 5820 |
| ggtcaggcat cttccctgcc gtcgtttctg ggaggttgaa aaattgatcc agaaagacct | 5880 |
| aaaacaaaaa a | 5891 |

<210> SEQ ID NO 151
<211> LENGTH: 2884
<212> TYPE: DNA
<213> ORGANISM: Homo sapiens

<400> SEQUENCE: 151

| | |
|---|---|
| tcgattctca agagggtttc attggtctca acctggcccc ccaggcaacc caccctgat | 60 |
| tggacagtct catcaagaag gttggtcaag agctcaagtg tttctgagaa tctgggtgat | 120 |
| ttataagaaa cccttagctg aatgcagggt ggggagaacg aaagacaaaa gcatcttttt | 180 |
| tcagaaggga aactgaaaga agagggaa gagtattaaa gaccatttct ggctgggcag | 240 |
| ggcactctca gcagctcaac tgcccagcgt gaccagtggc cacctctgca gtgtcttcca | 300 |
| caacctggtc ttgactcgtc tgctgaacaa atcctctgac ctcaggccgg ctgtgaacgt | 360 |
| agttcctgag agatagcaaa catgcccaac agtgagcccg catctctgct ggagctgttc | 420 |
| aacagcatcg ccacacaagg ggagctcgta aggtccctca agcgggaaa tgcgtcaaag | 480 |
| gatgaaattg attctgcagt aaagatgttg gtgtcattaa aaatgagcta caaagctgcc | 540 |
| gcggggagg attacaaggc tgactgtcct ccagggaacc cagcacctac cagtaatcat | 600 |
| ggcccagatg ccacagaagc tgaagaggat tttgtggacc catggacagt acagacaagc | 660 |
| agtgcaaaag gcatagacta cgataagctc attgttcggt ttggaagtag taaaattgac | 720 |
| aaagagctaa taaaccgaat agagagagcc accggccaaa gaccacacca cttcctgcgc | 780 |

```
agaggcatct tcttctcaca cagagatatg aatcaggttc ttgatgccta tgaaaataag    840
aagccatttt atctgtacac gggccggggc ccctcttctg aagcaatgca tgtaggtcac    900
ctcattccat ttattttcac aaagtggctc caggatgtat ttaacgtgcc cttggtcatc    960
cagatgacgg atgacgagaa gtatctgtgg aaggacctga ccctggacca ggcctatagc   1020
tatgctgtgg agaatgccaa ggacatcatc gcctgtggct ttgacatcaa caagactttc   1080
atattctctg acctggacta catggggatg agctcaggtt tctacaaaaa tgtggtgaag   1140
attcaaaagc atgttacctt caaccaagtg aaaggcattt tcggcttcac tgacagcgac   1200
tgcattggga gatcagtttt tcctgccatc caggctgctc cctccttcag caactcattc   1260
ccacagatct tccgagacag gacggatatc cagtgcctta tcccatgtgc cattgaccag   1320
gatccttact ttagaatgac aagggacgtc gcccccagga tcggctatcc taaaccagcc   1380
ctgctgcact ccaccttctt cccagccctg cagggcgccc agaccaaaat gagtgccagc   1440
gaccccaact cctccatctt cctcaccgac acggccaagc agatcaaaac caaggtcaat   1500
aagcatgcgt tttctggagg gagagacacc atcgaggagc acaggcagtt tgggggcaac   1560
tgtgatgtgg acgtgtcttt catgtacctg accttcttcc tcgaggacga cgacaagctc   1620
gagcagatca ggaaggatta ccagcggga gccatgctca ccggtgagct caagaaggca   1680
ctcatagagt tctgcagcc cttgatcgca gagcaccagg cccggcgcaa ggaggtcacg   1740
gatgagatag tgaaagagtt catgactccc cggaagctgt ccttcgactt tcagtagcac   1800
tcgttttaca tatgcttata aagaagtga tgtatcagta atgtatcaat aatcccagcc   1860
cagtcaaagc accgccacct gtaggcttct gtctcatggt aattactggg cctggcctct   1920
gtaagcctgt gtatgttatc aatactgttt cttcctgtga gttccattat ttctatctct   1980
tatgggcaaa gcattgtggg taattggtgc tggctaacat tgcatggtcg atagagaag   2040 tccagctgtg agtctctccc caaagcagcc ccacagtgga gcctttggct ggaagtccat   2100
gggccaccct gttcttgtcc atggaggact ccgagggttc caagtatact cttaagaccc   2160
actctgttta aaaatatata ttctatgtat gcgtatatgg aattgaaatg tcattattgt   2220
aacctagaaa gtgctttgaa atattgatgt ggggaggttt attgagcaca agatgtatt   2280 cagcccatgc ccctcccaa aaagaaattg ataagtaaaa gcttcgttat acatttgact   2340
aagaaatcac ccagctttaa agctgctttt aacaatgaag attgaacaga gttcagcaat   2400
tttgattaaa ttaagacttg ggggtgaaac tttccagttt actgaactcc agaccatgca   2460
tgtagtccac tccagaaatc atgctcgctt cccttggcac accagtgttc tcctgccaaa   2520
tgaccctaga ccctctgtcc tgcagagtca gggtggcttt tcccctgact gtgtccgatg   2580
ccaaggagtc ctggcctccg cagatgcttc attttgaccc ttggctgcag tggaagtcag   2640
cacagagcag tgccctggct gtgtccctgg acgggtggac ttagctaggg agaaagtcga   2700
ggcagcagcc ctcgaggccc tcacagatgt ctaggcaggc ctcatttcat cacgcagcat   2760
gtgcaggcct ggaagagcaa agccaaatct cagggaagtc cttggttgat gtatctgggt   2820
ctcctctgga gcactctgcc ctcctgtcac ccagtagagt aaataaactt ccttggctcc   2880
tgct                                                                2884
```

<210> SEQ ID NO 152
<211> LENGTH: 2387
<212> TYPE: DNA
<213> ORGANISM: Homo sapiens

<400> SEQUENCE: 152

```
agacacctct gccctcacca tgagcctctg gcagcccctg gtcctggtgc tcctggtgct    60
gggctgctgc tttgctgccc ccagacagcg ccagtccacc cttgtgctct tccctggaga   120
cctgagaacc aatctcaccg acaggcagct ggcagaggaa tacctgtacc gctatggtta   180
cactcgggtg gcagagatgc gtggagagtc gaaatctctg gggcctgcgc tgctgcttct   240
ccagaagcaa ctgtccctgc ccgagaccgg tgagctggat agcgccacgc tgaaggccat   300
gcgaacccca cggtgcgggg tcccagacct gggcagattc caaacctttg agggcgacct   360
caagtggcac caccacaaca tcacctattg gatccaaaac tactcggaag acttgccgcg   420
ggcggtgatt gacgacgcct tgcccgcgc cttcgcactg tggagcgcgg tgacgccgct   480
caccttcact cgcgtgtaca gccgggacgc agacatcgtc atccagtttg gtgtcgcgga   540
gcacggagac gggtatccct tcgacgggaa ggacgggctc ctggcacacg cctttcctcc   600
tggccccggc attcagggag acgcccattt cgacgatgac gagttgtggt ccctgggcaa   660
gggcgtcgtg gttccaactc ggtttggaaa cgcagatggc gcggcctgcc acttcccctt   720
catcttcgag ggccgctcct actctgcctg caccaccgac ggtcgctccg acggcttgcc   780
ctggtgcagt accacggcca actacgacac cgacgaccgg tttggcttct gccccagcga   840
gagactctac acccaggacg gcaatgctga tgggaaaccc tgccagtttc cattcatctt   900
ccaaggccaa tcctactccg cctgcaccac ggacggtcgc tccgacggct accgctggtg   960
cgccaccacc gccaactacg accgggacaa gctcttcggc ttctgcccga cccgagctga  1020
ctcgacggta tgggggggca actcggcggg ggagctgtgc gtcttcccct tcactttcct  1080
gggtaaggag tactcgacct gtaccagcga gggccgcgga gatgggcgcc tctggtgcgc  1140
taccacctcg aactttgaca gcgacaagaa gtggggcttc tgcccggacc aaggatacag  1200
tttgttcctc gtggcggcgc atgagttcgg ccacgcgctg gcttagatc attcctcagt  1260
gccggaggcg ctcatgtacc ctatgtaccg cttcactgag ggccccccct tgcataagga  1320
cgacgtgaat ggcatccggc acctctatgg tcctcgccct gaacctgagc cacggcctcc  1380
aaccaccacc acaccgcagc ccacggctcc ccgacggtc tgccccaccg accccccac   1440
tgtccacccc tcagagcgcc ccacagctgg ccccacaggt cccccctcag ctggccccac  1500
aggtccccc actgctggcc cttctacggc cactactgtg cctttgagtc cggtggacga  1560
tgcctgcaac gtgaacatct tcgacgccat cgcggagatt gggaaccagc tgtatttgtt  1620
caaggatggg aagtactggc gattctctga gggcaggggg agccggccgc agggccccct  1680
ccttatcgcc gacaagtggc ccgcgctgcc ccgcaagctg gactcggtct ttgaggagcg  1740
gctctccaag aagctttttct tcttctctgg gcgccaggtg tgggtgtaca caggcgcgtc  1800
ggtgctgggc ccgaggcgtc tggacaagct gggcctggga gccgacgtgg cccaggtgac  1860
cggggccctc cggagtggca gggggaagat gctgctgttc agcgggcggc gcctctggag  1920
gttcgacgtg aaggcgcaga tggtggatcc ccggagcgcc agcgaggtgg accggatgtt  1980
ccccgggggtg cctttggaca cgcacgacgt cttccagtac cgagagaaag cctatttctg  2040
ccaggaccgt tctactggc gcgtgagttc ccggagtgag ttgaaccagg tggaccaagt  2100
gggctacgtg acctatgaca tcctgcagtg ccctgaggac tagggctccc gtcctgcttt  2160
ggcagtgcca tgtaaatccc cactgggacc aaccctgggg aaggagccag tttgccggat  2220
acaaactggt attctgttct ggaggaaagg gaggagtgga ggtgggctgg gccctctctt  2280
ctcacctttg ttttttgttg gagtgtttct aataaacttg gattctctaa cctttaaaaa  2340
```

| | |
|---|---|
| aaaaaaaaaa aaaaaaaaaa aaaaaaaaaa aaaaaaaaaa aaaaaaa | 2387 |

<210> SEQ ID NO 153
<211> LENGTH: 7544
<212> TYPE: DNA
<213> ORGANISM: Homo sapiens

<400> SEQUENCE: 153

| | |
|---|---|
| gcggccgggc cgggccgcgg gagcaggcgg aggcggaggc ggcggggggca ggaggatgtc | 60 |
| gcagccgccg ctgctccccg cctcggcgga gactcggaag ttcacccggg cgctgagtaa | 120 |
| gccgggcacg gcgccgagc tgcggcagag cgtgtctgag gtggtgcgcg gctccgtgct | 180 |
| cctggcaaag ccaaagctaa ttgagccact cgactatgaa aatgtcatcg tccagaagaa | 240 |
| gactcagatc ctgaacgact gtttacggga gatgctgctc ttcccttacg atgactttca | 300 |
| gacggccatc ctgagacgac agggtcgata catatgctca acagtgcctg cgaaggcgga | 360 |
| agaggaagca cagagcttgt tgttacaga gtgcatcaaa acctataact ctgactggca | 420 |
| tcttgtgaac tataaatatg aagattactc aggagagttt cgacagcttc cgaacaaagt | 480 |
| ggtcaagttg gataaacttc cagttcatgt ctatgaagtt gacgaggagg tcgacaaaga | 540 |
| tgaggatgct gcctcccttg gttcccagaa gggtgggatc accaagcatg gctggctgta | 600 |
| caaaggcaac atgaacagtg ccatcagcgt gaccatgagg tcatttaaga gacgattttt | 660 |
| ccacctgatt caacttggcg atggatccta taatttgaat ttttataaag atgaaaagat | 720 |
| ctccaaagaa ccaaaaggat caatatttct ggattcctgt atgggtgtcg ttcagaacaa | 780 |
| caaagtcagg cgttttgctt ttgagctcaa gatgcaggac aaaagtagtt atctcttggc | 840 |
| agcagacagt gaagtggaaa tggaagaatg gatcacaatt ctaaataaga tcctccagct | 900 |
| caactttgaa gctgcaatgc aagaaaagcg aaatggcgac tctcacgaag atgatgaaca | 960 |
| aagcaaattg gaaggttctg gttccggttt agatagctac ctgccggaac ttgccaagag | 1020 |
| tgcaagagaa gcagaaatca aactgaaaag tgaaagcaga gtcaaacttt tttatttgga | 1080 |
| cccagatgcc cagaagcttg acttctcatc agctgagcca gaagtgaagt catttgaaga | 1140 |
| gaagtttgga aaaaggatcc ttgtcaagtg caatgattta tctttcaatt tgcaatgctg | 1200 |
| tgttgccgaa aatgaagaag gacccactac aaatgttgaa cctttctttg ttactctatc | 1260 |
| cctgtttgac ataaaataca accggaagat ttctgccgat ttccacgtag acctgaacca | 1320 |
| tttctcagtg aggcaaatgc tcgccaccac gtccccggcg ctgatgaatg cagtgggca | 1380 |
| gagcccatct gtcctcaagg gcatccttca tgaagccgcc atgcagtatc cgaagcaggg | 1440 |
| aatattttca gtcacttgtc ctcatccaga tatatttctt gtggccagaa ttgaaaaagt | 1500 |
| ccttcagggg agcatcacac attgcgctga gccatatatg aaaagttcag actcttctaa | 1560 |
| ggtggcccag aaggtgctga agaatgccaa gcaggcatgc aaagactag gacagtatag | 1620 |
| aatgccattt gcttgggcag caaggacatt gtttaaggat gcatctggaa atcttgacaa | 1680 |
| aaatgccaga ttttctgcca tctacaggca agacagcaat aagctatcca atgatgacat | 1740 |
| gctcaagtta cttgcagact ttcggaaacc tgagaagatg gctaagctcc cagtgatttt | 1800 |
| aggcaatcta gacattacaa ttgataatgt ttcctcagac ttccctaatt atgttaattc | 1860 |
| atcatacatt cccacaaaac aatttgaaac ctgcagtaaa actcccatca cgtttgaagt | 1920 |
| ggaggaattt gtgccctgca taccaaaaca cactcagcct tacaccatct acaccaatca | 1980 |
| cctttacgtt tatcctaagt acttgaaata cgacagtcag aagtctttg ccaaggctag | 2040 |

```
aaatattgcg atttgcattg aattcaaaga ttcagatgag gaagactctc agccccttaa    2100
gtgcatttat ggcagacctg gtgggccagt tttcacaaga agcgcctttg ctgcagtttt    2160
acaccatcac caaaacccag aattttatga tgagattaaa atagagttgc ccactcagct    2220
gcatgaaaag caccacctgt tgctcacatt cttccatgtc agctgtgaca actcaagtaa    2280
aggaagcacg aagaagaggg atgtcgttga aacccaagtt ggctactcct ggcttcccct    2340
cctgaaagac ggaagggtgg tgacaagcga gcagcacatc ccggtctcgg cgaaccttcc    2400
ttcgggctat cttggctacc aggagcttgg gatgggcagg cattatggtc cggaaattaa    2460
atgggtagat ggaggcaagc cactgctgaa aatttccact catctggttt ctacagtgta    2520
tactcaggat cagcatttac ataatttttt ccagtactgt cagaaaaccg aatctggagc    2580
ccaagcctta ggaaacgaac ttgtaaagta ccttaagagt ctgcatgcga tggaaggcca    2640
cgtgatgatc gccttcttgc ccactatcct aaaccagctg ttccgagtcc tcaccagagc    2700
cacacaggaa gaagtcgcgg ttaacgtgac tcgggtcatt attcatgtgg ttgcccagtg    2760
ccatgaggaa ggattggaga gccacttgag gtcatatgtt aagtacgcgt ataaggctga    2820
gccatatgtt gcctctgaat acaagacagt gcatgaagaa ctgaccaaat ccatgaccac    2880
gattctcaag ccttctgccg atttcctcac cagcaacaaa ctactgaagt actcatggtt    2940
tttctttgat gtactgatca aatctatggc tcagcatttg atagagaact ccaaagttaa    3000
gttgctgcga aaccagagat ttcctgcatc ctatcatcat gcagtggaaa ccgttgtaaa    3060
tatgctgatg ccacacatca ctcagaagtt tcgagataat ccagaggcat ctaagaacgc    3120
gaatcatagc cttgctgtct tcatcaagag atgtttcacc ttcatggaca ggggctttgt    3180
cttcaagcag atcaacaact acattagctg ttttgctcct ggagacccaa agaccctctt    3240
tgaatacaag tttgaatttc tccgtgtagt gtgcaaccat gaacattata ttccgttgaa    3300
cttaccaatg ccatttggaa aaggcaggat tcaaagatac caagacctcc agcttgacta    3360
ctcattaaca gatgagttct gcagaaaacca cttcttggtg ggactgttac tgagggaggt    3420
ggggacagcc ctccaggagt tccgggaggt ccgtctgatc gccatcagtg tgctcaagaa    3480
cctgctgata aagcattctt ttgatgacag atatgcttca aggagccatc aggcaaggat    3540
agccacccct cacctgcctc tgtttggtct gctgattgaa aacgtccagc ggatcaatgt    3600
gagggatgtg tcacccttcc ctgtgaacgc gggcatgact gtgaaggatg aatccctggc    3660
tctaccagct gtgaatccgc tggtgacgcc gcagaaggga agcaccctgg acaacagcct    3720
gcacaaggac ctgctgggcg ccatctccgg cattgcttct ccatatacaa cctcaactcc    3780
aaacatcaac agtgtgagaa atgctgattc gagaggatct ctcataagca cagattcggg    3840
taacagcctt ccagaaagga atagtgagaa gagcaattcc ctggataagc accaacaaag    3900
tagcacattg ggaaattccg tggttcgctg tgataaactt gaccagtctg agattaagag    3960
cctactgatg tgtttcctct acatcttaaa gagcatgtct gatgatgctt tgtttacata    4020
ttggaacaag gcttcaacat ctgaacttat ggattttttt acaatatctg aagtctgcct    4080
gcaccagttc cagtacatgg ggaagcgata catagccaga acaggaatga tgcatgccag    4140
attgcagcag ctgggcagcc tggataactc tctcactttt aaccacagct atggccactc    4200
ggacgcagat gttctgcacc agtcattact tgaagccaac attgctactg aggtttgcct    4260
gacagctctg gacacgcttt ctctatttac attggcgttt aagaaccagc tcctggccga    4320
ccatggacat aatcctctca tgaaaaagt ttttgatgtc tacctgtgtt ttcttcaaaa    4380
acatcagtct gaaacggctt taaaaaatgt cttcactgcc ttaaggtcct aatttataa    4440
```

```
gtttccctca acattctatg aagggagagc ggacatgtgt gcggctctgt gttacgagat   4500
tctcaagtgc tgtaactcca agctgagctc catcaggacg gaggcctccc agctgctcta   4560
cttcctgatg aggaacaact ttgattacac tggaaagaag tcctttgtcc ggacacattt   4620
gcaagtcatc atatctgtca gccagctgat agcagacgtt gttggcattg ggggaaccag   4680
attccagcag tccctgtcca tcatcaacaa ctgtgccaac agtgaccggc ttattaagca   4740
caccagcttc tcctctgatg tgaaggactt aaccaaaagg atacgcacgg tgctaatggc   4800
caccgcccag atgaaggagc atgagaacga cccagagatg ctggtggacc tccagtacag   4860
cctggccaaa tcctatgcca gcacgcccga gctcaggaag acgtggctcg acagcatggc   4920
caggatccat gtcaaaaatg gcgatctctc agaggcagca atgtgctatg tccacgtaac   4980
agccctagtg gcagaatatc tcacacgaaa agaagcagtc cagtgggagc cgccccttct   5040
cccccacagc catagcgcct gcctgaggag gagccgggga ggcgtgttta gacaaggatg   5100
caccgccttc agggtcatta ccccaaacat cgacgaggag gcctccatga tggaagacgt   5160
ggggatgcag gatgtccatt tcaacgagga tgtgctgatg gagctccttg agcagtgcgc   5220
agatggactc tggaaagccg agcgctacga gctcatcgcc gacatctaca aacttatcat   5280
ccccatttat gagaagcgga gggattttga gaggctggcc catctgtatg acacgctgca   5340
ccgggcctac agcaaagtga ccgaggtcat gcactcgggc cgcaggcttc tggggaccta   5400
cttccgggta gccttcttcg ggcaggcagc gcaataccag tttacagaca gtgaaacaga   5460
tgtggaggga ttctttgaag atgaagatgg aaaggagtat atttacaagg aacccaaact   5520
cacaccgctg tcggaaattt ctcagagact ccttaaactg tactcggata aatttggttc   5580
tgaaaatgtc aaaatgatac aggattctgg caaggtcaac cctaaggatc tggattctaa   5640
gtatgcatac atccaggtga ctcacgtcat ccccttcttt gacgaaaaag agttgcaaga   5700
aaggaaaaca gagtttgaga gatcccacaa catccgccgc ttcatgtttg agatgccatt   5760
tacgcagacc gggaagaggc agggcggggt ggaagagcag tgcaaacggc gcaccatcct   5820
gacagccata cactgcttcc cttatgtgaa gaagcgcatc cctgtcatgt accagcacca   5880
cactgacctg aaccccatcg aggtggccat tgacgagatg agtaagaagg tggcggagct   5940
ccggcagctg tgctcctcgg ccgaggtgga catgatcaaa ctgcagctca aactccaggg   6000
cagcgtgagt gttcaggtca atgctggccc actagcatat gcgcgagctt tcttagatga   6060
tacaaacaca aagcgatatc ctgacaataa agtgaagctg cttaaggaag ttttcaggca   6120
atttgtggaa gcttgcggtc aagccttagc ggtaaacgaa cgtctgatta agaagacca   6180
gctcgagtat caggaagaaa tgaaagccaa ctacaggaa atggcgaagg agctttctga   6240
aatcatgcat gagcagctgg gatgatctgc ccctggagg agaagacgag cgtcttaccg   6300
aattcccttc acatcttcaa cgccatcagt gggactccaa caagcacaat ggttcacggg   6360
atgaccagct cgtcttcggt cgtgtgatta catctcatgg cccgtgtgtg gggacttgct   6420
tgtcatttg caaactcagg atgctttcca aagccaatca ctggggagac cgagcacagg   6480
gaggaccaag gggaaggga gagaaaggaa ataaagaaca acgttatttc ttaacagact   6540
ttctatagga gttgtaagaa ggtgcacata tttttttaaa tctcactggc aatattcaaa   6600
gttttcattg tgtcttaaca aaggtgtggt agacactctt gagctggact tagattttat   6660
tcttccttgc agagtagtgt tagaatagat ggcctacaga aaaaaaaggt tctgggatct   6720
acatggcagg gagggctgca ctgacattga tgcctggggg accttttgcc tcgaggctga   6780
```

```
gctggaaaat cttgaaaata ttttttttt  cctgtggcac attcaggttg aatacaagaa      6840 ctattttgt  gactagtttt tgatgaccta agggaactga ccattgtaat ttttgtacca      6900
gtgaaccagg agatttagtg cttttatatt catttccttg catttaagaa aatatgaaag      6960
cttaaggaat tatgtgagct taaaactagt caagcagttt agaaccaaag gcctatatta      7020
ataaccgcaa ctatgctgaa agtacaaag  tagtacagta tattgttatg tacatatcat      7080
tgttaataca gtcctggcat tctgtacata tatgtattac atttctacat ttttaatact      7140
cacatgggct tatgcattaa gtttaattgt gataaatttg tgctgttcca gtatatgcaa      7200
tacactttaa tgttttattc ttgtacataa aaatgtgcaa tatggagatg tatacagtct      7260
ttactatatt aggtttataa acagttttaa gaatttcatc cttttgccaa aatggtggag      7320
tatgtaattg gtaaatcata aatcctgtgg tgaatggtgg tgtactttaa agctgtcacc      7380
atgttatatt ttcttttaag actttaattt agtaatttta tatttgggaa aataaaggtt      7440
tttaatttta tttaactgga atcactgccc tgctgtaatt aaacattctg taccacatct      7500
gtattaaaaa gacattgctg accattaaaa aaaaaaaaa  aaaa                       7544

<210> SEQ ID NO 154
<211> LENGTH: 2833
<212> TYPE: DNA
<213> ORGANISM: Homo sapiens

<400> SEQUENCE: 154
ttagcacagt gactacagga atcacagccc agacacaaaa gcaggaaacc ctttgaccgg        60
gctccttcct attgcaccaa cagccttgtg ttgctgcaat gaaaacactt ccccaagcag       120
ctgtggccaa gagacgcaga aactgccttg tccacgggcc ccgcctcaga ctccaacact       180
cacaagagag cagaggagcc ccaagtcttg ggaccacag  aagatgccat gtgctccacg       240
atgtcggccc ccacctgcct ggcccacttg cctccctgct tcctgctgct ggcactggtc       300
cttgtcccct cagatgcctc tgggcagagc agcaggaatg actggcaggt gctacagccc       360
gagggcccca tgctggtggc agaaggtgag acacttctac tgaggtgtat ggtggtcggc       420
tcctgcactg atggtatgat aaaatgggtg aaggtgagca ctcaggacca acaggaaatt       480
tataacttta aacgtggctc cttccctggg gtaatgccca tgatccaacg gacatcagaa       540
ccactgaatt gtgattattc catctatatc cacaatgtca ccaggagca  cactggaacc       600 taccactgtg tgaggtttga tggtttgagt gaacactcag aaatgaaatc ggatgaaggc       660
acctcagtgc ttgtgaaggg agctggggac cctgaaccag acctgtggat catccagccc       720
caggaattgg tgttggggac cactggagac actgtctttc tgaactgcac agtgcttgga       780
gacggtcccc ctgacccat  caggtggttc caggagctg  gtctgagccg ggaggccatt       840
tacaactttg gaggcatctc ccaccccaag gagacagcgg tgcaggcctc caacaatgac       900
ttcagcattc ttctgcaaaa cgtctccagt gaggatgcag gcacctatta ctgtgtaaag       960
tttcagagga acccaacag  gcaataccctg tctggacagg gcaccagcct gaaagtgaaa      1020
gcaaaatcta cctcttccaa agaggcagaa ttcaccagtg aacctgcaac tgagatgtct      1080
ccaacaggcc tcctggttgt gttcgcacct gtggtcctgg gctgaaggc  aattaccttg      1140 gctgcactcc tactggccct ggctacctct cggaggagcc ctgggcaaga gatgtcaag       1200 accacaggcc cagcaggagc catgaacacc ttagcatgga gcaagggtca agagtgaggg      1260 gtcagccca  gagtgaggac cctctgagtt ggagaggagc cagggctcct caaccatttc      1320
cctacctcca gtcccagcct ctaggtgccc ccaggcctca tgacaaactc ctagatccct      1380
```

```
acatctggtt ttggtccacc tagtgaaatt cccttctttg caccgggctt ccctctaaaa    1440
tgtctccctt tctctttttg gcctgttcaa gacctccttg cttttcagtc cctggctcag    1500
tctctcctca acaccettgc ccctgctgca gcccttcctg gtgcgccctg cccctttccc    1560
cacctcgcta catccttctt ggcctccaac atccaactca gagtcttctt cccaggagat    1620
gtctgtaaga atctctgaac tcaaccagcc agaccatctg tgcccctcca tctacacctt    1680
tctccccact ccttcctgcc ttccttccat cccctcatg gctggcttgg gcaggtataa     1740
tattagaatg caggttcagc aactataaca aagctcttaa ataacagtgg cttaaaccag    1800
tggaaatcaa ccagaaagtt gaccatcagc aggccaagca atacagagac tccctggtat    1860
tgagacccag gattcactga tctcattgct accaggtcca ccttctaggc agccagactg    1920
gaaaagaggg caggaaaggg gagcaggacc ctccccttta agtgcacagt caggaacttg    1980
gccacctcac ttatctctac ttggctggaa tgtggtcaca tggtcacacc tagctgcaag    2040
aaacactggg agatgtagtc tttatttctg gcagcaatgc gcccagctgc aagttttcac    2100
tagagaaacc agatggcaga tatcagggga taaccagtta tctccaccac agcagcatac    2160
agacagcctc tcacctgccc tgtgggacac ctgagttcaa tgcccagcta gctagccagc    2220
acttcttccc actatcacct cccctggggc agcatgatgt ggggcagtag ttcccaagat    2280
gagtgatttt gcccccactg gacttttggc aatgtctaga gatgtttttg gttggcacaa    2340 cctgggggg tgctaccacc atctagtgga ctgagaagcc ctgacatggg gaagagtgtg     2400
catgcccagg agtcagacac acctgccttt aaccctgagg cctctgcctc ctccctgtgc    2460
accctcagtg actaatcaga gtcccttccc atcacggaac atccaggata ctaatgtgga    2520
cttctctgca ttgtgtaaga accaattcaa gaccaggcac ggtggcttat gcatgtaatc    2580
ccagcacttt gggaggccga ggtgggtgga tcacctgagt tcaggagttt gagaccagcc    2640
tggctaacat ggtgaaacct cgtctctact aaaaatacaa aaaattagcc aggcgtggtg    2700
gtgtgcacct gtaatcccag ctacttggga ggatggggca ggagaaccgc ttgaactggg    2760
aggcagaggc tgcagtgagc tgagatcgcg ccattgcact ccagcctggg caacaagagc    2820
aaaactccgt ctc                                                      2833

<210> SEQ ID NO 155
<211> LENGTH: 3993
<212> TYPE: DNA
<213> ORGANISM: Homo sapiens

<400> SEQUENCE: 155
aatgtaagaa cttttcttcc tcccttaact ttgcttcctt ctttcctgca tgttaccact      60
ggcagagcaa atatgactca gaaaccggct cctcagggtt gtaacattag atgatacagg     120
cttgggtcgt tacacatgac accagtgcct ttgtttcatt gggctgggct ctctggaagg     180
tgtgctgctg cctgagctgc tggaaaagca ctgacaggtg tttgctagaa aagcactcct     240
ggagcttgcc accagcttgg acttctaggg actttcctct cagccaggaa ggattttgat     300
attcatcaga aatacctcca gaagattcaa ggagctgtag aggtgaagta agcctgtgaa     360
ggaccagcat gggaatccta tactctgagc ccatctgcca agcagcctat cagaatgact     420
ttggacaagt gtggcggtgg gtgaaagaag acagcagcta tgccaacgtt caagatggct     480
ttaatggaga cacgccctg atctgtgctt gcaggcgagg gcatgtgaga atcgtttcct      540
tccttttaag aagaaatgct aatgtcaacc tcaaaaacca gaaagagaga acctgcttgc     600
```

```
attatgctgt gaagaaaaaa tttaccttca ttgattatct actaattatc ctcttaatgc    660
ctgttctgct tattgggtat ttcctcatgg tatcaaagac aaagcagaat gaggctcttg    720
tacgaatgct acttgatgct ggcgtcgaag ttaatgctac agattgttat ggctgtaccg    780
cattacatta tgcctgtgaa atgaaaaacc agtctcttat ccctctgctc ttggaagccc    840
gtgcagaccc cacaataaag aataagcatg gtgagagctc actggatatt gcacggagat    900
taaaattttc ccagattgaa ttaatgctaa ggaaagcatt gtaatccttg tgaccacacc    960
gatggagata cagaaaaagt taacgactgg attctatctt cattttagac ttttggtctg   1020
tgggccattt aacctggatg ccaccatttt atggggataa tgatgcttac catggttaat   1080
gttttggaag agcttttat ttatagcatt gtttactcag tcaagttcac catggccgta    1140
atccttctaa gggaaacact aaagttgttg tagtctccac ttcagtcaga aactgatgtt   1200
tcagctaggc acagtggtac atgcctgtaa tcccagctac ttgggaggct gaggtgggag   1260
gatcacttga actcaggagt ttgagagcag ccagggcaac acagcgagac cctgtctcaa   1320
aaaaaaaaa aaaaaaaaa gccctggtgt tccaaactca gtctttcctg aagaagagga    1380
tctgagttat cttctgaaac agcgttctcc cttcccagtt gtatcactct tataaaaaga   1440
ctgtccagtc tatgtcatgc cctaggagac aaactgttcc tcccagcccc ctttgagtat   1500
tgagcagaag aatcaaatta ttaaatacgt atgtttgtac agaatggtat ttgtgtatgt   1560
gtgtgggctt agagattcac aagtaaatat tcctttggtg aaggaatttc aataaaaaca   1620
tctatcaagt gtcagcggtg agtgtgttta caccacagaa attggcaaat tgacaaatca   1680
gagtttgttt ttgttttttt gttttttact ttccataaag ttcgtttacc agcataccac   1740
tagagatttc ggtttacaaa taaaagccat cttggtttga gcaagactat gcaactatga   1800
aaatgttcgt ttaaaaaaat cttcatgatc cttttgtaaa tacaaggtgg ttgccaagct   1860
tgttagtttt gtttatttta ttgatagatg taaaatatta ttgtaactta tttggataaa   1920
gttcttcaaa agaaacagag ctatacaatg aggtaggatc tggattattt gtctaagtga   1980
gagattgcga atatcaaaat atctgtctca cttcttctgt gaatgacaca gagtagaaat   2040
aaattcactt taaaaatatg actgaatttt gaaaatcaag actgaatctc acatagctgc   2100
agacaggaac taagccagcc tctttgtatg tggtaacaag tacagtataa gaatgaaaga   2160
tttaccatcc ttgaaagctc taatgaaaat caaatccagc aatatatatt caactgtgta   2220
caggatttaa gaaacttatt ttatgaagga agtaatagtg tgtagatata gattctgaag   2280
tctttaaacg tgtcttaata aattaagatt cactggcatt gagctgagct accaggtgac   2340
ccttggggac aaaaaaccca cacaagtgaa tttcacacac cagtatacct tcaacaatat   2400
actttgaca cacacaaacc tttgatttgg tttcagagat tttgcaaaat agtaccaatg    2460
taatttacaa ctgtcatctt tgaaattgtg taaaagtgga ataattttct gaagaaataa   2520
atcatggttt gtcaatgagt tgcagagact gtctgacatt aactttgtca agattaaagg   2580
ataaagtata tgacaatttg tttcatcatg ctcatgacat tatgcaattt tctccctagc   2640
ttttaatttt tggaggcaga aaattgagcc agaaattttt agtcattagg tctcctagca   2700
acaagctgta aaccttccaa caagcttgga ctagaatcta gacactgaaa tgcacataca   2760
tgctttatgt aatgcagaat gcatttattg gagaactcat aaacatccta taaaattttc   2820
ttccctgaga tgcaactata aaacttggcc ttattctgag aatgcttaac atagatttca   2880
tccatactgt aacactgatt ttgttgttgt tgtccttaaa gcagctcagc ttcctgaggt   2940
agtgttatgt ctctgtggca acaaggtgaa aatgtctagc ttatttttgtc aaagtcaaca   3000
```

```
ataatccaca gactccagac ctcaatatct gtcccaattt gccattttac tttagtgctc    3060
caaaaatatg gcttatagaa aaacaatag gtgttttaaa gagatttacc tgaatgatat    3120
agagaatgtc tagatatttt ctggctatca ggtaaaacct acccttcaag atggtagaat    3180
atataatagc atacaaaacc tctatttacc taataagtac tttaatttac agaaaaaaaa    3240
tgtaaatgta agtgtcggat ttagtgccaa gtgcagggaa tctgaaaaat gtatactagg    3300
tctctgctct ccgtaattct gccttcatgg gtcctagccc catccctcag gaggttgtcc    3360
taagatcgtc agtgtcagat gcttcacaat acggcctcac accgtccctg ggaaaggttg    3420
gtctcctcct gctgcatcag atggatgatt tcattgtaca tacggtgagg agcatccaaa    3480
ccccagatga aatccacgtg agcccattca ggaatattct tatggtagat gaggttggtc    3540
acctcagaga gcagcatttt cacgtcttct ggatttgaaa gccagtcctg acctcctgtc    3600
cacattgctg tagggaccgt catatctctg actctgtacc ttacaggagt tggctagaga    3660
aaaggaatag ttcttaactc taggtaacat ttggactttc aggctcataa tttatgtttc    3720
aaatagacat aataaacatg ccatctgttg tggtgaaggg tacatgggtg ttagagccac    3780
acaactctgt taagaatttc tgttcccgcc cttactttaa ggtaaaatta cttaacatta    3840
ttgaacctca gtttcttctt ctgtgactgg ggataatatc tgtaataact tgctagatca    3900
aatgacaaaa cacataaaaa catgtaatgc cttgtatttc ttttttcttc ctattaaata    3960
ttttgtaaat aaattgtttt taaaaaaaaa aaa    3993

<210> SEQ ID NO 156
<211> LENGTH: 2405
<212> TYPE: DNA
<213> ORGANISM: Homo sapiens

<400> SEQUENCE: 156
ggcgtcacgc ggccccgcga ggtctgtggg atacatagta gtcctcaagg cgggtctcac      60
tcttggccgc tgcaacttga ggactacact tccaaggagg cagcgcggcg cgccgagaac     120
cacccgaggc cgtgattggc tggtgagccg ccgcacgcg gaggatccta aggagcagct     180
ctgttgcgac ataggccgag cagcgaggcc cagctccctg aaacaacagt aacctacccc     240
tgtgggtcat catcatgccc tccgacctgg ccaagaagaa ggcagccaaa agaaggagg     300 ctgccaaagc tcgacagcgg cccagaaaag gacatgaaga aaatggagat gttgtcacag     360
aaccacaggt ggcagagaag aatgaggcca atggcagaga gaccacagaa gtagatttgc     420
tgaccaagga gctagaggac tttgagatga agaaagctgc tgctcgagct gtcactggcg     480
tcctggcctc tcaccccaac agtactgatg ttcacatcat caacctctca cttacctttc     540
atggtcaaga gctgctcagt gacaccaaac tggaattaaa ctcaggccgt cgttatggcc     600
tcattggttt aaatggaatt ggaaagtcca tgctgctctc tgctattggg aagcgtgaag     660
tgcccatccc tgagcacatc gacatctacc atctgactcg agagatgccc cctagtgaca     720
agacaccctt gcattgtgtg atggaagtcg acacagagcg ggccatgctg gagaaagagg     780
cagagcggct ggctcatgag gatgcggagt gtgagaagct catggagctc tacgagcgcc     840
tggaggagct ggatgccgac aaggcagaga tgagggcctc gcggatcttg catggactgg     900
gtttcacacc tgccatgcag cgcaagaagc taaaagactt cagtggggc tggaggatga     960 gggttgccct tgccagagcc ctcttttattc ggccccttcat gctgctcctg gatgagccta    1020
ccaaccacct ggacctagat gcttgcgtgt ggttggaaga agaactaaaa acttttaagc    1080
```

```
gcatcttggt cctcgtctcc cattcccagg attttctgaa tggtgtctgt accaatatca      1140
ttcacatgca caacaagaaa ctgaagtatt atacgggtaa ttatgatcag tacgtgaaga      1200
cgcggctaga gctggaggag aaccagatga agaggtttca ctgggagcaa gatcagattg      1260
cacacatgaa gaactacatt gcgaggtttg gtcatggcag tgccaagctg gcccggcagg      1320
cccagagcaa ggagaagacg ctacagaaaa tgatggcatc aggactgaca gagagggtcg      1380
tgagcgataa gacactgtca ttttatttcc caccatgtgg caagatccct ccacctgtca      1440
ttatggtgca aaatgtgagc ttcaagtata caaaagatgg ccttgcatc tacaataatc       1500 tagaatttgg aattgacctt gacacacgag tggctctggt agggcccaat ggagcaggga      1560
agtcaactct tctgaagctg ctaactggag agctactacc cacagatggc atgatccgaa      1620
aacactctca tgtcaagata gggcgttacc atcagcattt acaagagcag ctggacttag      1680
atctctcacc tttggagtac atgatgaagt gctacccaga gatcaaggag aaggaagaaa      1740
tgaggaagat cattgggcga tacggtctca ctgggaaaca acaggtgagc ccaatccgga      1800
acttgtcaga cgggcagaag tgccgagtgt gtctggcctg gctggcctgg cagaaccccc      1860
acatgctctt cctggatgaa cccaccaatc acctggatat cgagaccatc gacgccctgg      1920
cagatgccat caatgagttt gagggtggta tgatgctggt cagccatgac ttcagactca      1980
ttcagcaggt tgcacaggaa atttgggtct gtgagaagca gacaatcacc aagtggcctg      2040 agacatcct ggcttacaag gagcacctca gtccaagct ggtggatgag gagccccagc       2100
tcaccaagag gacccacaac gtgtgcaccc tgacattggc atctctgcca aggccatgag      2160
catcatgaac tcgtttgtaa acgacgtgtt tgagcagctg gcgtgtgagg ctgcccggct      2220
ggcccagtac tcgggccgga ccaccctgac atcccgagaa gtccagacgg ctgtgcgtct      2280
gctgctgcct ggggagctgg ccaagcacgc tgtgtctgag gcaccaaagg ctgtcaccaa      2340
gtacaccagc tccaagtgac ccagggcctg acaaaaataa agggtgaact gttaaaaaaa      2400
aaaaa                                                                 2405

<210> SEQ ID NO 157
<211> LENGTH: 5371
<212> TYPE: DNA
<213> ORGANISM: Homo sapiens

<400> SEQUENCE: 157
tcactcactg gggagcccgg cggtggcggc acctttcgag gtagacccgc tgagctgcta        60
gcccgccggc cagcgagtga gaggtcggac agactgtgga gccgacagac tgaaggacag       120
cggcaccgcc agacggccag aaagttccgc catgagctgg ggcacggagc tgtgggatca       180
gttcgacagc ttagacaagc atacacaatg gggaattgac ttcttggaaa gatatgccaa       240
atttgttaaa gagaggatag aaattgaaca gaactatgcg aaacaattga gaatctggt        300 taagaagtac tgccccaaac gttcatccaa agatgaagag ccacggttta cctcgtgtgt       360 agccttttt aatatcctta atgagttaaa tgactatgca ggacagcgag aagttgtagc        420
agaagaaatg gcgcacagag tgtatggtga attaatgaga tatgctcatg atctgaaaac       480
tgaaagaaaa atgcatctgc aagaaggacg aaaagctcaa caatatcttg acatgtgctg       540
gaaacagatg gataatagta aaagaagtt tgaaagagaa tgtagagagg cagaaaaggc       600 acaacgagt tatgaaagat tggataatga tactaatgca accaaggcag atgttgaaaa       660
ggccaaacag cagttgaatc tgcgtacgca tatggccgat gaaaataaaa atgaatatgc       720
tgcacaatta caaaacttta atggagaaca acataaacat ttttatgtag tgattcctca       780
```

```
gatttacaag caactacaag aaatggacga acgaaggact attaaactca gtgagtgtta    840
cagaggattt gctgactcag aacgcaaagt tattcccatc atttcaaaat gtttggaagg    900
aatgattctt gcagcaaaat cagttgatga aagaagagac tctcaaatgg tggtagactc    960
cttcaaatct ggttttgaac ctccaggaga ctttccattt gaagattaca gtcaacatat   1020
atatagaacc atttctgatg ggactatcag tgcatccaaa caggagagtg ggaagatgga   1080
tgccaaaacc acagtaggaa aggccaaggg caaattgtgg ctctttggaa agaagccaaa   1140
gggcccagca ctagaagatt tcagtcatct gccaccagaa cagagacgta aaaaactaca   1200
gcagcgcatt gatgaactta acagagaact acagaaagaa tcagaccaaa agatgcact    1260 caacaaaatg aaagatgtat atgagaagaa tccacaaatg ggggatccag ggagtttgca   1320
gcctaaatta gcagagacca tgaataacat tgaccgccta cgaatggaaa tccataagaa   1380
tgaggcttgg ctctctgaag tcgaaggcaa acaggtgggg agaggagaca aagacatag    1440 cagtgacata aatcatcttg taacacaggg acgagaaagt cctgagggaa gttacactga   1500
tgatgcaaac caggaagtcc gtgggccacc ccagcagcat ggtcaccaca atgagtttga   1560
tgatgaattt gaggatgatg atcccttgcc tgctattgga cactgcaaag ctatctaccc   1620
ttttgatgga cataatgaag gtactctagc aatgaaagaa ggtgaagttc tctacattat   1680
agaggaggac aaaggtgacg gatggacaag agctcggaga cagaacggtg aagaaggcta   1740
cgttcccacg tcatacatag atgtaactct agagaaaaac agtaaggtg cagtaactta    1800 tatctaaact aaccaggcac ctttgtgcca tgtgtgacat aggaagagta acataaaatg   1860
aaaacacatt caacaggttg aaaaaaataa ggaaacttaa agggcatcca agattaattg   1920
ttcactatgt gagctgagtg taggcttgat cttgtgaata ttaccacaag aaacattttg   1980
tggcacttta ctgtttgagt aacgttggtg tgaagcttaa ttgatgcctt ttgctttatg   2040
tcccgcttaa gtctgtgtga aggatttgtg tttttctgcc ttacaaatag aatttgattt   2100
attgggcagg aattcatgga tagtaatgct ctctgccccc tttacttcag aaaacacagt   2160
gactttagtg aatttgaata gtgaaactgc tctgaaatgc tatggaaagc cgactcccca   2220
aagagtggtt tcttctagaa gtttgaattt gtagctacag tttccaagaa gaaaaatagt   2280
agttggataa tttagtaaaa taataacatc attttcattt tcttacctat tcttaacttt   2340
ggtttcctaa aggaagaaaa tgagcaggta gcacataatc tatttaagta gatttaaaga   2400
gagtttcaaa ataaatctcc tggtctagct cttaggtgaa taaaatagat tttgtttgag   2460
acctcaaaat attttgaggt tagctggtaa ttttcaataa tttacaagct tccttccaaa   2520
ctaatctcat acttttgtat gtttcatctt gaaaatatct tttgggaaat accactttag   2580
tgattattta gcatttagca gttacacata ggaaaataca cagttacata gaaaaataca   2640
catttgaaga tagaggaaac cttgaatgga ggggaagtgt tgacaaattt taattttaa    2700 aggagaaact ttttgactat ctgggttaga ggaagatatg tgtaccgcct ttagggcatt   2760
ttgttatttc cgctgaatca ttagttatta ggatagataa attttttccaa ttagtttcag   2820 caagcgttgt tggaaacact gtgcagtcaa ggattgtgca gtgctggttg tgtgaccaca   2880
ccctgagtca gtggtgtggg gaagtaaagt gtgaagaagc agtaagattg gttttaatt    2940 ttgcccatgt tttaaatttt cctggtgttt tcggtagctg actataaaat gatagagaca   3000
tttgggacag gcactttaaa ctgaacaccc cttttggttt taccaaaggt cttcagtaat   3060
tgttcttttc ttttccttcc tggactgcag gttcctgaag agggtttctg aggaaatggg   3120
```

```
caagatgttg aaggaggtta catgcagctg cttttggggg agggtattag agttgtcagg    3180
ctcaaagaga gtgagagaag caagttgcat gagtgcatgc agacatgatt ttttttttac    3240
taacttcatt agcatttcca tacattgttt ttaaaaatca aataccaac ccttaagttc     3300
ctagttcaca gttattccca caaaagaaaa agccaacaat agtgtaccat ttttctattt    3360
attttattgc tgtctaatca ataaagaatg cagagctgtc aaaaaatgtg tcttacatta    3420
gctgtcccaa caggattgtc ttccctccca gctctgtttt aattggcttt tagacccact    3480
atctgtcaga tccttgccat ctgtcagtgt ctgcctgcgc cacctccgtg cttgcttaac    3540
atcctgttgc atgtctagcg tgattgagct agattttca ggcatgtctt tagattccct     3600
tgttcttgtc aaagccttgt tttgttttac atttgtagtg caaatcactt tgtcaaacat    3660
ctccagcact aatgtttcca tcttagtatt tgtgcacact gctataactt ccccactgca    3720
aacattccag ttttggcatt acgaagaagt agctgtgaac ctgaagtatt tatgataaga    3780
aaagaaaac atctctgctg tagcctacag cccagttgaa agaactcttt gaaacgtgat     3840
acatcttcag cacctcagtc tgggaagaat ctagtcagca ctgaaatcct ggcataataa    3900
acacagaaga tattcaccac ctcaagacaa aggactattg tcaaaagtca gctgcttcca    3960
ttcaaatgct gccttaaact tgagtgccta aatctgttga ttgccaacac taccactaca    4020
gtatcccaca aagggcttta tgtgtcagct cagtgcgacc tgctttaact ctgcagcacc    4080
gctgcagctg ccgatgtagc ctcggtaggt ggctattaga gctctaccat atacagtggt    4140
gcatcttcaa atttatgcat caaactaaag acatgtccaa gtccatttta atttcctcag    4200
tggttttatg agaagtttta tgggcctccc ccaattgtct tttattttg ggttatgacg     4260
atcatgtttg ataattacaa tgatagtctc tttccacgtg atgcttttgt ttgaacctga    4320
taaaatttag tgaaactttg taatgatcta tgtgcacttt tacttgtaaa atggaatttc    4380
tgtatgttta tacttgtaaa tatgattgtt gttagtgctc ctgttgctca tggtgtcctg    4440
cctcgcattt gtgattctgt taatgacatg tatcttaact aatttcttag tggtgttgta    4500
ataggagat ggggcaggtg gggggttatt tgtaccactg aatcttcatt aatttggttc     4560
tttactgttt tgaggggaga aagaacgtga aatggtttgt gtattattga attttaagca    4620
atattttaga agctgtgtga ctgctttaat aacttttcc cagtgttatt tgaatcatac     4680
tacccgttat actaaagctg aatgacaatt gtgtgaaagt tactgccttc ataagatcaa    4740
gtcaccactg ttacacagct gacatatagt gtattacctt tgcagctagt aaactataaa    4800
gtttagatat tgaatctcgt tacagggtta tttatataat gtgacattat tcagtactga    4860
cagactacat gaagtagttt taaaatctag tgctattttt attttaaagg ttagcaatga    4920
ggaggaaatg tgatctggct gtgtttgtct tctgtacaaa gcctgaagtg cttatggttt    4980
tttggctaac agccacagag ggcaaagttt aagactttct tgtaaggact aactgttctt    5040
ttcaagctac tgtttgtttt tctaaaagca ggatttgctt ccgtaggagg caagttcctt    5100
gatgtggaat agtgcaacct gtatatgggt tattataata ggaaagacat ttgtacttgc    5160
acagtttaaa tcattcttaa attttgaaca tgtgaattgt cccaaaaaat ctttaatttt    5220
ttggtaattt ttactctttt tgtgcacatg ttgatttctt aatggtaaat ccttcattta    5280
aagatagtgt tctctgttga gaatatttac atggaataaa acaatctttt catggcctgt    5340
taaaaaaaaa aaaaaaaaaa aaaaaaaaaa a                                   5371

<210> SEQ ID NO 158
<211> LENGTH: 1459
```

<212> TYPE: DNA
<213> ORGANISM: Homo sapiens

<400> SEQUENCE: 158

```
agtgcattta aggcgcagcc tggaagtgcc agggagcact ggaggccacc cagtcatggg      60
ggacaccttc atccgtcaca tcgccctgct gggctttgag aagcgcttcg tacccagcca     120
gcactatgta catgttcctg gtgaaatggc aggacctgtc ggagaaggtg gtctaccggc     180
gcttcaccga gatctacgag ttccataaaa ccttaaaaga aatgttccct attgaggcag     240
gggcgatcaa tccagagaac aggatcatcc cccacctccc agctcccaag tggtttgacg     300
ggcagcgggc cgccgagaac caccagggca cacttaccga gtactgcagc acgtctcatga    360
gcctgcccac caagatctcc cgctgtcccc acctcctcga cttcttcaag gtgcgccctg     420
atgacctcaa gctccccacg gacaaccaga caaaaaagcc agagacatac ttgatgccca     480
aagatggcaa gagtaccgcg acagacatca ccggccccat catcctgcag acgtaccgcg     540
ccattgccga ctacgagaag acctcgggct ccgagatggc tctgtccacg ggggacgtgg     600
tggaggtcgt ggagaagagc gagagcggtt ggtggttctg tcagatgaaa gcaaagcgag     660
gctggatccc agcatccttc ctcgagcccc tggacagtcc tgacgagacg gaagaccctg     720
agcccaacta tgcaggtgag ccatacgtcg ccatcaaggc ctacactgct gtggagggg      780
acgaggtgtc cctgctcgag ggtgaagctg ttgaggtcat tcacaagctc ctggacggct     840
ggtgggtcat caggaaagac gacgtcacag gctactttcc gtccatgtac ctgcaaaagt     900
cggggcaaga cgtgtcccag gcccaacgcc agatcaagcg gggggcgccg cccgcaggt      960
cgtccatccg caacgcgcac agcatccatc agcggtcgcg gaagcgcctc agccaggacg    1020
cctatcgccg caacagcgtc cgttttctgc agcagcgacg ccgccaggcg cggccgggac    1080
cgcagagccc cgggagcccg ctcgaggagg agcggcagac gcagcgctct aaaccgcagc    1140
cggcggtgcc cccgcggccg agcgccgacc tcatcctgaa ccgctgcagc gagagcacca    1200
agcggaagct ggcgtctgcc gtctgaggct ggagcgcagt cccccagctag cgtctcggcc    1260
cttgccgccc cgtgcctgta catacgtgtt ctatagagcc tggcgtctgg acgccgaggg    1320
cagccccgac ccctgtccag cgcggctccc gccacccctca ataaatgttg cttggagtgg   1380
accgaggctc tgcaggaatg cagggagggc cgggctccgc cccagggtta tttctaagtt    1440
gaaaaaaaaa aaaaaaaa                                                   1459
```

<210> SEQ ID NO 159
<211> LENGTH: 2114
<212> TYPE: DNA
<213> ORGANISM: Homo sapiens

<400> SEQUENCE: 159

```
actggtgctt agcacctatc tgctctctgg cctgcgtcag tggtctacag cagttacaca      60
caggcagtgg tatctgtgag cagctctgtg gactcaaagg tttctccct gagaggcatg      120
acccaggcca gctgattcat cagaatcagg atggacgtgg tagaggtcgc gggtagttgg     180
tgggcacaag agcgagagga catcattatg aaatacgaaa agggacaccg agctgggctg     240
ccagaggaca aggggcctaa gccttttcga agctacaaca caacgtcga tcatttgggg      300
attgtacatg agacggagct gcctcctctg actgcgcggg aggcgaagca aattcggcgg     360
gagatcagcc gaaagagcaa gtgggtggat atgctgggag actgggagaa atacaaaagc    420
agcagaaagc tcatagatcg agcgtacaag ggaatgccca tgaacatccg gggcccgatg    480
```

```
tggtcagtcc tcctgaacat tgaggaaatg aagttgaaaa accccggaag ataccagatc    540
atgaaggaga agggcaagag gtcatctgag cacatccagc gcatcgaccg ggacataagc    600
gggacattaa ggaagcatat gttcttcagg gatcgatacg gaaccaagca gcgggaacta    660
ctccacatcc tcctggcata tgaggagtat aacccggagg tgggctactg cagggacctg    720
agccacatcg ccgccttgtt cctcctctat tttcctgagg aggatgcatt ctgggcactg    780
gtgcagctgc tggccagtga gaggcactcc ctgcagggat tcacagccc aaatggcggg     840 accgtccagg ggctccaaga ccaacaggag catgtggtag ccacgtcaca atccaagacc    900
atggggcatc aggacaagaa agatctatgt gggcagtgtt ccccgttagg ctgcctcatc    960
cggatattga ttgacgggat ctctctcggg ctcaccctgc gcctgtggga cgtgtatctg   1020
gtagaaggcg aacaggcgtt gatgccgata caagaatcg cctttaaggt tcagcagaag    1080
cgcctcacga agacgtccag gtgtggcccg tgggcacgtt tttgcaaccg gttcgttgat   1140
acctgggcca gggatgagga cactgtgctc aagcatctta gggcctctat gaagaaacta   1200
acaagaaagc aggggggacct gccaccccca gccaaaccg agcaagggtc gtcggcatcc   1260
aggcctgtgc cggcttcacg tggcgggaag accctctgca aggggagcag gcaggcccct   1320
ccaggcccac cagcccggtt cccgcggccc atttggtcag cttccccgcc acgggcacct   1380
cgttcttcca caccctgtcc tggtggggct gtccggggaag acacctaccc tgtgggcact   1440
cagggtgtgc ccagcccggc cctggctcag ggaggacctc agggttcctg agattcctg    1500 cagtggaact ccatgccccg cctcccaacg gacctggacg tagagggccc ttggttccgc   1560
cattatgatt tcagacagag ctgctgggtc cgtgccatat cccaggagga ccagctggcc   1620
ccctgctggc aggctgaaca ccctgcggag cgggtgagat cggctttcgc tgcacccagc   1680
actgattccg accagggcac ccccttcaga gctaggacg aacagcagta tgctcccacc     1740
tcagggcctt gcctctgcgg cctccacttg gaaagttctc agttccctcc aggcttctag   1800
aagcatctgg gccagggctc atggctggat aatttcccta ggcttaacaa cccaagcaag   1860
cttcgcgtcc tcgttttatt tttggttaaa cttatgaaaa tgtattaaga aagagtgcag   1920
ctcgagagag attcagagat ggaacacacc agacccaga tcacaaagcc aaccatgccc    1980 agccctcc agcaccccca gccccacgac catcgttctg aattctgacg acaccgtgag     2040
cctgcctttg tactttaaac tcatggaagg ataactacct tcacgttttg aaataaatgt   2100
ttcctgttga aatg                                                    2114

<210> SEQ ID NO 160
<211> LENGTH: 4129
<212> TYPE: DNA
<213> ORGANISM: Homo sapiens

<400> SEQUENCE: 160
acacagagca gagtggggct ctgagtatat aactgttagg tgcctccctc cagcaccatc      60
tcctgagaag cactctccct tgtcgtggag gtgggcaaat ctttatcagc cactgccttc     120
tgctgccagg aagccagcta gagtggtctt taaagaaaac tgggcatctc ctgctactta    180
aaatcaaaaa ctacctaaaa taagattat aaaaaagtaa ggatgaatgg acggtctttg     240
attggcggcg ctggtgacgc ccgtcatggt cctgtttgga aggacccttt tggaactaaa   300
gctggtgacg cagcgcgcag aggcatcgcc cggctaagct tggccctggc agatgggtcg    360
caggaacagg agccagagga agagatagcc atggaggaca gccccactat ggttagagtg   420
gacagcccca ctatggttag gggtgaaaac caggtttcgc catgtcaagg gagaaggtgc    480
```

```
ttccccaaag ctcttggcta tgtcaccggt gacatgaaag aacttgccaa ccagcttaaa    540
gacaaacccg tggtgctcca gttcattgac tggattctcc ggggcatatc ccaagtggtg    600
ttcgtcaaca accccgtcag tggaatcctg attctggtag gacttcttgt tcagaacccc    660
tggtgggctc tcactggctg gctgggaaca gtggtctcca ctctgatggc cctcttgctc    720
agccaggaca ggtcattaat agcatctggg ctctatggct acaatgccac cctggtggga    780
gtactcatgg ctgtcttttc ggacaaggga gactatttct ggtggctgtt actccctgta    840
tgtgctatgt ccatgacttg cccaattttt caagtgcat  tgaattccat gctcagcaaa    900
tgggacctcc ccgtcttcac cctccctttc aacatgcgt  tgtcaatgta cctttcagcc    960
acaggacatt acaatccatt ctttccagcc aaactggtca tacctataac tacagctcca   1020
aatatctcct ggtctgacct cagtgccctg gagttgttga aatctatacc agtgggagtt   1080
ggtcagatct atggctgtga taatccatgg acaggggca ttttcctggg agccatccta   1140
ctctcctccc cactcatgtg cctgcatgct gccataggat cattgctggg catagcagcg   1200
ggactcagtc tttcagcccc atttgaggac atctactttg gactctgggg tttcaacagc   1260
tctctggcct gcattgcaat gggaggaatg ttcatggcgc tcacctggca aacccacctc   1320
ctggctcttg gctgtgccct gttcacggcc tatcttggag tcggcatggc aaactttatg   1380
gctgaggttg gattgccagc ttgtacctgg cccttctgtt tggccacgct attgttcctc   1440
atcatgacca caaaaaattc caacatctac aagatgcccc tcagtaaagt tacttatcct   1500
gaagaaaacc gcatcttcta cctgcaagcc aagaaaagaa tggtggaaag ccctttgtga   1560
gaacaagccc catttgcagc catggtcacg agtcatttct gcctgactgc tccagctaac   1620
ttccagggtc tcagcaaact gctgttttc acgagtatca actttcatac tgacgcgtct    1680
gtaatctgtt cttatgctca ttttgtattt tcctttcaac tccaggaata tccttgagca   1740
tatgagagtc acatccaggt gatgtgctct ggtatggaat ttgaaacccc aatggggcct   1800
tggcactaag actggaatgt atataaagtc aaagtgctcc aacagaagga ggaagtgaaa   1860
acaaactatt agtatttatt gatattcttg gtgtttagct ggctcgatga tgttaacagt   1920
attaaaaatt aaacccata  aaccaactaa gccttatgga attcacagtc acaaaatcga   1980
agttaatcca gaattctgtg ataagcagct tggcttttt  tttaaatcaa tgcaagttac   2040
acattatagc cagaatctgt atcacagagg tgcaagctga cagcagagct cagtccccac   2100
ttcctgcaaa caatggcctg caccctatcc cttgtgtgtg tgacattctc tcatgggaca   2160
atgttggggt ttttcagact gacaggactg caagagggag aaaggaattt tgtcaatcaa   2220
aattattctg tattgcaact tttctcagag attgcaaagg attttttagg tagagattat   2280
ttttccttat gaaaatgat  ctgttttaaa tgagataaaa taggagaagt tcctggctta   2340
acctgttctt acatattaaa gaaaagttac ttactgtatt tatgaaatac tcagcttagg   2400 cattttact  ttaacccta  aattgatttt gtaaatgcca caaatgcata gaattgttac   2460
caacctccaa agggctcttt aaaatcatat ttttattca  tttgaggatg tcttataaag   2520
actgaaggca aaggtcagat tgcttacggg tgttatttt  ataagttgtt gaattcctta   2580
atttaaaaaa gctcattatt ttttgcacac tcacaatatt ctctctcaga aatcaatggc   2640
atttgaacca ccaaaaagaa ataagggct  gagtgcggtg gctcacgcct gtaatcccag   2700
cactttgggg agcccaggcg ggcagattgc ttgaacccag gagttcaaga ccagcctggg   2760
cagcatggtg aaaccctgta tctacaaaaa atacaaaaat tagccaggca tggtggtggg   2820
```

```
tgcctgtagt tccagctact tgggaggctg aggtgggaaa atgacttgag cccaggagga    2880
ggaggctgca gtgagctaag attgcaccac tgcactccaa cctgggcgac aagagtgaaa    2940
ctgtgtctct caaaaaaaaa aaaaaacaaa caaaaacaaa aacaaaacaa aacaaaacaa    3000
aacaaaacag gtaaggattc ccctgttttc ctctctttaa ttttaaagtt atcagttccg    3060
taaagtctct gtaaccaaac atactgaaga cagcaacaga agtcacgttc agggactggc    3120
tcacacctgt aatcccagca ctttgggaga tggaggtaaa aggatctctt gagcccagga    3180
gttcaagacc agcttgggca acatagcaag actccatctc ttaaaaaata aaatagtaa    3240 cattagccag gtgtagcagc acacatctgc agcagctact caggaggctg aggtggaaag    3300
atcgcttgtg cacagaagtt cgaggctgca gtgagctata tgatcatgtc actgcactcc    3360
agcctgtgtg accagcaag accctatctc aaaaaaatta attaattaat taattaatta    3420
atttaaaaag gaagtcatgt tcatttactt tccacttcag tgtgtatcgt gtagtatttt    3480
ggaggttgga aagtgaaacg taggaatcct gaagattttt tccacttcta gtttgcagtg    3540
ctcagtgcac aatatacatt ttgctgaatg aataaacaga aatagggaag taaacctaca    3600 aatatttttag ggagaagctc acttcttcct tttctcagga aaccaagcaa gcaaacatat    3660
cgttccaatt ttaaaaccca gtgaccaaag cctttggaac tatgaatttg caactgtcat    3720
aggtttatgg atattgctgt ggagaagctc aattttcagt gtttgaactg aacccttttct    3780 tgttagggaa cgtgtgaaag aagaattgtg gggaaaaaa agcaagcata accaaagatc    3840
atcagcagtg aagaatctag gctgtggctg agagaaccag aggcctctaa aatggacccg    3900
agtcgatctt cagaacaggg atctaccatg caggagcttc ttgtgctcac acaaatctgt    3960
aaatgggaac attgtacatt gtcgaattta aatgatatta attttctcaa gctattttg    4020 ttactatttt cctaaaattg aatatttgca gggagcactt atacttttttc ctaatgtctg    4080 tataacaaat ttctatgcaa gtacatgaat aaattatgct cacagctca                4129
```

```
<210> SEQ ID NO 161
<211> LENGTH: 3754
<212> TYPE: DNA
<213> ORGANISM: Homo sapiens

<400> SEQUENCE: 161
```

```
caggcgggac gggctctccc ttgggtgctt agccccgccc ccgtcccact ctgccctgtt      60
gctgtcgcgc cgctgctggt tgctgtccct ggaccctac catggaggag accatcaaag     120
atccccccac atcagctgtc ttgctggatc actgtcattt ctctcaggtc atctttaaca     180
gtgtggagaa gttctacatc cctggagggg acgtcacatg tcattatacc ttcacccagc     240
atttcatccc tcgtcgaaag gattggattg gcatctttag agcatttaaa tgtttccaag     300
acaaattgga acaagaacta ctcaaatgga ggagccaagg acagaaattg caggtggggt     360
ggaagacaac ccgtgagtat tacaccttca tgtgggttac tttgcccatt gacctaaaca     420
acaaatcagc taaacagcag gaagtccaat tcaaagctta ctacctgccc aaggatgatg     480
agtattacca gttctgctat gtggatgagg atggtgtggt ccggggagca agtattcctt     540
tccaattccg tccagaaaat gaggaagaca tcctggttgt taccactcag ggagaggtgg     600
aagagattga gcagcacaac aaggagcttt gcaaagaaaa ccaggagctg aaggacagct     660
gtatcagcct ccagaagcag aactcagaca tgcaggctga gctccaaaag aagcaggagg     720
agctagaaac cctacagagc atcaataaga agttggaact gaaagtgaaa gaacagaagg     780
actattggga gacagagctg cttcaactga aagaacaaaa ccagaagatg tcctcagaaa     840
```

```
atgagaagat gggaatcaga gtggatcagc ttcaggccca gctgtcaact caagagaaag    900
aaatggagaa gcttgttcag ggagatcaag ataagacaga gcagttagag cagctgaaaa    960
aggaaaatga ccacctcttt ctcagtttaa ctgaacagag gaaggaccag aagaagctcg   1020
agcagacagt ggagcaaatg aagcagaatg aaactactgc aatgaagaaa caacaggaat   1080
taatggatga aaactttgac ctgtcaaaaa gactgagtga gaacgaaatt atatgtaatg   1140
ctctgcagag acagaaagag agattggaag gagaaaatga tcttttgaag agggagaaca   1200
gcagattgct cagttacatg ggtctggatt ttaattcttt gccgtatcaa gtacctactt   1260
cagatgaagg aggcgcaaga caaaatccag gacttgccta tggaaaccca tattctggta   1320
tccaagaaag ttcttccccc agcccgctct ccatcaagaa atgccctatc tgcaaagcag   1380
atgatatttg tgatcacacc ttggagcaac agcagatgca gccccttttgt ttcaattgtc   1440 caatttgtga caagatcttc ccagctacag agaagcagat ctttgaagac cacgtgttct   1500
gccactctct ctgagtatcc caacctcttg gatgtataca gagattttat agaatagaac   1560
ctatagcttc taccatgagt tatatgagtc aagatcctgc ctaacctgaa attattaggg   1620
atttactcag ccctgctgcc gctaacagtg gagttatgtc actgatctga aggtcactgt   1680
taagggcttc tgctgccatc cttgtgggtt gctacccttta agtcgcataa ctctagctgt   1740
atcatcctct cacctgtcat tcttctgagg gtctcagtac aagggccctg ggatggagcc   1800
aacctgggta ttcacaacag gcctgacttg atactaagtg attagttttc caagttgtcc   1860
cactgccatt caaagtcagc ccttgagtgt atttgttctc agtcctaacc ctggggccag   1920
agattggtcc gaggttgaga attccttcct cctcatcctt ggtgttgctt tctccaaatg   1980
attgttttag actagccaaa aatgccgtgg caaagagctc agaaatccaa tttggatacc   2040
aaaggtttct catgttaatt tctcagcccc caaagaagca tcttactcct gaaccttaga   2100
caggaagtat tgtttcagtc acagaaagct tttctgggta cctctggtta gcactttcta   2160
ctctctgata tttcctatgt acatagcttt tattgttgta aatcctttct taatggttaa   2220
ataggattgt tagcaactat gggttttgcag ttttctgagt aggtgagttt tgaatatggg   2280
taaatcagaa taatgagaca acttgttaat ctctttaata ctaaaaataa attactcttc   2340
tatttcaggg acttaggtaa tttaaaataa accttcaatt tatggtcttc tgttttgaag   2400
ctcatgggaa aattgtgatc aaaagggcta tgggaagggc agaccccgcc aatgatttct   2460
cttcacctgt cttaagatta aataaaaaag agtgtcctgg cagttatctt gaggtgggga   2520
aggaggtgat gaaacattag tttgtgaaat ccaaggccct ggcttgcttt ctttcttttt   2580
tttttttttt ttttgaaaca gtctctctct gtcacccagg ctggcgtgca atggcgcagt   2640
tgactcacta cagcctctgc ctcccaggtt caagcgattc tcatgcctta gcctcccaag   2700
tagctgggat tacaggtgtg tgccgcaatg cccagctaat ttttgtgttt ttagtagaga   2760
cagggtttca ctatgttggc caggctggtc tcgaactcct ggcctcacgt gatctgtcca   2820
cttcagccgt ccaaagtgct gggattacaa gcgtgagcca ctgtgctggg cccgaggccc   2880
tgacttcttg ctgtaacttt ccatgcattt tttttaaaag gagcagtgtg gattttcgca   2940
ccctttgtga actaagttca atgcgctcta tccaaatttg cctaattgaa ctataagaaa   3000
gtaataattc cattttctat cccctcaggg actgaacaaa tggaaataac tcccaggcag   3060
tatcaggtgg tcactacaga gacttccaca aaaacttttg aatgatgtga aacacgatgt   3120
catgaataag ggttgagcca actatagctc tgtgttccta ctgggctttc cctaatgtgg   3180
```

-continued

| | |
|---|---|
| ttgggagtta tgccctagac taactgtatt gtcctagtca cagctccttg ctttgatttc | 3240 |
| atccttgata aaatgaagat gaaacttaca ctacttctcc aagcctttg ctgtcttaag | 3300 |
| aataagacct gagattaaca ctaaccctag aatagaaatg taatagggag atggtaataa | 3360 |
| aggagttttt ctggcacata ccctccctac agaatttctg ttgctcccca gatccagtga | 3420 |
| agaattgcag tttcatttat tttgtaccag tcagctctta attaagtaca tgaatggaga | 3480 |
| ggaacagtgg tgcacataat ccaaatcagt gaataccatt ttctggtgaa ttacccaccc | 3540 |
| cttttgcccct gctaccccga gggttaccat gattgtcaac agcagcagga gcccttccac | 3600 |
| agggcttggt aaaaaaacca gttgaggtgt taatgacccct ttttgctggg tgtaaaacaa | 3660 |
| agcatcttta accactgttc attatcccca gctgctctta ccaaggcttt gaaggggggaa | 3720 |
| attatgctct aggcagccac tagtagtaaa caat | 3754 |

<210> SEQ ID NO 162
<211> LENGTH: 1651
<212> TYPE: DNA
<213> ORGANISM: Homo sapiens

<400> SEQUENCE: 162

| | |
|---|---|
| acgactgcgt gggtgagtcg tctataaaaa ctcatctctg cgcgtctctt cgccacattc | 60 |
| gcttcctgct ttcggtgtgt ctgttgtgtc ttgttgcggg caccgcagtc gccgtgaaga | 120 |
| tggcgtctac cagccgtttg gatgctcttc caagagtcac atgtccaaac catccagatg | 180 |
| cgatttagt ggaggactac agagccggtg atatgatctg tcctgaatgt ggcttggttg | 240 |
| taggtgaccg ggttattgat gtgggatctg aatggcgaac tttcagcaat gacaaagcaa | 300 |
| caaaagatcc atctcgagtt ggagattctc agaatcctct tctgagtgat ggagatttgt | 360 |
| ctaccatgat tggcaagggc acaggagctg caagttttga cgaatttggc aattctaagt | 420 |
| accagaatcg gagaacaatg agcagttctg atcgggcaat gatgaatgca ttcaaagaaa | 480 |
| tcactaccat ggcagacaga atcaatctac ctcgaaatat agttgatcga acaaataatt | 540 |
| tattcaagca agtatatgaa cagaagagcc tgaagggaag agctaatgat gctatagctt | 600 |
| ctgcttgtct ctatattgcc tgtagacaag aaggggttcc taggacattt aaagaaatat | 660 |
| gtgccgtatc acgaatttct aagaaagaaa ttggtcggtg ttttaaactt attttgaaag | 720 |
| cgctagaaac cagtgtggat ttgattacaa ctggggactt catgtccagg ttctgttcca | 780 |
| acctttgtct tcctaaacaa gtacagatgg cagctacaca tatagcccgt aaagctgtgg | 840 |
| aattggactt ggttcctggg aggagcccca tctctgtggc agcggcagct atttacatgg | 900 |
| cctcacaggc atcagctgaa aagaggaccc aaaaagaaat tggagatatt gctggtgttg | 960 |
| ctgatgttac aatcagacag tcctatagac tgatctatcc tcgagcccca gatctgtttc | 1020 |
| ctacagactt caaatttgac accccagtgg acaaactacc acagctataa attgaggcag | 1080 |
| ctaacgtcaa attcttgaat acaaaacttt gcctgttgta catagcctat acaaaatgct | 1140 |
| gggttgagcc tttcatgagg aaaaacaaaa gacatggtac gcattccagg gctgaatact | 1200 |
| attgcttggc attctgtatg tatatactag tgaaacatat ttaatgattt aaatttctta | 1260 |
| tcaaatttct tttgtagcaa tctaggaaac tgtattttgg aagatatttg aaattatgta | 1320 |
| attcttgaat aaaacatttt tcaaaactca gttttttgtt atatgttaca tgtaacttat | 1380 |
| gatacataat tacaaataat gcaaatcatt gcagctaata aagctgatag actttatttc | 1440 |
| cattacttat atatacatag ttttttattt taataaattt atggaaagag caaaagcttt | 1500 |
| tgagaaccat tgttaacatc aacatcatag tttccagttt gaaggatgt gtatgtgaga | 1560 |

| | |
|---|---|
| tttattatgt atattattaa acaagaagtg atgagcttgg gccttgaaag gcaccagctt | 1620 |
| gagagacatt aaaatgttct aagtaaaaaa a | 1651 |

<210> SEQ ID NO 163
<211> LENGTH: 1578
<212> TYPE: DNA
<213> ORGANISM: Homo sapiens

<400> SEQUENCE: 163

| | |
|---|---|
| agttctaaag tccccacgca cccacccgga ctcagagtct cctcagacgc cgagatgctg | 60 |
| gtcatggcgc cccgaaccgt cctcctgctg ctctcggcgg ccctggccct gaccgagacc | 120 |
| tgggccggct cccactccat gaggtatttc tacacctccg tgtcccggcc cggccgcggg | 180 |
| gagccccgct tcatctcagt gggctacgtg gacgacaccc agttcgtgag gttcgacagc | 240 |
| gacgccgcga gtccgagaga ggagccgcgg gcgccgtgga tagagcagga ggggccggag | 300 |
| tattgggacc ggaacacaca gatctacaag gccaggcac agactgaccg agagagcctg | 360 |
| cggaacctgc gcggctacta caaccagagc gaggccgggt ctcacaccct ccagagcatg | 420 |
| tacggctgcg acgtggggcc ggacgggcgc ctcctccgcg gcatgaccca gtacgcctac | 480 |
| gacggcaagg attacatcgc cctgaacgag gacctgcgct cctggaccgc cgcggacacg | 540 |
| gcggctcaga tcacccagcg caagtgggag gcggcccgtg aggcggagca gcggagagcc | 600 |
| tacctggagg gcgagtgcgt ggagtggctc cgcagatacc tggagaacgg gaaggacaag | 660 |
| ctggagcgcg ctgacccccc aaagacacac gtgacccacc accccatctc tgaccatgag | 720 |
| gccaccctga ggtgctgggc cctgggtttc taccctgcgg agatcacact gacctggcag | 780 |
| cgggatggcg aggaccaaac tcaggacact gagcttgtgg agaccagacc agcaggagat | 840 |
| agaaccttcc agaagtgggc agctgtggtg gtgccttctg agaagagca gagatacaca | 900 |
| tgccatgtac agcatgaggg gctgccgaag ccccctcaccc tgagatggga gccgtcttcc | 960 |
| cagtccaccg tccccatcgt gggcattgtt gctggcctgg ctgtcctagc agttgtggtc | 1020 |
| atcggagctg tggtcgctgc tgtgatgtgt aggaggaaga gttcaggtgg aaaaggaggg | 1080 |
| agctactctc aggctgcgtg cagcgacagt gcccagggct ctgatgtgtc tctcacagct | 1140 |
| tgaaaagcct gagacagctg tcttgtgagg gactgagatg caggatttct tcacgcctcc | 1200 |
| cctttgtgac ttcaagagcc tctggcatct ctttctgcaa aggcacctga atgtgtctgc | 1260 |
| gtccctgtta gcataatgtg aggaggtgga gagacagccc acccttgtgt ccactgtgac | 1320 |
| ccctgttccc atgctgacct gtgtttcctc cccagtcatc tttcttgttc cagagaggtg | 1380 |
| gggctggatg tctccatctc tgtctcaact ttacgtgcac tgagctgcaa cttcttactt | 1440 |
| ccctactgaa aataagaatc tgaatataaa tttgttttct caaatatttg ctatgagagg | 1500 |
| ttgatggatt aattaaataa gtcaattcct ggaatttgag agagcaaata aagacctgag | 1560 |
| aaccttccag aaaaaaaa | 1578 |

<210> SEQ ID NO 164
<211> LENGTH: 1591
<212> TYPE: DNA
<213> ORGANISM: Homo sapiens

<400> SEQUENCE: 164

| | |
|---|---|
| tttctcactc ccattgggcg tcgcgtttct agagaagcca atcagtgtcg ccgcagttcc | 60 |
| caggttctaa agtcccacgc accccgcggg actcatattt ttcccagacg cggaggttgg | 120 |

```
ggtcatggcg ccccgaagcc tcctcctgct gctctcaggg gccctggccc tgaccgatac    180
ttgggcgggc tcccactcct tgaggtattt cagcaccgct gtgtcgcggc ccggccgcgg    240
ggagccccgc tacatcgccg tggagtacgt agacgacacg caattcctgc ggttcgacag    300
cgacgccgcg attccgagga tggagccgcg ggagccgtgg gtggagcaag aggggccgca    360
gtattgggag tggaccacag ggtacgccaa ggccaacgca cagactgacc gagtggccct    420
gaggaacctg ctccgccgct acaaccgagc gaggctgggg tctcacaccc tccagggaat    480
gaatggctgc gacatggggc ccgacggacg cctcctccgc gggtatcacc agcacgcgta    540
cgacggcaag gattacatct ccctgaacga ggacctgcgc tcctggaccg cggcggacac    600
cgtggctcag atcacccagc gcttctatga ggcagaggaa tatgcagagg agttcaggac    660
ctacctggag ggcgagtgcc tggagttgct ccgcagatac ttggagaatg ggaaggagac    720
gctacagcgc gcagatcctc caaaggcaca cgttgcccac caccccatct ctgaccatga    780
ggccaccctg aggtgctggg ccctgggctt ctaccctgcg agatcacgc tgacctggca    840 gcgggatggg gaggaacaga cccaggacac agagcttgtg gagaccaggc ctgcagggga    900
tggaaccttc cagaagtggg ccgctgtggt ggtgcctcct ggagaggaac agagatacac    960
atgccatgtg cagcacgagg ggctgcccca gcccctcatc ctgagatggg agcagtctcc   1020
ccagcccacc atccccatcg tgggcatcgt tgctggcctt gttgtccttg gagctgtggt   1080
cactggagct gtggtcgctg ctgtgatgtg gaggaagaag agctcagata gaaacagagg   1140
gagctactct caggctgcag cctactcagt ggtcagcgga aacttgatga taacatggtg   1200
gtcaagctta tttctcctgg gggtgctctt ccaaggatat ttgggctgcc tccggagtca   1260
cagtgtcttg ggccgccgga aggtgggtga catgtggatc ttgttttttt tgtggctgtg   1320
gacatctttc aacactgcct tcttggcctt gcaaagcctt cgctttggct tcggcttttag   1380 gaggggcagg agcttccttc ttcgttcttg gcaccatctt atgaaaaggg tccagattaa   1440
gatttttgac tgagtcattc taaagtaagt tgcaagaccc atgatactag accactaaat   1500
acttcatcac acacctccta agaataagaa ccaacattat cacaccaaag aaaataaata   1560
attccataat attaaaaaaa aaaaaaaaa a                                   1591
```

<210> SEQ ID NO 165
<211> LENGTH: 817
<212> TYPE: DNA
<213> ORGANISM: Homo sapiens

<400> SEQUENCE: 165

```
gctggccgtg ggagaggctt aaaacaaacg ccggaagcaa ctcccagccc cataaagatc     60
tgtgaccggc agcccagac ctgcctgcct tcctgacttc tgttccagag caaaggtcat    120
tcagccgctt gaatcagcct tttcccccca cccggtcccc aactttgttt acccgataag    180
gaaggtcagc attcaaagtc aagaagcgcc atttatcttc ccgtgcgctc tacaaatagt    240
tccgtgagaa agatggccgg gaactcgatc ctgctggctg ctgtctctat tctctcggcc    300
tgtcagcaaa gttattttgc tttgcaagtt ggaaaggcaa gattaaaata caaagttacg    360
cccccagcag tcactgggtc accagagttt gagagagtat tcgggcacac acaaaactgt    420
gtggagtttt atcctatatt cataattaca ttgtggatgg ctgggtggta tttcaaccaa    480 gttttttgcta cttgtctggg tctggtgtac atatatggcc gtcacctata cttctgggga    540
tattcagaag ctgctaaaaa acggatcacc ggtttccgac tgagtctggg gattttggcc    600
ttgttgaccc tcctaggtgc cctgggaatt gcaaacagct ttctggatga atatctggac    660
```

-continued

| | | |
|---|---|---|
| ctcaatattg ccaagaaact gaggcggcaa ttctaacttt ttctcttccc tttaatgctt | 720 | |
| gcagaagctg ttcccaccat gaaggtaata tggtatcatt tgttaaataa aaataaagtc | 780 | |
| tttattctgt ttttcttgaa aaaaaaaaaa aaaaaaa | 817 | |

<210> SEQ ID NO 166
<211> LENGTH: 5221
<212> TYPE: DNA
<213> ORGANISM: Homo sapiens

<400> SEQUENCE: 166

| | | |
|---|---|---|
| ggcccgagcc accgactgca ggaggagaag gggttgtgct cctggccgag gaaggagaaa | 60 | |
| ggggcggggc cggcgggcag cgtgcggcag tgcggagctc ctgagaccgg cgggcacacg | 120 | |
| ggggtctgtg gccccgccg tagcagtggc tgccgccgtc gcttggttcc cgtcggtctg | 180 | |
| cgggaggcgg gttatggcgg cggcggcagt gagagctgtg aatgaattct ccgggtggac | 240 | |
| gagggaagaa gaaaggctcc ggcggcgcca gcaacccggt gcctcccagg cctccgcccc | 300 | |
| cttgcctggc ccccgcccct cccgccgccg ggccggcccc tccgcccgag tcgccgcata | 360 | |
| agcggaacct gtactatttc tcctacccgc tgtttgtagg cttcgcgctg ctgcgtttgg | 420 | |
| tcgccttcca cctggggctc ctcttcgtgt ggctctgcca gcgcttctcc cgcgccctca | 480 | |
| tggcagccaa gaggagctcc ggggccgcgc cagcacctgc ctcggcctcg gcccggcgc | 540 | |
| cggtgccggg cggcgaggcc gagcgcgtcc gagtcttcca caaacaggcc ttcgagtaca | 600 | |
| tctccattgc cctgcgcatc gatgaggatg agaaagcagg acagaaggag caagctgtgg | 660 | |
| aatggtataa gaaggtatt gaagaactgg aaaaaggaat agctgttata gttacaggac | 720 | |
| aaggtgaaca gtgtgaaaga gctagacgcc ttcaagctaa aatgatgact aatttggtta | 780 | |
| tggccaagga ccgcttacaa cttctagaga agatgcaacc agttttgcca ttttccaagt | 840 | |
| cacaaacgga cgtctataat gacagtacta acttggcatg ccgcaatgga catctccagt | 900 | |
| cagaaagtgg agctgttcca aaaagaaaag accccttaac acacactagt aattcactgc | 960 | |
| ctcgttcaaa aacagttatg aaaactggat ctgcaggcct ttcaggccac catagagcac | 1020 | |
| ctagttacag tggtttatcc atggtttctg gagtgaaaca gggatctggt cctgctccta | 1080 | |
| ccactcataa gggtactccg aaaacaaata ggacaaataa accttctacc cctacaactg | 1140 | |
| ctactcgtaa gaaaaaagac ttgaagaatt ttaggaatgt ggacagcaac cttgctaacc | 1200 | |
| ttataatgaa tgaaattgtg gacaatggaa cagctgttaa atttgatgat atagctggtc | 1260 | |
| aagacttggc aaaacaagca ttgcaagaaa ttgttattct tccttctctg aggcctgagt | 1320 | |
| tgttcacagg gcttagagct cctgccagag gctgttact cttggtcca cctgggaatg | 1380 | |
| ggaagacaat gctggctaaa gcagtagctg cagaatcgaa tgcaaccttc tttaatataa | 1440 | |
| gtgctgcaag tttaacttca aaatacgtgg gagaaggaga gaaattggtg agggctcttt | 1500 | |
| ttgctgtggc tcgagaactt caaccttcta aatttttat agatgaagtt gatagccttt | 1560 | |
| tgtgtgaaag aagagaaggg gagcacgatg ctagtagacg cctaaaaact gaatttctaa | 1620 | |
| tagaatttga tggtgtacag tctgctggag atgacagagt acttgtaatg ggtgcaacta | 1680 | |
| ataggccaca agagcttgat gaggctgttc tcaggcgttt catcaaacgg gtatatgtgt | 1740 | |
| ctttaccaaa tgaggagaca agactacttt tgcttaaaaa tctgttatgt aaacaaggaa | 1800 | |
| gtccattgac ccaaaaagaa ctagcacaac ttgctagaat gactgatgga tactcaggaa | 1860 | |
| gtgacctaac agctttggca aaagatgcag cactgggtcc tatccgagaa ctaaaaccag | 1920 | |

-continued

| | |
|---|---|
| aacaggtgaa gaatatgtct gccagtgaga tgagaaatat tcgattatct gacttcactg | 1980 |
| aatccttgaa aaaataaaa cgcagcgtca gccctcaaac tttagaagcg tacatacgtt | 2040 |
| ggaacaagga ctttggagat accactgttt aaggaaatac ctttgtaaac ctgcagaaca | 2100 |
| ttttacttaa aagaggaaac acaagatctt caatgaacgt catcggctac agaaacagcc | 2160 |
| taagtttaca ggacttttta gagtcttaca tatttgtgca ccaaacttga agatgaacca | 2220 |
| gaaaacagac ttaaacaaaa tatacaatgc aaatgtaatt ttttgttgtt taaggccttg | 2280 |
| ccttgatggt cacagttatc ccaatggaca ctaagttaga gcacaacaaa acctgattct | 2340 |
| ggtcttcttt accaatataa tcataatgta aataataatt tgtatattgt gttgcagatg | 2400 |
| aaagtattcc aggaacagtg aatggtagaa gacacaagaa catttgtttg tttgtcttct | 2460 |
| gatgttttt cttaaaatag taatttctcc tacttttctt ttctactgtt gtcttaacta | 2520 |
| caggtgattg gaatgccaaa cactcttaag tttatttct ttttcgttt tataaattca | 2580 |
| gtgtgccaaa tgaactttt ttcctaagta actgtaatag gaaaaagttt attttgagag | 2640 |
| tttcttcttc ataaatctac agacattaaa caattgttgt gttctttta ccttttattt | 2700 |
| ttctattacc ttgctaccaa acagtttaga tagcaatata atagcaaaaa agcaaatatg | 2760 |
| gtaaaataga gaaggtttga aggtttgagt tactctgtca tataacatgt agatcagtct | 2820 |
| tcatgtgacc tgcagtattt ttttttctaa tgtatttgtc agaaatctgt tgtagactgt | 2880 |
| taacttcttc ctgatggaat ttattttctg caagaattat tctgatattt aagagagcca | 2940 |
| attttaactg ctgtgaaaat gtttccagtg caagagaagg gaaatactag gaactaagac | 3000 |
| atttctaatt tattgcttat tactttctta attttacagg ataattataa gcaagtggaa | 3060 |
| ctaccatctt ttattcttaa taattattaa tcccttcaat gaaactttaa aaaaactgaa | 3120 |
| tttttataca tggcatacat ttttctagtt ccttctgctt gctttattaa ctcaaaagtt | 3180 |
| ctagttctag tctgttgatc tgccttttgt tctcccaaaa tgtacagtaa ttccatttgt | 3240 |
| ttgtataaat atgcctggat tttcattata aaaatgtcat tgtagggagt agagactcat | 3300 |
| atcatggcct tttaaatatt gtaataaagg caaatagata tttgcccttg gtttactggt | 3360 |
| taaaagtttg tttacagaac ttttctctgg tgcttaaatg atgctatgta aaatgtcatg | 3420 |
| agtggaaaga atatttgtag tagtaacaag aattttttcat ttaggaaaga tttcttaggt | 3480 |
| tttgaaagaa tacattaaaa taaaaaactt gccccctacta ggtaagaact ttataatgaa | 3540 |
| gacatacatt cttcttaatt ttactcttgc tcttgttaaa gatttgtttg aatatagaag | 3600 |
| atgcatgatt tctgggtttt ttttttttt tgagacagag tttcgctctt gttgcccagg | 3660 |
| ctggagtgca atggcgcaat ctcgactcac cacaacctcc gcctcccagg ttcaagcaat | 3720 |
| tctcctgcct cagcctcccg agtagctggg attacaggca tgcgccacta ccccagctaa | 3780 |
| ttttgtattt ttagtagaga tggggtttct ccatgttggt caggctggtc ttgaactcct | 3840 |
| gacctcaggt gatccgcctg cctcggcctc ccaaagtgct gggattacag gcataagcca | 3900 |
| ctgcgcccag ccagaagatg catgatttct taggatcata tgctgtttgt agccataagg | 3960 |
| taaatcatgt ctcttccaat catgactttg gaactccctg aataataaaa atgagagttg | 4020 |
| agataaatag gggaaaaaa attttttca agccagagct atgcatatgt taggtgatgg | 4080 |
| gtagtatccc tttaaggtct caaacattac aacatcaatt atgaaatact gataacgaaa | 4140 |
| ggtagtaatg aaatatatat gatgaaaaga attgagaagt tctaaattaa gacatttcag | 4200 |
| ttaagctcat aaaatttcat tgttttcatt taaaagatta acgttattga tacttggata | 4260 |
| actggctaat catattaaag gactatgtgg ttccagctca acttttaata tattgtctcc | 4320 |

```
tttaaaacta tcatggttat aattctattg ggaaagactt ttagataaca aagatttcaa    4380
atgttaaaag agataaaagt caggttaata ctatcttaaa cactgagtca gaaaatcatt    4440
actgtataga agttgctttc ctgatcaagt ctgaacttca gctagtgcta gagaactatt    4500
ttctatgact taactctaac caagttttat tttaagctgt ttctttgata gaagggccat    4560
gaaaatagag taatgatata gtaggagata agggattggt ttggtctttt tcaataaaga    4620
tagaagttgc tgaagttttc tgaattaata atgacttaga ttgtgacctt ttagattcgg    4680
tgttgagctc tgtgttgtat tacttcctaa aagataatgc ttaaacatta agcattagtg    4740
tgctcttcat gttaatatgg cagagttttg taaactaaat taaaacttac tgatatattg    4800
gactttgagc caagggaaag aatgagtact atctttccag atatcttaag ggtaaaagct    4860
tattctaaga cagtctgtcc attgagaata ttagatttct gacttgcaaa tatgtttgta    4920
ctccagaaga attagaggaa aagcagatac tagaattcta atttaattac atatacagcc    4980
gtctttgttt atagtgtaga attctttata ttttgtacaa aaactaattc ttttggtaaa    5040
atgaaccatt tacagttcgg ttttggactc tgagtcaaag gattttcctt taaatgcttg    5100
tctcaatttt agtctggtct tttgtacttt tcttcagaag aaatgaatta aagggtacag    5160
ttgcataaag tgggttttta tcctaatgta ttggaaataa atgataaact ttaaaaaaaa    5220
a                                                                    5221
```

<210> SEQ ID NO 167
<211> LENGTH: 5537
<212> TYPE: DNA
<213> ORGANISM: Homo sapiens

<400> SEQUENCE: 167

```
cgcccgccgc cgccgccgcc tgcgcgcccg cccgcctttc gcggccgctc tcccccctcc      60
ccgacacaca ctcacaggcc gggcattgat ggtaatgtat gcgaggaaac agcagagact     120
cagtgatggc tgtcacgacc ggaggggga ctcgcagcct taccaggcac ttaagtattc     180
atcgaagagt caccccagta gcggtgatca cagacatgaa agatgcgag acgccggaga     240 tccttcacca ccaaataaaa tgttgcggag atctgatagt cctgaaaaca aatacagtga     300
cagcacaggt cacagtaagg ccaaaaatgt gcatactcac agagttagag agagggatgg     360
tgggaccagt tactctccac aagaaaattc acacaaccac agtgctcttc atagttcaaa     420
ttcacattct tctaatccaa gcaataaccc aagcaaaact tcagatgcac cttatgattc     480
tgcagatgac tggtctgagc atattagctc ttctgggaaa aagtactact acaattgtcg     540
aacagaagtt tcacaatggg aaaaaccaaa agagtggctt gaaagagaac agagacaaaa     600
agaagcaaac aagatggcag tcaacagctt cccaaaagat agggattaca gaagagaggt     660
gatgcaagca acagccacta gtgggtttgc cagtggaatg aagacaagc attccagtga     720 tgccagtagt ttgctcccac agaatatttt gtctcaaaca agcagacaca atgacagaga     780
ctacagactg ccaagagcag agactcacag tagttctacg ccagtacagc accccatcaa     840
accagtggtt catccaactg ctaccccaag cactgttcct tctagtccat ttacgctaca     900
gtctgatcac cagccaaaga aatcatttga tgctaatgga gcatctactt tatcaaaact     960
gcctacaccc acatcttctg tccctgcaca gaaaacagaa agaaagaat ctacatcagg    1020 agacaaaccc gtatcacatt cttgcacaac tccttccacg tcttctgcct ctggactgaa    1080
ccccacatct gcacctccaa catctgcttc agcggtccct gtttctcctg ttccacagtc    1140
```

```
gccaatacct cccttacttc aggacccaaa tcttcttaga caattgcttc ctgctttgca    1200
agccacgctg cagcttaata attctaatgt ggacatatct aaaataaatg aagttcttac    1260
agcagctgtg acacaagcct cactgcagtc tataattcat aagtttctta ctgctggacc    1320
atctgctttc aacataacgt ctctgatttc tcaagctgct cagctctcta cacaagccca    1380
gccatctaat cagtctccga tgtctttaac atctgatgcg tcatcccaa gatcatatgt    1440 ttctccaaga ataagcacac ctcaaactaa cacagtccct atcaaacctt tgatcagtac    1500
tcctcctgtt tcatcacagc caaaggttag tactccagta gttaagcaag gaccagtgtc    1560
acagtcagcc acacagcagc ctgtaactgc tgacaagcag caaggtcatg aacctgtctc    1620
tcctcgaagt cttcagcgct caagtagcca gagaagtcca tcacctggtc ccaatcatac    1680
ttctaatagt agtaatgcat caaatgcaac agttgtacca cagaattctt ctgcccgatc    1740
cacgtgttca ttaacgcctg cactagcagc acacttcagt gaaaatctca taaaacacgt    1800
tcaaggatgg cctgcagatc atgcagagaa gcaggcatca agattacgcg aagaagcgca    1860
taacatggga actattcaca tgtccgaaat ttgtactgaa ttaaaaaatt taagatcttt    1920
agtccgagta tgtgaaattc aagcaacttt gcgagagcaa aggatactat ttttgagaca    1980
acaaattaag gaacttgaaa agctaaaaaa tcagaattcc ttcatggtgt gaagatgtga    2040
ataattgcac atggttttga gaacaggaac tgtaaatctg ttgcccaatc ttaacatttt    2100
tgagctgcat ttaagtagac tttggaccgt taagctgggc aaaggaaatg acaagggac    2160 ggggtctgtg agagtcaatt caggggaaag atacaagatt gatttgtaaa acccttgaaa    2220
tgtagatttc ttgtagatgt atccttcacg ttgtaaatat gttttgtaga gtgaagccat    2280
gggaagccat gtgtaacaga gcttagacat ccaaaactaa tcaatgctga ggtggctaaa    2340
tacctagcct tttacatgta aacctgtctg caaaattagc tttttttaaaa aaaaaaaaa    2400 aaaaattggg ggggttaatt tatcattcag aaatcttgca ttttcaaaaa ttcagtgcaa    2460
gcgccaggcg atttgtgtct aaggatacga ttttgaacca tatgggcagt gtacaaaata    2520
tgaaacaact gtttccacac ttgcacctga tcaagagcag tgcttctcca tttgttttgc    2580
agagaaatgt ttttcatttc ccgtgtgttt ccatttcctt ctgaaattct gattttatcc    2640 attttttttaa ggctcctctt tatctccttt cttaaggcac tgttgctatg gcacttttct    2700 ataaccttt cattcctgtg tacagtagct taaaattgca gtgattgagc ataacctact    2760
tgtttgtata aattattgaa atccatttgc accctgttaa gaatggactt aaaagtactg    2820
ctggacaggc atgtgtgctc aaagtacatt gattgctcaa atataaggaa atggcccaat    2880
gaacgtggtt gtgggagggg aaagaggaaa cagagctagt cagatgtgaa ttgtatctgt    2940
tgtaataaac atgttaaaac aaacaaaaat tgttattttt cttttccttc ggtcagtgca    3000
cattagcatt tgaactacct ggggattctt tatcagaact gttcttgttg aatatttata    3060
cttaattgaa ataattcctt aagggaggtt ttgtttaaaa cgtattaaca ggaaattgtg    3120
tatgagatat ttaatgaaat aagaaattca acaagaatga ttaagtcact tcccaagtgg    3180
ttgtcatttg ttaaaccctg gtttacctgt cttgctatta tgacatttca tttggaagga    3240
tgtttgtgtt gtagctaact gttcaagtct ggtgctgact gctgttctta gccatcacaa    3300
aacgctaaat ttgtgtaatt ggagcttcct gctgttatct ggaaatagca ggaaagcgca    3360
gctttgtata ttgtttccta agtatatta aataaaaaaa agaaactatt gctactataa    3420
aattaccttg acttttttttt tcctttgctg aaatattagt cacatagcct tagcttcaca    3480
ctgccagtaa tgtatcaaat cacaagggtt tccgcatgaa aaaaatcttt tcttcccca    3540
```

-continued

```
caaaaaaacc tttaccatca aaatcttgcc atctgattta gaaaggtgtt tcttcttctt    3600
cttctttttt ttctttaaat tggtttaggg ttttttggtg atttttttt ttttttttt     3660
tctgttgggg cagataagtg cttccaaaac tggcagcacc aagggcttat tttttatgtt    3720
agacatcaat gtcaatgtta ctacattctc ggatgctaac ataaattttg aaattgctct    3780
tgtgctttaa gcatatattg aaagtatgga agttaaatgt tcaggctttt cagtaagctc    3840
aaaaagttaa ctgtaagcga tagtgttggt gttttctaaa atacaaaaat gttccagtgt    3900
aattaaaagg aattaaaatc ttgaagatat tttcctgtaa tttaaggata cttttaaat    3960
gtaagaaaag acatgtcatt aatttattgt catgtttata cctctgtgag attgttaaca    4020
tctgctgaat ttaactagtg catgtaaatg aaaccccaaa gagctgtgtg ttcagctaga    4080
aaccttactg tatctttcct ggaaagaagt gagcaatttg ttgtaatagg caaatgtttc    4140
ctgatcagat ggcaatttgt gatttaggta aatttgaatt tgatttgctt atagtctact    4200
ggtctgtgta cctatgtttt gttttcaaa aagtttaca tccctaaatg aattagtcac     4260
atatatttag gagaagatgc ctaatttggt atttcttaat agtgaatttt tttttttctt    4320
gagacagagt ttcactcttg ttgcccaggc tggagtgcaa tggcacgatc tcggctcacc    4380
gcaacctctg cctcctgggt tcaagcgatt ctcctgcctc ggcgttccga gtagctggga    4440
ttacaggcat gcaccaccac gcctggctaa ttttgtattt ttagtagaga tggggtttct    4500
ccatgttggt caggctggtc ttgaactgcc aacttcaggt gatctgcctg ccttggcctc    4560
ccaaagtgct gggattacag gcgtgagcca ccgctcctgg ccagtagtga atttttaaac    4620
acagaaaatc taaattttg tggaaatatt ttaaatattg caccttaata caaggtatcc    4680
agctcctaac cttaactagg gaatatctat taaaataagc ataatgttct ggactagagt    4740
attccttatc tagttggtta tggatttgaa catgtacctt ggtttagata ctttgaaaat    4800
agaagtactg aatagcctct agggaacttg agtggccttt ccctccccct gccccccccc    4860
cccccccccc gttttaaaag atcagtagtc tctattcaaa cttttaaaat gtcgtggtat    4920
tgtaacaata tatttgatga agaaggtta cagactcccc tgaagaacca gctttcctac    4980
gcttttatt tttctaactt gtctaacctg attttaaaat gactgcaatt ccagactaaa    5040
aacatgcttc agccctgttt caagacatta tgcttctttt aacagtccaa attagtagtt    5100
ttattttct tctaaatctt tgtttcacac ttgtaaaatc ttgggaagga ggttcttaaa    5160
actttgccag gaattgttac ccatttccaa aaacagttta ttatgttcaa aaaccaccat    5220
atctttgagg gactgtttga aaggggagag ggcaacgcgg gaaataattc actctgcgca    5280
ccggaactat tgtagttcag gacttccagc tactgtattt agatgttggg tttgaatata    5340
cagatttctt ttcaatacct gtaaatatgg ctatattctt gtatttgtac gggagtgtac    5400
aaaatgacac tgaaaagtaa taaatatgtt ttgactatat tgtgcagtta tttcagaact    5460
gtgttttgaa agtcttagaa tgcataattt gcatttgagt aaggaaattt aaaatacaga    5520
ttactgctga gatttta                                                   5537
```

<210> SEQ ID NO 168
<211> LENGTH: 70
<212> TYPE: DNA
<213> ORGANISM: Artificial Sequence
<220> FEATURE:
<223> OTHER INFORMATION: probe

<400> SEQUENCE: 168

```
ctgtgcagta tgcgatgttt tgtggatggc aaagacttat tcctgaggga atcgatatag        60
gggaacctct                                                               70

<210> SEQ ID NO 169
<211> LENGTH: 70
<212> TYPE: DNA
<213> ORGANISM: Artificial Sequence
<220> FEATURE:
<223> OTHER INFORMATION: probe

<400> SEQUENCE: 169
tgaggaagtg acacttatac gcaaagctga tttggagaac cataataaag atggaggctt        60
ctggactgtg                                                               70

<210> SEQ ID NO 170
<211> LENGTH: 70
<212> TYPE: DNA
<213> ORGANISM: Artificial Sequence
<220> FEATURE:
<223> OTHER INFORMATION: probe

<400> SEQUENCE: 170
ctgctcaatg acttttgagc agctggatct cctgcttcgg caggtgagtg aggggatgga        60
tggttccgcg                                                               70

<210> SEQ ID NO 171
<211> LENGTH: 70
<212> TYPE: DNA
<213> ORGANISM: Artificial Sequence
<220> FEATURE:
<223> OTHER INFORMATION: probe

<400> SEQUENCE: 171
accaaaaaac acaataccag gcatacattt ggcagaataa atgaaccagg tcagtctgcg        60
gtattttgtg                                                               70
```

BIOMARKERS AND COMBINATIONS THEREOF FOR DIAGNOSING TUBERCULOSIS

FIELD OF THE INVENTION

This invention relates to the detection and diagnosis of tuberculosis. More specifically, the invention relates to new biomarkers and combinations thereof that enable the accurate detection and diagnosis of tuberculosis.

BACKGROUND OF THE INVENTION

Tuberculosis (TB) is a progressive, often fatal, infectious disease, caused by the bacterial pathogen *Mycobacterium tuberculosis* (*M. tuberculosis*, MTB). This is a significant cause of mortality worldwide, being the eighth largest leading cause of death globally, and is primarily a disease of poverty, particularly in developing countries. Latent TB infection is believed to affect as much as one third of the world's population.

Tuberculosis is a notifiable disease and is a major concern for many governmental and other health bodies including the World Health Organisation (WHO), who have initiated numerous control and treatment programmes like the "Stop TB Partnership".

The WHO estimates that nearly nine million new cases of TB, and nearly two million deaths, occur globally each year. The largest number of new TB cases in 2005 occurred in South-East Asia (34% of incident cases globally), and the estimated incidence rate in sub-Saharan Africa is nearly 350 cases per 100,000 population. However, TB infection is not limited to the developing world: the UK has seen a resurgence of tuberculosis since the late 1980s and there are currently over 8000 new cases each year—a rate of 14.0 per 100,000 population. About 40% of these new cases occur in the London region, where the rate of infection is 44.8 per 100,000 population.

*M. tuberculosis* is capable of forming intracellular infections. These infections may be exclusively intracellular, or may contain both intracellular and extracellular components. Generally, *M. tuberculosis* bacilli do not circulate freely in the body, for example, in the bloodstream, and as such are often difficult to detect. They are also less amenable to drug treatment regimes. Intracellular survival and multiplication of mycobacteria is suspected to be a main contributory factor for mycobacterial disease progression.

The term "latency" is synonymous with "persistence", and describes a reversible state of low metabolic activity in which mycobacterial cells can survive for extended periods with limited or no cell division. During latency (i.e. latent infection), the clinical symptoms associated with a mycobacterial infection do not become manifest.

The presence of a large reservoir of asymptomatic individuals latently-infected with mycobacteria is a major problem for the control of *M. tuberculosis* infections. In addition, conventional methods for the detection of a latent mycobacterial infection by skin testing may be compromised by BCG vaccination and by exposure to environmental mycobacteria.

Timely, accurate and sensitive diagnosis is imperative for disease control. This is a key priority for many health and immigration authorities, particularly at "point of entry" for developed countries where the majority of TB cases are imported. Optimal patient management requires early initiation of drug therapy and isolation of infectious individuals as soon as possible. Left untreated, each person with active TB disease will infect on average between 10 and 15 people every year. TB infection can normally be treated by a 6 month course of antibiotics; however, patient compliance to long-term drug treatment is varied, with patients often stopping therapy when their symptoms cease. Failure to complete the treatment regime can promote the development of multiple drug-resistant mycobacteria.

Despite considerable investment in surveillance, control and treatment programmes, as well as in research and development for new diagnostics and therapeutics, TB control and eradication has proved challenging. The standard methods used for TB diagnosis have not changed significantly in recent years in many routine diagnostic laboratories, and there is substantial evidence that TB diagnosis is subject to significant error, with up to 52% under-diagnosis reported in some studies using comparative indices between TB diagnosis methods as measured against autopsy observations.

Early detection of a disease condition typically allows for a more effective therapeutic treatment with a correspondingly more favourable clinical outcome. In view of the increasing threat and global prevalence of TB, new strategies are required for more effective prevention, treatment, and diagnosis of TB and *M. tuberculosis* infection. Ideally, diagnosis would be made by a technique that accurately, rapidly, and simultaneously measures a plurality of biomarkers at a single point in time, thereby minimizing disease progression during the time required for diagnosis.

SUMMARY OF THE INVENTION

Previous attempts to develop new diagnostic methods for TB have proved problematic. In particular, earlier work attempting to enable the accurate and timely diagnosis of early stage or latent infection TB, where symptoms may not be apparent and where detection of *M. tuberculosis* by culture or specific polymerase chain reaction (PCR) is not achieved, has faced challenges.

Other groups have investigated host biomarkers in active and latent TB. However, these methods were unable to maintain the required level of specificity for TB across different subgroups, such as different ethnic groups.

The present inventors have conducted a temporal differential gene expression study in peripheral blood leukocytes (PBLs) in an aerosol *Macaca fascicularis* non-human primate model of TB. Using this method, the inventors have identified host biomarkers associated with early exposure to TB. Microarray hybridisation analyses to human whole genome arrays have revealed many significant gene expression changes, showing substantial temporal changes in PBL gene expression in response to *M. tuberculosis* challenge across the time-course of the study. Using parametric and non-parametric tools for data analysis, including artificial neural network analysis, the inventors have identified highly-significant host biomarkers associated with TB and *M. tuberculosis* infections. The biomarkers identified by the present invention have improved specificity for TB across different subgroups, such as different ethnic groups.

Therefore, the present invention allows for accurate, rapid, and sensitive prediction and diagnosis of TB through a measurement of one or more biomarker taken from a biological sample at a single point in time.

Accordingly, the present invention provides the use of one or more of SNX10, CPVL, PF4V1, HERC2, CD52, LYN, LGALS3BP, BAZ1A, KLRAP1, WSB1, BST1, SERPINB1, MVP, APBB1IP, MB21D1/C6orf150, TICAM2, DEFB128 and IL8 as a biomarker for tuberculosis.

The invention also provides a method for diagnosing tuberculosis in an individual comprising determining the presence and/or amount of one or more biomarker for tuberculosis in a sample obtained from the individual, wherein the one or more biomarker for tuberculosis is selected from SNX10, CPVL, PF4V1, HERC2, CD52, LYN, LGALS3BP, BAZ1A, KLRAP1, WSB1, BST1, SERPINB1, MVP, APBB1IP, MB21D1/C6orf150, TICAM2, DEFB128 and IL8.

The tuberculosis detected and/or diagnosed by the method or use of the present invention may be an active tuberculosis infection and the one or more biomarker a biomarker for an active tuberculosis infection.

Typically the one or more biomarker is selected from SNX10, CPVL, PF4V1 and HERC2, or any combination thereof. In a preferred embodiment, the one or more biomarker is selected from: (i) SNX10 and CREG1; and/or (ii) PF4V1 and HERC2.

The tuberculosis detected and/or diagnosed by the method or use of the present invention may be a latent tuberculosis infection and the one or more biomarker a biomarker for a latent tuberculosis infection. Typically the one or more biomarker for a latent tuberculosis infection is selected from PF4V1, LYN, CD52, HERC2, KLRAP1, DEFB128, LGALS3BP and IL8.

A use of the invention may comprise determining the presence and/or amount of the one or more biomarker for tuberculosis in a sample obtained from an individual.

The present invention also provides a use or method as defined herein, wherein said one or more biomarker is able to identify an individual with an active tuberculosis infection and/or an individual with a latent tuberculosis infection.

The present invention also provides a use or method as defined herein, wherein said one or more biomarker is able to identify an individual with an active tuberculosis infection and/or an individual with a latent tuberculosis infection and/or an individual uninfected with tuberculosis.

One or more additional biomarker for tuberculosis may be used in the method or use of the invention. The one or more additional biomarker may be (a) a biomarker for an active tuberculosis infection selected from: (i) LOC400759/GBP1P1, SNX10, CPVL, CREG1, PF4V1, PSMB9, LGALS3BP, BST1, BAZ1A, LYN, TAPBP, SERPINB1, WSB1, MVP, APBB1IP, FYB, MB21D1/C6orf150, TICAM2, CD52, KLRAP1, DEFB128 and IL8; and/or (ii) a biomarker listed in Table 3; and/or (b) a biomarker for a latent tuberculosis infection selected from: (i) a biomarker listed in Table 4; and/or (ii) a biomarker listed in Table 5. In a preferred embodiment, the one or more additional biomarker for an active tuberculosis infection is selected from LOC400759/GBP1P1, CREG1, PSMB9, ALPK1, GBP1, IRF1, HLA-B, IFITM3, S100A11, MMP9 and CD96. In a more preferred embodiment, the one or more biomarkers for tuberculosis are SNX10 and CPVL and the one or more additional biomarkers for tuberculosis are LOC400759/GBP1P1 and CREG1; and/or the one or more biomarkers for tuberculosis are PF4V1 and HERC2 and the one or more additional biomarkers for tuberculosis are LOC400759/GBP1P1 and ALPK1.

One or more further additional biomarkers may be used in the methods and/or uses of the invention. In one embodiment, the one or more further additional biomarker is PSMB9 and/or PF4V1. Alternatively and/or in addition, the one or more additional biomarker for an active tuberculosis infection, or the one or more further additional biomarker is: (i) GBP1, IRF1 and HLA-B; (ii) GBP1, IRF1, IFITM3 and S100A11; and/or (iii) GBP1, IRF1, MMP9 and CD96.

The presence and/or amount of the one or more biomarker for tuberculosis may be compared with the presence and/or amount of the one or more biomarker for tuberculosis in a control sample. The specificity of the comparison of the presence and/or amount of the one or more biomarker for tuberculosis in the sample and the presence and/or absence of the one or more biomarker for tuberculosis in the control diagnoses tuberculosis may be at least about 80%.

The presence and/or amount of the one or more biomarker for tuberculosis may be determined using an antibody and/or an oligonucleotide specific for said one or more biomarker. Typically, an oligonucleotide specific for said one or more biomarker is used. Preferably: (i) the one or more biomarker for tuberculosis is LOC400759/GBP1P1 and the oligonucleotide comprises at least one nucleic acid sequence having at least 90% sequence identity to the nucleic acid sequence of SEQ ID NOs: 1, 2 or 3; (ii) the one or more biomarker for tuberculosis is PF4V1 and the oligonucleotide comprises at least one nucleic acid sequence having at least 90% sequence identity to the nucleic acid sequence of SEQ ID NOs: 4 or 5; (iii) the one or more biomarker for tuberculosis is ALPK1 and the oligonucleotide comprises at least one nucleic acid sequence having at least 90% sequence identity to the nucleic acid sequence of SEQ ID NOs: 6 or 7; (iv) the one or more biomarker for tuberculosis is HERC2 and the oligonucleotide comprises at least one nucleic acid sequence having at least 90% sequence identity to the nucleic acid sequence of SEQ ID NOs: 8, 9 or 168 to 171; (v) the one or more biomarker for tuberculosis is LGALS3BP and the oligonucleotide comprises at least one nucleic acid sequence having at least 90% sequence identity to the nucleic acid sequence of SEQ ID NOs: 10 or 11; (vi) the one or more biomarker for tuberculosis is BST1 and the oligonucleotide comprises at least one nucleic acid sequence having at least 90% sequence identity to the nucleic acid sequence of SEQ ID NOs: 12 or 13; (vii) the one or more biomarker for tuberculosis is SNX10 and the oligonucleotide comprises at least one nucleic acid sequence having at least 90% sequence identity to the nucleic acid sequence of SEQ ID NOs: 14 or 15; (viii) the one or more biomarker for tuberculosis is CREG1 and the oligonucleotide comprises at least one nucleic acid sequence having at least 90% sequence identity to the nucleic acid sequence of SEQ ID NOs: 16 or 17; (ix) the one or more biomarker for tuberculosis is BAZ1A and the oligonucleotide comprises at least one nucleic acid sequence having at least 90% sequence identity to the nucleic acid sequence of SEQ ID NOs: 18 or 19; (x) the one or more biomarker for tuberculosis is LYN and the oligonucleotide comprises at least one nucleic acid sequence having at least 90% sequence identity to the nucleic acid sequence of SEQ ID NOs: 20 or 21; (xi) the one or more biomarker for tuberculosis is TAPBP and the oligonucleotide comprises at least one nucleic acid sequence having at least 90% sequence identity to the nucleic acid sequence of SEQ ID NOs: 22 or 23; (xii) the one or more biomarker for tuberculosis is SERPINB1 and the oligonucleotide comprises at least one nucleic acid sequence having at least 90% sequence identity to the nucleic acid sequence of SEQ ID NOs: 24 or 25; (xiii) the one or more biomarker for tuberculosis is PSMB9 and the oligonucleotide comprises at least one nucleic acid sequence having at least 90% sequence identity to the nucleic acid sequence of SEQ ID NOs: 26 or 27; (xiv) the one or more biomarker for tuberculosis is WSB1 and the oligonucleotide comprises at least one nucleic acid sequence having at least 90% sequence identity to the nucleic acid sequence of SEQ ID NOs: 28 or 29; (xv) the one or more biomarker for tuberculosis is MVP and the oligonucleotide comprises at least one nucleic acid sequence having at least 90% sequence identity to the nucleic acid sequence of SEQ ID NOs: 30 or 31; (xvi) the one or more biomarker for tuberculosis is APBB1IP and the oligonucleotide comprises at least one nucleic acid sequence having at least 90% sequence identity to the nucleic acid sequence of SEQ ID NOs: 32 or 33; (xvii) the one or more biomarker for tuberculosis is FYB and the oligonucleotide comprises at least one nucleic acid sequence having at least 90% sequence identity to the nucleic acid sequence of SEQ ID NOs: 34 or 35; (xviii) the one or more biomarker for tuberculosis is MB21D1/C6orf150 and the oligonucleotide comprises at least one nucleic acid sequence having at least 90% sequence identity to the nucleic acid sequence of SEQ ID NOs: 36 or 37; (xix) the one or more biomarker for tuberculosis is CPVL and the oligonucleotide comprises at least one nucleic acid sequence having at least 90% sequence identity to the nucleic acid sequence of SEQ ID NOs: 38 or 39; (xx) the one or more biomarker for tuberculosis is TICAM2 and the oligonucleotide comprises at least one nucleic acid sequence having at least 90% sequence identity to the nucleic acid sequence of SEQ ID NOs: 40 or 41; (xxi) the one or more biomarker for tuberculosis is CD52 and the oligonucleotide comprises at least one nucleic acid sequence having at least 90% sequence identity to the nucleic acid sequence of SEQ ID NOs: 42 or 43; (xxii) the one or more biomarker for tuberculosis is KLRAP1 and the oligonucleotide comprises at least one nucleic acid sequence having at least 90% sequence identity to the nucleic acid sequence of SEQ ID NOs: 44 or 45; (xxiii) the one or more biomarker for tuberculosis is DEFB128 and the oligonucleotide comprises at least one nucleic acid sequence having at least 90% sequence identity to the nucleic acid sequence of SEQ ID NOs: 46 or 47; (xxiv) the one or more biomarker for tuberculosis is IL8 and the oligonucleotide comprises at least one nucleic acid sequence having at least 90% sequence identity to the nucleic acid sequence of SEQ ID NOs: 48 or 49; (xxv) the one or more biomarker for tuberculosis is GBP1 and the oligonucleotide comprises at least one nucleic acid sequence having at least 90% sequence identity to the nucleic acid sequence of SEQ ID NOs: 50 or 51; (xxvi) the one or more biomarker for tuberculosis is IRF1 and the oligonucleotide comprises at least one nucleic acid sequence having at least 90% sequence identity to the nucleic acid sequence of SEQ ID NOs: 52 or 53; (xxvii) the one or more biomarker for tuberculosis is MMP9 and the oligonucleotide comprises at least one nucleic acid sequence having at least 90% sequence identity to the nucleic acid sequence of SEQ ID NOs: 54 or 55; (xxviii) the one or more biomarker for tuberculosis is CD96 and the oligonucleotide comprises at least one nucleic acid sequence having at least 90% sequence identity to the nucleic acid sequence of SEQ ID NOs: 56 or 57; (xxix) the one or more biomarker for tuberculosis is AIM2 and the oligonucleotide comprises at least one nucleic acid sequence having at least 90% sequence identity to the nucleic acid sequence of SEQ ID NOs: 58 or 59; (xxx) the one or more biomarker for tuberculosis is CD274 and the oligonucleotide comprises at least one nucleic acid sequence having at least 90% sequence identity to the nucleic acid sequence of SEQ ID NOs: 60 or 61; (xxxi) the one or more biomarker for tuberculosis is CDH23 and the oligonucleotide comprises at least one nucleic acid sequence having at least 90% sequence identity to the nucleic acid sequence of SEQ ID NOs: 62 or 63; (xxxii) the one or more biomarker for tuberculosis is IFIT3 and the oligonucleotide comprises at least one nucleic acid sequence having at least 90% sequence identity to the nucleic acid sequence of SEQ ID NOs: 64 or 65; (xxxiii) the one or more biomarker for tuberculosis is IFITM3 and the oligonucleotide comprises at least one nucleic acid sequence having at least 90% sequence identity to the nucleic acid sequence of SEQ ID NOs: 66 or 67; (xxxiv) the one or more biomarker for tuberculosis is GK and the oligonucleotide comprises at least one nucleic acid sequence having at least 90% sequence identity to the nucleic acid sequence of SEQ ID NOs: 68 or 69; (xxxv) the one or more biomarker for tuberculosis is NELL2 and the oligonucleotide comprises at least one nucleic acid sequence having at least 90% sequence identity to the nucleic acid sequence of SEQ ID NOs: 70 or 71; (xxxvi) the one or more biomarker for tuberculosis is S100A11 and the oligonucleotide comprises at least one nucleic acid sequence having at least 90% sequence identity to the nucleic acid sequence of SEQ ID NOs: 72 or 73; (xxxvii) the one or more biomarker for tuberculosis is SAMD9L and the oligonucleotide comprises at least one nucleic acid sequence having at least 90% sequence identity to the nucleic acid sequence of SEQ ID NOs: 74 or 75; (xxxviii) the one or more biomarker for tuberculosis is STAT1 and the oligonucleotide comprises at least one nucleic acid sequence having at least 90% sequence identity to the nucleic acid sequence of SEQ ID NOs: 76 or 77; (xxxix) the one or more biomarker for tuberculosis is TLR6 and the oligonucleotide comprises at least one nucleic acid sequence having at least 90% sequence identity to the nucleic acid sequence of SEQ ID NOs: 78 or 79; (xl) the one or more biomarker for tuberculosis is WARS and the oligonucleotide comprises at least one nucleic acid sequence having at least 90% sequence identity to the nucleic acid sequence of SEQ ID NOs: 80 or 81; (xli) the one or more biomarker for tuberculosis is DOCK5 and the oligonucleotide comprises at least one nucleic acid sequence having at least 90% sequence identity to the nucleic acid sequence of SEQ ID NOs: 82 or 83; (xlii) the one or more biomarker for tuberculosis is SIRPB2 and the oligonucleotide comprises at least one nucleic acid sequence having at least 90% sequence identity to the nucleic acid sequence of SEQ ID NOs: 84 or 85; (xliii) the one or more biomarker for tuberculosis is ANKRD22 and the oligonucleotide comprises at least one nucleic acid sequence having at least 90% sequence identity to the nucleic acid sequence of SEQ ID NOs: 86 or 87; (xliv) the one or more biomarker for tuberculosis is ABCF2 (NM 005692.3 and the oligonucleotide comprises at least one nucleic acid sequence having at least 90% sequence identity to the nucleic acid sequence of SEQ ID NOs: 88 or 89; (xlv) the one or more biomarker for tuberculosis is FNBP1L and the oligonucleotide comprises at least one nucleic acid sequence having at least 90% sequence identity to the nucleic acid sequence of SEQ ID NOs: 90 or 91; (xlvi) the one or more biomarker for tuberculosis is NCF1C and the oligonucleotide comprises at least one nucleic acid sequence having at least 90% sequence identity to the nucleic acid sequence of SEQ ID NOs: 92 or 93; (xlvii) the one or more biomarker for tuberculosis is TBC1D3B and the oligonucleotide comprises at least one nucleic acid sequence having at least 90% sequence identity to the nucleic acid sequence of SEQ ID NOs: 94 or 95; (xlviii) the one or more biomarker for tuberculosis is SLC14A1 and the oligonucleotide comprises at least one nucleic acid sequence having at least 90% sequence identity to the nucleic acid sequence of SEQ ID NOs: 96 or 97; (xlix) the one or more biomarker for tuberculosis is CALCOCO2 and the oligonucleotide comprises at least one nucleic acid sequence having at least 90% sequence identity to the nucleic acid sequence of SEQ ID NOs: 98 or 99; (l) the one or more biomarker for tuberculosis is GTF2B and the oligonucleotide comprises at least one nucleic acid sequence having at least 90% sequence identity to the nucleic acid sequence of SEQ ID NOs: 100 or 101; (li) the one or more biomarker for tuberculosis is HLA-B and the oligonucleotide comprises at least one nucleic acid sequence having at least 90% sequence identity to the nucleic acid sequence of SEQ ID NOs: 102 or 103; (lii) the one or more biomarker for tuberculosis is HLA-F and the oligonucleotide comprises at least one nucleic acid sequence having at least 90% sequence identity to the nucleic acid sequence of SEQ ID NOs: 104 or 105; (liii) the one or more biomarker for tuberculosis is MGST2 and the oligonucleotide comprises at least one nucleic acid sequence having at least 90% sequence identity to the nucleic acid sequence of SEQ ID NOs: 106 or 107; (liv) the one or more biomarker for tuberculosis is SPAST and the oligonucleotide comprises at least one nucleic acid sequence having at least 90% sequence identity to the nucleic acid sequence of SEQ ID NOs: 108 or 109; and/or (lv) the one or more biomarker for tuberculosis is WAC and the oligonucleotide comprises at least one nucleic acid sequence having at least 90% sequence identity to the nucleic acid sequence of SEQ ID NOs: 110 or 111 or 168 to 171.

The presence and/or absence of the at least one biomarker for tuberculosis in the individual may be determined at least twice using a separate sample taken each time the presence and/or absence of the at least one biomarker for tuberculosis is determined. The samples from the individual may be taken prior to, during and/or after treatment initiation.

The invention further provides a device for carrying out the use of the invention, or for use in a method of the invention, which comprises (i) one or more antibody specific for the one or more biomarker for tuberculosis; or (ii) one or more oligonucleotide specific for the one or more biomarker for tuberculosis. In a preferred embodiment, the one or more oligonucleotide specific for the one or more biomarker for tuberculosis comprised in the device is an oligonucleotide of the invention as defined herein.

DETAILED DESCRIPTION OF THE INVENTION

Figure 1:
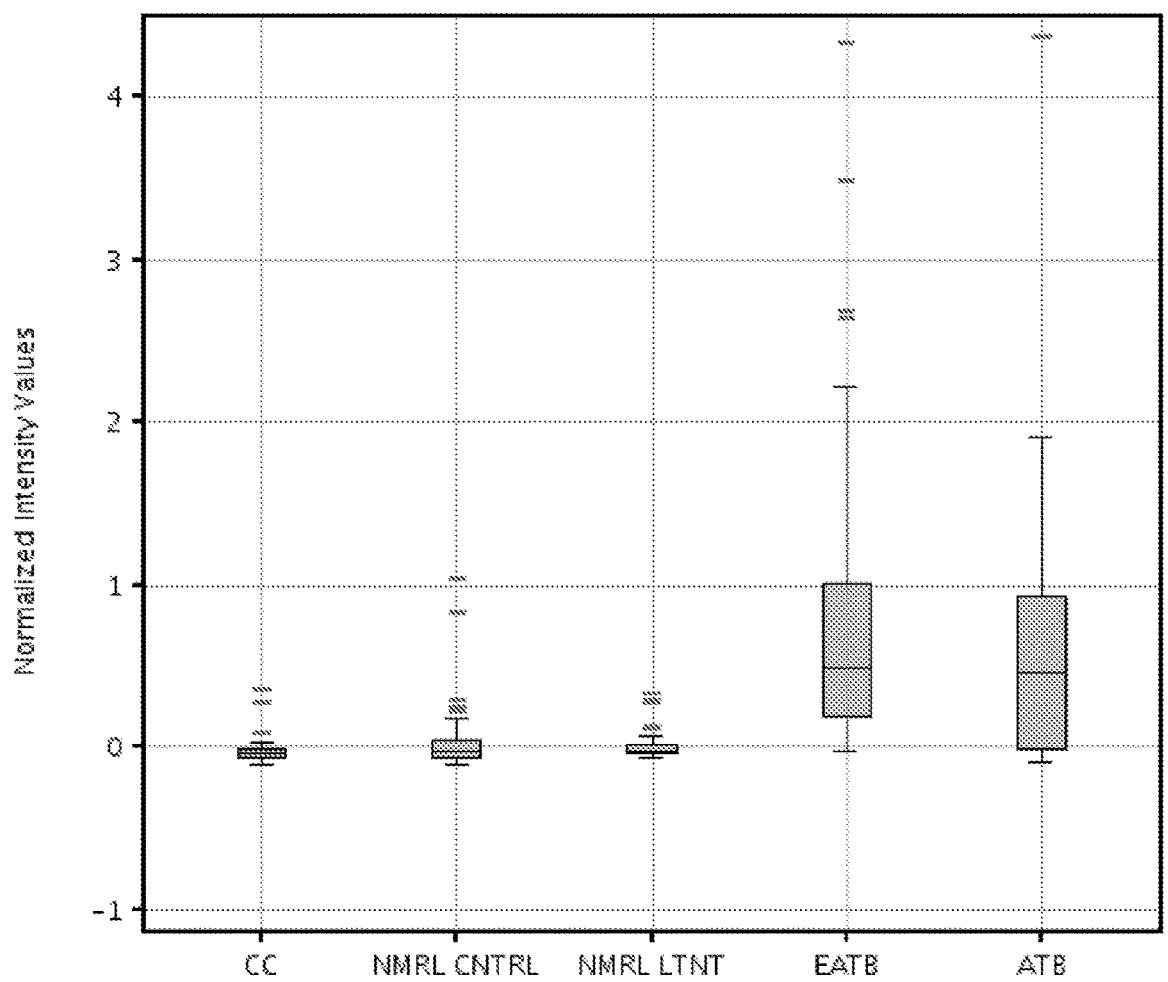
FIG. 1: shows a box plot of LOC400759 normalised gene expression in Caucasian controls (CC); Controls of Asian descent recruited from Hindu temples in London who tested negative for TB in skin and/or IFNγ tests and originate from high-incidence areas of TB (NMRL CNTRL); individuals of Asian descent recruited from Hindu temples in London and test positive for TB in Mantoux skin and/or IFNγ tests and diagnosed with latent TB (NMRL LTNT); individuals with early stage active TB recruited at St. Thomas's and Royal Free hospitals in London (EATB); and individuals of Asian descent recruited at the Jawaharlal Institute of Postgraduate Medical Education and Research (JIPMER), India, diagnosed with active TB (ATB). The box represents highest and lowest gene expression interquartile range and median gene expression. The error bars represent minimum and maximum values. Grey bars represent outlier values.

The present invention allows for the rapid, sensitive, and accurate diagnosis or prediction of TB using one or more biological samples obtained from an individual at a single time point ("snapshot") or during the course of disease progression. TB may be diagnosed or predicted prior to the onset of clinical symptoms, and/or as subsequent confirmation after the onset of clinical symptoms. Accordingly, the present invention allows for more effective therapeutic intervention and/or diagnosis in the pre-symptomatic stage of the disease.

Tuberculosis and *Mycobacterium tuberculosis*

Tuberculosis (TB) is a progressive, often fatal, infectious disease, caused by the bacterial pathogen *Mycobacterium tuberculosis* (*M. tuberculosis*, MTB). Pulmonary symptoms of TB include a productive, prolonged cough of three or more weeks, chest pain, and hemoptysis. Systemic symptoms include low grade remittent fever, chills, night sweats, appetite loss, weight loss, easy fatigability, and production of sputum that starts out mucoid but changes to purulent. A reference herein to the detection or diagnosis of TB is equivalent to the detection or diagnosis of *M. tuberculosis* infection. When the *M. tuberculosis* cells are metabolically active and/or undergoing cell division, this results in the symptoms of TB becoming overt, and is described as an active TB/*M. tuberculosis* infection.

In latent TB, an individual is infected with *M. tuberculosis*, but the individual does not display the symptoms of active TB disease. In latent TB, the mycobacterial cells survive for extended periods in a state of low metabolic activity and with limited or no cell division. Thus, during latency (i.e. latent infection), the clinical symptoms associated with a mycobacterial infection do not become manifest. This can make it difficult to distinguish between a latent TB infection and the absence of a TB infection using conventional methods and techniques. A reference herein to the detection or diagnosis of latent TB is equivalent to the detection or diagnosis of latent *M. tuberculosis* infection.

The present inventors have also found that there is a temporal aspect to the expression of some biomarkers for TB during the active phase of an infection. Specifically, some biomarkers for active TB are expressed at relatively low levels at an early stage in active TB, but become expressed at higher levels as the active stage of the infection progresses. In this context, the term "low level of expression" is relative. For example, the expression of these active TB biomarkers during the early active phase may be low relative to the expression level later in the active phase, and similar to (or slightly greater than) the expression level of the same biomarkers in an uninfected individual and/or an individual with latent TB. Typically the expression of these active TB biomarkers during the early active phase is low relative to the expression level later in the active phase, but still higher than the expression level of the same biomarkers in an uninfected individual and/or an individual with latent TB.

The present invention provides biomarkers for the detection and/or diagnosis of TB infection. In particular, the present invention provides biomarkers for the detection and/or diagnosis of an active TB infection, including an early stage active TB infection and/or a later stage active TB infection. The present invention also provides biomarkers for the detection and/or diagnosis of a latent TB infection. The present invention further provides biomarkers for distinguishing between active and latent TB infections. The present invention also provides biomarkers for distinguishing between a latent TB infection and an absence/lack of TB infection (active or latent). The present invention also provides biomarkers for distinguishing between early stage active TB and later stage active TB. The present invention also provides biomarkers for distinguishing between an individual who has no symptomatic TB infection (active or latent) and has not been exposed to TB (e.g. because they are from a non/low-TB endemic region) and an individual who has no symptomatic TB infection (active or latent) but has been exposed to TB (e.g. because they are from a high-TB endemic region).

Any appropriate technique may be used to confirm the diagnosis of active and/or latent TB according to the present invention. Standard techniques are known in the art. For example, chest x-ray, microbiological culture of *M. tuberculosis* in a sample (sputum, pus, cerebrospinal fluid, biopsied tissue, etc.) from the individual, CT scan, MMR, antibodies from lymphocyte secretion (ALS) assay, IFNγ assay and tuberculin skin tests (e.g. Mantoux and Heaf tests).

Biomarkers for Tuberculosis

A "biomarker" is virtually any biological compound, such as a protein and a fragment thereof, a peptide, a polypeptide, a proteoglycan, a glycoprotein, a lipoprotein, a carbohydrate, a lipid, a nucleic acid, an organic on inorganic chemical, a natural polymer, and a small molecule, that is present in the biological sample and that may be isolated from, or measured in, the biological sample. Furthermore, a biomarker can be the entire intact molecule, or it can be a portion thereof that may be partially functional or recognized, for example, by an antibody or other specific binding protein. A biomarker is considered to be informative if a measurable aspect or characteristic of the biomarker is associated with a given state of an individual, such as infection with TB. Such a measurable aspect or characteristic may include, for example, the presence, absence, or concentration of the biomarker in the biological sample from the individual and/or its presence as part of a profile of biomarkers. Such a measurable aspect of a biomarker is defined herein as a "feature." For example, the presence of a biomarker may be a feature. As another example, the amount of a biomarker in a sample, or the amount of a biomarker in a sample compared with a control or reference sample may be a feature. A feature may also be a ratio of two or more measurable aspects of biomarkers, which biomarkers may or may not be of known identity, for example. A "biomarker profile" comprises at least two such features, where the features can correspond to the same or different classes of biomarkers such as, for example, two nucleic acids or a nucleic acid and a carbohydrate. A biomarker profile may also comprise at least three, four, five, 10, 20, 30 or more features. In one embodiment, a biomarker profile comprises hundreds, or even thousands, of features. In another embodiment, the biomarker profile comprises at least one measurable aspect of at least one internal standard.

The present inventors have conducted a temporal differential gene expression study in peripheral blood leukocytes (PBLs) in an aerosol *Macaca fascicularis* non-human primate model of TB. Using this method, the inventors have identified host biomarkers associated with early exposure to TB.

The new biomarkers for TB identified by the present inventors are listed in Table 2 herein (together with corresponding sequence identifiers (SEQ ID NOs). In particular, the present inventors have identified LOC400759/GBP1P1, SNX10, CPVL, CREG1, PF4V1, PSMB9, ALPK1, HERC2, LGALS3BP, BST1, BAZ1A, LYN, TAPBP, SERPINB1, WSB1, MVP, APBB1IP, FYB, MB21D1/C6orf150, TICAM2, CD52, KLRAP1, DEFB128 and IL8 as biomarkers for TB. Therefore, the present invention provides the use of one or more of LOC400759/GBP1P1, SNX10, CPVL, CREG1, PF4V1, PSMB9, ALPK1, HERC2, LGALS3BP, BST1, BAZ1A, LYN, TAPBP, SERPINB1, WSB1, MVP, APBB1IP, FYB, MB21D1/C6orf150, TICAM2, CD52, KLRAP1, DEFB128 and IL8 as a biomarker for tuberculosis. Each of these biomarkers may be used alone, in combination with any of the other biomarkers, and/or in combination with one or more additional biomarker for tuberculosis as disclosed herein. For example, the invention may relate to the use of LOC400759/GBP1P1, SNX10, CPVL and/or CREG1 (alone or in any combination thereof), optionally in combination with PF4V1 and/or PSMB9 and/or in combination with any of the other biomarkers disclosed herein.

Typically the present invention provides the use of one or more of SNX10, CPVL, PF4V1, HERC2, CD52, LYN, LGALS3BP, BAZ1A, KLRAP1, WSB1, BST1, SERPINB1, MVP, APBB1IP, MB21D1/C6orf150, TICAM2, DEFB128 and IL8 as a biomarker for tuberculosis.

Any combination of these biomarkers may be used according to the present invention. For example, any two or more, three or more, four or more, five or more, six or more, seven or more, eight or more, nine or more, ten or more, up to and including all of these biomarkers may be used to diagnose TB according to the present invention.

The one or more biomarker of the invention may be a hormone, a growth factor, a transcription factor, a cell surface marker or a soluble protein derived from cells. The one or more biomarker of the invention may be a nucleic acid encoding for one of said proteins.

The one or more of biomarker of the invention may be used in the detection and/or diagnosis of an active TB infection. The one or more biomarker of the invention may be used in the detection and/or diagnosis of a latent TB infection. The one or more biomarker of the invention may be used to diagnose the absence of a TB infection (active or latent). The one or more biomarker of the invention may be used to identify an individual with an active TB infection and/or an individual with a latent TB infection. The one or more biomarker of the invention may be used to identify an individual with an active TB infection and/or an individual with a latent TB infection and/or an individual uninfected with TB. The one or more biomarker of the invention may be used in the detection and/or diagnosis of an early stage active TB infection or a late/later stage active TB infection. The one or more biomarker of the invention may be used to determine exposure of an individual to TB, even in the absence of a symptomatic active or asymptomatic latent TB infection. Thus, the one or more biomarker of the invention may be used to distinguish between one or more individual with an active (early or later stage) TB infection and/or one or more individual with a latent TB infection, and/or one or more individual uninfected with TB. The one or more biomarker of the invention may also be used to distinguish between one or more individual with an early stage active TB infection and one or more individual with a late/later stage active TB infection.

Typically, the present invention relates to the use of one or more of SNX10, CPVL, PF4V1, HERC2, CD52 and LYN as a biomarker for TB. One or more of these biomarkers may be used in the detection and/or diagnosis of an active TB infection (early or late/later stage), or to distinguish between an early stage active TB infection and a late/later stage active TB infection. Alternatively, one or more of these biomarkers may be used in the detection and/or diagnosis of a latent TB infection, or to diagnose the absence of a TB infection (active or latent). Any combination of SNX10, CPVL, PF4V1, HERC2 CD52 and LYN may be used as biomarkers for TB according to the present invention. As a non-limiting example: (i) SNX10 and CPVL; (ii) SNX10 and PF4V1; (iii) SNX10 and HERC2; (iv) CPVL and PF4V1; (v) CPVL and HERC2; (vi) PF4V1 and HERC2; (vii) SNX10, CPVL and PF4V1; (viii) SNX10, CPVL and HERC2; (ix) SNX10, PF4V1 and HERC2; (x) CPVL, PF4V1 and HERC2; and/or (xi) SNX10, CPVL, PF4V1 and HERC2 may be used in combination as biomarkers in the detection and/or diagnosis of TB according to the present invention. Any of these combinations may be used with CD52 and/or LYN. Similarly, CD52 and/or LYN may be used in combination with one or more of SNX10, CPVL, PF4V1 and HERC2, or with any combination of SNX10, CPVL, PF4V1 and HERC2. Thus, in one embodiment, the invention relates to the use of SNX10, CPVL, PF4V1, HERC2, CD52 and LYN.

Typically the invention relates to the use of (i) SNX10 and CPVL; and/or (ii) PF4V1 and HERC2 as biomarkers for tuberculosis. In a preferred embodiment, SNX10 and CPVL are used in combination with LOC400759/GBP1P1 and/or CREG1 as biomarkers in the diagnosis of TB according to the present invention. In another preferred embodiment, PF4V1 and HERC2 are used in combination with LOC400759/GBP1P1 and/or ALPK1 as biomarkers in the diagnosis of TB according to the present invention. Any of these combinations may be used with CD52 and/or LYN.

One or more additional biomarker for TB (or further additional biomarker for TB) may also be used in the detection and/or diagnosis of TB according to the present invention. Any combination of the one or more additional biomarker (or further additional biomarker) may be used in combination with the one or more biomarker of the invention. For example at least two, at least three, at least four, at least five, at least six, at least seven, at least eight, at least nine, at least ten or more additional biomarkers for TB may be used in combination with the one or more biomarker of the invention. As a non-limiting example, in the cases where the one or more biomarker is selected from SNX10 and/or CPVL, the one or more additional biomarker may be selected from LOC400759/GBP1P1, CREG1, PF4V1, PSMB9, ALPK1, HERC2, LGALS3BP, BST1, BAZ1A, LYN, TAPBP, SERPINB1, WSB1, MVP, APBB1IP, FYB, MB21D1/C6orf150, TICAM2, CD52, KLRAP1, DEFB128, HERC2 and IL8. As another non-limiting example, in the case where the one or biomarker is selected from PF4V1 and/or HERC2, the one or more additional biomarker may be selected from LOC400759/GBP1P1, SNX10, CPVL, CREG1, PSMB9, LGALS3BP, BST1, BAZ1A, LYN, TAPBP, SERPINB1, WSB1, MVP, APBB1IP, FYB, MB21D1/C6orf150, CPVL, TICAM2, CD52, KLRAP1, DEFB128 and IL8. Again, any of these combinations may be used with CD52 and/or LYN.

Typically, the one or more additional biomarker is selected from the biomarkers listed in Tables 2, 3, 4 and/or 5 herein (corresponding sequence identifiers (SEQ ID NOs) are also given in Tables 2 to 5).

In a preferred embodiment, the one or more biomarker of the invention is selected from SNX10 and CPVL and the one or more additional biomarker is selected from the biomarkers in Tables 2 and 3 or 5. In a more preferred embodiment, the one or more biomarker of the invention is selected from SNX10 and CPVL and the one or more additional biomarker is selected from LOC400759/GBP1P1, CREG1, PF4V1, PSMB9, GBP1, IRF1, HLA-B, IFITM3 and S100A11. In a more preferred embodiment, the present invention provides the use SNX10 and CPVL in combination with PF4V1 and/or PSMB9, and optionally in combination with one or more additional biomarker for TB as disclosed herein. Said one or more additional biomarker is preferably selected from LOC400759/GBP1P1, CREG1, GBP1, IRF1, HLA-B, IFITM3 and S100A11. Any of these combinations may be used with CD52 and/or LYN.

In a particularly preferred embodiment, the present invention relates to the use of SNX10, CPVL, LOC400759/GBP1P1 and CREG1, the combination of SNX10, CPVL, LOC400759/GBP1P1, CREG1, PSMB9, the combination of SNX10, CPVL, LOC400759/GBP1P1, CREG1, PF4V1, the combination of SNX10, CPVL, LOC400759/GBP1P1, CREG1, PSMB9, GBP1, IRF1 and HLA-B or the combination of SNX10, CPVL, LOC400759/GBP1P1, CREG1, PF4V1, GBP1, IRF1, IFITM3 and S100A11 as biomarkers for TB. Most preferably the combination of SNX10, CPVL, LOC400759/GBP1P1, CREG1, PSMB9, GBP1, IRF1 and HLA-B or the combination of SNX10, CPVL, LOC400759/GBP1P1, CREG1, PF4V1, GBP1, IRF1, IFITM3 and S100A11 is used. Any of these combinations may be used with CD52 and/or LYN.

In another preferred embodiment, the one or more biomarker of the invention is selected from PF4V1 and HERC2 and the one or more additional biomarker is selected from the biomarkers in Tables 2 and 3 or 5. In a preferred embodiment, the one or more biomarker of the invention is selected from PF4V1 and HERC2 and the one or more additional biomarker is selected from LOC400759/GBP1P1, CREG1, PF4V1, PSMB9, GBP1, IRF1, HLA-B, IFITM3 and S100A11, MMP9 and CD96. In a more preferred embodiment, the invention relates to the use of PF4V1 and HERC2 in combination with one or more additional biomarker for TB as disclosed herein. Said one or more additional biomarker is preferably selected from LOC400759/GBP1P1, CREG1, GBP1, IRF1, HLA-B, IFITM3, S100A11, MMP9, KLRA1, DEFB128 and IL8 and CD96. Thus, in one preferred embodiment, the present invention provides the use of PF4V1 and HERC2 in combination with one or more additional biomarker selected from LOC400759/GBP1P1, ALPK1, GBP1, IRF1, MMP9 and CD96; or in combination with one or more additional biomarker selected from of LOC400759/GBP1P1, ALPK1, GBP1, IRF1, MMP9, CD96, KLRA1, DEFB128 and IL8. In a more preferred embodiment, the present invention provides the use of the combination of PF4V1, HERC2, LOC400759/GBP1P1, ALPK1, GBP1, IRF1, MMP9 and CD96, or the combination of PF4V1, HERC2, LOC400759/GBP1P1, ALPK1, GBP1, IRF1, MMP9, CD96, KLRA1, DEFB128 and IL8 as biomarkers for TB. Any of these combinations may be used with CD52 and/or LYN.

Combinations of one or more of LOC400759/GBP1P1, SNX10, CPVL and CREG1 are particularly preferred. Such combinations include: (i) LOC400759/GBP1P1 and SNX10; (ii) LOC400759/GBP1P1 and CPVL; (iii) LOC400759/GBP1P1 and CREG1; (iv) SNX10 and CPVL; (v) SNX10 and CREG1; (vi) CPVL and CREG1; (vii) LOC400759/GBP1P1, SNX10 and CPVL; (viii) LOC400759/GBP1P1, SNX10 and CREG1; (ix) LOC400759/GBP1P, CPVL and CREG1; (x) SNX10, CPVL and CREG1; and/or (xi) LOC400759/GBP1P1, SNX10, CPVL and CREG1. These combinations may be used in combination with one or more further additional biomarker as disclosed herein, with one or more of GBP1, IRF1, HLA-B, IFITM3 and/or S100A11 being particularly preferred as disclosed herein. Any of these combinations may be used with CD52 and/or LYN.

Alternatively or in addition, combinations of one or more of LOC400759/GBP1P1, PF4V1, ALPK1 and HERC2 are preferred. Such combinations include: (i) LOC400759/GBP1P1 and PF4V1; (ii) LOC400759/GBP1P1 and ALPK1; (iii) LOC400759/GBP1P1 and HERC2; (iv) PF4V1 and ALPK1; (v) PF4V1 and HERC2; (vi) ALPK1 and HERC2; (vii) LOC400759/GBP1P1, PF4V1 and ALPK1; (viii) LOC400759/GBP1P1, PF4V1 and HERC2; (ix) LOC400759/GBP1P1, ALPK1 and HERC2; (x) PF4V1, ALPK1 and HERC2; and (xi) LOC400759/GBP1P1, PF4V1, ALPK1 and HERC2. These combinations may be used in combination with one or more further additional biomarker as disclosed herein, with one or more of GBP1, IRF1, MMP9, CD96, KLRA1, DEFB128 and IL8 being particularly preferred as disclosed herein. Any of these combinations may be used with CD52 and/or LYN.

The combination of SNX10, CPVL, PF4V1, HERC2, CD52 and LYN, optionally including one or more additional biomarker for TB, preferably selected from CREG1, PSMB9, LOC400759/GBP1P1, ALPK1, GBP1, IRF1, HLA-B, IFITM3, S100A11, MMP9, CD96, KLRA1, DEFB128 and/or IL8, or any combination thereof, is also preferred. Similarly, the combination of SNX10, CPVL, PF4V1, HERC2, CD52, LYN, LGALS3BP, BAZ1A, KLRA1 and WSB1, optionally including one or more additional biomarker for TB, preferably selected from CREG1, PSMB9, LOC400759/GBP1P1, ALPK1, GBP1, IRF1, HLA-B, IFITM3, S100A11, MMP9, CD96, KLRA1, DEFB128 and/or IL8, or any combination thereof, is also preferred.

The present inventors have also identified biomarkers for latent TB, and which can be used to distinguish between latent and active forms of TB, i.e. between latent and active forms of *M. tuberculosis* infection. These biomarkers for latent TB can also be used according to the present invention to distinguish between latent TB infection and the absence of TB infection. In particular, the present inventors have identified PF4V1, LYN, CD52, HERC2, KLRA1, DEFB128, LGALS3BP and IL8 as biomarkers for latent TB. These biomarkers may be used to distinguish between active TB and/or latent TB and/or the absence of TB. In a preferred embodiment, these biomarkers are used to distinguish between latent TB and the absence of TB infection, i.e. to identify one or more individual with a latent TB infection and/or one or more individual uninfected with TB.

Accordingly, the present invention provides the use of one or more of the biomarkers selected from PF4V1, LYN, CD52, HERC2, KLRA1, DEFB128, LGALS3BP and IL8 for distinguishing between latent and active *M. tuberculosis* infection, and hence latent and active TB. The present invention also provides the use of one or more of the biomarkers selected from PF4V1, LYN, CD52, HERC2, KLRA1, DEFB128, LGALS3BP and IL8 for distinguishing between active TB and/or latent TB and/or the absence of TB. In a preferred embodiment, the present invention provides the use of one or more of the biomarkers selected from PF4V1, LYN, CD52, HERC2, KLRA1, DEFB128, LGALS3BP and IL8 for distinguishing between one or more individual with a latent TB infection, and one or more individual uninfected with TB.

Any combination of these biomarkers may be used according to the present invention. For example, any two, three or four, or all five of these biomarkers may be used to distinguish between latent TB and/or active TB and/or the absence of TB according to the present invention. For example, the combination of the biomarkers PF4V1, LYN, CD52, HERC2, KLRA1, DEFB128, LGALS3BP and IL8 is used to distinguish between latent TB and/or active TB and/or the absence of TB according to the present invention. In a preferred embodiment, the combination of the biomarkers PF4V1, LYN, CD52, HERC2 is used to distinguish between latent TB and the absence of TB, and/or to identify one or more individual with a latent TB infection and/or one or more individual uninfected with TB. In another preferred embodiment, the combination of the biomarkers PF4V1, LYN, CD52, HERC2, KLRA1, DEFB128, LGALS3BP and IL8 is used to distinguish between latent TB and the absence of TB. Thus, the combination of the biomarkers PF4V1, LYN, CD52, HERC2, KLRA1, DEFB128 and IL8 may be used to identify an individual with a latent TB infection and/or an individual uninfected with TB. In a preferred embodiment, the combination of biomarkers PF4V1, LYN, CD52, HERC2, the combination of biomarkers, HERC2, KLRAP1, PF4V1, DEFB128, IL8 or the combination of biomarkers PF4V1, LYN, CD52, HERC2, KLRA1, DEFB128, LGALS3BP and IL8 is used to distinguish between one or more individual with a latent TB infection, and one or more individual uninfected with TB.

One or more additional biomarker for latent TB may also be used in combination with the one or more biomarker selected from PF4V1, LYN, CD52, HERC2, KLRA1, DEFB128, LGALS3BP and IL8. In a preferred embodiment, the one or more additional biomarker is selected from the biomarkers listed in Tables 4 and 5.

One or more additional biomarker for TB may also be used in to distinguish between latent TB and/or active TB and/or the absence of TB according to the present invention. Any combination of the one or more additional biomarker may be used in combination with the one or more biomarker of the invention. For example at least two, at least three, at least four, at least five, at least six, at least seven, at least eight, at least nine, at least ten or more additional biomarkers for TB may be used in combination with the one or more biomarker of the invention. The one or more additional biomarker for use in distinguishing between latent TB and/or active TB and/or the absence of TB can be any biomarker disclosed herein.

Other biomarkers for distinguishing between latent TB and/or active TB and/or the absence of TB, particularly for distinguishing between latent TB and the absence of TB (i.e. to identify one or more individual with a latent TB infection and/or one or more individual uninfected with TB) include HLA-B, NCF1C, ABCF2, FNBP1L, TBC1D3B, SLC14A1, CALCOCO2, GTF2B, HLA-F, MGST2, SPAST and WAC. These biomarkers are listed in Tables 4 and 5 herein.

The present inventors have also identified biomarkers which can be used to distinguish between early stage active TB and late/later stage active TB, i.e. between early stage active and late/later stage active forms of M. tuberculosis infection. In particular, the present inventors have identified GBP1 as such a biomarker. The GBP1 biomarker may be used to distinguish between early stage active TB and late/later stage active TB. As used herein, the term "early stage active TB" refers to patients on first presentation with low to moderate symptoms, such as persistent cough and/or fever, and/or suspected pulmonary tuberculosis which is subsequently confirmed using conventional methods such as smear positivity (graded 1-4 in terms of severity of bacterial load), M. tuberculosis culture or M. tuberculosis PCR positivity (such as using the Cepheid GeneXpert™), As used herein, the term "later or later stage active TB" refers to patients with fully symptomatic active pulmonary tuberculosis, such as persistent cough of some duration, prolonged fever, weight loss, subsequently confirmed using conventional methods as above.

Accordingly, the present invention provides the use of the GBP1 biomarker for distinguishing between early stage active TB and late/later stage active TB. The present invention also provides the use of the GBP1 biomarker for distinguishing between active (early or late active stage) TB and/or latent TB and/or the absence of TB.

One or more additional biomarker for TB may also be used to distinguish between early stage active TB and late/later stage active TB according to the present invention. Any combination of the one or more additional biomarkers may be used in combination with the GBP1 biomarker of the invention. For example at least two, at least three, at least four, at least five, at least six, at least seven, at least eight, at least nine, at least ten or more additional biomarkers for TB may be used in combination with the GBP1 biomarker of the invention. The one or more additional biomarker for use in distinguishing between early stage active TB and late/later stage active TB can be any biomarker disclosed herein.

The present inventors have also identified biomarkers which can be used to determine exposure of an individual to TB, even in the absence of an active or latent TB infection. In particular, the present inventors have identified IRF1, S100A11, CD52, LYN, IFITM3, NCF1C and HLA-B as such biomarkers for exposure to TB. One or more of the IRF1, S100A11, CD52, LYN, IFITM3, NCF1C and HLA-B biomarkers, or any combination thereof, may be used to determine exposure to TB. As used herein, the term "exposure to TB" is defined by comparison to non-exposed controls from regions of non/low-TB endemic regions. As an example, the Caucasian control group used in Example 2 below are an example of non-exposed individuals.

Accordingly, the present invention provides the use of one or more of the IRF1, S100A11, CD52, LYN, IFITM3, NCF1C and HLA-B biomarkers for determining exposure to TB. Any combination of these biomarkers may be used according to the present invention. For example, any one, two, or all three of these biomarkers may be used to determine exposure to TB according to the present invention. Typically, the combination of the biomarkers IRF1, S100A11, CD52, LYN, IFITM3, NCF1C and HLA-B or the combination of IRF1, S100A11, CD52, LYN, IFITM3 and NCF1C is used to determine exposure to TB according to the present invention.

One or more additional biomarker for TB may also be used to determine exposure to TB according to the present invention. Any combination of the one or more additional biomarkers may be used in combination with one or more of the IRF1, S100A11, CD52, LYN, IFITM3, NCF1C and HLA-B biomarkers of the invention. For example at least two, at least three, at least four, at least five, at least six, at least seven, at least eight, at least nine, at least ten or more additional biomarkers for TB may be used in combination with one or more of the IRF1, S100A11, CD52, LYN, IFITM3, NCF1C and HLA-B biomarkers of the invention. The one or more additional biomarker for use in determining exposure to TB can be any biomarker disclosed herein.

The one or more biomarker of the invention as described herein may have a nucleic acid sequence as shown in the sequences in the Sequence Information section herein. The relevant sequence identifiers are also shown in Tables 2 to 5. The one or more biomarker of the invention may have a sequence identity of at least 80% with the corresponding nucleic acid sequence shown in the Sequence Information section. Sequence identity may be calculated as described herein. A sequence identity of at least 80% includes at least 82%, at least 84%, at least 86%, at least 88%, at least 90%, at least 91%, at least 92%, at least 93%, at least 94%, at least 95%, at least 96%, at least 97%, at least 98%, at least 99%, and 100% sequence identity (to each and every nucleic acid sequence presented herein and/or to each and every SEQ ID NO presented herein).

Thus, as described herein, by studying both human and non-human primate biomarkers for TB, the present inventors have identified a robust set of biomarkers for TB that are mutually compatible (i.e. retain accurate binding specificity) within a single set of assay conditions (i.e. a singleplex format). Similarly, the present inventors have also identified robust sets of mutually compatible biomarkers for distinguishing between latent and active TB, for distinguishing between early active and late/later active TB and for determining exposure to TB. Combinations of biomarkers for use according to the present invention are discussed in detail herein. As discussed above, preferably, the present invention provides the use of the combination of: (i) LOC400759/GBP1P1, SNX10, CPVL, CREG1, PSMB9, GBP1, IRF1 and HLA-B; (ii) LOC400759/GBP1P1, SNX10, CPVL, CREG1, PF4V1, GBP1, IRF1, IFITM3 and S100A11; and/or (iii) LOC400759/GBP1P1, PF4V1, ALPK1, HERC2, GBP1, IRF1, MMP9, CD96, KLRA1, DEFB128 and IL8 as biomarkers for TB. These combinations (and the other combinations of biomarkers disclosed herein) may be used not only as biomarkers for TB, but also to distinguish between latent TB and/or active TB and/or the absence of TB, to distinguish between early active and late/later stage active TB and/or to determine exposure to TB.

The one or more biomarkers of the invention may be used in a decision tree process. For example, the present invention may first provide one or more biomarkers for the detection and/or diagnosis of active TB (an active TB infection) in an individual. Any suitable biomarker or combination of biomarkers disclosed herein may be used for the detection and/or diagnosis of active TB. In a preferred embodiment, the one or more biomarker for the detection and/or diagnosis of active TB is selected from (i) LOC400759/GBP1P1, SNX10, CPVL, CREG1, PSMB9, GBP1, IRF1 and HLA-B; (ii) LOC400759/GBP1P1, SNX10, CPVL, CREG1, PF4V1, GBP1, IRF1, IFITM3 and S100A11; and/or (iii) LOC400759/GBP1P1, PF4V1, ALPK1, HERC2, GBP1, IRF1, MMP9 and CD96; optionally in combination with one or more additional biomarker as disclosed herein. If the individual tests positive for active TB using this method, they may be treated appropriately.

If, however, the individual tests negative for active TB, they may then be tested for latent TB (a latent TB infection) according to the present invention. This is the next "branch" of the decision tree. Any suitable biomarker or combination of biomarkers disclosed herein may be used for the detection and/or diagnosis of latent TB. In a preferred embodiment, the one or more biomarker for the detection and/or diagnosis of latent TB is selected from PF4V1, LYN, CD52, HERC2, KLRA1, DEFB128 and IL8, optionally in combination with one or more additional biomarker as disclosed herein.

The present invention enables the rapid detection of TB, and also to rapidly distinguish between latent TB and/or active TB and/or the absence of TB. By way of example, the method of the invention is typically completed within 2.5 hours, preferably within 2 or 1.5 hours. In contrast, existing multiplex assays typically take at least 4-5 hours, typically at least 5 hours.

Biomarker Profiles

A "phenotypic change" is a detectable change in a parameter associated with a given state of the individual. For instance, a phenotypic change may include an increase or decrease of a biomarker in a bodily fluid, where the change is associated with TB or distinguishing between active and latent TB. The presence and/or amount of each of the one or more biomarkers of the invention is a feature or phenotypic change according to the present invention.

A phenotypic change may further include a change in a detectable aspect of a given state of the individual that is not a change in a measurable aspect of a biomarker. For example, a change in phenotype may include a detectable change in body temperature, weight loss, fatigue, respiration rate or other physiological parameter. Such changes can be determined via clinical observation and measurement using conventional techniques that are well-known to the skilled artisan. As used herein, "conventional techniques" are those techniques that classify an individual based on phenotypic changes without obtaining a biomarker profile according to the present invention.

A "decision rule" or a "decision tree" is a method used to classify individuals. This rule can take on one or more forms that are known in the art, as exemplified in Hastie et al., in "The Elements of Statistical Learning" Springer-Nerlag (Springer, New York (2001)). Analysis of biomarkers in the complex mixture of molecules within the sample generates features in a data set. A decision rule or a decision tree may be used to act on a data set of features to detect and/or diagnose, or to distinguish between active TB and/or latent TB and/or the absence of TB (for example uninfected control(s)).

The application of the decision rule or the decision tree does not require perfect classification. A classification may be made with at least about 90% certainty, or even more, in one embodiment. In other embodiments, the certainty is at least about 80%, at least about 70%, or at least about 60%. The useful degree of certainty may vary, depending on the particular method of the present invention. "Certainty" is defined as the total number of accurately classified individuals divided by the total number of individuals subjected to classification. As used herein, "certainty" means "accuracy".

Classification may also be characterized by its "sensitivity". The "sensitivity" of classification relates to the percentage of individuals with TB who were correctly identified as having TB, or in the case of distinguishing between active and latent TB, the percentage of individuals correctly identified as having active TB, or latent TB, or as uninfected with TB. "Sensitivity" is defined in the art as the number of true positives divided by the sum of true positives and false negatives.

The "specificity" of a method is defined as the percentage of patients who were correctly identified as not having TB, or in the case of distinguishing between active and latent TB, the percentage of individuals correctly identified as not having active or latent TB compared with an uninfected control(s). That is, "specificity" relates to the number of true negatives divided by the sum of true negatives and false positives.

Typically, the accuracy, sensitivity and/or specificity is at least about 90%, at least about 80%, at least about 70% or at least about 60%.

Diagnosing TB in an individual means to identify or detect TB in the individual. Distinguishing between active and latent TB in an individual means to identify or detect TB in the individual and to determine whether the TB is active or latent as described herein. Distinguishing between early stage active and late/later stage active TB in an individual means to identify or detect TB in the individual and to determine whether the TB is early stage active or late/later stage active as described herein. Distinguishing between latent TB and the absence of TB in an individual means to identify or detect latent TB in the individual compared with an uninfected control. Determining exposure of an individual to TB means to determine whether an individual has been exposed to TB, but is not themselves infected with active or latent TB.

Because of the sensitivity of the present invention to detect TB before an overtly observable clinical manifestation, the diagnosis, identification or detection of TB includes the detection of the onset of TB, as defined above.

According to the present invention, TB may be diagnosed or detected, or active and latent TB distinguished, by obtaining a profile of biomarkers from a sample obtained from an individual. As used herein, "obtain" means "to come into possession of". The present invention is particularly useful in predicting and diagnosing TB in an individual, who is suspected of having TB, or who is at risk of TB infection. In the same manner, the present invention may be used to distinguish between active TB and/or latent TB and/or the absence of TB in an individual. That is, the present invention may be used to confirm a clinical suspicion of TB.

The presence and/or amount of the one or more biomarker of the invention in an individual or the profile of biomarkers in an individual may be measured relative to a control or reference population, for example relative to the corresponding biomarker profile of a reference population. Similarly, the biomarker profile of an individual may be measured relative to a biomarker profile from a control or reference population. Herein the terms "control" and "reference population" are used interchangeably. The actual amount of the one or more biomarkers, such as the mass, molar amount, concentration or molarity of the one or more biomarker of the invention may be assessed and compared with the corresponding value from the control or reference population. Alternatively, the amount of one or more biomarker of the invention may be compared with that of the control or reference population without quantifying the mass, molar amount, concentration or molarity of the one or more biomarker.

The control or reference biomarker profile can be generated from one individual or a population of two or more individuals. The control or reference population, for example, may comprise three, four, five, ten, 15, 20, 30, 40, 50 or more individuals. Furthermore, the control or reference biomarker profile and the individual's (test) biomarker profile that are compared in the methods of the present invention may be generated from the same individual, provided that the test and reference biomarker profiles are generated from biological samples taken at different time points and compared to one another. For example, a sample may be obtained from an individual at the start of a study period. A control or reference biomarker profile taken from that sample may then be compared to biomarker profiles generated from subsequent samples from the same individual. Such a comparison may be used, for example, to determine the progression of TB in the individual by repeated classifications over time.

The control or reference may be obtained, for example, from a population of TB-negative individuals, TB-positive individuals, individuals with active TB and individuals with latent TB. In the Examples herein, the Caucasian control group consists of professional individuals recruited locally to the project team who constitute a low risk group, coming from non/low-TB endemic regions, such that their risk of having been exposed to TB is extremely low. Typically this is the preferred control group. The second control group in the Examples consists of individuals of Asian descent who tested negative for TB using the standard Mantoux skin test and IFNγ test and who come from regions where TB is endemic. The likelihood is that these individuals have been exposed to TB, even if they are not themselves (currently) infected. Thus, without being bound by theory, any differences in the detection of biomarkers of the invention between this control group and the Caucasian controls may result from the likely exposure of this Asian control group to TB.

Typically the control or reference population does not have TB and/or is not infected with *M. tuberculosis* (i.e. is TB-negative). The control or reference population may be TB-positive and are then subsequently diagnosed with TB using conventional techniques. For example, a population of TB-positive individuals used to generate the reference profile may be diagnosed with TB about 24, 48, 72, 96 or more hours after biological samples were taken from them for the purposes of generating a reference biomarker profile. In one embodiment, the population of TB-positive individuals is diagnosed with TB using conventional techniques about 0-36 hours, about 36-60 hours, about 60-84 hours, or about 84-108 hours after the biological samples were taken. If the biomarker profile is indicative of TB, a clinician may begin treatment prior to the manifestation of clinical symptoms of TB.

The amount of the one or more biomarker of the invention, for example in a biomarker profile, may differ by at least 10%, at least 20%, at least 30%, at least 40%, at least 50%, at least 60, at least 70%, at least 80%, at least 90%, at least 100%, at least 150%, at least 200% or more compared with a control or reference population.

For example, if the amount of the one or more biomarker of the invention, typically in a biomarker profile, is reduced compared with a control or reference population, the expression may be reduced partially or totally compared with the control or reference population. Typically the amount is reduced by at least 10%, at least 20%, at least 30%, at least 40%, at least 50%, at least 60, at least 70%, at least 80%, at least 90%, at least 95%, at least 99%, up to total elimination of the one or more biomarker.

If the amount of one or more biomarker of the invention, typically in a biomarker profile, is increased compared with a control or reference population, the amount may be increased by at least 10%, at least 20%, at least 30%, at least 40%, at least 50%, at least 60, at least 70%, at least 80%, at least 90&, at least 100%, at least 150%, at least 200% compared with the control or reference population.

The amount of the one or more biomarker of the invention may be increased or decreased compared with a control or reference population as shown in Tables 2 to 5 herein (where ↑ means the one or more biomarker is upregulated/an increased amount of the one or more biomarker and ↓ means the one or more biomarker is downregulated/a decreased amount of the one or more biomarker). In instances where more than one indication of up or downregulation is given in Tables 2 to 5, the first recited statement is preferred. For example, Table 2 discloses that ALPK1 is increased in monocytes, neutrophils and CD4 positive T cells compared with a control or reference population. In this example, the amount of ALPK1 may be increased in CD4 positive T cells, preferably increased in neutrophils and most preferably increased in monocytes. The amount of ALPK1 may be increased in CD4 positive T cells, neutrophils and monocytes, and may also be increased in other cell types not listed in Tables 2 to 5.

The amount of the one or more biomarker may be increased in some cell types and/or decreased in other cell types. For example, as shown in Table 2 herein, PF4V1 is upregulated (increased amount) in monocytes of individuals with TB, whereas PF4V1 is downregulated (decreased amount) in neutrophils of individuals with TB.

The presence and/or amount of the one or more biomarker of the invention may be determined by quantitative and/or qualitative analysis. The amount of the one or more biomarker of the invention encompasses the mass of the one or more biomarker, the molar amount of the one or more biomarker, the concentration of the one or biomarker and the molarity of the one or more biomarker. This amount may be given in any appropriate units. For example, the concentration of the one or more biomarker may be given in pg/ml, ng/ml or µg/ml.

The presence and/or amount of the one or more biomarker of the invention may be measured directly or indirectly. The relative presence and/or amount of the one or more biomarker of the invention relative to a control or reference population may be determined using any appropriate technique. Suitable standard techniques are known in the art, for example Western blotting and enzyme-linked immunosorbent assays (ELISAs). Preferred methods include microarray analysis (as used in Example 1) and quantitative real-time PCR (qPCR) (as used in Example 2). Different one or more biomarkers may be used with different detection methods according to the present invention. For example, in one embodiment, the one or more biomarker is selected from PF4V1/or HERC2, preferably in combination with LOC400759/GBP1P1 and/or ALPK1 as disclosed herein, for use with microarray analysis. Typically, the one or more biomarker is selected from SNX10 and/or CPVL, preferably in combination with LOC400759/GBP1P1 and/or CREG1, for use with qPCR analysis. Again, additional one or more biomarkers as disclosed herein can be selected dependent on the preferred detection method.

As used herein, "comparison" includes any means to discern at least one difference in the presence and/or amount of the one or more biomarker in the individual and the control or reference population, or at least one difference in the individual's and the control or reference profiles. Thus, a comparison may include a visual inspection of chromatographic spectra, and a comparison may include arithmetical or statistical comparisons of values assigned to the features of the profiles. Such statistical comparisons include, but are not limited to, applying a decision rule. If the biomarker profiles comprise at least one internal standard, the comparison to discern a difference in the biomarker profiles may also include features of these internal standards, such that features of the biomarker are correlated to features of the internal standards. The comparison can confirm the presence or absence of TB, and thus to detect or diagnose TB; or the comparison can distinguish between active and latent TB.

The presence and/or amount level of the one or more biomarker may be altered compared with a control or reference population for at least 12 hours, at least 24 hours, at least 30 hours, at least 48 hours, at least 72 hours, at least 96 hours, at least 120 hours, at least 144 hours, at least 1 week, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks or more.

Although the invention does not require a monitoring period to classify an individual, it will be understood that repeated classifications of the individual, i.e., repeated snapshots, may be taken over time until the individual is no longer at risk. Alternatively, a profile of biomarkers obtained from the individual may be compared to one or more profiles of biomarkers obtained from the same individual at different points in time.

As used herein, an "individual" is an animal, preferably a mammal, more preferably a human or non-human primate. The terms "individual," "subject" and "patient" are used interchangeably herein. The individual can be normal, suspected of having TB or at risk of a TB infection. In a preferred embodiment, the present invention relates to the detection and/or diagnosis of TB in adult humans (over the age of 16 years).

The progression of an individual from normalcy (i.e., a condition characterized by not having TB) to latent or active TB, and vice versa, will be characterized by changes in biomarker profiles, as certain biomarkers are expressed at increasingly higher levels and the expression of other biomarkers becomes down regulated. These changes in biomarker profiles may reflect the progressive establishment of a physiological response in the reference population to infection. The biomarker profile of the control or reference population also will change as a physiological response subsides. As stated above, one of the advantages of the present is the capability of classifying an individual, using a biomarker profile from a single biological sample, as having membership in a particular population. The determination of whether a particular physiological response is becoming established or is subsiding may be facilitated by a subsequent classification of the individual. To this end, the present invention provides numerous biomarkers that both increase and decrease in level of expression as a physiological response to TB is established or subsides. For example, a feature of an individual's biomarker profile that is known to change in intensity as a physiological response to TB becomes established may be selected. A comparison of the same feature in a profile from a subsequent biological sample from the individual can establish whether the individual is progressing toward more severe TB or is progressing toward normalcy.

Detection and Quantification of Biomarkers and Determination of Biomarker Profiles A feature as defined herein for the diagnosis of TB, a TB infection and/or a *M. tuberculosis* infection may be detected, quantified or determined by any appropriate means. For example, the one or more biomarker of the invention, a measurable aspect or characteristic of the one or more biomarker or a biomarker profile of the invention may be detected by any appropriate means. The presence and/or amount of the one or more biomarkers of the invention may be considered together as a "biomarker profile" of the invention. The presence and/or amount of the individual biomarkers within any of the biomarker combinations disclosed herein may be considered together as a "biomarker profile" of the invention. For example, in a preferred embodiment of the invention, the combination of biomarkers: (i) SNX10 and CPVL; (ii) LOC400759/GBP1P1, SNX10, CPVL and CREG1; (iii) LOC400759/GBP1P1, SNX10, CPVL, CREG1, PSMB9, GBP1, IRF1 and HLA-B; (iv) LOC400759/GBP1P1, SNX10, CPVL, CREG1, PF4V1, GBP1, IRF1, IFITM3 and S100A11; (v) PF4V1 and HERC2; (vi) SNX10, CPVL, PF4V1 and HERC2; (vii) SNX10, CPVL, PF4V1, HERC2, CD52, LYN, LGALS3BP, BAZ1A, KLRA1 and WSB1 and/or (viii) LOC400759/GBP1P1, PF4V1, ALPK1, HERC2, GBP1, IRF1, MMP9 and CD96 is used to detect and or diagnose TB. Thus, the presence and/or amount of: (i) SNX10 and CPVL; (ii) LOC400759/GBP1P1, SNX10, CPVL and CREG1; (iii) LOC400759/GBP1P1, SNX10, CPVL, CREG1, PSMB9, GBP1, IRF1 and HLA-B; (iv) LOC400759/GBP1P1, SNX10, CPVL, CREG1, PF4V1, GBP1, IRF1, IFITM3 and S100A11; (v) PF4V1 and HERC2; (vi) SNX10, CPVL, PF4V1 and HERC2; (vii) SNX10, CPVL, PF4V1, HERC2, CD52, LYN, LGALS3BP, BAZ1A, KLRA1 and WSB1 and/or (viii) LOC400759/GBP1P1, PF4V1, ALPK1, HERC2, GBP1, IRF1, MMP9 and CD96 may be considered as a biomarker profile according to the present invention. The presence and/or amount of any other combination of biomarkers according to the present invention may also be considered as a biomarker profile. A biomarker profile of the invention may comprise: (i) SNX10 and CPVL; (ii) LOC400759/GBP1P1, SNX10, CPVL and CREG1; (iii) LOC400759/GBP1P1, SNX10, CPVL, CREG1, PSMB9, GBP1, IRF1 and HLA-B; (iv) LOC400759/GBP1P1, SNX10, CPVL, CREG1, PF4V1, GBP1, IRF1, IFITM3 and S100A11; (v) PF4V1 and HERC2; (vi) SNX10, CPVL, PF4V1 and HERC2; (vii) SNX10, CPVL, PF4V1, HERC2, CD52, LYN, LGALS3BP, BAZ1A, KLRA1 and WSB1 and/or (viii) LOC400759/GBP1P1, PF4V1, ALPK1, HERC2, GBP1, IRF1, MMP9, CD96, KLRA1, DEFB128 and IL8.

The presence and/or amount of the one or more biomarker of the invention may be determined in a sample obtained from an individual. The sample may be any suitable biological material, for example blood, plasma, saliva, serum, sputum, urine, cerebral spinal fluid, cells, a cellular extract, a tissue sample, a tissue biopsy, a stool sample and the like. Typically the sample is blood sample. The precise biological sample that is taken from the individual may vary, but the sampling preferably is minimally invasive and is easily performed by conventional techniques. In a preferred embodiment, the sample is a whole blood sample, a purified peripheral blood leukocyte sample or a cell type sorted leukocyte sample, such as a sample of the individual's neutrophils. The biological sample may be taken from the individual before, during, and/or after treatment for TB infection. In one embodiment, the sample is taken after treatment for TB infection has been initiated.

Measurement of a phenotypic change may be carried out by any conventional technique. Measurement of body temperature, respiration rate, pulse, blood pressure, or other physiological parameters can be achieved via clinical observation and measurement. Measurements of biomarker molecules may include, for example, measurements that indicate the presence, concentration, expression level, or any other value associated with a biomarker molecule. The form of detection of biomarker molecules typically depends on the method used to form a profile of these biomarkers from a biological sample. For instance, biomarkers separated by 2D-PAGE are detected by Coomassie Blue staining or by silver staining, which are well-established in the art.

The biomarkers of the invention may be detected at the nucleic acid or protein level. Thus, the biomarkers of the invention may be DNA, RNA or protein and may be detected using any appropriate technique. The presence and/or amount of the one or more biomarker of the invention may be measured directly or indirectly. Any appropriate agent may be used to determine the presence and/or amount of the one or more biomarker of the invention. For example, the presence and/or amount of the one or more biomarker of the invention may be determined using an agent selected from peptides and peptidomimetics, antibodies, small molecules and single-stranded DNA or RNA molecules, as described herein. The relative presence and/or amount of the one or more biomarker of the invention relative to a control or reference population (see above) may be determined using any appropriate technique. Suitable standard techniques are known in the art.

For example, when the one or more biomarker is detected at the nucleic acid level this may be carried out using: (i) biomarker-specific oligonucleotide DNA or RNA or any other nucleic acid derivative probes bound to a solid surface; (ii) purified RNA (labelled by any method, for example using reverse transcription and amplification) hybridised to probes; (iii) whole lysed blood, from which the RNA is labelled by any method and hybridised to probes; (iv) purified RNA hybridised to probes and a second probe (labelled by any method) hybridised to the purified RNA; (v) whole lysed blood from which the RNA is hybridised to probes, and a second probe (labelled by any method) which is hybridised to the RNA; (vi) purified peripheral blood leukocytes, obtaining purified RNA (labelled by any method), and hybridising the purified labelled RNA to probes; (vii) purified peripheral blood leukocytes, obtaining purified RNA and hybridising the RNA to probes, then using a second probe (labelled by any method) which hybridises to the RNA; (viii) RT-PCR using any primer/probe combination or inter-chelating fluorescent label, for example Syber-Green; (ix) end-point PCR; (x) digital PCT; (xi) sequencing; (xii) array cards (RT-PCT); (xiii) lateral flow devices/methodology; and/or (xiv) digital microfluidics.

In a preferred embodiment, RNA from a sample (either purified or unpurified) is labelled via any method (typically amplification) and used to interrogate one or more probe immobilised on a surface. Typically the one or more probes are 50 to 100 nucleotides in length.

In another preferred embodiment, one or more probe is immobilised on a surface and the RNA from a sample is hybridised to one or more second probe (labelled by any method). The RNA hybridised with the second (labelled) probe is then used to interrogate the one or more probe immobilised on the surface. Examples of such methodology are known in the art, including the Vantix™ system.

For example, when the one or more biomarker is detected at the protein acid level this may be carried out using: (i) biomarker-specific primary antibodies or antibody fragments bound to a solid surface; (ii) whole lysed blood biomarker antigen bound to antibodies or antibody fragments; (iii) secondary biomarker-specific antibodies or antibody fragments used to detect biomarker antigen bound to primary antibody (labelled using any method); (iv) biomarker-specific primary aptamers bound to a solid surface; (v) whole lysed blood—biomarker antigen bound to aptamers; (vi) secondary biomarker-specific aptamer used to detect biomarker antigen bound to primary aptamer (labelled using any method); (vii) any antibody derivative i.e. phage display etc. used as above; (viii) lateral flow devices/methodology; (ix) chromatography; (x) mass spectrometry; (xi) nuclear magnetic resonance (NMR); (xii) protein gels/transfers to filter; and/or (xiii) immunoprecipitation.

Any agent for the detection of or for the determination of the amount of the one or more biomarker of the invention may be used to determine the presence of and/or amount of the one or more biomarker. Similarly, any method that allows for the detecting of the one or more biomarker, the quantification, or relative quantification of the one or more biomarker may be used.

Agents for the detection of or for the determination of the amount of one or more biomarker may be used to determine the amount of the one or more biomarker in a sample obtained from the individual. Such agents typically bind to the one or more biomarker. Such agents may bind specifically to the one or more biomarker. The agent for the detection of or for the determination of the amount of the one or more biomarker may be an antibody or other binding agent specific for the one or more biomarker. By specific, it will be understood that the agent or antibody binds to the molecule of interest, in this case the one or more biomarker, with no significant cross-reactivity to any other molecule, particularly any other protein. For example, an agent or antibody that is specific for LOC400759/GBP1P1 will show no significant cross-reactivity with human neutrophil elastase. Cross-reactivity may be assessed by any suitable method. Cross-reactivity of an agent or antibody for the one or more biomarker with a molecule other than the one or more biomarker may be considered significant if the agent or antibody binds to the other molecule at least 5%, 10%, 15%, 20%, 25%, 30%, 35%, 40%, 45%, 50%, 55%, 60%, 65%, 70%, 75%, 80%, 85%, 90% or 100% as strongly as it binds to the one or more biomarker. An agent or antibody that is specific for the one or more biomarker may bind to another molecule such as human neutrophil elastase at less than 90%, 85%, 80%, 75%, 70%, 65%, 60%, 55%, 50%, 45%, 40%, 35%, 30%, 25% or 20% the strength that it binds to the one or more biomarker. Preferably, the agent or antibody binds to the other molecule at less than 20%, less than 15%, less than 10% or less than 5%, less than 2% or less than 1% the strength that it binds to the one or more biomarker.

As described herein, the presence and/or amount of the one or more biomarker, and hence the biomarker profile may be determined immunologically by reacting antibodies, or functional fragments thereof, specific to the biomarkers. A functional fragment of an antibody is a portion of an antibody that retains at least some ability to bind to the antigen to which the complete antibody binds. The fragments, which include, but are not limited to, scFv fragments, Fab fragments, F(ab) fragments and F(ab)2 fragments, can be recombinantly produced or enzymatically produced. Specific binding molecules other than antibodies, such as aptamers, may be used to bind the biomarkers.

The antibody may be monoclonal or polyclonal. The antibody may be produced by any suitable method known in the art. For example, polyclonal antibodies may be obtained by immunizing a mammal, typically a rabbit or a mouse, with the one or more biomarker under suitable conditions and isolating antibody molecules from, for example, the serum of said mammal. Monoclonal antibodies may be obtained by hybridoma or recombinant methods.

Hybridoma methods may involve immunizing a mammal, typically a rabbit or a mouse, with the one or more biomarker under suitable conditions, then harvesting the spleen cells of said mammal and fusing them with myeloma cells. The mixture of fused cells is then diluted and clones are grown from single parent cells. The antibodies secreted by the different clones are then tested for their ability to bind to the one or more biomarker, and the most productive and stable clone is then grown in culture medium to a high volume. The secreted antibody is collected and purified.

Recombinant methods may involve the cloning into phage or yeast of different immunoglobulin gene segments to create libraries of antibodies with slightly different amino acid sequences. Those sequences which give rise to antibodies which bind to the one or more biomarker may be selected and the sequences cloned into, for example, a bacterial cell line, for production.

Typically the antibody is a mammalian antibody, such as a primate, human, rodent (e.g. mouse or rat), rabbit, ovine, porcine, equine or camel antibody. The antibody may be a camelid antibody or shark antibody. The antibody may be a nanobody. The antibody can be any class or isotype of antibody, for example IgM, but is preferably IgG. The antibody may be a humanised antibody.

The antibody or fragment may be associated with other moieties, such as linkers which may be used to join together 2 or more fragments or antibodies. Such linkers may be chemical linkers or can be present in the form of a fusion protein with the fragment or whole antibody. The linkers may thus be used to join together whole antibodies or fragments which have the same or different binding specificities, e.g. that can bind the same or different polymorphisms. The antibody may be a bispecific antibody which is able to bind to two different antigens, typically any two of the polymorphisms mentioned herein. The antibody may be a 'diabody' formed by joining two variable domains back to back. In the case where the antibodies used in the method are present in any of the above forms which have different antigen binding sites of different specificities then these different specificities are typically to polymorphisms at different positions or on different proteins. In one embodiment the antibody is a chimeric antibody comprising sequence from different natural antibodies, for example a humanised antibody.

Methods to assess an amount of the one or more biomarker may involve contacting a sample with an agent or antibody capable of binding specifically to the one or more biomarker. Such methods may include dipstick assays and Enzyme-linked Immunosorbant Assay (ELISA), or similar assays, such as those using a lateral flow device. Other immunoassay types may also be used to assess the one or more biomarker amounts. Typically dipsticks comprise one or more antibodies or proteins that specifically bind to the one or more biomarker. If more than one antibody is present, the antibodies preferably have different non-overlapping determinants such that they may bind to the one or more biomarker simultaneously.

ELISA is a heterogeneous, solid phase assay that requires the separation of reagents. ELISA is typically carried out using the sandwich technique or the competitive technique. The sandwich technique requires two antibodies. The first specifically binds the one or more biomarker and is bound to a solid support. The second antibody is bound to a marker, typically an enzyme conjugate. A substrate for the enzyme is used to quantify the one or more biomarker-antibody complex and hence the amount of the one or more biomarker in a sample. The antigen competitive inhibition assay also typically requires a one or more biomarker-specific antibody bound to a support. A biomarker-enzyme conjugate is added to the sample (containing the one or more biomarker) to be assayed. Competitive inhibition between the biomarker-enzyme conjugate and unlabelled biomarker allows quantification of the amount of the one or more biomarker in a sample. The solid supports for ELISA reactions preferably contain wells.

Antibodies capable of binding specifically to the one or more biomarker may be used in methods of immunofluorescence to detect the presence of the one or more biomarker and hence in methods of diagnosing TB, a TB infection, infection with *M. tuberculosis*, or to distinguish between active and latent TB according to the present invention.

The present invention may also employ methods of determining the amount of the one or more biomarker that do not comprise antibodies. High Performance Liquid Chromatography (HPLC) separation and fluorescence detection is preferably used as a method of determining the amount of the one or more biomarker. HPLC apparatus and methods as described previously may be used (Tsikas D et al. J Chromatogr B Biomed Sci Appl 1998; 705: 174-6) Separation during HPLC is typically carried out on the basis of size or charge. Prior to HPLC, endogenous amino acids and an internal standard L-homoarginine are typically added to assay samples and these are phase extracted on CBA cartridges (Varian, Harbor City, Calif.). Amino acids within the samples are preferably derivatized with o-phthalaldehyde (OPA). The accuracy and precision of the assay is preferably determined within quality control samples for all amino acids.

Other methods of determining the amount the one or more biomarker that do not comprise antibodies include mass spectrometry. Mass spectrometric methods may include, for example, matrix-assisted laser desorption/ionization mass spectrometry (MALDI MS), surface-enhanced laser desorption/ionization mass spectrometry (SELDI MS), time of flight mass spectrometry (TOF MS) and liquid chromatography mass spectrometry (LC MS).

A separation method may be used to determine the presence and/or amount of the one or more biomarker and hence to create a profile of biomarkers, such that only a subset of biomarkers within the sample is analysed. For example, the biomarkers that are analysed in a sample may consist of mRNA species from a cellular extract, which has been fractionated to obtain only the nucleic acid biomarkers within the sample, or the biomarkers may consist of a fraction of the total complement of proteins within the sample, which have been fractionated by chromatographic techniques. One or more, two or more, three or more, four or more, or five or more separation methods may be used according to the present invention.

Determination of the presence and/or amount of the one or more biomarker, and hence the creation of a profile of biomarkers may be carried out without employing a separation method. For example, a biological sample may be interrogated with a labelled compound that forms a specific complex with a biomarker in the sample, where the intensity of the label in the specific complex is a measurable characteristic of the biomarker. A suitable compound for forming such a specific complex is a labelled antibody. A biomarker may be measured using an antibody with an amplifiable nucleic acid as a label. The nucleic acid label may become amplifiable when two antibodies, each conjugated to one strand of a nucleic acid label, interact with the biomarker, such that the two nucleic acid strands form an amplifiable nucleic acid.

The presence and/or amount of the one or more biomarker, and hence the biomarker profile may be derived from an assay, such as an array, of nucleic acids, where the biomarkers are the nucleic acids or complements thereof. For example, the biomarkers may be ribonucleic acids. The presence and/or amount of the one or more biomarker, and hence the biomarker profile may be obtained using a method selected from nuclear magnetic resonance, nucleic acid arrays, dot blotting, slot blotting, reverse transcription amplification and Northern analysis.

The biomarker profile may comprise any measurable aspect of *M. tuberculosis* or a component thereof. For example, the biomarker profile may comprise measurable aspects of small molecules, which may include fragments of proteins or nucleic acids, or which may include metabolites.

The determination of the presence and/or amount of the one or more biomarker, and hence a biomarker profile may be generated by the use of one or more separation methods. For example, suitable separation methods may include a mass spectrometry method, such as electrospray ionization mass spectrometry (ESI-MS), ESI-MS/MS, ESI-MS/(MS)n (n is an integer greater than zero), matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SLMS), quadrupole time-of-flight (Q-TOF), atmospheric pressure chemical ionization mass spectrometry (APCI-MS), APCI-MS/MS, APCI-(MS)n, atmospheric pressure photoionization mass spectrometry (APPI-MS), APPI-MS/MS, and APPI-(MS)n. Other mass spectrometry methods may include, inter alia, quadrupole, fourier transform mass spectrometry (FTMS) and ion trap. Other suitable separation methods may include chemical extraction partitioning, column chromatography, ion exchange chromatography, hydrophobic (reverse phase) liquid chromatography, isoelectric focusing, one-dimensional polyacrylamide gel electrophoresis (PAGE), two-dimensional polyacrylamide gel electrophoresis (2D-PAGE) or other chromatography, such as thin-layer, gas or liquid chromatography, or any combination thereof. The sample may be fractionated prior to application of the separation method.

The determination of the presence and/or amount of the one or more biomarker, and hence a biomarker profile may be generated by methods that do not require physical separation of the biomarkers themselves. For example, nuclear magnetic resonance (NMR) spectroscopy may be used to resolve a profile of biomarkers from a complex mixture of molecules. An analogous use of NMR to classify tumours is disclosed in Hagberg, NMR Biomed. 11: 148-56 (1998), for example. Additional procedures include nucleic acid amplification technologies, which may be used to generate a profile of biomarkers without physical separation of individual biomarkers. (See Stordeur et al, J. Immunol. Methods 259: 55-64 (2002) and Tan et al, Proc. Nat'l Acad. Sci. USA 99: 11387-11392 (2002), for example.)

In one embodiment, laser desorption/ionization time-of-flight mass spectrometry is used to determine the presence and/or amount of the one or more biomarker, and hence create a biomarker profile where the biomarkers are proteins or protein fragments that have been ionized and vaporized off an immobilizing support by incident laser radiation. A profile is then created by the characteristic time-of-flight for each protein, which depends on its mass-to-charge ("m/z") ratio. A variety of laser desorption/ionization techniques are known in the art. (See, e.g., Guttman et al, Anal Chem. 73: 1252-62 (2001) and Wei et al, Nature 399: 243-46 (1999).)

Laser desorption/ionization time-of-flight mass spectrometry allows the generation of large amounts of information in a relatively short period of time. A sample is applied to one of several varieties of a support that binds all of the biomarkers, or a subset thereof, in the sample. Cell lysates or samples are directly applied to these surfaces in volumes as small as 0.5 μL, with or without prior purification or fractionation. The lysates or sample can be concentrated or diluted prior to application onto the support surface. Laser desorption/ionization is then used to generate mass spectra of the sample, or samples, in as little as three hours.

In a preferred embodiment, the total mRNA from a cellular extract of the individual is assayed, and the various mRNA species that are obtained from the sample are used as biomarkers. Biomarker profiles may be obtained, for example, by hybridizing these mRNAs to an array of probes, which may comprise oligonucleotides or cDNAs, using standard methods known in the art. Alternatively, the mRNAs may be subjected to gel electrophoresis or blotting methods such as dot blots, slot blots or Northern analysis, all of which are known in the art. (See, e.g., Sambrook et al. in "Molecular Cloning, 3rd ed.," Cold Spring Harbor Laboratory Press, Cold Spring Harbor, N.Y. (2001).) mRNA profiles also may be obtained by reverse transcription followed by amplification and detection of the resulting cDNAs, as disclosed by Stordeur et al, supra, for example. In another embodiment, the profile may be obtained by using a combination of methods, such as a nucleic acid array combined with mass spectroscopy.

Different methods have different advantages and may be preferred depending on numerous factors, such as the particular circumstances of the individuals to be tested and/or the availability of reagents/equipment in the diagnostics laboratory. For example, qPCR using probe/quencher hydrolysis probes as described herein is highly specific and stringent. As another example, microarray analysis can resolve subtle differences in expression of transcript variants, which may be important in disease pathology and diagnosis.

Probes

Any appropriate detection means can be used to detect or quantify the one or more biomarker of the invention, as described herein.

Typically when the one or more biomarker of the invention is a nucleic acid, the presence of the one or more biomarker may be detected, and/or the amount of the one or more biomarker determined using an oligonucleotide probe.

An oligonucleotide probe of the invention may have at least 80% sequence identity to the one or more biomarker of the invention, or a target region within said biomarker, measured over any appropriate length of sequence. Typically the % sequence identity is determined over a length of contiguous nucleic acid residues. An oligonucleotide probe of the invention may, for example, have at least 80% sequence identity to the one or more biomarker of the invention, or target region thereof, measured over at least 10, at least 20, at least 30, at least 40, at least 50, at least 60, at least 70, at least 80, at least 90, or more nucleic acid residues, up to the oligonucleotide probe having at least 80% sequence identity with the one or more biomarker of the invention, or target region thereof, over the entire length of the oligonucleotide probe.

An oligonucleotide probe of the invention may be complementary to the one or more nucleic acid biomarker of the invention, or a target region thereof. Typically the oligonucleotide probe of the invention is complementary over a length of contiguous nucleic acid residues. An oligonucleotide probe of the invention may, for example, be complementary to the one or more biomarker of the invention, or target region thereof, measured over at least 10, at least 20, at least 30, at least 40, at least 50, at least 60, at least 70, at least 80, at least 90, or more nucleic acid residues, up to the oligonucleotide probe having being complementary to the one or more biomarker of the invention, or target region thereof, over the entire length of the oligonucleotide probe.

An oligonucleotide probe of the invention may be complementary to a variant of the one or more biomarker of the invention, or a variant of a target region of said biomarker. Typically the oligonucleotide probe is complementary to a variant having at least 80% sequence identity to the one or more biomarker of the invention, or a variant having at least 80% sequence identity to the target region of said biomarker. The % sequence identity of the variant to the one or more biomarker of the invention, or a variant of a target region of said biomarker may be calculated over any appropriate length of sequence in the one or more biomarker, as described herein.

A sequence identity of at least 80% includes at least 82%, at least 84%, at least 86%, at least 88%, at least 90%, at least 91%, at least 92%, at least 93%, at least 94%, at least 95%, at least 96%, at least 97%, at least 98%, at least 99%, and 100% sequence identity (to each and every nucleic acid sequence presented herein and/or to each and every SEQ ID NO presented herein).

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22 (22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. MoI. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262 (5131) Science 208-214 (1993); Align-M, see, e.g., Ivo Van WaIIe et al., Align-M—A New Algorithm for Multiple Alignment of Highly Divergent Sequences, 20 (9) Bioinformatics: 1428-1435 (2004). Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992.

Variants of the specific sequences provided above may alternatively be defined by reciting the number of nucleotides that differ between the variant sequences and the specific reference sequences provided above. Thus, in one embodiment, the sequence may comprise (or consist of) a nucleotide sequence that differs from the specific sequences provided above at no more than 2 nucleotide positions, for example at no more than 1 nucleotide position. Conservative substitutions are preferred. The term variants as defined herein also encompasses splice variants.

An oligonucleotide probe of the invention may be at least 30, at least 40, at least 50, at least 60, at least 70, at least 80, at least 90, at least 100, or more nucleotides in length. In a preferred embodiment, the oligonucleotide probe is 40 to 100 nucleotides in length, more preferably 50 to 100 nucleotides in length, even more preferably 50 to 80 nucleotides in length and most preferably 50 to 70 nucleotides in length.

The probes of the invention are typically designed to hybridise to their target nucleic acid sequence present in the one or more biomarker of the invention.

A probe may comprise or be complementary to a nucleic acid sequence within a target nucleic acid sequence from the one or more biomarker of the invention, or to a nucleic acid sequence having at least 80% identity to said target nucleic acid sequence. Any suitable probe which comprises or is complementary (as defined herein) to a nucleic acid sequence within a target nucleic acid sequence of one or more biomarker of the invention may be used. Preferred target sequences within the one or more biomarkers of the invention are underlined in the nucleic acid sequences shown in the Sequence Information section.

In embodiments wherein the one or more biomarker for TB is LOC400759/GBP1P1, a target nucleic acid sequence may comprise bases 91 to 640 of SEQ ID NO: 112 or bases 13751 to 13950 of SEQ ID NO: 113, and a probe typically comprises or is complementary to a nucleic acid sequence having at least 80% sequence identity to a nucleic acid sequence from this target sequence.

In embodiments wherein the one or more biomarker for TB is PF4V1, a target nucleic acid sequence may comprise bases 21 to 450 of SEQ ID NO: 134, and a probe typically comprises or is complementary to a nucleic acid sequence having at least 80% sequence identity to a nucleic acid sequence from this target sequence.

In embodiments wherein the one or more biomarker for TB is ALPK1, a target nucleic acid sequence may comprise bases 511 to 3220 of SEQ ID NO: 117, and a probe typically comprises or is complementary to a nucleic acid sequence having at least 80% sequence identity to a nucleic acid sequence from this target sequence.

In embodiments wherein the one or more biomarker for TB is HERC2, a target nucleic acid sequence may comprise bases 2411 to 5641, 8141 to 9630 and/or 13651 to 14930 of SEQ ID NO: 132, and a probe typically comprises or is complementary to a nucleic acid sequence having at least 80% sequence identity to a nucleic acid sequence from this target sequence.

In embodiments wherein the one or more biomarker for TB is LGALS3BP, a target nucleic acid sequence may comprise bases 1431 to 1850 of SEQ ID NO: 114, and a probe typically comprises or is complementary to a nucleic acid sequence having at least 80% sequence identity to a nucleic acid sequence from this target sequence.

In embodiments wherein the one or more biomarker for TB is BST1, a target nucleic acid sequence may comprise bases 361 to 840 of SEQ ID NO: 115, and a probe typically comprises or is complementary to a nucleic acid sequence having at least 80% sequence identity to a nucleic acid sequence from this target sequence.

In embodiments wherein the one or more biomarker for TB is SNX10, a target nucleic acid sequence may comprise bases 1901 to 2480 of SEQ ID NO: 116, and a probe typically comprises or is complementary to at least one nucleic acid sequence having at least 80% sequence identity to a nucleic acid sequence from this target sequence.

In embodiments wherein the one or more biomarker for TB is CREG1, a target nucleic acid sequence may comprise bases 961 to 1620 of SEQ ID NO: 118, and a probe typically comprises or is complementary to at least one nucleic acid sequence having at least 80% sequence identity to a nucleic acid sequence from this target sequence.

In embodiments wherein the one or more biomarker for TB is BAZ1A, a target nucleic acid sequence may comprise bases 4561 to 5270 of SEQ ID NO: 119, and a probe typically comprises or is complementary to at least one nucleic acid sequence having at least 80% sequence identity to a nucleic acid sequence from this target sequence.

In embodiments wherein the one or more biomarker for TB is LYN, a target nucleic acid sequence may comprise bases 1681 to 2520 of SEQ ID NO: 120, and a probe typically comprises or is complementary to at least one nucleic acid sequence having at least 80% sequence identity to a nucleic acid sequence from this target sequence.

In embodiments wherein the one or more biomarker for TB is TAPBP, a target nucleic acid sequence may comprise bases 171 to 1820 of SEQ ID NO: 121, and a probe typically comprises or is complementary to at least one nucleic acid sequence having at least 80% sequence identity to a nucleic acid sequence from this target sequence.

In embodiments wherein the one or more biomarker for TB is SERPINB1, a target nucleic acid sequence may comprise bases 1201 to 2050 of SEQ ID NO: 122, and a probe typically comprises or is complementary to at least one nucleic acid sequence having at least 80% sequence identity to a nucleic acid sequence from this target sequence.

In embodiments wherein the one or more biomarker for TB is PSMB9, a target nucleic acid sequence may comprise bases 241 to 870 of SEQ ID NO: 123, and a probe typically comprises or is complementary to at least one nucleic acid sequence having at least 80% sequence identity to a nucleic acid sequence from this target sequence.

In embodiments wherein the one or more biomarker for TB is WSB1, a target nucleic acid sequence may comprise bases 851 to 2250 of SEQ ID NO: 124, and a probe typically comprises or is complementary to at least one nucleic acid sequence having at least 80% sequence identity to a nucleic acid sequence from this target sequence.

In embodiments wherein the one or more biomarker for TB is MVP, a target nucleic acid sequence may comprise bases 1901 to 2880 of SEQ ID NO: 125, and a probe typically comprises or is complementary to at least one nucleic acid sequence having at least 80% sequence identity to a nucleic acid sequence from this target sequence.

In embodiments wherein the one or more biomarker for TB is APBB1IP, a target nucleic acid sequence may comprise bases 301 to 1830 of SEQ ID NO: 126, and a probe typically comprises or is complementary to at least one nucleic acid sequence having at least 80% sequence identity to a nucleic acid sequence from this target sequence.

In embodiments wherein the one or more biomarker for TB is FYB, a target nucleic acid sequence may comprise bases 1621 to 2690 of SEQ ID NO: 127, and a probe typically comprises or is complementary to at least one nucleic acid sequence having at least 80% sequence identity to a nucleic acid sequence from this target sequence.

In embodiments wherein the one or more biomarker for TB is MB21D1/C6orf150, a target nucleic acid sequence may comprise bases 1051 to 1570 of SEQ ID NO: 128, and a probe typically comprises or is complementary to at least one nucleic acid sequence having at least 80% sequence identity to a nucleic acid sequence from this target sequence.

In embodiments wherein the one or more biomarker for TB is CPVL, a target nucleic acid sequence may comprise bases 381 to 1140 of SEQ ID NO: 129, and a probe typically comprises or is complementary to at least one nucleic acid sequence having at least 80% sequence identity to a nucleic acid sequence from this target sequence.

In embodiments wherein the one or more biomarker for TB is TICAM2, a target nucleic acid sequence may comprise bases 2671 to 3020 of SEQ ID NO: 130, and a probe typically comprises or is complementary to at least one nucleic acid sequence having at least 80% sequence identity to a nucleic acid sequence from this target sequence.

In embodiments wherein the one or more biomarker for TB is CD52, a target nucleic acid sequence may comprise bases 51 to 450 of SEQ ID NO: 131, and a probe typically comprises or is complementary to at least one nucleic acid sequence having at least 80% sequence identity to a nucleic acid sequence from this target sequence.

In embodiments wherein the one or more biomarker for TB is KLRA1, a target nucleic acid sequence may comprise bases 801 to 1310 of SEQ ID NO: 133, and a probe typically comprises or is complementary to at least one nucleic acid sequence having at least 80% sequence identity to a nucleic acid sequence from this target sequence.

In embodiments wherein the one or more biomarker for TB is DEFB128, a target nucleic acid sequence may comprise bases 11 to 270 of SEQ ID NO: 135, and a probe typically comprises or is complementary to at least one nucleic acid sequence having at least 80% sequence identity to a nucleic acid sequence from this target sequence.

In embodiments wherein the one or more biomarker for TB is IL8, a target nucleic acid sequence may comprise bases 241 to 1460 of SEQ ID NO: 136, and a probe typically comprises or is complementary to at least one nucleic acid sequence having at least 80% sequence identity to a nucleic acid sequence from this target sequence.

In embodiments wherein the one or more biomarker for TB is GBP1, a target nucleic acid sequence may comprise bases 2171 to 2800 of SEQ ID NO: 142, and a probe typically comprises or is complementary to at least one nucleic acid sequence having at least 80% sequence identity to a nucleic acid sequence from this target sequence.

In embodiments wherein the one or more biomarker for TB is IRF1, a target nucleic acid sequence may comprise bases 1411 to 2050 of SEQ ID NO: 141, and a probe typically comprises or is complementary to at least one nucleic acid sequence having at least 80% sequence identity to a nucleic acid sequence from this target sequence.

In embodiments wherein the one or more biomarker for TB is MMP9, a target nucleic acid sequence may comprise bases 1091 to 2190 of SEQ ID NO: 152, and a probe typically comprises or is complementary to at least one nucleic acid sequence having at least 80% sequence identity to a nucleic acid sequence from this target sequence.

In embodiments wherein the one or more biomarker for TB is CD96, a target nucleic acid sequence may comprise bases 641 to 3760 of SEQ ID NO: 138, and a probe typically comprises or is complementary to at least one nucleic acid sequence having at least 80% sequence identity to a nucleic acid sequence from this target sequence.

In embodiments wherein the one or more biomarker for TB is AIM2, a target nucleic acid sequence may comprise bases 541 to 1060 of SEQ ID NO: 137, and a probe typically comprises or is complementary to at least one nucleic acid sequence having at least 80% sequence identity to a nucleic acid sequence from this target sequence.

In embodiments wherein the one or more biomarker for TB is CD274, a target nucleic acid sequence may comprise bases 541 to 1930 of SEQ ID NO: 138, and a probe typically comprises or is complementary to at least one nucleic acid sequence having at least 80% sequence identity to a nucleic acid sequence from this target sequence.

In embodiments wherein the one or more biomarker for TB is CDH23, a target nucleic acid sequence may comprise bases 9681 to 10990 of SEQ ID NO: 140, and a probe typically comprises or is complementary to at least one nucleic acid sequence having at least 80% sequence identity to a nucleic acid sequence from this target sequence.

In embodiments wherein the one or more biomarker for TB is IFIT3, a target nucleic acid sequence may comprise bases 1041 to 1830 of SEQ ID NO: 143, and a probe typically comprises or is complementary to at least one nucleic acid sequence having at least 80% sequence identity to a nucleic acid sequence from this target sequence.

In embodiments wherein the one or more biomarker for TB is IFITM3, a target nucleic acid sequence may comprise bases 211 to 580 of SEQ ID NO: 144, and a probe typically comprises or is complementary to at least one nucleic acid sequence having at least 80% sequence identity to a nucleic acid sequence from this target sequence.

In embodiments wherein the one or more biomarker for TB is GK, a target nucleic acid sequence may comprise bases 1251 to 1970 of SEQ ID NO: 145, and a probe typically comprises or is complementary to at least one nucleic acid sequence having at least 80% sequence identity to a nucleic acid sequence from this target sequence.

In embodiments wherein the one or more biomarker for TB is NELL2, a target nucleic acid sequence may comprise bases 2401 to 3110 of SEQ ID NO: 146, and a probe typically comprises or is complementary to at least one nucleic acid sequence having at least 80% sequence identity to a nucleic acid sequence from this target sequence.

In embodiments wherein the one or more biomarker for TB is S100A11, a target nucleic acid sequence may comprise bases 291 to 580 of SEQ ID NO: 147, and a probe typically comprises or is complementary to at least one nucleic acid sequence having at least 80% sequence identity to a nucleic acid sequence from this target sequence.

In embodiments wherein the one or more biomarker for TB is SAMD9L, a target nucleic acid sequence may comprise bases 461 to 3260 of SEQ ID NO: 148, and a probe typically comprises or is complementary to at least one nucleic acid sequence having at least 80% sequence identity to a nucleic acid sequence from this target sequence.

In embodiments wherein the one or more biomarker for TB is STAT1, a target nucleic acid sequence may comprise bases 2261 to 3170 of SEQ ID NO: 149, and a probe typically comprises or is complementary to at least one nucleic acid sequence having at least 80% sequence identity to a nucleic acid sequence from this target sequence.

In embodiments wherein the one or more biomarker for TB is TLR6, a target nucleic acid sequence may comprise bases 1751 to 2430 of SEQ ID NO: 150, and a probe typically comprises or is complementary to at least one nucleic acid sequence having at least 80% sequence identity to a nucleic acid sequence from this target sequence.

In embodiments wherein the one or more biomarker for TB is WARS, a target nucleic acid sequence may comprise bases 1801 to 2860 of SEQ ID NO: 151, and a probe typically comprises or is complementary to at least one nucleic acid sequence having at least 80% sequence identity to a nucleic acid sequence from this target sequence.

In embodiments wherein the one or more biomarker for TB is DOCKS, a target nucleic acid sequence may comprise bases 5791 to 6460 of SEQ ID NO: 153, and a probe typically comprises or is complementary to at least one nucleic acid sequence having at least 80% sequence identity to a nucleic acid sequence from this target sequence.

In embodiments wherein the one or more biomarker for TB is SIRPB2, a target nucleic acid sequence may comprise bases 741 to 1950 of SEQ ID NO: 154, and a probe typically comprises or is complementary to at least one nucleic acid sequence having at least 80% sequence identity to a nucleic acid sequence from this target sequence.

In embodiments wherein the one or more biomarker for TB is ANKRD22, a target nucleic acid sequence may comprise bases 981 to 1320 of SEQ ID NO: 155, and a probe typically comprises or is complementary to at least one nucleic acid sequence having at least 80% sequence identity to a nucleic acid sequence from this target sequence.

In embodiments wherein the one or more biomarker for TB is ABCF2, a target nucleic acid sequence may comprise bases 1741 to 2370 of SEQ ID NO: 156, and a probe typically comprises or is complementary to at least one nucleic acid sequence having at least 80% sequence identity to a nucleic acid sequence from this target sequence.

In embodiments wherein the one or more biomarker for TB is FNBP1L, a target nucleic acid sequence may comprise bases 4591 to 5220 of SEQ ID NO: 157, and a probe typically comprises or is complementary to at least one nucleic acid sequence having at least 80% sequence identity to a nucleic acid sequence from this target sequence.

In embodiments wherein the one or more biomarker for TB is NCF1C, a target nucleic acid sequence may comprise bases 461 to 940 of SEQ ID NO: 158, and a probe typically comprises or is complementary to at least one nucleic acid sequence having at least 80% sequence identity to a nucleic acid sequence from this target sequence.

In embodiments wherein the one or more biomarker for TB is TBC1D3B, a target nucleic acid sequence may comprise bases 1421 to 2090 of SEQ ID NO: 159, and a probe typically comprises or is complementary to at least one nucleic acid sequence having at least 80% sequence identity to a nucleic acid sequence from this target sequence.

In embodiments wherein the one or more biomarker for TB is SLC14A1, a target nucleic acid sequence may comprise bases 2031 to 2950 of SEQ ID NO: 160, and a probe typically comprises or is complementary to at least one nucleic acid sequence having at least 80% sequence identity to a nucleic acid sequence from this target sequence.

In embodiments wherein the one or more biomarker for TB is CALCOCO2, a target nucleic acid sequence may comprise bases 2601 to 3600 of SEQ ID NO: 161, and a probe typically comprises or is complementary to at least one nucleic acid sequence having at least 80% sequence identity to a nucleic acid sequence from this target sequence.

In embodiments wherein the one or more biomarker for TB is GTF2B, a target nucleic acid sequence may comprise bases 661 to 1160 of SEQ ID NO: 162, and a probe typically comprises or is complementary to at least one nucleic acid sequence having at least 80% sequence identity to a nucleic acid sequence from this target sequence.

In embodiments wherein the one or more biomarker for TB is HLA-B, a target nucleic acid sequence may comprise bases 961 to 1430 of SEQ ID NO: 163, and a probe typically comprises or is complementary to at least one nucleic acid sequence having at least 80% sequence identity to a nucleic acid sequence from this target sequence.

In embodiments wherein the one or more biomarker for TB is HLA-F, a target nucleic acid sequence may comprise bases 461 to 1520 of SEQ ID NO: 164, and a probe typically comprises or is complementary to at least one nucleic acid sequence having at least 80% sequence identity to a nucleic acid sequence from this target sequence.

In embodiments wherein the one or more biomarker for TB is MGST2, a target nucleic acid sequence may comprise bases 161 to 760 of SEQ ID NO: 165, and a probe typically comprises or is complementary to at least one nucleic acid sequence having at least 80% sequence identity to a nucleic acid sequence from this target sequence.

In embodiments wherein the one or more biomarker for TB is SPAST, a target nucleic acid sequence may comprise bases 701 to 1770 of SEQ ID NO: 166, and a probe typically comprises or is complementary to at least one nucleic acid sequence having at least 80% sequence identity to a nucleic acid sequence from this target sequence.

In embodiments wherein the one or more biomarker for TB is WAC, a target nucleic acid sequence may comprise bases 2011 to 3590 of SEQ ID NO: 167, and a probe typically comprises or is complementary to at least one nucleic acid sequence having at least 80% sequence identity to a nucleic acid sequence from this target sequence.

It is preferred that the binding conditions for a probe hybridising to its target sequence are such that a high level of specificity is provided—i.e. hybridisation of the probe occurs under "stringent conditions". In general, stringent conditions are selected to be about 5° C. lower than the thermal melting point (Tm) for the specific sequence at a defined ionic strength and pH. The Tm is the temperature (under defined ionic strength and pH) at which 50% of the target (or complement) sequence hybridises to a perfectly matched probe. In this regard, the Tm of probes of the present invention, at a salt concentration of about 0.02M or less at pH 7, is for example above 60° C., such as about 70° C.

Premixed buffer solutions are commercially available (e.g. EXPRESSHYB Hybridisation Solution from CLONTECH Laboratories, Inc.), and hybridisation can be performed according to the manufacturer's instructions.

Probes of the present invention may be screened to minimise self-complementarity and dimer formation (probe-probe binding).

Any of the probes described herein may comprise a tag and/or label. The tag and/or label may, for example, be located (independently of one another) towards the middle or towards or at the 5' or 3' end of the herein described probes, for example at the 5' end.

Hence, following hybridisation of tagged/labelled probe to target nucleic acid, the tag/label is associated with the target nucleic acid in the one or more biomarker. Alternatively, if an amplification step is employed, the probes may act as primers during the method of the invention and the tag/label may therefore become incorporated into the amplification product as the primer is extended.

Examples of suitable labels include detectable labels such as radiolabels or fluorescent or coloured molecules, enzymatic markers or chromogenic markers—e.g. dyes that produce a visible colour change upon hybridisation of the probe. By way of example, the label may be digoxygenin, fluorescein-isothiocyanate (FITC), R-phycoerythrin, Alexa 532 or Cy3. The probes preferably contain a Fam label (e.g. a 5' Fam label), and/or a minor groove binder (MGB). The label may be a reporter molecule, which is detected directly, such as by exposure to photographic or X-ray film. Alternatively, the label is not directly detectable, but may be detected indirectly, for example, in a two-phase system. An example of indirect label detection is binding of an antibody to the label.

Examples of suitable tags include "complement/anti-complement pairs". The term "complement/anti-complement pair" denotes non-identical moieties that form a non-covalently associated, stable pair under appropriate conditions. Examples of suitable tags include biotin and streptavidin (or avidin). By way of example, a biotin tag may be captured using streptavidin, which may be coated onto a substrate or support such as a bead (for example a magnetic bead) or membrane. Likewise, a streptavidin tag may be captured using biotin, which may be coated onto a substrate or support such as a bead (for example a magnetic bead) or membrane. Other exemplary complement/anti-complement pairs include receptor/ligand pairs, antibody/antigen (or hapten or epitope) pairs, and the like. Another example is a nucleic acid sequence tag that binds to a complementary sequence. The latter may itself be pre-labelled, or may be attached to a surface (e.g. a bead) which is separately labelled. An example of the latter embodiment is the well-known LuminexR bead system. Other exemplary pairs of tags and capture molecules include receptor/ligand pairs and antibody/antigen (or hapten or epitope) pairs. Where subsequent dissociation of the complement/anti-complement pair is desirable, the complement/anti-complement pair has a binding affinity of, for example, less than $10^9$ $M^{-1}$. One exemplary tagged probe is a biotin-labelled probe, which may be detected using horse-radish peroxidase conjugated streptavidin.

The probes of the invention may be labelled with different labels or tags, thereby allowing separate identification of each probe when used in the method of the present invention.

Any conventional method may be employed to attach nucleic acid tags to a probe of the present invention (e.g. to the 5' end of the defined binding region of the probe). Alternatively, nucleic acid probes of the invention (with pre-attached nucleic acid tags) may be constructed by commercial providers.

If an amplification step is employed, this step may be carried out using methods and platforms known in the art, for example PCR (for example, with the use of "Fast DNA Polymerase", Life Technologies), such as real-time PCR, block-based PCR, ligase chain reaction, glass capillaries, isothermal amplification methods including loop-mediated isothermal amplification, rolling circle amplification transcription mediated amplification, nucleic acid sequence-based amplification, signal mediated amplification of RNA technology, strand displacement amplification, isothermal multiple displacement amplification, helicase-dependent amplification, single primer isothermal amplification, and circular helicase-dependent amplification. If employed, amplification may be carried using any amplification platform.

A general amplification step (e.g. pre-detection) may be employed to increase the amount of the one or more biomarker of the invention present in the sample. PCR amplification primers are typically employed to amplify approximately 100-400 base pair regions of the target/complementary nucleic acid that contain the nucleotide targets of the present invention. In the presence of a suitable polymerase and DNA precursors (dATP, dCTP, dGTP and dTTP), forward and reverse primers are extended in a 5' to 3' direction, thereby initiating the synthesis of new nucleic acid strands that are complementary to the individual strands of the target nucleic acid. The primers thereby drive amplification of target nucleic acid sequences in the one or more biomarker, thereby generating amplification products comprising said target nucleic acid sequences.

An amplification step may be employed in which the probes of the present invention act as primers. In this embodiment, the probes (acting as primers) are extended from their 3' ends (i.e. in a 5'-to-'3') direction. Such an amplification step may be employed in conjunction with a general amplification step, such as the one described above.

The detection step may be carried out by any known means. In this regard, the probe or amplification product may be tagged and/or labelled, and the detection method may therefore comprise detecting said tag and/or label.

In one embodiment, the probe(s) may comprise a tag and/or label. Thus, in one embodiment, following hybridisation of tagged/labelled probe to target nucleic acid in the one or more biomarker, the tag/label becomes associated with the target nucleic acid. Thus, in one embodiment, the assay may comprise detecting the tag/label and correlating presence of tag/label with presence of the one or more nucleic acid biomarker of the invention.

In one embodiment, tag and/or label may be incorporated during extension of the probe(s). In doing so, the amplification product(s) become tagged/labelled, and the assay may therefore comprise detecting the tag/label and correlating presence of tag/label with presence of amplification product, and hence the presence of one or more nucleic acid biomarker of the invention.

By way of example, in one embodiment, the amplification product may incorporate a tag/label (e.g. via a tagged/labelled dNTP such as biotin-dNTP) as part of the amplification process, and the assay may further comprise the use of a binding partner complementary to said tag (e.g. streptavidin) that includes a detectable tag/label (e.g. a fluorescent label, such as R-phycoerythrin). In this way, the amplified product incorporates a detectable tag/label (e.g. a fluorescent label, such as R-phycoerythrin).

In one embodiment, the probe(s) and/or the amplification product(s) may include a further tag/label (as the complement component) to allow capture of the amplification product(s).

By way of example, a "complement/anti-complement" pairing may be employed in which an anti-complement capture component binds to said further tag/label (complement component) and thereby permits capture of the probe(s) and/or amplification product(s). Examples of suitable "complement/anti-complement" partners have been described earlier in this specification, such as a complementary pair of nucleic acid sequences, a complementary antibody-antigen pair, etc. The anti-complement capture component may be attached (e.g. coated) on to a substrate or solid support—examples of suitable substrates/supports include membranes and/or beads (e.g. a magnetic or fluorescent bead). Capture methods are well known in the art. For example, LuminexR beads may be employed. Alternatively, the use of magnetic beads may be advantageous because the beads (plus captured, tagged/labelled amplification product) can easily be concentrated and separated from the sample, using conventional techniques known in the art.

Immobilisation provides a physical location for the anti-complement capture component (or probes), and may serve to fix the capture component/probe at a desired location and/or facilitate recovery or separation of probe. The support may be a rigid solid support made from, for example, glass, plastic or silica, such as a bead (for example a fluorescent or magnetic bead). Alternatively, the support may be a membrane, such as nylon or nitrocellulose membrane. 3D matrices are also suitable supports for use with the present invention—e.g. polyacrylamide or PEG gels. Immobilisation to a support/platform may be achieved by a variety of conventional means. By way of example, immobilisation onto a support such as a nylon membrane may be achieved by UV cross-linking. Alternatively, biotin-labelled molecules may be bound to streptavidin-coated substrates (and vice-versa), and molecules prepared with amino linkers may be immobilised on to silanised surfaces. Another means of immobilisation is via a poly-T tail or a poly-C tail, for example at the 3' or 5' end. Said immobilisation techniques apply equally to the probe component (and primer pair component, if present) of the present invention.

In one embodiment, the probes of the invention comprise a nucleic acid sequence tag/label (e.g. attached to each probe at the 5' end of the defined sequence of the probe that binds to target/complement nucleic acid). In more detail, each of the probes is provided with a different nucleic acid sequence tag/label, wherein each of said tags/labels (specifically) binds to a complementary nucleic acid sequence present on the surface of a bead. Each of the different tags/labels binds to its complementary sequence counterpart (and not to any of the complementary sequence counterparts of the other tags), which is located on a uniquely identifiable bead. In this regard, the beads are uniquely identifiable, for example by means of fluorescence at a specific wavelength. Thus, in use, probes of the invention bind to target nucleic acid (if present in the sample). Thereafter, (only) the bound probes may be extended (in the 3' direction) in the presence of one or more labelled dNTP (e.g. biotin labelled dNTPs, such as biotin-dCTPs).

The extended primers may be contacted with a binding partner counterpart to the labelled dNTPs (e.g. a streptavidin labelled fluorophore, such as streptavidin labelled R-phycoerythrin), which binds to those labelled dNTPs that have become incorporated into the extended primers. Thereafter, the labelled extended primers may be identified by allowing them to bind to their nucleic acid counterparts present on the uniquely identifiable beads. The latter may then be "called" (e.g. to determine the type of bead present by wavelength emission) and the nature of the primer extension (and thus the type of target/complement nucleic acid present) may be determined.

Typically, probes of the invention are oligonucleotides having sequence identity with a region of the one or more biomarker of the invention as disclosed herein. One or more probe may be immobilised on a solid support, and used to interrogate mRNA obtained from a test sample. If the mRNA from the test sample contains the one or more biomarker targeted by the immobilised probe, it will bind to the probe, and may then be detected. The biomarkers of the invention may also be detected using PCR, such as real time PCR.

Any oligonucleotide with the appropriate level of sequence identity with the one or more biomarker of the invention, or with one or more target sequences within said one or more biomarker of the invention may be used as a probe as described herein. Any oligonucleotide with the appropriate level of complementarity with the one or more biomarker of the invention, or with one or more target sequences within said one or more biomarker of the invention may be used as a probe as described herein. Exemplary sequences of the one or more biomarkers of the invention are given in SEQ ID NOs: 112 to 167 (see Tables 2 to 5 herein). Sequences of exemplary target regions within the one or more biomarkers of the invention are shown as underlined in the sequences of the Sequence Information section (as discussed herein). Exemplary probe nucleic acid sequences for the biomarkers disclosed herein are set out in Table 6 (SEQ ID NOs: 1 to 111 and 168 to 171) and are shown as double-underlined in the sequences of the Sequence Information section.

In embodiments wherein the one or more biomarker for TB is LOC400759/GBP1P1, the oligonucleotide probe typically comprises or is complementary to a nucleic acid sequence having at least 80% sequence identity to the nucleic acid sequence of SEQ ID NO: 1, 2 or 3.

In embodiments wherein the one or more biomarker for TB is PF4V1, the oligonucleotide probe typically comprises or is complementary to at least one nucleic acid sequence having at least 80% sequence identity to the nucleic acid sequence of SEQ ID NOs: 4 or 5.

In embodiments wherein the one or more biomarker for TB is ALPK1, the oligonucleotide probe typically comprises or is complementary to at least one nucleic acid sequence having at least 80% sequence identity to the nucleic acid sequence of SEQ ID NOs: 6 or 7.

In embodiments wherein the one or more biomarker for TB is HERC2, the oligonucleotide probe typically comprises or is complementary to at least one nucleic acid sequence having at least 80% sequence identity to the nucleic acid sequence of SEQ ID NOs: 8, 9 or 168 to 171.

In embodiments wherein the one or more biomarker for TB is LGALS3BP, the oligonucleotide probe typically comprises or is complementary to at least one nucleic acid sequence having at least 80% sequence identity to the nucleic acid sequence of SEQ ID NOs: 10 or 11.

In embodiments wherein the one or more biomarker for TB is BST1, the oligonucleotide probe typically comprises or is complementary to at least one nucleic acid sequence having at least 80% sequence identity to the nucleic acid sequence of SEQ ID NOs: 12 or 13.

In embodiments wherein the one or more biomarker for TB is SNX10, the oligonucleotide probe typically comprises or is complementary to at least one nucleic acid sequence having at least 80% sequence identity to the nucleic acid sequence of SEQ ID NOs: 14 or 15.

In embodiments wherein the one or more biomarker for TB is CREG1, the oligonucleotide probe typically comprises or is complementary to at least one nucleic acid sequence having at least 80% sequence identity to the nucleic acid sequence of SEQ ID NOs: 16 or 17.

In embodiments wherein the one or more biomarker for TB is BAZ1A, the oligonucleotide probe typically comprises or is complementary to at least one nucleic acid sequence having at least 80% sequence identity to the nucleic acid sequence of SEQ ID NOs: 18 or 19.

In embodiments wherein the one or more biomarker for TB is LYN, the oligonucleotide probe typically comprises or is complementary to at least one nucleic acid sequence having at least 80% sequence identity to the nucleic acid sequence of SEQ ID NOs: 20 or 21.

In embodiments wherein the one or more biomarker for TB is TAPBP, the oligonucleotide probe typically comprises or is complementary to at least one nucleic acid sequence having at least 80% sequence identity to the nucleic acid sequence of SEQ ID NOs: 22 or 23.

In embodiments wherein the one or more biomarker for TB is SERPINB1, the oligonucleotide probe typically comprises or is complementary to at least one nucleic acid sequence having at least 80% sequence identity to the nucleic acid sequence of SEQ ID NOs: 24 or 25.

In embodiments wherein the one or more biomarker for TB is PSMB9, the oligonucleotide probe typically comprises or is complementary to at least one nucleic acid sequence having at least 80% sequence identity to the nucleic acid sequence of SEQ ID NOs: 26 or 27.

In embodiments wherein the one or more biomarker for TB is WSB1, the oligonucleotide probe typically comprises or is complementary to at least one nucleic acid sequence having at least 80% sequence identity to the nucleic acid sequence of SEQ ID NOs: 28 or 29.

In embodiments wherein the one or more biomarker for TB is MVP, the oligonucleotide probe typically comprises or is complementary to at least one nucleic acid sequence having at least 80% sequence identity to the nucleic acid sequence of SEQ ID NOs: 30 or 31.

In embodiments wherein the one or more biomarker for TB is APBB1IP, the oligonucleotide probe typically comprises or is complementary to at least one nucleic acid sequence having at least 80% sequence identity to the nucleic acid sequence of SEQ ID NOs: 32 or 33.

In embodiments wherein the one or more biomarker for TB is FYB, the oligonucleotide probe typically comprises or is complementary to at least one nucleic acid sequence having at least 80% sequence identity to the nucleic acid sequence of SEQ ID NOs: 34 or 35.

In embodiments wherein the one or more biomarker for TB is MB21D1/C6orf150, the oligonucleotide probe typically comprises or is complementary to at least one nucleic acid sequence having at least 80% sequence identity to the nucleic acid sequence of SEQ ID NOs: 36 or 37.

In embodiments wherein the one or more biomarker for TB is CPVL, the oligonucleotide probe typically comprises or is complementary to at least one nucleic acid sequence having at least 80% sequence identity to the nucleic acid sequence of SEQ ID NOs: 38 or 39.

In embodiments wherein the one or more biomarker for TB is TICAM2, the oligonucleotide probe typically comprises or is complementary to at least one nucleic acid sequence having at least 80% sequence identity to the nucleic acid sequence of SEQ ID NOs: 40 or 41.

In embodiments wherein the one or more biomarker for TB is CD52, the oligonucleotide probe typically comprises or is complementary to at least one nucleic acid sequence having at least 80% sequence identity to the nucleic acid sequence of SEQ ID NOs: 42 or 43.

In embodiments wherein the one or more biomarker for TB is KLRA1, the oligonucleotide probe typically comprises or is complementary to at least one nucleic acid sequence having at least 80% sequence identity to the nucleic acid sequence of SEQ ID NOs: 44 or 45.

In embodiments wherein the one or more biomarker for TB is DEFB128, the oligonucleotide probe typically comprises or is complementary to at least one nucleic acid sequence having at least 80% sequence identity to the nucleic acid sequence of SEQ ID NOs: 46 or 47.

In embodiments wherein the one or more biomarker for TB is IL8, the oligonucleotide probe typically comprises or is complementary to at least one nucleic acid sequence having at least 80% sequence identity to the nucleic acid sequence of SEQ ID NOs: 48 or 49.

In embodiments wherein the one or more biomarker for TB is GBP1, the oligonucleotide probe typically comprises or is complementary to at least one nucleic acid sequence having at least 80% sequence identity to the nucleic acid sequence of SEQ ID NOs: 50 or 51.

In embodiments wherein the one or more biomarker for TB is IRF1, the oligonucleotide probe typically comprises or is complementary to at least one nucleic acid sequence having at least 80% sequence identity to the nucleic acid sequence of SEQ ID NOs: 52 or 53.

In embodiments wherein the one or more biomarker for TB is MMP9, the oligonucleotide probe typically comprises or is complementary to at least one nucleic acid sequence having at least 80% sequence identity to the nucleic acid sequence of SEQ ID NOs: 54 or 55.

In embodiments wherein the one or more biomarker for TB is CD96, the oligonucleotide probe typically comprises or is complementary to at least one nucleic acid sequence having at least 80% sequence identity to the nucleic acid sequence of SEQ ID NOs: 56 or 57.

In embodiments wherein the one or more biomarker for TB is AIM2, the oligonucleotide probe typically comprises or is complementary to at least one nucleic acid sequence having at least 80% sequence identity to the nucleic acid sequence of SEQ ID NOs: 58 or 59.

In embodiments wherein the one or more biomarker for TB is CD274, the oligonucleotide probe typically comprises or is complementary to at least one nucleic acid sequence having at least 80% sequence identity to the nucleic acid sequence of SEQ ID NOs: 60 or 61.

In embodiments wherein the one or more biomarker for TB is CDH23, the oligonucleotide probe typically comprises or is complementary to at least one nucleic acid sequence having at least 80% sequence identity to the nucleic acid sequence of SEQ ID NOs: 62 or 63.

In embodiments wherein the one or more biomarker for TB is IFIT3, the oligonucleotide probe typically comprises or is complementary to at least one nucleic acid sequence having at least 80% sequence identity to the nucleic acid sequence of SEQ ID NOs: 64 or 65.

In embodiments wherein the one or more biomarker for TB is IFITM3, the oligonucleotide probe typically comprises or is complementary to at least one nucleic acid sequence having at least 80% sequence identity to the nucleic acid sequence of SEQ ID NOs: 66 or 67.

In embodiments wherein the one or more biomarker for TB is GK, the oligonucleotide probe typically comprises or is complementary to at least one nucleic acid sequence having at least 80% sequence identity to the nucleic acid sequence of SEQ ID NOs: 68 or 69.

In embodiments wherein the one or more biomarker for TB is NELL2, the oligonucleotide probe typically comprises or is complementary to at least one nucleic acid sequence having at least 80% sequence identity to the nucleic acid sequence of SEQ ID NOs: 70 or 71.

In embodiments wherein the one or more biomarker for TB is S100A11, the oligonucleotide probe typically comprises or is complementary to at least one nucleic acid sequence having at least 80% sequence identity to the nucleic acid sequence of SEQ ID NOs: 72 or 73.

In embodiments wherein the one or more biomarker for TB is SAMD9L, the oligonucleotide probe typically comprises or is complementary to at least one nucleic acid sequence having at least 80% sequence identity to the nucleic acid sequence of SEQ ID NOs: 74 or 75.

In embodiments wherein the one or more biomarker for TB is STAT1, the oligonucleotide probe typically comprises or is complementary to at least one nucleic acid sequence having at least 80% sequence identity to the nucleic acid sequence of SEQ ID NOs: 76 or 77.

In embodiments wherein the one or more biomarker for TB is TLR6, the oligonucleotide probe typically comprises or is complementary to at least one nucleic acid sequence having at least 80% sequence identity to the nucleic acid sequence of SEQ ID NOs: 78 or 79.

In embodiments wherein the one or more biomarker for TB is WARS, the oligonucleotide probe typically comprises or is complementary to at least one nucleic acid sequence having at least 80% sequence identity to the nucleic acid sequence of SEQ ID NOs: 80 or 81.

In embodiments wherein the one or more biomarker for TB is DOCK8, the oligonucleotide probe typically comprises or is complementary to at least one nucleic acid sequence having at least 80% sequence identity to the nucleic acid sequence of SEQ ID NOs: 82 or 83.

In embodiments wherein the one or more biomarker for TB is SIRPB2, the oligonucleotide probe typically comprises or is complementary to at least one nucleic acid sequence having at least 80% sequence identity to the nucleic acid sequence of SEQ ID NOs: 84 or 85.

In embodiments wherein the one or more biomarker for TB is ANKRD22, the oligonucleotide probe typically comprises or is complementary to at least one nucleic acid sequence having at least 80% sequence identity to the nucleic acid sequence of SEQ ID NOs: 86 or 87.

In embodiments wherein the one or more biomarker for TB is ABCF2 (NM_005692.3), the oligonucleotide probe typically comprises or is complementary to at least one nucleic acid sequence having at least 80% sequence identity to the nucleic acid sequence of SEQ ID NOs: 88 or 89.

In embodiments wherein the one or more biomarker for TB is FNBP1L, the oligonucleotide probe typically comprises or is complementary to at least one nucleic acid sequence having at least 80% sequence identity to the nucleic acid sequence of SEQ ID NOs: 90 or 91.

In embodiments wherein the one or more biomarker for TB is NCF1C, the oligonucleotide probe typically comprises or is complementary to at least one nucleic acid sequence having at least 80% sequence identity to the nucleic acid sequence of SEQ ID NOs: 92 or 93.

In embodiments wherein the one or more biomarker for TB is TBC1D3B, the oligonucleotide probe typically comprises or is complementary to at least one nucleic acid sequence having at least 80% sequence identity to the nucleic acid sequence of SEQ ID NOs: 94 or 95.

In embodiments wherein the one or more biomarker for TB is SLC14A1, the oligonucleotide probe typically comprises or is complementary to at least one nucleic acid sequence having at least 80% sequence identity to the nucleic acid sequence of SEQ ID NOs: 96 or 97.

In embodiments wherein the one or more biomarker for TB is CALCOCO2, the oligonucleotide probe typically comprises or is complementary to at least one nucleic acid sequence having at least 80% sequence identity to the nucleic acid sequence of SEQ ID NOs: 98 or 99.

In embodiments wherein the one or more biomarker for TB is GTF2B, the oligonucleotide probe typically comprises or is complementary to at least one nucleic acid sequence having at least 80% sequence identity to the nucleic acid sequence of SEQ ID NOs: 100 or 101.

In embodiments wherein the one or more biomarker for TB is HLA-B, the oligonucleotide probe typically comprises or is complementary to at least one nucleic acid sequence having at least 80% sequence identity to the nucleic acid sequence of SEQ ID NOs: 102 or 103.

In embodiments wherein the one or more biomarker for TB is HLA-F, the oligonucleotide probe typically comprises or is complementary to at least one nucleic acid sequence having at least 80% sequence identity to the nucleic acid sequence of SEQ ID NOs: 104 or 105.

In embodiments wherein the one or more biomarker for TB is MGST2, the oligonucleotide probe typically comprises or is complementary to at least one nucleic acid sequence having at least 80% sequence identity to the nucleic acid sequence of SEQ ID NOs: 106 or 107.

In embodiments wherein the one or more biomarker for TB is SPAST, the oligonucleotide probe typically comprises or is complementary to at least one nucleic acid sequence having at least 80% sequence identity to the nucleic acid sequence of SEQ ID NOs: 108 or 109.

In embodiments wherein the one or more biomarker for TB is WAC, the oligonucleotide probe typically comprises or is complementary to at least one nucleic acid sequence having at least 80% sequence identity to the nucleic acid sequence of SEQ ID NOs: 110 or 111.

Use of a Data Analysis Algorithm

In one embodiment, comparison of the one or more biomarker or the biomarker profile to a reference or control comprises applying a decision rule, or using a decision tree, as described herein. The decision rule or decision tree can comprise a data analysis algorithm, such as a computer pattern recognition algorithm. Other suitable algorithms include, but are not limited to, logistic regression or a nonparametric algorithm that detects differences in the distribution of feature values (e.g., a Wilcoxon Signed Rank Test). The decision rule may be based upon one, two, three, four, five, 10, 20 or more features. In one embodiment, the decision rule or decision tree is based on hundreds or more of features. Applying the decision rule or decision tree may also comprise using a classification tree algorithm. For example, the control or reference biomarker profile may comprise at least three features or biomarkers, where the features are predictors in a classification tree algorithm. The data analysis algorithm predicts membership within a population (or class) with an accuracy of at least about 60%, at least about 70%, at least about 80% and at least about 90%.

Suitable algorithms are known in the art, some of which are reviewed in Hastie et al, supra. Such algorithms classify complex spectra from biological materials, such as a blood sample, to distinguish individuals as normal or as possessing biomarker expression levels characteristic of a particular disease state. While such algorithms may be used to increase the speed and efficiency of the application of the decision rule and to avoid investigator bias, one of ordinary skill in the art will realize that computer-based algorithms are not required to carry out the methods of the present invention.

Algorithms may be applied to the comparison of the one or more biomarker or the biomarker profiles, regardless of the method that was used to generate the data for the one or more biomarker or the biomarker profile. For example, suitable algorithms can be applied to biomarker profiles generated using gas chromatography, as discussed in Harper, "*Pyrolysis and GC in Polymer Analysis*" Dekker, New York (1985). Further, Wagner et al, Anal Chem 74: 1824-35 (2002) disclose an algorithm that improves the ability to classify individuals based on spectra obtained by static time-of-flight secondary ion mass spectrometry (TOF-SIMS). Additionally, Bright et al, J. Microbiol Methods 48: 127-38 (2002) disclose a method of distinguishing between bacterial strains with high certainty (79-89% correct classification rates) by analysis of MALDI-TOF-MS spectra. Dalluge, Fresenius J. Anal. Chem. 366: 701-11 (2000) discusses the use of MALDI-TOF-MS and liquid chromatography-electrospray ionization mass spectrometry (LC/ESI-MS) to classify profiles of biomarkers in complex biological samples.

Methods of Diagnosis

As described herein, the present invention provides a method for diagnosing TB in an individual, comprising determining the presence and/or amount of one or more biomarker for TB in a sample obtained from the individual, wherein the one or more biomarkers is selected from SNX10, CPVL, PF4V1, HERC2, LGALS3BP, BST1, BAZ1A, LYN, SERPINB1, WSB1, MVP, APBB1IP, MB21D1/C6orf150, TICAM2, CD52, KLRA1, DEFB128 and IL8. Any combination of biomarkers as disclosed herein may be used in a method according to the present invention.

The method may comprising obtaining a first biomarker profile from a first sample taken from the individual at a single initial point in time and multiple time points thereafter to monitor the efficacy of treatment and disease resolution; and comparing said individual's first biomarker profile to a reference or control biomarker profile, wherein said comparison determines the status of TB infection in the individual with an accuracy, sensitivity and/or specificity of at least about 90%, at least about 80%, at least about 70% or at least about 60%; and wherein the biomarker profiles comprise determining the presence and/or amount of one or more biomarker of the invention. Typically the accuracy, sensitivity and/or specificity is of at least about 80% or at least about 90%.

The method may comprise obtaining a first biomarker profile from a first sample from the individual; and comparing the individual's first biomarker profile to a reference or control biomarker profile obtained from a reference or control population, said comparison being capable of classifying the individual as belonging to or not belonging to the reference or control population, wherein the comparison determines the status of TB infection in the individual, and wherein the biomarker profiles comprise determining the presence and/or amount of one or more biomarker of the invention.

The method may comprise comparing a measurable characteristic of at least three biomarkers of the invention between (i) a first biomarker profile obtained from a first sample from the individual and (ii) a biomarker profile obtained from samples from a control or reference population; and classifying the individual as belonging to or not belonging to the control or reference population, wherein the comparison determines the status of TB infection in the individual, and wherein the measurable characteristic optionally comprises the presence and/or amount of the biomarker.

The method may comprise selecting at least two features from a set of biomarkers of the invention in a first biomarker profile generated from a first sample of the individual; and comparing the at least two features to a set of the same biomarkers in a biomarker profile generated from samples from a control or reference population, wherein the comparison is capable of classifying the individual as belonging to or not belonging to the control reference population with an accuracy, sensitivity and/or specificity of at least about 90%, at least about 80%, at least about 70% or at least about 60%, wherein the comparison determines the status of TB in the individual, and wherein the feature optionally comprises the presence and/or amount of the biomarker. Typically the accuracy, sensitivity and/or specificity is of at least about 80% or at least about 90%.

The method may comprise determining an abundance or a change in an abundance of at least three biomarkers contained in a first biomarker profile obtained from a first biological sample of the individual; and (b) comparing the abundance or the change in the abundance to an abundance or change in an abundance of said at least three biomarkers contained in biological samples from a control or reference population, wherein the comparison is capable of classifying the individual as belonging to or not belonging to the control or reference population; and wherein the comparison determines the status of TB in the individual.

The method may further comprise obtaining a second biomarker profile from a second sample taken from the individual; and comparing the individual's second biomarker profile to the control or reference biomarker profile; wherein the individual's second biomarker profile and the control or reference biomarker profile comprise features that are measurable characteristics of a biomarker of the invention, wherein the second comparison is capable of classifying the individual as belonging to or not belonging to the control or reference population, and wherein the second comparison determines the status TB infection in the individual. The biomarker profiles optionally comprise one or more of the biomarkers of the present invention, and the measurable characteristic optionally comprises the presence and/or amount of one or more biomarker of the invention.

The methods of the invention may be repeated at least once, at least twice, at least three times, at least four times, at least five times, or more. A separate biomarker profile can be obtained from the individual from a separate sample taken each time the method is repeated.

The methods of the invention may be used to diagnose, detect and/or predict TB, TB infection and/or infection with *M. tuberculosis*. The methods of the invention may be used to distinguish between active and latent TB, a TB infection and/or infection with *M. tuberculosis*. The methods of the invention may be used to distinguish between latent TB and the absence of TB. The methods of the invention may be used to identify an individual with an active TB infection and/or a latent TB infection. The methods of the invention may be used to identify an individual with an active TB infection and/or a latent TB infection and/or an individual uninfected with TB. The methods of the invention may be used to identify an individual with an early stage active TB infection and/or a late/later stage active TB infection. The methods of the invention may be used to distinguish between an early stage active TB infection and/or a late/later stage active TB infection. The methods of the invention may also be used to determine the status of TB, a TB infection and/or infection with *M. tuberculosis* in an individual. Determining the status of TB, a TB infection and/or infection with *M. tuberculosis* in an individual may comprise determining the progression or resolution of TB, a TB infection and/or infection with *M. tuberculosis* in the individual. Determining the status of TB, a TB infection and/or infection with *M. tuberculosis* in an individual may comprise determining the presence of active or latent TB, a TB infection and/or infection with *M. tuberculosis* in an individual. The methods of the invention may be used to determine whether an individual has been exposed to TB.

The methods of the invention may comprise applying a decision rule as described herein. Applying the decision rule may comprise using a data analysis algorithm, also as described herein. The data analysis algorithm may comprise at least two, at least three, at least four, at least five, at least six, at least seven, at least eight, at least nine, at least ten, at least 15, at least 20, at least 25, at least 50 or more input parameters. The data analysis algorithm may use any of the biomarkers of the invention, or combination of biomarkers of the invention as input parameters. Typically, the data analysis algorithm uses at least two, at least three, at least four, at least five, at least six, at least seven, at least eight, at least nine, at least ten, at least 15, at least 20, at least 25, at least 50 of the biomarkers of the invention (e.g. as listed in any one of Tables 2 to 5) as input parameters.

In a preferred embodiment, the features and/or biomarkers profile used in the methods of the invention are the one or more biomarkers of the present invention, as described herein, and preferably the methods relate to determining the presence and/or amount of the one or more biomarker. Similarly, the "measurable characteristic" in a method of the invention may be any quantitative or qualitative characteristic associated with one or more biomarker of the invention, and is preferably the presence and/or amount of said biomarker.

In a more preferred embodiment, the one or more biomarker of the invention is nucleic acids, selected from DNA or RNA, typically mRNA. The biomarker profile may comprise any measurable aspect of said nucleic acid biomarker, and is typically a measurable characteristic of an mRNA biomarker, such as the presence and/or amount of said mRNA biomarker. The one or more biomarker of the invention and/or the biomarker may comprise a measurable aspect of a nucleic acid biomarker that encodes a protein that is informative of the state of the immune system in response to TB, a TB infection and/or infection with *M. tuberculosis* in an individual.

As described herein, a method of the invention may comprise fractionation of the sample prior to determining the presence and/or amount of the one or more biomarker of the invention, or obtaining a biomarker profile. Typically, the method comprises at least one, at least two, at least three, at least four, at least five, or more separation methods as described herein. The at least one separation method may be selected from inflammatory cell separation, chemical extraction partitioning, ion exchange chromatography, gel electrophoresis, and any combination thereof.

The invention also provides the use of one or more biomarker for TB as defined herein in the manufacture of a diagnostic for TB. Said diagnostic may be for diagnosing active TB and/or latent TB and/or the absence of TB.

Kits and Devices

The invention also provides kits and devices that are useful in determining the status of TB, diagnosing or detecting TB, distinguishing between active and latent TB in an individual, distinguishing between early stage active TB and late/later stage active TB and/or to determine whether an individual has been exposed to TB. The kits and devices of the present invention comprise at least one biomarker of the invention and/or one or more agent for the detection of or for the determination of the amount of the one or more biomarker of the invention. Specific biomarkers and agents for the detection of said biomarkers useful in the present invention are set forth herein. The biomarkers of the kit or device can be used to generate biomarker profiles according to the present invention.

Generally, the biomarkers of the kit or biomarker will bind, with at least some specificity, to the biomarker molecules contained in the sample from which the biomarker profile is generated. Examples of classes of compounds of the kit or device include, but are not to, proteins (including antibodies of the invention), and fragments thereof, peptides, polypeptides, proteoglycans, glycoproteins, lipoproteins, carbohydrates, lipids, nucleic acids, organic and inorganic chemicals, and natural and synthetic polymers. The biomarker(s) and/or agent(s) for the detection of the one or more biomarker may be part of an array, or the biomarker(s) and/or agent(s) may be packaged separately and/or individually. The biomarker(s) and/or agent(s) may be immobilised on an inert support.

The kit or device may also comprise at least one internal standard to be used in generating the biomarker profiles of the present invention. Likewise, the internal standards can be any of the classes of compounds described above.

The kits and devices of the present invention also may contain reagents that can be used to detectably label biomarkers contained in the biological samples from which the biomarker profiles are generated. For this purpose, the kit or device may comprise a set of antibodies or functional fragments thereof that specifically bind at least two, three, four, five, 10, 20, 30, 40, 50 or more, up to all 55 of the biomarkers set forth in any one of Tables 2 to 6 that list biomarkers for use in the invention. The antibodies themselves may be detectably labelled. The kit or device also may comprise a specific biomarker binding component, such as an aptamer.

In a preferred embodiment, a kit or device of the invention comprises (i) one or more antibody specific for the one or more biomarker for tuberculosis; or (ii) one or more oligonucleotide specific for the one or more biomarker for tuberculosis. In a more preferred embodiment, the one or more oligonucleotide specific for the one or more biomarker for tuberculosis is an oligonucleotide is an oligonucleotide of the invention, more preferably one or more of SEQ ID NOs: 1 to 111 or 168 to 171.

If the biomarkers comprise a nucleic acid, the kit or device may provide one or more oligonucleotide probe that is capable of forming a duplex with the one or more biomarker or with a complementary strand of said one or more biomarker. The one or more oligonucleotide probe may be detectably labelled. Typically, the one or more oligonucleotide probe used in the methods of the invention is selected from one or more of the oligonucleotide described herein. In a preferred embodiment, the one or more oligonucleotide probe is selected from an oligonucleotide probe that comprises or is complementary to at least one nucleic acid sequence having at least 80% sequence identity to the nucleic acid sequence of any one or more of SEQ ID NOs: 1 to 111 or 168 to 171.

The kits and devices of the present invention may also include pharmaceutical excipients, diluents and/or adjuvants when the biomarker is to be used to raise an antibody. Examples of pharmaceutical adjuvants include, but are not limited to, preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid, and the like. It may also be desirable to include isotonic agents such as sugars, sodium chloride, and the like.

The Following Examples Illustrate the Invention

EXAMPLES

Example 1—TB-Specific Biomarker Identification

Naive Cynomologous macaques (*Macaca fascicularis*) aged between 2-4 yrs from two separate breeding colonies i.e. of Mauritian or Chinese origin, from established United Kingdom or Chinese breeding facilities were challenged with were challenged with live *M. tuberculosis* using aerosol challenge Erdman strain K 01. They were confirmed as naïve in terms of prior exposure to mycobacterial antigens (*M. tuberculosis* infection or environmental mycobacteria), by negative tuberculin test while in their original breeding colony and prior to the start of the study using the gamma interferon (IFN-$\gamma$)-based Primagam test kit (Biocor; CSL). All procedures involving animals were approved by the Ethical Review Committee of the Centre for Emergency Preparedness and Response, Salisbury, United Kingdom.

Mono-dispersed bacteria in particles were generated using a three-jet Collison nebulizer (BGI) and in conjunction with a modified Henderson apparatus, delivered to the nose of each sedated primate via a modified veterinary anaesthesia mask. The challenge was performed on sedated animals placed within a "head-out" plethysmography chamber (Buxco, Wilmington, N.C.), to enable the aerosol to be delivered simultaneously with the measurement of the respiration rate. None of the animals had been used previously for experimental procedures.

Whole heparinised blood was obtained at three independent time points prior to challenge and at one, two, four and six weeks post *M. tuberculosis* challenge. Within 1 hour of collection, 1 ml of blood from each animal was mixed with 5 ml of Erythrocyte Lysis (EL) Buffer (Qiagen) followed by incubation on ice for 10-15 min. Peripheral blood leukocytes (PBLs) were recovered from erythrocyte-lysed blood by centrifugation at 400×g for 10 min at 4° C. and re-suspended in a further 2 ml of EL buffer. PBLS were again recovered by centrifugation as described above and processed for recovery of total RNA.

One ml of TRIzol® was added to the PBL pellet and then total RNA was extracted from the lysed PBL pellet according to the manufacturer's instructions, using aqueous-phase separation with chloroform isoamyl alcohol and the precipitation using 2-isopropanol. Recovered, dried RNA pellets were re-suspended in 10 µl of diethylpyrocarbonate (DECP) water (Invitrogen), then concentration and purity (A260/A280 ratio ≥1.8) assessed by spectrophotometry using a NanoDrop™ ND-1000 spectrophotometer (Thermo Scientific). Genomic DNA was removed prior to its use in further procedures using the DNase I kit (Qiagen), according to the manufacturer's instructions. The GeniSphere SenseAmp RNA amplification kit according to manufacturer's instructions. The resulting amplified cRNA was purified using RNeasy® Min-Elute Cleanup kit (Qiagen), again according to the manufacturer's protocol. The cRNA concentration and purity (A260/A280 ratio ≥1.8) was then assessed by spectrophotometry using a NanoDrop™ ND-1000 spectrophotometer.

Total amplified cRNAs were then labelled with Cy3 and hybridised to replicate Operon Human Genome AROS V4.0 slides (n=3/sample/time point), using established protocols. The slides were air-dried and scanned using an Affymetrix 480 microarray scanner, at a gain threshold of 65. Feature extraction was then conducted using the microarray quantification package BlueFuse™ (BlueGnome ltd.). Raw data were then exported and hybridisation fluorescence intensities quantified using the software analysis program BlueFuse™, using default background subtraction and normalisation methods, to remove data generated from poor-quality spots, hybridisation artifacts. All raw data were then processed further using the microarray analysis package Genespring 12.5.

Data output files from BlueFuse were imported into GeneSpring 12.5 (GX12) for differential gene expression and statistical analysis. Raw data was normalized to the 50th percentile followed by median baseline transformed to the corresponding animal pre-bleed. This was conducted to normalise data across all time points and assess differential gene expression of each gene entity, relative to a baseline i.e. pre-bleed level of expression prior to M. tuberculosis challenge. The mean value across three replicate samples slides for each feature was used for further analysis. Data were assessed for quality, then filtered on gene expression where entities in at least 100 percent of samples and in any one out of one conditions had normalised expression values within the cut-off-10.699 to 7.037. Statistically significant features were identified using one-way ANOVA analysis across all entities and time points, using the Benjamini-Hochberg False Discovery Rate (BH-FDR) at a cut-off p<0.05. To identify temporally, differentially expressed entities between time-points post-infection, fold-change cut-off analysis was conducted, all against the pre-bleed condition and where the minimum number of pairs was equal to 1 out of the 4 condition pairs i.e. weeks 1, 2, 4 or 6 and using the default cut-off setting >2.0.

Data outputs were also analysed using Artificial Neural Network Analysis (ANN). Normalised expression data was analysed using ANN based data mining approach (Lancashire L J et al (2010), Breast Cancer Res Treat. February; 120(1):83-93). This approach comprised a supervised learning approach where the data for a given single probe was used to classify a known sample. The classifier consisted of a multi-layer perceptron ANN, where weights were updated by a back propagation algorithm (Rumelhart D E et al (1986) Nature 323: 533-536). The ANN architecture utilised a constrained architecture to prevent over-fitting, having only 2 hidden nodes in the hidden layer. ANN training incorporated Monte Carlo Cross Validation, where, the data was randomly divided into three subsets; 60% for training the classifier, 20% for testing (to assess model performance during the training process) and 20% for validation (to independently test the model on data completely blind to the model). This process of random sample cross validation was utilised to prevent over-fitting of the data and assess how well the model would perform on a blind data set. This random re-sampling and training process was repeated 50 times to generate predictions and associated error values for each sample with respect to the validation (blind) data. Probes were ranked in ascending order based on predictive error for test data from the Monte Carlo Cross validation. Significant hits were identified by cross-comparison between ANOVA p value-based (lowest to highest) and ANN test error-based ranked order lists (lowest to highest) and further filtered using the heat map and cluster functions in Genespring 12.0, using default settings. Highly significant biomarker datasets were refined by cross comparison of entity lists obtained using either one way ANOVA (P≥0.05) or ANN analysis (top one thousand entities ranked on average test error). Fifty-five biomarkers were selected for further progression from these gene lists.

All fifty-five biomarkers and individual smaller panels of up to ten biomarkers each were used to interrogate previously published human datasets using the cluster algorithm of GeneSpring 12.5, using the unsupervised hierarchical Euclidean clustering setting on conditions and entities. Small, select panels of biomarkers more amenable to use on point of care diagnostic platforms were identified which exhibited the best sensitivity and specificity in discriminating active Tuberculosis patients from Latent Tuberculosis and controls in one analysis and also in discrimination Latent Tuberculosis from uninfected controls in a second tier analysis. These are given below in Table 1.

All TB 55 Panel; all Biomarkers combined from Tables 2-5
Active TB 8 Panel; LOC400759, PF4V1, ALPK1, HERC2, IRF1, MMP9, GBP1, CD96
Latent TB 5 Panel; HERC2, KLRAP1, PF4V1, DEFB128, IL8

TABLE 1

Select Biomarkers for TB

| Data Set | Biomarker Panel | No. True Negatives | No. False Negatives | No. True Positives | No. False Positives | Sensitivity (%) | Specificity (%) |
|---|---|---|---|---|---|---|---|
| Human Dataset 1[a] | All TB 55 panel | 82 | 21 | 53 | 10 (9 Latent TB, 1 uninfected) | 84.1 | 79.6 |

TABLE 1-continued

Select Biomarkers for TB

| Data Set | Biomarker Panel | No. True Negatives | No. False Negatives | No. True Positives | No. False Positives | Sensitivity (%) | Specificity (%) |
|---|---|---|---|---|---|---|---|
| Human Dataset 2[b] | All TB 55 panel | 60 | 14 | 32 | 4 (all Latent TB) | 88.9 | 81.1 |
| Human Dataset 1[a] | Active TB 8 panel | 88 | 18 | 56 | 10 (9 Latent TB, 1 uninfected) | 84.8 | 83 |
| Human Dataset 2[b] | Active TB 8 panel | 62 | 16 | 30 | 2 (all Latent TB) | 93.75 | 79.5 |
| Human Dataset 1[a] | Latent TB 5 panel | 20 | 17 | 52 | 3 | 94.5 | 54.1 |

[a]Berry MPR. et al (2010) Nature 466(7309): 973-977
[b]Maertzdorf J et al (2011) PLoS One 6(10): e26938

Table 2 lists the genes newly identified as biomarkers for TB using the above methods. Also given are the sequence identifiers for the identified genes and an indication of whether expression of the various genes are up or down regulated in TB compared with a control/reference population, and in what cell types (all white blood cells in a sample, monocytes, neutrophils, CD4 positive T cells, CD8 positive T cells, etc.) the change was observed. Where more than one indication is given, the first listed is the most preferred.

TABLE 2

Biomarkers for TB

| Probe Number | Gene Symbol | SEQ ID NO: | Corrected P value NHP Dataset BH FDR | Cell Type |
|---|---|---|---|---|
| AA1 | LOC400759/ GBP1P1 (RP4-644F6.3) | 112/113 | 1.95E-20 | Mainly Monocytes↑/ Neutrophils↑ |
| AA2 | LGALS3BP | 114 | 7.46E-09 | All↑ |
| AB1 | BST1 | 115 | 2.05E-09 | Monocytes↑/ Neutrophils↑/ CD8 positive T cells (CD8↑ |
| AB2 | SNX10 | 116 | 8.02E-12 | Monocytes↑/ Neutrophils↑/ CD4 positive T cells(CD4)↑ |
| AC1 | ALPK1 | 117 | 1.33E-03 | Monocytes↑/ Neutrophils↑/ CD4↑ |
| AC2 | CREG1 | 118 | 1.52E-09 | Monocytes↑/ Neutrophils↑/ CD4↑ |
| AD1 | BAZ1A | 119 | 5.46E-04 | Monocytes↑/ Neutrophils↑ |
| AD2 | LYN | 120 | 3.14E-11 | Monocytes↑/ Neutrophils↑ |
| AD3 | TAPBP | 121 | 1.63E-04 | Monocytes↑/ Neutrophils↑ |
| AE1 | SERPINB1 | 122 | 1.61E-14 | Monocytes↑/ Neutrophils↑ |
| AE2 | PSMB9 | 123 | 9.98E-17 | All↑ |
| AE3 | WSB1 | 124 | 3.82E-04 | Monocytes↑/ Neutrophils↑ |
| AF1 | MVP | 125 | 3.49E-11 | Monocytes↑/ Neutrophils↑ |
| AF2 | APBB1IP | 126 | 1.21E-08 | Monocytes↑/ Neutrophils↑ |

TABLE 2-continued

Biomarkers for TB

| Probe Number | Gene Symbol | SEQ ID NO: | Corrected P value NHP Dataset BH FDR | Cell Type |
|---|---|---|---|---|
| AF3 | FYB | 127 | 3.09E-10 | All↑ |
| AG1 | MB21D1/ C6orf150 | 128 | 1.76E-02 | All↑ |
| AG2 | CPVL | 129 | 2.30E-15 | Monocytes↑/ CD4↑ |
| AG3 | TICAM2 | 130 | 5.98E-10 | Neutrophils↑ |
| AH1 | CD52 | 131 | 9.66E-04 | Monocytes↓/ Neutrophils↓ |
| AI1 | HERC2 | 132 | 2.07E-09 | Neutrophils↓ |
| AJ2 | KLRAP1 (KLRA1) | 133 | 7.81E-07 | CD4 & CD8 positive T cells (CD4, CD8)↑ |
| AK1 | PF4V1 | 134 | 4.37E-02 | Monocytes↑/ Neutrophils↓ |
| AL1 | DEFB128 | 135 | 7.22E-03 | CD8↑/ Monocytes↑ |
| AM1 | IL8 | 136 | | Neutrophils↓ |

Table 3 lists further biomarkers for TB. Also given are the sequence identifiers for the identified genes and an indication of whether expression of the various genes are up or down regulated in TB compared with a control/reference population, and in what cell types the change was observed. Where more than one indication is given, the first listed is the most preferred.

TABLE 3

Further Biomarkers for TB

| Probe Number | Gene Symbol | SEQ ID NO: | Corrected P value NHP Dataset BH FDR | |
|---|---|---|---|---|
| B1 | AIM2 | 137 | 4.63E-02 | Monocytes↑/ Neutrophil↑/ CD4↑ |
| B2 | CD274 | 138 | 8.31E-04 | All↑ |
| B3 | CD96 | 139 | 4.02E-04 | CD4 & CD8 positive T cells (CD4, CD8) ↑ |
| B4 | CDH23 | 140 | 8.26E-10 | CD8↑/ Neutrophils↓ |

TABLE 3-continued

Further Biomarkers for TB

| Probe Number | Gene Symbol | SEQ ID NO: | Corrected P value NHP Dataset BH FDR | |
|---|---|---|---|---|
| B5 | IRF1 | 141 | 2.36E−19 | Monocytes↑/Neutrophil↑ |
| B6 | GBP1 | 142 | 7.95E−06 | All↑ |
| B7 | IFIT3 | 143 | 7.13E−04 | All ↑ |
| B8 | IFITM3 | 144 | 8.38E−12 | Monocytes↑/Neutrophil↑/CD4↑ |
| B9 | GK | 145 | 3.50E−02 | Monocytes↑/Neutrophils↑/CD4↑ |
| B10 | NELL2 | 146 | 4.63E−04 | CD8 positive T cells (CD8)↓ |
| B11 | S100A11 | 147 | 7.31E−03 | CD4↑/CD8↑ |
| B12 | SAMD9L | 148 | 1.60E−04 | All↑ |
| B13 | STAT1 | 149 | 3.42E−05 | All↑ |
| B14 | TLR6 | 150 | 2.13E−03 | Monocytes↑/Neutrophils↑ |
| B15 | WARS | 151 | 2.43E−06 | Monocytes↑/Neutrophils↑/CD4↑ |
| B16 | MMP9 | 152 | 3.39E−01 | Monocytes↓/Neutrophils↓/CD8 positive T cells (CD8)↓ |
| B17 | DOCK9 | 153 | 1.43E−04 | CD4 & CD8 positive T cells (CD4, CD8)↓/Neutrophils↑ |
| B18 | SIRPB2 | 154 | 3.03E−01 | Monocytes↑ |
| B19 | ANKRD22 | 155 | | Monocytes↑/Neutrophils↑/CD4↑ |

Table 4 lists the genes identified as biomarkers for latent TB using the above methods. Also given are the sequence identifiers for the identified genes and an indication of whether expression of the various genes are up or down regulated in TB compared with a control/reference population, and in what cell types the change was observed. Where more than one indication is given, the first listed is the most preferred.

TABLE 4

Biomarkers for Latent TB

| Probe Number | Gene Symbol | SEQ ID NO: | Corrected P value NHP Dataset BH FDR | |
|---|---|---|---|---|
| C1 | ABCF2 (NM_005692.3) | 156 | 5.10E−03 | CD4 & CD8 positive T cells (CD4, CD8)↑/Monocytes↓/Neutrophils↓ |
| C2 | FNBP1L | 157 | 1.92E−04 | Neutrophils↑ |
| C3 | NCF1C | 158 | 3.60E−04 | Monocytes↑/Neutrophils↑/CD4↑ |
| C4 | TBC1D3B | 159 | 1.83E−03 | Neutrophils↓↑ (differing splice variants) |
| C5 | SLC14A1 | 160 | | Neutrophils↑ |

Table 5 lists further biomarkers for latent TB. Also given are the sequence identifiers for the identified genes and an indication of whether expression of the various genes are up or down regulated in TB compared with a control/reference population, and in what cell types the change was observed. Where more than one indication is given, the first listed is the most preferred.

TABLE 5

Further Biomarkers for TB

| Probe Number | Gene Symbol | SEQ ID NO: | Corrected P value NHP Dataset BH FDR | |
|---|---|---|---|---|
| D1 | CALCOCO2 | 161 | 1.77E−03 | Monocytes↑/Neutrophils ↑ |
| D2 | GTF2B | 162 | 2.68E−09 | Neutrophils↑ |
| D3 | HLA-B | 163 | 4.02E−11 | Neutrophils↑ |
| D4 | HLA-F | 164 | 3.23E−09 | Neutrophils↑ |
| D5 | MGST2 | 165 | 4.59E−08 | Neutrophils↑ |
| D6 | SPAST | 166 | 1.28E−02 | CD8 positive T cells (CD8)↓/Neutrophils↑ |
| D7 | WAC | 167 | 6.57E−10 | All↑/Neutrophils↑ |

Table 6 lists the various probes used to detect the various biomarkers of the invention

TABLE 6

Oligonucleotide probes

| Probe No. | Gene Symbol | Probes 1a & 1b | SEQ ID NO: | Probe 2 | SEQ ID NO: |
|---|---|---|---|---|---|
| AA1 | LOC40075/GBP1P1 | CAGGCCCAATGTGCCTCATTGAGAACACTAATGGGCG ACTGATGGCGAATCCAGAAGCTCTGAAGATCCT GAACAGCACCAAGTGGAACGTGTGAAAGCTGAGTCTG CACAGGCTTCAGCAAAAATGTTGCAGCAAATGC | 1<br><br>2 | CTTCTTCCCAGACTTTGTGTTGACACTGAGAGATTT CTAGCATTACAGAAAGCGCTTTTGGACAAAACTGT | 3 |
| AA2 | LGALS3BP | GCCTTTGGTCAAATATTCTTCTGATTACTTCCAAGCC CCCTCTGACTACAGATACTACCCCTACCAGTCC | 10 | CACCATTGCCTACGAAAACAAAGCCCTGATGCTCTG CGAAGGGCTCTTCGTGGCAGACGTCACCGATTTC | 11 |
| AB1 | BST1 | TGGGAAAATAGCCACCTCCTTGTTAACAGCTTTGCAG ACAACACCCGTCGTTTTATGCCCCTGAGCGATG | 12 | TAGTTCTGGGGTGATCCACGTCATGCTGAATGGTTC AGAGCCAACAGGAGCCTATCCCATCAAAGGTTTT | 13 |
| AB2 | SNX10 | AGTTCATGCCATCCAGGCATTTAAGAGCGATCCTCAT CCCTTCAGCAATATGTATTTGAGTTCACACTA | 14 | GATAACTAGGATAACTTGTTGCTTTGTTACCCAGCC TAATTGAAGAGTGGCAGAGGCTACTACAAAAAGC | 15 |

TABLE 6-continued

Oligonucleotide probes

| Probe No. | Gene Symbol | Probes 1a & 1b | SEQ ID NO: | Probe 2 | SEQ ID NO: |
|---|---|---|---|---|---|
| AC1 | ALPK1 | TTCCAGTGGGAGTTCTTGGGTTTCATTGCCGGGAAAG ATGAGGAAAGAGATCCTTGAGGCTCGCACCTTG | 6 | GTTCCTGTATGGGCTCGACGTCTCTGGAAAACTTCT GCAGGTCGCCAAAGGTCTCCACAAGTTGCAGCCA | 7 |
| AC2 | CREG1 | CCTGGTATTCTTTTATAAGTAAAGTTTACCCAGGCAT GGACCAGCTTCAGCCAGGGACAAAATCCCCTC | 16 | TGGTGCTTCTGAATAAATCTTGCCAAGATAGACAAA CAATGATGAAACTCAGATGGAGCTTCCTACTCAC | 17 |
| AD1 | BAZ1A | CACCCAGTAATGTGGACCAAGTTAGCACACCACCGGC TGCGAAAAAGTCACGAATCTGACTTTGTCCTTC | 18 | GAGTCATTGCCACAAAGTCAAGTGAACAGTCAAGAT CTGTAAATATTGCTTCAAAACTTTCTCTCCAAGA | 19 |
| AD2 | LYN | AAAAGTAACCATCACTGGTTGCACTTATGATTTCATG TGCGGGGATCATCTGCCGTGCCTGGATCCTGAA | 20 | TCTTCTATGAACACTGCTCAGACCTGCTAGACATGC CATAGGAGTGGCGTGCACATCTCTCTCTCTTCCA | 21 |
| AD3 | TAPBP | TCCACCGCCCCTCATGCCGCCCTTTGGAGGAAAGTGA AAGTGAAAGGAGGAAGAGGAGGCTTCATGGCTG | 22 | ACCTGCAAGGATTCAAAGAAGAAAGCAGAGTGAGGG CACTCACTGCCATCCTGTGGAAGCCACCATCATC | 23 |
| AE1 | SERPINB1 | ACAGCAGGCATCGCAACTTTCTGCATGTTGATGCCCG AAGAAAATTTCACTGCCGACCATCCATTCCTTT | 24 | ACATCCGATGCGTAGATTCTTGACCATGTAGTAATC TATAAAATTGCTATATCCTCCTGATAGCCATGGG | 25 |
| AE2 | PSMB9 | TGCCGGTGTGGACCATCGAGTCATCTTGGGCAATGAA CTGCCAAAATTCTATGATGAGTGAACCTTCCCC | 26 | AATAAACTCTCTAGGGCAAAACCTGGTATGGTCAT TGGGAAATGAGTGCTCAGGGAGATGGAGCTTAGG | 27 |
| AE3 | WSB1 | AGATGGTAAATACTGACTTACGAAAGTTGAATTGGGT GAGGCGGGCAAATCACCTGAGGTCAGCAGTTT | 28 | CGTATCGTATTTAGAAGATTCTGCCTTCCCTAGTAG TAGGGACTGACAGAATACACTTAACACAAACCTC | 29 |
| AF1 | MW | CTCAAGCTCCTGGAGACAACCACGTGGTGCCTGTACT GCGCTAACTCCTGATTAATACAATGGAAGTTTC | 30 | CTGGCTGAGGTGGAGGTGAAGAAGTTCAAGCAGATG ACAGAGGCCATAGGCCCCAGCACCATCAGGGACC | 31 |
| AF2 | APBB1IP | TGTGGCAAAGGCTGGACTTGCCTCTCGGTGGACAAAC TTGGGGACAGTCAATGCAGCTGCACCAGCTCAG | 32 | ATGAATGATAACAGCACAAAGTCACTGATGGTGGAT GAGCGGCAGCTGGCCCGAGATGTTCTGGACAACC | 33 |
| AF3 | FYB | AAATGGTTGGGCAGAACAGCAAGGGGTTCATATGGCT ATATTAAAACAACTGCTGTAGAGATTGACTATG | 34 | ATGGCTGCATCTATGACAATGACTAGCACTCAACTT TGGTCATTCTGCTGTGTTCATTAGGTGCCAATGT | 35 |
| AG1 | MB21D1/ C6orf150 | CGTATGTACCCAGAACCCTCAAGCAGTCAGTGGGAC CGCAAAGACCTGGGCCTCTGCTTTGATAACTGC | 36 | CCAAGAAGGCCTGCGCATTCAAAACTGGCTTTCAGC AAAAGTTAGGAAGCAACTACGACTAAAGCCATTT | 37 |
| AG2 | CPVL | ATATTCTGATCCCGAATCAATTATAGGGGCTATGCA GAATTCCTGTACCAAATTGGCTTGTTGGATGAG | 38 | TGTCACAAGTAACATGACCTTGCGTGACAGAGACTT CCCCTGGACCACAACGCTCTCCATGCTTTACATT | 39 |
| AG3 | TICAM2 | TATATACTAATAAAACATGAACTGCCCACTCTTCATG CCTGCCAAACTTGGGGCAATTGATGCTAAATGG | 40 | TTGTATATCCCCTACCAGTACCGGGATCTGCACACA TCTTTTTGCAGTTACCTCTTCATAGCCATGAACC | 41 |
| AH1 | CD52 | GTTGATGCCAGACATCACCAGGTTGTAGAAGTTGACA GGCAGTGCCATGGGGGCAACAGCCAAAATAGGG | 42 | CAATGCCATAATCCACCTCTTCTGCTTCAGTTGAGG TGACACGTCTCAGCCTTAGCCCTGTGCCCCTGA | 43 |
| AI1 | HERC2 | GATGTCGACTCCTTTGCTTCGGACTCTACACAAGATT ATTTAACAGGACACTAAGATGGGGAAACGTCCT CTGTGCAGTATGCGATGTTTTGTGGATGCAAAGACT TATTCCTGAGGGAATCGATATAGGGGAACCTCT CTGCTCAATGACTTTTGAGCAGCTGGATCTCCTGCTT CGGCAGGTGAGTGAGGGGATGGATGGTTCCGCG | 8 168 170 | GGTTGATAAGGATTTTATTCCTGGACTCATGTACAT CCGAGACAATGAAGCCACCTCAGAGGAGTTTGAA TGAGGAAGTGACACTTATACGCAAAGCTGATTTGGA GAACCATAATAAAGATGGAGGCTTCTGGACTGTG ACCAAAAAACACAATACCAGGCATACATTTGGCAGA ATAAATGAACCAGGTCAGTCTGCGGTATTTTGTG | 9 169 171 |
| AJ1 | KLRAP1 (KLRA1) | GCATTCAAACGTACAATTGTATCTGTGGGAAGAGAAT AGACTCTATTTTCTCTGATTCGGTGTGCGCCAA | 44 | ACTCTGTTTCTCAATGTTGGACCTAAGATATTGAAG ACAGGCTGGAGCCCAGAGCCTTCATTCAATCTCA | 45 |
| AK1 | PF4V1 | AGGAGATGCTGTTCTTGGCGTTGCTGCTCCTGCCAGT TGTGGTCGCCTTCGCCAGAGCTGAAGCTGAAGA | 4 | AGCTACTAGCTGCCTAAGTGTGCACTTTCAATCTAA CTGTGAAAGAATCTTCTGATGTTTGTATTATCCT | 5 |
| AL1 | DEFB128 | TGCTTCAATAAAGTAACAGGCTATTGCAGGAAGAAAT GCAAGGTAGGAGAAAGATATGAAATAGGATGTC | 46 | TGTGTCATTTAAGAAGCCACATCAACATTCTGGTGA GAAGCTGAGTGTGCTGCAGGATTACATCATCTTA | 47 |
| AM1 | IL8 | ATTTTAATTGAACTAACAATCCTAGTTTGATACTCCC AGTCTTGTCATTGCCAGCTGTGTTGGTAGTGCT | 48 | AAAGAACTGAGAGTGATTGAGAGTGGACCACACTGC GCCAACACAGAAATTATTGTAAAGCTTTCTGATG | 49 |
| B1 | AIM2 | TGTCCCGCTGAACATTATCAGAAAAGCTGGTGAAACC CCGAAGATCAACACGCTTCAAACTCAGCCCCTT | 58 | TAGCAAGATATTATCGGCACAGTGGTTTCTTAGAGG TAAATAGCGCCTCACGTGTGTTAGATGCTGAATC | 59 |
| B2 | CD274 | AGACCACCACCACCAATTCCAAGAGAGAGGAGAAGCT TTTCAATGTGACCAGCACACTGAGAATCAACAC | 60 | TAACCCATTAATACTCTGGTTGACCTAATCTTATTC TCAGACCTCAAGTGTCTGTGCAGTATCTGTTCCA | 61 |
| B3 | CD96 | TGCATGGTCGGTGGAAAACAGCAGCACGGATTCTTGG GTCCTTCTTTCTAAGGGTATAAAGGAGGATAAT | 56 | GGAGGTATTCACACTCAGGGTCATGCACTTGCACAA TGTTGAGAATGAGTACCACTCTCACCATTGGTAT | 57 |

TABLE 6-continued

Oligonucleotide probes

| Probe No. | Gene Symbol | Probes 1a & 1b | SEQ ID NO: | Probe 2 | SEQ ID NO: |
|---|---|---|---|---|---|
| B4 | CDH23 | ATCCCACTTTTGCCAGACGCTCATTCAGCATCTGACC TCTACCTTCATAAGATCTGTTATTTTTATAAGA | 62 | TGCTGAAGGTGGTCCTGGAGGATTACCTGCGGCTCA AAAAGCTCTTTGCACAGCGGATGGTGCAAAAAGC | 63 |
| B5 | IRF1 | ATCCCAGGGCTGGCTCTGCACTAAGAGAAAATTGCAC TAAATGAATCTCGTTCCCAAAGAACTACCCCCT | 52 | AGCCCTCAACAGGCCCAGGGAGGGAAGTGTGAGCGC CTTGGTATGACTTAAAATTGGAAATGTCATCTAA | 53 |
| B6 | GBP1 | AGCTGGTACCACTCAGGAGAAGTTTATTCTTCCAGAT GACCAGCAGTAGACAAATGGATACTGAGCAGAG | 50 | TCTCCAGAGGAAGGTGGAAGAAACCATGGGCAGGAG TAGGAATTGAGTGATAAACAATTGGGCTAATGAA | 51 |
| B7 | IFIT3 | GGGACTGAATCCTCTGAATGCATACTCCGATCTCGCT GAGTTCCTGGAGACGGAATGTTATCAGACACCA | 64 | GAGACAGAGGAGGAAAACAGAGCATCAGAAGCCTGC AGTGGTGGTTGTGACGGGTAGGACGATAGGAAGA | 65 |
| B8 | IFITM3 | AGGCCTATGCCTCCACCGCCAAGTGCCTGAACATCTG GCCCTGATTCTGGGCATCCTCATGACCATTCT | 66 | TGATCTTCCAGGCCTATGGATAGATCAGGAGGCATC ACTGAGGCCAGGAGCTCTGCCCATGACCTGTATC | 67 |
| B9 | GK | GACCAGCAACAAAATTCTTATGCAGCTACAAGCAGAC ATTCTGTATATACCAGTAGTGAAGCCCTCAATG | 68 | AACTCATGGATTCCCAAGATGTGAGCTTTTTACATA ATGAAAGAACCCAGCAATTCTGTCTCTTAATGCA | 69 |
| B10 | NELL2 | TTGATTGTTGGCCCCTGCCTTGCCCAGATGTGGAGTG TGAATTCAGCATTCTCCCAGAGAATGAGTGCTG | 70 | TACCGTGACATCCTGAACCCTGGATAGAAAGCCTGA GCCCATTGGATCTGTGAAAGCCTCTAGCTTCACT | 71 |
| B11 | S100A11 | CAGCCTTTCTGTCATCATCTCCACAGCCCACCCATCC CCTGAGCACACTAACCACCTCATGCAGGCCCCA | 72 | TTGGTGGCCTAGCTATGGCTTGCCATGACTCCTTCC TCAAGGCTGTCCCTTCCCAGAAGCGGACCTGAGG | 73 |
| B12 | SAMD9L | ATAACAGCAAGAGGGAACCTGGCAAGGAAGCTATTCC TATAATCCAGGAAAGAGATGAGGAAGGCTTGGA | 74 | ACTGGAAATCCTCTGTGAAAATGAGTGTACAGAGAC AGACATCGAGAAAGACAAATCTAAATTCCTGGAG | 75 |
| B13 | STAT1 | CCTGACATCATTCGCAATTACAAAGTCATGGCTGCTG AGAATATTCCTGAGAATCCCCTGAAGTATCTGT | 76 | GATACACCCAAAGTATCAGGACGAGAATGAGGGTCC TTTGGGAAAGGAGAAGTTAAGCAACATCTAGCAA | 77 |
| B14 | TLR6 | GACTGTGACCTCCCTCTGCATCTACTTGGATCTGCCC TGGTATCTCAGGATGGTGTGCCAGTGGACCCAG | 78 | ATTCCCAACAAGTACCACAAGCTGAAGGCTCTCATG ACGCAGCGGACTTATTTGCAGTGGCCCAAGGAGA | 79 |
| B15 | WARS | CCAAGGAGTCCTGGCCTCCGCAGATGCTTCATTTTGA CCCTTGGCTGCAGTGGAAGTCAGCACAGAGCAG | 80 | CCTGGCCTCTGTAAGCCTGTGTATGTTATCAATACT GTTTCTTCCTGTGAGTTCCATTATTTCTATCTCT | 81 |
| B16 | MMP9 | TACCACCTCGAACTTTGACAGCGACAAGAAGTGGGGC TTCTGCCCGGACCAAGGATACAGTTTGTTCCTC | 54 | TTCTACTGGCGCGTGAGTTCCCGGAGTGAGTTGAAC CAGGTGGACCAAGTGGGCTACGTGACCTATGACA | 55 |
| B17 | DOCK9 | GGAAGAGCAGTGCAAACGGCGCACCATCCTGACAGCC ATACACTGCTTCCCTTATGTGAAGAAGCGCATC | 82 | ACATCTTCAACGCCATCAGTGGGACTCCAACAAGCA CAATGGTTCACGGGATGACCAGCTCGTCTTCGGT | 83 |
| B18 | SIRPB2 | TTCTGCAAAACGTCTCCAGTGAGGATGCAGGCACCTA TTACTGTGTAAAGTTTCAGAGGAAACCCAACAG | 84 | TATTAGAATGCAGGTTCAGCAACTATAACAAAGCTC TTAAATAACAGTGGCTTAAACCAGTGGAAATCAA | 85 |
| B19 | ANKRD22 | AGACTTTTGGTCTGTGGGCCATTTAACCTGGATGCCA CCATTTTATGGGGATAATGATGCTTACCATGGT | 86 | TCAAGTTCACCATGGCCGTAATCCTTCTAAGGGAAA CACTAAAGTTGTTGTAGTCTCCACTTCAGTCAGA | 87 |
| C1 | ABCF2 | CATCATGAACTCGTTTGTAAACGACGTGTTTGAGCAG CTGGCGTGTGAGGCTGCCCGGCTGGCCCAGTAC | 88 | CAGCCATGACTTCAGACTCATTCAGCAGGTTGCACA GGAAATTTGGGTCTGTGAGAAGCAGACAATCACC | 89 |
| C2 | FNBP1L | TACTGCCTTCATAAGATCAAGTCACCACTGTTACACA GCTGACATATAGTGTATTACCTTTGCAGCTAGT | 90 | GGAGGAAATGTGATCTGGCTGTGTTTGTCTTCTGTA CAAAGCCTGAAGTGCTTATGGTTTTTTGGCTAAC | 91 |
| C3 | NCF1C | GGTGGTTCTGTCAGATGAAAGCAAAGCGAGGCTGGAT CCCAGCATCCTTCCTCGAGCCCCTGGACAGTCC | 92 | GACGTCACAGGCTACTTTCCGTCCATGTACCTGCAA AAGTCGGGGCAAGACGTGTCCCAGGCCCAACGCC | 93 |
| C4 | TBC1D3B | ACTGATTCCGACCAGGGCACCCCCTTCAGAGCTAGGG ACGAACAGCAGTATGCTCCCACCTCAGGGCCTT | 94 | AGGCTTCTAGAAGCATCTGGGCCAGGGCTCATGGCT GGATAATTTCCCTAGGCTTAACAACCCAAGCAAG | 95 |
| C5 | SLC14A1 | TGACATTCTCTCATGGGACAATGTTGGGGTTTTTCAG ACTGACAGGACTGCAAGAGGGAGAAAGGAATTT | 96 | TCACAATATTCTCTCAGAAATCAATGGCATTTGA ACCACCAAAAAGAAATAAAGGGCTGAGTGCGGTG | 97 |
| D1 | CALCOCO2 | CATTTTCTATCCCCTCAGGGACTGAACAAATGGAAAT AACTCCCAGGCAGTATCAGGTGGTCACTACAGA | 98 | CTGGGCTTTCCCTAATGTGGTTGGGAGTTATGCCCT AGACTAACTGTATTGTCCTAGTCACAGCTCCTTG | 99 |
| D2 | GTF2B | CGCTAGAAACCAGTGTGGATTTGATTACAACTGGGGA CTTCATGTCCAGGTTCTGTTCCAACCTTTGTCT | 100 | TCTCTGTGGCAGCGGCAGCTATTTACATGGCCTCAC AGGCATCAGCTGAAAAGAGGACCCAAAAAGAAAT | 101 |
| D3 | HLA-B | AGCTACTCTCAGGCTGCGTGCAGCGACAGTGCCCAGG GCTCTGATGTGTCTCTCACAGCTTGAAAAGCCT | 102 | GCATAATGTGAGGAGGTGGAGAGACAGCCCACCCTT GTGTCCACTGTGACCCCTGTTCCCATGCTGACCT | 103 |
| D4 | HLA-F | ATCACCCAGCGCGCTTCTATGAGGCAGAGGAATATGCAG AGGAGTTCAGGACCTACCTGGAGGGCGAGTGCC | 104 | GAGATCACGCTGACCTGGCAGCGGGATGGGGAGGAA CAGACCCAGGACACAGAGCTTGTGGAGACCAGGC | 105 |

TABLE 6-continued

Oligonucleotide probes

| Probe No. | Gene Symbol | Probes 1a & 1b | SEQ ID NO: | Probe 2 | SEQ ID NO: |
|---|---|---|---|---|---|
| D5 | MGST2 | TCACTGGGTCACCAGAGTTTGAGAGAGTATTTCGGGC ACAACAAAACTGTGTGGAGTTTTATCCTATATT | 106 | ACGGATCACCGGTTTCCGACTGAGTCTGGGGATTTT GGCCTTGTTGACCCTCCTAGGTGCCCTGGGAATT | 107 |
| D6 | SPAST | CACAAACGGACGTCTATAATGACAGTACTAACTTGGC ATGCCGCAATGGACATCTCCAGTCAGAAAGTGG | 108 | TTAGGAATGTGGACAGCAACCTTGCTAACCTTATAA TGAATGAAATTGTGGACAATGGAACAGCTGTTAA | 109 |
| D7 | WAC | GTTTTGTAGAGTGAAGCCATGGGAAGCCATGTGTAAC AGAGCTTAGACATCCAAAACTAATCAATGCTGA | 110 | GGTGCTGACTGCTGTTCTTAGCCATCACAAAACGCT AAATTTGTGTAATTGGAGCTTCCTGCTGTTATCT | 111 |

Example 2—TB-Specific Biomarker Identification in a Cohort of UK Controls, TB Test Negative Controls, TB Test Positive Suspected Latent TB, Early Active and Established Active TB Volunteers Whole blood samples were obtained from the following cohorts: (1) Caucasian controls-professional individuals recruited locally to the project team who constitute a low risk group, coming from non/low-TB endemic regions, such that their risk of having been exposed to TB is extremely low (CC); (2) Controls of Asian descent recruited from Hindu temples in London who tested negative for TB in skin and/or IFNγ tests and originate from high-incidence areas of TB (LC or NMRL CNTRL); (3) individuals of Asian descent recruited from Hindu temples in London and test positive for TB in Mantoux skin and/or IFNγ tests and diagnosed with latent TB (LTB or NMRL LTNT); (4) individuals with early stage active TB recruited at St. Thomas's and Royal Free hospitals in London (EATB); and (5) individuals of Asian descent recruited at the Jawaharlal Institute of Postgraduate Medical Education and Research (JIPMER), India, diagnosed with active TB (ATB).

Whole blood was obtained at a single time point in PaxGene or Tempus RNA stabilization tubes. Control and Latent TB Blood were collected using PaxGene tubes. Early Active and Active TB blood were collected using Tempus tubes. Blood collected in PaxGene tubes was mixed by inversion and incubated at Room Temperature (~25° C.) for 2 hours before storing at −80° C. Blood collected in Tempus tubes was vortexed at full speed for 10 seconds and then stored at −20/−80° C. RNA was extracted from these respective tubes according to the manufacturer's instructions. Concentration and purity (A260/A280 ratio ≥1.8) were assessed by spectrophotometry using a NanoDrop ND-1000 spectrophotometer. The purity of the extracted RNA was analysed using Agilent Bioanalyzer according to the manufacturer's instructions. cDNA was synthesized from the extracted RNA using the Roche Transcriptor First Strand cDNA Synthesis Kit according to the manufacturer's instructions.

Quantitative real-time PCR analyses were performed using the Roche Lightcycler (LC) 480 in 384 well plate format. The LC 480 is a plate-based, highly adaptable and versatile real-time PCR system used for gene expression analysis and has been designed for enhanced throughput and efficiency without compromising sensitivity and specificity. Roche provide an online 'target to assay' design and build system, the 'Realtime Ready configurator', which can be used to generate quantitative real-time PCR (qPCR) assays in a number of plate formats. Assays for the biomarker targets of interest were designed using this system and the assay plates configured, tested and quality assured by Roche. It uses a dual-colour assay, 165-FAM labelled Universal Probe Library (UPL) probe system and Roche provide all platform-specific dedicated reagents. Assay plates are dispatched in desiccated format, each well containing a target-specific primer pair and assay-specific human LC 480 Universal Probe Library (UPL) probe, coated in the bottom of each of the 384 wells.

All assays were performed using default protocols according to the manufacturer's instructions. Four human reference genes were used throughout, for quantifying the expression of genes of interest. In short, synthesized cDNA was mixed with Roche LC480 probes master mix at a constant dilution and pipetted into the 384 well assay plates using a Qiagility™ robotic pipetter. This reduced manual handling minimised pipetting errors and ensured reagent distribution uniformity throughout the plate wells. Data outputs were quantified using the Lightcycler 480 software and then expressed as a numeric figure of the ratio of the fold-change difference of the target vs the mean of all four reference genes. All raw data were then exported and processed further using the microarray analysis package Genespring GX 12.5 ((GX 12.5).

Data output files from BlueFuse were imported into GX 12.5 for differential gene expression and statistical analysis. Averaged data were imported without further normalisation and then baseline transformed to the median of all samples. Data were assessed for quality, then filtered on gene expression where entities in at least 100 percent of samples and in any one out of one conditions had normalised expression values within the cut-off 0 to 329.0 where at least 1 feature out of all samples had values within range. Statistically significant features were identified using one-way ANOVA analysis across all entities and time points at a cut-off $p<0.05$. To identify differentially expressed entities between the groups T-tests (unpaired, unequal variance) were performed on the samples arranged by group at a $p<0.05$ using the cut-off fold-change setting >1.2. The outputs were visualised using the boxplot graphical output facility.

Table 7 lists the genes newly identified as biomarkers for TB in Example 1 (see Table 2 above). Also given are the results of t-tests comparing the expression of a given marker between different test/control groups. The final two columns give ANOVA p values illustrating the significance of the biomarkers as determined using the qPCR technique.

Table 8 provides the results of the qPCR analysis of the human cohort samples using the further biomarkers for TB listed in Table 3 above. Also given are the results oft-tests comparing the expression of a given marker between different test/control groups. The final two columns give ANOVA p values illustrating the significance of the biomarkers as determined using the qPCR technique.

Table 9 provides the results of the qPCR analysis of the human cohort samples using the genes identified as biomarkers for latent TB in Example 1 (see Table 4 above). Also given are the results of t-tests comparing the expression of a given marker between different test/control groups. The final two columns give ANOVA p values illustrating the significance of the biomarkers as determined using the qPCR technique.

Table 10 provides the results of the qPCR analysis of the human cohort samples using the further biomarkers for latent TB listed in Table 5 above. Also given are the results of t-tests comparing the expression of a given marker between different test/control groups. The final two columns give ANOVA p values illustrating the significance of the biomarkers as determined using the qPCR technique.

Figure 2:
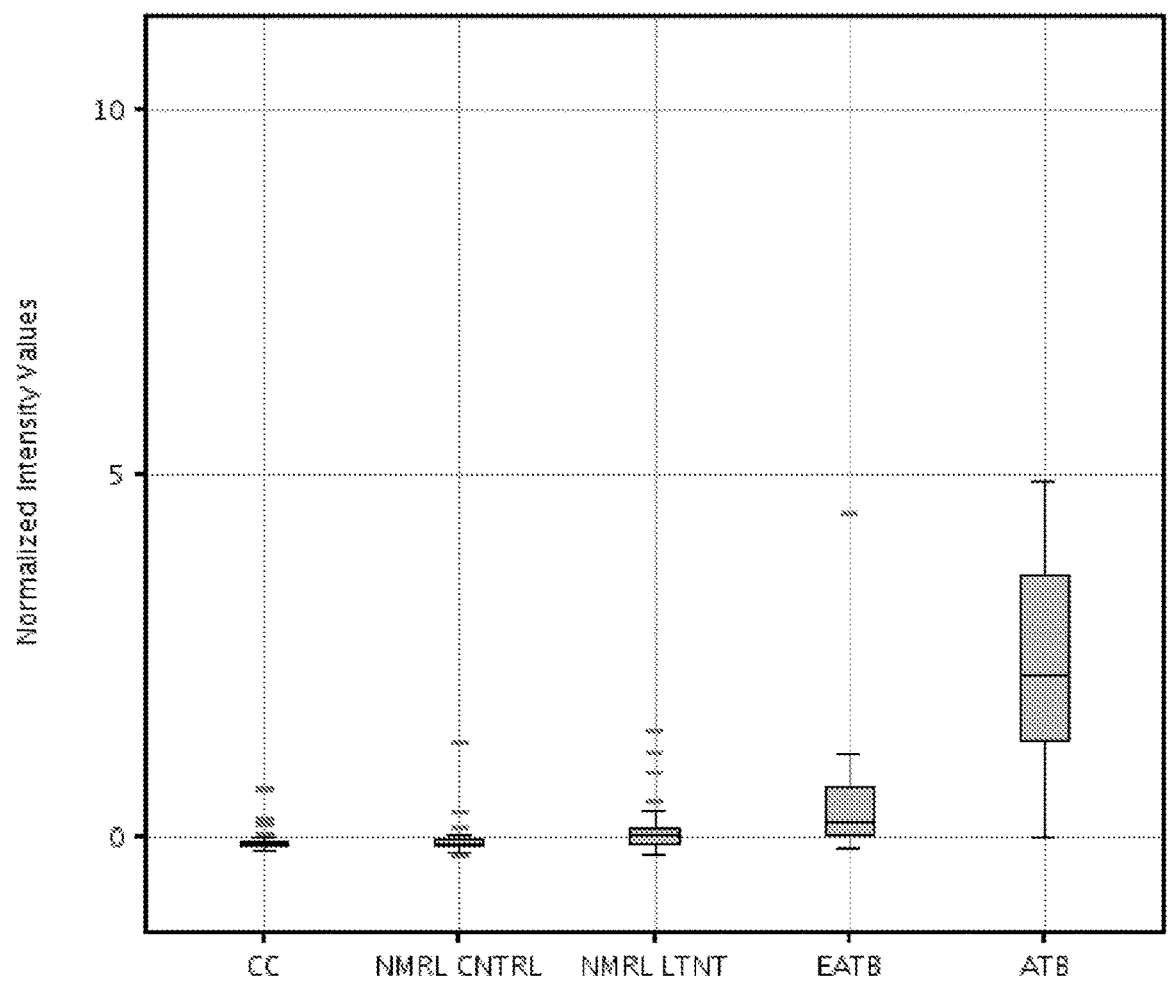
FIG. 2: shows a box plot of GBP1 normalised gene expression in CC, NMRL CNTRL, NMRL LTNT, EATB and ATB. The box represents highest and lowest gene expression interquartile range and median gene expression. The error bars represent minimum and maximum values. Grey bars represent outlier values.
Figure 3:
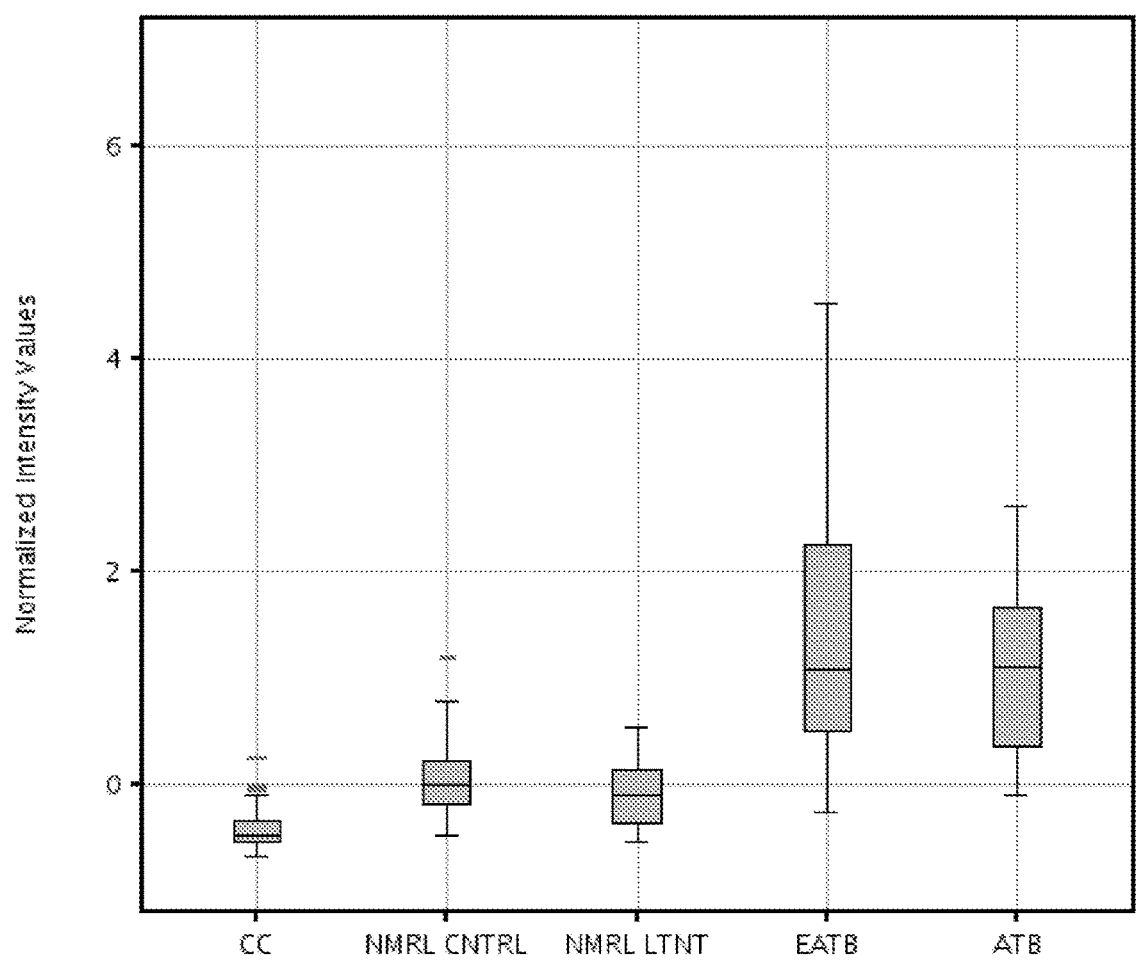
FIG. 3: shows a box plot of IRF1 normalised gene expression in CC, NMRL CNTRL, NMRL LTNT, EATB and ATB. The box represents highest and lowest gene expression interquartile range and median gene expression. The error bars represent minimum and maximum values. Grey bars represent outlier values.
Figure 4:
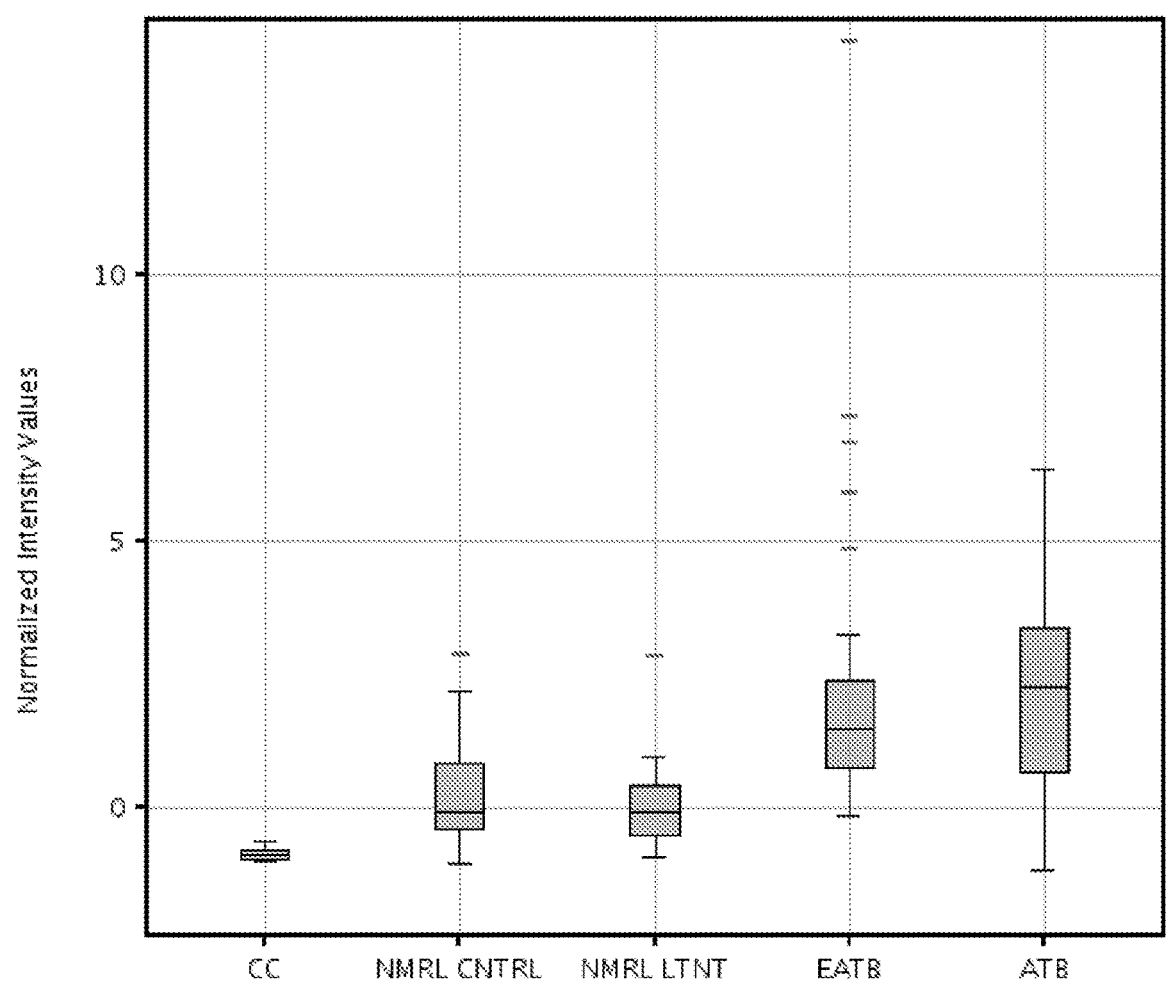
FIG. 4: shows a box plot of S100A11 normalised gene expression in CC, NMRL CNTRL, NMRL LTNT, EATB and ATB. The box represents highest and lowest gene expression interquartile range and median gene expression. The error bars represent minimum and maximum values. Grey bars represent outlier values.
Figure 5:
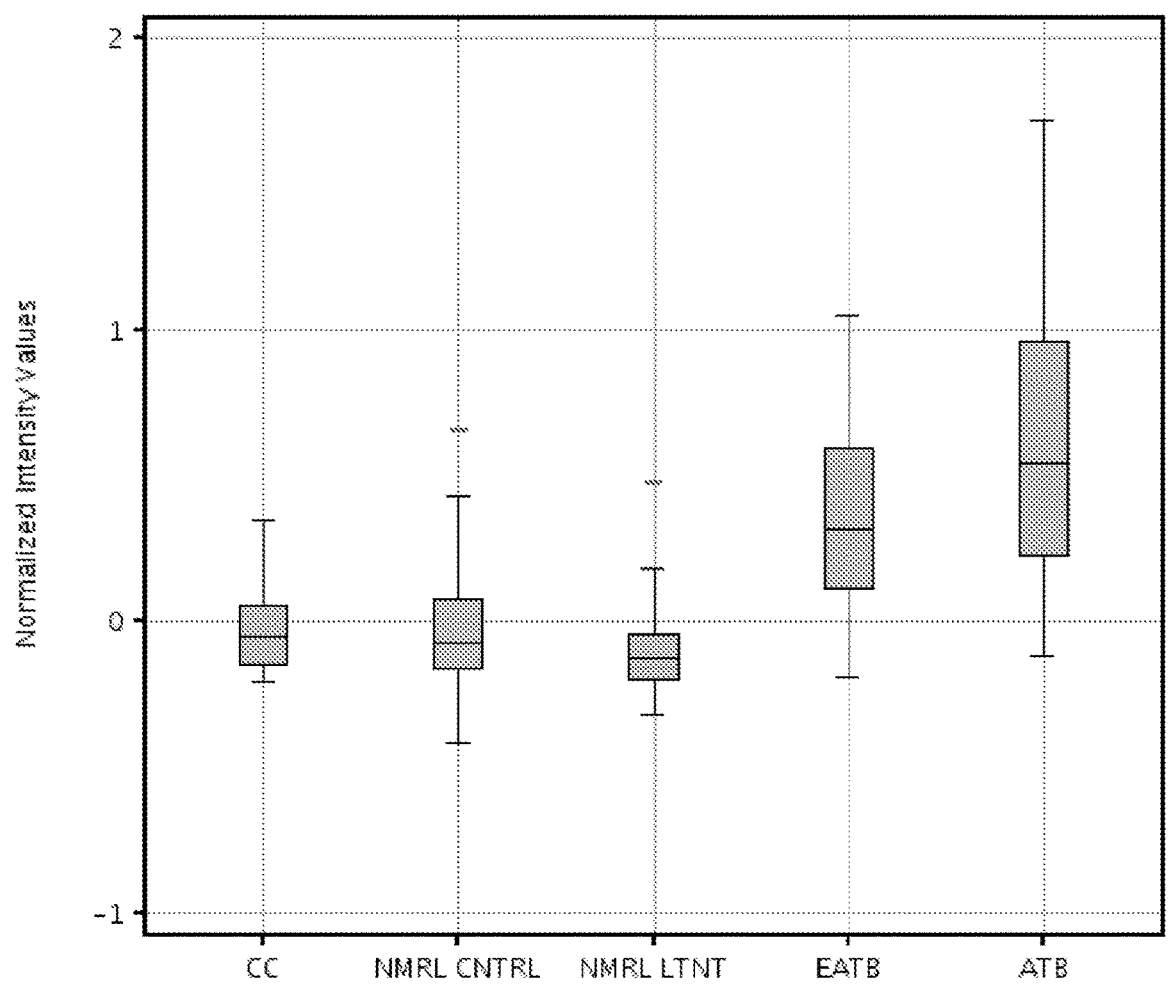
FIG. 5: shows a box plot of CPVL normalised gene expression in CC, NMRL CNTRL, NMRL LTNT, EATB and ATB. The box represents highest and lowest gene expression interquartile range and median gene expression. The error bars represent minimum and maximum values. Grey bars represent outlier values.
Figure 6:
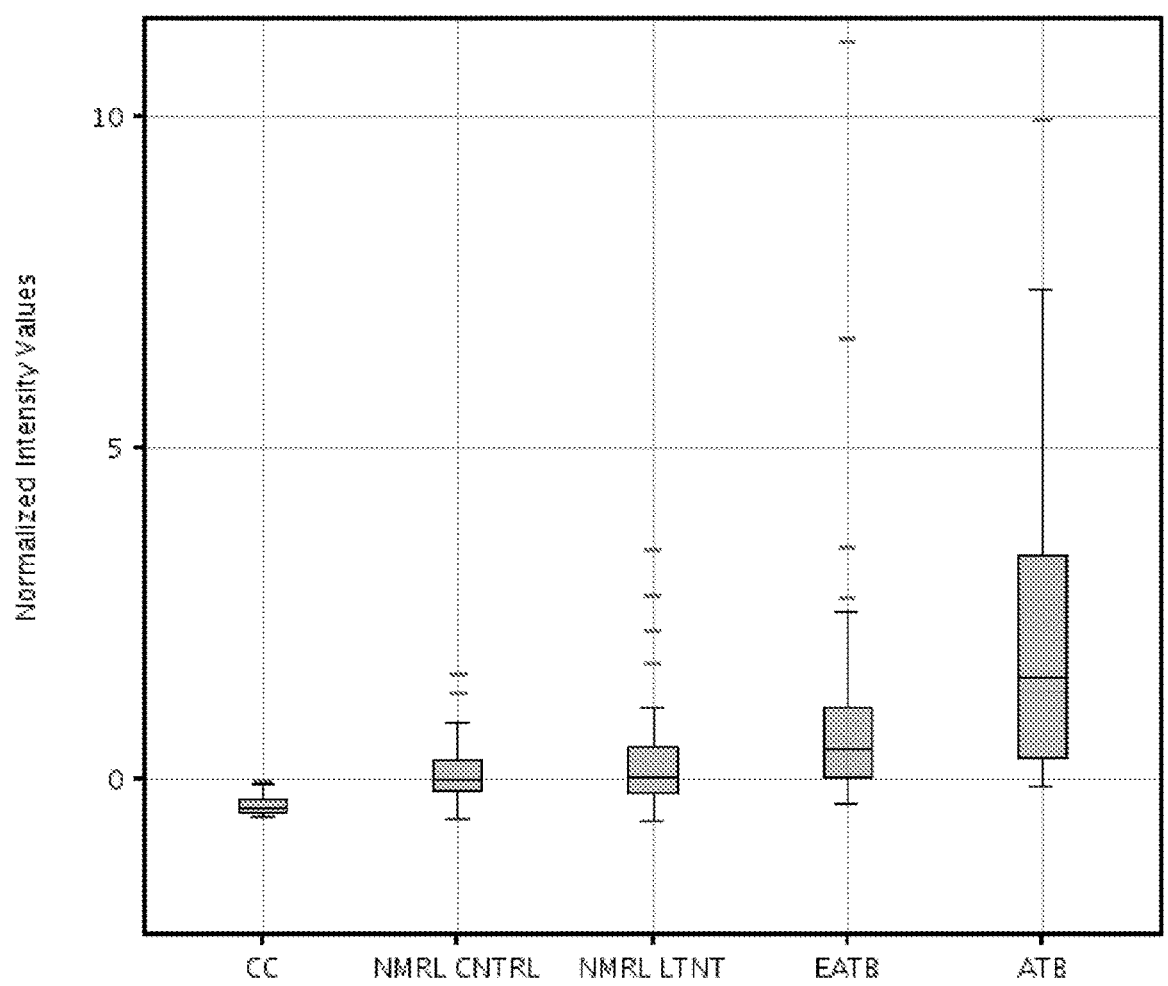
FIG. 6: shows a box plot of IFITM3 normalised gene expression in CC, NMRL CNTRL, NMRL LTNT, EATB and ATB. The box represents highest and lowest gene expression interquartile range and median gene expression. The error bars represent minimum and maximum values. Grey bars represent outlier values.
Figure 7:
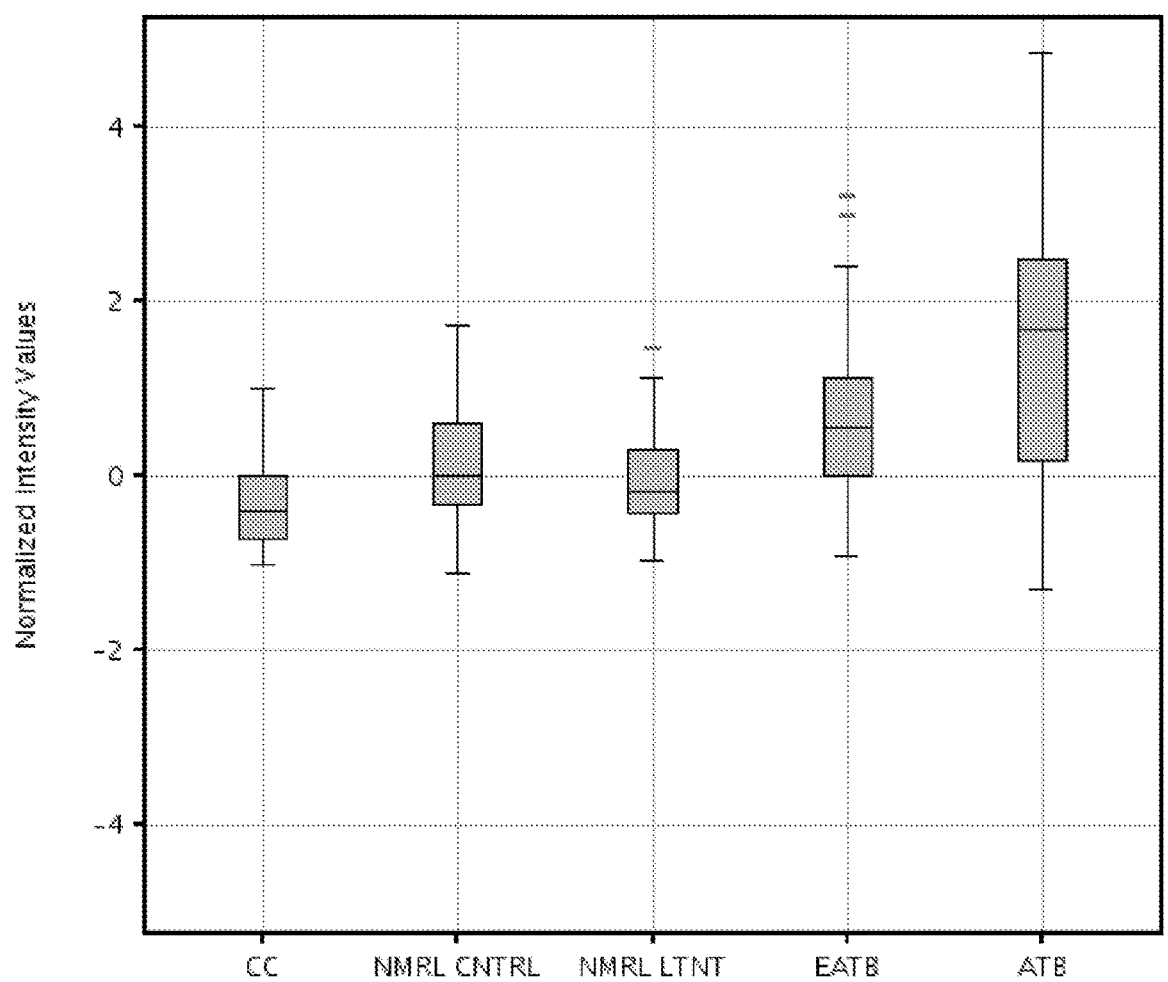
FIG. 7: shows a box plot of NCF1C normalised gene expression in CC, NMRL CNTRL, NMRL LTNT, EATB and ATB. The box represents highest and lowest gene expression interquartile range and median gene expression. The error bars represent minimum and maximum values. Grey bars represent outlier values.
Figure 8:
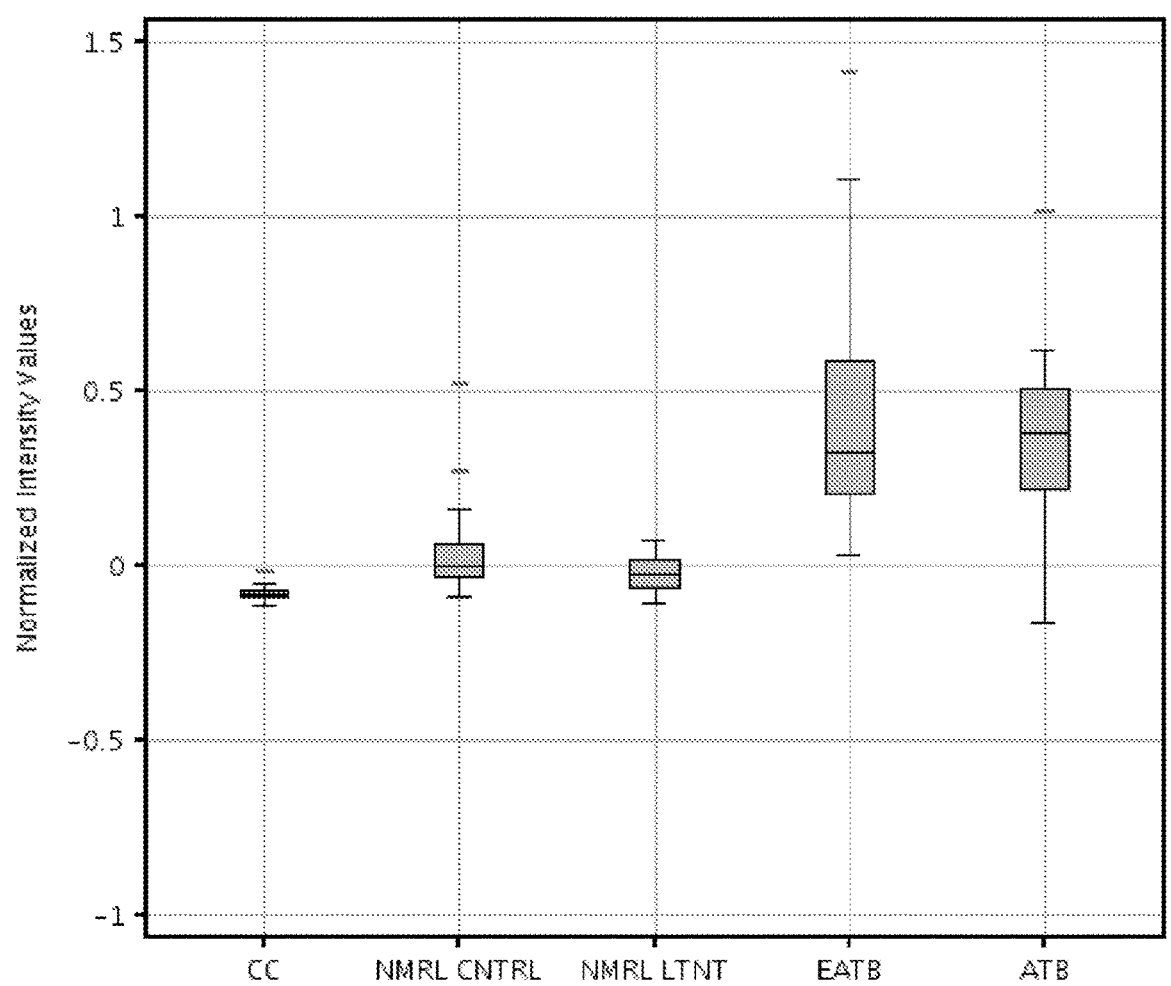
FIG. 8: shows a box plot of SNX10 normalised gene expression in CC, NMRL CNTRL, NMRL LTNT, EATB and ATB. The box represents highest and lowest gene expression interquartile range and median gene expression. The error bars represent minimum and maximum values. Grey bars represent outlier values.
Figure 9:
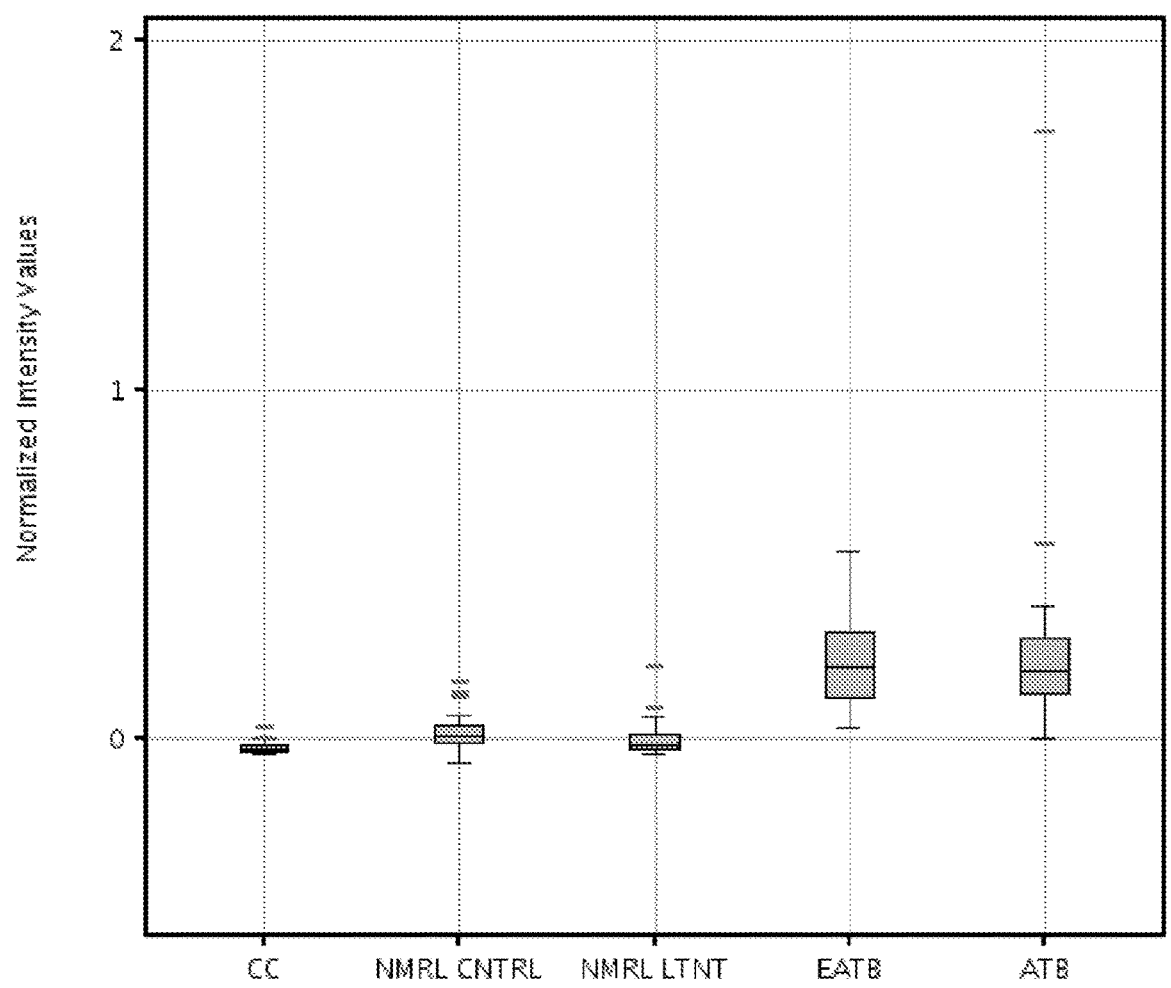
FIG. 9: shows a box plot of CREG1 normalised gene expression in CC, NMRL CNTRL, NMRL LTNT, EATB and ATB. The box represents highest and lowest gene expression interquartile range and median gene expression. The error bars represent minimum and maximum values. Grey bars represent outlier values.
Figure 10:
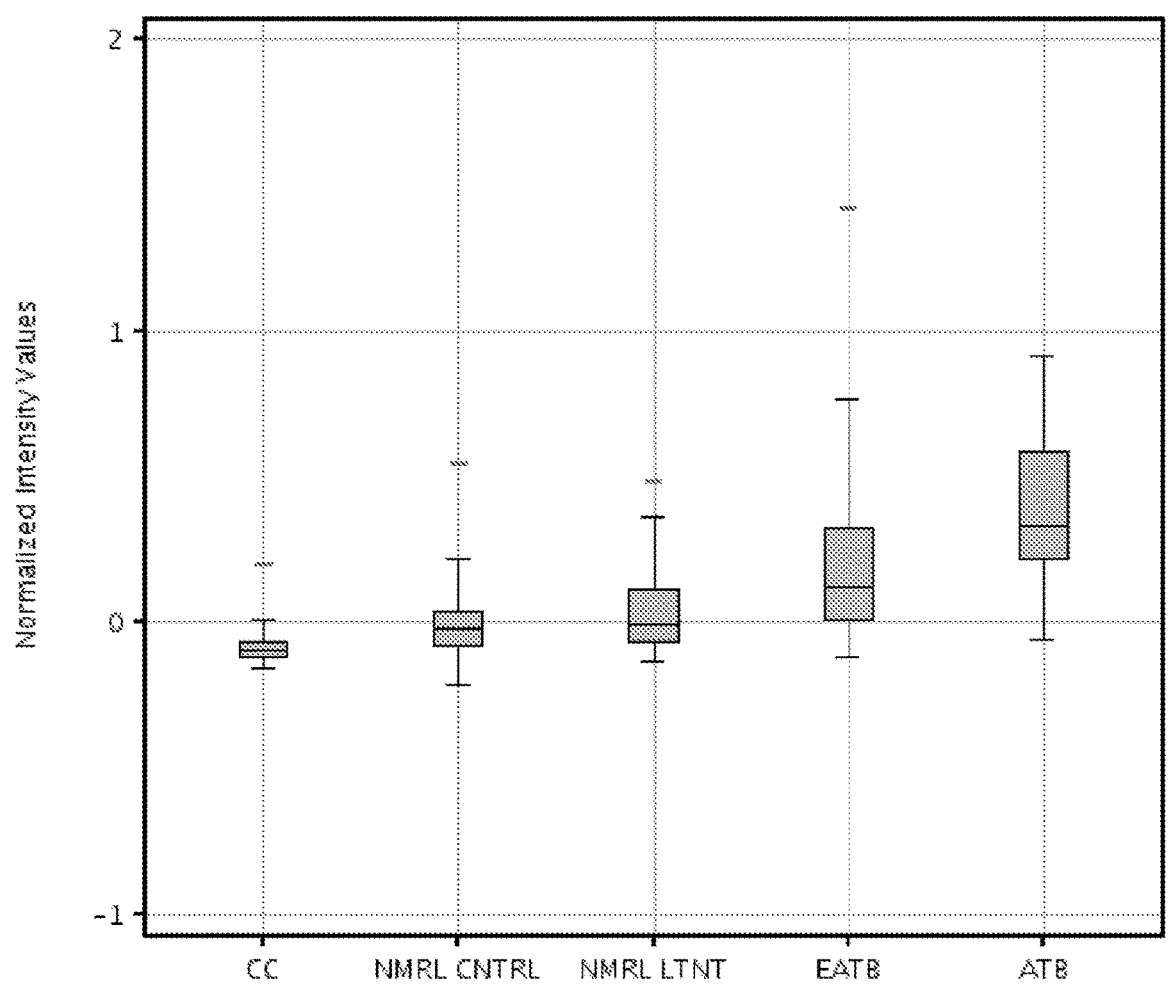
FIG. 10: shows a box plot of PSMB9 normalised gene expression in CC, NMRL CNTRL, NMRL LTNT, EATB and ATB. The box represents highest and lowest gene expression interquartile range and median gene expression. The error bars represent minimum and maximum values. Grey bars represent outlier values.
Figure 11:
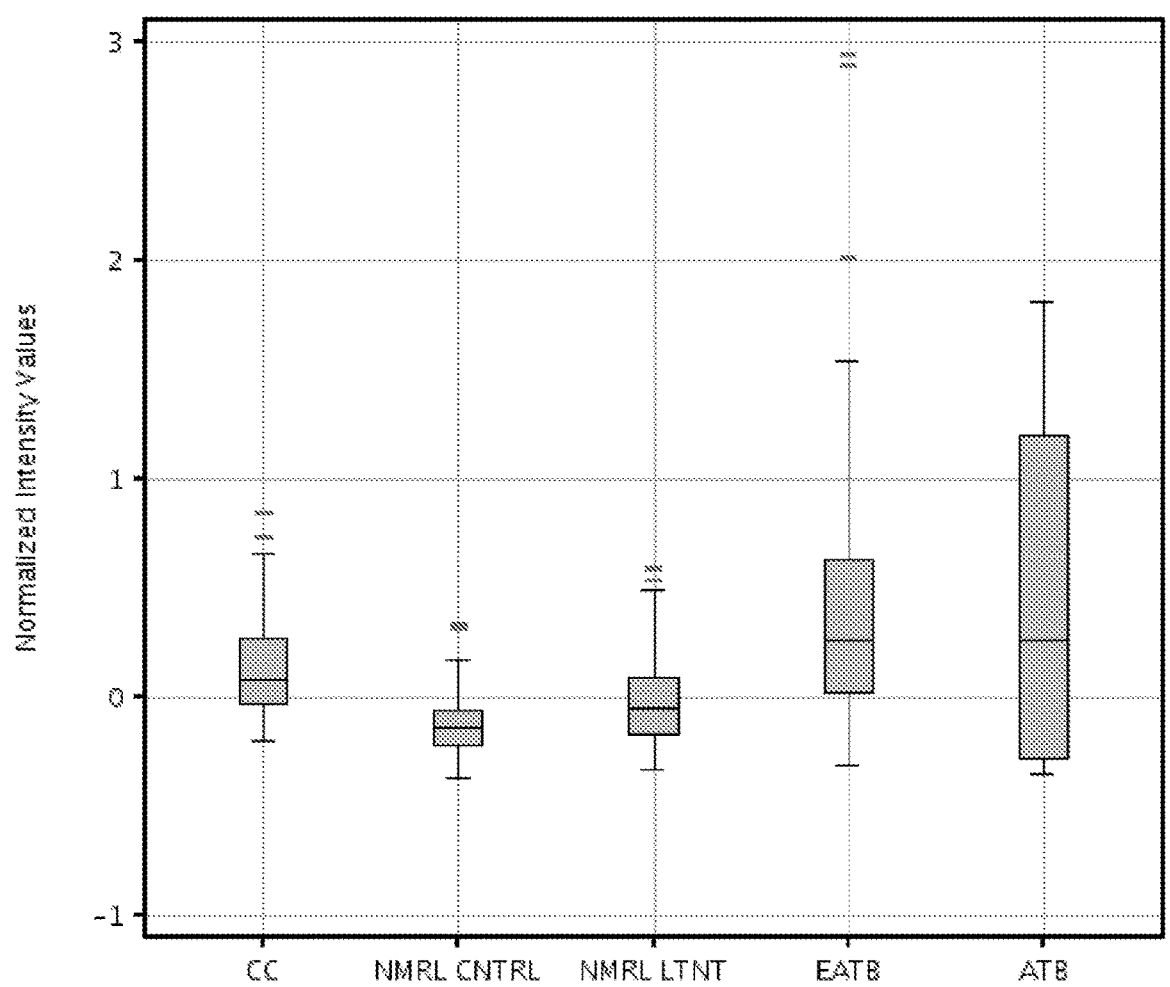
FIG. 11: shows a box plot of PF4V1 normalised gene expression in CC, NMRL CNTRL, NMRL LTNT, EATB and ATB. The box represents highest and lowest gene expression interquartile range and median gene expression. The error bars represent minimum and maximum values. Grey bars represent outlier values.
Figure 12:
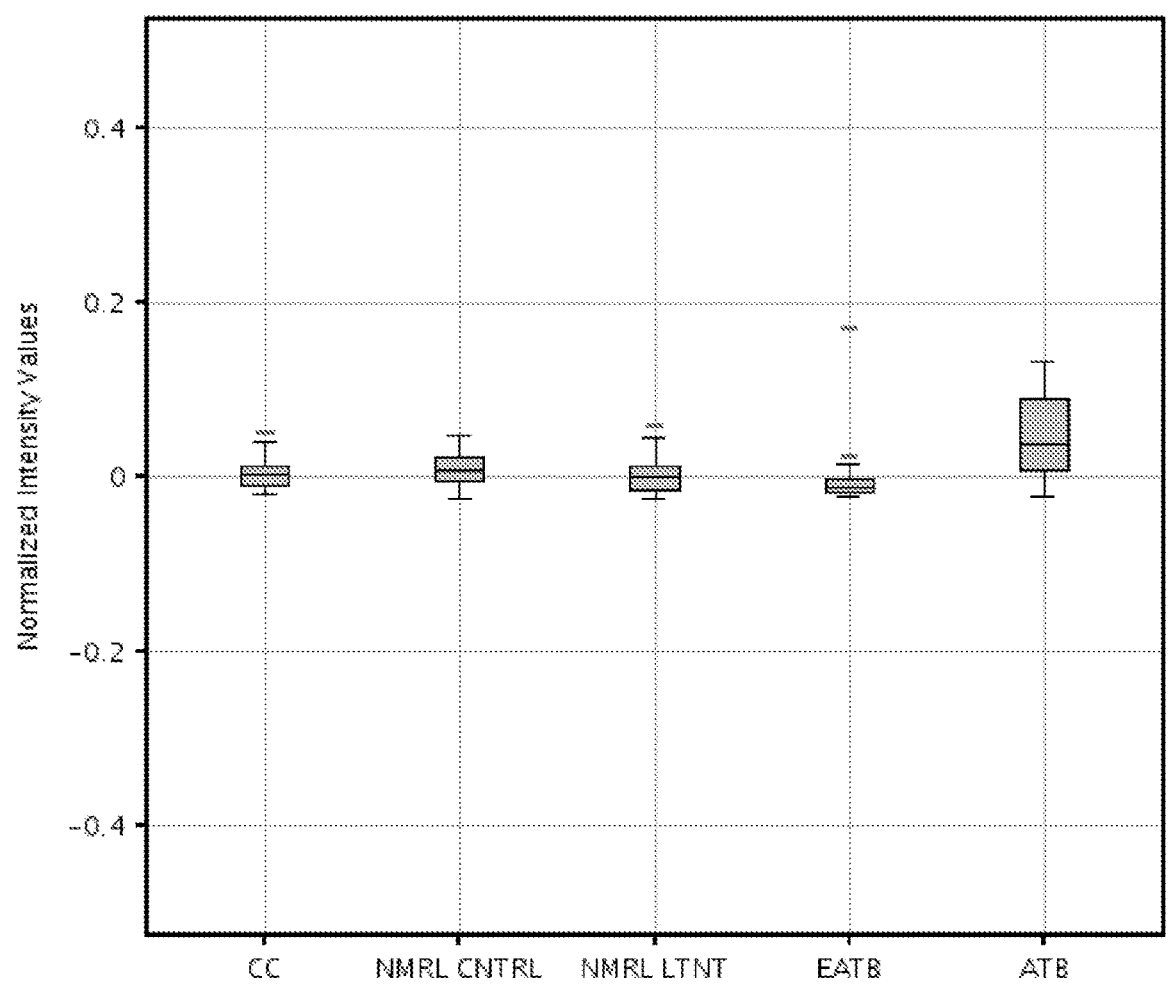
FIG. 12: shows a box plot of ALPK1 normalised gene expression in CC, NMRL CNTRL, NMRL LTNT, EATB and ATB. The box represents highest and lowest gene expression interquartile range and median gene expression. The error bars represent minimum and maximum values. Grey bars represent outlier values.

In Tables 7 to 10 and FIGS. 1 to 12, the terms CC, LC (or NMRL CNTRL), LTB (or NMRL LTNT), EATB and ATB are as defined above. The term ND stands for not detected.

TABLE 7

Biomarkers for TB - qPCR Validation Data on New Cohort of TB infected and Uninfected Donors

| Probe Number | Gene Symbol | Corrected P value CC vs LC | Corrected P value CC vs LTB | Corrected P value CC vs EATB | Corrected P value CC vs ATB | Corrected P value LC VS LTB | Corrected P value LC VS EATB | Corrected P value LC VS ATB |
|---|---|---|---|---|---|---|---|---|
| AA1 | LOC400759/GBP1P1 (RP4-644F6.3) | ND | ND | 3.76E−06 | 1.47E−02 | ND | 1.82E−05 | 2.51E−02 |
| AA2 | LGALS3BP | ND | ND | ND | ND | ND | ND | ND |
| AB1 | BST1 | ND | ND | ND | ND | ND | ND | ND |
| AB2 | SNX10 | ND | ND | 4.99E−13 | 2.44E−06 | ND | 8.17E−10 | 6.11E−05 |
| AC1 | ALPK1 | ND | ND | ND | ND | ND | ND | ND |
| AC2 | CREG1 | ND | ND | ND | 4.05E−03 | ND | ND | 1.07E−02 |
| AD2 | LYN | ND | 3.64E−12 | 2.15E−06 | 3.66E−05 | ND | ND | 7.57E−03 |
| AD3 | TAPBP | ND | ND | 3.57E−04 | 4.32E−02 | ND | 7.37E−04 | ND |
| AE1 | SERPINB1 | ND | ND | ND | 9.12E−04 | ND | ND | 4.03E−03 |
| AE2 | PSMB9 | ND | ND | 2.94E−07 | 1.02E−06 | ND | ND | 9.44E−06 |
| AE3 | WSB1 | ND | ND | ND | ND | ND | ND | ND |
| AF1 | MVP | ND | ND | ND | ND | ND | ND | ND |
| AF2 | APBB1IP | ND | ND | ND | ND | ND | ND | ND |
| AF3 | FYB | ND | ND | 7.26E−05 | 7.02E−03 | ND | ND | 1.45E−02 |
| AG1 | MB21D1/C6orf150 | ND | ND | ND | ND | ND | ND | ND |
| AG2 | CPVL | ND | ND | 6.64E−10 | 1.02E−04 | ND | 1.21E−08 | 1.27E−04 |
| AH1 | CD52 | 3.84E−05 | 1.84E−05 | ND | ND | ND | 9.08E−04 | ND |
| AJ2 | KLRAP1 (KLRA1) | ND | ND | ND | ND | ND | ND | ND |
| AK1 | PF4V1 | 4.67E−07 | ND | 0.016029 | ND | ND | 1.74E−05 | 1.30E−02 |
| AL1 | DEFB128 | ND | ND | ND | ND | ND | ND | ND |
| AM1 | IL8 | ND | ND | ND | ND | ND | ND | ND |

| Probe Number | Gene Symbol | Corrected P value LTB VS EATB | Corrected P value LTB VS ATB | Corrected P value EATB VS ATB | Corrected p value ANOVA | Uncorrected p value ANOVA |
|---|---|---|---|---|---|---|
| AA1 | LOC400759/GBP1P1 (RP4-644F6.3) | 6.51E−06 | 0.018 | ND | 5.74E−12 | 1.99E−12 |
| AA2 | LGALS3BP | ND | ND | ND | 5.45E−17 | 1.21E−17 |
| AB1 | BST1 | ND | ND | ND | 1.67E−10 | 6.71E−11 |
| AB2 | SNX10 | 2.09E−11 | 1.34E−05 | ND | 3.86E−32 | 1.61E−33 |
| AC1 | ALPK1 | ND | ND | ND | 2.15E−09 | 9.87E−10 |
| AC2 | CREG1 | ND | 0.006925 | ND | 5.04E−20 | 6.30E−21 |
| AD2 | LYN | ND | ND | ND | 2.78E−10 | 1.16E−10 |
| AD3 | TAPBP | 9.60E−04 | ND | ND | 6.55E−06 | 4.00E−06 |
| AE1 | SERPINB1 | ND | 0.002271 | ND | 6.22E−06 | 3.71E−06 |
| AE2 | PSMB9 | ND | 3.95E−05 | ND | 1.47E−17 | 3.06E−18 |
| AE3 | WSB1 | ND | ND | ND | 1.58E−08 | 7.92E−09 |
| AF1 | MVP | ND | ND | ND | 6.74E−09 | 3.18E−09 |
| AF2 | APBB1IP | ND | ND | ND | 0.027901 | 0.024026 |
| AF3 | FYB | 1.13E−04 | 0.006217 | ND | 1.48E−09 | 6.38E−10 |
| AG1 | MB21D1/C6orf150 | ND | ND | ND | 4.59E−12 | 1.53E−12 |
| AG2 | CPVL | 4.75E−12 | 3.42E−05 | ND | 1.06E−24 | 7.35E−26 |
| AH1 | CD52 | 1.03E−03 | ND | ND | 1.83E−04 | 1.40E−04 |
| AJ2 | KLRAP1 (KLRA1) | ND | ND | ND | 3.51E−06 | 2.05E−06 |
| AK1 | PF4V1 | 4.66E−04 | ND | ND | 1.49E−07 | 8.06E−08 |
| AL1 | DEFB128 | ND | ND | ND | 0.028874 | 0.025666 |
| AM1 | IL8 | ND | ND | ND | 2.84E−07 | 1.58E−07 |

TABLE 8

Biomarkers for TB - qPCR Validation Data on New Cohort of TB infected and Uninfected Donors

| Probe Number | Gene Symbol | Corrected P value CC vs LC | Corrected P value CC vs LTB | Corrected P value CC vs EATB | Corrected P value CC vs ATB | Corrected P value LC VS LTB | Corrected P value LC VS EATB | Corrected P value LC VS ATB |
|---|---|---|---|---|---|---|---|---|
| B2 | CD274 | ND | ND | ND | ND | ND | ND | ND |
| B3 | CD96 | ND | ND | ND | ND | ND | ND | ND |
| B4 | CDH23 | ND | ND | ND | ND | ND | ND | ND |
| B5 | IRF1 | 1.03E-09 | 4.40E-08 | 5.78E-10 | 5.08E-07 | ND | 5.34E-07 | 5.31E-05 |
| B6 | GBP1 | ND | ND | 9.63E-04 | 4.63E-04 | ND | 8.76E-04 | 4.47E-04 |
| B7 | IFIT3 | ND | ND | 2.09E-06 | 1.16E-03 | ND | 3.35E-05 | 4.08E-03 |
| B8 | IFITM3 | 2.33E-08 | 5.38E-07 | 9.03E-05 | 6.71E-04 | ND | 9.70E-03 | 3.53E-03 |
| B9 | GK | ND | ND | ND | ND | ND | ND | ND |
| B10 | NELL2 | ND | ND | ND | ND | ND | ND | ND |
| B11 | S100A11 | 9.55E-10 | 5.65E-11 | 5.64E-09 | 9.54E-06 | ND | 4.83E-05 | 1.15E-03 |
| B12 | SAMD9L | ND | ND | ND | ND | ND | ND | 2.94E-02 |
| B14 | TLR6 | ND | ND | ND | ND | ND | ND | ND |
| B16 | MMP9 | ND | ND | 0.001241 | ND | ND | 9.03E-03 | ND |
| B17 | DOCK9 | ND | ND | ND | ND | ND | ND | ND |
| B18 | SIRPB2 | ND | ND | ND | ND | ND | ND | ND |
| B19 | ANKRD22 | ND | ND | ND | ND | ND | ND | ND |

| Probe Number | Gene Symbol | Corrected P value LTB VS EATB | Corrected P value LTB VS ATB | Corrected P value EATB VS ATB | Corrected p value ANOVA | Uncorrected p value ANOVA |
|---|---|---|---|---|---|---|
| B2 | CD274 | ND | ND | ND | 2.58E-18 | 4.31E-19 |
| B3 | CD96 | ND | ND | ND | 8.66E-05 | 6.38E-05 |
| B4 | CDH23 | ND | ND | ND | 8.31E-06 | 5.43E-06 |
| B5 | IRF1 | 6.08E-08 | 1.13E-05 | ND | 4.08E-23 | 3.40E-24 |
| B6 | GBP1 | 1.48E-02 | 6.65E-04 | 0.001967 | 4.51E-23 | 4.38E-24 |
| B7 | IFIT3 | 2.63E-05 | 0.003847 | ND | 1.98E-12 | 5.77E-13 |
| B8 | IFITM3 | 3.62E-02 | 0.006008 | ND | 4.85E-11 | 1.89E-11 |
| B9 | GK | ND | ND | ND | 0.002047 | 0.001706 |
| B10 | NELL2 | ND | ND | ND | 6.81E-21 | 7.57E-22 |
| B11 | S100A11 | 5.12E-06 | 3.35E-04 | ND | 2.73E-18 | 4.93E-19 |
| B12 | SAMD9L | ND | ND | ND | 7.26E-07 | 4.13E-07 |
| B14 | TLR6 | ND | ND | ND | 4.31E-04 | 3.35E-04 |
| B16 | MMP9 | 3.15E-03 | ND | ND | 7.83E-06 | 4.89E-06 |
| B17 | DOCK9 | ND | ND | ND | 9.70E-19 | 1.48E-19 |
| B18 | SIRPB2 | ND | ND | ND | 0.001946 | 0.001595 |
| B19 | ANKRD22 | ND | ND | ND | 1.54E-09 | 6.86E-10 |

TABLE 9

Biomarkers for TB - qPCR Validation Data on New Cohort of TB infected and Uninfected Donors

| Probe Number | Gene Symbol | Corrected P value CC vs LC | Corrected P value CC vs LTB | Corrected P value CC vs EATB | Corrected P value CC vs ATB | Corrected P value LC VS LTB | Corrected P value LC VS EATB | Corrected P value LC VS ATB |
|---|---|---|---|---|---|---|---|---|
| C2 | FNBP1L | ND | ND | ND | ND | ND | ND | ND |
| C3 | NCF1C | 0.006398 | ND | 1.71E-06 | 5.51E-04 | ND | 2.21E-03 | 3.89E-03 |
| Ifit3 C4 | TBC1D3B | ND | ND | ND | ND | ND | ND | ND |
| C5 | SLC14A1 | ND | ND | ND | ND | ND | ND | ND |

| Probe Number | Gene Symbol | Corrected P value LTB VS EATB | Corrected P value LTB VS ATB | Corrected P value EATB VS ATB | Corrected p value ANOVA | Uncorrected p value ANOVA |
|---|---|---|---|---|---|---|
| C2 | FNBP1L | ND | ND | ND | 4.63E-05 | 3.35E-05 |
| C3 | NCF1C | 2.25E-04 | 0.002172 | ND | 2.47E-12 | 7.55E-13 |
| Ifit3 C4 | TBC1D3B | ND | ND | ND | 0.044403 | 0.040086 |
| C5 | SLC14A1 | ND | ND | ND | 1.86E-05 | 1.27E-05 |

TABLE 10

Biomarkers for TB - qPCR Validation Data on New Cohort of TB infected and Uninfected Donors

| Probe Number | Gene Symbol | Corrected P value CC vs LC | Corrected P value CC vs LTB | Corrected P value CC vs EATB | Corrected P value CC vs ATB | Corrected P value LC VS LTB | Corrected P value LC VS EATB | Corrected P value LC VS ATB |
|---|---|---|---|---|---|---|---|---|
| D1 | CALCOCO2 | ND | ND | ND | ND | ND | ND | ND |
| D2 | GTF2B | ND | ND | ND | ND | ND | ND | ND |
| D3 | HLA-B | ND | 5.27E−04 | 5.27E−04 | ND | 4.87E−03 | 4.35E−02 | ND |
| D4 | HLA-F | ND | ND | ND | ND | ND | ND | ND |
| D5 | MGST2 | ND | ND | ND | ND | ND | ND | ND |
| D6 | SPAST | ND | ND | ND | ND | ND | ND | ND |
| D7 | WAC | ND | ND | ND | ND | ND | ND | ND |

| Probe Number | Gene Symbol | Corrected P value LTB VS EATB | Corrected P value LTB VS ATB | Corrected P value EATB VS ATB | Corrected p value ANOVA | Uncorrected p value ANOVA |
|---|---|---|---|---|---|---|
| D1 | CALCOCO2 | ND | ND | ND | 9.07E−15 | 2.14E−15 |
| D2 | GTF2B | ND | ND | ND | 8.31E−06 | 5.39E−06 |
| D3 | HLA-B | 9.79E−04 | ND | ND | 9.05E−04 | 7.17E−04 |
| D4 | HLA-F | ND | ND | ND | 3.35E−12 | 1.07E−12 |
| D5 | MGST2 | ND | ND | ND | 8.92E−06 | 5.95E−06 |
| D6 | SPAST | ND | ND | ND | 5.88E−08 | 3.11E−08 |
| D7 | WAC | ND | ND | ND | 0.00189 | 0.001523 |

SEQUENCE INFORMATION

Set out below are the nucleotide sequences of the TB biomarkers disclosed herein. Exemplary target regions within the biomarker sequences are underlined, and exemplary probe sequences are double underlined.

```
A1 LOC400759 GBP1P1-guanylate binding protein 1, interferon-inducible
pseudogene 1 GBP1P1, mRNA-NR 003133.2
                                                       (SEQ ID NO: 112)
    1 aaaatattag tccaaggatc cagtgagaga cacagaagtg ctagaagcca ctcctcatga 61 actaaggaga aaaagaacag acaagggaac acccccagaca tggtatcaga gatccacatg 121 acaggcccaa tgtgcctcat tgagaacact aatgggcgac tgatggcgaa tccagaagct 181 ctgaagatcc tttctgccat tacgcagcct gtggtggtgg tggcgactgt gggccgctag 241 cgcacaggaa aatcctacct gattaacaag ctggctcaga agaaaaaggg cttctctctg 301 ggctccacag tgcagtctca cactaaagga atctggatgt ggtgtatgcc ccatcccaag 361 aagccaggcc acatcctagt tctgctggac accgagggtc tgggagatgt agagaagggt 421 gacaaccaga atgactcctg gatcttcgcc ctggccgtcc tcctgaacag cacttccatg 481 tacaatagca taggaaccat taaccagcag gccatggacc aactgcagta cctttgtga 541 cccagaacag caccaagtgg aacgtgtgaa agctgagtct gcacaggctt cagcaaaaat 601 gttgcagcaa atgcaaagaa agaatgagca gatgatggaa cagaaggaga ggagttatca 661 ggaacacttg aaacaactga ctgagaagat ggagagcgac agggtccagt tgctggaaga 721 gcaagagagg accctcgctc ttaaacttca ggtgtctaat tgcatcacct tgaggtttct 781 gttttctgt tttctctcca ttctccccga tcacaggctt actgtggcag agagaacatg 841 aagcccaggg gaagaaccct gcttgcttac ttgtactttt caattcctgt ctgtccagcc 901 tgaactggct actgccaagt ctggtcacta aactgcaaat attgcagttg tgtcacattc 961 agtgctttat ctatatatcc ttcatttcaa ggcaggtatt atctgctagc catcattaaa 1021 gtatctgtat ctcttgctta ataccatgtg aagcaagaac tatattctta ttacttagga 1081 gaagaaacaa agtttccaaa aataataaat aaatagagtc acacagctag taaatgtatc
```

-continued

```
1141  aaagctgtct tcatcactta gtggaatcca caatgattat ttttttctgt gacacctagt
1201  atgaaattaa acttaagaaa acctttgtga gcag
```

GBP1P1 Genomic Sequence AL691464

(SEQ ID NO: 113)
```
   1  aaaatattag tccaaggatc cagtgagaga cacagaagtg ctagaagcca ctcctcatga
  61  actaaggaga aaaagaacag gtaagaactt ttactacttc tcattaagca gctttctctt
 121  tagctccaaa ggatctcagc tcagggatat ggaacccata aggttgtggc agggatggga
 181  aggaatttat aaaggtcagt tcattttctt aaacatcgtc agaaccaaat taggctgcag
 241  atgagcctga agtgggacgc aggtcagatg aaatcctggt gttatcaggg acagcatggc
 301  cttaagtgac actacagtgt ttgtgttgaa ttaggcacca gtagacaggg gctaaactga
 361  gagtttgaaa tgcactagga tagtcttttct ctttgttgtc attctctgtg ttgactggag
 421  acatgattac atttccatta tcagtgatgg agcttgctga atcctgctcc tatgcagcta
 481  agaaatggaa agagctacaa atgggttctt ttcataagga aagaacagca aatgagaagc
 541  agagtaatca gcccactgac atggttaaag acaaagaaaa aactgaaact cagcctgaaa
 601  gatgaagatt catgaaaaca gtatactttt tattcacttt gtgaacttcg tttcagaatg
 661  gattactttc tttagaaata gtccagactc actaatttcc tagtgcccac tgatccctgt
 721  cccttagaag tgaaattcaa ccccactgct tcactaaagt gcttccaatt ttgtcttctt
 781  ttagtagaga ctggggccta aagtgtttcc tctttaattc tcctgtaatg catctctaga
 841  gaaaatatct ttgcttattt taacctctct atgcaatcag actactttaa tcctgccttc
 901  tggaaagtcc tcgcctgaat tccttgtcaa gacactagcc tcattcatca ccttctggtc
 961  tgatagctct ttctcgctct ctctctctct ctctctctct ctctctctct ctctctctca
1021  cacacacaca cacacacaca caaacacaca cacaccttcc cagcccttc tcctcctcct
1081  ctccactcct actattcctc ctctatttct ctttctccta ccctaccaaa tggaaaacag
1141  aacaaaacag aaatcctaaa gctgtatcgc tggaaatata tttcatttga caacttcct
1201  aggtagctct ctttatctgc ctcttgatct tttaatcctt atttcattat ctgggggaaa
1261  cattcagcat ttgcaatttt gcattcatac cctcactgag ttagaggcta ccttattgtg
1321  actctaacgc agcttaagtt tcagggcccct tctcttggac atgacccttc agagtccttg
1381  gaaggttcct cagccatgtg tttcacatgt ttgtatagtt ttctaaaatt tgcaaaagta
1441  tgttacgttg tttccacttc cagaatggca ccgtgaaaag ctttattgat cctcattgcg
1501  gtgaaataag cataaccact tgaagatgga ggaaggaaca catttaaaaa tctttggaaa
1561  ttgttctaag ggtaaacatc aaactatgaa tactgattca ctgtattatt cactgtaaga
1621  attaataagt aaatcaatat tgaattcctt atacacagcc aggatgcaaa ataaatcctc
1681  taaatcctgt tctatcttcc attaattgac tagtgaaaat atttaaaaag aatccaaaaa
1741  gaaagttttc cactataaat taaatgaaat atttgagttg tgagcatagt tgagtgttga
1801  tgaggcagga aattaaagaa aaatacaatt aaaaataaaa agaaataagt tttcctgtat
1861  taggctgact tgtcccagag gcagcaacag gcacagacca gacccaggaa aagtcttgat
1921  aatactatct aaggtgctct ggagactctc ccagcactcc ctcaacatag gaagaagaaa
1981  aataaatttt cctttgtttt atggaaaagt ttgtagattc ctgttctctg taactagtga
2041  cttcaagtat tctgtttttat ctaagaagta gagtgaaggt catgagaagc ctgaataggc
2101  ctgaactaca gctgcctggg caccatagtg aaggttataa tataaaccag tgcaaggctc
2161  tttagagcaa aacgtagata acagacatct gggttgcttg gcaatggtca tgtgtaatcc
2221  tgagtttgtc ctgcctctat atccctgctt tcatgccact gtaagcttgc ttcaagctag
```

-continued

```
2281  cccacctgct tttgtgaagt gtgtataaaa gtcaagtgct gtctttgcat gtgagtgtgc
2341  tggggcctga gtgtactcaa taaaaattct cctgttttaa cccgaggtct ctctctcgtc
2401  ctcctggatc ccacaacatt gataagtcac tgtcatgcta acatttttttg taatgagcta
2461  ctttgacaat acttccataa ttttctcaaa tgatacagat tttgcctcat ctctctcgct
2521  gtcacacaca aaacttttgg ccataatggg gaatcttatg attctcccctt ataattgcaa
2581  aacactagaa actctcattt atttcacctc ttctcttgca gacaagggaa cacccccagac
2641  atggtatcag agatccacat gacaggccca atgtgcctca ttgagaacac taatgggcga
2701  ctgatggcga atccagaagc tctgaagatc ctttctgcca ttacgcagcc tgtggtggtg
2761  gtggcgactg tgggccgcta gcgcacagga aaatcctacc tgattaacaa gctggctcag
2821  aagaaaaagg gtgagtggca tgagcaaagc tctgccaagt cccttctgtc catctacaca
2881  gtcagcctcc atcatgagga tgtgaagaga gaaagagatg aggatgaata tggaaagcta
2941  actttccatt cacagtcggg ctccttatct tcacgctgct ctaagggata attttaaatt
3001  cattaattat tcccatgata cattagtttc cctttcaaaa gcacaaactg tgcctttcct
3061  aaaaggagta agactgtaat aaaaataatt aatgtacata ataataacta taataaacta
3121  caattttttat gccataacag cgagtttaca gtgatcttta aggttgaaaa aatgtttgtc
3181  tgtattggat attcttttttt attgttgtaa aaaaataaca taaaatttaa cctcgtaacc
3241  atttttaagt gtacagctct gtggcattaa ttaaattcac attgttatac agctgtcacc
3301  tccatccata tccagaaatc tttcatcttg cctaacagaa actctgtact aactaaacaa
3361  aagctccaca taaacccatt gcctgccatc attctacatt ctatctctat gaattttact
3421  actacagaaa cctcatataa gtggaattat tcaatatttg tccttttatg actggcttat
3481  ttcaattcat atgtcttcaa ggttcatcag tgtgttagca tgtgtcaaaa ctcttccttt
3541  ttaaggctta gtaattgtac atgtatacta atttgtttat ctcttcatct gtcaatggac
3601  aattggattg cttccacctt ttgtctatta taaataatgc taataggaac atgggtgtct
3661  gaatatctgt tcaagtccct gctttcactt cttttgggaa tatacccaga agggtaattg
3721  ctggctcatg cagtcattcc atgttaactt ttttttttttt taagaaatca ctatactatt
3781  ttccacagtg actgtactgt tttacattcc caacagaaat gcacaagggc tctaatttct
3841  ctacctcctc accaacattt tttattttca gtgttttttt tgatagtggc catatgaatg
3901  gatgttaagt agtatctcac tatggttttg attttcattt tcctaatgac tggtgatact
3961  gggcatcttt tcatgtgctt attggccacc tgtatatctt ctttgggaaa tgtctattc
4021  aagtcctttc ttcatttatt ttttttttttt aaattcagaa aaattttctt ccacttgaaa
4081  atgttaaaac tcttcattaa acaactatta gatcaagtag aaaatacaaa tcaaaatagg
4141  tgaacatata aacatcaaaa tagtgatata tatatcagaa tctatggaat ataatgaaaa
4201  taattatcaa aaacaatttg tagtctttaa atcatatatc aatagaatta taaattaaaa
4261  tacataaatc taatgtgaaa cacagaaagc tagaaaaaag atcaagaaaa taaagcaaaa
4321  ggaaacataa cagacataaa gagataagag cagaacttca gttagttctg attgtaagct
4381  atgttataaa ttaatcaaca tgctagttct ttgaatagaa cataaacaaa atatgcaaac
4441  caacatccaa cctaatcaag aaaacaggg agaaaacaaa gttacacaga ataatacacg
4501  aaacaagagg aaatcatact aaaactaagg acatttttaa actttttgagt taaatcattt
4561  tacacagctc taagcaggta gatataaaag cctacataaa atgggtaatc ccataggaa
4621  attattaaca gtgataccaa tggagacaga aagtttaaga aaatgagaaa gttattaaat
```

-continued

```
4681  tactactccc acccaaaagt acaagacaca gatgacttta taatggaatt ttatgaattt
4741  ttcaaatatt agataatacc aatgctacat agactgttct taaaaagaga ttgccaagct
4801  atggccagtg ggacaaatat ggcctgccgg ttattatttt attttatttt attttatttt
4861  ttaaatcaat gtatatttta ttttatttta ttatttattt atttatttat ttttattata
4921  ctttaagttt tagggtacat gtgcacattg tgcaggttag ttacatatgt atacatgtgc
4981  catgctgctg cgctgcaccc actaacttgt catctagcat taggtatatc ccccaatgct
5041  atccctcccc cctccccca ccccacaaca gtccccagag tgtgatattc cccttcctgt
5101  gtccatgtga tctcattgtt caattcccac ctatgagtga gaatatgcgg tgtttggttt
5161  tttgttcttg tgatagttta ctgagaatga tgatttccaa tttcatccat gtccctacaa
5221  aggacatgaa ctcatcattt tttatggctg catagtattc catggtgtat atgtgccaca
5281  ttttcttaat ccagtctatc attgttggac atttggggttg gttccaagtc tttgctattg
5341  tgaataatgc cacaataaac atacgtgtgc atgtgtcttt atagcagcat gatttatagt
5401  cctttggata tatacccagt agtgggatgg ctgggtcaaa tggtatttct agttctagat
5461  tcctgaggaa tcgccacact gacttccgca atggttgaac tagtttacag tcccaccaac
5521  agtgtaaaag tgttcctatt tctccacatc ctctccagca cctgttgttt cctgactttt
5581  taatgatcgc cattctaact ggtgtgagat gatatctcat gtggttttg atttgcattt
5641  ctctgatggc cagtgatgat gagcattttt tcaagtgttt tttggctgca taaaggtctt
5701  cttttgagaa gtgtctgttc atgtcctttg cccactttt gatgggttg tttgtttttt
5761  tcttgtaaat ttgttggagt tcattgtaga ttctggatat tagccctttt tcagatgaat
5821  aggttgcaaa aattttctcc cattttatag gttgcctgtt cactctgatg gtagtttctt
5881  ttgctgtgca gaagctcttc agttcaatta gatcccattt gtcaattttg gcttttgttg
5941  ccattgcttt tggtgtttta gacatgaaat ccttgcccat gcctatgtcc tgaatggtaa
6001  tgcctagatt ttcttctagg gttttatgg ttttaggtct aacttttaag tctttaatcc
6061  accttgaatt aattttttgta taaggtgtaa ggaagggatc cagtttcagc tatctacata
6121  tggctagcca gttttcccag caccatttat taaataggga atcctctccc cattgcttgt
6181  ttttctcagg tttgtcaaag atcagatagt tgtagatatg cggcgttatt tctgagggct
6241  ctgttctgtt ccattgatct atatctctgt tttggtacca gtaccatgct gttttggtta
6301  ctgtagcctt gtagtatagt ttgaagttag gtagtgtgat gcctccagct ttgttctttt
6361  ggcttaggat tgacttggtg atgtgggctc ttttttggtt ccatatgaac tttaaagtag
6421  ttttttccaa ttctgtgaag aaagtcattg gtagcttgat ggggatggca ttgaatctgt
6481  aaattacctt gggcagtacg gccattttca cgatattgag tcttcctact catgagcatg
6541  gaatgttctt ccatttgttt gtatcctctt ttatttcctt gagcagtggt ttgtagttct
6601  ccttgaagag gtccttcaca tcccttgtaa gttgtattcc taggtatttt attctctttg
6661  aagcaattgt gaatgggagt tcactcatga tttggctctc tgtttgtctg ttgttggtgt
6721  acaagaatgc ttgtgatttt ggtacattga ttttgtatcc tgagactttg ctaaagttgc
6781  ttatcagctt aaggagattt tgggctgaga cgatgggtt ttctagatat acaatcatgt
6841  cgtctgcaaa cagggacaat ttgacttcct ctttttcctaa ttgaataccc tttatttcct
6901  tctcctgcct aattgccctg gccagaactt ccaacactat gttgaatagg agtggtgaga
6961  gagggcatcc ctgtcttgtg ccagtttca aagggaatgc ttccagtttt tgcccattca
7021  gtatgatatt ggctgtgggt ttgtcataga tagctcttat tatttttgaaa tatgtcccat
7081  caatacctaa tttattgaga gttttttagca tgaagggttg ttgaatttg tcaaaggctt
```

-continued

```
7141  tttctgcatc tattgagata atcatgtggt ttttgtcttt ggctctgttt atatgctgga
7201  ttacatttat tgatttgcat atattgaacc agccttgcat cccagggatg aagcccactt
7261  gatcatggtg gataagcttt ttgatgtgct gctggattcg gtttgccagt attttattga
7321  ggatttttgc atcaatgttc atcaaggata ttggtctaaa attctctttt ttggttgtgt
7381  ctctgcccgg ctttggtatc agaatgatgc tggcctcata aaatgagtta gggaggattc
7441  cctctttttc tattgattgg aatagtttca gaaggaatgg taccattcc tccttgtacc
7501  tctggtagaa ttcggctgtg aatccatctg gtcctggact cttttggtt ggtaagctat
7561  tgattattgc cacaatttca gagcctgtta ttggtctatt cagagattca acttcttcct
7621  ggtttagtct tgggagagtg tatgtgtcca ggaatttatc catttcttct agatgttcta
7681  gtttatttgc atagaggtgt ttgtagtata ctctgatggt agtttgtatt tctgtgggat
7741  cgctggtgat atccccttta tcatttttta ttgcgtctat ttgattcttc tctctttttt
7801  tctttattag tcttgctagc ggtctatcaa ttttgttgat cctttcaaaa aaccagctcc
7861  tggattcatt gatttttga agggtttttt gtgtctctat ttccttcagt tctgctctga
7921  ttttagttat ttcttgcctt ctgctagctt tgaatgtgt ttgctcttgc ttttctagtt
7981  cttttaattg tgatgttagg gtgtcaattt tggatctttc ctgcttttct tgtgggcatt
8041  tagtgctata aatttcccctt tacacactgc tttgaatgcg tcccagagat tctggtatgt
8101  tgtgtcgttg ttctcgttgg tttcaaagaa catctttatt tctgccttca tttcattatg
8161  tacccagtag tcattcaggt gcaggttgtt cagtttccat gtagttgagc cgttttgagt
8221  gagattctta atcctgagtc ctagtttgat tgcactgtgg tctgagaaat agtttgttat
8281  aatctctgtt cttttacatt tgctgaggag agcttactt ccaagtatgt ggtcaatttt
8341  ggaataggtg tggtgtggtg ctgaaaaata tgtatattct gttgatttgg ggtggagagt
8401  tctgtagatg tctattaggt ctgcttggtg cagagctgag ttcaattcct gggtatcctt
8461  gttgacttc tgtctcgttg atctgtctaa tgttgacagt ggggtgttaa agtctcccat
8521  tattaatgtg tgggagtcta agtctctttg taggtcactc aggacttgct ttatgaatct
8581  gggtgctcct gtattgggtg catatatatt taggatagtt agctcttctt gttgaattga
8641  tcccttacc attatgtaat ggccttcttt gtctcttttg atctttttg ttttgacatc
8701  tgttttatca gagactagga ttgcaacccc tgcctttttt tgttttccat ttgcttggta
8761  gatcttcctc catccttta ttttgagcct atgtgtgtct ctgcacgtga gatgggtttc
8821  ctgggtacag cacactgatg ggtcttgact ctttatccaa tttgccagtc tgtgtctttt
8881  aattggagca tttagtccat ttacatttaa agttaatatt gttatgtgtg aatttgatcc
8941  tgttgttatg atgttagctg gttattttgc tcattagttg atgcaatttc ttcctagact
9001  tgatgatcat gcaaaatttt ggcatgattt tgcagcggct ggtaccggtt gttcctttcc
9061  atgtttagcg tttccttcag gagctctttt agggcaggcc tggtggtgac aaaaatctct
9121  cagcatttga ttgtctgtaa agtatttat ttctccttca cttatgaagc ttagtttggc
9181  tggatatgaa attctgggtt gaaaattctt ttctttaaga atgttgaata ttggccccca
9241  ctctcttctg gcttgtaggg tttctgccga gagatctgct gttagtctga tgggcttccc
9301  tttgtgggta acccgacctt tctctctggc tgcccttaac atttttttcct tcatttcaac
9361  tttggtgaat ctgacaatta tgtgtcttgg agttgctctt cttgaggagt atctttgtgg
9421  cgttctctgt atttcctgaa tctgaacgtt ggcctgcctt gctagattgg ggaagttctc
9481  ctggataata tcctgcagag tgttttccaa cttggttcca ttctccccat cactttcagg
```

-continued

```
 9541 tacaccaatc agacgtagat ttggtctttt cacatagtcc catatttctt ggaggctttg
 9601 ctcatttctt tttattcttt tgtctctaaa cttcccttct cacttcattt cattcatttc
 9661 atcttccatt gctgataccc tttcttccag ttgatcgcat cggctcctca ggcttctgca
 9721 ttcttcacgt agttctcgag ccttggcttt cagctccatc agctccttta agcacttctc
 9781 tgtattggtt attctagtta tacattcttc taaattttttt ttcaaagttt tcaacttctt
 9841 tgcctttggt ttgaatgtcc tcctgtagtt cagtgtaatt tgatagtctg aagccttctt
 9901 ctctcagctc gtcaaagtca ttctccatcc agctttgttc cgttgctggt gaggaactgc
 9961 gttcctttgg aggaggagag gcgctctgct ttttagagtt tccagttttt ctgttctgtt
10021 ttttccccat ctttgtggtt ttatctactt ttggtctttg atgatggtga tgtacggatg
10081 ggtttttggt gtggatgtcc tttctgtttg ttagtcttcc ttctaacaga caggaccctc
10141 agctgcaggt ctgttggaat accctgccgt gtgaggtgtc agtgtgcccc tgctgggggg
10201 tgcctcccag ttaggctgct cggggtcag gggtcaggga accacttgag gaggcagtct
10261 gcccgttctc agatctccag ctgcgtgctg ggagaaccac tgctctcttc aaagctgtca
10321 gacagggaca tttaagtctg cagaggttgc tgctgtcttt tgtttgtct gtgccctgcc
10381 cccagaggtg gagcctacag aggcaggcag gcctccttga gctgtggtgg gctccaccca
10441 gttcgagctt cctggctgct tgtttacct aagcaagcct gggcaatggt gggcgcccct
10501 cccccagcct cgctgccgcc ttgcagtttg atctcagact gctgtgctag caatcagcga
10561 gactccgtgg gcgtaggacc ctccgagcca ggtgcgggat ataatctcgt ggtgcaccgt
10621 ttttttaagc ccgtcggaaa agcgcagtat tcgggtggga gtgacccgat tttccaggtg
10681 cgtccgtcac tcctttcttt gactgggaaa gggaactccc tgaccccttg cacttcccaa
10741 gtgaggcaat gcctcgcccct gcttcggctc gcgcacggtg cgcgcaccca ctgacctgtg
10801 cccactgtct ggcactccct agtgagatga acccgttacc tcagatggaa atgcagaaat
10861 cacccgtctt ctgcgtcgct caggctggga gctgtagacc ccagctgttc ctattcggcc
10921 atcttggctc ctcctccttt attcatttat taatctggtt gtttatctgt gttgctttgt
10981 aaattttttt tatattttct agatataaat cccttatcat atacatgttt aacaaatatt
11041 ttcttacatt ctgtgtgttg cttttttttta actctgttga tagtgtctgt taatacacaa
11101 aagttttaaa tgttgatgaa gtcaactaat ctattttttc ttttattgtc tatactttg
11161 gtttcttatt aaaaaaaatc attgccaaat ccaatattat ataactttta cccttgtttt
11221 cttctacaaa ttttatagtt ttaactctaa tgtttggttc tttgatccat tttgagttca
11281 tatttgtaag ttataaggta agagcccaac ttttttttaag gagatatctc atttcctcaa
11341 catcatttgt taaagagact cttctttctt aattaaatga tcttgacacc catcctggaa
11401 atcactgacc atatatgtca gagtatattc atgggctgtc tttttctattc cattggttta
11461 tatgtcagtc tttataccag taccacacat ggttttgtaa taagtttcag aactcagaaa
11521 ctgtaagact ccaactttgc tcttcctctc ttccttttta agattatttt cataattagg
11581 ggatctctgg aaatttcata tgaaagttat ggtagatttt tctatttata caaagtaatt
11641 ggaatgttgg tagaattacc tcaaacctgt acatcacttt gggtagtagt gacatcttaa
11701 gaatattaag tcttccaatt cataaacgca ggatgttttt ctaatgattt atgtcatcta
11761 caattctttt aaagggtgtt tgaagttttc actcgacaac tcttgcgcct gcttggttaa
11821 gcttattcct aagtgattta ttcttttgat gctgttaaat gggattgttt tcaaaatttc
11881 cttttctttt tgtttaggaa ggaaattaga attcctgttc taattctatt tttatacact
11941 agcaactgat ttctccatat tggctttgca tcctgcaact ttgatgaatt cttttaatag
```

```
-continued
12001  ttctaatagt tttttgtgga atatttaatg ttttccacaa attagatact accgtcggca
12061  gacagagata attttacttt ttcattacca attaggatgc ctcctttatg cttttcttgt
12121  ctaattactc tggataggac ttgcagtgtt ctgtggaatg caattggcaa aagtaggcat
12181  ccttttcttg ttcctgatgt tataggaaaa gctatgacac ttcatcatta aatgtgaagt
12241  gagctgtggg ttttaatat atggcctttta ttatgttgag gtattgtctt tctatttcta
12301  ctttgttgat tattttttatc gtgaaagcct cctgaatttt tccatgcatt ggatattcaa
12361  atttcctatt tctttgattg taagtaagta aggtgaatac tgattgttgt ttcagttctc
12421  tctcttaacc ttaaaatacg ctaccttttc cttcagttgc tagaactgcc tgttactaaa
12481  tccccatctc tggtctcctc tctcccttgc aggcttctct ctgggctcca cagtgcagtc
12541  tcacactaaa ggaatctgga tgtggtgtat gccccatccc aagaagccag gccacatcct
12601  agttctgctg gacaccgagg gtctgggaga tgtagagaag gtgagactca aggatccaat
12661  tgtggagtga gcccctcttc tctgaatatt ttatgcactg tttaattgtt tattaaccat
12721  taactacagg ctgtaatatg tgtgggttaa cacagatgca taaagggagc acaaataatc
12781  ccagtgtcat gagtcttatc ctgcacagaa ctttagttaa gaatttgggt gctaaagccc
12841  cgtgactttg tatttaaatt taaattctgt cactaattca gtagcctgag aaaattgacc
12901  tattttagcc tcagcattct aagctttaaa atgtatggaa aagacctatg ttggccacat
12961  agtataattt tgaatattta ataagaaaat acgtgtcagg tgtatattaa ttattcgata
13021  aaacagcaac taatagtacc aatcttatat gtgaattctg ttattgaaaa aagaagagaa
13081  aattttaaat ttacattgta ctcaggcctt aaaatgccca ccaaccttga attttaattt
13141  tacaattatc tgttgatgat cattagaaga cctagtaagg atcattgtaa cccaaaacat
13201  tcatcgaaaa actacccaaa agccacatcc tactgagaat acttttttgta tttggcttct
13261  ttgataggtc attagtgcta aagaacaaac aaacaaaaaa ccaaaaaccc tctaacatat
13321  gaacatagtt ttactactct tactctggaa agtgctgtga ctacgaaacg tgctcctgac
13381  tccagtgtgt cttgacttcc agggtgacaa ccagaatgac tcctggatct tcgccctggc
13441  cgtcctcctg aacagcactt ccatgtacaa tagcatagga accattaacc agcaggccat
13501  ggaccaactg cagtatcctt tgtgacccag aacagcacca aggtcagagg gcacctgtgt
13561  tcataaacca gctgcctgac tgtgaatcct gatgaatcaa gctcaaaagg agaaaacata
13621  aaatacataa agtacagagg agtgatccca tatatccact ttagacttga cacttaggtt
13681  aagaacaaag gaaatgaaa ggtttgggaa tgtgttgaac taatatggga tgaggtccat
13741  gttcattttg tcacatttct ttagttagct actcagctat gtgacagagc tgacacatcg
13801  agtccaacca aaatcttcac ctgatgagaa tgagaatgag gattcagctg actttgagag
13861  cttcttccca gactttgtgt tgacactgag agatttctag cattacagaa agcgcttttg
13921  gacaaaactg tgataaaata aactaaatgg aggactttt tttattggaa tagtttcatt
13981  tgtttcatac atattgatca aatgcttact atgaatagac tgaagataca gatataaatg
14041  aaatagatat ggttcctgtc ctaatgttgc ttggggttaa aatggatgca aacattcaat
14101  taacacaggt ctatgtaatc tagtacaaga actctcaaat gttggtatgc atacgtatct
14161  tctgaggatc ttaccaagga caaaagtcta attcaataga tcttggacag ggtctaagag
14221  tctgtatttc tgaaaaaaaa aaaaaaaaaa aaaaaaaaaa agaattacag ggaatagaga
14281  ctttctttac tacaagaaac attagcattt gttctccata ggcaggtcta gagagcctgg
14341  tgctgaccta tgtcaatgcc atcagcagtg gggatctacc ctgcatggag aacgcagtcc
```

-continued

```
14401  tggccttggc ccagatagag aactcagccg cagtgcaaaa ggctattgcc cactatgaaa
14461  agcagatggg ccagaaggtg cagctgccca cagaaaccct ccaggagctg ctggacctgc
14521  acagggacag tgagagcaag gccactgaag ttttcatcag gagttccttc aaagatgtgg
14581  accatctatt tcaaaaggag ttagcggtaa tttttgtctc aaatttatat ggtttagggt
14641  catggaagac aaagtactac aaagaaagaa aacgagtatt attttgatag aagtaattct
14701  tcctagcttt cataatggtg acaacaacag atttgtaatc acatcaatca agaggaccaa
14761  ctgtattatt acagactcaa agttttaaaa cattttttcc tgaataattt ccctttacc
14821  taaatgcata caactgataa ccagagcttc taataaaatt acctgcccac tcttctcaga
14881  ctgatttgat attctagcca aacacaaaga aaactttcat cctgcttatc ttgagcatgc
14941  ttctgttcag ccacatttat tccatatgaa atcattagtc caatatgcaa aaccagagtt
15001  ttcctctaac ggttgacata aagctatcaa tctcggtcct gaacctcacc tccaaaaaga
15061  aagcgacttc agtagaaagt ggggtcagaa ggaagagtgt ggtcctggtg aggagtctgt
15121  caatttctcc agcatcattg acttttattt tcagaagtca ttcccgaaat tctgaggtca
15181  agctaacatc ctttccctgt tactcttttt acttcctatt tttacattaa aggcccagct
15241  agacaaaaag cgggatgact tttgtaaaca gaatcaggaa gcatcatcag atcgttgctc
15301  agctttactt caggtcattt tcagtcctct agaagaagaa gtgaaggcgg aatttattc
15361  gaaaccaggg ggctatcgtc tctttattca gaagttacaa gacctggaga aaaagtacta
15421  tgaggaaccg aggaagggga tacaggtaac caaaattcat ctgtcgatta tggaaacctg
15481  ctgacctgcc tcctacaaac accaaggtga ccaagcttca ctgcacacag atgtgctttt
15541  ttgtttgcat aacattcatg cttttcattca ataacatatg caaagaggct gttattccag
15601  atatgcccta ggtgctcatc aaggagagtg caattaacta ctgagttaca aattcaacta
15661  gcagatgaag caccaagttg tcattatcat cattacagct gggcttttcc tgttgcaaga
15721  gacaggaacc taatgatggc tgcttaaaca aaaatagtaa ttcattgatt taggctgcaa
15781  actggcttta caggacaggt gggtctaagg tttcaagtaa catcatgaac tgtctctctg
15841  tccagtgttc ccccatcccc acagttttct ccctcccacc ctccctctat ctgagtcact
15901  ctgatatttg ctttctcaat gatggcttca ttccccagca ggctcagccc atatgggacc
15961  acagcattaa cagttccaaa cttagagccc ttaatctaaa caggacagag actctccttt
16021  tcccagtatc tatattagcc tactaaaaat gactgctaag taggatgctc tgatcagctt
16081  gccaggagca tgtgcctctc gctctgacag ggaatttcac caccaaggac aacagggcaa
16141  aggaaagaat tcccagagga aaggatggca ggaagacaaa caggaacacc tgcttacagc
16201  cgtctcctac ttctcacttt gtgttctctg ggtcctaagg ctgaagagat tctgcagaca
16261  tacttgaaat ccaaggagtc tatgactgat gcaattctcc agacagacca gactctcaca
16321  gaaaaagaaa aggagattga aggtgaggag tgagttaaga gattagatgg cctcaaaagc
16381  tccaaaaatt gaaataactt gactggataa acatgggacc ctttaactag agcaagatcc
16441  acaaaggtgt gtcttacttg ccgaggtcat ctctgagtag ggcatatgca gtcagcaaca
16501  acgacaggta agtgtataag gaacaatgag gcaacaagat aaccccacac aaatttcct
16561  tctttctttt cctccacagt ggaacgtgtg aaagctgagt ctgcacaggc ttcagcaaaa
16621  atgttgcagc aaatgcaaag aaagaatgag cagatgatgg aacagaagga gaggagttat
16681  caggaacact tgaaacaact gactgagaag atggagagcg acagggtcca gttgctggaa
16741  gagcaagaga ggaccctcgc tcttaaactt caggtgtcta attgcatcac cttgaggttt
16801  ctgttttcct gttttctctc cattctcccc gatcacaggc ttactgtggc agagagaaca
```

-continued

```
16861 tgaagcccag gggaagaacc ctgcttgctt acttgtactt ttcaattcct gtctgtccag
16921 cctgaactgg ctactgccaa gtctggtcac taaactgcaa atattgcagt tgtgtcacat
16981 tcagtgcttt atctatatat ccttcatttc aaggcaggta ttatctgcta gccatcatta
17041 aagtatctgt atctcttgct taataccatg tgaagcaaga actatattct tattacttag
17101 gagaagaaac aaagtttcca aaataataa ataaatagag tcacacagct agtaaatgta
17161 tcaaagctgt cttcatcact tagtggaatc cacaatgatt atttttttct gtgacaccta
17221 gtatgaaatt aaacttaaga aaacctttgt gagcaga
```

AA2 LGALS3BP-galectin-3-binding protein precursor, mRNA-NM_005567.3
(SEQ ID NO: 114)

```
   1 aatcgaaagt agactctttt ctgaagcatt tcctgggatc agcctgacca cgctccatac
  61 tgggagaggc ttctgggtca aggaccagt ctgcagaggg atcctgtggc tggaagcgag
 121 gaggctccac acggccgttg cagctaccgc agccaggatc tgggcatcca ggcacggcca
 181 tgaccctcc gaggctcttc tgggtgtggc tgctggttgc aggaacccaa ggcgtgaacg
 241 atggtgacat gcggctggcc gatggggcg ccaccaacca gggccgcgtg agatcttct
 301 acagaggcca gtggggcact gtgtgtgaca acctgtggga cctgactgat gccagcgtcg
 361 tctgccgggc cctgggcttc gagaacgcca cccaggctct gggcagagct gccttcgggc
 421 aaggatcagg ccccatcatg ctggatgagg tccagtgcac gggaaccgag gcctcactgg
 481 ccgactgcaa gtccctgggc tggctgaaga gcaactgcag gcacgagaga gacgctggtg
 541 tggtctgcac caatgaaacc aggagcaccc acaccctgga cctctccagg gagctctcgg
 601 aggcccttgg ccagatctt gacagccagc ggggctgcga cctgtccatc agcgtgaatg
 661 tgcagggcga ggacgccctg ggcttctgtg ccacacggt catcctgact gccaacctgg
 721 aggcccaggc cctgtggaag gagccgggca gcaatgtcac catgagtgtg gatgctgagt
 781 gtgtgcccat ggtcagggac cttctcaggt acttctactc ccgaaggatt gacatcaccc
 841 tgtcgtcagt caagtgcttc acaagctgg cctctgccta tggggccagg cagctgcagg
 901 gctactgcgc aagcctcttt gccatcctcc tccccagga ccccctcgttc cagatgcccc
 961 tggacctgta tgcctatgca gtggccacag gggacgccct gctggagaag ctctgcctac
1021 agttcctggc ctggaacttc gaggccttga cgcaggccga ggcctggccc agtgtcccca
1081 cagacctgct ccaactgctg ctgcccagga cgacctggc ggtgcccagc gagctggccc
1141 tactgaaggc cgtggacacc tggagctggg gggagcgtgc ctcccatgag gaggtggagg
1201 gcttggtgga aagatccgc ttcccccatga tgctccctga ggagctcttt gagctgcagt
1261 tcaacctgtc cctgtactgg agccacgagg ccctgttcca agaagagact ctgcaggccc
1321 tggaattcca cactgtgccc ttccagttgc tgcccggta caaggcctg aacctcaccg
1381 aggataccta caagcccgg atttacacct cgcccacctg gagtgccttt gtgacagaca
1441 gttcctggag tgcacggaag tcacaactgg tctatcagtc cagacggggg cctttggtca
1501 aatattcttc tgattacttc caagcccct ctgactacag atactacccc taccagtcct
1561 tccagactcc acaacacccc agcttcctct tccaggacaa gagggtgtcc tggtccctgg
1621 tctacctccc caccatccag agctgctgga actacggctt ctcctgctcc tcggacgagc
1681 tccctgtcct gggcctcacc aagtctggcg gtcagatcg caccattgcc tacgaaaaca
1741 aagccctgat gctctgcgaa gggctcttcg tggcagacgt caccgatttc gagggctgga
1801 aggctgcgat tcccagtgcc ctggacacca acagtcgaa gagcacctcc tccttcccct
1861 gcccggcagg gcacttcaac ggcttccgca cggtcatccg cccccttcctac ctgaccaact
```

-continued

```
1921  cctcaggtgt ggactagacg gcgtggccca agggtggtga gaaccggaga accccaggac
1981  gccctcactg caggctcccc tcctcggctt ccttcctctc tgcaatgacc ttcaacaacc
2041  ggccaccaga tgtcgcccta ctcacctgag cgctcagctt caagaaatta ctggaaggct
2101  tccactaggg tccaccagga gttctcccac cacctcacca gtttccaggt ggtaagcacc
2161  aggacgccct cgaggttgct ctgggatccc cccacagccc ctggtcagtc tgcccttgtc
2221  actggtctga ggtcattaaa attacattga ggttcctaca aaaaaaaaaa aaaaaaa
```

AB1 BST1-bone marrow stromal cell antigen 1, mRNA NM_004334.2

(SEQ ID NO: 115)

```
   1  aaagtgctgg gattacaggc atgagccgcc gcgccccgcc ccacgctcag tcttgaaatt
  61  gtctggaacg ggaaacggca acagcgaga tatccgagcg agagtcccgc cctgcatcag
 121  tttgcggaac cgccttggta aaggagaga aggggagtgg aggaagcacg ggactggagg
 181  gaccaaagtt ccccgatggc ggcccagggg tgcgcggcat cgcggctgct ccagctgctg
 241  ctgcagcttc tgcttctact gttgctgctg gcggcgggcg gggcgcgcg gcggtggcgc
 301  ggggagggca ccagcgcaca cttgcggac atcttcctgg gccgctgcgc cgagtaccgc
 361  gcactgctga gtcccgagca gcggaacaag aactgcacag ccatctggga agcctttaaa
 421  gtggcgctgg acaaggatcc ctgctccgtg ctgcccctcag actatgacct ttttattaac
 481  ttgtccaggc actctattcc cagagataag tccctgttct gggaaaatag ccacctcctt
 541  gttaacagct ttgcagacaa caccccgtcgt tttatgcccc tgagcgatgt tctgtatggc
 601  agggttgcag atttcttgag ctggtgtcga cagaaaaatg actctggact cgattaccaa
 661  tcctgcccta catcagaaga ctgtgaaaat aatcctgtgg attccttttg gaaaagggca
 721  tccatccagt attccaagga tagttctggg gtgatccacg tcatgctgaa tggttcagag
 781  ccaacaggag cctatcccat caaaggtttt tttgcagatt atgaaattcc aaacctccag
 841  aaggaaaaaa ttacacgaat cgagatctgg gttatgcatg aaattggggg acccaatgtg
 901  gaatcctgcg gggaaggcag catgaaagtc ctggaaaaga ggctgaagga catgggggttc
 961  cagtacagct gtattaatga ttaccgacca gtgaagctct acagtgcgt ggaccacagc
1021  acccatcctg actgtgcctt aaagtcggca gcagccgcta ctcaaagaaa agccccaagt
1081  ctttatacag aacaagggc gggtcttatc attcccctct ttctggtgct ggcttccagg
1141  actcaactgt aactggaaac tgtgttgctc taaccctcct ccagccctg agcctcccct
1201  tgcagtcatc attcgtgttc tgtgtatacc aaatgattct gttatctaaa gaagcttttt
1261  gctgggaaaa cgatgtcctg aaaatggtat ttcaatgagg catatgttca ggatttcaga
1321  aacaagaagt tagttctatt tagcaggtta aaaaatgctg cattagaatt aaagcaagtt
1381  attttcttat tgtataatg acacaaagca tgggagtca gactgcttgt atattatcaa
1441  acattttaag agaattctaa taaagctgta ttttacatca aaaaaaaaaa aaaaaaa
```

AB2 SNX10-sorting nexin-10, mRNA NM_001199835.1

(SEQ ID NO: 116)

```
   1  gctgagcgcg ggcgcggggc cgctacgtgc gcggggagcg cggggagcgc ggggagcgcg
  61  gggctgcgct cgtgtgcgct cctgggcgct cgccgccgcc gctgccgccg cgcgcctttg
 121  agtcagcaaa ctccgcgcc cgcaagcccg gtcggcccg gccctgctct gttctgcccg
 181  gaggagccgc ccgtaagtga caagagaccc gctgaggggg cctcccctgc accgcccaga
 241  ttgatcgtgt cctgtgctga agatgtttcc ggaacaacag aaagaggaat tgtaagtgt
 301  ctgggttcga gatcctagga ttcagaagga ggacttctgg cattcttaca ttgactatga
 361  gatatgtatt catactaata gcatgtgttt tacaatgaaa acatcctgtg tacgaagaag
 421  atatagagaa ttcgtgtggc tgaggcagag actccaaagt aatgcgttgc tggtacaact
```

-continued

```
 481 gccagaactt ccatctaaaa acctgttttt caacatgaac aatcgccagc acgtggatca
 541 gcgtcgccag ggtctggaag atttcctcag aaaagtccta cagaatgcac ttttgctttc
 601 agatagcagc cttcacctct tcttacagag ccatctgaat tcagaagaca ttgaggcgtg
 661 tgtttctggg cagactaagt actctgtgga agaagcaatt cacaagtttg ccttaatgaa
 721 tagacgtttc cctgaagaag atgaagaagg aaaaaaagaa atgatatag attatgattc
 781 agaaagttca tcctctgggc ttggacacag tagtgatgac agcagttcac atggatgtaa
 841 agtaaataca gctccgcagg aatcctgaaa ataattcta atgttactat cttaggaata
 901 gcaaattatg tccagtcata gagaagaaag cttcataata atacattctt acctaaagct
 961 cactgtcatg atgttaggta tttaaattct taaagatgtt gggttgttta ttagtggtat
1021 ttttatgttg tcttatttta ggtaagcttc tgtgtaaagc taaaaatcct gtgaatacaa
1081 tactatcctt tacaggcaga cattattggt aaacaagatc ttgccctcca atgaaatgac
1141 ttacatgttt taaaaaaccg agttggtttt attgaattta aaagataggt aactaagta
1201 gcatttaaaa tcaagataga gcattccttc ttgtatcagt ggggcagtgt taccataaac
1261 acggtgtata tgttgttaaa ccctatgaag agtaacagtg tagaccagac tgcctctctc
1321 agatatgtgc ctgatatttt gtggataccc ccctgcact ggcaaaacac tatgcttttg
1381 ggtgttagac tgaaatattt taagagtatt taacctttcc agtattctgt ttcacgctta
1441 gatggaaatg tatcttatga atagagacat attaaaataa tgtttacatc ttagaaaaaa
1501 catagatagt gctagtaata ttacttataa ctgtaatata tagattcaga aatacatttt
1561 cattatccaa aatcagcttc aacaaatggt ttctggagac aaataatttg ttttcattat
1621 cattgtataa tcaggttaat gattttatttt ttgactaaat gtgcaatttc ttatcactag
1681 ataactttca gtatcagtgg tggttactta ttacttaaat cagaggaagg attttataaa
1741 gattaataaa tttaatttta ccaataaata ttcccataat ttagaaaagg atgtcgactt
1801 gctaatttca gaaataatta ttcatttta aaaagcccct tttaaagcat ctacttgaag
1861 attggtataa ttttcataaa atgtctttttt ttttagtgtc caaagatat cttagataaa
1921 ctattttgaa gttcagattt cagatgaggc aacatttctct tgagataatt acccaagttt
1981 catccatgtt gaatggtaca aatatttctct gtgaaactaa caggaagata ttttcagata
2041 actaggataa cttgttgctt tgttacccag cctaattgaa gagtggcaga ggctactaca
2101 aaaagcaacc ttttcatttt cactaagagt ttaaaagcta ttgtattatt aaaaagtctt
2161 tacaatgctt gtttcaaaga accaacagaa aaaaaagcta agaaaactga gaactaacat
2221 taaaaaaatt aaatttagaa taagaatgat ttctttaatt tgtccttttt ttctttggtc
2281 taaaacatta ttaaattttt gtaaatattt tgatttaatg tgtcttagat cctcattatt
2341 ttaatacagg aaaagaaaag atttagtaat ttcttaccat gctaatatgt aaagttcatg
2401 ccatccaggc atttaagagc gatcctcatc ccttcagcaa tatgtatttg agttcacact
2461 atttctgttt tacagcagtt ttgaaaaaca catactatgc caccaattgt catattattt
2521 ttagatgatg taacatagcc atcaaaatta atattatgta atgcctaata cttagtatgt
2581 aaatgtcacg agatcatttt tacattaaac gtgaaaaaaa atcaaaaaaa aaaaaaaa
```

AC1 ALPK1-alpha-kinase 1, mRNA-NM_025144.3

(SEQ ID NO: 117)

```
   1 aattcctact tcctgaaact gaagccgttt atgagaaaca gtgtgtttca gagaggctgt
  61 accagaatta actctgctca gagttagatt tgctggtctt aaagtacttt tcctctttaa
 121 gataaaagaa gttcttctaa atcaggaatg gattgaaatc taatgaaccg aaactttggg
```

-continued

```
 181  tacttcggcc ttcaagggggc tcctttattg agaatcaatg tcttctccta ggtaattgat
 241  caccctagac ccagggacac ccaattcatc gtaatcatca tgaataatca aaaagtggta
 301  gctgtgctac tgcaagagtg caagcaagtg ctggatcagc tcttgttgga agcgccagat
 361  gtgtcggaag aggacaagag cgaggaccag cgctgcagag ctttactccc cagcgagtta
 421  aggaccctga tccaggaggc aaaggaaatg aagtggccct tcgtgcctga aaagtggcag
 481  tacaaacaag ccgtgggccc agaggacaaa acaaacctga aggatgtgat tggcgccggg
 541  ttgcagcagt tactggcgtc cctgagggcc tccatcctcg ctcgggactg tgcggctgcg
 601  gcggctattg tgttcttggt ggaccggttc ctgtatgggc tcgacgtctc tggaaaactt
 661  ctgcaggtcg ccaaaggtct ccacaagttg cagccagcca cgccaattgc cccgcaggtg
 721  gttattcgcc aagcccgaat ctccgtgaac tcaggaaaac ttttaaaagc agagtatatt
 781  ctgagcagtc taataagcaa caatggagca acgggtacct ggctgtacag aaatgaaagt
 841  gacaaggtcc tggtgcagtc ggtctgtata cagatcagag ggcagattct gcaaaagctg
 901  gggatgtggt acgaagcagc agagttaata tgggcctcca ttgtaggata tttggcactt
 961  cctcagccgg ataaaaaggg cctctccacg tcgctaggta tactggcaga catctttgtt
1021  tccatgagca agaacgatta tgaaaagttt aaaaacaatc cacaaattaa tttgagcctg
1081  ctgaaggagt ttgaccacca tttgctgtcc gctgcagaag cctgcaagct ggcagctgcc
1141  ttcagtgcct atacgccgct cttcgtgctc acagctgtga atatccgtgg cacgtgttta
1201  ttgtcctaca gtagttcaaa tgactgtcct ccagaattga aaaacttaca tctgtgtgaa
1261  gccaaagagg cctttgagat tggcctcctc accaagagag atgatgagcc tgttactgga
1321  aaacaggagc ttcacagctt tgtcaaagct gctttcggtc tcaccacagt gcacagaagg
1381  ctccatgggg agacaggac ggtccatgca gcaagtcagc tctgtaagga agcaatgggg
1441  aagctgtaca atttcagcac ttcctccaga agtcaggaca gagaagctct gtctcaagaa
1501  gttatgtctg tgattgccca ggtgaaggaa catttacaag ttcaaagctt ctcaaatgta
1561  gatgacagat cttatgttcc cgagagtttc gagtgcaggt tggataaact tatcttgcat
1621  gggcaagggg atttccaaaa aatccttgac acctattcac agcaccatac ttcggtgtgt
1681  gaagtatttg aaagtgattg tggaaacaac aaaaatgaac agaaagatgc aaaaacagga
1741  gtctgcatca ctgctctaaa acagaaaata aaaaacatag atactgtgag tactactcaa
1801  gaaaagccac attgtcaaag agacacagga atatcttcct ccctaatggg taagaatgtt
1861  cagagggaac tcagaagggg aggaaggaga aactggaccc attctgatgc atttcgagtc
1921  tccttggatc aagatgtgga gactgagact gagccatcgg actacagcaa tggtgaggga
1981  gctgttttca acaagtctct gagtggcagc cagacttcca gtgcttggag caacttatca
2041  gggtttagtt cctctgcaag ctgggaggaa gtgaattatc acgttgacga caggtcagcc
2101  agaaaagagc ctggcaaaga acatctggtg gacactcagt gttccactgc cttgtctgag
2161  gagctagaga atgacaggga aggcagagct atgcattcat tgcattcaca gcttcatgat
2221  ctctctcttc aggaacccaa caatgacaat ttggagcctt ctcaaaatca gccacagcaa
2281  cagatgccct tgacacccct tctcgcctcat aatacccccag gcattttctt ggcccctggt
2341  gcagggcttc tagaaggagc tccagaaggt atccaggaag tcagaaatat gggacccaga
2401  aatacttctg ctcactccag accctcatat cgttctgctt cttggtcttc tgattctggt
2461  aggcccaaga atatgggcac acatccttca gtccaaaaag aagaagcctt tgaaataatt
2521  gttgagtttc cagaaaccaa ctgcgatgtc aaagacaggc aggggaaaga gcagggagaa
2581  gaaattagtg aaagaggcgc aggccctaca tttaaagcta gtccctcctg ggttgaccca
```

-continued

```
2641  gaaggagaaa cagcagaaag cactgaagat gcacccttag actttcacag ggtcctgcac 2701  aattctctgg gaaacatttc catgctgcca tgtagctcct tcacccctaa ttggcctgtt 2761  caaaatcctg actccagaaa aagtggtggc ccagtcgcag agcagggcat cgaccctgat 2821  gcctccacag tggatgagga ggggcaactg ctcgacagca tggatgttcc ctgcacaaat 2881  gggcacggct ctcatagact gtgcattctg agacagccgc ctggtcagag ggcggagacc 2941  cccaattcct ctgtaagcgg taacatcctc ttccctgtcc tcagcgagga ctgcactacc 3001  acagaggaag gaaatcagcc tggaaacatg ctaaactgca gccagaactc cagctcatcc 3061  tcagtgtggt ggctgaaatc acctgcattt tccagtggtt cttctgaggg ggacagccct 3121  tggtcctatc tgaattccag tgggagttct tgggtttcat tgccgggaaa gatgaggaaa 3181  gagatccttg aggctcgcac cttgcaacct gatgactttg aaaagctgtt ggcaggagtg 3241  aggcatgatt ggctgtttca gagactagag aatacggggg ttttttaagcc cagtcaactc 3301  caccgagcac atagtgctct tttgttaaaa tattcaaaaa atctgaact gtggacggcc 3361  caggaaacta ttgtctattt gggggactac ttgactgtga agaaaaagg cagacaaaga 3421  aatgctttt gggttcatca tcttcatcaa gaagaaattc tggggaggta tgttgggaaa 3481  gactataagg agcagaaggg gctctggcac cacttcactg atgtggagcg acagatgacc 3541  gcacagcact atgtgacaga atttaacaag agactctatg aacaaaacat tcccacccag 3601  atattctaca tcccatccac aatactactg attttagagg acaagacaat aaagggatgt 3661  atcagtgtgg agccttacat actgggagaa tttgtaaaat tgtcaaataa cacgaaagtg 3721  gtgaaaacag aatacaaagc cacagaatat ggcttggcct atggccattt ttcttatgag 3781  ttttctaatc atagagatgt tgtggtcgat ttacaaggtt gggtaaccgg taatggaaaa 3841  ggactcatct acctcacaga tccccagatt cactccgttg atcagaaagt tttcactacc 3901  aattttggaa agagaggaat ttttttacttc tttaataacc agcatgtgga atgtaatgaa 3961  atctgccatc gtctttcttt gactagacct tcaatggaga aaccatgcac atagaatacg 4021  gcacagtctg gtcctttggg gcttgggcag ggccgtgaca caggttctgg ccaatgattt 4081  gcaagaggaa ttgatcagta tcactttaag tcctgcattt aattggcagc acaagatcct 4141  gcagagcctc tttccctctg ccacagttat caagaatggg tcaggagacc gctgcttctg 4201  ggcataagtc ctgcaaggaa agcaacatgg aaaacagccc caactcaccc atgagggatg 4261  aaaagcactc ttgagaaagg catgtgttgt ttaagccatt gagattttag agcttttttgt 4321  cactatctgt caagactgat actactgggg cttttcctat tgatttggga gttcttttaca 4381  tattaaaaaa atgtgagcct ttgtgatacg aattcaattt gttttcctgt cttttgacat 4441  ttgactttgc ataaaagttt atctgtgcat aattttatat gtagttgaat tcatcaatct 4501  tttatttttgt atggcttttt ggttatgtat aatacttaga tcctccttat actctgagtt 4561  tcttttcttttt taattctcct gtatttcctt ctagtataat taaatctgta aaaagtaaga 4621  tggaagagtg gtacagtttt ctttatccag tctgtccttg atgggcattt aggtagactg 4681  gataaagaaa atgtggtaca tatacaccat ggaacactat gtgtattaat ccactctcac 4741  actgctatga agagatacct gagactgggt aatttagaaa gaaagaggt ttaattaact 4801  cacagttcca catggctggg gagacctcag gaaacttaca atcatggcag aaggcacctc 4861  ttcatagggt agcaggagag agaatgagtg ccagcagggg aaatgccaga tgcttataaa 4921  gccatcagat cttgtgagaa ttcattcact ctcacgagaa cagcatggga aaaactgcct 4981  caattacctc ctaccaggtc cttcccatga cacatgggaa ttatgggact acaattcgag
```

-continued

```
5041  atgagatttg gtgggggaca caaagccaaa ccatatcaca atgtaaccat aaaaaagaat
5101  gagatcatgt cctttgcagg gacatggata gagctggagg ccattatttt tagcaaacta
5161  atgcaagaac agaaaactaa ataccacttg ttctcactta taggtgagag ctaagtgatg
5221  agagtaggtg gacacataga gggaacaaca cacaccaggg cttatcagag ggtggacagt
5281  gggaggaggg agaggatcag gaaaaataac taatgggtac taggctgaat acctgggtga
5341  tgaagtaatt cgcacaacaa accccccatga cacaaacctg cacatgtacc cctgaactta
5401  aaataaaagt aaaaaaaaaa aaaaaaaaa aaaaaaaaa a
```

AC2 CREG1-cellular repressor of E1A-stimulated genes 1, mRNA NM_003851.2
(SEQ ID NO: 118)

```
   1  ggcggggcct gggcgcgccg agctccggct gggtccctgc aggtcttggg gcccgggact
  61  cttcctggag acaccgccat ggccgggcta tcccgcgggt ccgcgcgcgc actgctcgcc
 121  gccctgctgg cgtcgacgct gttggcgctg ctcgtgtcgc ccgcgcgggg tcgcggcggc
 181  cgggaccacg gggactggga cgaggcctcc cggctgccgc cgctaccacc ccgcgaggac
 241  gcggcgcgcg tggccccgctt cgtgacgcac gtctccgact ggggcgctct ggccaccatc
 301  tccacgctgg aggcggtgcg cggccggccc ttcgccgacg tcctctcgct cagcgacggg
 361  cccccgggcg cgggcagcgg cgtgccctat ttctacctga gcccgctgca gctctccgtg
 421  agcaacctgc aggagaatcc atatgctaca ctgaccatga ctttggcaca gaccaacttc
 481  tgcaagaaac atggatttga tccacaaagt ccccctttgtg ttcacataat gctgtcagga
 541  actgtgacca aggtgaatga aacagaaatg gatattgcaa agcattcgtt attcattcga
 601  caccctgaga tgaaaacctg gccttccagc cataattggt tctttgctaa gttgaatata
 661  accaatatct gggtcctgga ctactttggt ggaccaaaaa tcgtgacacc agaagaatat
 721  tataatgtca cagttcagtg aagcagactg tggtgaattt agcaacactt atgaagtttc
 781  ttaaagtggc tcatacacac ttaaaaggct taatgttct ctggaaagcg tcccagaata
 841  ttagccagtt ttctgtcaca tgctggtttg tttgcttgct tgtttacttg cttgtttacc
 901  aatagagttg acctgttatt ggatttcctg gaagatgtgg tagctacttt tttcctattt
 961  tgaagccatt ttcgtagaga aatatccttc actataatca aataagtttt gtcccatcaa
1021  ttccaaagat gtttccagtg gtgctcttga agaggaatga gtaccagttt taaattgccc
1081  attggcattt gaaggtagtt gagtatgtgt tctttattcc tagaagccac tgtgcttggt
1141  agagtgcatc actcaccaca gctgcctcct gagctgcctg agcctggtgc aaaaggattg
1201  gccccccatta tggtgcttct gaataaatct tgccaagata gacaaacaat gatgaaactc
1261  agatggagct tcctactcac gttgattat gtctcacaat cctgggtatt gttaattcaa
1321  catagggtga aactatttct gataaagaac ttttgaaaaa ctttttatac tctaaagtga
1381  tactcagaac aaaagaaagt cataaaactc ctgaatttaa tttccccacc taagtcgaaa
1441  cagtattatc aaaacacatg tgcacacaga ttattttttg gctccaaaac tggattgcaa
1501  aagaaagagg agaagaatat tttgtgtgtt cctggtattc ttttataagt aaagtttacc
1561  caggcatgga ccagcttcag ccagggacaa aatcccctcc caaaccactc tccacagctt
1621  tttaaaaata cttctactct taacaattac ctaggcttc ctcaactgcc caaatctct
1681  taatagcttc tagtgctgct acaatctaag tcaggtcacc agagggaaga gaacatggca
1741  ttaaaagaat cacatcttca gaagagaaga cactaatatt attacccata tacatgattt
1801  cagaagatga cataagattc ctcttaaaga ggaaatgtca ggaatcaagc cactgaatcc
1861  ttaaagagaa aagttgaata tgagtcattg tgtctgaaaa ctgcaaagtg aacttaactg
1921  agatccagca aacaggttct gtttaagaaa ataatttat actaaattta gtaaaatgga
```

-continued

```
1981 cttcttattc aaagcatcaa taattaaaag aattattttta atgaaaaaaa aaaaaaaaaa
2041 aaaaaaaa
```

AD1 BAZ1A-bromodomain adjacent to zinc finger domain protein 1A, mRNA
NM_013448.2
(SEQ ID NO: 119)

```
   1 cttttcccat cgtgtagtca agagtctgtg ccagacttga aggctttact ttgttagcca
  61 tgtgtttatg aaccccagc gctttcccta gatcttttgg ctgataatct caaacatgga
 121 ggatgcttct gaatcttcac gaggggttgc tccattaatt aataatgtag ttctcccagg
 181 ctctccgctg tctcttcctg tatcagtgac aggctgtaaa agtcatcgag tagccaataa
 241 aaaggtagaa gcgaggagtg aaaagctcct cccaacagct cttcctcctt cagagccgaa
 301 agtagatcag aaacttccca ggagctccga gaggcgggga agtggcggtg ggacgcaatt
 361 ccccgcgcgg agtcgggcag tggcagcggg agaagcggca gccaggggcg cggcggggcc
 421 ggagagaggc ggtcccctgg gaggacgggg tctcccctcg ttgcctttgt agtggagaag
 481 gtggacaagt ggcagtcggc gtgatcgcag ggaagcgggg ccggcgcggg cggccgaggg
 541 tccaggcgag cccgcgggcg gacgggagat gccgctgcta caccgaaagc cgtttgtgag
 601 acagaagccg cccgcggacc tgcgcccga cgaggaagtt ttctactgta aagtcaccaa
 661 cgagatcttc cgccactacg atgactttt tgaacgaacc attctgtgca acagccttgt
 721 gtggagttgt gctgtgacgg gtagacctgg actgacgtat caggaagcac ttgagtcaga
 781 aaaaaagca agacagaatc ttcagagttt tccagaacca ctaattattc cagttttata
 841 cttgaccagc cttacccatc gttcgcgctt acatgaaatt tgtgatgata tctttgcata
 901 tgtcaaggat cgatatttg tcgaagaaac tgtggaagtc attaggaaca atggtgcaag
 961 gttgcagtgt aggattttgg aagtcctccc tccatcacat caaaatggtt ttgctaatgg
1021 acatgttaac agtgtggatg gagaaactat tatcatcagt gatagtgatg attcagaaac
1081 acaaagctgt tcttttcaaa atgggaagaa aaaagatgca attgatccct actattcaa
1141 gtataaagtg caacccacta aaaagaatt acatgagtct gctattgtta agcaacaca
1201 aatcagccgg agaaaacacc tattttctcg tgataaacta agctttttc tgaagcaaca
1261 ctgtgaacca caagatggag tcattaaaat aaaggcatca tctctttcaa cgtataaaat
1321 agcagaacaa gatttttctt atttcttccc tgatgatcca cccacattta tcttcagtcc
1381 tgctaacaga cgaagaggga gacctcccaa acgaatacat attagtcaag aggacaatgt
1441 tgctaataaa cagactcttg caagttatag gagcaaagct actaaagaaa gagataaact
1501 tttgaaacaa gaagaaatga agtcactggc ttttgaaaag gctaaattaa aaagagaaaa
1561 agcagatgcc ctagaagcga agaaaaaaga aaagaagat aaagagaaaa agagggaaga
1621 attgaaaaaa attgttgaag aagagagact aaagaaaaaa gaagaaaaag agaggcttaa
1681 agtagaaaga gaaaaggaaa gagagaagtt acgtgaagaa aagcgaaagt atgtggaata
1741 cttaaaacag tggagtaaac ctagagaaga tatggaatgt gatgacctta aggaacttcc
1801 agaaccaaca ccagtgaaaa ctagactacc tcctgaaatc tttggtgatg ctctgatggt
1861 tttggagttc cttaatgcat ttggggaact tttgatctt caagatgagt ttcctgatgg
1921 agtaacccta gaagtattag aggaagctct tgtaggaaat gacagtgaag gcccactgtg
1981 tgaattgctt ttttctcc tgactgcaat cttccaggca atagctgaag aagaagagga
2041 agtagccaaa gagcaactaa ctgatgctga caccaaagat ttaacagagg ctttggatga
2101 agatgcagac cccacaaaat ctgcactgtc tgcagttgca tctttggcag ctgcatggcc
2161 acagttacac cagggctgca gtttgaaaag tttggatctt gatagctgca ctctttcaga
```

-continued

```
2221  aatcctcaga ctgcacatct tagcttcagg tgctgatgta acatcagcaa atgcaaagta
2281  tagatatcaa aaacgaggag gatttgatgc tacagatgat gcttgtatgg agcttcgttt
2341  gagcaatccc agtctagtga agaaactgtc aagcacctca gtgtatgatt tgacaccagg
2401  agaaaaaatg aagatactcc atgctctctg tggaaagcta ctgacccag tttcaactag
2461  ggattttatt gaagattatg ttgatatatt acgacaggca agcaggagt tccgggaatt
2521  aaaagcagaa caacatcgaa agagaggga agaagcagct gccagaattc gtaaaggaa
2581  ggaagaaaaa cttaaggagc aagaacaaaa aatgaaagag aaacaagaaa aactgaaaga
2641  agatgagcaa agaaattcaa cggcagatat atctattggg gaggaagaaa gggaagattt
2701  tgatactagc attgagagca agacacaga gcaaaaggaa ttagatcaag atatggtcac
2761  tgaagatgaa gatgacccag gatcacataa aagaggcaga aggggaaaa gaggacaaaa
2821  tggatttaaa gaatttacaa ggcaagaaca gatcaactgt gtaacaagag agcctcttac
2881  tgctgatgag gaagaagcat taaaacagga acaccaacga aaagagaaag agctcttaga
2941  aaaaatccaa agtgccatag cctgtaccaa tatctttccc ttgggtcgcg accgcatgta
3001  tagacgatac tggattttcc cttctattcc tggactcttt attgaagagg attattctgg
3061  tcttactgaa gacatgctgt tgcctagacc ttcatcattt cagaataatg tacagtctca
3121  agatcctcag gtatccacta aaactggaga gccttttgatg tctgaatcta cctccaacat
3181  tgaccaaggt ccacgtgacc attctgtgca gctgccaaaa ccagtgcata agccaaatcg
3241  gtggtgcttt tacagttctt gtgaacagct agaccagctt attgaagctc ttaattctag
3301  aggacataga gaaagtgcct taaaagaaac tttgttacaa gagaaaagca gaatatgtgc
3361  acagctagcc cgttttttctg aagagaaatt tcattttttca gacaaacctc agcctgatag
3421  caaaccaaca tatagtcggg gaagatcttc caatgcatat gatccatctc agatgtgtgc
3481  agaaaagcaa cttgaactaa ggctgagaga ttttcttta gatattgaag atagaatcta
3541  ccaaggaaca ttaggagcca tcaaggttac agatcgacat atctggagat cagcattaga
3601  aagtggacgg tatgagctgt taagtgagga aaacaaggaa aatgggataa ttaaaactgt
3661  gaatgaagac gtagaagaga tggaaattga tgaacaaaca aaggtcatag taaaagacag
3721  acttttgggg ataaaaacag aaactccaag tactgtatca acaaatgcaa gtacaccaca
3781  atcagtgagc agtgtggttc attatctggc aatggcactc tttcaaatag agcagggcat
3841  tgagcggcgt tttctgaaag ctccacttga tgccagtgac agtgggcgtt cttataaaac
3901  agttctggac cgttggagag agtctctcct ttcttctgct agtctatccc aagtttttct
3961  tcacctatcc accttggatc gtagcgtgat atggtctaaa tctatactga atgcgcgttg
4021  caagatatgt cgaaagaaag gcgatgctga aaacatggtt ctttgtgatg gctgtgatag
4081  gggtcatcat acctactgtg ttcgaccaaa gctcaagact gtgcctgaag gagactggtt
4141  ttgtccagaa tgtcgaccaa agcaacgttc tagaagactc tcctctagac agagaccatc
4201  cttggaaagt gatgaagatg tggaagacag tatgggaggt gaggatgatg aagttgatgg
4261  cgatgaagaa gaaggtcaaa gtgaggagga agagtatgag gtagaacaag atgaagatga
4321  ctctcaagaa gaggaagaag tcagcctacc caaacgagga agaccacaag ttagattgcc
4381  agttaaaaca agagggaaac ttagctcttc ttctctcaagt cgtggccaac aacaagaacc
4441  tggaagatac ccttcaagga gtcagcagag cacacccaaa caactgtttt cttctaaaac
4501  tggtagaagc ctaagaaaga taaaactctgc cctcctaca gaaacaaaat ctttaagaat
4561  tgccagtcgt tctactcgcc acagtcatgg cccactgcaa gcagatgtat ttgtggaatt
```

-continued

```
4621  gcttagtcct cgtagaaaac gcagaggcag gaaaagtgct aataatacac cagaaaatag 4681  tcccaacttc cctaacttca gagtcattgc cacaaagtca agtgaacagt caagatctgt 4741  aaatattgct tcaaaacttt ctctccaaga gagtgaatcc aaaagaagat gcagaaaaag 4801  acaatctcca gagccatcgc ctgtgacact gggtcgaagg agttctggcc gacagggagg 4861  agttcatgaa ttgtctgctt ttgaacaact tgttgtagaa ttggtacgac atgatgacag 4921  ctggcctttt ttgaaacttg tttctaaaat ccaggtccca gactactatg acatcatcaa 4981  aaagcccatt gccttaaata taattcgtga aaaagtgaat aagtgtgaat ataaattagc 5041  atctgagttt attgatgaca ttgagttaat gttttcgaac tgctttgaat acaaccctcg 5101  taacacaagt gaagcaaaag ctggaactag gcttcaagca ttttttcata ttcaggctca 5161  aaagcttgga ctccacgtca cacccagtaa tgtggaccaa gttagcacac caccggctgc 5221  gaaaaagtca cgaatctgac tttgtccttc taaggatat atttgaagaa aaacaaattg 5281  ttcatgaaaa tggaacatta aatcatgctg tataaagcaa taacaattga ttgaccacat 5341  gaaagtgtgg cctgcactat attctcaatt ttaatattaa gcactcagga gaatgtagga 5401  aagatatcct ttgctacagt tttgttcagt atctaataag tttgatagat gtattggata 5461  cagtactggt ttacagaggt tttgtacat ttttgagatc attcatgtgt ccagagatct 5521  tggaaaatat ttttttcaccc acgatttatt ttgttattga tgattttttt ttaaagtggt 5581  ggtattaagg gagagttatc tacatggatg agtcttccgc tatagcacag tttagaaaag 5641  gtgtttatgt cttaattaat tgtttgagta cattctttca acactacaca tgaatgaatc 5701  caatcttata accttgaagt gctgtaccag tgctggctgc aggtattaag tccaagttta 5761  ttaactagat atttatttag tattgagagt aatttgtgaa tttgtttgt atttataaaa 5821  tttatacctg aaaaatgttc cttaatgttt taaaccttt actgtgtttt tattcctcta 5881  acttccttaa tgatcaatca aaaaaagtaa caccctccct ttttcctgac agttctttca 5941  gctttacaga actgtattat aagtttctat gtataacttt ttaactgtac aaataaaata 6001  acatttttc aaataaaaaa aaaaaaaaa a
```

AD2 LYN-v-yes-1 Yamaguchi sarcoma viral related oncogene homolog,
mRNA NM_001111097.2
(SEQ ID NO: 120)

```
  1  agacagccag ttcctctccc gccgcgccgg gccgcgctgc cgctcgctcc ccggccgtgg 61  cgcctccggg ccagacgcgc tgcagcctcc agcccgcggc aagcggggcg gccgcgccac 121  ccccggcccc gcgccagcag cccctcgccg cgcgtccagc gttcccggcc agcagcctcc 181  ccatacgcag gtcctgctgg gccgccccgt cgcgccccc actctgaact caagtcaccg 241  tggagctccg ccgccccgaa actttcaccg cgagcgggaa atatgggatg tataaaatca 301  aaagggaaag acagcttgag tgacgatgga gtagatttga agactcaacc agttccagaa 361  tctcagcttt tacctggaca gaggtttcaa actaaagatc cagaggaaca aggagacatt 421  gtggtagcct tgtaccccta tgatggcatc caccccggacg acttgtcttt caagaaagga 481  gagaagatga aagtcctgga ggagcatgga aatggtgga aagcaaagtc ccttttaaca 541  aaaaaagaag gcttcatccc cagcaactat gtggccaaac tcaacacctt agaaacagaa 601  gagtggtttt tcaaggatat aaccaggaag gacgcagaaa ggcagctttt ggcaccagga 661  aatagcgctg gagctttcct tattagagaa agtgaaacat aaaaggaag cttctctctg 721  tctgtcagag actttgaccc tgtgcatggt gatgttatta gcactacaa aattagaagt 781  ctggataatg ggggctatta catctctcca cgaatcactt ttccctgtat cagcgacatg 841  attaaacatt accaaaagca ggcagatggc ttgtgcagaa gattggagaa ggcttgtatt
```

-continued

```
 901 agtcccaagc cacagaagcc atgggataaa gatgcctggg agatccccg ggagtccatc
 961 aagttggtga aaaggcttgg cgctgggcag tttggggaag tctggatggg ttactataac
1021 aacagtacca aggtggctgt gaaaaccctg aagccaggaa ctatgtctgt gcaagccttc
1081 ctggaagaag ccaacctcat gaagaccctg cagcatgaca agctcgtgag gctctacgct
1141 gtggtcacca gggaggagcc catttacatc atcaccgagt acatggccaa gggcagtttg
1201 ctggatttcc tgaagagcga tgaaggtggc aaagtgctgc ttccaaagct cattgacttt
1261 tctgctcaga ttgcagaggg aatggcatac atcgagcgga agaactacat tcaccgggac
1321 ctgcgagcag ctaatgttct ggtctccgag tcactcatgt gcaaaattgc agattttggc
1381 cttgctagag taattgaaga taatgagtac acagcaaggg aaggtgctaa gttccctatt
1441 aagtggacgg ctccagaagc aatcaacttt ggatgtttca ctattaagtc tgatgtgtgg
1501 tcctttggaa tcctcctata cgaaattgtc acctatggga aaattcccta cccagggaga
1561 actaatgccg acgtgatgac cgccctgtcc cagggctaca ggatgccccg tgtggagaac
1621 tgcccagatg agctctatga cattatgaaa atgtgctgga agaaaaggc agaagagaga
1681 ccaacgtttg actacttaca gagcgtcctg gatgatttct acacagccac ggaagggcaa
1741 taccagcagc agcctagag cacagggaga cccgtccatt tggcaggggt ggctgcctca
1801 tttagagagg aaaagtaacc atcactggtt gcacttatga tttcatgtgc ggggatcatc
1861 tgccgtgcct ggatcctgaa atagaggcta aattactcag gaagaacacc ctctaaatgg
1921 gaaagtattc tgtactctta gatggattct ccactcagtt gcaacttgga cttgtcctca
1981 gcagctggta atcttgctct gcttgacaac atctgagtgc agccgtttga gaagaaaaca
2041 tctattctct ccaaaaatgc acccaactag ctctatgttt acaaatggac ataggactca
2101 aagtttcaga gaccattgca atgaatcccc ataattgca gaactaaact catttataaa
2161 gctaaaataa ccggatatat acatagcatg acatttcttt gtgctttggc ttacttgttt
2221 aaaaaaaaa aaaaactaat ccaacctgtt agattttgca ggtgaagtca gcagcttaaa
2281 aatgtctttc ccagatttca atgattttt tccccctacc tcccaaaatc tgagactgtt
2341 aaaacatttt tcttctatga acactgctca gacctgctag acatgccata ggagtggcgt
2401 gcacatctct ctctcttcca gcaggaggag cccgtgagca cgcacagctg ccctgtctgc
2461 tcacccgaag gcaccgggct caccctggacc tcccaggaaa gggagaagag cctcagaaac
2521 tgctctgtgt ttagaaggaa tatttttaag agtccagctt tttcattttcc acaattttcct
2581 atatccagat ttgttttgac aatgtagttt ggaagaacta agattctaat ctctgaagaa
2641 ccttataggg ccttctaaaa cataagagtt tccttttgttg cttcaaatat ttgaacatta
2701 tgttaaagat caagtattaa ttttagttgt actctagaaa gctaaagtgc acattcggg
2761 gctattttta tgattcagca atcttttcta aattgtgtag catgtgtatg agactattta
2821 tacccaagga tatgaaggaa cataagtgac tacaaggctc taataagcca cggtggcagg
2881 aggttcaagc ggttctgttc actaaatttt tctcctgtaa gctttgaatg gaaacttctg
2941 tatcacatga tgtgtttcac ttatgctgtt gtgtatatac ctaatatttc tattttgat
3001 tttatttaa tacacctcgt ccaataacat ctcaagcttt ttatttgcat ttacattttc
3061 agctgtggtc agtgtaaaaa ttggtcatca gctggggcg gggtggttag aagtgattca
3121 acagagctac atgctttaaa cttgcccaag ttctacctcc ttcctttgaa catttcagat
3181 tggagaacca aggagttgat tgcctgaaca cctgaacatc cgtttatggg ggccagatag
3241 aatttgtttt caataggct taacaggcat cattaaaatt tcattctgtg tgttttgttt
3301 aggcttgagg tgcttagaag atgggataaa atattctact ttttttctaaa ttttaacttt
```

-continued

```
3361  gtttcctatg tgattttttt aaatgtcctt tctaaaatat tctaaaatta ttgattcaca
3421  agtgccatgt tcagaactat agaatattac tgttacataa tgtctgcaca gctggtccct
3481  tgattcagtg gtaaggtttt tgtgtacacc ccctgcttg cattttattt cagaaccaca
3541  agtattaccc aatatgttac atggagagga actataaaga atccctaagg caaaaagaag
3601  tctctagaaa atgactagag gttttttttt tagcataaca aatttattta agaaaatta
3661  ttaaatttat cttcgccttg ttttgcttct cccagttcct cctcttcttg ccattttcca
3721  cttgtctttc cctcccaatc aagcctgtga tccttacctc catgtgggcc cttcaccagc
3781  ttgggcctca tctctggtgt ccagcatgtg tggaagtcac acgttccctt gatgaacagc
3841  acacacagtc tccttactta gctataggtt tccagcctcc ctgtgacaga caggcataat
3901  gaggggctga ataggtgttt gtagcatttt cgggtatcca gtggtgtgca aaatggctca
3961  tgtcatcaca cctcaggtta ttgtagagaa ctggaaagac agaatccata ctccctaccg
4021  ccaagattct gacttagctg ttgtgcagcg ggagatgtat gtcagtctat tttaaaagct
4081  tctccagtca gctag
```

AD3 TAPBP-tapasin isoform 1 precursor, mRNA NM_003190.4

(SEQ ID NO: 121)

```
   1  ggggacgcgg cacagatagg gggaagccgg agtaatggtt ttcgggcaag tggatgttgg
  61  agagcacaca caggagttgg ggggcggggg agggcctggg gttggggagg gctcgaactc
 121  ggggctgctg ggtagtccag gagggcgcgg taaggctggg gtgtcctggt gagaactgga
 181  gaggatctac ccgggtccct gcctggccag tggggaaaca ccggtccccc aggcaccttc
 241  acctaaccag agcgggatt tccaccgccc ctcatgccgc cctttggagg aaagtgaaag
 301  tgaaggagg aagaggaggc ttcatggctg aggaggtcgc agcgccatga agtccctgtc
 361  tctgctcctc gctgtggctt tgggcctggc gaccgccgtc tcagcaggac ccgcggtgat
 421  cgagtgttgg ttcgtggagg atgcgagcgg aaagggcctg gccaagagac ccggtgcact
 481  gctgttgcgc cagggaccgg gggaaccgcc gccccggccg gacctcgacc ctgagctcta
 541  tctcagtgta cacgaccccg cgggcgccct ccaggctgcc ttcaggcgga tccccggggg
 601  cgcccccgca ccacactgcg agatgagccg cttcgtgcct ctcccgcct ctgcgaaatg
 661  ggccagcggc ctgacccccg cgcagaactg cccgcgggcc ctggatgggg cttggctgat
 721  ggtcagcata tccagcccag tcctcagcct ctccagcctc ttgcgaccac agccagagcc
 781  tcagcaggag cctgttctca tcaccatggc aacagtggta ctgactgtcc tcacccacac
 841  ccctgcccct cgagtgagac tgggacaaga tgctctgctg gacttgagct ttgcctacat
 901  gccccccacc tccgaggccg cctcatctct ggctccgggt cccccctcct ttgggctaga
 961  gtgcgacgc cagcacctgg gtaagggaca tctgctcctg gctgcaactc ctgggctgaa
1021  tggccagatg ccagcagccc aagaaggggc cgtggcattt gctgcttggg atgatgatga
1081  gccatggggc ccatggaccg gaaatggaac cttctggctg cctacagttc aaccctttca
1141  ggagggcacc tatctggcca ccatacacct gccataccctg caaggacagg tcaccctgga
1201  gcttgctgtg tacaaacccc ccaaagtgtc cctgatgcca gcaacccttg cacgggccgc
1261  cccagggag gcaccccgg aattgctctg ccttgtgtcc cacttctacc cttctggggg
1321  cctggaggtg gagtgggaac tccggggtgg cccaggggc cgctctcaga aggccgaggg
1381  gcagaggtgg ctctcggccc tgccgccacca ttccgatggc tctgtcagcc tctctgggca
1441  cttgcagccg ccccccagtca ccactgagca gcatgggggca cgctatgcct gtcgaattca
1501  ccatcccagc ctgcctgcct cggggcgcag cgctgaggtc acctggagg tagcaggtct
```

-continued

```
1561  ttcagggccc tcccttgagg acagcgtagg cctttcctg tctgcctttc ttctgcttgg
1621  gctcttcaag gcactgggct gggctgctgt ctacctgtcc acctgcaagg attcaaagaa
1681  gaaagcagag tgagggcact cactgccatc ctgtggaagc caccatcatc tctggcccaa
1741  gcttctgtag tagctcccta aaataatacc ctatcatctg ctcctaatcc ctccaatctc
1801  tctccactga gtggctggaa tgctttttt ttttctttc acttatataa gggataattt
1861  ttcttttttt tttttttttg agacggagtc tcactcttcc gcccaggctg cagtgcagtg
1921  gcatgatctt ggcttactgc aacctccgcc tcctgggttc aagcaattct gtggcttcag
1981  cctccggagt agctgggatt acaggcacat gccaccacac ccagtgaatt tttgtatttt
2041  tagtagagac ggggtttcac catgttggcc aggctggtct tgaattcctg acctcaggtg
2101  atctgcccac ctcagcctcc caaagtgctg ggattacagg cgtgagccac cacaccaggc
2161  ccgagaaatg ctttttaaa aaacacacat cttatggcat tcaccttctt ggagctctag
2221  gacagtggtt ctcaaaattt ttttctctca ggacctctta aaaatcatca aggaccccaa
2281  aaagcttttg ggtatgtggg ttatagctat caatatttat ggtactagaa cttaaaagtg
2341  agaaaattt aaaacacgag aatacatagg cacacattct attcatcgtg ggaaccatgg
2401  tgtcaataca tatcatgtag cttctgaaaa actccactgt acacttatag aatgaagaag
2461  gcaaaaaact ttttttttt tttttttgag acggagtctc gctctgtcgc ccaggctgga
2521  gtgcagtggc gcgatctcgg ctcactgcaa gctccgcctc tcgggttcac gccattctcc
2581  tgcctcagcc tcccaagtag ctcggactac aggcgtcctc caccatgcct ggctaatatt
2641  ttgtatttt tagtagagac ggggtttcac cgtgttagcc aggatggtct cgatctccta
2701  acctggtgat ccgcccgcct cggcctccca aagtattggg attacccgcg tgagccaccg
2761  cgcccggctg caaataatct ttctttttt ctgagacaga gtctcgtctc gttgcccagg
2821  ctggagtgca gtggcacgat ctcggctcac ggcacgctcc gcctcccggg ttcacgccat
2881  tctcctgcct cagcttcccg agtagctggg actacagggg cccgccacca cgcccggcta
2941  actttttgtg tttttagtag agacggggtt tcaccgtgtt agccaggatg gtctcgatct
3001  cctgaccttg tgatctgccc gcctcggcct cccaaagtgc tgggattaca ggcgtgagcc
3061  accgcgcccg gcggcgaaac acgatattgt actaacatct taattttgtt ataaaatctc
3121  acaaaccccc tgacatagtc tcagagatct gtagggccga ggttacattt ggagaacccg
3181  tactctaggg ccaaatccat tcttcttgcc ctggctcact tgtccccccc accgccccgc
3241  gctggagcca ctgcctagtt cttcagccct agatggtgct cgccagacct cctctcaatg
3301  ctcatcacac acagggctat tccttcctc caatgaacca aacgcctccc gcccacctcc
3361  aggtcccagt cctctgttcc ctttgcctgg tccaccttg ccctccctg gtcgcagacg
3421  aggtcggcct cgtcattccc cgcagaccgc cgcgcgtccc tcttgtgcgg ttcaccacag
3481  ttgtatttaa gtgatcgtgt gagtcgtcgt taaatgcctg tctccccgcg gatcatgggc
3541  tcctcgagga cagggactgg cctgtctgtc cactgctgta accccgcgcc ggcataggga
3601  cctaaggccc actggagggc gctcatcaag tagctgctgg atgttgacga aggaagcggc
3661  ggcgcagctc agggatctcc gagtcaggac ggtcggccag acccacgggg taacgggtct
3721  aatcgtgtag gaataaagct gtattccagt gcttccaaaa aaaaaaaaaa aaaaaaaa
```

AE1 SERPINB1-serpin peptidase inhibitor, clade B (ovalbumin) member 1, mRNA-NM_030666.3

(SEQ ID NO: 122)

```
  1  agaaagaagc cgcgcccctg aggagggcgc tgcccggaag ccacgctcac ttctgcttgc
 61  acttaggcga cctcgggagc tcggactcct acgcagtcac cgggaagggc cgccgccccg
```

-continued

```
 121   cccgcggctg ctggcccggg tgacgcttcc gcctgctata agagcagcgg ccctcggtgc
 181   ctccttcctg acctcgcacc cagctcggag cccggagcgt gcctcggcgg cctgtcggtt
 241   ttcaccatgg agcagctgag ctcagcaaac acccgcttcg ccttggacct gttcctggcg
 301   ttgagtgaga acaatccggc tggaaacatc ttcatctctc ccttcagcat ttcatctgct
 361   atggccatgg ttttctgggg accagaggt aacacggcag cacagctgtc caagactttc
 421   catttcaaca cggttgaaga ggttcattca agattccaga gtctgaatgc tgatatcaac
 481   aaacgtggag cgtcttatat tctgaaactt gctaatagat tatatggaga gaaaacttac
 541   aatttccttc ctgagttctt ggtttcgact cagaaaacat atggtgctga cctggccagt
 601   gtggattttc agcatgcctc tgaagatgca aggaagacca taaaccagtg ggtcaaagga
 661   cagacagaag gaaaaattcc ggaactgttg gcttcgggca tggttgataa catgaccaaa
 721   cttgtgctag taaatgccat ctatttcaag ggaaactgga aggataaatt catgaaagaa
 781   gccacgacga atgcaccatt cagattgaat aagaaagaca gaaaaactgt gaaaatgatg
 841   tatcagaaga aaaaatttgc atatggctac atcgaggacc ttaagtgccg tgtgctggaa
 901   ctgccttacc aaggcgagga gctcagcatg gtcatcctgc tgccggatga cattgaggac
 961   gagtccacgg gcctgaagaa gattgaggaa cagttgactt ggaaaagtt gcatgagtgg
1021   actaaacctg agaatctcga tttcattgaa gttaatgtca gcttgcccag gttcaaactg
1081   gaagagagtt acactctcaa ctccgacctc gcccgcctag gtgtgcagga tctctttaac
1141   agtagcaagg ctgatctgtc tggcatgtca ggagccagag atatttttat atcaaaaatt
1201   gtccacaagt catttgtgga agtgaatgaa gagggaacag aggcggcagc tgcc acagca
1261   ggcatcgcaa ctttctgcat gttgatgccc gaagaaaatt tcactgccga ccatccattc
1321   cttt tcttta ttcggcataa ttcctcaggt agcatcctat tcttggggag attttcttcc
1381   ccttagaaga aagagactgt agcaatacaa aaatcaagct tagtgcttta ttacctgagt
1441   ttttaataga gccaatatgt cttatatctt taccaataaa accactgttc agaaacaagt
1501   ctttcatttt ctttgtaagt ttggctctgt tggctgttta cacccatgaa ttttggcatg
1561   ggtatctatt tttctttttt acattgaaaa aaatccagtg gttgcttttg aatgcatcaa
1621   gtaaagaaga agaaaagaat acatccgatg cgtagattct tgaccatgta gtaatctata
1681   aaattgctat atcctcctga tagccatggg aaaacatgat aagatggtca tttattttgc
1741   agttagaatt tggaagcca caaaatagac agacaccctg actgttgaag ggaggtttaa
1801   aaacagatat tcaattgaaa tgtaagagag caccccaatt gagagcccag gttacgaaga
1861   caagcttgcc tcgcctgact tttctgtccc ttgttctgca ggattagtat tctgttacag
1921   acctctagtt tttagactct tcaattaaag ggccaatggt tataacctgc attcccttt
1981   ttgttcttct ttatgtataa tatatagttc atgtggcgct gcatgaaatc aagaagtggg
2041   tgtcttagga taaaagatac aagagtctc aaaaataac catgtagtaa gataaactgc
2101   tgaacaaagg ttttactgtt agccaccttc tcatgtgttt tcttttctct ttttcttttt
2161   ctttctttct ttctttttt tttttttgag acagagtctt gctctgttac ccaggctgga
2221   gtgcagtggc acgatctcag ctcaccgcaa cctctgcctc ctgggttcaa gtgattctct
2281   tgcttcagcc tcctgagtag ctgggattat aggcatgcac cactaggcct ggctaatttt
2341   tgtattttta gtagagatgg ggttttttcca tgttggccag gctggtcccg aactcctgac
2401   ctcaggtgat ccgcgcacct cagcctccca agtgctggga ttacaggca tgagctacca
2461   tgcctggcct tctcatgtgt tttctgatta aggctcttga cttccaaggc tgtgtgggga
2521   gatggggtgg gggctcttgg actgatataa aactttgtca aatgtagttc tttgaatgga
```

-continued

```
2581 gcttgaaacg ccgcatattc ttgctcccac aaggatagtg ggcatcatga attaataaaa
2641 cgtcctagga ttctgcaagc taaaaaaaaa aaaaaaaa
```

AE2 PSMB9-proteasome (prosome, macropain) subunit, beta type 9, mRNA NM_002800.4
(SEQ ID NO: 123)
```
   1 gcgcgttgtg cgctgtccca ggttggaaac cagtgcccca ggcggcgagg agagcggtgc
  61 cttgcaggga tgctgcgggc gggagcacca accggggact taccccgggg gggagaagtc
 121 cacaccggga ccaccatcat ggcagtggag tttgacgggg cgttgtgat gggttctgat
 181 tcccgagtgt ctgcaggcga ggcggtggtg aaccgagtgt ttgacaagct gtccccgctg
 241 cacgagcgca tctactgtgc actctctggt tcagctgctg atgcccaagc cgtggccgac
 301 atggccgcct accagctgga gctccatggg atagaactgg aggaacctcc acttgttttg
 361 gctgctgcaa atgtggtgag aaatatcagc tataaatatc gagaggactt gtctgcacat
 421 ctcatggtag ctggctggga ccaacgtgaa ggaggtcagg tatatggaac cctgggagga
 481 atgctgactc gacagccttt tgccattggt ggctccggca gcacctttat ctatggttat
 541 gtggatgcag catataagcc aggcatgtct cccgaggagt gcaggcgctt caccacagac
 601 gctattgctc tggccatgag ccgggatggc tcaagcgggg gtgtcatcta cctggtcact
 661 attacagctg ccggtgtgga ccatcgagtc atcttgggca atgaactgcc aaaattctat
 721 gatgagtgaa ccttccccag acttctcttt cttatttgt aataaactct ctagggccaa
 781 aacctggtat ggtcattggg aaatgagtgc tcagggagat ggagcttagg ggaggtgggt
 841 gcttccctcc tagatgtcag catacactct ttcttctttt gtcccaggtc taaaacatct
 901 ttcctagaga aaacaaaagg gactaaacta gaaatataaa gagccctata catgacaggt
 961 gatcacgtac tgaatgattt tgaagtagta caaacaataa aaattctcat tccgcatcat
1021 catgcggtcc atgatgatga ggccgcaa
```

AE3 WSB1-WD repeat and SOCS box containing 1 mRNA-NM_015626.8
(SEQ ID NO: 124)
```
   1 agatatctcc ggcgccgccc gccattttga ctccagtgtc tcgtttgcag tcggcgcttt
  61 aggggaactg tcttcctccg caggcgcgag gctgggtaca gggtctattg tctgtggttg
 121 actccgtact ttggtctgag gccttcggga gctttcccga ggcagttagc agaagccgca
 181 gcggccgccc ccgcccgtct cctctgtccc tgggcccggg agggaccaac ttggcgtcac
 241 gccccctcagc ggtcgccact ctcttctctg ttgttgggtc cgcatcgtat tcccggaatc
 301 agacggtgcc ccatagatgg ccagctttcc cccgagggtc aacgagaaag agatcgtgag
 361 attacgtact ataggtgaac ttttagctcc tgcagctcct tttgacaaga atgtggtcg
 421 tgaaaattgg actgttgctt ttgctccaga tggttcatac tttgcttggt cacaaggaca
 481 tcgcacagta aagcttgttc cgtggtccca gtgccttcag aactttctct tgcatggcac
 541 caagaatgtt accaattcaa gcagtttaag attgccaaga caaaatagtg atggtggtca
 601 gaaaaataag cctcgtgaac atattataga ctgtggagat atagtctgga gtcttgcttt
 661 tgggtcatca gttccagaaa aacagagtcg ctgtgtaaat atagaatggc atcgcttcag
 721 atttggacaa gatcagctac ttcttgctac agggttgaac aatgggcgta tcaaatatg
 781 ggatgtatat acaggaaaac tcctccttaa cttggtagat catactgaag tggtcagaga
 841 tttaactttt gctccagatg gaagcttgat cctggtgtca gcttcaagag acaaaactct
 901 cagagtatgg gacctgaaag atgatggaaa catgatgaaa gtattgaggg ggcatcagaa
 961 ttgggtgtac agctgtgcat tctctcctga ctcttctatg ctgtgttcag tcggagccag
1021 taaagcagtt ttcctttgga atatgggtaa atacaccatg atacggaaac tagaaggaca
```

```
1081  tcaccatgat gtggtagctt gtgactttc tcctgatgga gcattactgg ctactgcatc
1141  ttatgatact cgagtatata tctgggatcc acataatgga gacattctga tggaatttgg
1201  gcacctgttt cccccaccta ctccaatatt tgctggagga gcaaatgacc ggtgggtacg
1261  atctgtatct tttagccatg atggactgca tgttgcaagc cttgctgatg ataaaatggt
1321  gaggttctgg agaattgatg aggattatcc agtgcaagtt gcacctttga gcaatggtct
1381  ttgctgtgcc ttctctactg atggcagtgt tttagctgct gggacacatg acggaagtgt
1441  gtattttgg gccactccac ggcaggtccc tagcctgcaa catttatgtc gcatgtcaat
1501  ccgaagagtg atgcccaccc aagaagttca ggagctgccg attccttcca agcttttgga
1561  gtttctctcg tatcgtattt agaagattct gccttccta gtagtaggga ctgacagaat
1621  acacttaaca caaacctcaa gctttactga cttcaattat ctgtttaa agacgtagaa
1681  gatttattta atttgatatg ttcttgtact gcatttgat cagttgagct tttaaaatat
1741  tatttataga caatagaagt atttctgaac atatcaaata taaattttt taaagatcta
1801  actgtgaaaa catacatacc tgtacatatt tagatataag ctgctatatg ttgaatggac
1861  ccttttgctt ttctgatttt tagttctgac atgtatatat tgcttcagta gagccacaat
1921  atgtatcttt gctgtaaagt gcaaggaaat tttaaattct gggacactga gttagatggt
1981  aaatactgac ttacgaaagt tgaattgggt gaggcgggca aatcacctga ggtcagcagt
2041  ttgagactag cctggcaaac atgatgaaac cctgtctcta ctaaaaatac aaaaaaaaa
2101  aaaattagcc aggcgtggtg gtgcacacct gtagtcctag ctacttggga ggctgaggca
2161  ggagaattgc ttgaacccag gaggtggagg ttgcagtaag ccaagatcac accactgcac
2221  tccaacctgg acaacagagc gagactccat ctcaaaaaaa aaaaaaatt gtgttgcctc
2281  atacgaaatg tatttggttt tgttggagag tgtcagactg atctggaagt gaaacacagt
2341  ttatgtacag ggaaaaggat tttattatcc ttaggaatgt catccaagac gtagagcttg
2401  aatgtgacgt tatttaaaaa caacaacaaa gaaggcagag ccaggatata actagaaaaa
2461  ggatgtcttt ttttttttt ttactcccc tctaaacact gctgctgcct taattttaga
2521  aagcagctta ctagtttacc cttgtggtat aaagtattat aaattgttgt gaatttgaag
2581  aatccgtcta ctgtattatt gctaaatatt ttgttatac taagggacaa ttattttaag
2641  accatggatt taaaaaaaaa aaaaaaact ctgtttctgc aggggatgat attggtgagt
2701  tgccaaagaa gcaatacagc atatctgctt ttgccttctg ttgtttatct tacctgcaga
2761  tattaagaat gtatgcatta tgtaaaatgc tcaattatat attttgttg agttttttaa
2821  ttaaagactt gttaaaaaaa aaaaaaaa
```

AF1 MVP-major vault protein, mRNA-NM_005115.4

(SEQ ID NO: 125)

```
  1   aactcccaag ccccacccct gggcttggcc tgccttgccc tgccgggaag tgatccccaa
 61   ggcagggtga gagttcccca tctgaggcgt tgttgcagc tacctgcact tctagattca
121   tcttcttgtg agccctgggc ttaggagtca ccatggcaac tgaagagttc atcatccgca
181   tccccccata ccactatatc catgtgctgg accagaacag caacgtgtcc cgtgtggagg
241   tcgggccaaa gacctacatc cggcaggaca atgagagggt actgtttgcc cccatgcgca
301   tggtgaccgt cccccacgt cactactgca cagtggccaa ccctgtgtct cgggatgccc
361   agggcttggt gctgtttgat gtcacagggc aagttcggct tcgccacgct gacctcgaga
421   tccggctggc ccaggacccc ttccccctgt acccagggga ggtgctggaa aaggacatca
481   cacccctgca ggtggttctg cccaacactg ccctccatct aaaggcgctg cttgattttg
```

-continued

```
 541  aggataaaga tggagacaag gtggtggcag gagatgagtg gcttttcgag ggacctggca
 601  cgtacatccc ccggaaggaa gtggaggtcg tggagatcat tcaggccacc atcatcaggc
 661  agaaccaggc tctgcggctc agggcccgca aggagtgctg ggaccgggac ggcaaggaga
 721  gggtgacagg ggaagaatgg ctggtcacca cagtaggggc gtacctccca gcggtgtttg
 781  aggaggttct ggatttggtg gacgccgtca tccttacgga aaagacagcc ctgcacctcc
 841  gggctcggcg gaacttccgg gacttcaggg gagtgtcccg ccgcactggg gaggagtggc
 901  tggtaacagt gcaggacaca gaggcccacg tgccagatgt ccacgaggag gtgctggggg
 961  ttgtgcccat caccaccctg gcccccaca actactgcgt gattctcgac cctgtcggac
1021  cggatggcaa gaatcagctg gggcagaagc gcgtggtcaa gggagagaag tcttttttcc
1081  tccagccagg agagcagctg gaacaaggca tccaggatgt gtatgtgctg tcggagcagc
1141  aggggctgct gctgagggcc ctgcagcccc tggaggaggg ggaggatgag gagaaggtct
1201  cacaccaggc tggggaccac tggctcatcc gcggacccct ggagtatgtg ccatctgcca
1261  aagtggaggt ggtggaggag cgccaggcca tccctctaga cgagaacgag ggcatctatg
1321  tgcaggatgt caagaccgga aaggtgcgcg ctgtgattgg aagcacctac atgctgaccc
1381  aggacgaagt cctgtgggag aaagagctgc ctcccggggt ggaggagctg ctgaacaagg
1441  ggcaggaccc tctggcagac aggggtgaga aggacacagc taagagcctc cagcccttgg
1501  cgccccggaa caagacccgt gtggtcagct accgcgtgcc ccacaacgct gcggtgcagg
1561  tgtacgacta ccgagagaag cgagcccgcg tggtcttcgg gcctgagctg gtgtcgctgg
1621  gtcctgagga gcagttcaca gtgttgtccc tctcagctgg gcggcccaag cgtccccatg
1681  cccgccgtgc gctctgcctg ctgctggggc ctgacttctt cacagacgtc atcaccatcg
1741  aaacggcgga tcatgccagg ctgcaactgc agctgcccta caactggcac tttgaggtga
1801  atgaccggaa ggaccccaa gagacggcca agctcttttc agtgccagac tttgtaggtg
1861  atgcctgcaa agccatcgca tcccgggtgc gggggggccgt ggcctctgtc actttcgatg
1921  acttccataa gaactcagcc cgcatcattc gcactgctgt ctttggcttt gagacctcgg
1981  aagcgaaggg ccccgatggc atggccctgc ccaggcccg ggaccaggct gtcttccccc
2041  aaaacgggct ggtggtcagc agtgtggacg tgcagtcagt ggagcctgtg atcagagga
2101  cccgggacgc cctgcaacgc agcgtccagc tggccatcga gatcaccacc aactcccagg
2161  aagcggcggc caagcatgag gctcagagac tggagcagga agcccgcggc cggcttgagc
2221  ggcagaagat cctggaccag tcagaagccg agaaagctcg caaggaactt ttggagctgg
2281  aggctctgag catggccgtg gagagcaccg ggactgccaa ggcggaggcc gagtcccgtg
2341  cggaggcagc ccggattgag ggagaagggt ccgtgctgca ggccaagcta aaagcacagg
2401  ccttggccat tgaaacggag gctgagctcc agagggtcca gaaggtccga gagctggaac
2461  tggtctatgc ccgggcccag ctggagctgg aggtgagcaa ggctcagcag ctggctgagg
2521  tggaggtgaa gaagttcaag cagatgacag aggccatagg ccccagcacc atcagggacc
2581  ttgctgtggc tgggcctgag atgcaggtaa aactgctcca gtccctgggc ctgaaatcaa
2641  ccctcatcac cgatggctcc actcccatca acctcttcaa cacagccttt gggctgctgg
2701  ggatggggcc cgagggtcag cccctggca gaagggtggc cagtgggccc agccctgggg
2761  agggggatatc cccccagtct gctcaggccc ctcaagctcc tggagacaac cacgtggtgc
2821  ctgtactgcg ctaactcctg attaatacaa tggaagtttc tgggcattta caatttcaac
2881  acttaaaaaa aaaaaaaaaa aa
```

-continued

AF2 APBB1IP-amyloid beta (A4) precursor protein-binding, family B,
member 1 interacting protein, mRNA NM_019043.3

(SEQ ID NO: 126)

```
   1 tctcagtctt tggtggaacc atcactaggc cccaatccct tagtccctct tgcgtcgagg
  61 ctgcaaaatg gttccattcg ccaggagacg ctcctgagag aagggcgcgc gcggcacagg
 121 ggccttcctt gcacctcgga gcaaagcagc tcggatagcg ccacacgtct gcgcgctgcg
 181 tgggaagggc agggctgaca gcacttcctc cccggggcag cgacctggag cccgggtgcg
 241 gcagtctgca ccgcgcgtcg ctttcccggc cggagtctcg ccgccttccc gcgccccgca
 301 gcgccccgca gagcagtcga gatgggtgag tcaagtgaag acatagacca aatgttcagc
 361 actttgctgg gagagatgga tcttctgact cagagtttag gagttgacac tctccctcct
 421 cctgacccta atccacccag agctgaattt aactacagtg tgggtttaa agatttaaat
 481 gagtccttaa atgcactgga agaccaagat ttagatgctc tcatggcaga tctggtagca
 541 gacataagtg aggctgagca gaggacaatc caggcacaga aagagtcctt gcagaatcaa
 601 catcattcag catctctaca agcatcaatt ttcagtggtg cagcctctct tggttatgga
 661 acaaatgttg ctgccactgg tatcagccaa tatgaggatg acttaccacc tccaccagcc
 721 gatcctgtgt tagaccttcc actgccacca ccacctcctg aacctctctc tcaggaagag
 781 gaagaagccc aagccaaggc tgataaaatt aagctggcgc tggaaaaact gaaggaggcc
 841 aaggttaaga agctcgtcgt caaggtgcac atgaatgata acagcacaaa gtcactgatg
 901 gtggatgagc ggcagctggc ccgagatgtt ctggacaacc ttttcgagaa aactcattgt
 961 gactgcaatg tagactggtg tctttatgaa atctacccgg aactacaaat tgagaggttt
1021 tttgaagacc atgaaaatgt tgttgaagtc ttatcagact ggacaagaga cacagaaaat
1081 aaaatactat ttttggagaa agaggagaaa tatgctgtat ttaaaaaccc ccagaatttc
1141 tacttggata acagaggaaa aaaagaaagc aaggaaacta atgagaaaat gaatgctaaa
1201 aacaaggaat ccttacttga ggaaagtttc tgtggaacat ctatcattgt accagaactg
1261 gaaggagctc tttatttgaa agaagatgga aagaaatcct ggaaaaggcg ctattttctt
1321 ttacgggctt ctggaattta ttatgtaccc aaaggaaaga ctaagacatc tcgagatctg
1381 gcgtgttttta tacagtttga aaatgtcaac atttactatg ggactcagca taaaatgaaa
1441 tataaagcgc ccactgacta ttgctttgtt ttaaagcacc cccaaattca gaaggagtcc
1501 cagtatatca agtatctctg ctgtgatgac acaagaaccc ttaaccagtg ggtcatggga
1561 atacggatag ccaagtatgg gaagactctc tatgataact accagcgggc tgtggcaaag
1621 gctggacttg cctctcggtg gacaaacttg gggacagtca atgcagctgc accagctcag
1681 ccatctacag gacctaaaac aggcaccacc cagcccaatg gacagattcc ccaggctaca
1741 cattctgtca gtgctgttct ccaagaggcc cagagacatg ctgaaacatc gaaggataag
1801 aagccagccc tcgggaacca ccacgacccg gcagtgcccc gggccccgca cgcccccaag
1861 tccagcctgc cccgcccccc tccggtgcgg aggtcctccg acaccagcgg cagtcccgcc
1921 acgcccctca aggccaaggg cacaggcggc ggggcttgc cgccccacc cgacgacttc
1981 ctgccgccgc cgccaccgcc gccgcccctc gatgacccctg agctcccgcc gccgcccccg
2041 gacttcatgg agccgccccc agacttcgtg ccccgcccc cgccgtcgta cgcagggatc
2101 gcgggctcag agctgccccc gccgccgccg ccgccgcccg cgccccgcgcc gccccccgtc
2161 cccgactccg ccaggccgcc cccgccggtg gccaagaggc ctcctgtgcc cccaagagg
2221 caagagaacc cagggcaccc cggcggagca ggaggcgggg agcaagattt catgtcagac
2281 ctcatgaaag ctttgcaaaa gaagagaggc aacgtgtcct agggacgggc atgatgagtg
```

-continued

```
2341  ttccagaggg agaagcatcg ctgaccccga gcgcaggttt tgctagcaga ttgccctgac 2401  atcttgttca tttcagataa aatgtgatgg gaaacttctc actgatgtgc tcaagtacag 2461  gcataaccat taacccagta gagttcagaa tatctgccca aatgtacata tcgttcccat 2521  gtattttaac ctaaatggaa tgtatcttcc cttccaagct gcctaaagcg ctgttttagg 2581  ttcatttatt ttattatgtt cagaagcatc aaataaaagt taaacgtttt tccggaaaaa 2641  aaaaaaaaaa aaaaaaaaa
```

AF3 FYB-FYN binding protein, mRNA NM_001243093.1

(SEQ ID NO: 127)

```
   1  gcatagctaa cttgcacatt cactatccaa gctgcaccat cttcggggtc attgtgtgcc 61  aggcatatca actcttttca ataaaaatgg atggaaaggc agatgtaaag tccctcatgg 121  cgaaatataa cacgggggc aacccgacag aggatgtctc agtcaatagc cgaccttca 181  gagtcacagg gccaaactca tcttcaggaa tacaagcaag aaagaactta ttcaacaacc 241  aaggaaatgc cagccctcct gcaggaccca gcaatgtacc taagtttggg tccccaaagc 301  cacctgtggc agtcaaacct tcttctgagg aaaagcctga caaggaaccc aagcccccgt 361  ttctaaagcc cactggagca ggccaaagat tcggaacacc agccagcttg accaccagag 421  accccgaggc gaaagtggga tttctgaaac ctgtaggccc caagcccatc aacttgccca 481  aagaagattc caaacctaca tttccctggc ctcctggaaa caagccatct cttcacagtg 541  taaaccaaga ccatgactta aagccactag gcccgaaatc tgggcctact cctccaacct 601  cagaaaatga acagaagcaa gcgtttccca aattgactgg ggttaaaggg aaatttatgt 661  cagcatcaca agatcttgaa cccaagcccc tcttccccaa acccgccttt ggccagaagc 721  cgcccctaag taccgagaac tcccatgaag acgaaagccc catgaagaat gtgtcttcat 781  caaaagggtc cccagctccc ctgggagtca ggtccaaaag cggcccttta aaaccagcaa 841  gggaagactc agaaaataaa gaccatgcag gggagatttc aagtttgccc tttcctggag 901  tggttttgaa acctgctgcg agcaggggag gcccaggtct ctccaaaaat ggtgaagaaa 961  aaaaggaaga taggaagata gatgctgcta agaacaccTT ccagagcaaa ataaatcagg 1021  aagagttggc ctcagggact ctcctgcca ggttccctaa ggcccttct aagctgacag 1081  tgggggggcc atggggccaa agtcaggaaa aggaaagggg agacaagaat tcagccaccc 1141  cgaaacagaa gccattgcct cccttgttta ccttgggtcc acctccacca aaacccaaca 1201  gaccaccaaa tgttgacctg acgaaattcc acaaaacctc ttctggaaac agtactagca 1261  aaggccagac gtcttactca acaacttccc tgccaccacc tccaccatcc catccggcca 1321  gccaaccacc attgccagca tctcacccat cacaaccacc agtcccaagc ctacctccca 1381  gaaacattaa acctcgtttt gacctaaaaa gccctgtcaa tgaagacaat caagatggtg 1441  tcacgcactc tgatggtgct ggaaatctag atgaggaaca agacagtgaa ggagaaacat 1501  atgaagacat agaagcatcc aaagaaagag agaagaaaag ggaaaaggaa gaaagaagaa 1561  ggttagagct ggagaaaaag gaacagaaag agaaagaaaa gaagaacaa gaaataaaga 1621  agaaatttaa actaacaggc cctattcaag tcatccatct tgcaaagct tgttgtgatg 1681  tcaaaggagg aaagaatgaa ctgagcttca gcaaggaga gcaaattgaa atcatccgca 1741  tcacagacaa cccagaagga aaatggttgg gcagaacagc aaggggttca tatggctata 1801  ttaaaacaac tgctgtagag attgactatg attctttgaa actgaaaaaa gactctcttg 1861  gtgccccttc aagacctatt gaagatgacc aagaagtata tgatgatgtt gcagagcagg 1921  atgatattag cagccacagt cagagtggaa gtgagggat attccctcca ccaccagatg 1981  atgacatttta tgatgggatt gaagaggaag atgctgatga tggctccaca ctacaggttc
```

-continued

```
2041  aagagaagag taatacgtgg tcctggggga ttttgaagat gttaaaggga aaagatgaca
2101  gaaagaaaag tatacgagag aaacctaaag tctctgactc agacaataat gaaggttcat
2161  ctttccctgc tcctcctaaa caattggaca tgggagatga agtttacgat gatgtggata
2221  cctctgattt ccctgtttca tcagcagaga tgagtcaagg aactaatgtt ggaaaagcta
2281  agacagaaga aaaggacctt aagaagctaa aaaagcagga aaaagaagaa aaagacttca
2341  ggaaaaaatt taaatatgat ggtgaaatta gagtcctata ttcaactaaa gttacaactt
2401  ccataacttc taaaaagtgg ggaaccagag atctacaggt aaaacctggt gaatctctag
2461  aagttataca aaccacagat gacacaaaag ttctctgcag aaatgaagaa gggaaatatg
2521  gttatgtcct tcggagttac ctagcggaca atgatggaga gatctatgat gatattgctg
2581  atggctgcat ctatgacaat gactagcact caactttggt cattctgctg tgttcattag
2641  gtgccaatgt gaagtctgga ttttaattgg catgttattg ggtatcaaga aaattaatgc
2701  acaaaaccac ttattatcat ttgttatgaa atcccaatta tctttacaaa gtgtttaaag
2761  tttgaacata gaaataatc tctctgctta attgttaact cagaagacta cattagtgag
2821  atgtaagaat tattaaatat tccatttccg ctttggctac aattatgaag aagttgaagg
2881  tacttctttt agaccaccag taaataatcc tccttcaaaa aataaaaata aagaaaaag
2941  gaaaatcatt caggaagaaa tgacctgtct aaaaaaacct aaggaagaat aataatataa
3001  gaaaggaaat ttaaaaacat tccacaagaa gaaaaattat tgtttatact tctacttatg
3061  gttatatctt atattctcta ttcaagtgac ctgtctttta aaaaggcagt gctgtcttac
3121  ctcttgctag tgggttaaat gttttcaaaa attatagcag tagtagaagt tttgtataaa
3181  atttgtcctt atttgttaat tgtatataaa tgttaattat ttgatacgaa tgttatgcat
3241  ttagtatgca cattgaagtc taaactgtag aagagtctaa acaagttct cttttttgcag
3301  attcacatac taatggttta attctgtgct ctgtttaaag tactattata actagagtag
3361  atctgaatga ggataaccct aaaatcatga ggaatggaag aatggaccct gaaactacct
3421  aggcttttat gcatggcacc tctttataat gaagcacatt tttaaagttt tgttttttgt
3481  ttcaattacc gctagatttt ttttctctt ttttaaaat ccattttact ggaaagttgg
3541  ccagcagagg gagtagaaat tattaaaatt ctagtgttg gattgggccc ttctctaaca
3601  gtacatactc attcccaaag caatccaaaa acaaaatgtg aaccatttgg gtttcaaatg
3661  ttaagaacac taaatagcat gatttaaaa atgaaaatg ctaacaccca agaaagaag
3721  atattaagtg ctttttaaca actcctagag tacaaaatga gtacatcata atgctggctc
3781  ttctactaat gaaccatcga gtgatattga ataaattatt tatcttctca gtttccttat
3841  ctgtaaatta caatattaga ctaagtaagt ttttccaact cttcactacc aattaccta
3901  ggcttttata atgctccgcc tacttcagtc ccatgtttca gaagcttttg tctatttttt
3961  aaactcattg attaaataat gattaatgca ttctccacat tttaatattg caaaggccca
4021  ttggagtttc tgaagtggct ccacagaatt gaaataattt caaataactg taaaggaact
4081  gaaaatcttc acagagatga agtggggttt ccattaggtg ctttgaaatt tgataacaaa
4141  tcatcaactt ccactggtca atatatagat tttgggtgtc tgaggcccca agattagatg
4201  ccactaatct ccaaagattc cctccaatta tgaaatattt taatgtctac ttttagagag
4261  cactagccag tatatgacca tgtgattaat ttcttttcac actagataaa attacctggt
4321  tcaaaagtgg ttttgtttta ttaaatttgg taataaatat atataataca cagacaggat
4381  agtttttatg ctgaagtttt tggccagctt tagtttgagg actccttgat aagcttgcta
```

-continued

```
4441 aactttcaga gtgccctgag acacttccag ccatccctcc tcctgccttc attggggcag 4501 acttgcattg cagtctgaca gtaattttttt ttctgattga gaattatgta aattcagtac 4561 aatgtcagtt tttaaaagtc aaagttagat caagagaata tttcagagtt ttggtttaca 4621 catcaagaaa cagacacaca tacctaggaa agatttacac aatagataat catcttaatg 4681 tgaaagatat ttgaagtatt aatttttaata tattaaatat gatttctgtt atagtcttct 4741 gtatggaatt ttgtcactta agatgagctg caaataaata ataccttcaa tggataaaaa 4801 aaaaaaaaa a
```

AG1 MB21D1/C6orf150-Mab-21 domain containing 1, mRNA NM_138441.2
(SEQ ID NO: 128)

```
   1 agcctggggt tccccttcgg gtcgcagact cttgtgtgcc cgccagtagt gcttggtttc 61 caacagctgc tgctggctct tcctcttgcg gccttttcct gaaacggatt cttctttcgg 121 ggaacagaaa gcgccagcca tgcagccttg gcacggaaag gccatgcaga gagcttccga 181 ggccggagcc actgccccca aggcttccgc acggaatgcc aggggcgccc cgatggatcc 241 caccgagtct ccggctgccc ccgaggccgc cctgcctaag gcgggaaagt tcggccccgc 301 caggaagtcg ggatcccggc agaaaaagag cgccccggac acccaggaga ggccgcccgt 361 ccgcgcaact ggggcccgcg ccaaaaaggc ccctcagcgc gcccaggaca cgcagccgtc 421 tgacgccacc agcgcccctg ggcagaggg gctggagcct cctgcggctc gggagccggc 481 tctttccagg gctggttctt gccgccagag gggcgcgcgc tgctccacga agccaagacc 541 tccgcccggg ccctgggacg tgcccagccc cggcctgccg gtctcggccc ccattctcgt 601 acggagggat gcggcgcctg gggcctcgaa gctccgggcg gttttggaga agttgaagct 661 cagccgcgat gatatctcca cggcggcggg gatggtgaaa ggggttgtgg accacctgct 721 gctcagactg aagtgcgact ccgcgttcag aggcgtcggg ctgctgaaca ccgggagcta 781 ctatgagcac gtgaagattt ctgcacctaa tgaatttgat gtcatgttta aactggaagt 841 ccccagaatt caactagaag aatattccaa cactcgtgca tattactttg tgaaatttaa 901 aagaaatccg aaagaaaatc ctctgagtca gttttttagaa ggtgaaatat tatcagcttc 961 taagatgctg tcaaagttta ggaaaatcat taaggaagaa attaacgaca ttaaagatac 1021 agatgtcatc atgaagagga aaagaggagg gagccctgct gtaacacttc ttattagtga 1081 aaaaatatct gtggatataa ccctggcttt ggaatcaaaa agtagctggc ctgctagcac 1141 ccaagaaggc ctgcgcattc aaaactggct ttcagcaaaa gttaggaagc aactacgact 1201 aaagccattt taccttgtac ccaagcatgc aaaggaagga aatggtttcc aagaagaaac 1261 atgcggcta tccttctctc acatcgaaaa ggaaattttg aacaatcatg gaaaatctaa 1321 aacgtgctgt gaaaacaaag aagagaaatg ttgcaggaaa gattgtttaa aactaatgaa 1381 ataccttta gaacagctga agaaaggtt taaagacaaa aaacatctgg ataaattctc 1441 ttcttatcat gtgaaaactg ccttctttca cgtatgtacc cagaaccctc aagacagtca 1501 gtgggaccgc aaagacctgg gcctctgctt tgataactgc gtgacatact ttcttcagtg 1561 cctcaggaca gaaaaacttg agaattattt tattcctgaa ttcaatctat tctctagcaa 1621 cttaattgac aaaagaagta aggaatttct gacaaagcaa attgaatatg aagaaacaa 1681 tgagttttcca gttttttgatg aattttgaga ttgtatttttt agaaagatct aagaactaga 1741 gtcaccctaa atcctggaga atacaagaaa aatttgaaaa ggggccagac gctgtggctc 1801 ac
```

AG2 CPVL-carboxypeptidase, vitellogenic-like, mRNA NM_019029.2
(SEQ ID NO: 129)

```
   1 gtgactgggt ggggctgcct cacttctgcc tgatttggga agcgctgcaa ggacaaccgg
  61 ctgggtcct tgcgcgccgc ggctcaggga ggagcaccga ctgcgccgcg taagtgccgc
 121 ctgccctgcg tgggtcgtgc cagctcagcg ggacaggtcc tcgcctcggt ccctcggact
 181 tagggagcgc ggggcagacc ctgagagatg gttggtgcca tgtggaaggt gattgtttcg
 241 ctggtcctgt tgatgcctgg cccctgtgat gggctgtttc gctccctata cagaagtgtt
 301 tccatgccac ctaagggaga ctcaggacag ccattatttc tcaccccttc cattgaagct
 361 gggaagatcc aaaaaggaag agaattgagt ttggtcggcc ctttcccagg actgaacatg
 421 aagagttatg ccggcttcct caccgtgaat aagacttaca acagcaacct cttcttctgg
 481 ttcttcccag ctcagataca gccagaagat gccccagtag ttctctggct acagggtggg
 541 ccgggaggtt catccatgtt tggactcttt gtggaacatg ggccttatgt tgtcacaagt
 601 aacatgacct tgcgtgacag agacttcccc tggaccacaa cgctctccat gctttacatt
 661 gacaatccag tgggcacagg cttcagtttt actgatgata cccacggata tgcagtcaat
 721 gaggacgatg tagcacggga tttatacagt gcactaattc agttttttcca gatatttcct
 781 gaatataaaa ataatgactt ttatgtcact ggggagtctt atgcagggaa atatgtgcca
 841 gccattgcac acctcatcca ttccctcaac cctgtgagag aggtgaagat caacctgaac
 901 ggaattgcta ttggagatgg atattctgat cccgaatcaa ttataggggg ctatgcagaa
 961 ttcctgtacc aaattggctt gttggatgag aagcaaaaaa agtacttcca gaagcagtgc
1021 catgaatgca tagaacacat caggaagcag aactggtttg aggcctttga aatactggat
1081 aaactactag atggcgactt aacaagtgat ccttcttact tccagaatgt tacaggatgt
1141 agtaattact ataacttttt gcggtgcacg gaacctgagg atcagcttta ctatgtgaaa
1201 tttttgtcac tcccagaggt gagacaagcc atccacgtgg ggaatcagac ttttaatgat
1261 ggaactatag ttgaaaagta cttgcgagaa gatacagtac agtcagttaa gccatggtta
1321 actgaaatca tgaataatta taaggttctg atctacaatg gccaactgga catcatcgtg
1381 gcagctgccc tgacagagcg ctccttgatg gcatggact ggaaaggatc ccaggaatac
1441 aagaaggcag aaaaaaagt ttggaagatc tttaaatctg acagtgaagt ggctggtta
1501 atccggcaag cgggtgactt ccatcaggta attattcgag gtggaggaca tattttaccc
1561 tatgaccagc tctgagagc ttttgacatg attaatcgat tcatttatgg aaaaggatgg
1621 gatccttatg ttggataaac taccttccca aaagagaaca tcagaggttt tcattgctga
1681 aaagaaaatc gtaaaaacag aaaatgtcat aggaataaaa aaattatctt ttcatatctg
1741 caagattttt ttcatcaata aaaattatcc ttgaaacaa
```

AG3 TICAM2-toll-like receptor adaptor molecule 2, mRNA NM_021649.6
(SEQ ID NO: 130)

```
   1 acattaaccc ctgactcaca gctggaccgc cccggcccgc agcgccacgt cccgggtggg
  61 gcctgccacg gcaaagcagc agtccggcct cgagcggccc ctcggggcg gcggggtggg
 121 cgccaacagc agtcaggcct gacaagcggc gacctccaag ggtgaggcct ctgcgggccc
 181 ccgactcacg cgcgtccggg ctctgcaagc gcggtgggga gcaggctgct gtggtcgcgg
 241 ggactgggtt gcggcgcgcc gcgtacggga cggccccaaa ctctcgacgc ccggggcaag
 301 acgcccaccc cctgggcgct ctcgctgggc cagaaaggaa gacagaaaag ccgcgggctg
 361 actgtggtgg cgctcgcctg cagattgaaa agaaatgctg agaaatacat aaagttttcc
 421 tcttctgcct tggatattta atgggtat cggaagtct aaataaatt cctgccctct
 481 ttctctctct tggggtaaaa ggcacagtgt ggatacaagt ccaggatatc atgagtcaga
```

-continued

```
 541   ttccaagaag tctgaagatc tatccttgtg taatgttgct gagcacagca atacaacaga
 601   ggggccaaca ggaaagcagg agggagctca gagcgtggaa gagatgtttg aagaagaagc
 661   tgaagaagag gtgttcctca aatttgtgat attgcatgca aagatgaca cagatgaagc
 721   cctcagagtc cagaatctgc tacaagatga ctttggtatc aaaccgggaa taatctttgc
 781   tgagatgcca gtgtggcagac agcatttaca gaatttagat gatgctgtaa atgggtctgc
 841   atggacaatc ttattactga ctgaaaactt tttaagagat acttggtgta atttccagtt
 901   ctatacgtcc ctaatgaact ccgttaacag gcagcataaa tacaactctg ttatacccat
 961   gcggcccctg aacaatcccc ttccccgaga aaggactccc tttgccctcc aaaccatcaa
1021   tgccttagag gaagaaagtc gtggatttcc tacacaagta gaaagaattt ttcaggagtc
1081   tgtgtataag acacaacaaa ctatatggaa agagacaaga aatatggtac aagacaatt
1141   tattgcctga gatgaaacat ataacatgtg gctggctctt gttttgtaaa ccaaatgatt
1201   aatcttcact tgagaaagca gtttctagga aatgtttaaa taaaagagag tcttcacctt
1261   aaagaaacct atggagcaca agaaagataa atttctgcag gacagcctat aaaattgtgg
1321   tacttttttga tgtttcagta aacttgacat tgtcagagtt tcaaggactt ttcttttcaca
1381   attttcctag ttcatggata tgaaaaagga attctcaatc catattcctt gtattgaacc
1441   ttgaacaaaa acttgtatga cagacatttt taaaaatgtg acaacacttt tattctctga
1501   attttgatct caaaggacac agaaaaaaaa tggccccagg agatctgatc acacttcctc
1561   ctgaggcacc tctcatggat gttgcaataa gcattcgggt actatcaccc agaaatatga
1621   attgccagaa tagaacattt agcatgttaa gcgttgatgc atataaaatc agaaatagat
1681   gtgagaatgg tggaactttt taaaagaacc cagtcaaatg tatttttctgc tgaaatctgc
1741   atatttggag gcatttccca ccaccgattc acagcccatt tgatagtgtg gtagttaggg
1801   acttcgtgga gtggtgttca gacgtcccct ggggcttaaa tctcttcata ttagtcatca
1861   tttgtaacta tggctttatt tgcagagctt ctaaaaggcg tataactgtg tgagtggcca
1921   gatattcact ttttaaatca aaaacctctc ttatggaagc tttaaaagtt tccgtcacac
1981   acaattctct tctcaggaag tatttctcat ttaggtcttc aaagtagcct gactgtgtgc
2041   atgtgtgtgt gtgataggtt attttataaag actttggata gaaggagatg tattttatta
2101   cctcctattc tagagcccca tgctcctaac aagccagaga ggccccaaac aggattgttt
2161   ctttcctcca cagcccttct gcccatctga gattgaggga gcatcgtcca cttgagatca
2221   gggatggggt ggagaatggg tcatgtcatg taatgagaaa agccctcttc gggatcatga
2281   gacttggttc tagtccaatt tctgccactg aggatgaatg taactgtggg caaactattt
2341   accctccttt atctgtgaaa tgaagggtt gaattgatgg atctctaaag gcttttgtcc
2401   tctatgagga tgtgaaaaac tagggaccac aaaagggaac aagcaaaaaa gtttggattc
2461   gataaagtga tatgtaatag ttgcagaagg cttatatat gcttataatg aaaagatatt
2521   ttttgtatat tgacagcata atttattttt aatgctgtca ttacacttaa agtcacagga
2581   aaaaaatata catgcttact caggctttct taaaaataaa ttttttataga gatccttgag
2641   taaagacatt ttgcttaatt tctttttttct tatt*ccccac* ttgtatatcc cctaccagta
2701   ccgggatctg cacacatctt tttgcagtta cctcttcata gccatgaacc aaaacgttct
2761   atgaggagca tgcaagtaag tcaagcctcc tattctgtta gtacttatta gaggaggaga
2821   tggttttcat tgcatagtga catttttctta gccttaacgt tctgatagta gcttactact
2881   cacttctctt tttcagtttt cataataagt attcattttt ttgccataat gcttcctgta
```

-continued

```
2941  aagccaattt tatatactaa taaaacatga actgcccact cttcatgcct gccaaacttg 3001  gggcaattga tgctaaatgg tatttttaaa ataaatgttt ttattcttta ctcttgaaaa 3061  aaaaaaaaaa aaaa
```

AH1 CD52-CD52 molecule/CAMPATH1, mRNA NM_001803.2
(SEQ ID NO: 131)

```
   1  ctcctggttc aaaagcagct aaaccaaaag aagcctccag acagccctga gatcacctaa 61  aaagctgcta ccaagacagc cacgaagatc ctaccaaaat gaagcgcttc ctcttcctcc 121  tactcaccat cagcctcctg gttatggtac agatacaaac tggactctca ggacaaaacg 181  acaccagcca aaccagcagc ccctcagcat ccagcaacat aagcggaggc atttttcttt 241  tcttcgtggc caatgccata atccacctct tctgcttcag ttgaggtgac acgtctcagc 301  cttagccctg tgccccctga aacagctgcc accatcactc gcaagagaat cccctccatc 361  tttgggaggg gttgatgcca gacatcacca ggttgtagaa gttgacaggc agtgccatgg 421  gggcaacagc caaaataggg gggtaatgat gtagggggcca agcagtgccc agctgggggt 481  caataaagtt acccttgtac ttgcaaaaaa aaaaaaaaaa aaa
```

AI1 HERC2 *Homo sapiens* HECT and RLD domain containing E3 ubiquitin protein ligase 2, mRNA NM_004667.5
(SEQ ID NO: 132)

```
   1  gcgccggctg agccagcggc tcttgggagg ctgcgtccgc gcgccggcga ggcgaggcgg 61  ccgggccctg cgcgtcaggc ctgagacctg ggaggaagct ggagaaaaga tgccctctga 121  atctttctgt ttggctgccc aggctcgcct cgactccaaa tggttgaaaa cagatataca 181  gcttgcattc acaagagatg ggctctgtgg tctgtggaat gaaatggtta agatggagaa 241  aattgtatac actggaacag aatcaaccca gaacggagag ctccctccta gaaaagatga 301  tagtgtcgaa ccaagtggaa caaagaaaga agatctgaat gacaaagaga aaaagatga 361  agaagaaact cctgcaccta tatagggc caagtcaatt ctggacagct gggtatgggg 421  caagcaacca gatgtgaatg aactgaagga gtgtctttct gtgctggtta aagagcagca 481  ggccctggcc gtccagtcag ccaccaccac cctctcagcc ctgcgactca agcagaggct 541  ggtgatcttg gagcgctatt tcattgcctt gaatagaacc gttttttcagg agaatgtcaa 601  agttaagtgg aaaagcagcg gtatttctct gcctcctgtg gacaaaaaaa gttcccggcc 661  tgcgggcaaa ggtgtggagg ggctcgccag agtgggatcc cgagcggcgc tgtcttttgc 721  ctttgccttc ctgcgcaggg cctggcgatc aggcgaggat gcggaccct gcagtgagct 781  gttgcaggag tccctggacg ccctgcgagc acttcccgag gcctcgctct tgacgagag 841  caccgtgtcc tctgtgtggc tggaggtggt ggagagagcg accaggttcc tcaggtccgt 901  cgtgacgggg gatgttcacg gaacgccagc caccaaaggg ccaggaagca tccccctgca 961  ggaccagcac ttggccctgg ccatcctgct ggagctggct gtgcagagag gcacgctgag 1021  ccaaatgttg tctgccatcc tgttgttgct tcagctgtgg acagcgggg cacaggagac 1081  tgacaatgag cgttccgccc agggcaccag cgcccacttt tgcccttgc tgcaaaggtt 1141  ccagagcatc atttgcagga aggatgcacc ccactccgag ggcgacatgc acctttttgtc 1201  tggccctctg agcccaatg agagtttcct gaggtacctc acccttccac aagacaacga 1261  gcttgccatt gatctgcgac aaacggcggt tgttgtcatg gcccatttag accgtctggc 1321  tacgccctgt atgcctccgc tgtgtagctc tccgacatct cataaggat cattgcaaga 1381  ggtcataggt tgggggttaa taggatggaa atactatgcc aatgtgattg gtccaatcca 1441  gtgcgaaggc ctggccaacc tgggagtcac acagattgcc tgtgcagaga agcgtttcct 1501  gattctgtca cgcaatggcc gcgtgtacac acaggcctat aatagtgaca cgctggcccc
```

-continued

```
1561  acagctggtc caaggccttg cctccagaaa cattgtaaaa attgctgccc attctgatgg
1621  tcaccactac ctagccttgg ctgctactgg agaggtgtac tcctggggct gtggggacgg
1681  cggacggctg ggccatgggg acactgtgcc tttggaggag cctaaggtga tctccgcctt
1741  ctctggaaag caggccggga agcacgtggt gcacatcgct tgcgggagca cttacagtgc
1801  ggccatcact gccgaggggg agctgtacac ctggggccgc gggaactacg gccggctggg
1861  ccatggctcc agtgaggacg aggccattcc gatgctggta gccgggctta aggactgaa
1921  ggtcatcgat gtggcgtgtg ggagtgggga tgctcaaacc ctggctgtca ctgagaacgg
1981  gcaagtgtgg tcttggggag atggtgacta tgggaaattg gcagaggtg gtagtgatgg
2041  ctgcaaaacc ccaaagctga ttgaaaagct tcaagacttg gatgtggtca aagtccgctg
2101  tggaagtcag ttttccattg ctttgacgaa agatggccaa gtttattcat ggggaaaagg
2161  tgacaaccag agacttggac atggaacaga ggaacatgtt cgttatccaa aactcttaga
2221  aggcttgcaa gggaagaagg tgattgatgt ggctgcaggc tccacccact gcctggctct
2281  gactgaggac agcgaggtcc acagctgggg gagcaacgac cagtgccagc actttgacac
2341  cttgcgcgtg accaagccag aacctgcagc attgccagga ctggacacca aacacatagt
2401  gggaattgcc tgtgggcctg cccagagctt tgcttggtca tcatgttctg agtggtccat
2461  tggcctccgt gtccctttg tggtggacat ctgctcaatg acttttgagc agctggatct
2521  cctgcttcgg caggtgagtg agggatgga tggttccgcg gactggcccc cgccccagga
2581  gaaagagtgt gtggccgtgg caacgctgaa tcttctacga cttcagttgc atgctgccat
2641  tagtcaccag gttgacccgg aattccttgg tttaggtctg ggcagcatcc tcctgaacag
2701  cctgaagcag acggtggtga ccctggccag cagtgcgggc gtgctgagca ccgtgcagtc
2761  ggccgcccag gccgtgctgc agagtgctg gtccgtgctg ctgcccaccg cggaggagcg
2821  ggcccgggca ctctctgctc tcctgccctg cgcagtttca ggcaatgaag tgaacataag
2881  tccaggtcgt cgattcatga ttgatcttct ggtggggcagc ttgatggctg atggagggtt
2941  ggagtcagcc ttacacgcag ccattactgc agagatccag gatattgaag ccaaaaaaga
3001  agcacagaag gaaaagaaa ttgatgaaca ggaagcgaat gcctcaacat tcatagaag
3061  caggactcca ctggataaag accttattaa tacggggatc tgtgagtctt ctggcaaaca
3121  gtgtttgcct ctggttcagc tcatacaaca gcttcttaga aacattgctt ctcagactgt
3181  agccagattg aaagatgttg cccgtcggat ttcatcatgt ctggactttg agcaacacag
3241  tcgtgaaaga tctgcttcat tggatttgtt actgcgtttt caacgtttgc ttattagtaa
3301  actttatcca ggagaaagta ttggtcagac ctcagatatt tctagtccag agctaatgga
3361  tgttggttcc ttgctgaaga agtacacagc cctcctgtgc acgcacattg gagatatact
3421  gcctgtggcc gccagcattg cttctaccag ctggcggcac ttcgcggagg tggcttacat
3481  tgtggaaggg gactttactg gtgttctcct tccagaacta gtagtttcta tagtgcttct
3541  gctcagtaaa aatgctggtc tcatgcaaga ggctggagct gtacctctgc tgggtggcct
3601  gttggaacat ctggatcggt tcaaccatct ggcaccagga aaggaacggg atgatcatga
3661  agagttagcc tggcctggca taatggagtc attttttaca ggtcagaact gtagaaataa
3721  tgaggaagtg acacttatac gcaaagctga tttggagaac cataataaag atggaggctt
3781  ctggactgtg attgacggga aggtgtatga tataaaggac ttccagacac agtcgttaac
3841  aggaaatagt attcttgctc agtttgcagg ggaagaccca gtggtagctt tggaagctgc
3901  tttgcagttt gaagacaccc gggaatccat gcacgcgttt tgtgttggcc agtatttgga
3961  gcctgaccaa gaaatcgtca ccataccaga tctgggagt ctctcttcac ctctgatag
```

-continued

```
4021  cacagagagg aatctgggcc tgcttctcgg attacacgct tcgtatttgg caatgagcac
4081  accgctgtct cctgtcgaga ttgaatgtgc caaatggctt cagtcatcca tcttctctgg
4141  aggcctgcag accagccaga tccactacag ctacaacgag gagaaagacg aggaccactg
4201  cagctcccca gggggcacac ctgccagcaa atctcgactc tgctcccaca gacgggccct
4261  gggggaccat tcccaggcat ttctgcaagc cattgcagac aacaacattc aggatcacaa
4321  cgtgaaggac ttttgtgtc aaatagaaag gtactgtagg cagtgccatt tgaccacacc
4381  gatcatgttt cccccgagc atcccgtgga agaggtcggt cgcttgttgt tatgttgcct
4441  cttaaaacat gaagatttag gtcatgtggc attatcttta gttcatgcag gtgcacttgg
4501  tattgagcaa gtaaagcaca gaacgttgcc taagtcagtg gtggatgttt gtagagttgt
4561  ctaccaagca aaatgttcgc tcattaagac tcatcaagaa cagggccgtt cttacaagga
4621  ggtctgcgct cctgtcatcg aacgtttgag attcctcttt aatgaattga gacctgctgt
4681  ttgtaatgac ctctctataa tgtctaagtt taaattgtta agttctttgc cccgttggag
4741  gaggatagct caaaagataa ttcgagaacg aaggaaaaag agagttccta agaagccaga
4801  atctacggat gatgaagaaa aaattggaaa cgaagagagt gatttagaag aagcttgcat
4861  tttgcctcat agtccaataa atgtggacaa gagacccatt gcaattaaat cacccaagga
4921  caaatggcag ccgctgttga gtactgttac aggtgttcac aaatacaagt ggttgaagca
4981  gaatgtgcag ggtctttatc cgcagtctcc actcctcagt acaattgctg aatttgccct
5041  taaagaagag ccagtggatg tggaaaaaat gagaaagtgc ctactaaaac agttggagag
5101  agcagaggtt cgcctggaag ggatagatac aattttaaaa ctggcgagca agaatttctt
5161  acttccatct gtgcagtatg cgatgttttg tggatggcaa agacttattc ctgagggaat
5221  cgatataggg gaacctctta ctgattgttt aaaggatgtt gatttgatcc cgcctttaa
5281  tcggatgctg ctggaagtca ccttggcaa gctgtacgct tgggctgtac agaacattcg
5341  aaatgttttg atggatgcca gtgccaaatt taaagagctt ggtatccagc cggttcccct
5401  gcaaaccatc accaatgaga acccgtcagg accgagcctg ggaccatcc cgcaagccca
5461  cttcctcctg gtgatgctca gcatgctcac cctgcagcac ggcgcaaaca acctcgacct
5521  tctgctcaat tccggcatgc tggccctcac gcagacggca ctgcgcctga ttggccccag
5581  ttgtgacaac gttgaggaag atatgaatgc ttctgctcaa ggtgcttctg ccacagtttt
5641  ggaagaaaca aggaaggaaa cggctcctgt gcagctccct gtttcaggac cagaactggc
5701  tgccatgatg aagattgaa caagggtcat gagaggtgtg gactggaaat ggggcgatca
5761  ggatgggcct cctccaggcc taggccgcgt gattggtgag ctgggagagg acggatggat
5821  aagagtccag tgggacacag gcagcaccaa ctcctacagg atggggaaag aaggaaaata
5881  cgacctcaag ctggcagagc tgccggctgc tgcacagccc tcagcagagg attcggacac
5941  agaggatgac tctgaagccg aacaaactga aggaacatt caccccactg caatgatgtt
6001  taccagcact attaacttac tgcagactct ttgtctgtct gctggagttc atgctgagat
6061  catgcagagc gaagccacca agactttatg cggactgctg cgaatgttag tggaaagcgg
6121  aacgacggac aagacatctt ctccaaacag gctggtgtac agggagcaac accggagctg
6181  gtgcacgctg ggtttgtgc ggagcatcgc tctcacgccg caggtatgcg gcgccctcag
6241  ctccccgcag tggatcacgc tgctcatgaa ggtcgtggaa gggcacgcac ccttcactgc
6301  cacctcgctg cagaggcaga tcttagctgt gcatttgttg caagcagtcc ttccatcatg
6361  ggacaagacc gaaagggcga gggacatgaa atgcctcgtg gagaagctgt ttgacttctt
```

-continued

```
6421  gggaagcttg ctcactacct gctcctctga cgtgccatta ctcagagagt ccacgctgag
6481  gcggcgcagg gtgcgcccgc aggcctcgct gactgccacc cacagcagca cactggcgga
6541  ggaggtggtg gcactgctgc gcacgctgca ctccctgact cagtggaatg ggctcatcaa
6601  caagtacatc aactcccagc tccgctccat cacccacagc tttgtgggaa ggccttccga
6661  aggggcccag ttagaggact acttccccga ctccgagaac cctgaagtgg ggggcctcat
6721  ggcagtcctg gctgtgattg aggcatcga tggtcgcctg cgcctggggc gtcaagttat
6781  gcacgatgag tttggagaag gcactgtgac tcgcatcacc ccaaagggca aaatcaccgt
6841  gcagttctct gacatgcgga cgtgtcgcgt ttgcccattg aatcagctga aaccactccc
6901  tgccgtggcc tttaatgtga acaacctgcc cttcacagag cccatgctgt ctgtctgggc
6961  tcagttggtg aacctcgctg aagcaagtt agaaaagcac aaaataaaga aatcgactaa
7021  acaggccttt gcaggacaag tggacctgga cctgctgcgg tgccagcagt tgaagctata
7081  catcctgaaa gcaggtcggg cgctgctctc ccaccaggat aaactgcggc agatcctgtc
7141  tcagccagct gttcaggaga ctggaactgt tcacacagat gatggagcag tggtatcacc
7201  tgaccttggg gacatgtctc ctgaagggcc gcagccccc atgatcctct gcagcagct
7261  gctggcctcg gccacccagc cgtctcctgt gaaggccata tttgataaac aggaacttga
7321  ggctgctgca ctggccgttt gccagtgctt ggctgtggag tccactcacc cttcgagccc
7381  aggatttgaa gactgcagct ccagtgaggc caccacgcct gtcgccgtgc agcacatccg
7441  ccctgccaga gtgaagaggc gcaagcagtc gcccgttccc gctctgccga tcgtggtgca
7501  gctcatggag atgggatttt ccagaaggaa catcgagttt gccctgaagt ctctcactgg
7561  tgcttccggg aatgcatcca gcttgctgg tgtggaagcc ttggtcgggt ggctgctgga
7621  ccactccgac atacaggtca cggagctctc agatgcagac acggtgtccg acgagtattc
7681  tgacgaggag gtggtggagg acgtggatga tgccgcctac tccatgtcta ctggtgctgt
7741  tgtgacggag agccagacgt acaaaaaacg agctgatttc ttgagtaatg atgattatgc
7801  tgtatatgtg agagagaata ttcaggtggg aatgatggtt agatgctgcc gagcgtatga
7861  agaagtgtgc gaaggtgatg ttggcaaagt catcaagctg acagagatg gattgcatga
7921  tctcaatgtg cagtgtgact ggcagcagaa agggggcacc tactgggtta ggtacattca
7981  tgtggaactt ataggctatc ctccaccaag ttcttcttct cacatcaaga ttggtgataa
8041  agtgcgggtc aaagcctctg tcaccacacc aaaatacaaa tggggatctg tgactcatca
8101  gagtgtgggg gttgtgaaag ctttcagtgc caatgaaaaa gatatcattg tcgactttcc
8161  ccagcagtct cactggactg ggttgctatc agaaatggag ttggtaccca gtattcatcc
8221  tggggttacg tgtgatggat gtcagatgtt tcctatcaat ggatccagat tcaaatgcag
8281  aaactgtgat gactttgatt tttgtgaaac gtgtttcaag accaaaaaac acaataccag
8341  gcatacattt ggcagaataa atgaaccagg tcagtctgcg gtattttgtg gccgttctgg
8401  aaaacagctg aagcgttgcc acagcagcca gccaggcatg ctgctggaca gctggtcccg
8461  catggtgaag agcctgaatg tgtcgtcctc cgtgaaccag gcatcccgtc tcattgacgg
8521  cagcgagccc tgctggcagt catcgggtg gcaaggaaag cactggattc gtttggagat
8581  tttcccagat gttcttgttc atagattaaa aatgatcgta gatcctgctg acagtagcta
8641  catgccgtcc ctggttgtag tgtcaggtgg aaattccctg aataacctta ttgaactaaa
8701  gacaatcaat attaacccctt ctgacaccac agtgcccctt ctgaatgact gcacagagta
8761  tcacaggtat attgaaattg ctataaagca gtgcaggagc tcaggaatcg attgtaaaat
8821  ccatggtctc atcctgctgg gacggatccg tgcagaagag gaagatttgg ctgcagttcc
```

-continued

```
 8881  tttcttagct tcggataatg aagaggagga ggatgagaaa ggcaacagcg gaagcctcat
 8941  tagaaagaag gctgctgggc tggaatcagc agctacgata agaaccaagg tgtttgtgtg
 9001  gggcctgaat gacaaggacc agctgggcgg gctgaaaggc tccaagataa aggttccttc
 9061  gttctctgag acactgtcag ctttgaatgt ggtacaggtg gctggtggat ctaaaagttt
 9121  gtttgcagtg actgtggaag ggaaggtgta tgcctgtgga gaagccacga atggccggct
 9181  ggggctgggc atttccagcg ggacggtgcc catcccacgg cagatcacag ctctcagcag
 9241  ctacgtggtc aagaaggtgg ctgttcactc aggtggccgg cacgcgacgg ctttaactgt
 9301  cgatggaaaa gtgttttcgt ggggcgaagg tgacgatgga aaacttggac acttcagcag
 9361  aatgaactgt gacaaaccaa ggctgatcga ggccctgaaa accaagcgta tccgggatat
 9421  cgcctgtggg agctcgcaca gcgcagccct cacatccagc ggagaactgt acacctgggg
 9481  cctcggcgag tacggccggc tgggacatgg ggataatacg acacagctaa agcccaaaat
 9541  ggtgaaagtc cttctcggtc acagagtaat ccaggttgca tgtgggagta gagacgcgca
 9601  gaccctggct ctgaccgatg aaggtttggt attttcctgg ggtgatggtg actttggaaa
 9661  actgggccgg ggcggaagtg aaggctgtaa cattccccag aacattgaga gactaaatgg
 9721  acagggggtg tgccagattg agtgtggagc tcagttctcc ctggcgctca ccaagtctgg
 9781  agtggtgtgg acatgggaa aggggattg cttcagattg gccacggct ctgacgtgca
 9841  cgtgcggaaa ccacaggtgg tggaagggct gagagggaag aagatcgtgc atgtggctgt
 9901  cggggcctg cactgcctgg cggtcacgga ctcggggcag gtgtatgctt ggggtgacaa
 9961  cgaccacggc cagcagggca atggcacgac cacggttaac aggaagccca cactcgtgca
10021  aggcttagaa ggccagaaga tcacacgcgt ggcttgtggg tcgtcccaca gtgtggcgtg
10081  gacaactgtg gatgtggcca cgccctctgt ccacgagccc gtcctcttcc agactgcaag
10141  agaccctta ggtgcttcct atttaggcgt gccttcagat gctgattctt ctgctgccag
10201  taataaaata agtggtgcaa gtaattctaa gccaaatcgc ccttctcttg ccaagattct
10261  cttgtcattg gatggaaatc tggccaaaca gcaggcctta tcacatattc ttacagcatt
10321  gcaaatcatg tatgccagag atgctgttgt cggggccctg atgccggccg ccatgatcgc
10381  cccggtggag tgcccctcgt tctcctcggc ggccccttcc gacgcatctg cgatggctag
10441  tcccatgaat ggagaagaat gcatgctggc tgttgatatc gaagacagac tgagtccaaa
10501  tccatggcaa gaaaagagag agattgtttc ctctgaggac gcagtgaccc cctctgcagt
10561  gactccgtcg gcccctcag cctccgctcg gccttttatc ccagtgacgg atgacctggg
10621  agccgcaagc atcattgcag aaaccatgac caaaaccaaa gaggatgttg aaagccaaaa
10681  taaagcagca ggtccggagc ctcaggcctt ggatgagttc accagtctgc tgattgcgga
10741  tgacactcgt gtggtggtag acctgctcaa gctgtcagtg tgcagccggg ccgggacag
10801  gggcagggat gtgctctccg cggtgctttc cggcatgggg accgcctacc cacaggtggc
10861  agatatgctg ttggagctct gtgtcaccga gttggaggat gtggccacag actcgcagag
10921  cggccgcctc tcttctcagc ctgtggtggt ggagagtagc caccccttaca ccgacgacac
10981  ctccaccagt ggcacagtga agataccagg tgcagaagga ctcagggtag aatttgaccg
11041  gcagtgctcc acagagaggc gccacgaccc tctcacagtc atggacggcg tcaacaggat
11101  cgtctccgtg cggtcaggcc gagagtggtc cgactggtcc agcgagctgc gcatcccagg
11161  ggatgagtta aagtggaagt tcatcagcga tgggtctgtg aatgctggg gctggcgctt
11221  caccgtctat cccatcatgc cagctgctgg ccctaaagaa ctcctctctg accgctgcgt
```

-continued

```
11281   cctctcctgt ccatccatgg acttggtgac gtgtctgtta gacttccgac tcaaccttgc 11341   ctctaacaga agcatcgtcc ctcgccttgc ggcctcgctg gcagcttgtg cacagctgag 11401   tgccctagct gccagtcaca gaatgtgggc ccttcagaga ctgaggaagc tgcttacaac 11461   tgaatttggg cagtcaatta acataaatag gctgcttgga gaaaatgatg gggaaacaag 11521   agctttgagt tttacaggta gtgctcttgc tgctttggtg aaaggtcttc cagaagcttt 11581   gcaaaggcag tttgaatatg aagatcctat tgtgaggggt ggcaaacagc tgctccacag 11641   cccattcttt aaggtactgg tagctcttgc ttgtgacctg gagctggaca ctctgccttg 11701   ctgtgccgag acgcacaagt gggcctggtt ccggaggtac tgcatggcct cccgtgttgc 11761   tgtggcccett gacaaaagaa caccgttgcc ccgtctgttt cttgatgagg tggctaagaa 11821   aattcgtgaa ttaatggcag acagcgaaaa catggatgtt ctgcatgaga gccatgacat 11881   ttttaaaaga gagcaagacg aacaacttgt gcagtggatg aacaggcgac cagatgactg 11941   gactctctct gctggtggca gtggaacaat ttatgatgg ggacataatc acaggggcca 12001   gctcgggggc attgaaggcg caaaagtcaa agttcccact ccctgtgaag cccttgcaac 12061   tctcagaccc gtgcagttaa tcggagggga acagaccctc tttgctgtga cggctgatgg 12121   gaagctgtat gccactgggt atggtgcagg tggcagacta ggcattggag ggacagagtc 12181   ggtgtccacc ccaacattgc ttgaatccat tcagcatgtg tttattaaga aagtagctgt 12241   gaactctgga ggaaagcact gccttgccct gtcttcagaa ggagaagttt actcttgggg 12301   tgaggcagaa gatgggaagt tggggcatgg caacagaagt ccgtgtgacc gccctcgtgt 12361   catcgagtct ctgagaggaa ttgaagtggt cgatgttgct gctggcggag cccacagcgc 12421   ctgtgtcaca gcagccgggg acctctacac atggggcaaa ggccgctacg gccggctggg 12481   gcacagcgac agtgaggacc agctgaagcc gaagctggtg gaggcgctgc agggccaccg 12541   tgtggttgac atcgcctgtg gcagtggaga tgcccagacc ctctgcctca cagatgacga 12601   cactgtctgg tcctgggggg acggggacta cggcaagctc ggccggggag gcagcgatgg 12661   ctgtaaagtg cctatgaaga ttgattctct tactggtctt ggagtagtta aagtggaatg 12721   cggatcccag ttttctgttg cccttaccaa atctggagct gtttatacct ggggcaaagg 12781   cgattatcac aggttgggcc atggatcaga tgaccatgtt cgaaggcctc ggcaggtcca 12841   agggttgcag gggaagaaag tcatcgccat cgccactggc tccctgcact gtgtgtgctg 12901   cacagaggat ggtgaggttt atacatgggg cgacaatgat gagggacaac tgggagacgg 12961   aaccaccaat gccatccaga ggcctcggtt ggtagctgcc cttcagggta agaaggtcaa 13021   ccgtgtggcc tgtggctcag cacatacccct cgcctggtcg accagcaagc ccgccagtgc 13081   tggcaaactc cctgcacagg tccccatgga gtacaatcac ctgcaggaga tccccatcat 13141   tgcgctgagg aaccgtctgc tgctgctgca ccacctctcc gagctcttct gcccctgcat 13201   cccatgttc gacctggaag gctcgctcga cgaaactgga ctcgggcctt ctgtttgggtt 13261   cgacactctc cgaggaattc tgatatccca gggaaaggag gcggctttcc ggaaagtagt 13321   acaagcaact atggtacgcg atcgtcagca tggccccgtc gtggagctga accgcatcca 13381   ggtcaaacga tcaaggagca aaggcgggct ggccggcccc gacggcacca agtctgtctt 13441   tgggcagatg tgtgctaaga tgagctcgtt tggtcccgac agcctcctcc ttcctcaccg 13501   tgtctggaaa gtcaagtttg tgggtgaatc tgtggatgac tgtgggggcg gctacagcga 13561   gtccatagct gagatctgtg aggagctgca gaacggactc acgccctgc tgatcgtgac 13621   acccacggg agggatgagt ctggggccaa ccgagactgc tacctgctca gcccggccgc 13681   cagagcaccc gtgcacagca gcatgttccg cttcctgggt gtgttgctgg gcattgccat
```

-continued

```
13741  ccgaaccggg agtcccctga gcctcaacct tgccgagcct gtctggaagc agctggctgg 13801  gatgagcctc accatcgcgg acctcagtga ggttgataag gattttattc ctggactcat 13861  gtacatccga gacaatgaag ccacctca a ggagtttgaa gccatgagcc tgcccttcac 13921  agtgccaagt gccagtggcc aggacattca gttgagctcc aagcacacac acatcaccct 13981  ggacaaccgc gcggagtacg tgcggctggc gataaactat agactccatg aatttgatga 14041  gcaggtggct gctgttcggg aaggaatggc ccgcgttgtg cctgttcccc tcctctctct 14101  gttcaccggc tacgaactgg agacgatggt gtgtggcagc cctgacatcc cgctgcacct 14161  tctcaagtcg gtggccacct ataaaggcat cgagccttcc gcatcgctga tccagtggtt 14221  ctgggaggtg atggagtcct tctccaacac agagcgctct ctttccttc gcttcgtctg 14281  gggccggacg aggctgccca ggaccatcgc cgacttccgg ggccgagact tcgtcatcca 14341  ggtgttggat aaatacaacc ctccagacca cttcctccct gagtcctaca cctgtttctt 14401  cttgctgaag ctgcccaggt attcctgcaa gcaggtgctg gaggagaagc tcaagtacgc 14461  catccacttc tgcaagtcca tagacacaga tgactacgct cgcatcgcac ttacaggaga 14521  gccagccgcc gacgacagca gcgacgattc agataacgag gatgtcgact ccttttgcttc 14581  ggactctaca caagattatt taacaggaca ctaagatggg gaaacgtcct cgtgagatga 14641  gagcctgagc caggcagcag agcgctcgct gctgtgtaga ctgtaggctg cctggtgtgt 14701  ctgatgagaa gcgtccgtcc tcgagccagg cgggaggagg gagtggagag actgactggc 14761  cgtgatggga atgacagtga gaaggtccgc ctgtgcgcgt ggaacactgt ggacgctcga 14821  cttccaaggg tcttctcacc cgtaatgctg cattacatgt aggactgtgt ttactaaagt 14881  gtgtaaatgt ttatataaat accaaattgc agcatcccca aaatgaataa agccttttta 14941  cttgtgggtg caatcgattt ttttcttc tcctttcttt caagtgtcgt gagtcgtctt 15001  gattgtatat tggaaataac tgtgtaacaa atcgtattat aaatatttca attaatttta 15061  ctctgaattt gtttattaaa agactttga acatgaaatg attagtatta cttgaatgca 15121  tccagaggat atttaaacca aaatgaaaaa ccagaaggcc atttggtgtc cccctccca 15181  ggtgtcccct tgtagcatat gcattatgtc atctgaattg aggcctttct gtgaacagca 15241  tcataacttc tatcatggaa agtgtactat atataatgtt tgtgtcatgt atatgcctaa 15301  attttaatta tctataaata aaacatctga cataaaagtg
```

AI2 KLRAP1 (KLRA1)-KLRAP1 killer cell lectin-like receptor subfamily A pseudogene 1, mRNA NR_028045.1

(SEQ ID NO: 133)

```
  1  ttcagccctc aaatattgat tttgaacatt attttgcaaa gagtactaag tggttggtta 61  gttgagatag aggaatatgc agcttttgac tatctttcct ttcccgtcag taccagcttt 121  catgatacaa tttcctctta tcactttggt caagaggtgg ggcagaaaat tttgagttac 181  agtatcattc gaagagaatt tatttctgcc tttcatgtta tagccctaa gggatccagg 241  acccgaaagg ccagcttctc cctcattttg aaatcagttt tctccacctg caccactgca 301  tagcacagat acagaaacca tcctatttca ggatttgaat gcaaaactta ccttcttact 361  ctaaagatga atgatcaggg agagatttat tcaaccctga gattttgca gtctccttca 421  gagtcacaga atagattaag gcctgatgat actcaaaggc tgggaaaac tgatgacaaa 481  gaattttcag tgccctggca cctcattgca gtgactcttg ggatcctctg tttacttctt 541  ctgatgatag tcacagtgtt ggtgacaaat atctttcagt gtattcaaga aaacatcaa 601  cggcaggaaa ttctaagaaa ctgtagtgaa agtacatca tgcaaaatga caactactta 661  aaagagcaga ttttgacaaa taagactttta aaatttgacg ttctcaaaaa tagctttcag
```

```
 721 cagaaaaagg aactggattc acgccttata caaagaaca gatgtcatag agaaaatgag
 781 atcgttttta aagttttgca aaatacaggc aaattctctg aagaccacgg gtcctgttgt
 841 ggagtaaact gttattattt taccatgcag aagaaagact ggaagggatg taaacagact
 901 tgtcaacatt gtagatcatc ccttttgaag atagatgaca aagatgaact cgtatttac
 961 attcactttt attctcttgg actctgtttc tcaatgttgg acctaagata ttgaagacag
1021 gctggagccc agagccttca ttcaatctca gatttatgaa aataattact ggattggatt
1081 atcatatgat gaaagggaaa gtaagtggaa atggattgat aatggcacat ctcctggaat
1141 taattctaca ataatgcgtt tttcttctgg gagaggagaa tgtgcatttt tgacctcaac
1201 aagaatggca actattgatt gcattcaaac gtacaattgt atctgtggga agagaataga
1261 ctctattttc tctgattcgg tgtgcgccaa gaagaaaagg tgaaaatgga atgttttctt
1321 tttttgtttc ccataataat ttctgattat aaatcattgc ttttaactgt gggacttagt
1381 taattcttca aaagataaag atgaacagga agaaaagaa aattattttg gactatgact
1441 ttaaagatca gatgccatct ttcttcctgg agaagaggag attttctctt ttgagagtgg
1501 ttgttccttc ctttaatgtc cctgaggaat tattcattct ttctaattca cagaactacc
1561 tatacaacca gttagagaac tctgatatta tatcctgggt ctttttcttt atcaatagga
1621 taaatcattc cagcatcttc tggttttgaa agcagttgtg aactagaatg tagttatttt
1681 tttcttccca tctagaagtt acctcatctt ttaaaacatt tgttttgcta caaaatataa
1741 cttcaaactt actgaaagtt gcaagcatag tacaaggaac ttctatataa ccttttactca
1801 tacttactag ttgtttatat tttgctctgc tttatatttc tctctttcta tcttccactt
1861 aataataaat tgaggacttc atgtcccttt gtctaaatat tttccaagat caagggcttt
1921 gttttatata atcacagtgc aattatcaaa ctcaggaaat ttagcattag tacagtacta
1981 tgatctaatc tgtaatccat gttcaaattt tgtcaattgt cccaataatg ccatttatgt
2041 gtatttctta aaaatccatg ttcaggataa ttcaatgcat ttgattgtaa tgtctcttta
2101 gtcttcttta atctgaaaca gttcttttagg ctttttcttg accttgacat tttaaaaatt
2161 aactttattg agttatactt ttcatgcaat aaaatgcact cactttaa
```
AJ1 *Homo sapiens* platelet factor 4 variant 1 (PF4V1/CXCL4L1), mRNA
NM_0026202

(SEQ ID NO: 134)
```
   1 actgcctgca gaaccccagc ccgactttcc ctgcgcactg ggatcctgct ggaacctcag
  61 ctgcaacatg agctccgcag ccaggtcccg cctcacccgc gccacccgcc aggagatgct
 121 gttcttggcg ttgctgctcc tgccagttgt ggtcgccttc gccagagctg aagctgaaga
 181 agatgggac ctgcagtgcc tgtgtgtgaa gaccacctcc caggtccgtc ccaggcacat
 241 caccagcctg gaggtgatca aggccggacc ccactgcccc actgcccaac tcatagccac
 301 gctgaagaat gggaggaaaa tttgcttgga tctgcaagcc ctgctgtaca agaaaatcat
 361 taaggaacat ttggagagtt agctactagc tgcctaagtg tgcactttca atctaactgt
 421 gaaagaatct tctgatgttt gtattatcct tcttatatta tattaacaaa ataaatcaag
 481 ttgtggtata gtcaatctat ttccttaataa tactgcaaaa ataatgctga cacatcacaa
 541 tttcatattt taaaattccc agaattttaa gcaaaagca ttatgaagga aggcttggtt
 601 taataaagac tgattttgtt cagtgttata tgttagctga tacatatttg ttcatttatg
 661 tgattgcagt actttatagc tacatattta ccttgaatgt tacaattagc ttgccaataa
 721 atattagtag ctcttaagca t
```

-continued

AL1 DEFB128 defensin, beta 128, mRNA NM_001037732.1
(SEQ ID NO: 135)

```
  1 atgaagctgt ttctggttct cattattctg ctgtttgagg tactcacaga cggggcaaga
 61 ctcaaaaaat gcttcaataa agtaacaggc tattgcagga agaaatgcaa ggtaggagaa
121 agatatgaaa taggatgtct aagtgggaaa ttatgttgtg ctaatgatga agaagagaaa
181 aaacatgtgt catttaagaa gccacatcaa cattctggtg agaagctgag tgtgctgcag
241 gattacatca tcttacccac catcaccatt ttcacagtct aa
```

AM1 IL8 interleukin 8, mRNA NM_000584.3
(SEQ ID NO: 136)

```
  1 gagggtgcat aagttctcta gtagggtgat gatataaaaa gccaccggag cactccataa
 61 ggcacaaact ttcagagaca gcagagcaca caagcttcta ggacaagagc caggaagaaa
121 ccaccggaag gaaccatctc actgtgtgta acatgactt ccaagctggc cgtggctctc
181 ttggcagcct tcctgatttc tgcagctctg tgtgaaggtg cagttttgcc aaggagtgct
241 aaagaactta gatgtcagtg cataaagaca tactccaaac ctttccaccc caaatttatc
301 aaagaactga gagtgattga gagtggacca cactgcgcca acacagaaat tattgtaaag
361 ctttctgatg gaagagagct ctgtctggac cccaaggaaa actgggtgca gagggttgtg
421 gagaagtttt tgaagagggc tgagaattca taaaaaaatt cattctctgt ggtatccaag
481 aatcagtgaa gatgccagtg aaacttcaag caaatctact tcaacacttc atgtattgtg
541 tgggtctgtt gtaggggttgc cagatgcaat acaagattcc tggttaaatt tgaatttcag
601 taaacaatga atagttttc attgtaccat gaaatatcca gaacatactt atatgtaaag
661 tattatttat ttgaatctac aaaaaacaac aataattttt taaatataag gattttccta
721 gatattgcac gggagaatat acaaatagca aaattgaggc caagggccaa gagaatatcc
781 gaactttaat ttcaggaatt gaatgggttt gctagaatgt gatatttgaa gcatcacata
841 aaaatgatgg gacaataaat tttgccataa agtcaaattt agctggaaat cctggatttt
901 tttctgttaa atctggcaac cctagtctgc tagccaggat ccacaagtcc ttgttccact
961 gtgccttggt ttctccttta tttctaagtg gaaaaagtat tagccaccat cttacctcac
1021 agtgatgttg tgaggacatg tggaagcact ttaagttttt tcatcataac ataaattatt
1081 ttcaagtgta acttattaac ctatttatta tttatgtatt tatttaagca tcaaatattt
1141 gtgcaagaat ttggaaaaat agaagatgaa tcattgattg aatagttata aagatgttat
1201 agtaaattta ttttattta gatattaaat gatgttttat tagataaatt tcaatcaggg
1261 tttttagatt aaacaaacaa acaattgggt acccagttaa attttcattt cagataaaca
1321 acaaataatt ttttagtata agtacattat tgtttatctg aaattttaat tgaactaaca
1381 atcctagttt gatactccca gtcttgtcat tgccagctgt gttggtagtg ctgtgttgaa
1441 ttacggaata atgagttaga actattaaaa cagccaaaac tccacagtca atattagtaa
1501 tttcttgctg gttgaaactt gtttattatg tacaaataga ttcttataat attatttaaa
1561 tgactgcatt tttaaataca aggctttata ttttaacttt aagatgtttt tatgtgctc
1621 tccaaatttt ttttactgtt tctgattgta tggaaatata aaagtaaata tgaaacattt
1681 aaaatataat ttgttgtcaa agtaaaaaaa aaaaaaaa
```

B1 AIM2-interferon-inducible protein AIM2/absent in melanoma 2 mRNA NM_004833.1
(SEQ ID NO: 137)

```
  1 tcagccaatt agagctccag ttgtcactcc tacccacact gggcctgggg gtgaagggaa
 61 gtgtttatta ggggtacatg tgaagccgtc cagaagtgtc agagtctttg tagctttgaa
121 agtcacctag gttatttggg catgctctcg tgagtcctct gctagttaag ctctctgaaa
```

-continued

```
  181 agaaggtggc agacccggtt tgctgatcgc cccagggatc aggaggctga tcccaaagtt
  241 gtcagatgga gagtaaatac aaggagatac tcttgctaac aggcctggat aacatcactg
  301 atgaggaact ggataggttt aagttctttc tttcagacga gtttaatatt gccacaggca
  361 aactacatac tgcaaacaga atacaagtag ctaccttgat gattcaaaat gctggggcgg
  421 tgtctgcagt gatgaagacc attcgtattt ttcagaagtt gaattatatg cttttggcaa
  481 aacgtcttca ggaggagaag gagaaagttg ataagcaata caaatcggta caaaaaccaa
  541 agccactaag tcaagctgaa atgagtcctg ctgcatctgc agccatcaga aatgatgtcg
  601 caaagcaacg tgctgcacca aagtctctc ctcatgttaa gcctgaacag aaacagatgg
  661 tggcccagca ggaatctatc agagaagggt tcagaagcg ctgtttgcca gttatggtac
  721 tgaaagcaaa gaagcccttc acgtttgaga cccaagaagg caagcaggag atgtttcatg
  781 ctacagtggc tacagaaaag gaattcttct ttgtaaaagt ttttaataca ctgctgaaag
  841 ataaattcat tccaaagaga ataattataa tagcaagata ttatcggcac agtggtttct
  901 tagaggtaaa tagcgcctca cgtgtgttag atgctgaatc tgaccaaaag gttaatgtcc
  961 cgctgaacat tatcagaaaa gctggtgaaa ccccgaagat caacacgctt caaactcagc
 1021 cccttggaac aattgtgaat ggtttgtttg tagtccagaa ggtaacagaa agaagaaaa
 1081 acatattatt tgacctaagt gacaacactg ggaaaatgga agtactgggg gttagaaacg
 1141 aggacacaat gaaatgtaag gaaggagata aggttcgact acattcttc acactgtcaa
 1201 aaaatggaga aaaactacag ctgacatctg gagttcatag caccataaag gttattaagg
 1261 ccaaaaaaa aacatagaga agtaaaaagg accaattcaa gccaactggt ctaagcagca
 1321 tttaattgaa gaatatgtga tacagcctct tcaatcagat tgtaagttac ctgaaagctg
 1381 cagttcacag gctcctctct ccaccaaatt aggatagaat aattgctgga taaacaaatt
 1441 cagaatatca acagatgatc acaataaaca tctgtttctc attcc
```

B2 CD274-CD274 molecule/B7-H, mRNA NM_014143.3

(SEQ ID NO: 138)

```
    1 ggcgcaacgc tgagcagctg gcgcgtcccg cgcggcccca gttctgcgca gcttcccgag
   61 gctccgcacc agccgcgctt ctgtccgcct gcagggcatt ccagaaagat gaggatattt
  121 gctgtcttta tattcatgac ctactggcat ttgctgaacg catttactgt cacggttccc
  181 aaggacctat atgtggtaga gtatggtagc aatatgacaa ttgaatgcaa attcccagta
  241 gaaaaacaat tagacctggc tgcactaatt gtctattggg aaatggagga taagaacatt
  301 attcaatttg tgcatggaga ggaagacctg aaggttcagc atagtagcta cagacagagg
  361 gcccggctgt gaaggacca gctctccctg ggaaatgctg cacttcagat cacagatgtg
  421 aaattgcagg atgcaggggg tgtaccgctg catgatcagc tatggtggtg cgactacaag
  481 cgaattactg tgaaagtcaa tgccccatac aacaaaatca ccaaagaat tttggttgtg
  541 gatccagtca cctctgaaca tgaactgaca tgtcaggctg agggctaccc caaggccgaa
  601 gtcatctgga caagcagtga ccatcaagtc ctgagtggta agaccaccac caccaattcc
  661 aagagagagg agaagctttt caatgtgacc agcacactga gaatcaacac aacaactaat
  721 gagattttct actgcacttt taggagatta gatcctgagg aaaaccctac agctgaattg
  781 gtcatcccag aactacctct ggcacatcct ccaaatgaaa ggactcactt ggtaattctg
  841 ggagccatct tattatgcct tggtgtagca ctgacattca tcttccgttt aagaaaaggg
  901 agaatgatgg atgtgaaaaa atgtggcatc caagatacaa actcaaagaa gcaaagtgat
  961 acacatttgg aggagacgta atccagcatt ggaacttctg atcttcaagc agggattctc
 1021 aacctgtggt ttaggggttc atcggggctg agcgtgacaa gaggaaggaa tgggcccgtg
```

-continued

```
1081  ggatgcaggc aatgtgggac ttaaaaggcc caagcactga aaatggaacc tggcgaaagc 1141  agaggaggag aatgaagaaa gatggagtca acagggagc ctggagggag accttgatac 1201  tttcaaatgc ctgaggggct catcgacgcc tgtgacaggg agaaaggata cttctgaaca 1261  aggagcctcc aagcaaatca tccattgctc atcctaggaa gacgggttga gaatccctaa 1321  tttgagggtc agttcctgca gaagtgccct ttgcctccac tcaatgcctc aatttgtttt 1381  ctgcatgact gagagtctca gtgttggaac gggacagtat ttatgtatga gttttccta 1441  tttattttga gtctgtgagg tcttcttgtc atgtgagtgt ggttgtgaat gatttctttt 1501  gaagatatat tgtagtagat gttacaattt tgtcgccaaa ctaaacttgc tgcttaatga 1561  tttgctcaca tctagtaaaa catggagtat ttgtaaggtg cttggtctcc tctataacta 1621  caagtataca ttggaagcat aaagatcaaa ccgttggttg cataggatgt cacctttatt 1681  taacccatta atactctggt tgacctaatc ttattctcag acctcaagtg tctgtgcagt 1741  atctgttcca tttaaatatc agctttacaa ttatgtggta gcctacacac ataatctcat 1801  ttcatcgctg taaccaccct gttgtgataa ccactattat tttacccatc gtacagctga 1861  ggaagcaaac agattaagta acttgcccaa accagtaaat agcagacctc agactgccac 1921  ccactgtcct tttataatac aatttacagc tatattttac tttaagcaat tcttttattc 1981  aaaaaccatt tattaagtgc ccttgcaata tcaatcgctg tgccaggcat tgaatctaca 2041  gatgtgagca agacaaagta cctgtcctca aggagctcat agtataatga ggagattaac 2101  aagaaaatgt attattacaa tttagtccag tgtcatagca taaggatgat gcgagcggaa 2161  aacccgagca gtgttgccaa gaggaggaaa taggccaatg tggtctggga cggttggata 2221  tacttaaaca tcttaataat cagagtaatt ttcatttaca aagagaggtc ggtacttaaa 2281  ataaccctga aaaataacac tggaattcct tttctagcat tatatttatt cctgatttgc 2341  ctttgccata taatctaatg cttgttttata tagtgtctgg tattgtttaa cagttctgtc 2401  ttttctattt aaatgccact aaatttttaaa ttcataccttt tccatgattc aaaattcaaa 2461  agatcccatg ggagatggtt ggaaaatctc cacttcatcc tccaagccat tcaagtttcc 2521  tttccagaag caactgctac tgcctttcat tcatatgttc ttctaaagat agtctacatt 2581  tggaaatgta tgttaaaagc acgtatttt aaaatttttt tcctaaatag taacacattg 2641  tatgtctgct gtgtactttg ctatttttat ttattttagt gtttcttata tagcagatgg 2701  aatgaatttg aagttcccag ggctgaggat ccatgccttc tttgtttcta agttatcttt 2761  cccatagctt ttcattatct ttcatatgat ccagtatatg ttaaatatgt cctacatata 2821  catttagaca accaccattt gttaagtatt tgctctagga cagagtttgg atttgtttat 2881  gtttgctcaa aaggagaccc atgggctctc cagggtgcac tgagtcaatc tagtcctaaa 2941  aagcaatctt attattaact ctgtatgaca gaatcatgtc tggaactttt gttttctgct 3001  ttctgtcaag tataaacttc actttgatgc tgtacttgca aaatcacatt ttctttctgg 3061  aaattccggc agtgtacctt gactgctagc taccctgtgc cagaaaagcc tcattcgttg 3121  tgcttgaacc cttgaatgcc accagctgtc atcactacac agccctccta agaggcttcc 3181  tggaggtttc gagattcaga tgccctggga gatcccagag tttcctttcc ctcttggcca 3241  tattctggtg tcaatgacaa ggagtacctt ggcttgcca catgtcaagg ctgaagaaac 3301  agtgtctcca acagagctcc ttgtgttatc tgtttgtaca tgtgcatttg tacagtaatt 3361  ggtgtgacag tgttcttgt gtgaattaca ggcaagaatt gtggctgagc aaggcacata 3421  gtctactcag tctattccta agtcctaact cctccttgtg gtgttggatt tgtaaggcac
```

-continued

```
3481  tttatcccct  ttgtctcatg  tttcatcgta  aatggcatag  gcagagatga  tacctaattc 3541  tgcatttgat  tgtcactttt  tgtacctgca  ttaatttaat  aaaatattct  tatttatttt 3601  gttacttggt  acaccagcat  gtccattttc  ttgtttattt  tgtgtttaat  aaaatgttca 3661  gtttaacatc  ccagtggaga  aagttaaaaa  a
```

B3 CD96-CD96 antigen; T cell activation mRNA NM_198196.2

(SEQ ID NO: 139)

```
   1  ttcctgtcta  cgtttcattt  cctgggggct  tgccaagtga  taaacagacc  caggcgtgtg 61  tggtagagtt  cgggtttttt  agcacgaagt  gggtggctgg  agtttgcttg  aaaacatcaa 121  ttgactttgt  gatcattaca  gaaatgctgg  tgtaaggtgt  tcagaagaca  atggagaaaa 181  aatggaaata  ctgtgctgtc  tattacatca  tccagataca  ttttgtcaag  ggagtttggg 241  aaaaaacagt  caacacagaa  gaaaatgttt  atgctacact  tggctctgat  gtcaacctga 301  cctgccaaac  acagacagta  ggcttcttcg  tgcagatgca  atggtccaag  gtcaccaata 361  agatagacct  gattgctgtc  tatcatcccc  aatacggctt  ctactgtgcc  tatgggagac 421  cctgtgagtc  acttgtgact  ttcacagaaa  ctcctgagaa  tgggtcaaaa  tggactctgc 481  acttaaggaa  tatgtcttgt  tcagtcagtg  gaaggtacga  gtgtatgctt  gttctgtatc 541  cagagggcat  tcagactaaa  atctacaacc  ttctcattca  gacacacgtt  acagcagatg 601  aatggaacag  caaccatacg  atagaaatag  agataaatca  gactctggaa  ataccatgct 661  tcaaaatag  ctcctcaaaa  atttcatctg  agttcaccta  tgcatggtcg  gtggaaaaca 721  gcagcacgga  ttcttgggtc  cttctttcta  agggtataaa  ggaggataat  ggaactcagg 781  aaacacttat  ctcccaaaat  cacctcatca  gcaattccac  attacttaaa  gatagagtca 841  agcttggtac  agactacaga  ctccacctct  ctccagtcca  aatcttcgat  gatgggcgga 901  agttctcttg  ccacattaga  gtcggtccta  acaaaatctt  gaggagctcc  accacagtca 961  aggttttgc  taaaccagaa  atccctgtga  ttgtggaaaa  taactccacg  gatgtcttgg 1021  tagagagaag  atttacctgc  ttactaaaga  atgtatttcc  caaagcaaat  atcacatggt 1081  ttatagatgg  aagttttctt  catgatgaaa  agaaggaat  atatattact  aatgaagaga 1141  gaaaaggcaa  agatggattt  ttggaactga  agtctgtttt  aacaagggta  catagtaata 1201  aaccagccca  atcagacaac  ttgaccattt  ggtgtatggc  tctgtctcca  gtcccaggaa 1261  ataaagtgtg  gaacatctca  tcagaaaaga  tcacttttct  cttaggttct  gaaattcct 1321  caacagaccc  tccactgagt  gttacagaat  ctacccttga  cacccaacct  tctccagcca 1381  gcagtgtatc  tcctgcaaga  tatccagcta  catcttcagt  gacccttgta  gatgtgagtg 1441  ccttgaggcc  aaacaccact  cctcaaccca  gcaattccag  tatgactacc  cgaggcttca 1501  actatccctg  gacctccagt  gggacagata  ccaaaaaatc  agtttcacgg  atacctagtg 1561  aaacatacag  ttcatccccg  tcaggtgcag  gctcaacact  tcatgacaat  gtctttacca 1621  gcacagccag  agcattttca  gaagtcccca  caactgccaa  tggatctacg  aaaactaatc 1681  acgtccatat  cactggtatt  gtggtcaata  agcccaaaga  tggaatgtcc  tggccagtga 1741  ttgtagcagc  tttactcttt  tgctgcatga  tattgtttgg  tcttggagtg  agaaaatggt 1801  gtcagtacca  aaaagaaata  atggaaagac  ctccaccttt  caagccacca  ccacctccca 1861  tcaagtacac  ttgcattcaa  gagcccaacg  aaagtgatct  gcccttatcat  gagatggaga 1921  ccctctagtc  tcgtgagact  ttgccccatg  gcagaactct  gctggaatcc  tattgagaag 1981  gtagacattg  tgctttatta  atatagtcgc  tcttcagcca  tgcctttgct  gcagctgaaa 2041  tggaagtcag  aagtgagtga  cctgttttcc  cagcaactca  ccctcttcca  tctccaaacg 2101  cctgaagctt  aaccaagagt  gagaggatat  gtcatgttca  cactcaatgc  aattcgtagt
```

-continued

```
2161  ggttttcttg cttatgtaag aagtacatat tagtctgcca tctttaaaaa aaaatacagt
2221  attttcattt aaattctctg atggagggac aacaatggtt tcaactgtat gcccatgcct
2281  gatcctctta tttgaacatc tatcaacatt gtaaactctt tgccaaaatc ctggggcttt
2341  gctgcattcc ctaagataat tacaggaaaa agaaaatgta aaagtgctaa caaggctgcc
2401  aagtaatgga gaagtatggt tagtcttcat attgaaattc tgttgcttat tttcatggaa
2461  ggaaacagaa tactttgcac aggaaccaca ttttcaatcc tccttcactg tcttcctacc
2521  atgttcagcc cagactcctg ccacatggac caggatgaag agggatcaaa gagataatta
2581  gccaaaaacc cagtagccta aagatacaa aactccactg gcctctaaaa ttatattagc
2641  caagagtggt ttcatttgag tgccttcgtg tgtatgtcca tcaaactgga accaaactgt
2701  tttgtaagta aacaggcagc ctaagcccaa ccctactttc taattccagt tattctcttt
2761  ttcatctggg gatttacctg ttcatttaat ctgcctgttt tgatctgttt tgaaaaagat
2821  aaagagcctc aaatcagacc agcactgatt aattaaccct gctcctacca atctttttta
2881  aagcagttga agcagaatgt ataggtgtca gagaagaaac ctagtcagcc agacgtgctc
2941  tgtattcagc aatagtttgt gaatgaataa attactaatc ctccttgtcg cttgaaacct
3001  tcccacactc cctgctccag gagggaaaaa cagatgttgt tgacagatag agtgataggc
3061  aaattctgtg tggactttag tcccaaaagg aaactttagt tcacttgcag tatgcttatc
3121  cttgactgca catgagaatg ccttgtgcag agttatttgg agattatgtc tttttcttaa
3181  acaccatggc tgtcacactt cagttcaatt aaatcagaat gtctgaggag tgagacacag
3241  gcatcaacac tctcaaatga ttcacatgtt cagccaaagt tgagaaccat cgagcctgtg
3301  gaagttcttt ctcatggctc agaatcttag gtaggtgctt aactcttgtg gtggccagcc
3361  tccaagatga gccccagtgt tcttgcctcc tactattcac atctttatgt ggtcccctcc
3421  aatgctgaat acagatgatt tgtgtaacct gaggccagga ttaaggggag gcaatcaatg
3481  cacctaggga aaaaatttaa ggaggtattc acactcaggg tcatgcactt gcacaatgtt
3541  gagaatgagt accactctca ccattggtat agccaaaaaa gcttggaagt gaccaaggct
3601  aggtcacaaa atacactgtg gcttcttctt tgatctctct ttgaccatac tgcactggg
3661  aaaagcccat tcccatgcca tgaagacacc aaggcagccc tattgagaaa tctacctgtc
3721  gtggccgggc gcagtggctc acgcctgtaa tcccagcact ttgggaggcc gaggtgggtg
3781  gatcacgagg tcaggagatc gagaccatcc tggctaacac agtgaaaccc cgtctctact
3841  aaaaatacaa aaaattagcc gggtgtggtg tcgggcacct gtagtcccag ctactcagga
3901  ggctgaggca ggagaagggt gggaacccgg gaggcagagc ttgcagtgag ccgagattgt
3961  gccactgcac actccaatct gggtgaaaga ccgagactcc gcctcaaaaa aaaaaaaaa
4021  agaaagaaag aaagaaagaa agaaatctac ctgtcaagga actaaggtat tttgctaaca
4081  agcaccaact tgccagccat gtaagggagc catcttggaa gcagatcctc cagcctccag
4141  tcaagtcttc agataattgc aacttcagtt gatcttttga ccaagacctc aagagagcca
4201  gaactaccca gctaagcctt ttactaaatt tctgaacttc taacactatt agataataag
4261  tgcttattgt ttaacaccat taattttgag tataatttgt tacatagcga cagataacta
4321  tacagctcaa caactagaaa aataaactgt ttacctgcct taattatta tctttagttc
4381  cttattagtt ctcaagaaac aaatgctagc ttcatatgta tggctgttgc tttgcttcat
4441  gtgtatggct atttgtattt aacaagactt aatcatcagt a
```

-continued

B4 CDH23-cadherin-related 23 mRNA NM_022124.5

(SEQ ID NO: 140)

```
   1 gcggcggcgg cggctcggga gagagggacg cgggctgcag gcgcgatgct tggctagagg
  61 acgcgtccga cggcggccgg acgctgaggt ggtcggggct agtcagcccg gcctgggcat
 121 ggagcgcggg gtggcagagc ctctggacgt ttggggcgcg cccagtccga gccccggcg
 181 cgcctgaagt tgcgagcggc gagcggcgag cggcgagcgg cccgcggaga cccaggagct
 241 gccggcacgc cgcggatgag ccttcgcgcc ggcgggaaga cgcggcggtg gccagggcca
 301 gagcaggcgg cccgcggggg ccgatccggc ggagagcaga gcccgaggcg aggcgaggcg
 361 cggcgccgct gcacacacgc acacggagcc atgggggcgcc atgttgccac cagctgccac
 421 gtggcctggc ttttggtgct gatctctgga tgctggggcc aggtgaaccg gctgcccttc
 481 ttcaccaacc acttctttga tacatacctg ctgatcagcg aggacacgcc tgtgggttct
 541 tctgtgaccc agttgctggc ccaagacatg gacaatgacc ccctggtgtt tggcgtgtct
 601 ggggaggagg cctctcgctt ctttgcagtg gagcctgaca ctggcgtggt gtggctccgg
 661 cagccactgg acagagagac caagtcagag ttcaccgtgg agttctctgt cagcgaccac
 721 caggggggtga tcacacggaa ggtgaacatc caggttgggg atgtgaatga caacgcgccc
 781 acatttcaca atcagcccta cagcgtccgc atccctgaga atacaccagt ggggacgccc
 841 atcttcatcg tgaatgccac agaccccgac ttgggggcag ggggcagcgt cctctactcc
 901 ttccagcccc cctcccaatt cttcgccatt gacagcgccc gcggtatcgt cacagtgatc
 961 cgggagctgg actacgagac cacacaggcc taccagctca cggtcaacgc cacagatcaa
1021 gacaagacca ggcctctgtc caccctggcc aacttggcca tcatcatcac agatgtccag
1081 gacatggacc ccatcttcat caacctgcct tacagcacca acatctacga gcattctcct
1141 ccgggcacga cggtgcgcat catcaccgcc atagaccagg ataaaggacg tccccggggc
1201 attggctaca ccatcgtttc agggaatacc aacagcatct tgccctgga ctacatcagc
1261 ggagtgctga ccttgaatgg cctgctggac cggagagaacc ccctgtacag ccatggcttc
1321 atcctgactg tgaagggcac ggagctgaac gatgaccgca ccccatctga cgctacagtc
1381 accacgacct tcaatatcct ggttattgac atcaatgaca atgccccgga gttcaacagc
1441 tccgagtaca gcgtggccat cactgagctg gcacaggtcg gctttgccct tccactcttc
1501 atccaggtgg tggacaagga tgagaatttg gcctgaaca gcatgtttga ggtgtacttg
1561 gtggggaaca actcccacca cttcatcatc tccccgacct ccgtccaggg gaaggcggac
1621 attcgtattc gggtggccat cccactggac tacgagaccg tggaccgcta cgactttgat
1681 ctctttgcca atgagagtgt gcctgaccat gtgggctatg ccaaggtgaa gatcactctc
1741 atcaatgaaa atgacaaccg gcccatcttc agccagccac tgtacaacat cagcctgtac
1801 gagaacgtca ccgtggggac ctctgtgctg acagtcctgg caactgacaa tgatgcaggc
1861 acctttgggg aagtcagcta cttcttcagt gatgaccctg acaggttctc gctggacaag
1921 gacacgggac tcatcatgct gattgccagg ctggactatg agctcatcca gcgcttcacc
1981 ctgacgatca ttgcccggga cggggcgcgc gaggagacca caggccgggt caggatcaat
2041 gtgttggatg tcaacgacaa cgtgcccacc ttccagaagg atgcctacgt gggtgctctg
2101 cgggagaacg agccttctgt cacacagctg gtgcggctcc gggcaacaga tgaagactcc
2161 cctcccaaca accagatcac ctacagcatt gtcagtgcat ctgcctttgg cagctacttc
2221 gacatcagcc tgtacgaggg ctatggagtg atcagcgtca gtcgccccct ggattatgaa
2281 cagatatcca atgggctgat ttatctgacg gtcatggcca tggatgctgg caacccccct
2341 ctcaacagca ccgtccctgt caccatcgag gtgtttgatg agaatgacaa ccctcccacc
```

-continued

```
2401  ttcagcaagc cgcctactt cgtctccgtg gtggagaaca tcatggcagg agccacggtg
2461  ctgttcctga atgccacaga cctggaccgc tcccgggagt acggccagga gtccatcatc
2521  tactccttgg aaggctccac ccagtttcgg atcaatgccc gctcagggga aatcaccacc
2581  acgtctctgc ttgaccgaga gaccaagtct gaatacatcc tcatcgttcg cgcagtggac
2641  gggggtgtgg gccacaacca gaaaactggc atcgccaccg taaacatcac cctcctggac
2701  atcaatgaca accaccccac gtggaaggac gcaccctact acatcaacct ggtggagatg
2761  accccctccag actctgatgt gaccacggtg gtggctgttg acccagacct gggggagaat
2821  ggcacccctgg tgtacagcat ccagccaccc aacaagttct acagcctcaa cagcaccacg
2881  ggcaagatcc gcaccaccca cgccatgctg gaccgggaga ccccgaccc ccatgaggcc
2941  gagctgatgc gcaaaatcgt cgtctctgtt actgactgtg caggccccc tctgaaagcc
3001  accagcagtg ccacagtgtt tgtgaacctc ttggatctca atgacaatga ccccaccttt
3061  cagaacctgc cttttgtggc cgaggtgctt gaaggcatcc cggcgggggt ctccatctac
3121  caagtggtgg ccatcgacct cgatgagggc ctgaacggcc tggtgtccta ccgcatgccg
3181  gtgggcatgc cccgcatgga cttcctcatc aacagcagca gcggcgtggt ggtcaccacc
3241  accgagctgg accgcgagcg catcgcggag taccagctgc gggtggtggc cagtgatgca
3301  ggcacgccca ccaagagctc caccagcacg ctcaccatcc atgtgctgga tgtgaacgac
3361  gagacgccca ccttcttccc ggccgtgtac aatgtgtctg tgtccgagga cgtgccacgc
3421  gagttccggg tggtctggct gaactgcacg gacaacgacg tgggcctcaa tgcagagctc
3481  agctacttca tcacaggtgg caacgtggat gggaagttca gcgtgggtta ccgcgatgcc
3541  gttgtgagaa ccgtggtggg cctggaccgg gagaccacag ccgcctacat gctcatcctg
3601  gaggccatcg acaacggccc tgtagggaag cgacacacgg gcacagccac cgtgttcgtc
3661  actgtcctgg atgtgaatga caaccggccc atctttctgc agagcagcta tgaggccagc
3721  gtccctgagg acatccctga aggccacagc atcttgcagc tgaaagccac ggacgcagat
3781  gagggcgagt ttgggcgtgt gtggtaccgc atcctccatg taaccatgg caacaacttc
3841  cggatccatg tcagcaatgg gctcctgatg cgagggcccc ggcccctgga ccgggagcgg
3901  aactcatccc acgtgctgat agtggaggcc tacaaccacg acctgggccc catgcggagc
3961  tccgtcaggg tgattgtgta cgtggaggac atcaacgatg aggcccccgt gttcacacag
4021  cagcagtaca gccgtctggg gcttcgagag accgcaggca ttggaacgtc agtcatcgtg
4081  gtccaagcca cagaccgaga ctctggggat ggtggcctgg tgaactaccg catcctgtcg
4141  ggcgcagagg ggaagtttga gattgacgag agcacagggc ttatcatcac cgtgaattac
4201  ctggactacg agaccaagac cagctacatg atgaatgtgt cggccactga ccaggcccg
4261  cccttcaacc agggcttctg cagcgtctac atcactctgc tcaacgagct ggacgaggcc
4321  gtgcagttct ccaatgcctc atacgaggct gccatcctgg agaatctggc actgggtact
4381  gagattgtgc gggtccaggc ctactccatc gacaacctca accaaatcac gtaccgcttc
4441  aacgcctaca ccagcaccca ggccaaagcc ctcttcaaga tagacgccat cacgggtgtg
4501  atcacagtcc agggcctggt ggaccgtgag aagggcgact tctatacctt gacagtggtg
4561  gcagatgacg gcggcccaa ggtggactcc accgtgaagg tctacatcac tgtgctggac
4621  gagaatgaca cagcccccg gtttgacttc acctccgact cggcggtcag catacccgag
4681  gactgccctg tgggccagcg agtggcgtact gtcaaggcct gggaccctga tgctggcagc
4741  aatgggcagg tggtcttctc cctggcctct ggcaacatcg cgggggcctt tgagatcgtc
```

-continued

```
4801  accaccaatg actccattgg cgaagtgttt gtggccaggc ccctggacag agaagagctg
4861  gatcactaca tcctccaggt tgtggcttct gaccgaggca cccctccacg gaagaaggac
4921  cacatcctgc aggtgaccat cctggacatc aatgacaacc ctccagtcat cgagagcccc
4981  tttggataca atgtcagtgt gaatgagaac gtgggtggag gtactgctgt ggtccaggtg
5041  agagccactg accgtgacat cgggatcaac agtgttctgt cctactacat caccgagggc
5101  aacaaggaca tggccttccg catggaccgc atcagcggtg agatcgccac acggcctgcc
5161  ccgcctgacc gcgagcgcca gagcttctac cacctggtgg ccactgtgga ggacgagggc
5221  accccaaccc tgtcggccac acgcacgtg tacgtgacca ttgtggatga gaatgataac
5281  gcgcccatgt tccagcagcc ccactatgag gtgctgctgg atgagggccc agacacgctc
5341  aacaccagcc tcatcaccat ccaggcactg gacctggatg agggtcccaa cggcacagtc
5401  acctatgcca tcgtcgcagg caacatcgtc aacaccttcc gcatcgacag acacatgggt
5461  gtcatcactg ctgccaaaga gctggactac gagatcagcc acggccgcta caccctgatc
5521  gtcactgcca cagaccagtg ccccatctta tcccaccgcc tcacctctac caccacggtg
5581  cttgtgaatg tgaatgacat caacgacaat gtgcctacct tccccgggga ctatgaggga
5641  ccatttgaag tcactgaggg ccagccgggg cccagagtgt ggaccttcct ggcccatgac
5701  cgagactcag gacccaacgg gcaggtggag tacagcatca tggatggaga ccctctgggg
5761  gagtttgtga tctctcctgt ggagggggtg ctaagggtcc ggaaggacgt ggagctggac
5821  cgggagacca tcgccttcta caacctgacc atctgtgccc gtgaccgggg gatgccccca
5881  ctcagctcca caatgctggt ggggatccgg gtgctggaca tcaacgacaa cgaccctgtg
5941  ctgctgaacc tgcccatgaa catcaccatc agcgagaaca gccctgtctc cagctttgtc
6001  gcccatgtcc tggccagtga cgctgacagt ggctgcaatg cacgcctcac cttcaacatc
6061  actgcgggca accgcgagcg ggccttcttc atcaatgcca cgacagggat cgtcactgtg
6121  aaccggcccc tggaccgcga gcggatccca gagtacaagc tgaccatttc tgtgaaggac
6181  aacccggaga tccacgcat agccaggagg gattatgact tgcttctgat cttcctttct
6241  gatgagaatg acaaccaccc cctcttcact aaaagcacct accaggcaga ggtgatggaa
6301  aactctcccg ctggcacccc tctcacggtg ctcaatgggc ccatcctggc cctggatgca
6361  gaccaagaca tctacgccgt ggtgacctac cagctgctgg gtgcccagag tggcctcttt
6421  gacatcaaca gcagcaccgg tgtggtgacc gtgaggtcag gtgtcatcat tgaccgggag
6481  gcattctcgc cacccatcct ggagctgctg ctgctggctg aggacatcgg gctgctcaac
6541  agcacggccc acctgctcat caccatcctg atgacaatg acaaccggcc caccttagc
6601  cctgccaccc tcactgtcca tctgctagag aactgcccgc ctggattctc agtccttcaa
6661  gtcacagcca cagatgagga cagtggcctc aatgggagc tggtctaccg aatagaagct
6721  ggggctcagg accgcttcct cattcatctg gtcaccgggg tcatccgtgt tggtaatgcc
6781  accatcgaca gagaggagca ggagtcctac aggctaacgg tggtggccac cgaccggggc
6841  accgttcctc tctcgggcac agccattgtc accattctga tcgatgacat caatgactcc
6901  cgccccgagt tcctcaaccc catccagaca gtgagcgtgc tggagtcggc tgagccaggc
6961  actgtcattg ccaatatcac ggccattgac cacgacctca acccaaagct agagtaccac
7021  attgtcggca ttgtggccaa ggacgacact gatcgcctgg tgcccaacca ggaggacgcc
7081  tttgctgtga atatcaacac aggatctgta atggtgaagt ccccccatgaa tcgggagctg
7141  gttgccacct atgaggtcac tctctcagtg attgacaatg ccagcgacct accagagcgc
7201  tctgtcagtg tgccaaatgc caagctgact gtcaacgtcc tggacgtcaa tgacaatacg
```

-continued

```
7261  ccccagttca agcccctttgg gatcacctac tacatggagc ggatcctgga gggggccacc
7321  cctgggacca cactcattgc tgtggcagcc gtggaccctg acaagggcct taatgggctg
7381  gtcacctaca ccctgctgga cctggtgccc ccagggtatg tccagctgga ggactcctcg
7441  gcagggaagg tcattgccaa ccggacagtg gactacgagg aggtgcactg gctcaacttt
7501  accgtgaggg cctcagacaa cgggtccccg ccccgggcag ctgagatccc tgtctacctg
7561  gaaatcgtgg acatcaatga caacaacccc atcttttgacc agccctccta ccaggaggct
7621  gtctttgagg atgtgcctgt gggcacaatc atcctgacag tcactgccac tgatgctgac
7681  tcaggcaact ttgcactcat tgagtacagc cttggagatg gagagagcaa gtttgccatc
7741  aaccccacca cgggtgacat ctatgtgctg tcttctctgg accgggagaa gaaggaccac
7801  tatatcctga ctgccttggc caaagacaac cctggggatg tagccagcaa ccgtcgcgaa
7861  aattcagtgc aggtggtgat ccaagtgctg gatgtcaatg actgccggcc acagttctcc
7921  aagccccagt tcagcacaag cgtgtatgag aatgagccgg cgggcaccctc ggtcatcacc
7981  atgatggcca ctgaccagga tgaaggtccc aatggagagt tgacctactc acttgagggc
8041  cctggcgtgg aggccttcca tgtggacatg gactcgggct tggtgaccac acagcggcca
8101  ctgcagtcct acgagaagtt cagtctgacc gtggtggcca cagatggtgg agagccccca
8161  ctctggggca ccaccatgct cctggtggag gtcatcgacg tcaatgacaa ccgccctgtc
8221  tttgtgcgcc cacccaacgg caccatcctc cacatcagag aggagatccc gctgcgctcc
8281  aacgtgtacg aggtctacgc cacggacaag gatgagggcc tcaacggggc ggtgcgctac
8341  agcttcctga agactgcggg caaccgggac tgggagttct tcatcatcga cccaatcagc
8401  ggcctcatcc agactgctca gcgcctggac cgcgagtcgc aggcggtgta cagcctcatc
8461  ttggtggcca gcgacctggg ccagccagtg ccatacgaga ctatgcagcc gctgcaggtg
8521  gccctggagg acatcgatga caacgaaccc cttttcgtga ggcctccaaa aggcagcccc
8581  cagtaccagc tgctgacagt gcctgagcac tcaccacgcg gcaccctcgt gggcaacgtg
8641  acaggcgcag tggatgcaga tgagggcccc aacgcgatcg tgtactactt catcgcagcc
8701  ggcaacgaag agaagaactt ccatctgcag cccgatgggt gtctgctggt gctgcgggac
8761  ctggaccggg agcgagaagc catcttctcc ttcatcgtca aggcctccag caatcgcagc
8821  tggacacctc cccgtggacc ctccccaacc ctcgacctgg ttgctgacct cacactgcag
8881  gaggtgcgcg ttgtgctaga ggacatcaac gaccagccac cacgcttcac caaggctgag
8941  tacactgcag gggtggccac cgacgccaag gtgggctcag agttgatcca ggtgctggcc
9001  ctggatgcag acattggcaa caacagcctt gtcttctaca gcattctggc catccactac
9061  ttccgggccc ttgccaacga ctctgaagat gtgggccagg tcttcaccat ggggagcatg
9121  gacggcattc tgcgcacctt cgacctcttc atggcctaca gccccggcta cttcgtggtg
9181  gacattgtgg cccgagacct ggcaggccac aacgacacgg ccatcatcgg catctacatc
9241  ctgagggacg accagcgcgt caagatcgtc attaacgaga tccccgaccg tgtgcgcggc
9301  ttcgaggagg agttcatcca cctgctctcc aacatcactg ggccattgt caatactgac
9361  aatgtgcagt ccatgtggga caagaagggc cgggtgaact tgcgcagac agaactgctt
9421  atccacgtgg tgaaccgcga taccaaccgc atcctggacg tggaccgggt gatccagatg
9481  atcgatgaga acaaggagca gctacggaat cttttccgga actacaacgt cctggacgtg
9541  cagcctgcca tctctgtccg gctgccggat gacatgtctg ccctgcagat ggcgatcatc
9601  gtcctggcta tcctcctgtt cctggccgcc atgctctttg tcctcatgaa ctggtactac
```

-continued

```
 9661 aggactgtac acaagaggaa gctcaaggcc attgtggctg gctcagctgg gaatcgtggc
 9721 ttcatcgaca tcatggacat gcctaacacc aacaagtact cctttgatgg agccaaccct
 9781 gtgtggctgg atcccttctg tcggaacctg gagctggccg cccaggcgga gcatgaggat
 9841 gacctaccgg agaacctgag tgagatcgcc gacctgtgga acagccccac gcgcacccat
 9901 ggaactttg ggcgtgagcc agcagctgtc aagcctgatg atgaccgata cctgcgggct
 9961 gccatccagg agtatgacaa cattgccaag ctgggccaga tcattcgtga ggggccaatc
10021 aagggctcgc tgctgaaggt ggtcctggag gattacctgc ggctcaaaaa gctctttgca
10081 cagcggatgg tgcaaaaagc ctcctcctgc cactcctcca tctctgagct gatacagact
10141 gagctggacg aggagccagg agaccacagc ccagggcagg gtagcctgcg cttccgccac
10201 aagccaccag tggagctcaa ggggcccgat gggatccatg tggtgcacgg cagcacgggc
10261 acgctgctgg ccaccgacct caacagcctg cccgaggaag accagaaggg cctgggccgc
10321 tcgctggaga cgctgaccgt tgccgaggcc actgccttcg agcgcaacgc ccgcacagaa
10381 tccgccaaat ccacacccct gcacaaactt cgcgacgtga tcatggagac cccctggag
10441 atcacagagc tgtgactaga cagggaagcc ttgtgggtgt gagcagcacc catccaccgt
10501 cccctcccag ggagcaaggg cagggacagg gccggtcggg ggggaccctc caaggccagg
10561 ccttggggac aaccttggct tggccctggc agcccgcatc agctgctcag atcccacttt
10621 tgccagacgc tcattcagca tctgacctct accttcataa gatctgttat ttttataaga
10681 aaaccaaaca aaaatgttaa gcatctaagg acaaggtaag gagggtcact ggggcccaag
10741 agtctgggga ccagcttggc tcaggctgag ctgaaagagg ccaaacaggc cctcctccct
10801 cccagctcca ccccgcaagc accatcccct ccggctaagc aggcgcaagg gaggcccagc
10861 gcggacatcc cctgctgcc ggacacccga ctccagtcca agtctcgcta catttccgcc
10921 acatccctct ctgctggacg tccaggtgga ggtggcatcc ccacgtggac aagaaagtca
10981 atgtcaatga acaagcattc tctccatttc actggcttcc caaatgtgtg cccagcttat
11041 aaacagaagt gactgatgtt ccctccggtt ttgaatgtgg agtgtttgtg tgtgttcctt
11101 ttttaaatta agttattccc tcaaaaaaaa aaaa
```

B5 IRF1-interferon regulatory factor 1 mRNA-NM_002198.2
(SEQ ID NO: 141)

```
   1 agagctcgcc actccttagt cgaggcaaga cgtgcgcccg agcccgccg aaccgaggcc
  61 acccggagcc gtgcccagtc cacgccggcc gtgcccggcg gccttaagaa cccggcaacc
 121 tctgccttct tccctcttcc actcggagtc gcgctccgcg cgccctcact gcagcccctg
 181 cgtcgccggg accctcgcgc gcgaccgccg aatcgctcct gcagcagagc caacatgccc
 241 atcactcgga tgcgcatgag accctggcta gagatgcaga ttaattccaa ccaaatcccg
 301 gggctcatct ggattaataa agaggagatg atcttccaga tcccatggaa gcatgctgcc
 361 aagcatggct gggacatcaa caaggatgcc tgtttgttcc ggagctgggc cattcacaca
 421 ggccgataca aagcagggga aaaggagcca gatcccaaga cgtggaaggc caactttcgc
 481 tgtgccatga actccctgcc agatatcgag gaggtgaaag accagagcag gaacaagggc
 541 agctcagctg tgcgagtgta ccggatgctt ccacctctca ccaagaacca gagaaagaa
 601 agaaagtcga gtccagccg agatgctaag agcaaggcca agaggaagtc atgtgggat
 661 tccagccctg ataccttctc tgatggactc agcagctcca ctctgcctga tgaccacagc
 721 agctacacag ttccaggcta catgcaggac ttggaggtgg agcaggccct gactccagca
 781 ctgtcgccat gtgctgtcag cagcactctc cccgactggc acatcccagt ggaagttgtg
```

```
 841 ccggacagca ccagtgatct gtacaacttc caggtgtcac ccatgccctc cacctctgaa
 901 gctacaacag atgaggatga ggaagggaaa ttacctgagg acatcatgaa gctcttggag
 961 cagtcggagt ggcagccaac aaacgtggat gggaaggggt acctactcaa tgaacctgga
1021 gtccagccca cctctgtcta tggagacttt agctgtaagg aggagccaga aattgacagc
1081 ccaggggggg atattgggct gagtctacag cgtgtcttca cagatctgaa gaacatggat
1141 gccacctggc tggacagcct gctgacccca gtccggttgc cctccatcca ggccattccc
1201 tgtgcaccgt agcagggccc ctgggcccct cttattcctc taggcaagca ggacctggca
1261 tcatggtgga tatggtgcag agaagctgga cttctgtggg ccctcaaca gccaagtgtg
1321 accccactgc caagtgggga tggggcctcc ctccttgggt cattgacctc tcagggcctg
1381 gcaggccagt gtctgggttt ttcttgtggt gtaaagctgg ccctgcctcc tgggaagatg
1441 aggttctgag accagtgtat caggtcaggg acttggacag gagtcagtgt ctggcttttt
1501 cctctgagcc cagctgcctg gagagggtct cgctgtcact ggctggctcc tagggaaca
1561 gaccagtgac cccagaaaag cataacacca atcccagggc tggctctgca ctaagagaaa
1621 attgcactaa atgaatctcg ttcccaaaga actacccct tttcagctga gccctgggga
1681 ctgttccaaa gccagtgaaa tgtgaaggaa agtggggtcc ttcggggcga tgctccctca
1741 gcctcagagg agctctaccc tgctccctgc tttggctgag gggcttggga aaaaaacttg
1801 gcacttttc gtgtggatct tgccacattt ctgatcagag gtgtacacta acatttcccc
1861 cgagctcttg gcctttgcat ttatttatac agtgccttgc tcggcgccca ccacccctc
1921 aagcccagc agccctcaac aggcccaggg agggaagtgt gagcgccttg gtatgactta
1981 aaattggaaa tgtcatctaa ccattaagtc atgtgtgaac ataaggac gtgtgtaaat
2041 atgtacattt gtctttttat aaaagtaaa ttgtttataa gggtgtggc cttttttagag
2101 agaaatttaa cttgtagatg attttacttt ttatggaaac actgatggac ttattattgg
2161 catcccgcct gaacttgact ttggggtgaa cagggacatg catctattat aaaatccttt
2221 cggccaggcg cggtggctca cacctgtaat cccagcactt tgggaggccg agatgggtgg
2281 atcacctgag gtcaggagtt cgagaccagc ctggtgaaac tccatttcta ctaaaaatgc
2341 aaaaattagc tgggcgtggt tgcgggtgct tgtaatccca gctactcagg aggctgaggc
2401 aagagaatcg cttgaacctg ggaggtggag gttgcagtga gccgagaaca tgccattgca
2461 ctccagcccg ggcaccaaaa aaaaaaaaa aaaaaaaac ctttcatttg gccgggcatg
2521 gtggcttatg cctgtaatcc tggcactttg ggaggccaag gtgggcagat cacctgaggt
2581 caggagtttg agaccagcct ggccaacatg gtgaaacctc atctctacta aaaatacaaa
2641 aattaggccg ggcacggtgg ctcacgcctg taatcccagc actttgggag gcagaggcgg
2701 gcggatcacg aggtcaggag atcaagacca tcctggctaa cacggtgaaa ccccgtctct
2761 actaaaaata taaaaaatta gccgggccta gtggcgggtg cctgtagtcc cagctactcg
2821 ggaggctgag gcaggagaat ggcatgaacc ccgaggcag agcttgcagt gagccgagat
2881 tgcaccactg cactacagcc tgggcgacag agcgagactc cgtctcaaaa aaaaaaaaa
2941 aaattagccg ggcctggtgg cgggcgcctg taatcccagc tactgtggag gctgaagcac
3001 aagaatcact tgaacccggg agatggaggt tgcagtgagc tgagactgtg ccactgcact
3061 ccagcctggg tgacaagagt gagactttgt ctcaaaaaaa aaaaatcct tttgtttatg
3121 ttcacataga caatggcaga aggagggac attcctgtca taggaacatg cttatataaa
3181 catagtcacc tgtccttgac tatcaccagg gctgtcagtt gattctgggc tcctggggcc
3241 caaggagtgt taagttttga ggcatgtgcc ataggtgatg tgtcctgcta acacacagat
```

-continued

```
3301 gctgctccaa aaagtcagtt gatatgacac agtcacagac agaacagtca gcagcccaag
3361 aaaggtcctc acggctgctg tgctgggtag cacttgccat ccagtttcta gagtgatgaa
3421 atgctctgtc tgtaccgttc aatacagtag gcactggcac tagccacatg tgccagctaa
3481 gcacttgaaa tgtggccagt gcaataagga attgaacttt taattgcatt taataaactg
3541 tatgtaaata gtcaaaaaaa aaaaaaa
```

B6 GBP1-interferon-induced guanylate-binding protein 1 mRNA
NM_002053.2

(SEQ ID NO: 142)

```
   1 ggagtcagtg atttgaacga agtactttca gtttcatatt actctaaatc cattacaaat
  61 ctgcttagct tctaaatatt tcatcaatga ggaaatccca gccctacaac ttcggaacag
 121 tgaaatatta gtccagggat ccagtgagag acacagaagt gctagaagcc agtgctcgtg
 181 aactaaggag aaaaagaaca gacaagggaa cagcctggac atggcatcag agatccacat
 241 gacaggccca atgtgcctca ttgagaacac taatgggcga ctgatggcga atccagaagc
 301 tctgaagatc ctttctgcca ttacacagcc tatggtggtg gtggcaattg tgggcctcta
 361 ccgcacaggc aaatcctacc tgatgaacaa gctggctgga agaaaaagg gcttctctct
 421 gggctccacg gtgcagtctc acactaaagg aatctggatg tggtgtgtgc cccaccccaa
 481 gaagccaggc cacatcctag ttctgctgga caccgagggt ctgggagatg tagagaaggg
 541 tgacaaccag aatgactcct ggatcttcgc cctggccgtc ctcctgagca gcaccttcgt
 601 gtacaatagc ataggaacca tcaaccagca ggctatggac caactgtact atgtgacaga
 661 gctgacacat agaatccgat caaaatcctc acctgatgag aatgagaatg aggttgagga
 721 ttcagctgac tttgtgagct tcttcccaga cttttgtgtgg acactgagag atttctccct
 781 ggacttggaa gcagatggac acccctcac accagatgag tacctgacat actccctgaa
 841 gctgaagaaa ggtaccagtc aaaaagatga aactttaac ctgcccagac tctgtatccg
 901 gaaattcttc ccaaagaaaa atgctttgt ctttgatcgg cccgttcacc gcaggaagct
 961 tgcccagctc gagaaactac aagatgaaga gctggacccc gaatttgtgc aacaagtagc
1021 agacttctgt cctacatct ttagtaattc caaaactaaa actctttcag gaggcatcca
1081 ggtcaacggg cctcgtctag agagcctggt gctgacctac gtcaatgcca tcagcagtgg
1141 ggatctgccg tgcatggaga acgcagtcct ggccttggcc cagatagaga actcagctgc
1201 agtgcaaaag gctattgccc actatgaaca gcagatgggc cagaaggtgc agctgcccac
1261 agaaaccctc caggagctgc tggacctgca cagggacagt gagagagagg ccattgaagt
1321 cttcatcagg agttccttca agatgtggga ccatctattt caaaaggagt tagcggccca
1381 gctagaaaaa agcgggatg acttttgtaa acagaatcag gaagcatcat cagatcgttg
1441 ctcagcttta cttcaggtca ttttcagtcc tctagaagaa gaagtgaagg cgggaattta
1501 ttcgaaacca gggggctatc gtctctttgt tcagaagcta caagacctga gaaaaagta
1561 ctatgaggaa ccgaggaagg ggatacaggc tgaagagatt ctgcagacat acttgaaatc
1621 caaggagtct atgactgatg caattctcca gacagaccag actctcacag aaaaagaaaa
1681 ggagattgaa gtggaacgtg tgaaagctga gtctgcacag gcttcagcaa aaatgttgca
1741 ggaaatgcaa agaaagaatg agcagatgat ggaacagaag gagaggagtt atcaggaaca
1801 cttgaaacaa ctgactgaga agatggaaaa cgacagggtc cagttgctga agagcaaga
1861 gaggaccctc gctcttaaac ttcaggaaca ggagcaacta ctaaagagg gatttcaaaa
1921 agaaagcaga ataatgaaaa atgagataca ggatctccag acgaaaatga gacgacgaaa
1981 ggcatgtacc ataagctaaa gaccagagcc ttcctgtcac ccctaaccaa ggcataattg
```

-continued

```
2041 aaacaatttt agaatttgga acaagcgtca ctacatttga taataattag atcttgcatc 2101 ataacaccaa aagtttataa aggcatgtgg tacaatgatc aaaatcatgt tttttcttaa 2161 aaaaaaaaaa agactgtaaa ttgtgcaaca aagatgcatt tacctctgta tcaactcagg 2221 aaatctcata agctggtacc actcaggaga agtttattct tccagatgac cagcagtaga 2281 caaatggata ctgagcagag tcttaggtaa aagtcttggg aaatatttgg gcattggtct 2341 ggccaagtct acaatgtccc aatatcaagg acaaccaccc tagcttctta gtgaagacaa 2401 tgtacagtta tccgttagat caagactaca cggtctatga gcaataatgt gatttctgga 2461 cattgcccat gtataatcct cactgatgat ttcaagctaa agcaaaccac cttatacaga 2521 gatctagaat ctctttatgt tctccagagg aaggtggaag aaaccatggg caggagtagg 2581 aattgagtga taaacaattg ggctaatgaa gaaaacttct cttattgttc agttcatcca 2641 gattataact tcaatgggac actttagacc attagacaat tgacactgga ttaaacaaat 2701 tcacataatg ccaaatcaca aatgtattta tagcaacgta taatttgcaa agatggactt 2761 taaaagatgc tgtgtaacta aactgaaata attcaattac ttattattta gaatgttaaa 2821 gcttatgata gtcttttcta actcttaaca ctcatacttg aaaactttct gagtttcccc 2881 agaagagaat atgggatttt ttttgacatt tttgactcat ttaataatgc tcttgtgttt 2941 acctagtata tgtagacttt gtcttatgtg tgaaaagtcc taggaaagtg gttgatgttt 3001 cttatagcaa ttaaaaatta tttttgaact gaaaatacaa tgtatttcac
```

B7 IFIT3-interferon-induced protein with tetratricopeptide repeats 3 mRNA NM_001549.4

(SEQ ID NO: 143)

```
   1 attttcctcc tcccaacgat tttaaattag tttcactttc cagtttcctc ttccttcccc 61 taaaagcaat tactcaaaaa cggagaaaac atcagctgat gcgtgcccta ctctcccacc 121 cctttatata gttccttcag tatttacttg aggcagacag gaagacttct gaagaacaaa 181 tcagcctggt caccagcttt tcggaacagc agagacacag agggcagtca tgagtgaggt 241 caccaagaat tccctggaga aaatccttcc acagctgaaa tgccatttca cctggaactt 301 attcaaggaa gacagtgtct caagggatct agaagataga gtgtgtaacg agattgaatt 361 tttaaacact gagttcaaag ctacaatgta caacttgttg gcctacataa aacacctaga 421 tggtaacaac gaggcagccc tggaatgctt acggcaagct gaagagttaa tccagcaaga 481 acatgctgac caagcagaaa tcagaagtct agtcacttgg ggaaactacg cctgggtcta 541 ctatcacttg ggcagactct cagatgctca gatttatgta gataaggtga acaaacctg 601 caagaaattt tcaaatccat acagtattga gtattctgaa cttgactgtg aggaagggtg 661 gacacaactg aagtgtggaa gaaatgaaag ggcgaaggtg tgttttgaga aggctctgga 721 agaaaagccc aacaacccag aattctcctc tggactggca attgcgatgt accatctgga 781 taatcaccca gagaaacagt tctctactga tgttttgaag caggccattg agctgagtcc 841 tgataaccaa tacgtcaagg ttctcttggg cctgaaactg cagaagatga ataaagaagc 901 tgaaggagag cagtttgttg aagaagcctt ggaaagtct ccttgccaaa cagatgtcct 961 ccgcagtgca gccaaatttt acagaagaaa aggtgaccta gacaaagcta ttgaactgtt 1021 tcaacgggtg ttggaatcca caccaaacaa tggctacctc tatcaccaga ttgggtgctg 1081 ctacaaggca aaagtaagac aaatgcagaa tacaggagaa tctgaagcta gtggaaataa 1141 agagatgatt gaagcactaa agcaatatgc tatggactat tcgaataaag tcttgagaa 1201 gggactgaat cctctgaatg catactccga tctcgctgag ttcctggaga cggaatgtta 1261 tcagacacca ttcaataagg aagtccctga tgctgaaaag caacaatccc atcagcgcta
```

```
1321  ctgcaacctt cagaaatata atgggaagtc tgaagacact gctgtgcaac atggtttaga 1381  gggtttgtcc ataagcaaaa aatcaactga caaggaagag atcaaagacc aaccacagaa 1441  tgtatctgaa aatctgcttc cacaaaatgc accaaattat tggtatcttc aaggattaat 1501  tcataagcag aatggagatc tgctgcaagc agccaaatgt tatgagaagg aactgggccg 1561  cctgctaagg gatgcccctt caggcatagg cagtattttc ctgtcagcat ctgagcttga 1621  ggatggtagt gaggaaatgg gccagggcgc agtcagctcc agtcccagag agctcctctc 1681  taactcagag caactgaact gagacagagg aggaaaacag agcatcagaa gcctgcagtg 1741  gtggttgtga cgggtaggac gataggaaga cagggggccc caacctggga ttgctgagca 1801  gggaagcttt gcatgttgct ctaaggtaca tttttaaaga gttgtttttt ggccgggcgc 1861  agtggctcat gcctgtaatc ccagcacttt gggaggccga ggtgggcgga tcacgaggtc 1921  tggagtttga gaccatcctg gctaacacag tgaaatcccg tctctactaa aaatacaaaa 1981  aattagccag gcgtggtggc tggcacctgt agtcccagct acttgggagg ctgaggcagg 2041  agaatggcgt gaacctggaa ggaagaggtt gcagtgagcc aagattgcgc cctgcactc 2101  cagcctgggc aacagagcaa gactccatct caaaaaaaaa aaaaaaaaaa aaaagagtt 2161  gttttctcat gttcattata gttcattaca gttacatagt ccgaaggtct tacaactaat 2221  cactggtagc aataaatgct tcaggcccac atgatgctga ttagttctca gttttcattc 2281  agttcacaat ataaccacca ttcctgccct ccctgccaag ggtcataaat ggtgactgcc 2341  taacaacaaa atttgcagtc tcatctcatt ttcatccaga cttctggaac tcaaagatta 2401  acttttgact aaccctggaa tatctcttat ctcacttata gcttcaggca tgtatttata 2461  tgtattcttg atagcaatac cataatcaat gtgtattcct gatagtaatg ctacaataaa 2521  tccaaacatt tcaactctgt taaaaaaaaa aa
```

B8 IFITM3-interferon induced transmembrane protein 3 mRNA-
NM_021034.2
(SEQ ID NO: 144)
```
   1  aggaaaagga aactgttgag aaaccgaaac tactggggaa agggagggct cactgagaac 61  catcccagta acccgaccgc cgctggtctt cgctggacac catgaatcac actgtccaaa 121  ccttcttctc tcctgtcaac agtggccagc cccccaacta tgagatgctc aaggaggagc 181  acgaggtggc tgtgctgggg gcgccccaca accctgctcc ccgacgtcc accgtgatcc 241  acatccgcag cgagacctcc gtgcccgacc atgtcgtctg gtccctgttc aacaccctct 301  tcatgaaccc ctgctgcctg ggcttcatag cattcgccta ctccgtgaag tctagggaca 361  ggaagatggt tggcgacgtg accggggccc aggcctatgc ctccaccgcc aagtgcctga 421  acatctgggc cctgattctg ggcatcctca tgaccattct gctcatcgtc atcccagtgc 481  tgatcttcca ggcctatgga tagatcagga ggcatcactg aggccaggag ctctgcccat 541  gacctgtatc ccacgtactc caacttccat tcctcgccct gccccggag ccgagtcctg 601  tatcagccct ttatcctcac acgcttttct acaatggcat tcaataaagt gcacgtgttt 661  ctggtgctaa aaaaaaaa
```

B9 GK-glycerol kinase mRNA NM_203391.3
(SEQ ID NO: 145)
```
   1  gggccggagg ggcggggtga gaaggctgcg cgcgggtaaa ggggccgcct cgagcgcggt 61  ccgagcgttc agcggacgcg cgcggcctcg atctctggac tcgtcacctg ccctcccc 121  tcccgccgcc gtcacccagg aaaccgccg caatcgccgg ccgacctgaa gctggtttca 181  tggcagcctc aaagaaggca gttttgggc cattggtggg gcggtggac cagggcacca 241  gttcgacgcg ctttttggtt ttcaattcaa aaacagctga actacttagt catcatcaag
```

-continued

```
 301 tagaaataaa acaagagttc caagagaag gatgggtgga acaggaccct aaggaaattc
 361 tacattctgt ctatgagtgt atagagaaaa catgtgagaa acttggacag ctcaatattg
 421 atatttccaa cataaaagct attggtgtca gcaaccagag ggaaaccact gtagtctggg
 481 acaagataac tggagagcct ctctacaatg ctgtggtgtg gcttgatcta agaacccagt
 541 ctaccgttga gagtcttagt aaaagaattc caggaaataa taactttgtc aagtccaaga
 601 caggccttcc acttagcact tacttcagtg cagtgaaact tcgttggctc cttgacaatg
 661 tgagaaaagt tcaaaaggcc gttgaagaaa aacgagctct ttttgggact attgattcat
 721 ggcttatttg gagtttgaca ggaggagtca atggaggtgt ccactgtaca gatgtaacaa
 781 atgcaagtag gactatgctt ttcaacattc attctttgga atgggataaa caactctgcg
 841 aattttttgg aattccaatg gaaattcttc caaatgtccg gagttcttct gagatctatg
 901 gcctaatgaa atctctcat agcgtgaaag ctggggcctt ggaaggtgtg ccaatatctg
 961 ggtgtttagg ggaccagtct gctgcattgg tgggacaaat gtgcttccag attggacaag
1021 ccaaaaatac gtatggaaca ggatgtttct tactatgtaa tacaggccat aagtgtgtat
1081 tttctgatca tggccttctc accacagtgg cttacaaact tggcagagac aaaccagtat
1141 attatgcttt ggaaggttct gtagctatag ctggtgctgt tattcgctgg ctaagagaca
1201 atcttggaat tataaagacc tcagaagaaa ttgaaaaact tgctaaagaa gtaggtactt
1261 cttatggctg ctacttcgtc ccagcatttt cggggttata tgcaccttat tgggagccca
1321 gcgcaagagg gataatctgt ggactcactc agttcaccaa taatgccat attgcttttg
1381 ctgcattaga agctgtttgt ttccaaactc gagagatttt ggatgccatg aatcgagact
1441 gtggaattcc actcagtcat ttgcaggtag atggaggaat gaccagcaac aaaattctta
1501 tgcagctaca agcagacatt ctgtatatac cagtagtgaa gccctcaatg cccgaaacca
1561 ctgcactggg tgcggctatg gcgcagggg ctgcagaagg agtcggcgta tggagtctcg
1621 aacccgagga tttgtctgcc gtcacgatgg agcggtttga acctcagatt aatgcggagg
1681 aaagtgaaat tcgttattct acatggaaga aagctgtgat gaagtcaatg ggttgggtta
1741 caactcaatc tccagaaagt ggtattccat aaaacctacc aactcatgga ttcccaagat
1801 gtgagctttt tacataatga aagaacccag caattctgtc tcttaatgca atgacactat
1861 tcatagactt tgatttttatt tataagccac ttgctgcatg accctccaag tagacctgtg
1921 gcttaaaata aagaaatgc agcaaaaga atgctataga aatatttggt ggtttttttt
1981 ttttttaaac atccacagtt aaggttgggc cagctacctt tggggctgac cccctccatt
2041 gccataacat cctgctccat tccctctaag atgtaggaag aattcggatc cttaccattg
2101 gaatcttcca tcgaacatac tcaaacactt ttggaccagg atttgagtct ctgcatgaca
2161 tatacttgat taaaaggtta ttactaacct gttaaaaatc agcagctctt tgcttttaac
2221 agacacccta aaagtcttct tttctacata gttgaagaca gcaacatctt cactgaatgt
2281 ttgaatagaa acctctacta aattattaaa atagacattt agtgttctca cagcttggat
2341 attttttctga aaagttattt gccaaaactg aaatccttca gatgttttcc atggtcccac
2401 taattataat gactttctgt ctggatctta taggaaaaga actttctttt tttcttccat
2461 ctttccttttt tatatttttt actttgtatg tataacatac atgcctatat attttataca
2521 ctgagggtag cccatttata aattaagagc acattatatt cagaaggttc taacagggct
2581 ggtcttaagt gaaccactgt gtatataaat atgttggaaa acagctgtat acatttttgg
2641 gcaacggtta tgcataatat ttaccaggag aattttttttc ttaacaagcc aacatttaaa
```

-continued

```
2701 atttatgttt tatgtcaata aaagaaaata tactttattg tgacttcaac tatatttctt
2761 atcccttaca tttttattta attgtcttag cttaaaaaaa gaagaaactg tggaatacta
2821 cagtaaatat tgttttcaaa cacaagcaat aattcaaata gttattttc ttttgaatta
2881 attttagaca tattttggat cctattgagg ggataagagg atgtcaaaaa agttaaatac
2941 ctaagtagaa aaaatatag aaataaagcc aagaatctct ttcagttcaa atgttatcaa
3001 ttgttaataa gaaattgcta tctgggatga cagaattacc tctgcttagt atctcattat
3061 aactgaaaga aggtttatca ttacaaatac cttccaatga aaccaagaat ttctcaaaat
3121 atttaatgtc acatattata agaagttacc taatcctgct tcttaacatc aattttaaa
3181 aatatcttaa aattactttg ttttgtagta aacagtgaag aaaagattgc ctcctaatta
3241 ttttttcaa tgagtgctga atgggaaaac atttatatct tactataaaa ggttctgttt
3301 tgtttggaat caatggtagc tttattgact gttctgattg tgctgtttct aatttattga
3361 atctgctagg ttttattgat gcagccacca cttaagtgac ataaatatta tagaaaggta
3421 ctgtgaaatg atcactttgt ggcaggggta cttttaaaca taaatgtttc tacaaaagta
3481 ggttgagttc attgtaaata attgtgaaag ccactgttca ataattta agattacatt
3541 aatttttcta taaattggaa gatttataaa tgtttgaaat tgtacacatt gatatttaat
3601 gacaaattta cttaaaataa attgacccct tgttcttact tgcatttctc atttacagac
3661 tagaacttag ttgaaagtta aattaagaaa gatgtttcag aggccgggca cggtggctga
3721 cgcctgtaat cccagcactt tgggaggccg aggtgggcag atcacctgag gtcaggagtt
3781 cgggactagc ctaaccgaca tggagaaacc ctatctctac taaaaaaaaa aaagatgtt
3841 tcaggacatg tgaaacttgg ctgttagcgc ttgataggc acactctgaa gagttaacca
3901 acagccaaag aagtaatttc tgtaatgatg aacactttaa tcattctatt agaagaaact
3961 acactgtccc atctcagcat ttgcaaaaaa taatgttggt aaggtcagca gccattatca
4021 acagggcctt gcatggctaa ctttgaccac cattttctc tcaacctgat aggcaacacc
4081 tcaatccttt gttctccaac taatcagtaa aataagtaat gcatctctgc ttctgtaatg
4141 atatcttaga attttagta tgtttctttt gaagtgccca agcccaatt ctttgggata
4201 tcttttgggt atctggtatc atgtgggagt gaagaaagaa agtttttgga gaaaccaaca
4261 aatgaaagct gtgatagcac agaagctaat ggcattgaca gtggagtagg tagtatttaa
4321 tctgtagtgt ttacaacata gtagatagaa gtacaaaaat tttttaact ataactcttt
4381 aatagcttgt tttatctagt aatatttaaa taatgaagtt tccttgatcc tttgcttttg
4441 caacctaaca actttaataa taagttcaca caataaacaa attagtagaa aaaaaaaaa
4501 aaa
```

B10 NELL2-NEL-like 2 (chicken) mRNA NM_001145107.1

(SEQ ID NO: 146)
```
   1 ctctacctac tttgcccagc tccacctcgg cagtgcagcg tgttttggtg gccttcctcc
  61 gcacgccctg gaggggagt gccctgcacc ccggggctgc tccggagccc agtgcacgag
 121 tgcacatggg cttccctcct ttgcttaaag ggcaggcgag cgctactcgc tccagccttg
 181 cctcctgcag ctgggtggtc tttttttctct cctgtctttc aagacacgcg cccgaaatcg
 241 agggagggag acgatggact gagctgatcc gcaccatgga gtctcgggtc ttactgagaa
 301 cattctgttt gatcttcggt ctcgagcag tttgggggct tggtgtggac ccttccctac
 361 agattgacgt cttaacagag ttagaacttg gggagtccac gaccggagtg cgtcaggtcc
 421 cggggctgca taatgggacg aaagcctttc tctttcaaga tactcccaga agcataaaag
 481 catccactgc tacagctgaa cagttttttc agaagctgag aaataaacat gaatttacta
```

-continued

```
 541 ttttggtgac cctaaaacag acccacttaa attcaggagt tattctctca attcaccact
 601 tggatcacag gtacctggaa ctggaaagta gtggccatcg gaatgaagtc agactgcatt
 661 accgctcagg cagtcaccgc cctcacacag aagtgtttcc ttacattttg gctgatgaca
 721 agtggcacaa gctctcctta gccatcagtg cttcccattt gattttacac attgactgca
 781 ataaaattta tgaaagggta gtagaaaagc cctccacaga cttgcctcta ggcacaacat
 841 tttggctagg acagagaaat aatgcgcatg gatattttaa gggtataatg caagatgtcc
 901 aattacttgt catgccccag ggatttattg ctcagtgccc agatcttaat cgcacctgtc
 961 caacttgcaa tgacttccat ggacttgtgc agaaaatcat ggagctacag gatattttag
1021 ccaaaacatc agccaagctg tctcgagctg aacagcgaat gaatagattg gatcagtgct
1081 attgtgaaag gacttgcacc atgaagggaa ccacctaccg agaatttgag tcctggatag
1141 acggctgtaa gaactgcaca tgcctgaatg gaaccatcca gtgtgaaact ctaatctgcc
1201 caaatcctga ctgcccactt aagtcggctc ttgcgtatgt ggatggcaaa tgctgtaagg
1261 aatgcaaatc gatatgccaa tttcaaggac gaacctactt tgaaggagaa agaaatacag
1321 tctattcctc ttctggagta tgtgttctct atgagtgcaa ggaccagacc atgaaacttg
1381 ttgagagttc aggctgtcca gctttggatt gtccagagtc tcatcagata accttgtctc
1441 acagctgttg caaagtttgt aaaggttatg acttttgttc tgaaaggcat aactgcatgg
1501 agaattccat ctgcagaaat ctgaatgaca gggctgtttg tagctgtcga gatggtttta
1561 gggctcttcg agaggataat gcctactgtg aagacatcga tgagtgtgct gaagggcgcc
1621 attactgtcg tgaaaataca atgtgtgtca cacccgggg ttcttttatg tgcatctgca
1681 aaactggata catcagaatt gatgattatt catgtacaga acatgatgag tgtatcacaa
1741 atcagcacaa ctgtgatgaa aatgctttat gcttcaacac tgttggagga cacaactgtg
1801 tttgcaagcc gggctataca gggaatggaa cgacatgcaa agcattttgc aaagatggct
1861 gtaggaatgg aggagcctgt attgccgcta atgtgtgtgc ctgcccacaa ggcttcactg
1921 gacccagctg tgaaacggac attgatgaat gctctgatgg ttttgttcaa tgtgacagtc
1981 gtgctaattg cattaacctg cctggatggt accactgtga gtgcagagat ggctaccatg
2041 acaatgggat gttttcacca agtggagaat cgtgtgaaga tattgatgag tgtgggaccg
2101 ggaggcacag ctgtgccaat gataccattt gcttcaattt ggatggcgga tatgattgtc
2161 gatgtcctca tggaaagaat tgcacagggg actgcatcca tgatggaaaa gttaagcaca
2221 atggtcagat ttgggtgttg gaaaatgaca ggtgctctgt gtgctcatgt cagaatggat
2281 tcgttatgtg tcgacggatg gtctgtgact gtgagaatcc cacagttgat ctttttttgct
2341 gccctgaatg tgaccaaggc ttagtagtc agtgcctcca tcaaaatggg gaaactttgt
2401 ataacagtgg tgacacctgg gtccagaatt gtcaacagtg ccgctgcttg caagggggaag
2461 ttgattgttg gcccctgcct tgcccagatg tggagtgtga attcagcatt ctcccagaga
2521 atgagtgctg cccgcgctgt gtcacagacc cttgccaggc tgacaccatc cgcaatgaca
2581 tcaccaagac ttgcctggac gaaatgaatg tggttcgctt caccgggtcc tcttggatca
2641 aacatggcac tgagtgtact ctctgccagt gcaagaatgg ccacatctgt tgctcagtgg
2701 atccacagtg ccttcaggaa ctgtgaagtt aactgtctca tgggagattt ctgttaaaag
2761 aatgttcttt cattaaaaga ccaaaaagaa gttaaaactt aaattgggtg atttgtgggc
2821 agctaaatgc agctttgtta atagctgagt gaacttttcaa ttatgaaatt tgtggagctt
2881 gacaaaatca caaaaggaaa attactgggg caaaattaga cctcaagtct gcctctactg
```

```
2941  tgtctcacat caccatgtag aagaatgggc gtacagtata taccgtgaca tcctgaaccc
3001  tggatagaaa gcctgagccc attggatctg tgaaagcctc tagcttcact ggtgcagaaa
3061  attttcctct agatcagaat cttcaagaat cagttaggtt cctcactgca agaaataaaa
3121  tgtcaggcag tgaatgaatt atattttcag aagtaaagca agaagctat aacatgttat
3181  gtacagtaca ctctgaaaag aaatctgaaa caagttattg taatgataaa aataatgcac
3241  aggcatggtt acttaatatt ttctaacagg aaaagtcatc cctatttcct tgttttactg
3301  cacttaatat tatttggttg aatttgttca gtataagctc gttcttgtgc aaaattaaat
3361  aaatatttct cttaccttat aacac
```

B11 S100A11 S100 calcium binding protein A11 mRNA NM_005620.1

(SEQ ID NO: 147)
```
   1  gggcaaggct gggccgggaa gggcgtgggt tgaggagagg ctccagaccc gcacgccgcg
  61  cgcacagagc tctcagcgcc gctcccagcc acagcctccc gcgcctcgct cagctccaac
 121  atggcaaaaa tctccagccc tacagagact gagcggtgca tcgagtccct gattgctgtc
 181  ttccagaagt atgctggaaa ggatggttat aactacactc tctccaagac agagttccta
 241  agcttcatga atacagaact agctgccttc acaaagaacc agaaggaccc tggtgtcctt
 301  gaccgcatga tgaagaaact ggacaccaac agtgatggtc agctagattt ctcagaattt
 361  cttaatctga ttggtggcct agctatggct tgccatgact ccttcctcaa ggctgtccct
 421  tcccagaagc ggacctgagg acccccttggc cctggccttc aaacccaccc ccttcttc
 481  cagcctttct gtcatcatct ccacagccca cccatcccct gagcacacta accacctcat
 541  gcaggcccca cctgccaata gtaataaagc aatgtcactt ttttaaaaca tgaaa
```

B12 SAMD9L-sterile alpha motif domain containing 9-like mRNA
NM_152703.2

(SEQ ID NO: 148)
```
   1  aaagtcagag tactgggaga acagaagact tcacaattta atgcctcagt ttttaaaaaa
  61  ggatccttac acttcatgtc tcctagccat cagaagagga atgagacagc aaaagttcaa
 121  atggcctgtt tcaagtttct gatataaaac gatgacattt tcaggaaaat cctgcatttc
 181  cagagagaga ctggctggtt aaatttctga agaggacac cagctaaaag aaggtattgc
 241  atctcacccg agcagactgt gtctgtggaa agtgtaagcc ccttgccaga agagcagctt
 301  cccagcaaag gcagagggtg aaaacagcaa aggtcttaag acactggga cctagagtca
 361  aaagggacct cctccaggga aaacgctgtg tgagaaatgg cctcattcgg tgactgtgag
 421  tgacacagca gaaagttggg tcattccggc tgcttttttg agaagtccct gaagagatca
 481  ataacagcaa gagggaacct ggcaaggaag ctattcctat aatccaggaa agagatgagg
 541  aaggcttgga ccaggtggta gtgtgtcag gtagtcaaat gctgggtata ttttgaagat
 601  acaccccata ggatttgctc cacattgaat gtggaatgct ggaagagaga taaagtgtac
 661  ctgtcacata cttttttgagt tttattttatt ttcttagaag taagtacaca aagagatgct
 721  acctaggaga agggtattct tttcactatt ctttcaaatt ttctgtatgt tcgaacattt
 781  tcatagtaga aagttgggg gaaaatctgt tcataaaca tttcctcagc agcagtccag
 841  tctattgcat tttaattggt tgtgatatca ttgttttatg caatacgttc tcaacaagta
 901  tatcctccgg caaactgaac aaggaccaag tctgttctgc ctacagctct gcttcctcat
 961  agctgctttc cagaacgtga ctcttgcaaa ttatcaagaa aggggaacta atctaaggga
1021  tccagatcaa acagcctcat gaagacttat tttatgtttc taatataaag atagaagttt
1081  tcagaaaagc cctgctacac agaggatcag agcaggggtg ggcctgctgg gctgcagctg
1141  ggattctgag catccttttcc cggaggcacg gaaagtgagt gagtgagccc agtgaggaag
```

-continued

```
1201   aagttgaagc tttgatatga gtaaacaagt atctctacct gaaatgatta aagactggac
1261   caaagagcat gtgaaaaaat gggtaaatga agaccttaag attaatgagc aatacgggca
1321   aattctgctc agtgaagaag taacaggatt agtcctgcag gaattaactg agaaggacct
1381   tgtagaaatg gggctaccat ggggtccagc acttttgata aacgttcat acaacaaatt
1441   gaatagtaag tcccctgaaa gtgacaatca tgatccggga caattagata attcaaaacc
1501   gtccaaaaca gaacaccaga aaaatccaaa acacaccaaa aaggaagaag aaaattcaat
1561   gtcatctaat attgattatg atcccagaga gatcagagat atcaaacaag aagaatcaat
1621   tcttatgaaa gaaatgtgt tagatgaagt agcaaatgct aaacacaaga aaaagggtaa
1681   gctaaaacct gaacaattga cttgtatgcc atatccttt gatcagttcc atgacagcca
1741   tcgctacata gaacattata ctctacaacc tgaaacagga gcactcaatc tcattgatcc
1801   aatacatgag ttcaaagctc tcacaaacac agaaacagcc acggaagtgg acattaagat
1861   gaaattcagc aatgaagtct tccgatttgc atcagcttgt atgaattcac gcaccaatgg
1921   caccatccat tttggagtca aggacaaacc ccatggagaa attgttggtg tgaaaatcac
1981   cagtaaggct gccttcattg accacttcaa tgtaatgatc aaaaagtatt ttgaagaaag
2041   tgagatcaat gaagccaaga agtgtattcg ggagccaagg tttgtggaag tccttctgca
2101   gaacaataca ccatctgaca gatttgtcat tgaagttgat actattccaa aacactctat
2161   atgtaatgat aagtatttct acattcagat gcaaatttgt aaagataaaa tatggaaaca
2221   aaaccaaaat ctttcactgt ttgtaagaga aggggctagc tctagggata tcctggccaa
2281   ttccaagcaa cgggatgtag atttcaaggc atttttacaa aatttaaagt cactggtagc
2341   atctagaaaa gaggctgaag aagagtatgg aatgaaggca atgaagaagg agagtgaagg
2401   actaaagctg gttaaacttc tcataggaaa ccgagactca ctggataatt catactatga
2461   ctggtacatt cttgtaacaa ataaatgcca tccaaaccaa ataaagcact tagatttttt
2521   aaaagaaatt aaatggtttg ctgtgttgga gtttgatcct gaatctatga tcaatggagt
2581   ggtcaaagct tacaaagaaa gtcgggtggc aaaccttcac tttccaaatc aatatgaaga
2641   caagacaact aacatgtggg agaagatttc tactcttaat ctttaccaac agcccagctg
2701   gattttctgc aacggcagat cagacctgaa aagcgagaca tataaacctc tagaaccaca
2761   tttatggcag agagaaagag cttcagaagt caggaaacta attttatttc tcacagatga
2821   aaatataatg acaagaggaa aatttttggt agtgtttcta ttactctctt cagtggaaag
2881   cccaggagat ccactcattg aaactttctg ggctttctat caagctctca aggaatgga
2941   aaatatgttg tgtatctctg taaactcaca tatttatcaa cgatggaaag atctactaca
3001   aacaagaatg aagatggaag atgaactaac aaaccacagt atttccactt taaatataga
3061   actggtaaac agcactatcc ttaaactaaa atcggtgact cggtcatcaa gaaggttttt
3121   gcccgcccgt ggatcttctt cagttatcct agagaaaaag aaagaggatg tcttgactgc
3181   actggaaatc ctctgtgaaa atgagtgtac agagacagac atcgagaaag acaaatctaa
3241   attcctggag tttaagaaat caaaagaaga acactttat cgaggtggca agtatcctg
3301   gtggaacttc tattttctt ctgaaaacta ttcttcagat tttgttaaaa gggacagtta
3361   tgaaaagctt aaagatttaa tacactgctg ggcagagtct cctaaaccaa tatttgcaaa
3421   aatcatcaat ctttatcatc atccaggctg tggaggtacc acactggcta tgcatgttct
3481   ctgggactta agaaaaact tcagatgtgc tgtgttaaaa aacaagcaa ctgattttgc
3541   agaaattgca gagcaagtga tcaatctggt cacctatagg gcaaagagcc atcaggatta
```

-continued

```
3601 cattcctgtg cttctccttg tggatgattt tgaagaacaa gaaaatgtct actttctaca
3661 aaatgccatc cattccgttt tagcagaaaa ggatttgcga tatgaaaaaa cattggtaat
3721 tatcttaaac tgcatgagat cccggaatcc agatgaaagt gcaaaattgg cagacagtat
3781 tgcactaaat taccaacttt cttccaagga acaaagagct tttggtgcca aactgaagga
3841 aattgaaaag cagcacaaga actgtgaaaa cttttattcc ttcatgatca tgaaaagcaa
3901 ttttgatgaa acatatatag aaaatgtagt caggaatatc ctaaaaggac aggatgttga
3961 cagcaaggaa gcacaactca tttccttcct ggctttactc agctcttatg ttactgactc
4021 tacaatttca gtttcacagt gtgaaatatt tttgggaatc atatacacta gtacaccctg
4081 ggaacctgaa agcttagaag acaagatggg aacttattct acacttctaa taaaaacaga
4141 agttgcagaa tatgggagat acacaggtgt gcgtatcatt cacccctctga ttgccctgta
4201 ctgtctaaaa gaactggaaa gaagctatca cttggataaa tgtcaaattg cattgaatat
4261 attagaagag aatttattct atgattctgg aataggaaga gacaaatttc aacatgatgt
4321 tcaaactctt ctgcttacaa gacagcgcaa ggtgtatgga gatgaaacag acactctgtt
4381 ttccccatta atggaagctt tacagaataa agacattgaa aaggtcttga gtgcaggaag
4441 tagacgattc ccacaaaatg cattcatttg tcaagcctta gcaagacatt tctacattaa
4501 agagaaggac tttaacacag ctctggactg ggcacgtcag gccaaaatga aagcacctaa
4561 aaattcctat atttcagata cactaggtca agtctacaaa agtgaaatca atggtggtt
4621 ggatgggaac aaaaactgta ggagcattac tgttaatgac ctaacacatc tcctagaagc
4681 tgcggaaaaa gcctcaagag cttttcaaaga atcccaaagg caaactgata gtaaaaacta
4741 tgaaaccgag aactggtcac cacagaagtc ccagagacga tatgacatgt ataacacagc
4801 ttgtttcttg ggtgaaatag aagttggtct ttacactatc cagattcttc agctcactcc
4861 cttttcccac aaagaaaatg aattatccaa aaaacatatg gtgcaatttt tatcaggaaa
4921 gtggaccatt cctcctgatc ccagaaatga atgttatttg gctcttagca agttcacatc
4981 ccacctaaaa aatttacaat cagatctgaa aaggtgcttt gacttttta ttgattatat
5041 ggttcttctg aaaatgaggt atacccaaaa agaaattgca gaaatcatgt taagcaagaa
5101 agtcagtcgt tgtttcagga aatacacaga acttttctgt catttggatc catgtctatt
5161 acaaagtaaa gagagtcaat tactccagga ggagaattgc aggaaaaagc tagaagctct
5221 gagagcagat aggtttgctg gactcttgga atatcttaat ccaaactaca agatgctac
5281 caccatggaa agtatagtga atgaatatgc cttcctactg cagcaaaact caaaaaagcc
5341 catgacaaat gagaaacaaa attccatttt ggccaacatt attctgagtt gtctaaagcc
5401 caactccaag ttaattcaac cacttaccac gctaaaaaaa caactccgag aggtcttgca
5461 atttgtagga ctaagtcatc aatatccagg tccttatttc ttggcctgcc tcctgttctg
5521 gccagaaaat caagagctag atcaagattc caaactaata gaaaagtatg tttcatcctt
5581 aaatagatcc ttcagggac agtacaagcg catgtgcagg tccaagcagg caagcacact
5641 tttctatctg ggcaaaagga agggtctaaa cagtattgtt cacaaggcca aaatagagca
5701 gtactttgat aaagcacaaa atacaaattc cctctggcac agtggggatg tgtggaaaaa
5761 aaatgaagtc aaagacctcc tgcgtcgtct aactggtcag gctgaaggca agctaatctc
5821 tgtagaatat ggaacagagg aaaaaataaa aataccagta atatctgttt attcaggtcc
5881 actcagaagt ggtaggaaca tagaaagagt gtctttctac ctaggatttt ccattgaagg
5941 ccctctggca tatgatatag aagtaattta agacaataca tcacctgtag ttcaaatacg
6001 tttatttata tctttatgat tttattctct ctctctattc tcatggcact ttcataacat
```

-continued

```
6061 tatggctaac ctctaattac agattttgct tttgcctccc tgaatgaatt acaagccttt
6121 ttaagatatg aaatatgcct acccgcagag cttggcacaa agtggagtca atcttttaat
6181 gttttaaata tgcattttca gactcaaata attaagaagt ttcattgata tccactggtc
6241 acatcataac tgtctatagg gcaataaaat ctgtgttaaa ctcaattgct tttataagtt
6301 ttctaaatta tttcttcact gtgacagcaa agatttaaat aagatgaatg taaaagagaa
6361 agcttattgg actcaaaccc acagatccac accagagttc tatttacctc atcttggtat
6421 caataaaaac ttatgtggaa ggtaaatata ttgttcccca tccaccacat aacactctcc
6481 ccaacacaca cacacacaca cacacacaca cacacactcc ttgtacccct
6541 tgcccttctc ccagctcatt gctccaggag agagaagagt tcaaaaaata aagtaatcat
6601 aaacttgaac tctctccatt ctcttgttcc catttacagg tgaatctctt cctttaagcc
6661 attttttgtct cctgtgaata cagccttatc tccacctgtt tcttagatcc catctcccct
6721 ggcttatttt ttccattcat tacccctcttt gttcccttta cttctcaacc tgtgctatat
6781 acatgctgtt ctctctgttg agattgcctt atttccatct aacattctct ctcctgctat
6841 tctgatttgt cattcacaac tgatttcaag agtcaccttc accaggaagt cttccttgac
6901 caccatcatt cctgcctgat tagagggctt cctcatggta atatgtgttc tcaagttttc
6961 agtgtcaagg aatgccatcc cagaagctca ttctcagatg cacaacagcc agaacagtct
7021 caagcagcat tctagagctt ggaatttaag aactacgcat tgcctataaa gtgaaacata
7081 ggctaatata gattaaattg aatattgaat aaaaaatata tttatttatc cac
```

B13 STAT1-signal transducer and activator of transcription 1-alpha/beta isoform alpha mRNA NM_007315.3

(SEQ ID NO: 149)

```
   1 gctgagcgcg gagccgcccg tgattggtg ggggcggaag ggggccgggc gccagcgctg
  61 ccttttctcc tgccgggtag tttcgctttc ctgcgcagag tctgcggagg ggctcggctg
 121 caccgggggg atcgcgcctg cagaccccca gaccgagcag aggcgaccca gcgcgctcgg
 181 gagaggctgc accgccgcgc ccccgcctag cccttccgga tcctgcgcgc agaaaagttt
 241 catttgctgt atgccatcct cgagagctgt ctaggttaac gttcgcactc tgtgtatata
 301 acctcgacag tcttggcacc taacgtgctg tgcgtagctg ctcctttggt tgaatcccca
 361 ggcccttgtt ggggcacaag gtggcaggat gtctcagtgg tacgaacttc agcagcttga
 421 ctcaaaattc ctggagcagg ttcaccagct ttatgatgac agttttccca tggaaatcag
 481 acagtacctg gcacagtggt tagaaaagca agactgggag cacgctgcca atgatgtttc
 541 atttgccacc atccgttttc atgacctcct gtcacagctg gatgatcaat atagtcgctt
 601 ttcctttgga aataacttct tgctacagca taacataagg aaaagcaagc gtaatcttca
 661 ggataatttt caggaagacc caatccagat gtctatgatc atttacagct gtctgaagga
 721 agaaaggaaa attctggaaa acgcccagag atttaatcag gctcagtcgg gaatattca
 781 gagcacagtg atgttagaca aacagaaaga gcttgacagt aaagtcagaa atgtgaagga
 841 caaggttatg tgtatagagc atgaaatcaa gagcctggaa gatttacaag atgaatatga
 901 cttcaaatgc aaaaccttgc agaacagaga acacgagacc aatggtgtgg caaagagtga
 961 tcagaaacaa gaacagctgt tactcaagaa gatgtattta atgcttgaca ataagagaaa
1021 ggaagtagtt cacaaaataa tagagttgct gaatgtcact gaacttaccc agaatgccct
1081 gattaatgat gaactagtgg agtggaagcg gagacagcag agcgcctgta ttggggggcc
1141 gcccaatgct tgcttggatc agctgcagaa ctggttcact atagttgcgg agagtctgca
1201 gcaagttcgg cagcagctta aaaagttgga ggaattggaa cagaaataca cctacgaaca
```

-continued

```
1261   tgaccctatc acaaaaaaca aacaagtgtt atgggaccgc accttcagtc ttttccagca 1321   gctcattcag agctcgtttg tggtggaaag acagccctgc atgccaacgc accctcagag 1381   gccgctggtc ttgaagacag gggtccagtt cactgtgaag ttgagactgt tggtgaaatt 1441   gcaagagctg aattataatt tgaaagtcaa agtcttattt gataaagatg tgaatgagag 1501   aaatacagta aaaggattta ggaagttcaa cattttgggc acgcacacaa aagtgatgaa 1561   catggaggag tccaccaatg gcagtctggc ggctgaattt cggcacctgc aattgaaaga 1621   acagaaaaat gctggcacca aacgaatga gggtcctctc atcgttactg aagagcttca 1681   ctcccttagt tttgaaaccc aattgtgcca gcctggtttg gtaattgacc tcgagacgac 1741   ctctctgccc gttgtggtga tctccaacgt cagccagctc ccgagcggtt gggcctccat 1801   cctttggtac aacatgctgg tggcggaacc caggaatctg tccttcttcc tgactccacc 1861   atgtgcacga tgggctcagc tttcagaagt gctgagttgg cagttttctt ctgtcaccaa 1921   aagaggtctc aatgtggacc agctgaacat gttgggagag aagcttcttg gtcctaacgc 1981   cagccccgat ggtctcattc cgtggacgag gttttgtaag gaaaatataa atgataaaaa 2041   ttttcccttc tggctttgga ttgaaagcat cctagaactc attaaaaaac acctgctccc 2101   tctctggaat gatgggtgca tcatgggctt catcagcaag gagcgagagc gtgccctgtt 2161   gaaggaccag cagccgggga ccttcctgct gcggttcagt gagagctccc gggaaggggc 2221   catcacattc acatgggtgg agcggtccca gaacggaggc gaacctgact tccatgcggt 2281   tgaaccctac acgaagaaag aactttctgc tgttactttc cctgacatca ttcgcaatta 2341   caaagtcatg gctgctgaga atattcctga gaatcccctg aagtatctgt atccaaatat 2401   tgacaaagac catgcctttg gaaagtatta ctccaggcca aaggaagcac cagagccaat 2461   ggaacttgat ggccctaaag gaactggata tatcaagact gagttgattt ctgtgtctga 2521   agttcaccct tctagacttc agaccacaga caacctgctc ccatgtctc ctgaggagtt 2581   tgacgaggtg tctcggatag tgggctctgt agaattcgac agtatgatga acacagtata 2641   gagcatgaat ttttttcatc ttctctggcg acagttttcc ttctcatctg tgattccctc 2701   ctgctactct gttccttcac atcctgtgtt tctagggaaa tgaaagaaag gccagcaaat 2761   tcgctgcaac ctgttgatag caagtgaatt tttctctaac tcagaaacat cagttactct 2821   gaagggcatc atgcatctta ctgaaggtaa aattgaaagg cattctctga agagtgggtt 2881   tcacaagtga aaaacatcca gatacaccca agtatcagg acgagaatga gggtcctttg 2941   ggaaaggaga agttaagcaa catctagcaa atgttatgca taaagtcagt gcccaactgt 3001   tataggttgt tggataaatc agtggttatt tagggaactg cttgacgtag gaacggtaaa 3061   tttctgtggg agaattctta catgttttct ttgctttaag tgtaactggc agttttccat 3121   tggtttacct gtgaaatagt tcaaagccaa gtttatatac aattatatca gtcctctttc 3181   aaaggtagcc atcatggatc tggtagggg aaaatgtgta ttttattaca tcttttcacat 3241   tggctatttta aagacaaaga caaattctgt ttcttgagaa gagaatatta gctttactgt 3301   ttgttatggc ttaatgacac tagctaatat caatagaagg atgtacattt ccaaattcac 3361   aagttgtgtt tgatatccaa agctgaatac attctgcttt catcttggtc acatacaatt 3421   attttttacag ttctcccaag ggagttaggc tattcacaac cactcattca aaagttgaaa 3481   ttaaccatag atgtagataa actcagaaat ttaattcatg tttcttaaat gggctacttt 3541   gtccttttg ttattagggt ggtatttagt ctattagcca caaaattggg aaaggagtag 3601   aaaaagcagt aactgacaac ttgaataata caccagagat aatatgagaa tcagatcatt
```

-continued

```
3661  tcaaaactca tttcctatgt aactgcattg agaactgcat atgtttcgct gatatatgtg
3721  tttttcacat ttgcgaatgg ttccattctc tctcctgtac ttttttccaga cacttttttg
3781  agtggatgat gtttcgtgaa gtatactgta tttttacctt tttccttcct tatcactgac
3841  acaaaaagta gattaagaga tgggtttgac aaggttcttc ccttttacat actgctgtct
3901  atgtggctgt atcttgtttt tccactactg ctaccacaac tatattatca tgcaaatgct
3961  gtattcttct ttggtggaga taaagatttc ttgagttttg ttttaaaatt aaagctaaag
4021  tatctgtatt gcattaaata taatatgcac acagtgcttt ccgtggcact gcatacaatc
4081  tgaggcctcc tctctcagtt tttatataga tggcgagaac ctaagtttca gttgattta
4141  caattgaaat gactaaaaaa caaagaagac aacattaaaa caatattgtt tctaattgct
4201  gaggtttagc tgtcagttct ttttgccctt tgggaattcg gcatggtttc attttactgc
4261  actagccaag agactttact tttaagaagt attaaaattc taaaattcaa aaaaaaaaa
4321  aaaaaa
```

B14 TLR6-toll-like receptor 6 mRNA NM_006068.4

(SEQ ID NO: 150)

```
   1  aattgtattt ccgttcattt acaagttatt ttctcttctt ctgaaaaaga gatcttgaat
  61  ttggactcat atcaagatgc tctgaagaag aacaacccct taggatagcc actgcaacat
 121  catgaccaaa gacaaagaac ctattgttaa aagcttccat tttgtttgcc ttatgatcat
 181  aatagttgga accagaatcc agttctccga cggaaatgaa tttgcagtag acaagtcaaa
 241  aagaggtctt attcatgttc caaaagacct accgctgaaa accaaagtct tagatatgtc
 301  tcagaactac atcgctgagc ttcaggtctc tgacatgagc tttctatcag agttgacagt
 361  tttgagactt tcccataaca gaatccagct acttgattta agtgttttca agttcaacca
 421  ggatttagaa tatttggatt tatctcataa tcagttgcaa aagatatcct gccatcctat
 481  tgtgagtttc aggcatttag atctctcatt caatgatttc aaggccctgc ccatctgtaa
 541  ggaatttggc aacttatcac aactgaattt cttgggattg agtgctatga gctgcaaaa
 601  attagatttg ctgccaattg ctcacttgca tctaagttat atccttctgg atttaagaaa
 661  ttattatata aaagaaaatg agacagaaag tctacaaatt ctgaatgcaa aaaccccttca
 721  ccttgttttt cacccaacta gtttattcgc tatccaagtg aacatatcag ttaatacttt
 781  agggtgctta caactgacta atattaaatt gaatgatgac aactgtcaag ttttcattaa
 841  attttatca gaactcacca gaggttcaac cttactgaat tttaccctca accacataga
 901  aacgacttgg aaatgcctgg tcagagtctt tcaatttctt tggcccaaac ctgtggaata
 961  tctcaatatt tacaatttaa caataattga aagcattcgt gaagaagatt ttacttattc
1021  taaaacgaca ttgaaagcat tgacaataga acatatcacg aaccaagttt tctgttttc
1081  acagacagct ttgtacaccg tgttttctga gatgaacatt atgatgttaa ccatttcaga
1141  tacaccttt atacacatgc tgtgtcctca tgcaccaagc acattcaagt ttttgaactt
1201  tacccagaac gttttcacag atagtatttt tgaaaaatgt tccacgttag ttaaattgga
1261  gacacttatc ttacaaaaga atggattaaa agaccttttc aaagtaggtc tcatgacgaa
1321  ggatatgcct tctttggaaa tactggatgt tagctggaat ctttggaat ctggtagaca
1381  taaagaaaac tgcacttggg ttgagagtat agtggtgtta aatttgtctt caaatatgct
1441  tactgactct gttttcagat gtttacctcc caggatcaag gtacttgatc ttcacagcaa
1501  taaaataaag agcgttccta aacaagtcgt aaaactggaa gctttgcaag aactcaatgt
1561  tgctttcaat tctttaactg accttcctgg atgtggcagc tttagcagcc tttctgtatt
1621  gatcattgat cacaattcag tttcccaccc atcggctgat ttcttccaga gctgccagaa
```

-continued

```
1681  gatgaggtca ataaaagcag gggacaatcc attccaatgt acctgtgagc taagagaatt
1741  tgtcaaaaat atagaccaag tatcaagtga agtgttagag ggctggcctg attcttataa
1801  gtgtgactac ccagaaagtt atagaggaag cccactaaag gactttcaca tgtctgaatt
1861  atcctgcaac ataactctgc tgatcgtcac catcggtgcc accatgctgg tgttggctgt
1921  gactgtgacc tccctctgca tctacttgga tctgccctgg tatctcagga tggtgtgcca
1981  gtggacccag actcggcgca gggccaggaa catacccta gaagaactcc aaagaaacct
2041  ccagtttcat gcttttattt catatagtga acatgattct gcctgggtga aaagtgaatt
2101  ggtaccttac ctagaaaaag aagatataca gatttgtctt catgagagaa actttgtccc
2161  tggcaagagc attgtggaaa atatcatcaa ctgcattgag aagagttaca agtccatctt
2221  tgttttgtct cccaactttg tccagagtga gtggtgccat tacgaactct attttgccca
2281  tcacaatctc tttcatgaag gatctaataa cttaatcctc atcttactgg aacccattcc
2341  acagaacagc attcccaaca agtaccacaa gctgaaggct ctcatgacgc agcggactta
2401  tttgcagtgg cccaaggaga aaagcaaacg tgggctcttt tgggctaaca ttagagccgc
2461  ttttaatatg aaattaacac tagtcactga aaacaatgat gtgaaatctt aaaaaaattt
2521  aggaaattca acttaagaaa ccattattta cttggatgat ggtgaatagt acagtcgtaa
2581  gtaactgtct ggaggtgcct ccattatcct catgccttca ggaaagactt aacaaaaaca
2641  atgtttcatc tggggaactg agctaggcgg tgaggttagc ctgccagtta gagacagccc
2701  agtctcttct ggtttaatca ttatgtttca aattgaaaca gtctcttttg agtaaatgct
2761  cagttttca gctcctctcc actctgcttt cccaaatgga ttctgttgtg agcaagagtt
2821  tatatggctt catggcagca agggaacagt caacttcagc atcatatgca ccagtcctcg
2881  gagtgccctg tgaatcatat tggtctttgg gtcagtgtca tcattctctt caagtctggg
2941  gcttgggaa aaattgat cagctacggc atataaaaaa gtcttttgtt tcacatatgt
3001  gtaatagctt atttaatttt ttatcctgct acacaaatat gtaattaacc aatgaggact
3061  catgacttga tagtgtatgt atgtaaaggg atatatggac ttaatcataa gctgttgagg
3121  tgaaagacgt ggatccacct gctttccaag aaaactcggc caaatttatt tgcagctgga
3181  tattgaatgg gacttttctg gttgtcttag aattctggct aaaggctcaa agctgacgaa
3241  agacagtaac tgcaccaaca tgatactaga cacagccagt ctggacttat caaaagagca
3301  gaaagagacc aatgactccc agtccgtatt atccatctct agaagactag agtcaaaagc
3361  gtgattaaag agtcattaag cggaggttct aggccatagg gagattgctt tgaatttctt
3421  gcagacaagt gtgagggact cagcatggta gaaggtagcc tggcatccca ctccaagact
3481  gaaagcttgc agagtaacag gagcacacag gttcagtgca gcagatgtgg tgtggcttga
3541  gaattcttgg aagagcttga tgagtgtttg ctggagtccg agggtgggca ctgggaacac
3601  agagactggt aaatagtgtt tggcaaatac aagtgcttga tgaatatttg ttgaatgaat
3661  agatgagttc ttccccctg gggaattcag gaggtgaaag gttggcttga gcacccaaaa
3721  tggcaggatg agagaagaga agcactgata gcaacctgcc ctcccattat tgacatggta
3781  aaaggatgtg aatttcttca catggctttg actatggaag agtagctggg cttgcattgt
3841  catgacggga tatcagccaa cagggtagcc tgttgtgcaa agaaactata gcagtaagag
3901  gacacggggt taggcagaag aggggtttgg ggtggaggtt gctgcaagag gtcagccaga
3961  taatgtggcc ctgcatcatg gaactgtgca atgtggggta cactcaaggc cctccaataa
4021  ctcacagatg tgccctatga aaaagccagc atttggactc tgccatagca gctggcagga
```

-continued

```
4081 tcatgctggc ctgtctgcct tattcaatag ttaactacag gaagatctgc tcctctttgt
4141 gtaataccct cttcccttgc aatggcatag ggacatctag aatatagaga agacagagac
4201 aatggaggaa gagtaaagaa actgactata tgccttcgtc atttcactgc aaggaaggcc
4261 aagcagattt ttgaatgagg tgtgagattg ctgttaaatt ggactggcct ggacatttta
4321 atcccttaaa tagaggtgca atgactaaag tgagatttgt cactaaaatt tatggtatct
4381 gcccaagatt caggagtgat gatgggagga gatccaacag aactttgttg taaggcaatg
4441 gttagagaaa aatgaagccc tcgctttctg gacttagttc attcaataaa ccagtttcgg
4501 ccaggcacgt tggctcacat ctataatccc agtactgtgg gaggctgagg caggtggatc
4561 acttgaggtc aggagttcga gaccagcctg gccaacatgg tgaaaccctg tctgtactaa
4621 aaatacaaaa attagccggg tgtggtggtg tgcacctgta gtcccagcta ctcgggaggc
4681 tgaggcagga aaatcacttg aacctgggag acagaggctg tagtgagctg agacagcgct
4741 actgtactcc ccgctgggca acagagtgag actccatctc aaaaaagtta aagaaaaaa
4801 aatctggttt cataatagct gtaacgaaat aagccttaat gatattttat tagcatcatc
4861 ttctgtctgc attagcccct ccttgctctt caggagaaca acatttgttt tcctccctag
4921 gctctatccc aaacggcaca ttcttccaca accctgttg aacagatttt ttaaactgtt
4981 gcctaatcta aaaacaataa aaacaacaaa caaccacagt aacaacaacg acaaaaaaa
5041 ctgccacaga ttctaaataa tcagatcttt ttaaatggta tcaatgtttc cacaaaata
5101 ttgttgacat tgaaaatata gaattttagc attaattttg ttaaacctac atccctcgg
5161 cagaggggcc tccctgcatc ccagtggaaa gtaggttcct cacagtcctc tccgtcacat
5221 tcttcccatt tctttcttc acagaacaca tcactgtcta aaattatctt gtttgcttag
5281 ttgcttactc atcttcttct tctctcctct gaagtctaag ctccaggaaa aagggagact
5341 tctccacctg ttccctgcct ctccccagtg ccgaggggac actgtgcacc ccattgtaga
5401 tgcgcagtaa aaactcgtgg gatgagcaaa tgactctgaa acggtcccat gcgggaaatg
5461 tccatgaagt cctggatttt atctaaaaag cccaggcagg gggggcggg ggcggcgggg
5521 ctacagttcc acgctgagct gcctcctggc cgctcgtccc cgccgcagtc cctgggcggc
5581 ccgggcgccc gaccttggcc gtggacacct tcgcggtggg tgctgctcct ccccatctgc
5641 cactggaaga tgctggggcg acccggctcc aggtttagca ggacactgag aaaagggaat
5701 ggctgccttt cggaggctgg gtgagcccctt ctctgtgcct cacctgcccg ccccacagcg
5761 gccctgcacc tcgtcccacg gggcccattg ccccggtagg atgcgcgctt ttgttttgag
5821 ggtcaggcat cttccctgcc gtcgtttctg ggaggttgaa aaattgatcc agaaagacct
5881 aaaacaaaaa a
```

B15 WARS-tryptophanyl-tRNA synthetase, cytoplasmic isoform a mRNA
NM_004184.3

(SEQ ID NO: 151)

```
  1 tcgattctca agagggtttc attggtctca acctggcccc ccaggcaacc caccccctgat
 61 tggacagtct catcaagaag gttggtcaag agctcaagtg tttctgagaa tctgggtgat
121 ttataagaaa cccttagctg aatgcagggt ggggagaacg aaagacaaaa gcatctttt
181 tcagaaggga aactgaaaga aagaggggaa gagtattaaa gaccatttct ggctgggcag
241 ggcactctca gcagctcaac tgcccagcgt gaccagtggc cacctctgca gtgtcttcca
301 caacctggtc ttgactcgtc tgctgaacaa atcctctgac ctcaggccgg ctgtgaacgt
361 agttcctgag agatagcaaa catgcccaac agtgagcccg catctctgct ggagctgttc
421 aacagcatcg ccacacaagg ggagctcgta aggtcccctca aagcgggaaa tgcgtcaaag
```

```
 481  gatgaaattg attctgcagt aaagatgttg gtgtcattaa aaatgagcta caaagctgcc
 541  gcggggagg  attacaaggc tgactgtcct ccagggaacc cagcacctac cagtaatcat
 601  ggcccagatg ccacagaagc tgaagaggat tttgtggacc catggacagt acagacaagc
 661  agtgcaaaag gcatagacta cgataagctc attgttcggt ttggaagtag taaaattgac
 721  aaagagctaa taaaccgaat agagagagcc accggccaaa gaccacacca cttcctgcgc
 781  agaggcatct tcttctcaca cagagatatg aatcaggttc ttgatgccta tgaaaataag
 841  aagccatttt atctgtacac gggccggggc ccctcttctg aagcaatgca tgtaggtcac
 901  ctcattccat ttattttcac aaagtggctc caggatgtat ttaacgtgcc cttggtcatc
 961  cagatgacgg atgacgagaa gtatctgtgg aaggacctga ccctggacca ggcctatagc
1021  tatgctgtgg agaatgccaa ggacatcatc gcctgtggct ttgacatcaa caagactttc
1081  atattctctg acctggacta catggggatg agctcaggtt tctacaaaaa tgtggtgaag
1141  attcaaaagc atgttacctt caaccaagtg aaaggcattt tcggcttcac tgacagcgac
1201  tgcattggga agatcagttt tcctgccatc caggctgctc cctccttcag caactcattc
1261  ccacagatct tccgagacag gacggatatc cagtgcctta tcccatgtgc cattgaccag
1321  gatccttact ttagaatgac aagggacgtg gcccccagga tcggctatcc taaaccagcc
1381  ctgctgcact ccaccttctt cccagccctg cagggcgccc agaccaaaat gagtgccagc
1441  gaccccaact cctccatctt cctcaccgac acgccaagc  agatcaaaac caaggtcaat
1501  aagcatgcgt tttctggagg gagagacacc atcgaggagc acaggcagtt tgggggcaac
1561  tgtgatgtgg acgtgtcttt catgtacctg accttcttcc tcgaggacga cgacaagctc
1621  gagcagatca ggaaggatta caccagcgga gccatgctca ccggtgagct caagaaggca
1681  ctcatagagg ttctgcagcc cttgatcgca gagcaccagg cccggcgcaa ggaggtcacg
1741  gatgagatag tgaaagagtt catgactccc cggaagctgt ccttcgactt tcagtagcac
1801  tcgttttaca tatgcttata aagaagtga  tgtatcagta atgtatcaat aatcccagcc
1861  cagtcaaagc accgccacct gtaggcttct gtctcatggt aattactggg cctggcctct
1921  gtaagcctgt gtatgttatc aatactgttt cttcctgtga gttccattat ttctatctct
1981  tatgggcaaa gcattgtggg taattggtgc tggctaacat tgcatggtcg gatagagaag
2041  tccagctgtg agtctctccc caaagcagcc ccacagtgga gcctttggct ggaagtccat
2101  gggccaccct gttcttgtcc atggaggact ccgagggttc caagtatact cttaagaccc
2161  actctgttta aaaatatata ttctatgtat gcgtatatgg aattgaaatg tcattattgt
2221  aacctagaaa gtgctttgaa atattgatgt ggggaggttt attgagcaca agatgtattt
2281  cagcccatgc cccctcccaa aaagaaattg ataagtaaaa gcttcgttat acatttgact
2341  aagaaatcac ccagctttaa agctgctttt aacaatgaag attgaacaga gttcagcaat
2401  tttgattaaa ttaagacttg gggtgaaac  tttccagttt actgaactcc agaccatgca
2461  tgtagtccac tccagaaatc atgctcgctt cccttggcac accagtgttc tcctgccaaa
2521  tgaccctaga ccctctgtcc tgcagagtca gggtggcttt tcccctgact gtgtccgatg
2581  ccaaggagtc ctggcctccg cagatgcttc attttgaccc ttggctgcag tggaagtcag
2641  cacagagcag tgccctggct gtgtccctgg acgggtggac ttagctaggg agaaagtcga
2701  ggcagcagcc ctcgaggccc tcacagatgt ctaggcaggc ctcatttcat cacgcagcat
2761  gtgcaggcct ggaagagcaa agccaaatct cagggaagtc cttggttgat gtatctgggt
2821  ctcctctgga gcactctgcc ctcctgtcac ccagtagagt aaataaactt ccttggctcc
2881  tgct
```

-continued

B16 MMP9-matrix metallopeptidase 9, mRNA NM_0049942

(SEQ ID NO: 152)

```
   1 agacacctct gccctcacca tgagcctctg gcagccctg gtcctggtgc tcctggtgct
  61 gggctgctgc tttgctgccc ccagacagcg ccagtccacc cttgtgctct ccctggaga
 121 cctgagaacc aatctcaccg acaggcagct ggcagaggaa tacctgtacc gctatggtta
 181 cactcgggtg cagagatgc gtggagagtc gaaatctctg gggcctgcgc tgctgcttct
 241 ccagaagcaa ctgtccctgc ccgagaccgg tgagctggat agcgccacgc tgaaggccat
 301 gcgaacccca cggtgcgggg tcccagacct gggcagattc caaacctttg agggcgacct
 361 caagtggcac caccacaaca tcacctattg gatccaaaac tactcggaag acttgccgcg
 421 ggcggtgatt gacgacgcct ttgcccgcgc cttcgcactg tggagcgcgg tgacgccgct
 481 caccttcact cgcgtgtaca gccgggacgc agacatcgtc atccagtttg tgtcgcgga
 541 gcacggagac gggtatccct tcgacgggaa ggacgggctc ctggcacacg cctttcctcc
 601 tggcccgggc attcaggag acgcccattt cgacgatgac gagttgtggt ccctgggcaa
 661 gggcgtcgtg gttccaactc ggtttggaaa cgcagatggc gcggcctgcc acttcccctt
 721 catcttcgag ggccgctcct actctgcctg caccaccgac ggtcgctccg acggcttgcc
 781 ctggtgcagt accacggcca actacgacac cgacgaccgg tttggcttct gccccagcga
 841 gagactctac acccaggacg gcaatgctga tgggaaaccc tgccagtttc cattcatctt
 901 ccaaggccaa tcctactccg cctgcaccac ggacggtcgc tccgacggct accgctggtg
 961 cgccaccacc gccaactacg accgggacaa gctcttcggc ttctgcccga cccgagctga
1021 ctcgacggtg atgggggca actcggcggg ggagctgtgc gtcttcccct tcactttcct
1081 gggtaaggag tactcgacct gtaccagcga gggccgcgga gatgggcgc tctggtgcgc
1141 taccacctcg aactttgaca gcgacaagaa gtggggcttc tgcccggacc aaggatacag
1201 tttgttcctc gtggcggcgc atgagttcgg ccacgcgctg ggcttagatc attcctcagt
1261 gccggaggcg ctcatgtacc ctatgtaccg cttcactgag ggcccccct tgcataagga
1321 cgacgtgaat ggcatccggc acctctatgg tcctcgccct gaacctgagc cacggcctcc
1381 aaccaccacc acaccgcagc ccacggctcc cccgacggtc tgccccaccg gaccccccac
1441 tgtccacccc tcagagcgcc ccacagctgg ccccacaggt ccccctcag ctggccccac
1501 aggtcccccc actgctggcc cttctacggc cactactgtg cctttgagtc cggtggacga
1561 tgcctgcaac gtgaacatct tcgacgccat cgcggagatt gggaaccagc tgtatttgtt
1621 caaggatggg aagtactggc gattctctga gggcagggg agccggccgc agggccctt
1681 ccttatcgcc gacaagtggc ccgcgctgcc ccgcaagctg gactcggtct ttgaggagcg
1741 gctctccaag aagcttttct tcttctctgg gcgccaggtg tgggtgtaca caggcgcgtc
1801 ggtgctgggc ccgaggcgtc tggacaagct gggcctggga gccgacgtgg cccaggtgac
1861 cggggccctc cggagtgcca ggggaagat gctgctgttc agcgggcggc gcctctggag
1921 gttcgacgtg aaggcgcaga tggtggatcc ccggagcgcc agcgaggtgg accggatgtt
1981 ccccgggtg cctttggaca cgcacgacgt cttccagtac cgagagaaag cctatttctg
2041 ccaggaccgc ttctactggc gcgtgagttc ccggagtgag ttgaaccagg tggaccaagt
2101 gggctacgtg acctatgaca tcctgcagtg ccctgaggac taggctccc gtcctgcttt
2161 ggcagtgcca tgtaaatccc cactgggacc aaccctgggg aaggagccag tttgccggat
2221 acaaactggt attctgttct ggaggaaagg gaggagtgga ggtgggctgg gccctctctt
```

-continued

```
2281 ctcacctttg tttttttgttg gagtgtttct aataaacttg gattctctaa cctttaaaaa
2341 aaaaaaaaaa aaaaaaaaaa aaaaaaaaaa aaaaaaaaaa aaaaaaa
```

B17 DOCK9-dedicator of cytokinesis 9 mRNA NM_015296.2

(SEQ ID NO: 153)

```
   1 gcggccgggc cgggccgcgg gagcaggcgg aggcggaggc ggcggggggca ggaggatgtc
  61 gcagccgccg ctgctccccg cctcggcgga gactcggaag ttcacccggg cgctgagtaa
 121 gccgggcacg gcggccgagc tgcggcagag cgtgtctgag gtggtgcgcg gctccgtgct
 181 cctggcaaag ccaaagctaa ttgagccact cgactatgaa aatgtcatcg tccagaagaa
 241 gactcagatc ctgaacgact gtttacggga gatgctgctc ttcccttacg atgactttca
 301 gacggccatc ctgagacgac agggtcgata catatgctca acagtgcctg cgaaggcgga
 361 agaggaagca cagagcttgt ttgttacaga gtgcatcaaa acctataact ctgactggca
 421 tcttgtgaac tataaatatg aagattactc aggagagttt cgacagcttc gaacaaagt
 481 ggtcaagttg gataaacttc cagttcatgt ctatgaagtt gacgaggagg tcgacaaaga
 541 tgaggatgct gcctcccttg gttcccagaa gggtgggatc accaagcatg ctggctgta
 601 caaaggcaac atgaacagtg ccatcagcgt gaccatgagg tcatttaaga gacgattttt
 661 ccacctgatt caacttggcg atggatccta taatttgaat ttttataaag atgaaaagat
 721 ctccaaagaa ccaaaaggat caatatttct ggattcctgt atgggtgtcg ttcagaacaa
 781 caaagtcagg cgttttgctt ttgagctcaa gatgcaggac aaaagtagtt atctcttggc
 841 agcagacagt gaagtggaaa tggaagaatg gatcacaatt ctaaataaga tcctccagct
 901 caactttgaa gctgcaatgc aagaaaagcg aaatggcgac tctcacgaag atgatgaaca
 961 aagcaaattg gaaggttctg gttccggttt agatagctac ctgccggaac ttgccaagag
1021 tgcaagagaa gcagaaatca aactgaaaag tgaaagcaga gtcaaacttt tttatttgga
1081 cccagatgcc cagaagcttg acttctcatc agctgagcca gaagtgaagt catttgaaga
1141 gaagtttgga aaaaggatcc ttgtcaagtg caatgattta tcttttcaatt tgcaatgctg
1201 tgttgccgaa aatgaagaag gacccactac aaatgttgaa ccttttctttg ttactctatc
1261 cctgtttgac ataaaataca accggaagat ttctgccgat ttccacgtag acctgaacca
1321 tttctcagtg aggcaaatgc tcgccaccac gtccccggcg ctgatgaatg cagtgggca
1381 gagcccatct gtcctcaagg catccttca tgaagccgcc atgcagtatc cgaagcaggg
1441 aatattttca gtcacttgtc ctcatccaga tatatttctt gtggccagaa ttgaaaaagt
1501 ccttcagggg agcatcacac attgcgctga gccatatatg aaaagttcag actcttctaa
1561 ggtggcccag aaggtgctga agaatgccaa gcaggcatgc caaagactag gacagtatag
1621 aatgccattt gcttgggcag caaggacatt gtttaaggat gcatctggaa atcttgacaa
1681 aaatgccaga ttttctgcca tctacaggca agacagcaat aagctatcca atgatgacat
1741 gctcaagtta cttgcagact ttcggaaacc tgagaagatg gctaagctcc cagtgatttt
1801 aggcaatcta gacattacaa ttgataatgt ttcctcagac ttccctaatt atgttaattc
1861 atcatacatt cccacaaaac aatttgaaac ctgcagtaaa actcccatca cgtttgaagt
1921 ggaggaattt gtgccctgca taccaaaaca cactcagcct tacaccatct acaccaatca
1981 cctttacgtt tatcctaagt acttgaaata cgacagtcag aagtcttttg ccaaggctag
2041 aaatattgcg atttgcattg aattcaaaga ttcagatgag gaagactctc agcccttaa
2101 gtgcatttat ggcagacctg gtgggccagt tttcacaaga agcgcctttg ctgcagtttt
2161 acaccatcac caaaacccag aattttatga tgagattaaa atagagttgc ccactcagct
2221 gcatgaaaag caccacctgt tgctcacatt cttccatgtc agctgtgaca actcaagtaa
```

-continued

```
2281  aggaagcacg aagaagaggg atgtcgttga aacccaagtt ggctactcct ggcttcccct
2341  cctgaaagac ggaagggtgg tgacaagcga gcagcacatc ccgtctcgg cgaaccttcc
2401  ttcgggctat cttggctacc aggagcttgg gatgggcagg cattatggtc cggaaattaa
2461  atgggtagat ggaggcaagc cactgctgaa aatttccact catctggttt ctacagtgta
2521  tactcaggat cagcatttac ataatttttt ccagtactgt cagaaaaccg aatctggagc
2581  ccaagcctta ggaaacgaac ttgtaaagta ccttaagagt ctgcatgcga tggaaggcca
2641  cgtgatgatc gccttcttgc ccactatcct aaaccagctg ttccgagtcc tcaccagagc
2701  cacacaggaa gaagtcgcgg ttaacgtgac tcgggtcatt attcatgtgg ttgcccagtg
2761  ccatgaggaa ggattggaga gccacttgag gtcatatgtt aagtacgcgt ataaggctga
2821  gccatatgtt gcctctgaat acaagacagt gcatgaagaa ctgaccaaat ccatgaccac
2881  gattctcaag ccttctgccg atttcctcac cagcaacaaa ctactgaagt actcatggtt
2941  tttctttgat gtactgatca aatctatggc tcagcatttg atagagaact ccaaagttaa
3001  gttgctgcga aaccagagat ttcctgcatc ctatcatcat gcagtggaaa ccgttgtaaa
3061  tatgctgatg ccacacatca ctcagaagtt tcgagataat ccagaggcat ctaagaacgc
3121  gaatcatagc cttgctgtct tcatcaagag atgtttcacc ttcatggaca ggggctttgt
3181  cttcaagcag atcaacaact acattagctg ttttgctcct ggagacccaa agaccctctt
3241  tgaatacaag tttgaatttc tccgtgtagt gtgcaaccat gaacattata ttccgttgaa
3301  cttaccaatg ccatttggaa aaggcaggat tcaaagatac caagacctcc agcttgacta
3361  ctcattaaca gatgagttct gcagaaacca cttcttggtg ggactgttac tgagggaggt
3421  ggggacagcc ctccaggagt tccgggaggt ccgtctgatc gccatcagtg tgctcaagaa
3481  cctgctgata aagcattctt ttgatgacag atatgcttca aggagccatc aggcaaggat
3541  agccaccctc tacctgcctc tgtttggtct gctgattgaa aacgtccagc ggatcaatgt
3601  gagggatgtg tcacccttcc ctgtgaacgc gggcatgact gtgaaggatg aatccctggc
3661  tctaccagct gtgaatccgc tggtgacgcc gcagaaggga agcaccctgg acaacagcct
3721  gcacaaggac ctgctgggcg ccatctccgg cattgcttct ccatatacaa cctcaactcc
3781  aaacatcaac agtgtgagaa atgctgattc gagaggatct ctcataagca cagattcggg
3841  taacagcctt ccagaaagga atagtgagaa gagcaattcc ctggataagc accaacaaag
3901  tagcacattg ggaaattccg tggttcgctg tgataaactt gaccagtctg agattaagag
3961  cctactgatg tgtttcctct acatcttaaa gagcatgtct gatgatgctt tgtttacata
4021  ttggaacaag gcttcaacat ctgaacttat ggattttttt acaatatctg aagtctgcct
4081  gcaccagttc cagtacatgg ggaagcgata catagccaga acaggaatga tgcatgccag
4141  attgcagcag ctgggcagcc tggataactc tctcactttt aaccacagct atggccactc
4201  ggacgcagat gttctgcacc agtcattact tgaagccaac attgctactg aggtttgcct
4261  gacagctctg gacacgcttt ctctatttac attggcgttt aagaaccagc tcctggccga
4321  ccatggacat aatcctctca tgaaaaagt ttttgatgtc tacctgtgtt tcttcaaaa
4381  acatcagtct gaaacggctt taaaaaatgt cttcactgcc ttaaggtcct taatttataa
4441  gtttccctca acattctatg aagggagagc ggacatgtgt gcggctctgt gttacgagat
4501  tctcaagtgc tgtaactcca agctgagctc catcaggacg gaggcctccc agctgctcta
4561  cttcctgatg aggaacaact tgattacac tggaaagaag tcctttgtcc ggacacattt
4621  gcaagtcatc atatctgtca gccagctgat agcagacgtt gttggcattg ggggaaccag
```

-continued

```
4681  attccagcag tccctgtcca tcatcaacaa ctgtgccaac agtgaccggc ttattaagca
4741  caccagcttc tcctctgatg tgaaggactt aaccaaaagg atacgcacgg tgctaatggc
4801  caccgcccag atgaaggagc atgagaacga cccagagatg ctggtggacc tccagtacag
4861  cctggccaaa tcctatgcca gcacgcccga gctcaggaag acgtggctcg acagcatggc
4921  caggatccat gtcaaaaatg gcgatctctc agaggcagca atgtgctatg tccacgtaac
4981  agcccctagtg gcagaatatc tcacacggaa agaagcagtc cagtgggagc cgcccccttct
5041  cccccacagc catagcgcct gcctgaggag gagccgggga ggcgtgttta gacaaggatg
5101  caccgccttc agggtcatta ccccaaacat cgacgaggag gcctccatga tggaagacgt
5161  ggggatgcag gatgtccatt tcaacgagga tgtgctgatg gagctccttg agcagtgcgc
5221  agatggactc tggaaagccg agcgctacga gctcatcgcc gacatctaca aacttatcat
5281  ccccatttat gagaagcgga gggattttga gaggctggcc catctgtatg acacgctgca
5341  ccgggcctac agcaaagtga ccgaggtcat gcactcgggc cgcaggcttc tggggaccta
5401  cttccgggta gccttcttcg ggcaggcagc gcaataccag tttacagaca gtgaaacaga
5461  tgtggaggga ttctttgaag atgaagatgg aaaggagtat atttacaagg aacccaaact
5521  cacaccgctg tcggaatttt ctcagagact ccttaaactg tactcggata atttggttc
5581  tgaaaatgtc aaaatgatac aggattctgg caaggtcaac cctaaggatc tggattctaa
5641  gtatgcatac atccaggtga ctcacgtcat ccccttcttt gacgaaaaag agttgcaaga
5701  aaggaaaaca gagtttgaga gatcccacaa catccgccgc ttcatgtttg agatgccatt
5761  tacgcagacc gggaagaggc agggcggggt ggaagagcag tgcaaacggc gcaccatcct
5821  gacagccata cactgcttcc cttatgtgaa gaagcgcatc cctgtcatgt accagcacca
5881  cactgacctg aacccatcg aggtggccat tgacgagatg agtaagaagg tggcggagct
5941  ccggcagctg tgctcctcgg ccgaggtgga catgatcaaa ctgcagctca aactccaggg
6001  cagcgtgagt gttcaggtca atgctggccc actagcatat gcgcgagctt cttagatga
6061  tacaaacaca aagcgatatc ctgacaataa agtgaagctg cttaaggaag ttttcaggca
6121  atttgtggaa gcttgcggtc aagccttagc ggtaaacgaa cgtctgatta agaagacca
6181  gctcgagtat caggaagaaa tgaaagccaa ctacagggaa atggcgaagg agctttctga
6241  aatcatgcat gagcagctgg gatgatctgc cccctggagg agaagacgag cgtcttaccg
6301  aattcccttc acatcttcaa cgccatcagt gggactccaa caagcacaat ggttcacggg
6361  atgaccagct cgtcttcggt cgtgtgatta catctcatgg cccgtgtgtg gggacttgct
6421  ttgtcatttg caaactcagg atgctttcca aagccaatca ctggggagac cgagcacagg
6481  gaggaccaag gggaagggga gagaaaggaa ataaagaaca acgttatttc ttaacagact
6541  ttctatagga gttgtaagaa ggtgcacata ttttttaaa tctcactggc aatattcaaa
6601  gttttcattg tgtcttaaca aaggtgtggt agacactctt gagctggact tagattttat
6661  tcttccttgc agagtagtgt tagaatagat ggcctacaga aaaaaaggt tctgggatct
6721  acatggcagg gagggctgca ctgacattga tgcctggggg accttttgcc tcgaggctga
6781  gctggaaaat cttgaaaata ttttttttttt cctgtggcac attcaggttg aatacaagaa
6841  ctattttgt gactagtttt tgatgaccta agggaactga ccattgtaat ttttgtacca
6901  gtgaaccagg agatttagtg ctttatatt catttccttg catttaagaa aatatgaaag
6961  cttaaggaat tatgtgagct taaaactagt caagcagttt agaaccaaag gcctatatta
7021  ataccgcaa ctatgctgaa aagtacaaag tagtacagta tattgttatg tacatatcat
7081  tgttaataca gtcctggcat tctgtacata tatgtattac atttctacat ttttaatact
```

```
7141  cacatgggct tatgcattaa gtttaattgt gataaatttg tgctgttcca gtatatgcaa
7201  tacactttaa tgtttttattc ttgtacataa aaatgtgcaa tatggagatg tatacagtct
7261  ttactatatt aggtttataa acagttttaa gaatttcatc ctttttgccaa aatggtggag
7321  tatgtaattg gtaaatcata aatcctgtgg tgaatggtgg tgtactttaa agctgtcacc
7381  atgttatatt ttcttttaag actttaattt agtaatttta tatttgggaa aataaaggtt
7441  tttaatttta tttaactgga atcactgccc tgctgtaatt aaacattctg taccacatct
7501  gtattaaaaa gacattgctg accattaaaa aaaaaaaaa aaaa
```

B18 SIRPB2 signal-regulatory protein beta 2, mRNA NM_001122962.1
(SEQ ID NO: 154)

```
   1  ttagcacagt gactacagga atcacagccc agacacaaaa gcaggaaacc ctttgaccgg
  61  gctccttcct attgcaccaa cagccttgtg ttgctgcaat gaaaacactt ccccaagcag
 121  ctgtggccaa gagacgcaga aactgccttg tccacgggcc ccgcctcaga ctccaacact
 181  cacaagagag cagaggagcc ccaagtcttg ggaccacag aagatgccat gtgctccacg
 241  atgtcggccc ccacctgcct ggcccacttg cctcctgct tcctgctgct ggcactggtc
 301  cttgtcccct cagatgcctc tgggcagagc agcaggaatg actggcaggt gctacagccc
 361  gagggcccca tgctggtggc agaaggtgag acacttctac tgaggtgtat ggtggtcggc
 421  tcctgcactg atggtatgat aaaatgggtg aaggtgagca ctcaggacca acaggaaatt
 481  tataacttta aacgtggctc cttccctggg gtaatgccca tgatccaacg gacatcagaa
 541  ccactgaatt gtgattattc catctatatc cacaatgtca ccagggagca cactggaacc
 601  taccactgtg tgaggtttga tggtttgagt gaacactcag aaatgaaatc ggatgaaggc
 661  acctcagtgc ttgtgaaggg agctggggac cctgaaccag acctgtggat catccagccc
 721  caggaattgg tgttggggac cactggagac actgtctttc tgaactgcac agtgcttgga
 781  gacggtcccc ctggacccat caggtggttc cagggagctg gtctgagccg ggaggccatt
 841  tacaactttg gaggcatctc ccaccccaag gagacagcgg tgcaggcctc caacaatgac
 901  ttcagcattc ttctgcaaaa cgtctccagt gaggatgcag gcacctatta ctgtgtaaag
 961  tttcagagga aacccaacag gcaataccctg tctggacagg gcaccagcct gaaagtgaaa
1021  gcaaaatcta cctcttccaa agaggcagaa ttcaccagtg aacctgcaac tgagatgtct
1081  ccaacaggcc tcctggttgt gttcgcacct gtggtcctgg ggctgaaggc aattaccttg
1141  gctgcactcc tactggccct ggctacctct cggaggagcc ctgggcaaga agatgtcaag
1201  accacaggcc cagcaggagc catgaacacc ttagcatgga gcaagggtca agagtgaggg
1261  gtcagcccca gagtgaggac cctctgagtt ggagaggagc cagggctcct caaccatttc
1321  cctacctcca gtcccagcct ctaggtgccc ccaggcctca tgacaaactc ctagatccct
1381  acatctggtt ttggtccacc tagtgaaatt ccccttctttg caccgggctt ccctctaaaa
1441  tgtctccctt tctcttttttg gcctgttcaa gacctccttg cttttcagtc cctggctcag
1501  tctctcctca acacccttgc ccctgctgca gcccttttctg gtgcgccctg cccctttccc
1561  cacctcgcta catccttctt ggcctcaac atccaactca gagtcttctt cccaggagat
1621  gtctgtaaga atctctgaac tcaaccagcc agaccatctg tgccctcca tctacacctt
1681  tctccccact ccttcctgcc ttccttccat ccccctcatg gctggcttgg gcaggtataa
1741  tattagaatg caggttcagc aactataaca aagctcttaa ataacagtgg cttaaaccag
1801  tggaaatcaa ccagaaagtt gaccatcagc aggccaagca atacagagac tccctggtat
1861  tgagacccag gattcactga tctcattgct accaggtcca ccttctaggc agccagactg
```

-continued

```
1921  gaaaagaggg caggaaaggg gagcaggacc ctcccctttta agtgcacagt caggaacttg 1981  gccacctcac ttatctctac ttggctggaa tgtggtcaca tggtcacacc tagctgcaag 2041  aaacactggg agatgtagtc tttatttctg gcagcaatgc gcccagctgc aagttttcac 2101  tagagaaacc agatggcaga tatcagggga taaccagtta tctccaccac agcagcatac 2161  agacagcctc tcacctgccc tgtgggacac ctgagttcaa tgcccagcta gctagccagc 2221  acttcttccc actatcacct cccctggggc agcatgatgt ggggcagtag ttcccaagat 2281  gagtgatttt gcccccactg gacttttggc aatgtctaga gatgttttg gttggcacaa 2341  cctgggggg tgctaccacc atcagtgga ctgagaagcc ctgacatggg gaagagtgtg 2401  catgcccagg agtcagacac acctgccttt aaccctgagg cctctgcctc ctccctgtgc 2461  accctcagtg actaatcaga gtcccttccc atcacggaac atccaggata ctaatgtgga 2521  cttctctgca ttgtgtaaga accaattcaa gaccaggcac ggtggcttat gcatgtaatc 2581  ccagcacttt gggaggccga ggtgggtgga tcacctgagt tcaggagttt gagaccagcc 2641  tggctaacat ggtgaaacct cgtctctact aaaaatacaa aaaattagcc aggcgtggtg 2701  gtgtgcacct gtaatcccag ctacttggga ggatggggca ggagaaccgc ttgaactggg 2761  aggcagaggc tgcagtgagc tgagatcgcg ccattgcact ccagcctggg caacaagagc 2821  aaaactccgt ctc
```

B19 ANKRD22 ankyrin repeat domain 22, mRNA NM_1445902

(SEQ ID NO: 155)

```
   1  aatgtaagaa cttttcttcc tcccttaact ttgcttcctt ctttcctgca tgttaccact 61  ggcagagcaa atatgactca gaaaccggct cctcagggtt gtaacattag atgatacagg 121  cttgggtcgt tacacatgac accagtgcct ttgtttcatt gggctgggct ctctggaagg 181  tgtgctgctg cctgagctgc tggaaaagca ctgacaggtg tttgctagaa aagcactcct 241  ggagcttgcc accagcttgg acttctaggg actttcctct cagccaggaa ggattttgat 301  attcatcaga atacctcca gaagattcaa ggagctgtag aggtgaagta agcctgtgaa 361  ggaccagcat gggaatccta tactctgagc ccatctgcca agcagcctat cagaatgact 421  ttggacaagt gtggcggtgg gtgaaagaag acagcagcta tgccaacgtt caagatggct 481  ttaatggaga cacgcccctg atctgtgctt gcaggcgagg gcatgtgaga atcgtttcct 541  tccttttaag aagaaatgct aatgtcaacc tcaaaaacca gaaagagaga acctgcttgc 601  attatgctgt gaagaaaaaa tttaccttca ttgattatct actaattatc ctcttaatgc 661  ctgttctgct tattgggtat ttcctcatgg tatcaaagac aaagcagaat gaggctcttg 721  tacgaatgct acttgatgct ggcgtcgaag ttaatgctac agattgttat ggctgtaccg 781  cattacatta tgcctgtgaa atgaaaaacc agtctcttat ccctctgctc ttggaagccc 841  gtgcagaccc cacaataaag aataagcatg tgagagctc actggatatt gcacggagat 901  taaattttc ccagattgaa ttaatgctaa ggaaagcatt gtaatccttg tgaccacacc 961  gatggagata cagaaaaagt taacgactgg attctatctt catttttagac ttttggtctg 1021  tgggccattt aacctggatg ccaccatttt atggggataa tgatgcttac catggttaat 1081  gttttggaag agctttttat ttatagcatt gtttactcag tcaagttcac catggccgta 1141  atccttctaa gggaaacact aaagttgttg tagtctccac ttcagtcaga aactgatgtt 1201  tcagctaggc acagtggtac atgcctgtaa tcccagctac ttgggaggct gaggtgggag 1261  gatcacttga actcaggagt ttgagagcag ccaggcaac acagcgagac cctgtctcaa 1321  aaaaaaaaa aaaaaaaaa gccctgtgt tccaaactca gtctttcctg aagaagagga 1381  tctgagttat cttctgaaac agcgttctcc cttcccagtt gtatcactct tataaaaga
```

-continued

```
1441  ctgtccagtc tatgtcatgc cctaggagac aaactgttcc tcccagcccc ctttgagtat 1501  tgagcagaag aatcaaatta ttaaatacgt atgtttgtac agaatggtat tgtgtatgt 1561  gtgtgggctt agagattcac aagtaaatat tcctttggtg aaggaatttc aataaaaaca 1621  tctatcaagt gtcagcggtg agtgtgttta caccacagaa attggcaaat tgacaaatca 1681  gagtttgttt ttgtttttttt gttttttact ttccataaag ttcgtttacc agcataccac 1741  tagagatttc ggtttacaaa taaaagccat cttggtttga gcaagactat gcaactatga 1801  aaatgttcgt ttaaaaaaat cttcatgatc cttttgtaaa tacaaggtgg ttgccaagct 1861  tgttagtttt gtttatttta ttgatagatg taaaatatta ttgtaactta tttggataaa 1921  gttcttcaaa agaaacagag ctatacaatg aggtaggatc tggattattt gtctaagtga 1981  gagattgcga atatcaaaat atctgtctca cttcttctgt gaatgacaca gagtagaaat 2041  aaattcactt taaaaatatg actgaatttt gaaaatcaag actgaatctc acatagctgc 2101  agacaggaac taagccagcc tctttgtatg tggtaacaag tacagtataa gaatgaaaga 2161  tttaccatcc ttgaaagctc taatgaaaat caaatccagc aatatatatt caactgtgta 2221  caggatttaa gaaacttatt ttatgaagga agtaatagtg tgtagatata gattctgaag 2281  tctttaaacg tgtcttaata aattaagatt cactggcatt gagctgagct accaggtgac 2341  ccttggggac aaaaaaccca cacaagtgaa tttcacacac cagtatacct tcaacaatat 2401  acttttgaca cacacaaacc tttgatttgg tttcagagat tttgcaaaat agtaccaatg 2461  taatttacaa ctgtcatctt tgaaattgtg taaagtgga ataattttct gaagaaataa 2521  atcatggttt gtcaatgagt tgcagagact gtctgacatt aactttgtca agattaaagg 2581  ataaagtata tgacaatttg tttcatcatg ctcatgacat tatgcaattt tctccctagc 2641  ttttaatttt tggaggcaga aaattgagcc agaattttt agtcattagg tctcctagca 2701  acaagctgta aaccttccaa caagcttgga ctagaatcta gacactgaaa tgcacataca 2761  tgctttatgt aatgcagaat gcatttattg gagaactcat aaacatccta taaaattttc 2821  ttccctgaga tgcaactata aaacttggcc ttattctgag aatgcttaac atagatttca 2881  tccatactgt aacactgatt ttgttgttgt tgtccttaaa gcagctcagc ttcctgaggt 2941  agtgttatgt ctctgtggca acaaggtgaa aatgtctagc ttattttgtc aaagtcaaca 3001  ataatccaca gactccagac ctcaatatct gtcccaattt gccattttac tttagtgctc 3061  caaaaatatg gcttatagaa aaacaatag gtgtttttaaa gagatttacc tgaatgatat 3121  agagaatgtc tagatatttt ctggctatca ggtaaaacct acccttcaag atggtagaat 3181  atataatagc atacaaaacc tctatttacc taataagtac tttaatttac agaaaaaaaa 3241  tgtaaatgta agtgtcggat ttagtgccaa gtgcagggaa tctgaaaaat gtatactagg 3301  tctctgctct ccgtaattct gccttcatgg gtcctagccc catccctcag gaggttgtcc 3361  taagatcgtc agtgtcagat gcttcacaat acggcctcac accgtccctg gaaaggttg 3421  gtctcctcct gctgcatcag atggatgatt tcattgtaca tacggtgagg agcatccaaa 3481  ccccagatga aatccacgtg agcccattca ggaatattct tatggtagat gaggttggtc 3541  acctcagaga gcagcatttt cacgtcttct ggatttgaaa gccagtcctg acctcctgtc 3601  cacattgctg tagggaccgt catatctctg actctgtacc ttacaggagt tggctagaga 3661  aaaggaatag ttcttaactc taggtaacat ttggactttc aggctcataa tttatgtttc 3721  aaatagacat aataaacatg ccatctgttg tggtgaaggg tacatgggtg ttagagccac 3781  acaactctgt taagaatttc tgttcccgcc cttactttaa ggtaaaatta cttaacatta
```

```
3841 ttgaacctca gtttcttctt ctgtgactgg ggataatatc tgtaataact tgctagatca 3901 aatgacaaaa cacataaaaa catgtaatgc cttgtatttc ttttttcttc ctattaaata 3961 ttttgtaaat aaattgtttt taaaaaaaaa aaa
```

C1 ABCF2-ATP-binding cassette, sub-family F (GCN20), member 2 mRNA
NM_005692.4
(SEQ ID NO: 156)

```
   1 ggcgtcacgc ggccccgcga ggtctgtggg atacatagta gtcctcaagg cgggtctcac 61 tcttggccgc tgcaacttga ggactacact tccaaggagg cagcgcggcg cgccgagaac 121 cacccgaggc cgtgattggc tggtgagccg gccgcacgcg gaggatccta aggagcagct 181 ctgttgcgac ataggccgag cagcgaggcc cagctccctg aaacaacagt aacctacccc 241 tgtgggtcat catcatgccc tccgacctgg ccaagaagaa ggcagccaaa agaaggagg 301 ctgccaaagc tcgacagcgg cccagaaaag acatgaaga aaatggagat gttgtcacag 361 aaccacaggt ggcagagaag aatgaggcca atggcagaga gaccacagaa gtagatttgc 421 tgaccaagga gctagaggac tttgagatga agaaagctgc tgctcgagct gtcactggcg 481 tcctggcctc tcaccccaac agtactgatg ttcacatcat caacctctca cttacctttc 541 atggtcaaga gctgctcagt gacaccaaac tggaattaaa ctcaggccgt cgttatggcc 601 tcattggttt aaatggaatt ggaaagtcca tgctgctctc tgctattggg aagcgtgaag 661 tgcccatccc tgagcacatc gacatctacc atctgactcg agagatgccc cctagtgaca 721 agacacccct tgcattgtgtg atggaagtcg acacagagcg ggccatgctg gagaaagagg 781 cagagcggct ggctcatgag gatgcggagt gtgagaagct catggagctc tacgagcgcc 841 tggaggagct ggatgccgac aaggcagaga tgagggcctc gcggatcttg catggactgg 901 gtttcacacc tgccatgcag cgcaagaagc taaagacttc cagtgggggc tggaggatga 961 gggttgccct tgccagagcc ctctttattc ggcccttcat gctgctcctg gatgagccta 1021 ccaaccacct ggacctagat gcttgcgtgt ggttggaaga agaactaaaa acttttaagc 1081 gcatcttggt cctcgtctcc cattcccagg attttctgaa tggtgtctgt accaatatca 1141 ttcacatgca caacaagaaa ctgaagtatt atacgggtaa ttatgatcag tacgtgaaga 1201 cgcggctaga gctggaggag aaccagatga agaggtttca ctgggagcaa gatcagattg 1261 cacacatgaa gaactacatt gcgaggtttg gtcatggcag tgccaagctg gcccggcagg 1321 cccagagcaa ggagaagacg ctacagaaaa tgatggcatc aggactgaca gagagggtcg 1381 tgagcgataa gacactgtca tttttatttcc caccatgtgg caagatccct ccacctgtca 1441 ttatggtgca aaatgtgagc ttcaagtata caaagatgg gccttgcatc tacaataatc 1501 tagaatttgg aattgacctt gacacacgag tggctctggt agggcccaat ggagcaggga 1561 agtcaactct tctgaagctg ctaactggag agctactacc cacagatggc atgatccgaa 1621 aacactctca tgtcaagata gggcgttacc atcagcattt acaagagcag ctggacttag 1681 atctctcacc tttggagtac atgatgaagt gctacccaga gatcaaggag aaggaagaaa 1741 tgaggaagat cattgggcga tacggtctca ctgggaaaca acaggtgagc ccaatccgga 1801 acttgtcaga cggcagaag tgccgagtgt gtctggcctg gctggcctgg cagaaccccc 1861 acatgctctt cctggatgaa cccaccaatc acctggatat cgagaccatc gacgccctgg 1921 cagatgccat caatgagttt gagggtggta tgatgctggt cagccatgac ttcagactca 1981 ttcagcaggt tgcacaggaa atttgggtct gtgagaagca gacaatcacc aagtggcctg 2041 gagacatcct ggcttacaag gagcacctca gtccaagct ggtggatgag gagcccagc 2101 tcaccaagag gacccacaac gtgtgcaccc tgacattggc atctctgcca aggccatgag
```

-continued

```
2161  catcatgaac tcgtttgtaa acgacgtgtt tgagcagctg gcgtgtgagg ctgcccggct
2221  ggcccagtac tcgggccgga ccaccctgac atcccgagaa gtccagacgg ctgtgcgtct
2281  gctgctgcct ggggagctgg ccaagcacgc tgtgtctgag ggcaccaagg ctgtcaccaa
2341  gtacaccagc tccaagtgac ccagggcctg acaaaaataa agggtgaact gttaaaaaaa
2401  aaaaa
```

C2 FNBP1L formin binding protein 1-like, mRNA NM_0010249482
(SEQ ID NO: 157)

```
   1  tcactcactg gggagcccgg cggtggcggc acctttcgag gtagacccgc tgagctgcta
  61  gcccgccggc cagcgagtga gaggtcggac agactgtgga gccgacagac tgaaggacag
 121  cggcaccgcc agacggccag aaagttccgc catgagctgg ggcacggagc tgtgggatca
 181  gttcgacagc ttagacaagc atacacaatg gggaattgac ttcttggaaa gatatgccaa
 241  atttgttaaa gagaggatag aaattgaaca gaactatgcg aaacaattga gaaatctggt
 301  taagaagtac tgccccaaac gttcatccaa agatgaagag ccacggttta cctcgtgtgt
 361  agcctttttt aatatcctta atgagttaaa tgactatgca ggacagcgag aagttgtagc
 421  agaagaaatg gcgcacagag tgtatggtga attaatgaga tatgctcatg atctgaaaac
 481  tgaaagaaaa atgcatctgc aagaaggacg aaaagctcaa caatatcttg acatgtgctg
 541  gaaacagatg gataatagta aaagaagtt tgaaagagaa tgtagagagg cagaaaaggc
 601  acaacagagt tatgaaagat tggataatga tactaatgca accaaggcag atgttgaaaa
 661  ggccaaacag cagttgaatc tgcgtacgca tatggccgat gaaaataaaa atgaatatgc
 721  tgcacaatta caaaacttta atggagaaca acataaacat ttttatgtag tgattcctca
 781  gatttacaag caactacaag aaatggacga acgaaggact attaaactca gtgagtgtta
 841  cagaggattt gctgactcag aacgcaaagt tattcccatc atttcaaaat gtttggaagg
 901  aatgattctt gcagcaaaat cagttgatga agaagagac tctcaaatgg tggtagactc
 961  cttcaaatct ggttttgaac ctccaggaga ctttccattt gaagattaca gtcaacatat
1021  atatagaacc atttctgatg ggactatcag tgcatccaaa caggagagtg ggaagatgga
1081  tgccaaaacc acagtaggaa aggccaaggg caaattgtgg ctctttggaa agaagccaaa
1141  gggcccagca ctagaagatt tcagtcatct gccaccagaa cagagacgta aaaaactaca
1201  gcagcgcatt gatgaactta acagagaact acagaaagaa tcagaccaaa aagatgcact
1261  caacaaaatg aaagatgtat atgagaagaa tccacaaatg ggggatccag ggagtttgca
1321  gcctaaatta gcagagacca tgaataacat tgaccgccta cgaatggaaa tccataagaa
1381  tgaggcttgg ctctctgaag tcgaaggcaa acaggtggg agaggagaca gaagacatag
1441  cagtgacata aatcatcttg taacacaggg acgagaaagt cctgagggaa gttacactga
1501  tgatgcaaac caggaagtcc gtgggccacc ccagcagcat ggtcaccaca atgagtttga
1561  tgatgaattt gaggatgatg atcccttgcc tgctattgga cactgcaaag ctatctaccc
1621  ttttgatgga cataatgaag gtactctagc aatgaaagaa ggtgaagttc tctacattat
1681  agaggaggac aaaggtgacg gatggacaag agctcggaga cagaacggtg aagaaggcta
1741  cgttcccacg tcatacatag atgtaactct agagaaaaac agtaaaggtg cagtaactta
1801  tatctaaact aaccaggcac ctttgtgcca tgtgtgacat aggaagagta acataaaatg
1861  aaaacacatt caacaggttg aaaaaaataa ggaaacttaa agggcatcca agattaattg
1921  ttcactatgt gagctgagtg taggcttgat cttgtgaata ttaccacaag aaacatttg
1981  tggcacttta ctgtttgagt aacgttggtg tgaagcttaa ttgatgcctt ttgctttatg
2041  tcccgcttaa gtctgtgtga aggatttgtg ttttctgcc ttacaaatag aatttgattt
```

-continued

```
2101  attgggcagg aattcatgga tagtaatgct ctctgccccc tttacttcag aaaacacagt
2161  gactttagtg aatttgaata gtgaaactgc tctgaaatgc tatggaaagc cgactcccca
2221  aagagtggtt tcttctagaa gtttgaattt gtagctacag tttccaagaa gaaaaatagt
2281  agttggataa tttagtaaaa taataacatc attttcattt tcttacctat tcttaacttt
2341  ggtttcctaa aggaagaaaa tgagcaggta gcacataatc tatttaagta gatttaaaga
2401  gagtttcaaa ataaatctcc tggtctagct cttaggtgaa taaaatagat tttgtttgag
2461  acctcaaaat attttgaggt tagctggtaa ttttcaataa tttacaagct tccttccaaa
2521  ctaatctcat acttttgtat gtttcatctt gaaatatct tttgggaaat accactttag
2581  tgattattta gcatttagca gttacacata ggaaaataca cagttacata gaaaaataca
2641  catttgaaga tagaggaaac cttgaatgga ggggaagtgt tgacaaattt taatttttaa
2701  aggagaaact ttttgactat ctgggttaga ggaagatatg tgtaccgcct ttagggcatt
2761  ttgttatttc cgctgaatca ttagttatta ggatagataa attttttccaa ttagtttcag
2821  caagcgttgt tggaaacact gtgcagtcaa ggattgtgca gtgctggttg tgtgaccaca
2881  ccctgagtca gtggtgtggg gaagtaaagt gtgaagaagc agtaagattg gttttttaatt
2941  ttgcccatgt tttaaattt cctggtgttt tcggtagctg actataaaat gatagagaca
3001  tttgggacag gcactttaaa ctgaacaccc cttttggttt taccaaaggt cttcagtaat
3061  tgttcttttc tttttcctcc tggactgcag gttcctgaag agggtttctg aggaaatggg
3121  caagatgttg aaggaggtta catgcagctg cttttggggg agggtattag agttgtcagg
3181  ctcaaagaga gtgagagaag caagttgcat gagtgcatgc agacatgatt ttttttttac
3241  taacttcatt agcatttcca tacattgttt ttaaaaatca taataccaac ccttaagttc
3301  ctagttcaca gttattccca caaagaaaa agccaacaat agtgtaccat ttttctattt
3361  attttattgc tgtctaatca ataaagaatg cagagctgtc aaaaaatgtg tcttacatta
3421  gctgtcccaa caggattgtc ttccctccca gctctgtttt aattggcttt tagacccact
3481  atctgtcaga tccttgccat ctgtcagtgt ctgcctgcgc cacctccgtg cttgcttaac
3541  atcctgttgc atgtctagcg tgattgagct agattttca ggcatgtctt tagattccct
3601  tgttcttgtc aaagccttgt tttgttttac atttgtagtg caaatcactt tgtcaaacat
3661  ctccagcact aatgtttcca tcttagtatt tgtgcacact gctataactt ccccactgca
3721  aacattccag ttttggcatt acgaagaagt agctgtgaac ctgaagtatt tatgataaga
3781  aaaagaaaac atctctgctg tagcctacag cccagttgaa agaactcttt gaaacgtgat
3841  acatcttcag cacctcagtc tgggaagaat ctagtcagca ctgaaatcct ggcataataa
3901  acacagaaga tattcaccac ctcaagacaa aggactattg tcaaaagtca gctgcttcca
3961  ttcaaatgct gccttaaact tgagtgccta aatctgttga ttgccaacac taccactaca
4021  gtatcccaca aagggcttta tgtgtcagct cagtgcgacc tgctttaact ctgcagcacc
4081  gctgcagctg ccgatgtagc ctcggtaggt ggctattaga gctctaccat atacagtggt
4141  gcatcttcaa atttatgcat caaactaaag acatgtccaa gtccatttta atttcctcag
4201  tggttttatg agaagttta tgggcctccc ccaattgtct ttttattttg ggttatgacg
4261  atcatgtttg ataattacaa tgatagtctc tttccacgtg atgctttgt ttgaacctga
4321  taaaatttag tgaaactttg taatgatcta tgtgcacttt tacttgtaaa atggaatttc
4381  tgtatgttta tacttgtaaa tatgattgtt gttagtgctc ctgttgctca tggtgtcctg
4441  cctcgcattt gtgattctgt taatgacatg tatcttaact aatttcttag tggtgttgta
```

```
-continued
4501  atagggagat ggggcaggtg gggggttatt tgtaccactg aatcttcatt aatttggttc 4561  tttactgttt tgaggggaga agaacgtga aatggtttgt gtattattga attttaagca 4621  atattttaga agctgtgtga ctgcttaat aacttttcc cagtgttatt tgaatcatac 4681  tacccgttat actaaagctg aatgacaatt gtgtgaaagt tactgccttc ataagatcaa 4741  gtcaccactg ttacacagct gacatatagt gtattacctt tgcagctagt aaactataaa 4801  gtttagatat tgaatctcgt tacaggggta tttatataat gtgacattat tcagtactga 4861  cagactacat gaagtagttt taaaatctag tgctatttt atttaaagg ttagcaatga 4921  ggaggaaatg tgatctggct gtgtttgtct tctgtacaaa gcctgaagtg cttatggttt 4981  tttggctaac agccacagag ggcaaagttt aagactttct tgtaaggact aactgttctt 5041  ttcaagctac tgtttgtttt tctaaaagca ggatttgctt ccgtaggagg caagttcctt 5101  gatgtggaat agtgcaacct gtatatgggt tattataata ggaaagacat ttgtacttgc 5161  acagtttaaa tcattcttaa attttgaaca tgtgaattgt cccaaaaaat ctttaatttt 5221  ttggtaattt ttactcttt tgtgcacatg ttgattcctt aatggtaaat ccttcattta 5281  aagatagtgt tctctgttga gaatattac atggaataaa acaatctttt catggcctgt 5341  taaaaaaaa aaaaaaaaa aaaaaaaaa a
```

C3 NCF1C neutrophil cytosolic factor 1C pseudogene, mRNA NR_0031872

(SEQ ID NO: 158)
```
   1  agtgcattta aggcgcagcc tggaagtgcc agggagcact ggaggccacc cagtcatggg 61  ggacaccttc atccgtcaca tcgccctgct gggctttgag aagcgcttcg tacccagcca 121  gcactatgta catgttcctg gtgaaatggc aggacctgtc ggagaaggtg gtctaccggc 181  gcttcaccga gatctacgag ttccataaaa ccttaaaaga aatgttccct attgaggcag 241  gggcgatcaa tccagagaac aggatcatcc cccacctccc agctcccaag tggtttgacg 301  ggcagcgggc cgccgagaac caccagggca cacttaccga gtactgcagc acgctcatga 361  gcctgcccac caagatctcc cgctgtcccc acctcctcga cttcttcaag gtgcgccctg 421  atgacctcaa gctccccacg gacaaccaga caaaaaagcc agagacatac ttgatgccca 481  aagatggcaa gagtaccgcg acagacatca ccggcccccat catcctgcag acgtaccgcg 541  ccattgccga ctacgagaag acctcgggct ccgagatggc tctgtccacg ggggacgtgg 601  tggaggtcgt ggagaagagc gagagcggtt ggtggttctg tcagatgaaa gcaaagcgag 661  gctggatccc agcatccttc ctcgagcccc tggacagtcc tgacgagacg gaagaccctg 721  agcccaacta tgcaggtgag ccatacgtcg ccatcaaggc ctacactgct gtgaggggg 781  acgaggtgtc cctgctcgag ggtgaagctg ttgaggtcat tcacaagctc ctggacggct 841  ggtgggtcat caggaaagac gacgtcacag gctactttcc gtccatgtac ctgcaaaagt 901  cggggcaaga cgtgtcccag gcccaacgcc agatcaagcg ggggggcgccg ccccgcaggt 961  cgtccatccg caacgcgcac agcatccatc agcggtcgcg gaagcgcctc agccaggacg 1021  cctatcgccg caacagcgtc cgttttctgc agcagcgacg ccgccaggcg cggccgggac 1081  cgcagagccc cgggagcccc ctcgaggagg agcggcagac gcagcgctct aaaccgcagc 1141  cggcggtgcc cccgcggccg agcgccgacc tcatcctgaa ccgctgcagc gagagcacca 1201  agcggaagct ggcgtctgcc gtctgaggct ggagcgcagt ccccagctag cgtctcggcc 1261  cttccgcccc cgtgcctgta catacgtgtt ctatagagcc tggcgtctgg acgccgaggg 1321  cagccccgac ccctgtccag cgcggctccc gccaccctca ataaatgttg cttggagtgg 1381  accgaggctc tgcaggaatg cagggagggc cggctccgc cccagggtta tttctaagtt 1441  gaaaaaaaaa aaaaaaaaa
```

-continued

C4 TBC1D3B TBC1 domain family, member 3B, mRNA NM_001001417.5
(SEQ ID NO: 159)

```
   1 actggtgctt agcacctatc tgctctctgg cctgcgtcag tggtctacag cagttacaca
  61 caggcagtgg tatctgtgag cagctctgtg gactcaaagg ttttctccct gagaggcatg
 121 acccaggcca gctgattcat cagaatcagg atggacgtgg tagaggtcgc gggtagttgg
 181 tgggcacaag agcgagagga catcattatg aaatacgaaa agggacaccg agctgggctg
 241 ccagaggaca aggggcctaa gccttttcga agctacaaca caacgtcga tcatttgggg
 301 attgtacatg agacggagct gcctcctctg actgcgcggg aggcgaagca aattcggcgg
 361 gagatcagcc gaaagagcaa gtgggtggat atgctgggag actgggagaa atacaaaagc
 421 agcagaaagc tcatagatcg agcgtacaag ggaatgccca tgaacatccg ggcccgatg
 481 tggtcagtcc tcctgaacat tgaggaaatg aagttgaaaa accccggaag ataccagatc
 541 atgaaggaga agggcaagag gtcatctgag cacatccagc gcatcgaccg ggacataagc
 601 gggacattaa ggaagcatat gttcttcagg gatcgatacg gaaccaagca gcgggaacta
 661 ctccacatcc tcctggcata tgaggagtat aacccggagg tgggctactg cagggacctg
 721 agccacatcg ccgccttgtt cctcctctat tttcctgagg aggatgcatt ctgggcactg
 781 gtgcagctgc tggccagtga gaggcactcc ctgcagggat tcacagccc aaatggcggg
 841 accgtccagg ggctccaaga ccaacaggag catgtggtag ccacgtcaca atccaagacc
 901 atgggcatc aggacaagaa agatctatgt gggcagtgtt cccgttagg ctgcctcatc
 961 cggatattga ttgacgggat ctctctcggg ctcaccctgc gcctgtggga cgtgtatctg
1021 gtagaaggcg aacaggcgtt gatgccgata caagaatcg cctttaaggt tcagcagaag
1081 cgcctcacga agacgtccag gtgtggcccg tgggcacgtt tttgcaaccg gttcgttgat
1141 acctgggcca gggatgagga cactgtgctc aagcatctta gggcctctat gaagaaacta
1201 acaagaaagc agggggacct gccaccccca gccaaacccg agcaagggtc gtcggcatcc
1261 aggcctgtgc cggcttcacg tggcgggaag accctctgca aggggacag gcaggcccct
1321 ccaggcccac cagcccggtt cccgcggccc atttggtcag cttccccgcc acgggcacct
1381 cgttcttcca caccctgtcc tggtggggct gtccgggaag acacctaccc tgtgggcact
1441 cagggtgtgc ccagcccggc cctggctcag ggaggacctc agggttcctg gagattcctg
1501 cagtggaact ccatgccccg cctcccaacg gacctggacg tagagggccc ttggttccgc
1561 cattatgatt tcagacagag ctgctgggtc cgtgccatat cccaggagga ccagctggcc
1621 ccctgctggc aggctgaaca ccctgcggag cgggtgagat cggctttcgc tgcacccagc
1681 actgattccg accagggcac cccttcaga gctagggacg aacagcagta tgctcccacc
1741 tcagggcctt gcctctgcgg cctccacttg gaaagttctc agttccctcc aggcttctag
1801 aagcatctgg gccagggctc atggctggat aatttcccta ggcttaacaa cccaagcaag
1861 cttcgcgtcc tcgttttatt tttggttaaa cttatgaaaa tgtattaaga aagagtgcag
1921 ctcgagagag attcagagat ggaacacacc agacccaga tcacaaagcc aaccatgccc
1981 agccctccc agcacccca gcccacgac catcgttctg aatttctacg acaccgtgag
2041 cctgcctttg tactttaaac tcatggaagg ataactacct tcacgttttg aaataaatgt
2101 ttcctgttga aatg
```

C5 SLC14A1 solute carrie family 14 (urea transporter), member 1, mRNA NM_001128588.3
(SEQ ID NO: 160)

```
   1 acacagagca gagtggggct ctgagtatat aactgttagg tgcctccctc cagcaccatc
  61 tcctgagaag cactctccct tgtcgtggag gtgggcaaat ctttatcagc cactgccttc
```

```
 121   tgctgccagg aagccagcta gagtggtctt taaagaaaac tgggcatctc ctgctactta
 181   aaatcaaaaa ctacctaaaa taaagattat aaaaaagtaa ggatgaatgg acggtctttg
 241   attggcggcg ctggtgacgc ccgtcatggt cctgtttgga aggaccctt  tggaactaaa
 301   gctggtgacg cagcgcgcag aggcatcgcc cggctaagct tggccctggc agatgggtcg
 361   caggaacagg agccagagga agagatagcc atggaggaca gccccactat ggttagagtg
 421   gacagcccca ctatggttag gggtgaaaac caggtttcgc catgtcaagg gagaaggtgc
 481   ttccccaaag ctcttggcta tgtcaccggt gacatgaaag aacttgccaa ccagcttaaa
 541   gacaaacccg tggtgctcca gttcattgac tggattctcc ggggcatatc ccaagtggtg
 601   ttcgtcaaca accccgtcag tggaatcctg attctggtag acttcttgt  tcagaacccc
 661   tggtgggctc tcactggctg gctgggaaca gtggtctcca ctctgatggc cctcttgctc
 721   agccaggaca ggtcattaat agcatctggg ctctatggct acaatgccac cctggtggga
 781   gtactcatgg ctgtcttttc ggacaaggga gactatttct ggtggctgtt actccctgta
 841   tgtgctatgt ccatgacttg cccaattttc tcaagtgcat tgaattccat gctcagcaaa
 901   tgggacctcc ccgtcttcac cctcccttc  aacatggcgt tgtcaatgta cctttcagcc
 961   acaggacatt acaatccatt cttccagcc  aaactggtca tacctataac tacagctcca
1021   aatatctcct ggtctgacct cagtgccctg gagttgttga atctatacc  agtgggagtt
1081   ggtcagatct atggctgtga taatccatgg acaggggca  ttttcctggg agccatccta
1141   ctctcctccc cactcatgtg cctgcatgct gccataggat cattgctggg catagcagcg
1201   ggactcagtc tttcagcccc atttgaggac atctactttg gactctgggg tttcaacagc
1261   tctctggcct gcattgcaat gggaggaatg ttcatggcgc tcacctggca aacccacctc
1321   ctggctcttg gctgtgccct gttcacggcc tatcttggag tcggcatggc aaactttatg
1381   gctgaggttg gattgccagc ttgtacctgg cccttctgtt tggccacgct attgttcctc
1441   atcatgacca caaaaaattc caacatctac aagatgcccc tcagtaaagt tacttatcct
1501   gaagaaaacc gcatcttcta cctgcaagcc aagaaaagaa tggtggaaag cccttttgtga
1561   gaacaagccc catttgcagc catggtcacg agtcatttct gcctgactgc tccagctaac
1621   ttccagggtc tcagcaaact gctgttttc  acgagtatca actttcatac tgacgcgtct
1681   gtaatctgtt cttatgctca ttttgtattt tcctttcaac tccaggaata tccttgagca
1741   tatgagagtc acatccaggt gatgtgctct ggtatggaat tgaaacccc  aatggggcct
1801   tggcactaag actggaatgt atataaagtc aaagtgctcc aacagaagga ggaagtgaaa
1861   acaaactatt agtatttatt gatattcttg gtgtttagct ggctcgatga tgttaacagt
1921   attaaaaatt aaaccccata accaactaa  gccttatgga attcacagtc acaaaatcga
1981   agttaatcca gaattctgtg ataagcagct tggcttttt  tttaaatcaa tgcaagttac
2041   acattatagc cagaatctgt atcacagagg tgcaagctga cagcagagct cagtccccac
2101   ttcctgcaaa caatggcctg caccctatcc cttgtgtgtg tgacattctc tcatgggaca
2161   atgttggggt ttttcagact gacaggactg caagagggag aaaggaattt tgtcaatcaa
2221   aattattctg tattgcaact tttctcagag attgcaaagg attttttagg tagagattat
2281   ttttccttat gaaaatgat  ctgttttaaa tgagataaaa taggagaagt tcctggctta
2341   acctgttctt acatattaaa gaaaagttac ttactgtatt tatgaaatac tcagcttagg
2401   catttttact ttaaccccta aattgatttt gtaaatgcca caaatgcata gaattgttac
2461   caacctccaa agggctcttt aaaatcatat tttttattca tttgaggatg tcttataaag
```

-continued

```
2521 actgaaggca aaggtcagat tgcttacggg tgttattttt ataagttgtt gaattcctta 2581 atttaaaaaa gctcattatt ttttgcacac tcacaatatt ctctctcaga aatcaatggc 2641 atttgaacca ccaaaaagaa ataaagggct gagtgcggtg gctcacgcct gtaatcccag 2701 cactttgggg agcccaggcg ggcagattgc ttgaacccag gagttcaaga ccagcctggg 2761 cagcatggtg aaaccctgta tctacaaaaa atacaaaaat tagccaggca tggtggtggg 2821 tgcctgtagt tccagctact gggaggctg aggtgggaaa atgacttgag cccaggagga 2881 ggaggctgca gtgagctaag attgcaccac tgcactccaa cctgggcgac aagagtgaaa 2941 ctgtgtctct caaaaaaaaa aaaaacaaa caaaaacaaa aacaaaacaa aacaaaacaa 3001 aacaaaacag gtaaggattc ccctgttttc ctctctttaa ttttaaagtt atcagttccg 3061 taaagtctct gtaaccaaac atactgaaga cagcaacaga agtcacgttc agggactggc 3121 tcacacctgt aatcccagca ctttgggaga tggaggtaaa aggatctctt gagcccagga 3181 gttcaagacc agcttgggca acatagcaag actccatctc ttaaaaaata aaaatagtaa 3241 cattagccag gtgtagcagc acacatctgc agcagctact caggaggctg aggtggaaag 3301 atcgcttgtg cacagaagtt cgaggctgca gtgagctata tgatcatgtc actgcactcc 3361 agcctgtgtg accgagcaag accctatctc aaaaaaatta attaattaat taattaatta 3421 atttaaaaag gaagtcatgt tcatttactt tccacttcag tgtgtatcgt gtagtatttt 3481 ggaggttgga aagtgaaacg taggaatcct gaagattttt tccacttcta gtttgcagtg 3541 ctcagtgcac aatatacatt ttgctgaatg aataaacaga aatagggaag taaacctaca 3601 aatattttag ggagaagctc acttcttcct tttctcagga aaccaagcaa gcaaacatat 3661 cgttccaatt ttaaaaccca gtgaccaaag cctttggaac tatgaatttg caactgtcat 3721 aggtttatgg atattgctgt ggagaagctc aattttcagt gtttgaactg aacccttct 3781 tgttagggaa cgtgtgaaag aagaattgtg gggaaaaaa agcaagcata accaaagatc 3841 atcagcagtg aagaatctag gctgtggctg agagaaccag aggcctctaa aatggacccg 3901 agtcgatctt cagaacaggg atctaccatg caggagcttc ttgtgctcac acaaatctgt 3961 aaatgggaac attgtacatt gtcgaattta aatgatatta atttctcaa gctattttg 4021 ttactatttt cctaaaattg aatatttgca gggagcactt atactttttc ctaatgtctg 4081 tataacaaat ttctatgcaa gtacatgaat aaattatgct cacagctca
```

D1 CALCOCO2-calcium binding and coiled-coildomain 2 mRNA NM_001261390.1
(SEQ ID NO: 161)

```
  1 caggcgggac gggctctccc ttgggtgctt agcccccgccc ccgtcccact ctgcccctgtt 61 gctgtcgcgc cgctgctggt tgctgtccct ggacccctac catggaggag accatcaaag 121 atccccccac atcagctgtc ttgctggatc actgtcattt ctctcaggtc atctttaaca 181 gtgtggagaa gttctacatc cctggagggg acgtcacatg tcattatacc ttcacccagc 241 atttcatccc tcgtcgaaag gattggattg gcatctttag agcatttaaa tgtttccaag 301 acaaattgga acaagaacta ctcaaatgga ggagccaagg acagaaattg caggtggggt 361 ggaagacaac ccgtgagtat tacaccttca tgtgggttac tttgcccatt gacctaaaca 421 acaaatcagc taaacagcag gaagtccaat tcaaagctta ctacctgccc aaggatgatg 481 agtattacca gttctgctat gtggatgagg atggtgtggt ccggggagca agtattcctt 541 tccaattccg tccagaaaat gaggaagaca tcctggttgt taccactcag ggagaggtgg 601 aagagattga gcagcacaac aaggagcttt gcaaagaaaa ccaggagctg aaggacagct 661 gtatcagcct ccagaagcag aactcagaca tgcaggctga gctccaaaag aagcaggagg 721 agctagaaac cctacagagc atcaataaga agttggaact gaaagtgaaa gaacagaagg
```

-continued

```
 781 actattggga gacagagctg cttcaactga agaacaaaa ccagaagatg tcctcagaaa
 841 atgagaagat gggaatcaga gtggatcagc ttcaggccca gctgtcaact caagagaaag
 901 aaatggagaa gcttgttcag ggagatcaag ataagacaga gcagttagag cagctgaaaa
 961 aggaaaatga ccacctcttt ctcagtttaa ctgaacagag gaaggaccag aagaagctcg
1021 agcagacagt ggagcaaatg aagcagaatg aaactactgc aatgaagaaa caacaggaat
1081 taatggatga aaactttgac ctgtcaaaaa gactgagtga gaacgaaatt atatgtaatg
1141 ctctgcagag acagaaagag agattggaag gagaaaatga tcttttgaag agggagaaca
1201 gcagattgct cagttacatg ggtctgactt ttaattcttt gccgtatcaa gtacctactt
1261 cagatgaagg aggcgcaaga caaaatccag gacttgccta tggaaaccca tattctggta
1321 tccaagaaag ttcttccccc agcccgctct ccatcaagaa atgccctatc tgcaaagcag
1381 atgatatttg tgatcacacc ttggagcaac agcagatgca gccccttttgt ttcaattgtc
1441 caatttgtga caagatcttc ccagctacag agaagcagat cttgaagac cacgtgttct
1501 gccactctct ctgagtatcc caacctcttg gatgtataca gagattttat agaatagaac
1561 ctatagcttc taccatgagt tatatgagtc aagatcctgc ctaacctgaa attattaggg
1621 atttactcag ccctgctgcc gctaacagtg gagttatgtc actgatctga aggtcactgt
1681 taagggcttc tgctgccatc cttgtgggtt gctacccttta agtcgcataa ctctagctgt
1741 atcatcctct cacctgtcat tcttctgagg gtctcagtac aagggccctg ggatggagcc
1801 aacctgggta ttcacaacag gcctgacttg atactaagtg attagttttc caagttgtcc
1861 cactgccatt caaagtcagc ccttgagtgt atttgttctc agtcctaacc ctggggccag
1921 agattggtcc gaggttgaga attccttcct cctcatcctt ggtgttgctt tctccaaatg
1981 attgttttag actagccaaa aatgccgtgg caaagagctc agaaatccaa tttggatacc
2041 aaaggtttct catgttaatt tctcagcccc caagaagca tcttactcct gaaccttaga
2101 caggaagtat tgtttcagtc acagaaagct tttctgggta cctctggtta gcactttcta
2161 ctctctgata tttcctatgt acatagcttt tattgttgta atcctttct taatggttaa
2221 ataggattgt tagcaactat gggttttgcag ttttctgagt aggtgagttt tgaatatggg
2281 taaatcagaa taatgagaca acttgttaat ctctttaata ctaaaaataa attactcttc
2341 tatttcaggg acttaggtaa tttaaaataa accttcaatt tatggtcttc tgttttgaag
2401 ctcatgggaa aattgtgatc aaaagggcta tgggaagggc agaccccgcc aatgatttct
2461 cttcacctgt cttaagatta aataaaaaag agtgtcctgg cagttatctt gaggtgggga
2521 aggaggtgat gaaacattag tttgtgaaat ccaaggccct ggcttgcttt ctttcttttt
2581 tttttttttt ttttgaaaca gtctctctct gtcacccagg ctggcgtgca atggcgcagt
2641 tgactcacta cagcctctgc ctcccaggtt caagcgattc tcatgcctta gcctcccaag
2701 tagctgggat tacaggtgtg tgccgcaatg cccagctaat ttttgtgttt tagtagaga
2761 cagggtttca ctatgttggc caggctggtc tcgaactcct ggcctcacgt gatctgtcca
2821 cttcagccgt ccaaagtgct gggattacaa gcgtgagcca ctgtgctggg cccgaggccc
2881 tgacttcttg ctgtaacttt ccatgcattt tttttaaaag gagcagtgtg gattttcgca
2941 ccctttgtga actaagttca atgcgctcta tccaaatttg cctaattgaa ctataagaaa
3001 gtaataattc catttctat cccctcaggg actgaacaaa tggaaataac tcccaggcag
3061 tatcaggtgg tcactacaga gacttccaca aaaactttg aatgatgtga aacacgatgt
3121 catgaataag ggttgagcca actatagctc tgtgttccta ctgggctttc cctaatgtgg
```

-continued

```
3181 ttgggagtta tgccctagac taactgtatt gtcctagtca cagctccttg ctttgatttc 3241 atccttgata aaatgaagat gaaacttaca ctacttctcc aagccttttg ctgtcttaag 3301 aataagacct gagattaaca ctaaccctag aatagaaatg taatagggag atggtaataa 3361 aggagttttt ctggcacata ccctccctac agaatttctg ttgctcccca gatccagtga 3421 agaattgcag tttcatttat tttgtaccag tcagctctta attaagtaca tgaatggaga 3481 ggaacagtgg tgcacataat ccaaatcagt gaataccatt ttctggtgaa ttacccaccc 3541 ctttgcccct gctacccgga gggttaccat gattgtcaac agcagcagga gcccttccac 3601 agggcttggt aaaaaaacca gttgaggtgt taatgaccct ttttgctggg tgtaaaacaa 3661 agcatcttta accactgttc attatcccca gctgctctta ccaaggcttt gaagggggaa 3721 attatgctct aggcagccac tagtagtaaa caat
```

D2 GTF2B-general transcription factor IIB mRNA NM_001514.5

(SEQ ID NO: 162)

```
   1 acgactgcgt gggtgagtcg tctataaaaa ctcatctctg cgcgtctctt cgccacattc 61 gcttcctgct ttcggtgtgt ctgttgtgtc ttgttgcggg caccgcagtc gccgtgaaga 121 tggcgtctac cagccgtttg gatgctcttc caagagtcac atgtccaaac catccagatg 181 cgattttagt ggaggactac agagccggtg atatgatctg tcctgaatgt ggcttggttg 241 taggtgaccg ggttattgat gtgggatctg aatggcgaac tttcagcaat gacaaagcaa 301 caaaagatcc atctcgagtt ggagattctc agaatcctct tctgagtgat ggagatttgt 361 ctaccatgat tggcaagggc acaggagctg caagttttga cgaatttggc aattctaagt 421 accagaatcg gagaacaatg agcagttctg atcgggcaat gatgaatgca ttcaaagaaa 481 tcactaccat ggcagacaga atcaatctac ctcgaaatat agttgatcga caaataattt 541 tattcaagca agtatatgaa cagaagagcc tgaagggaag agctaatgat gctatagctt 601 ctgcttgtct ctatattgcc tgtagacaag aaggggttcc taggacattt aaagaaatat 661 gtgccgtatc acgaatttct aagaaagaaa ttggtcggtg ttttaaactt attttgaaag 721 cgctagaaac cagtgtggat ttgattacaa ctgggacttt catgtccagg ttctgttcca 781 accttttgtct tcctaaacaa gtacagatgg cagctacaca tatagcccgt aaagctgtgg 841 aattggactt ggttcctggg aggagcccca tctctgtggc agcggcagct atttacatgg 901 cctcacaggc atcagctgaa aagaggaccc aaaaagaaat tggagatatt gctggtgttg 961 ctgatgttac aatcagacag tcctatagac tgatctatcc tcgagcccca gatctgtttc 1021 ctacagactt caaatttgac accccagtgg acaaactacc acagctataa attgaggcag 1081 ctaacgtcaa attcttgaat acaaaacttt gcctgttgta catagcctat acaaaatgct 1141 gggttgagcc tttcatgagg aaaaacaaaa gacatggtac gcattccagg gctgaatact 1201 attgcttggc attctgtatg tatatactag tgaaacatat ttaatgattt aaatttctta 1261 tcaaatttct tttgtagcaa tctaggaaac tgtattttgg aagatatttg aaattatgta 1321 attcttgaat aaaacatttt tcaaaactca gttttttgtt atatgttaca tgtaacttat 1381 gatacataat tacaaataat gcaaatcatt gcagctaata aagctgatag actttatttc 1441 cattacttat atatacatag ttttttattt taataaattt atggaaagag caaaagcttt 1501 tgagaaccat tgttaacatc aacatcatag tttccagttt gaaaggatgt gtatgtgaga 1561 tttattatgt atattattaa acaagaagtg atgagcttgg gccttgaaag gcaccagctt 1621 gagagacatt aaaatgttct aagtaaaaaa a
```

-continued

D3 HLA-B-major histocompatibility complex, class I, B mRNA NM_005514.6

(SEQ ID NO: 163)

```
   1  agttctaaag tccccacgca cccaccggga ctcagagtct cctcagacgc cgagatgctg
  61  gtcatggcgc cccgaaccgt cctcctgctg ctctcggcgg ccctggccct gaccgagacc
 121  tgggcggct cccactccat gaggtatttc tacacctccg tgtcccggcc cggccgcggg
 181  gagccccgct tcatctcagt gggctacgtg gacgacaccc agttcgtgag gttcgacagc
 241  gacgccgcga gtccgagaga ggagccgcgg gcgccgtgga tagagcagga ggggccggag
 301  tattgggacc ggaacacaca gatctacaag gcccaggcac agactgaccg agagagcctg
 361  cggaacctgc gcggctacta caaccagagc gaggccgggt ctcacaccct ccagagcatg
 421  tacggctgcg acgtggggcc ggacgggcgc ctcctccgcg gcatgaccg gtacgcctac
 481  gacggcaagg attacatcgc cctgaacgag gacctgcgct cctggaccgc cgcggacacg
 541  gcggctcaga tcacccagcg caagtgggag gcggccgtg aggcggagca ggggagagcc
 601  tacctggagg gcgagtgcgt ggagtggctc cgcagatacc tggagaacgg gaaggacaag
 661  ctggagcgcg ctgacccccc aaagacacac gtgacccacc ccccatctc tgaccatgag
 721  gccaccctga ggtgctgggc cctgggtttc taccctgcgg agatcacact gacctggcag
 781  cgggatggcg aggaccaaac tcaggacact gagcttgtgg agaccagacc agcaggagat
 841  agaaccttcc agaagtgggc agctgtggtg gtgccttctg agaagagca gagatacaca
 901  tgccatgtac agcatgaggg ctgccgaag cccctcaccc tgagatggga gccgtcttcc
 961  cagtccaccg tccccatcgt gggcattgtt gctggcctgg ctgtcctagc agttgtggtc
1021  atcggagctg tggtcgctgc tgtgatgtgt aggaggaaga gttcaggtgg aaaaggaggg
1081  agctactctc aggctgcgtg cagcgacagt gcccagggct ctgatgtgtc tctcacagct
1141  tgaaaagcct gagacagctg tcttgtgagg gactgagatg caggatttct tcacgcctcc
1201  cctttgtgac ttcaagagcc tctggcatct ctttctgcaa aggcacctga atgtgtctgc
1261  gtccctgtta gcataatgtg aggaggtgga gagacagccc acccttgtgt ccactgtgac
1321  ccctgttccc atgctgacct gtgtttcctc cccagtcatc tttcttgttc cagagaggtg
1381  gggctggatg tctccatctc tgtctcaact ttacgtgcac tgagctgcaa cttcttactt
1441  ccctactgaa ataagaatc tgaatataaa tttgttttct caaatatttg ctatgagagg
1501  ttgatggatt aattaaataa gtcaattcct ggaatttgag agagcaaata aagacctgag
1561  aaccttccag aaaaaaaa
```

D4 HLA-F-major histocompatibility complex, class I, F mRNA
NM_001098479.1

(SEQ ID NO: 164)

```
   1  tttctcactc ccattgggcg tcgcgtttct agagaagcca atcagtgtcg ccgcagttcc
  61  caggttctaa agtcccacgc accccgcggg actcatattt ttcccagacg cggaggttgg
 121  ggtcatggcg ccccgaagcc tcctcctgct gctctcaggg gccctggccc tgaccgatac
 181  ttgggcggc tcccactcct tgaggtattt cagcaccgct gtgtcgcggc ccggccgcgg
 241  ggagccccgc tacatcgccg tggagtacgt agacgacacg caattcctgc ggttcgacag
 301  cgacgccgcg attccgagga tggagccgcg ggagccgtgg gtggagcaag aggggccgca
 361  gtattgggag tggaccacag ggtacgccaa ggccaacgca cagactgacc gagtggccct
 421  gaggaacctg ctccgccgct acaaccagag cgaggctggg tctcacaccc tccagggaat
 481  gaatggctgc gacatgggc ccgacggacg cctcctccgc gggtatcacc agcacgcgta
 541  cgacggcaag gattacatct ccctgaacga ggacctgcgc tcctggaccg cggcggacac
 601  cgtggctcag atcacccagc gcttctatga ggcagaggaa tatgcagagg agttcaggac
```

```
 661 ctacctggag ggcgagtgcc tggagttgct ccgcagatac ttggagaatg ggaaggagac 721 gctacagcgc gcagatcctc caaaggcaca cgttgcccac caccccatct ctgaccatga 781 ggccaccctg aggtgctggg ccctgggctt ctaccctgcg gagatcacgc tgacctggca 841 gcgggatggg gaggaacaga cccaggacac agagcttgtg gagaccaggc ctgcagggga 901 tggaaccttc cagaagtggg ccgctgtggt ggtgcctcct ggagaggaac agagatacac 961 atgccatgtg cagcacgagg ggctgcccca gccccctcatc ctgagatggg agcagtctcc 1021 ccagcccacc atccccatcg tgggcatcgt tgctggcctt gttgtccttg gagctgtggt 1081 cactggagct gtggtcgctg ctgtgatgtg gaggaagaag agctcagata gaaacagagg 1141 gagctactct caggctgcag cctactcagt ggtcagcgga aacttgatga taacatggtg 1201 gtcaagctta tttctcctgg gggtgctctt ccaaggatat ttgggctgcc tccggagtca 1261 cagtgtcttg ggccgccgga aggtgggtga catgtggatc ttgttttttt tgtggctgtg 1321 gacatctttc aacactgcct tcttggcctt gcaaagcctt cgctttggct tcggctttag 1381 gaggggcagg agcttccttc ttcgttcttg gcaccatctt atgaaaaggg tccagattaa 1441 gattttgac tgagtcattc taaagtaagt tgcaagaccc atgatactag accactaaat 1501 acttcatcac acacctccta agaataagaa ccaacattat cacaccaaag aaaataaata 1561 attccataat attaaaaaaa aaaaaaaaa a
```

D5 MGST2-microsomal glutathione S-transferase 2 mRNA NM_002413.4
(SEQ ID NO: 165)
```
   1 gctggccgtg ggagaggctt aaaacaaacg ccggaagcaa ctcccagccc cataaagatc 61 tgtgaccggc agcccagac ctgcctgcct tcctgacttc tgttccagag caaaggtcat 121 tcagccgctt gaatcagcct tttccccca cccggtcccc aactttgttt acccgataag 181 gaaggtcagc attcaaagtc aagaagcgcc atttatcttc ccgtgcgctc tacaaatagt 241 tccgtgagaa agatggccgg gaactcgatc ctgctggctg ctgtctctat tctctcggcc 301 tgtcagcaaa gttattttgc tttgcaagtt ggaaaggcaa gattaaaata caaagttacg 361 cccccagcag tcactgggtc accagagttt gagagagtat tcgggcaca acaaaactgt 421 gtggagtttt atcctatatt cataattaca ttgtggatgg ctgggtggta tttcaaccaa 481 gtttttgcta cttgtctggg tctggtgtac atatatggcc gtcacctata cttctgggga 541 tattcagaag ctgctaaaaa acggatcacc ggtttccgac tgagtctggg gattttggcc 601 ttgttgaccc tcctaggtgc cctgggaatt gcaaacagct ttctggatga atatctggac 661 ctcaatattg ccaagaaact gaggcggcaa ttctaacttt ttctcttccc tttaatgctt 721 gcagaagctg ttcccaccat gaaggtaata tggtatcatt tgttaaataa aaataaagtc 781 tttattctgt ttttcttgaa aaaaaaaaa aaaaaaa
```

D6 SPAST-spastin mRNA NM_014946.3
(SEQ ID NO: 166)
```
   1 ggcccgagcc accgactgca ggaggagaag gggttgtgct cctggccgag gaaggagaaa 61 ggggcgggc cggcgggcag cgtgcgcag tgcggagctc ctgagaccgg cgggcacacg 121 ggggtctgtg gccccgccg tagcagtggc tgccgccgtc gcttggttcc cgtcggtctg 181 cgggaggcgg gttatggcgg cggcggcagt gagagctgtg aatgaattct ccgggtggac 241 gagggaagaa gaaaggctcc ggcggcgcca gcaacccggt gcctcccagg cctccgcccc 301 cttgcctggc cccgcccct ccgccgccg gccggcccc tccgcccgag tgccgcata 361 agcggaacct gtactatttc tcctacccgc tgtttgtagg cttcgcgctg ctgcgtttgg 421 tcgccttcca cctggggctc ctcttcgtgt ggctctgcca gcgcttctcc cgcgccctca 481 tggcagccaa gaggagctcc ggggccgcgc cagcacctgc ctcggcctcg gcccgggcgc
```

-continued

```
 541   cggtgccggg cggcgaggcc gagcgcgtcc gagtcttcca caaacaggcc ttcgagtaca
 601   tctccattgc cctgcgcatc gatgaggatg agaaagcagg acagaaggag caagctgtgg
 661   aatggtataa gaaaggtatt gaagaactgg aaaaaggaat agctgttata gttacaggac
 721   aaggtgaaca gtgtgaaaga gctagacgcc ttcaagctaa aatgatgact aatttggtta
 781   tggccaagga ccgcttacaa cttctagaga agatgcaacc agttttgcca ttttccaagt
 841   cacaaacgga cgtctataat gacagtacta acttggcatg ccgcaatgga catctccagt
 901   cagaaagtgg agctgttcca aaaagaaaag acccccttaac acacactagt aattcactgc
 961   ctcgttcaaa aacagttatg aaaactggat ctgcaggcct ttcaggccac catagagcac
1021   ctagttacag tggtttatcc atggtttctg gagtgaaaca gggatctggt cctgctccta
1081   ccactcataa gggtactccg aaaacaaata ggacaaataa accttctacc cctacaactg
1141   ctactcgtaa gaaaaagac ttgaagaatt ttaggaatgt ggacagcaac cttgctaacc
1201   ttataatgaa tgaaattgtg gacaatggaa cagctgttaa atttgatgat atagctggtc
1261   aagacttggc aaaacaagca ttgcaagaaa ttgttattct tccttctctg aggcctgagt
1321   tgttcacagg gcttagagct cctgccagag ggctgttact ctttggtcca cctgggaatg
1381   ggaagacaat gctggctaaa gcagtagctg cagaatcgaa tgcaaccttc tttaatataa
1441   gtgctgcaag tttaacttca aaatacgtgg gagaaggaga gaaattggtg agggctcttt
1501   ttgctgtggc tcgagaactt caaccttcta aatttttat agatgaagtt gatagcctttt
1561   tgtgtgaaag aagagaaggg gagcacgatg ctagtagacg cctaaaaact gaatttctaa
1621   tagaatttga tggtgtacag tctgctggag atgacagagt acttgtaatg ggtgcaacta
1681   ataggccaca agagcttgat gaggctgttc tcaggcgttt catcaaacgg gtatatgtgt
1741   ctttaccaaa tgaggagaca agactacttt tgcttaaaaa tctgttatgt aaacaaggaa
1801   gtccattgac ccaaaaagaa ctagcacaac ttgctagaat gactgatgga tactcaggaa
1861   gtgacctaac agctttggca aaagatgcag cactgggtcc tatccgagaa ctaaaaccag
1921   aacaggtgaa gaatatgtct gccagtgaga tgagaaatat tcgattatct gacttcactg
1981   aatccttgaa aaaataaaa cgcagcgtca gccctcaaac tttagaagcg tacatacgtt
2041   ggaacaagga ctttggagat accactgttt aaggaaatac ctttgtaaac ctgcagaaca
2101   ttttacttaa aagaggaaac acaagatctt caatgaacgt catcggctac agaaacagcc
2161   taagtttaca ggacttttta gagtcttaca tatttgtgca ccaaacttga agatgaacca
2221   gaaaacagac ttaaacaaaa tatacaatgc aaatgtaatt ttttgttgtt taaggccttg
2281   ccttgatggt cacagttatc ccaatggaca ctaagttaga gcacaacaaa acctgattct
2341   ggtcttcttt accaatataa tcataatgta aataataatt tgtatattgt gttgcagatg
2401   aaagtattcc aggaacagtg aatggtagaa gacacaagaa catttgtttg tttgtcttct
2461   gatgtttttt cttaaaatag taatttctcc tacttttctt ttctactgtt gtcttaacta
2521   caggtgattg gaatgccaaa cactcttaag tttatttttct ttttttcgttt tataaattca
2581   gtgtgccaaa tgaaactttt ttcctaagta actgtaatag gaaaaagttt attttgagag
2641   tttcttcttc ataaatctac agacattaaa caattgttgt gttctttta ccttttattt
2701   ttctattacc ttgctaccaa acagtttaga tagcaatata atagcaaaaa agcaaatatg
2761   gtaaaataga gaaggtttga aggtttgagt tactctgtca tataacatgt agatcagtct
2821   tcatgtgacc tgcagtattt ttttttctaa tgtatttgtc agaaatctgt tgtagactgt
2881   taacttcttc ctgatggaat ttattttctg caagaattat tctgatattt aagagagcca
```

-continued

```
2941  attttaactg ctgtgaaaat gtttccagtg caagagaagg gaaatactag gaactaagac
3001  atttctaatt tattgcttat tactttctta atttacagg ataattataa gcaagtggaa
3061  ctaccatctt ttattcttaa taattattaa tcccttcaat gaaactttaa aaaaactgaa
3121  tttttataca tggcatacat ttttctagtt ccttctgctt gctttattaa ctcaaaagtt
3181  ctagttctag tctgttgatc tgccttttgt tctcccaaaa tgtacagtaa ttccatttgt
3241  ttgtataaat atgcctggat tttcattata aaaatgtcat tgtagggagt agagactcat
3301  atcatggcct tttaaatatt gtaataaagg caaatagata tttgccctta gtttactggt
3361  taaaagtttg tttacagaac ttttctctgg tgcttaaatg atgctatgta aaatgtcatg
3421  agtggaaaga atatttgtag tagtaacaag aattttttcat ttaggaaaga tttcttaggt
3481  tttgaaagaa tacattaaaa taaaaaactt gccctacta ggtaagaact ttataatgaa
3541  gacatacatt cttcttaatt ttactcttgc tcttgttaaa gatttgtttg aatatagaag
3601  atgcatgatt tctgggtttt ttttttttt tgagacagag tttcgctctt gttgcccagg
3661  ctggagtgca atggcgcaat ctcgactcac cacaacctcc gcctcccagg ttcaagcaat
3721  tctcctgcct cagcctcccg agtagctggg attacaggca tgcgccacta ccccagctaa
3781  ttttgtattt ttagtagaga tggggtttct ccatgttggt caggctggtc ttgaactcct
3841  gacctcaggt gatccgcctg cctcggcctc ccaaagtgct gggattacag gcataagcca
3901  ctgcgcccag ccagaagatg catgatttct taggatcata tgctgtttgt agccataagg
3961  taaatcatgt ctcttccaat catgactttg gaactccctg aataataaaa atgagagttg
4021  agataaatag gggaaaaaaa atttttttca agccagagct atgcatatgt taggtgatgg
4081  gtagtatccc tttaaggtct caaacattac aacatcaatt atgaaatact gataacgaaa
4141  ggtagtaatg aaatatatat gatgaaaaga attgagaagt tctaaattaa gacatttcag
4201  ttaagctcat aaaatttcat tgttttcatt taaaagatta acgttattga tacttggata
4261  actggctaat catattaaag gactatgtgg ttccagctca acttttaata tattgtctcc
4321  tttaaaacta tcatggttat aattctattg ggaaagactt ttagataaca aagatttcaa
4381  atgttaaaag agataaaagt caggttaata ctatcttaaa cactgagtca gaaaatcatt
4441  actgtataga agttgctttc ctgatcaagt ctgaacttca gctagtgcta gagaactatt
4501  ttctatgact taactctaac caagttttat tttaagctgt ttctttgata gaagggccat
4561  gaaaatagag taatgatata gtaggagata agggattggt ttggtctttt tcaataaaga
4621  tagaagttgc tgaagttttc tgaattaata atgacttaga ttgtgacctt ttagattcgg
4681  tgttgagctc tgtgttgtat tacttcctaa aagataatgc ttaaacatta agcattagtg
4741  tgctcttcat gttaatatgg cagagttttg taaactaaat taaaacttac tgatatattg
4801  gactttgagc caagggaaag aatgagtact atctttccag atatcttaag ggtaaaagct
4861  tattctaaga cagtctgtcc attgagaata ttagatttct gacttgcaaa tatgtttgta
4921  ctccagaaga attagaggaa aagcagatac tagaattcta atttaattac atatacagcc
4981  gtctttgttt atagtgtaga attctttata ttttgtacaa aaactaattc ttttggtaaa
5041  atgaaccatt tacagttcgg ttttggactc tgagtcaaag gattttcctt taaatgcttg
5101  tctcaatttt agtctggtct tttgtacttt tcttcagaag aaatgaatta aagggtacag
5161  ttgcataaag tgggttttta tcctaatgta ttggaaataa atgataaact ttaaaaaaaa
5221  a
```

-continued

D7 WAC-WW domain containing adaptor with coiled-coil mRNA NM_016628.4

(SEQ ID NO: 167)

```
   1 cgcccgccgc cgccgccgcc tgcgcgcccg cccgcctttc gcggccgctc tcccccctcc
  61 ccgacacaca ctcacaggcc gggcattgat ggtaatgtat gcgaggaaac agcagagact
 121 cagtgatggc tgtcacgacc ggagggggga ctcgcagcct taccaggcac ttaagtattc
 181 atcgaagagt caccccagta gcggtgatca cagacatgaa aagatgcgag acgccggaga
 241 tccttcacca ccaaataaaa tgttgcggag atctgatagt cctgaaaaca aatacagtga
 301 cagcacaggt cacagtaagg ccaaaaatgt gcatactcac agagttagag agagggatgg
 361 tgggaccagt tactctccac aagaaaattc acacaaccac agtgctcttc atagttcaaa
 421 ttcacattct tctaatccaa gcaataaccc aagcaaaact tcagatgcac cttatgattc
 481 tgcagatgac tggtctgagc atattagctc ttctgggaaa aagtactact acaattgtcg
 541 aacagaagtt tcacaatggg aaaaaccaaa agagtggctt gaaagagaac agagacaaaa
 601 agaagcaaac aagatggcag tcaacagctt cccaaaagat agggattaca aagagaggt
 661 gatgcaagca acagccacta gtgggtttgc cagtggaatg gaagacaagc attccagtga
 721 tgccagtagt ttgctcccac agaatatttt gtctcaaaca agcagacaca atgacagaga
 781 ctacagactg ccaagagcag agactcacag tagttctacg ccagtacagc accccatcaa
 841 accagtggtt catccaactg ctaccccaag cactgttcct tctagtccat ttacgctaca
 901 gtctgatcac cagccaaaga aatcatttga tgctaatgga gcatctactt tatcaaaact
 961 gcctacaccc acatcttctg tccctgcaca gaaaacagaa agaaaagaat ctacatcagg
1021 agacaaaccc gtatcacatt cttgcacaac tccttccacg tcttctgcct ctggactgaa
1081 ccccacatct gcacctccaa catctgcttc agcggtccct gtttctcctg ttccacagtc
1141 gccaatacct cccttacttc aggacccaaa tcttcttaga caattgcttc ctgctttgca
1201 agccacgctg cagcttaata attctaatgt ggacatatct aaaataaatg aagttcttac
1261 agcagctgtg acacaagcct cactgcagtc tataattcat aagtttctta ctgctggacc
1321 atctgctttc aacataacgt ctctgatttc tcaagctgct cagctctcta cacaagccca
1381 gccatctaat cagtctccga tgtcttaac atctgatgcg tcatcccaa gatcatatgt
1441 ttctccaaga ataagcacac ctcaaactaa cacagtccct atcaaacctt tgatcagtac
1501 tcctcctgtt tcatcacagc caaaggttag tactccagta gttaagcaag gaccagtgtc
1561 acagtcagcc acacagcagc ctgtaactgc tgacaagcag caaggtcatg aacctgtctc
1621 tcctcgaagt cttcagcgct caagtagcca gagaagtcca tcacctggtc ccaatcatac
1681 ttctaatagt agtaatgcat caaatgcaac agttgtacca cagaattctt ctgcccgatc
1741 cacgtgttca ttaacgcctg cactagcagc acacttcagt gaaaatctca taaaacacgt
1801 tcaaggatgg cctgcagatc atgcagagaa gcaggcatca agattacgcg aagaagcgca
1861 taacatggga actattcaca tgtccgaaat ttgtactgaa ttaaaaaatt taagatcttt
1921 agtccgagta tgtgaaattc aagcaacttt gcgagagcaa aggatactat ttttgagaca
1981 acaaattaag gaacttgaaa agctaaaaaa tcagaattcc ttcatggtgt gaagatgtga
2041 ataattgcac atggtttga gaacaggaac tgtaaatctg ttgcccaatc ttaacatttt
2101 tgagctgcat ttaagtagac tttggaccgt taagctgggc aaaggaaatg acaagggggac
2161 ggggtctgtg agagtcaatt caggggaaag atacaagatt gatttgtaaa acccttgaaa
2221 tgtagatttc ttgtagatgt atccttcacg ttgtaaatat gttttgtaga gtgaagccat
2281 gggaagccat gtgtaacaga gcttagacat ccaaaactaa tcaatgctga ggtggctaaa
2341 tacctagcct tttacatgta aacctgtctg caaaattagc ttttttaaaa aaaaaaaaa
```

-continued

```
2401  aaaaattggg ggggttaatt tatcattcag aaatcttgca ttttcaaaaa ttcagtgcaa
2461  gcgccaggcg atttgtgtct aaggatacga ttttgaacca tatgggcagt gtacaaaata
2521  tgaaacaact gtttccacac ttgcacctga tcaagagcag tgcttctcca tttgttttgc
2581  agagaaatgt ttttcatttc ccgtgtgttt ccatttcctt ctgaaattct gattttatcc
2641  atttttttaa ggctcctctt tatctccttt cttaaggcac tgttgctatg cacttttct
2701  ataaccttt cattcctgtg tacagtagct taaaattgca gtgattgagc ataacctact
2761  tgtttgtata aattattgaa atccatttgc accctgttaa gaatggactt aaaagtacta
2821  ctggacaggc atgtgtgctc aaagtacatt gattgctcaa atataaggaa atggcccaat
2881  gaacgtggtt gtgggagggg aaagaggaaa cagagctagt cagatgtgaa ttgtatctgt
2941  tgtaataaac atgttaaaac aaacaaaaat tgttatttt cttttccttc ggtcagtgca
3001  cattagcatt tgaactacct ggggattctt tatcagaact gttcttgttg aatatttata
3061  cttaattgaa ataattcctt aagggaggtt ttgtttaaaa cgtattaaca ggaaattgtg
3121  tatgagatat ttaatgaaat aagaaattca acaagaatga ttaagtcact tcccaagtgg
3181  ttgtcatttg ttaaaccctg gtttacctgt cttgctatta tgacatttca tttggaagga
3241  tgtttgtgtt gtagctaact gttcaagtct ggtgctgact gctgttctta gccatcacaa
3301  aacgctaaat ttgtgtaatt ggagcttcct gctgttatct ggaaatagca ggaaagcgca
3361  gctttgtata ttgttccta aagtatatta aaataaaaaa agaaactatt gctactataa
3421  aattaccttg actttttttt tcctttgctg aaatattagt cacatagcct tagcttcaca
3481  ctgccagtaa tgtatcaaat cacaagggtt tccgcatgaa aaaaatcttt tcttccccca
3541  caaaaaaacc tttaccatca aaatcttgcc atctgattta gaaggtgtt tcttcttctt
3601  cttcttttt ttctttaaat tggtttaggg ttttttggtg attttttttt tttttttt
3661  tctgttgggg cagataagtg cttccaaaac tggcagcacc aagggcttat ttttatgtt
3721  agacatcaat gtcaatgtta ctacattctc ggatgctaac ataaatttg aaattgctct
3781  tgtgctttaa gcatatattg aaagtatgga agttaaatgt tcaggctttt cagtaagctc
3841  aaaaagttaa ctgtaagcga tagtgttggt gttttctaaa atacaaaaat gttccagtgt
3901  aattaaaagg aattaaaatc ttgaagatat tttcctgtaa tttaaggata cttttttaaat
3961  gtaagaaaag acatgtcatt aatttattgt catgtttata cctctgtgag attgttaaca
4021  tctgctgaat ttaactagtg catgtaaatg aaaccccaaa gagctgtgtg ttcagctaga
4081  aaccttactg tatctttcct ggaaagaagt gagcaatttg ttgtaatagg caaatgtttc
4141  ctgatcagat ggcaatttgt gatttaggta aatttgaatt tgatttgctt atagtctact
4201  ggtctgtgta cctatgtttt gttttcaaa aaagtttaca tccctaaatg aattagtcac
4261  atatatttag gagaagatgc ctaatttggt atttcttaat agtgaatttt ttttttttctt
4321  gagacagagt ttcactcttg ttgcccaggc tggagtgcaa tggcacgatc tcggctcacc
4381  gcaacctctg cctcctgggt tcaagcgatt ctcctgcctc ggcgttccga gtagctggga
4441  ttacaggcat gcaccaccac gcctggctaa ttttgtattt ttagtagaga tggggtttct
4501  ccatgttggt caggctggtc ttgaactgcc aacttcaggt gatctgcctg ccttggcctc
4561  ccaaagtgct gggattacag gcgtgagcca ccgctcctgg ccagtagtga atttttaaac
4621  acagaaaatc taaaattttg tggaaatatt ttaaatattg cacctttaata caaggtatcc
4681  agctcctaac cttaactagg gaatatctat taaaataagc ataatgttct ggactagagt
4741  attccttatc tagttggtta tggatttgaa catgtacctt ggtttagata cttttgaaaat
```

```
4801  agaagtactg aatagcctct agggaacttg agtggccttt ccctccccct gccccccccc 4861  cccccccccc gttttaaaag atcagtagtc tctattcaaa cttttaaaat gtcgtggtat 4921  tgtaacaata tatttgatga aagaaggtta cagactcccc tgaagaacca gctttcctac 4981  gctttttatt tttctaactt gtctaacctg attttaaaat gactgcaatt ccagactaaa 5041  aacatgcttc agccctgttt caagacatta tgcttctttt aacagtccaa attagtagtt 5101  ttatttttct tctaaatctt gtttcacac ttgtaaaatc ttgggaagga ggttcttaaa 5161  actttgccag gaattgttac ccatttccaa aaacagttta ttatgttcaa aaaccaccat 5221  atctttgagg gactgtttga aaggggagag ggcaacgcgg gaaataattc actctgcgca 5281  ccggaactat tgtagttcag gacttccagc tactgtattt agatgttggg tttgaatata 5341  cagatttctt ttcaatacct gtaaatatgg ctatattctt gtatttgtac gggagtgtac 5401  aaaatgacac tgaaaagtaa taaatatgtt ttgactatat tgtgcagtta tttcagaact 5461  gtgttttgaa agtcttagaa tgcataattt gcatttgagt aaggaaattt aaaatacaga 5521  ttactgctga gatttta
```

The invention claimed is:

1. A kit for diagnosing tuberculosis in an individual based on determining the presence or amount of a sorting nexin 10 (SNX10) biomarker encoded by a nucleotide corresponding to SEQ ID NO:116 and an interferon-induced guanylate-binding protein-1 (GBP1) biomarker encoded by a nucleotide corresponding to SEQ ID NO:142 in a sample, wherein the kit comprises antibodies:
wherein the antibodies consist essentially of:
   (a) one or more antibodies specific for SNX10 biomarkers
   (b) one or more antibodies specific for GBP1 biomarkers;
   (c) one or more detectably labeled antibodies specific for the SNX10 biomarkers; and
   (d) one or more detectably labeled antibodies specific for the GBP1 biomarkers; and optionally
wherein the kit further comprises at least one internal standard.

2. The kit according to claim 1, wherein the one or more antibodies specific for SNX10 and/or the one or more antibodies specific for GBP1 is immobilized on an inert support.

3. The kit according to claim 1, wherein the sample is a blood sample, a purified peripheral blood leukocyte sample, a sputum sample, a saliva sample, or a urine sample.

4. A kit for diagnosing tuberculosis in an individual based on determining the presence or amount of the sorting nexin 10 (SNX10) biomarker encoded by a nucleotide corresponding to SEQ ID NO:116 and the interferon-induced guanylate-binding protein-1 (GBP1) biomarker encoded by a nucleotide corresponding to SEQ ID NO:142 in a sample, wherein the kit comprises oligonucleotides; wherein
said oligonucleotides consist essentially of:
   (a)(i) one or more oligonucleotides which hybridize under stringent conditions to a SNX10 nucleic acid sequence corresponding to SEQ ID NO:116;
   (a)(ii) one or more oligonucleotides which hybridize under stringent conditions to a GBP1 nucleic acid sequence corresponding to SEQ ID NO: 142;
   (b)(i) one or more oligonucleotides which are detectably labeled and which hybridize under stringent conditions to a SNX10 nucleic acid sequence corresponding to SEQ ID NO:116;
   (b)(ii) one or more oligonucleotides which are detectably labeled and which hybridize under stringent conditions to a GBP1 nucleic acid sequence corresponding to SEQ ID NO: 142; and
   (c) one or more oligonucleotides which hybridize under stringent conditions to one or more additional biomarkers for tuberculosis;

wherein
(i) the one or more additional biomarkers for tuberculosis is a biomarker for an active tuberculosis infection selected from:
LOC400759/GBP1P1 (SEQ ID NO:112/113), CPVL (SEQ ID NO:129), CREG1 (SEQ ID NO:118), PF4V1 (SEQ ID NO:134), PSMB9 (SEQ ID NO:123), ALPK1 (SEQ ID NO:117), HERC2 (SEQ ID NO:132), LGALS3BP (SEQ ID NO:114), BST1 (SEQ ID NO:115), BAZ1A (SEQ ID NO:119), LYN (SEQ ID NO:120), TAPBP (SEQ ID NO:121), SERPINB1 (SEQ ID NO:122), WSB1 (SEQ ID NO:124), MVP (SEQ ID NO:125), APBB1IP (SEQ ID NO:126), FYB (SEQ ID NO:127), MB21D1/C6orf150 (SEQ ID NO:128), TICAM2 (SEQ ID NO:130), CD52 (SEQ ID NO:131), KLRA1 (SEQ ID NO:133), DEFB128 (SEQ ID NO:135) and IL8 (SEQ ID NO:136); and/or
AIM2 (SEQ ID NO:137), CD274 (SEQ ID NO:138), CD96 (SEQ ID NO:139), CDH23 (SEQ ID NO:140), IRF1 (SEQ ID NO:141), GBP1 (SEQ ID NO:142), IFIT3 (SEQ ID NO:143), IFITM3 (SEQ ID NO:144), GK (SEQ ID NO:145), NELL2 (SEQ ID NO:146), S100A11 (SEQ ID NO:147), SAMD9L (SEQ ID NO:148), STAT1 (SEQ ID NO:149), TLR6 (SEQ ID NO:150), WARS (SEQ ID NO:151), MMP9 (SEQ ID NO:152), DOCK9 (SEQ ID NO:153), SIRPB2 (SEQ ID NO:154), and/or ANKRD22 (SEQ ID NO:155); and/or
(ii) the one or more additional biomarkers for tuberculosis is a biomarker for a latent tuberculosis infection selected from:
ABCF2 (SEQ ID NO:156), FNBP1L (SEQ ID NO:157), NCF1C (SEQ ID NO:158), TBC1D3B (SEQ ID NO:159), and/or SLC14A1 (SEQ ID NO:160); and/or
CALCOCO2 (SEQ ID NO:161), GTF2B (SEQ ID NO:162), HLA B (SEQ ID NO:163), HLA-F (SEQ ID NO:164), MGST2 (SEQ ID NO:165), SPAST (SEQ ID NO:166), and/or WAC (SEQ ID NO:167);
wherein
the stringent conditions are selected to be 5° C. lower than the thermal melting point (Tm) for the specific sequence at a defined ionic strength and pH or above 60° C. at a salt concentration of 0.02 M or less at a pH of 7; and
optionally the kit further comprises at least one internal standard.

5. The kit of claim 4, wherein
(i) the one or more oligonucleotides which hybridize under stringent conditions to a SNX10 nucleic acid sequence corresponding to SEQ ID NO: 116 and/or the one or more oligonucleotides which are detectably labeled and which hybridize under stringent conditions to a SNX10 nucleic acid sequence corresponding to SEQ ID NO:116 is an oligonucleotide comprising at least one nucleic acid sequence having at least 90% sequence identity to SEQ ID NOs:14 or 15; and/or
(ii) the one or more oligonucleotides which hybridize under stringent conditions to a GBP1 nucleic acid sequence corresponding to SEQ ID NO: 142 and/or the one or more oligonucleotides which are detectably labeled and hybridize under stringent conditions to a GBP1 nucleic acid sequence corresponding to SEQ ID NO: 142 is an oligonucleotide comprising at least one nucleic acid sequence having at least 90% sequence identity to SEQ ID NOs:50 or 51.

6. The kit of claim 4, wherein the one or more oligonucleotides which hybridize under stringent conditions to one or more additional biomarkers are selected from:
(i) an oligonucleotide which comprises at least one nucleic acid sequence having at least 90% sequence identity to the nucleic acid sequence of SEQ ID NOs: 1, 2, or 3 and which hybridizes under stringent conditions to a LOC400759/GBP1P1 biomarker (SEQ ID NO:112/113);
(ii) an oligonucleotide which comprises at least one nucleic acid sequence having at least 90% sequence identity to the nucleic acid sequence of SEQ ID NOs:4 or 5 and which hybridizes under stringent conditions to a PF4V1 biomarker (SEQ ID NO:134);
(iii) an oligonucleotide which comprises at least one nucleic acid sequence having at least 90% sequence identity to the nucleic acid sequence of SEQ ID NOs:6 or 7 and which hybridizes under stringent conditions to a ALPK1 biomarker (SEQ ID NO:117);
(iv) an oligonucleotide which comprises at least one nucleic acid sequence having at least 90% sequence identity to the nucleic acid sequence of SEQ ID NOs:8, 9, or 168 to 171 and which hybridizes under stringent conditions to a HERC2 biomarker (SEQ ID NO:132);
(v) an oligonucleotide which comprises at least one nucleic acid sequence having at least 90% sequence identity to the nucleic acid sequence of SEQ ID NOs:10 or 11 and which hybridizes under stringent conditions to a LGALS3BP biomarker (SEQ ID NO:114);
(vi) an oligonucleotide which comprises at least one nucleic acid sequence having at least 90% sequence identity to the nucleic acid sequence of SEQ ID NOs:12 or 13 and which hybridizes under stringent conditions to a BST1 biomarker (SEQ ID NO:115);
(vii) an oligonucleotide which comprises at least one nucleic acid sequence having at least 90% sequence identity to the nucleic acid sequence of SEQ ID NOs:16 or 17 and which hybridizes under stringent conditions to a CREG1 biomarker (SEQ ID NO:118);
(viii) an oligonucleotide which comprises at least one nucleic acid sequence having at least 90% sequence identity to the nucleic acid sequence of SEQ ID NOs:18 or 19 and which hybridizes under stringent conditions to a BAZ1A biomarker (SEQ ID NO:11);
(ix) an oligonucleotide which comprises at least one nucleic acid sequence having at least 90% sequence identity to the nucleic acid sequence of SEQ ID NOs:20 or 21 and which hybridizes under stringent conditions to a LYN biomarker (SEQ ID NO:120);
(x) an oligonucleotide which comprises at least one nucleic acid sequence having at least 90% sequence identity to the nucleic acid sequence of SEQ ID NOs:22 or 23 and which hybridizes under stringent conditions to a TAPBP biomarker (SEQ ID NO:121);
(xi) an oligonucleotide which comprises at least one nucleic acid sequence having at least 90% sequence identity to the nucleic acid sequence of SEQ ID NOs:24 or 25 and which hybridizes under stringent conditions to a SERPINB1 biomarker (SEQ ID NO:122);
(xii) an oligonucleotide which comprises at least one nucleic acid sequence having at least 90% sequence identity to the nucleic acid sequence of SEQ ID NOs:26 or 27 and which hybridizes under stringent conditions to a PSMB9 biomarker (SEQ ID NO:123);
(xiii) an oligonucleotide which comprises at least one nucleic acid sequence having at least 90% sequence identity to the nucleic acid sequence of SEQ ID NOs:28 or 29 and which hybridizes under stringent conditions to a WSB1 biomarker (SEQ ID NO:124);

(xiv) an oligonucleotide which comprises at least one nucleic acid sequence having at least 90% sequence identity to the nucleic acid sequence of SEQ ID NOs:30 or 31 and which hybridizes under stringent conditions to an MVP biomarker (SEQ ID NO:125);

(xv) an oligonucleotide which comprises at least one nucleic acid sequence having at least 90% sequence identity to the nucleic acid sequence of SEQ ID NOs:32 or 33 and which hybridizes under stringent conditions to a APBB1IP biomarker (SEQ ID NO:126);

(xvi) an oligonucleotide which comprises at least one nucleic acid sequence having at least 90% sequence identity to the nucleic acid sequence of SEQ ID NOs:34 or 35 and which hybridizes under stringent conditions to a FYB biomarker (SEQ ID NO:127);

(xvii) an oligonucleotide which comprises at least one nucleic acid sequence having at least 90% sequence identity to the nucleic acid sequence of SEQ ID NOs:36 or 37 and which hybridizes under stringent conditions to a MB21D1/C6orf150 biomarker (SEQ ID NO:128);

(xviii) an oligonucleotide which comprises at least one nucleic acid sequence having at least 90% sequence identity to the nucleic acid sequence of SEQ ID NOs:38 or 39 and which hybridizes under stringent conditions to a CPVL biomarker (SEQ ID NO:129);

(xix) an oligonucleotide which comprises at least one nucleic acid sequence having at least 90% sequence identity to the nucleic acid sequence of SEQ ID NOs:40 or 41 and which hybridizes under stringent conditions to a TICAM2 biomarker (SEQ ID NO:130);

(xx) an oligonucleotide which comprises at least one nucleic acid sequence having at least 90% sequence identity to the nucleic acid sequence of SEQ ID NOs:42 or 43 and which hybridizes under stringent conditions to a CD52 biomarker (SEQ ID NO:131);

(xxi) an oligonucleotide which comprises at least one nucleic acid sequence having at least 90% sequence identity to the nucleic acid sequence of SEQ ID NOs:44 or 45 and which hybridizes under stringent conditions to a KLRA1 biomarker (SEQ ID NO:133);

(xxii) an oligonucleotide which comprises at least one nucleic acid sequence having at least 90% sequence identity to the nucleic acid sequence of SEQ ID NOs:46 or 47 and which hybridizes under stringent conditions to a DEFB128 biomarker (SEQ ID NO:135);

(xxiii) an oligonucleotide which comprises at least one nucleic acid sequence having at least 90% sequence identity to the nucleic acid sequence of SEQ ID NOs:48 or 49 and which hybridizes under stringent conditions to a IL8 biomarker (SEQ ID NO:136);

(xxiv) an oligonucleotide which comprises at least one nucleic acid sequence having at least 90% sequence identity to the nucleic acid sequence of SEQ ID NOs:52 or 53 and which hybridizes under stringent conditions to a IRF1 biomarker (SEQ ID NO:141);

(xxv) an oligonucleotide which comprises at least one nucleic acid sequence having at least 90% sequence identity to the nucleic acid sequence of SEQ ID NOs:54 or 55 and which hybridizes under stringent conditions to a MMP9 biomarker (SEQ ID NO:152);

(xxvi) an oligonucleotide which comprises at least one nucleic acid sequence having at least 90% sequence identity to the nucleic acid sequence of SEQ ID NOs:56 or 57 and which hybridizes under stringent conditions to a CD96 biomarker (SEQ ID NO:139);

(xxvii) an oligonucleotide which comprises at least one nucleic acid sequence having at least 90% sequence identity to the nucleic acid sequence of SEQ ID NOs:58 or 59 and which hybridizes under stringent conditions to a AIM2 biomarker (SEQ ID NO:137);

(xxviii) an oligonucleotide which comprises at least one nucleic acid sequence having at least 90% sequence identity to the nucleic acid sequence of SEQ ID NOs:60 or 61 and which hybridizes under stringent conditions to a CD274 biomarker (SEQ ID NO:138);

(xxix) an oligonucleotide which comprises at least one nucleic acid sequence having at least 90% sequence identity to the nucleic acid sequence of SEQ ID NOs:62 or 63 and which hybridizes under stringent conditions to a CDH23 biomarker (SEQ ID NO:140);

(xxx) an oligonucleotide which comprises at least one nucleic acid sequence having at least 90% sequence identity to the nucleic acid sequence of SEQ ID NOs:64 or 65 and which hybridizes under stringent conditions to a IFIT3 biomarker (SEQ ID NO:143);

(xxxi) an oligonucleotide which comprises at least one nucleic acid sequence having at least 90% sequence identity to the nucleic acid sequence of SEQ ID NOs:66 or 67 and which hybridizes under stringent conditions to a IFITM3 biomarker (SEQ ID NO:144);

(xxxii) an oligonucleotide which comprises at least one nucleic acid sequence having at least 90% sequence identity to the nucleic acid sequence of SEQ ID NOs:68 or 69 and which hybridizes under stringent conditions to a GK biomarker (SEQ ID NO:145);

(xxxiii) an oligonucleotide which comprises at least one nucleic acid sequence having at least 90% sequence identity to the nucleic acid sequence of SEQ ID NOs:70 or 71 and which hybridizes under stringent conditions to a NELL2 biomarker (SEQ ID NO:146);

(xxxiv) an oligonucleotide which comprises at least one nucleic acid sequence having at least 90% sequence identity to the nucleic acid sequence of SEQ ID NOs:72 or 73 and which hybridizes under stringent conditions to a S100A11 biomarker (SEQ ID NO:147);

(xxxv) an oligonucleotide which comprises at least one nucleic acid sequence having at least 90% sequence identity to the nucleic acid sequence of SEQ ID NOs:74 or 75 and which hybridizes under stringent conditions to a SAMD9L biomarker (SEQ ID NO:148);

(xxxvi) an oligonucleotide which comprises at least one nucleic acid sequence having at least 90% sequence identity to the nucleic acid sequence of SEQ ID NOs:76 or 77 and which hybridizes under stringent conditions to a STAT1 biomarker (SEQ ID NO:149);

(xxxvii) an oligonucleotide which comprises at least one nucleic acid sequence having at least 90% sequence identity to the nucleic acid sequence of SEQ ID NOs:78 or 79 and which hybridizes under stringent conditions to a TLR6 biomarker (SEQ ID NO:150);

(xxxviii) an oligonucleotide which comprises at least one nucleic acid sequence having at least 90% sequence identity to the nucleic acid sequence of SEQ ID NOs:80 or 81 and which hybridizes under stringent conditions to a WARS biomarker (SEQ ID NO:151);

(xxxix) an oligonucleotide which comprises at least one nucleic acid sequence having at least 90% sequence identity to the nucleic acid sequence of SEQ ID NOs:82 or 83 and which hybridizes under stringent conditions to a DOCK9 biomarker (SEQ ID NO:153);

(xl) an oligonucleotide which comprises at least one nucleic acid sequence having at least 90% sequence identity to the nucleic acid sequence of SEQ ID NOs:84 or 85 and which hybridizes under stringent conditions to a SIRPB2 biomarker (SEQ ID NO:154);
(xli) an oligonucleotide which comprises at least one nucleic acid sequence having at least 90% sequence identity to the nucleic acid sequence of SEQ ID NOs:86 or 87 and which hybridizes under stringent conditions to a ANKRD22 biomarker (SEQ ID NO:155);
(xlii) an oligonucleotide which comprises at least one nucleic acid sequence having at least 90% sequence identity to the nucleic acid sequence of SEQ ID NOs:88 or 89 and which hybridizes under stringent conditions to a ABCF2 (NM_005692.3) biomarker (SEQ ID NO:156);
(xliii) an oligonucleotide which comprises at least one nucleic acid sequence having at least 90% sequence identity to the nucleic acid sequence of SEQ ID NOs:90 or 91 and which hybridizes under stringent conditions to a FNBP1L biomarker (SEQ ID NO:157);
(xliv) an oligonucleotide which comprises at least one nucleic acid sequence having at least 90% sequence identity to the nucleic acid sequence of SEQ ID NOs:92 or 93 and which hybridizes under stringent conditions to a NCF1C biomarker (SEQ ID NO:158);
(xlv) an oligonucleotide which comprises at least one nucleic acid sequence having at least 90% sequence identity to the nucleic acid sequence of SEQ ID NOs:94 or 95 and which hybridizes under stringent conditions to a TBC1D3B biomarker (SEQ ID NO:159);
(xlvi) an oligonucleotide which comprises at least one nucleic acid sequence having at least 90% sequence identity to the nucleic acid sequence of SEQ ID NOs:96 or 97 and which hybridizes under stringent conditions to a SLC14A1 biomarker (SEQ ID NO:160);
(xlvii) an oligonucleotide which comprises at least one nucleic acid sequence having at least 90% sequence identity to the nucleic acid sequence of SEQ ID NOs:98 or 99 and which hybridizes under stringent conditions to a CALCOCO2 biomarker (SEQ ID NO:161);
(xlviii) an oligonucleotide which comprises at least one nucleic acid sequence having at least 90% sequence identity to the nucleic acid sequence of SEQ ID NOs: 100 or 101 and which hybridizes under stringent conditions to a GTF2B biomarker (SEQ ID NO:162);
(xlix) an oligonucleotide which comprises at least one nucleic acid sequence having at least 90% sequence identity to the nucleic acid sequence of SEQ ID NOs: 102 or 103 and which hybridizes under stringent conditions to an HLA-B biomarker (SEQ ID NO:163);
(l) an oligonucleotide which comprises at least one nucleic acid sequence having at least 90% sequence identity to the nucleic acid sequence of SEQ ID NOs: 104 or 105 and which hybridizes under stringent conditions to an HLA-F biomarker (SEQ ID NO:164);
(li) an oligonucleotide which comprises at least one nucleic acid sequence having at least 90% sequence identity to the nucleic acid sequence of SEQ ID NOs: 106 or 107 and which hybridizes under stringent conditions to a MGST2 biomarker (SEQ ID NO:165);
(lii) an oligonucleotide which comprises at least one nucleic acid sequence having at least 90% sequence identity to the nucleic acid sequence of SEQ ID NOs: 108 or 109 and which hybridizes under stringent conditions to a SPAST biomarker (SEQ ID NO:166); and/or
(liii) an oligonucleotide which comprises at least one nucleic acid sequence having at least 90% sequence identity to the nucleic acid sequence of SEQ ID NOs: 110 or 111 and which hybridizes under stringent conditions to a WAC biomarker (SEQ ID NO:167).

7. The kit according to claim 4, wherein:
(a) the one or more oligonucleotides which hybridize under stringent conditions to a SNX10 nucleic acid sequence corresponding to SEQ ID NO:116 and one or more oligonucleotides which hybridize under stringent conditions to a GBP1 nucleic acid sequence corresponding to SEQ ID NO: 142 are immobilized on an inert support; or
(b) the one or more oligonucleotides which are detectably labeled and which hybridize under stringent conditions to a SNX10 nucleic acid sequence corresponding to SEQ ID NO:116 and one or more oligonucleotides which are detectably labeled and which hybridize under stringent conditions to a GBP1 nucleic acid sequence corresponding to SEQ ID NO: 142 are immobilized on an inert support.

8. The kit according to claim 4, wherein the sample is a blood sample, a purified peripheral blood leukocyte sample, a sputum sample, a saliva sample, or a urine sample.

9. The kit according to claim 4, which is a kit for determining the presence or amount of SNX10 and GBP1 biomarker by qPCR, wherein
(i) two of the oligonucleotides which hybridize under stringent conditions to a SNX10 nucleic acid sequence corresponding to SEQ ID NO:116 are amplification primers;
(ii) two of the oligonucleotides which hybridize under stringent conditions to a GBP1 nucleic acid sequence corresponding to SEQ ID NO: 142 are amplification primers;
(iii) the oligonucleotide which is labeled and which hybridizes under stringent conditions to a SNX10 nucleic acid sequence corresponding to SEQ ID NO:116 is a probe; and
(iv) the oligonucleotide which is labeled and which hybridizes under stringent conditions to a GBP1 nucleic acid sequence corresponding to SEQ ID NO: 142 is a probe.

10. A kit for diagnosing tuberculosis in an individual based on determining the presence or amount of a sorting nexin 10 (SNX10) biomarker encoded by a nucleotide corresponding to SEQ ID NO: 116 and an interferon-induced guanylate-binding protein-1 (GBP1) biomarker encoded by a nucleotide corresponding to SEQ ID NO: 142 in a sample, wherein the kit comprise antibodies, and wherein said antibodies consist essentially of:
(a) one or more antibodies specific for SNX10 biomarkers;
(b) one or more antibodies specific for GBP1 biomarkers;
(c) one or more detectably labeled antibodies specific for the SNX10 biomarkers;
(d) one or more detectably labeled antibodies specific for the GBP1 biomarkers;
(e) one or more antibody specific for one or more additional biomarker;
(f) one or more detectably labeled antibodies specific for the one or more additional biomarkers,
wherein
(i) the one or more additional biomarkers for tuberculosis is a biomarker for an active tuberculosis infection, wherein said additional biomarker is encoded by a nucleic acid selected from:
LOC400759/GBP1P1 (SEQ ID NO:112/113), CPVL (SEQ ID NO:129), CREG1 (SEQ ID NO:118), PF4V1 (SEQ ID NO:134), PSMB9 (SEQ ID NO:123), ALPK1 (SEQ ID NO:117), HERC2 (SEQ ID NO:132), LGALS3BP (SEQ ID NO:114), BST1 (SEQ ID NO:115), BAZ1A (SEQ ID NO:119), LYN (SEQ ID NO:120), TAPBP (SEQ ID NO:121), SERPINB1 (SEQ ID NO:122), WSB1 (SEQ ID NO:124), MVP (SEQ ID NO:125), APBB1IP (SEQ ID NO:126), FYB (SEQ ID NO:127), MB21D1/C6orf150 (SEQ ID NO:128), TICAM2 (SEQ ID NO:130), CD52 (SEQ ID NO:131), KLRA1 (SEQ ID NO:133), DEFB128 (SEQ ID NO:135) and IL8 (SEQ ID NO:136); and/or AIM2 (SEQ ID NO:137), CD274 (SEQ ID NO:138), CD96 (SEQ ID NO:139), CDH23 (SEQ ID NO:140), IRF1 (SEQ ID NO:141), GBP1 (SEQ ID NO:142), IFIT3 (SEQ ID NO:143), IFITM3 (SEQ ID NO:144), GK (SEQ ID NO:145), NELL2 (SEQ ID NO:146), S100A11 (SEQ ID NO:147), SAMD9L (SEQ ID NO:148), STAT1 (SEQ ID NO:149), TLR6 (SEQ ID NO:150), WARS (SEQ ID NO:151), MMP9 (SEQ ID NO:152), DOCK9 (SEQ ID NO:153), SIRPB2 (SEQ ID NO:154), and/or ANKRD22 (SEQ ID NO:155); and/or (ii) the one or more additional biomarkers for tuberculosis is a biomarker for a latent tuberculosis infection, wherein said additional biomarker is encoded by a nucleic acid selected from:

ABCF2 (SEQ ID NO:156), FNBP1L (SEQ ID NO:157), NCF1C (SEQ ID NO:158), TBC1D3B (SEQ ID NO:159), and/or SLC14A1 (SEQ ID NO:160); and/or CALCOCO2 (SEQ ID NO:161), GTF2B (SEQ ID NO:162), HLA B (SEQ ID NO:163), HLA-F (SEQ ID NO:164), MGST2 (SEQ ID NO:165), SPAST (SEQ ID NO:166), and/or WAC (SEQ ID NO:167); and optionally wherein the kit further comprises at least one internal standard.

11. A kit for diagnosing tuberculosis in an individual based on determining the presence or amount of the sorting nexin 10 (SNX10) biomarker encoded by a nucleotide corresponding to SEQ ID NO:116 and the interferon-induced guanylate-binding protein-1 (GBP1) biomarker encoded by a nucleotide corresponding to SEQ ID NO:142 in a sample, wherein the kit comprises oligonucleotides; wherein said oligonucleotides consist essentially of:
(a)(i) one or more oligonucleotides which hybridize under stringent conditions to a SNX10 nucleic acid sequence corresponding to SEQ ID NO:116;
(a)(ii) one or more oligonucleotides which hybridize under stringent conditions to a GBP1 nucleic acid sequence corresponding to SEQ ID NO: 142;
(b)(i) one or more oligonucleotides which are detectably labeled and which hybridize under stringent conditions to a SNX10 nucleic acid sequence corresponding to SEQ ID NO:116;
(b)(ii) one or more oligonucleotides which are detectably labeled and which hybridize under stringent conditions to a GBP1 nucleic acid sequence corresponding to SEQ ID NO: 142;

and wherein the stringent conditions are selected to be 5° C. lower than the thermal melting point (Tm) for the specific sequence at a defined ionic strength and pH or above 60° C. at a salt concentration of 0.02 M or less at a pH of 7; and optionally the kit further comprises at least one internal standard.

12. The kit according to claim 11, wherein:
(a) the one or more oligonucleotides which hybridize under stringent conditions to a SNX10 nucleic acid sequence corresponding to SEQ ID NO:116 and one or more oligonucleotides which hybridize under stringent conditions to a GBP1 nucleic acid sequence corresponding to SEQ ID NO: 142 are immobilized on an inert support; or
(b) the one or more oligonucleotides which are detectably labeled and which hybridize under stringent conditions to a SNX10 nucleic acid sequence corresponding to SEQ ID NO:116 and one or more oligonucleotides which are detectably labelled and which hybridize under stringent conditions to a GBP1 nucleic acid sequence corresponding to SEQ ID NO: 142 are immobilized on an inert support.

13. The kit according to claim 11, wherein the sample is a blood sample, a purified peripheral blood leukocyte sample, a sputum sample, a saliva sample, or a urine sample.

14. The kit according to claim 11, which is a kit for determining the presence or amount of SNX10 and GBP1 biomarker by qPCR, wherein
(i) two of the oligonucleotides which hybridize under stringent conditions to a SNX10 nucleic acid sequence corresponding to SEQ ID NO:116 are amplification primers;
(ii) two of the oligonucleotides which hybridize under stringent conditions to a GBP1 nucleic acid sequence corresponding to SEQ ID NO: 142 are amplification primers;
(iii) the oligonucleotide which is labeled and which hybridizes under stringent conditions to a SNX10 nucleic acid sequence corresponding to SEQ ID NO:116 is a probe; and
(iv) the oligonucleotide which is labeled and which hybridizes under stringent conditions to a GBP1 nucleic acid sequence corresponding to SEQ ID NO: 142 is a probe.

* * * * *